US009150874B2

(12) United States Patent
Damude et al.

(10) Patent No.: US 9,150,874 B2
(45) **Date of Patent: *Oct. 6, 2015**

(54) DELTA-9 ELONGASES AND THEIR USE IN MAKING POLYUNSATURATED FATTY ACIDS

(71) Applicant: E. I. du Pont de Nemours And Company, Wilmington, DE (US)

(72) Inventors: Howard Glenn Damude, Hockessin, DE (US); Brian McGonigle, Wilmington, DE (US); Quinn Qun Zhu, West Chester, PA (US); Zhixiong Xue, Chadds Ford, PA (US)

(73) Assignee: E I DU PONT DE NEMOURS AND COMPANY, Wilmington, DE (US)

(*) Notice: Subject to any disclaimer, the term of this patent is extended or adjusted under 35 U.S.C. 154(b) by 224 days.

This patent is subject to a terminal disclaimer.

(21) Appl. No.: 13/834,813

(22) Filed: Mar. 15, 2013

(65) Prior Publication Data

US 2013/0254931 A1 Sep. 26, 2013

Related U.S. Application Data

(62) Division of application No. 12/725,482, filed on Mar. 17, 2010, now Pat. No. 8,420,892.

(60) Provisional application No. 60/739,989, filed on Nov. 23, 2005.

(51) Int. Cl.

| | |
|---|---|
| ***A01H 5/10*** | (2006.01) |
| ***A01H 1/00*** | (2006.01) |
| ***C12N 15/82*** | (2006.01) |
| ***C11B 1/02*** | (2006.01) |
| ***C12N 9/10*** | (2006.01) |
| ***C12P 7/64*** | (2006.01) |
| *C12N 15/00* | (2006.01) |

(52) U.S. Cl.

CPC ............ *C12N 15/8247* (2013.01); *C11B 1/025* (2013.01); *C12N 9/1029* (2013.01); *C12P 7/6427* (2013.01); *C12P 7/6463* (2013.01); *C12P 7/6472* (2013.01)

(58) Field of Classification Search

None

See application file for complete search history.

(56) References Cited

U.S. PATENT DOCUMENTS

| | | | |
|---|---|---|---|
| 6,075,183 | A | 6/2000 | Knutzon et al. |
| 6,403,349 | B1 | 6/2002 | Mukerji et al. |
| 6,459,018 | B1 | 10/2002 | Knutzon |
| 6,677,145 | B2 | 1/2004 | Mukerji et al. |
| 6,825,017 | B1 | 11/2004 | Browse et al. |
| 2004/0111763 | A1 | 6/2004 | Heinz et al. |
| 2004/0253621 | A1 | 12/2004 | Picataggio et al. |
| 2006/0094092 | A1 | 5/2006 | Damude et al. |
| 2006/0110806 | A1 | 5/2006 | Damude et al. |
| 2006/0115881 | A1 | 6/2006 | Damude et al. |
| 2006/0195939 | A1 | 8/2006 | Damude et al. |

FOREIGN PATENT DOCUMENTS

| | | |
|---|---|---|
| WO | WO 98/46764 | 10/1998 |
| WO | WO 98/55625 | 10/1998 |
| WO | WO 00/12720 | 3/2000 |
| WO | WO 00/34439 | 6/2000 |
| WO | WO 02/26946 | 4/2002 |
| WO | WO 02/077213 | 10/2002 |
| WO | WO 2004/057001 | 7/2004 |
| WO | WO 2004/071178 | 8/2004 |
| WO | WO 2004/071467 | 8/2004 |
| WO | WO 2004/090123 | 10/2004 |
| WO | WO 2004/101753 | 11/2004 |
| WO | WO 2004/101757 | 11/2004 |

OTHER PUBLICATIONS

Abbadi et al., Biosyntheses of Very-Long-Chain Polyunsaturated Fatty Acids in Transgenic Oilseeds: Constraints on their Accumulation. The Plant Cell, vol. 16, p. 2734-2748, Oct. 2004.

Barsanti et al., Fatty Acid Content in Wild Type and wzsl Mutant of *Euglena gracilis*, Journal of Applied Phycology, vol. 12, pp. 515-520, 2000.

Browse et al., Trends in Biochemical Sciences, Polyunsaturated fatty acid synthesis: what will they think of next? vol. 27(9), pp. 467-473, 2002,.

Guhaniyogi et al., Regulation of MRNA Stability in Mammalian Cells, Gene, vol. 183, pp. 626-645, 1990.

Jotun Hein, Unified Approach to Alignment and Phylogenies, Methods in Enzymology, vol. 183, pp. 626-645, 1990.

Lassner, et al., A Jojoba Beta-Ketoacyl-Coa Synthase cDNA Complements the Canola Fatty Acid Elongation Mutation in Transgenic Plants, The Plant Cell, vol. 8, pp. 281-292, 1996.

Napier, Trends in Plant Sciences, Plumbing the depths of PUFA biosynthesis: a novel polyketide synthase-like pathway from marine organisms, vol. 7(2), pp. 51-54, 2002.

National Center for Biotechnology Information General Identifier No. 17226123, Accession No. AAL37626, Mar. 9, 2006, Qi et al., Identification of a cDNA encoding a novel C18-Delta(9) polyunsaturated fatty acid-specific elongating activity from the docosahexaenoic acid (DHA)-producing microalga, *Isochrysis galbana*.

National Center for Biotechnology Information General Identifier No. 86565568, Accession No. NM_068396, The *C. elegans* Sequencing Consortium, Mar. 23, 2007.

National Center for Biotechnology Information General Identifier No. 21899501, Accession No. AX464731, Jul. 16, 2002, Elongase Genes and Uses Mukerji et al.

National Center for Biotechnology Information General Identifier No. 30690063, Accession No. NM_119617, Apr. 20, 2007.

(Continued)

*Primary Examiner* — Phoung Bui

(57) ABSTRACT

Isolated nucleic acid fragments and recombinant constructs comprising such fragments encoding delta-9 elongases along with a method of making long-chain polyunsaturated fatty acids (PUFAs) using these delta-9 elongases in plants.

11 Claims, 24 Drawing Sheets

(56) References Cited

OTHER PUBLICATIONS

National Center for Biotechnology Information General Identifier No. 31981652, Accession No. NM_134255, Jun. 3, 2007, The Status, Quality and Expansion of the NIH Full-Length cDNA Project: Mammalian Gene Collection.

National Center for Biotechnology Information General Identifier No. 148298785, Accession No. NM_134383, Jun. 26, 2007, Identification and Expression of a Rat Fatty Acid Elongase Involved in the Biosynthesis of C18 Fatty Acids. Inagaki et al.

National Center for Biotechnology Information General Identifier No. 19705492, Accession No. NM_134382, Nov. 17, 2006, Identification and Expression of a Rat Fatty Acid Elongase Involved in the Biosynthesis of C18 Fatty, Inagaki et al.

National Center for Biotechnology Information General Identifier No. 86565567, Accession No. NM_068392, Mar. 23, 2007.

National Center for Biotechnology Information General Identifier No. 86565488, Accession No. NM_070713, Mar. 23, 2007.

National Center for Biotechnology Information General Identifier No. 71985633, Accession No. NM_068746, Mar. 23, 2007.

National Center for Biotechnology Information General Identifier No. 17537430, Accession No. NM_064685, Mar. 23, 2007.

National Center for Biotechnology Information General Identifier No. 17226122, Accession No. AF390174, Qi et al., Identification of a cDNA Encoding a Novel C18-Delta(9) Polyunsaturated Fatty Acid-Specific Elongating Activity from the Docosahexaenoic Acid (DHA)-Producing Microalga, *Isochrysis galbana*, 2006.

National Center for Biotechnology Information General Identifier No. 2440162, Accession No. Y14837, Markausakas et al., A New Cloning Vector PUC57, Feb. 11, 1999.

Qi et al., Production of Very Long Chain Polyunsaturated Omega-3 and Omega-6 Fatty Acids in Plants, Nature Biotechnology, vol. 22(6), pp. 739-745, 2004.

Qi et al., FEBS Lett., Identification of a cDNA encoding a novel C18-Delta(9) polyunsaturated fatty acid-specific elongating activity from the docosahexaenoic acid (DHA)-producing microalga, *Isochrysis galbana*, vol. 510(3), pp. 159-165, 2002.

Qi, B., et al., "Identification of a cDNA encoding a novel C18-Delta (9) polyunsaturated . . . ", GenBank Database Accession No. AF390174, Jun. 11, 2001.

Smith et al., Planta, Heterologous expression of a fatty acid hydroxylase gene in developing seeds of *Arabidopsis thaliana*, vol. 217, pp. 507-516, 2003.

Spychalla et al., Proc. Natl. Acad. Sci. USA, Identification of an animal w-3 fatty acid desaturase by heterologous expression in *Arabidopsis*, vol. 94, pp. 1142-1147, 1997.

Wallis et al., The Delta8-Desaturase of *Euglena gracilis*: An Alternate Pathway for Synthesis of 20-Carbon Polyunsaturated Fatty Acids, Archives of Biochemistry & Biophysics, vol. 365(2), pp. 307-316, 1999.

U.S. Appl. No. 12/725,482, Restriction Election, mailed Mar. 11, 2011.

U.S. Appl. No. 12/725,482, Non Final Rejection, mailed Feb. 9, 2012.

U.S. Appl. No. 12/725,482, Final Rejection, mailed Jul. 26, 2012.

U.S. Appl. No. 12/725,482, Notice of Allowance and Fees Due, mailed Dec. 13, 2012.

| | | | | | | | | | | | | | | | | | | | | |
|---|---|---|---|---|---|---|---|---|---|---|---|---|---|---|---|---|---|---|---|---|
| pY119-5 | | 12.5 | 55.2 | 3.5 | 27.3 | 0.0 | 0.0 | 0.0 | 0.0 | 0.6 | 0.0 | 0.0 | 0.0 | 0.0 | 0.0 | 0.0 | 0.0 | 0.0 | 0.7 | |
| pY119-6 | | 13.0 | 53.8 | 3.6 | 28.3 | 0.0 | 0.0 | 0.0 | 0.0 | 0.5 | 0.0 | 0.0 | 0.0 | 0.0 | 0.0 | 0.0 | 0.0 | 0.0 | 0.6 | |
| pY119-8 | | 12.5 | 52.8 | 3.5 | 30.2 | 0.0 | 0.0 | 0.0 | 0.0 | 0.5 | 0.0 | 0.0 | 0.0 | 0.0 | 0.1 | 0.0 | 0.0 | 0.0 | 0.5 | |
| pY75 | LA | 17.4 | 20.5 | 4.6 | 11.1 | **45.3** | 0.0 | 0.0 | 0.0 | **0.6** | 0.0 | 0.0 | 0.0 | 0.0 | 0.0 | 0.0 | 0.0 | 0.0 | 0.5 | 1.2 |
| pY119-5 | | 13.6 | 30.9 | 3.1 | 12.2 | **32.0** | 0.0 | 0.0 | 0.0 | **7.7** | 0.0 | 0.0 | 0.0 | 0.0 | 0.0 | 0.0 | 0.0 | 0.0 | 0.5 | 19.3 |
| pY119-6 | | 15.2 | 26.7 | 4.0 | 13.4 | **30.7** | 0.0 | 0.0 | 0.0 | **8.7** | 0.0 | 0.0 | 0.5 | 0.0 | 0.0 | 0.2 | 0.0 | 0.0 | 0.6 | 22.1 |
| pY119-8 | | 14.0 | 29.1 | 3.9 | 15.2 | **27.1** | 0.0 | 0.0 | 0.0 | **10.1** | 0.0 | 0.0 | 0.0 | 0.0 | 0.0 | 0.2 | 0.0 | 0.0 | 0.4 | 27.2 |
| pY75 | ALA | 11.1 | 6.2 | 4.4 | 4.4 | 0.2 | 0.0 | **72.7** | 0.0 | 0.4 | 0.0 | 0.0 | **0.3** | 0.0 | 0.0 | 0.0 | 0.0 | 0.0 | 0.3 | 0.4 |
| pY119-5 | | 11.7 | 17.3 | 4.9 | 13.3 | 0.1 | 0.0 | **41.0** | 0.0 | 0.3 | 0.0 | 0.0 | **11.2** | 0.0 | 0.0 | 0.0 | 0.0 | 0.0 | 0.4 | 21.4 |
| pY119-6 | | 11.7 | 16.1 | 5.0 | 12.6 | 0.1 | 0.0 | **42.1** | 0.0 | 0.3 | 0.0 | 0.0 | **11.7** | 0.0 | 0.0 | 0.1 | 0.0 | 0.0 | 0.4 | 21.7 |
| pY119-8 | | 11.1 | 17.3 | 4.7 | 13.1 | 0.1 | 0.0 | **41.1** | 0.0 | 0.2 | 0.0 | 0.0 | **12.2** | 0.0 | 0.0 | 0.0 | 0.0 | 0.0 | 0.4 | 22.9 |
| pY75 | GLA | 16.4 | 7.0 | 5.4 | 6.0 | 0.0 | **62.3** | 0.0 | 0.2 | 0.4 | **0.4** | 0.0 | 0.0 | 0.0 | 0.0 | 0.4 | 0.0 | 0.0 | 0.6 | 0.6 |
| pY119-5 | | 16.4 | 10.1 | 5.3 | 8.4 | 0.0 | **57.1** | 0.0 | 0.2 | 0.4 | **0.5** | 0.0 | 0.0 | 0.0 | 0.0 | 0.5 | 0.0 | 0.0 | 0.7 | 0.8 |
| pY119-6 | | 14.6 | 9.8 | 4.7 | 7.0 | 0.0 | **61.9** | 0.0 | 0.2 | 0.3 | **0.4** | 0.0 | 0.0 | 0.0 | 0.0 | 0.6 | 0.0 | 0.0 | 0.5 | 0.7 |
| pY119-8 | | 16.4 | 8.0 | 4.9 | 6.1 | 0.0 | **62.5** | 0.0 | 0.2 | 0.2 | **0.6** | 0.0 | 0.0 | 0.0 | 0.0 | 0.5 | 0.0 | 0.0 | 0.5 | 0.9 |
| pY75 | STA | 11.5 | 5.9 | 4.9 | 5.9 | 0.0 | 0.0 | 0.0 | **70.7** | 0.2 | 0.0 | 0.0 | 0.0 | **0.4** | 0.0 | 0.0 | 0.0 | 0.0 | 0.5 | 0.5 |
| pY119-5 | | 12.5 | 5.4 | 5.0 | 5.0 | 0.0 | 0.0 | 0.0 | **70.5** | 0.3 | 0.0 | 0.0 | 0.2 | **0.5** | 0.0 | 0.0 | 0.0 | 0.0 | 0.7 | 0.7 |
| pY119-6 | | 11.4 | 6.6 | 5.2 | 7.0 | 0.0 | 0.1 | 0.0 | **68.5** | 0.3 | 0.0 | 0.0 | 0.0 | **0.4** | 0.0 | 0.0 | 0.0 | 0.0 | 0.5 | 0.6 |
| pY119-8 | | 11.3 | 5.0 | 3.9 | 4.5 | 0.0 | 0.1 | 0.0 | **74.1** | 0.2 | 0.0 | 0.0 | 0.0 | **0.5** | 0.0 | 0.0 | 0.0 | 0.0 | 0.5 | 0.6 |
| pY75 | ARA | 19.2 | 33.2 | 4.9 | 17.3 | 0.0 | 0.0 | 0.0 | 0.0 | 0.6 | 0.1 | **24.0** | 0.0 | 0.0 | 0.0 | 0.0 | **0.0** | 0.0 | 0.7 | 0.0 |
| pY119-5 | | 18.6 | 34.4 | 4.2 | 19.0 | 0.0 | 0.0 | 0.0 | 0.0 | 0.5 | 0.1 | **21.7** | 0.0 | 0.0 | 0.0 | 0.0 | **0.1** | 0.0 | 0.8 | 0.5 |
| pY119-6 | | 16.9 | 34.4 | 5.5 | 24.4 | 0.0 | 0.0 | 0.0 | 0.0 | 0.3 | 0.1 | **17.6** | 0.0 | 0.0 | 0.0 | 0.0 | **0.1** | 0.0 | 0.6 | 0.6 |
| pY119-8 | | 17.7 | 36.5 | 4.4 | 16.7 | 0.0 | 0.0 | 0.0 | 0.0 | 0.5 | 0.1 | **21.5** | 0.0 | 0.0 | 0.0 | 0.0 | **0.1** | 0.0 | 0.4 | 0.5 |
| pY75 | FPA | 16.7 | 27.7 | 4.7 | 16.4 | 0.0 | 0.0 | 0.0 | 0.0 | 0.4 | 0.0 | 0.1 | 0.0 | 0.0 | **33.7** | 0.0 | 0.0 | **0.0** | 0.4 | 0.0 |
| pY119-5 | | 16.0 | 29.9 | 5.0 | 18.7 | 0.0 | 0.0 | 0.0 | 0.0 | 0.0 | 0.0 | 0.1 | 0.0 | 0.0 | **29.6** | 0.0 | 0.0 | **0.1** | 0.5 | 0.4 |
| pY119-6 | | 17.4 | 27.3 | 6.0 | 20.8 | 0.0 | 0.0 | 0.0 | 0.0 | 0.0 | 0.0 | 0.1 | 0.0 | 0.0 | **27.7** | 0.1 | 0.0 | **0.1** | 0.5 | 0.4 |
| pY119-8 | | 16.5 | 28.8 | 5.9 | 22.1 | 0.0 | 0.0 | 0.0 | 0.0 | 0.0 | 0.0 | 0.1 | 0.0 | 0.0 | **25.9** | 0.0 | 0.0 | **0.1** | 0.6 | 0.4 |

FIG. 14

```
    M...N..................W......E.L........LK..L...G  Consensus #1
             10        20        30        40        50
1   MEVVNEIVSIGQEVLPKVDYAQLWSDASHCEVLYLSIAFVILKFTLGPLG  SEQ ID NO5.pro
1   MALANDAGE------------RIWAAVTDPEILIGTFSYLLLKPLLRNSG  SEQ ID NO27.pro

    ...............YN.L....S..SF...A.A....Y..G........  Consensus #1
             60        70        80        90       100
51  PKGQSRMKF--VFTNYNLLMSIYSLGSFLSMAYAM---YTIGV-----MS  SEQ ID NO5.pro
39  LVDEKKGAYRTSMIWYNVLLALFSALSFYVTATALGWDYGTGAWLRRQTG  SEQ ID NO27.pro

    D.....F.......D...F..T...FY.SK..EY.D...L.L.GK....L  Consensus #1
            110       120       130       140       150
91  DNCEKAF-------DNNVFRITTQLFYLSKFLEYIDSFYLPLMGKPLTWL  SEQ ID NO5.pro
89  DTPQPLFQCPSPVWDSKLPTWTAKAFYYSKYVEYLDTAWLVLKGKRVSFL  SEQ ID NO27.pro

    Q.FHH.GAP.D..L.....NE.VWIF...N.FIH.IMY.YY.......KF  Consensus #1
            160       170       180       190       200
134 QFFHHLGAPMDMWLFYNYRNEAVWIFVLLNGFIHWIMYGYYWTRLIKLKF  SEQ ID NO5.pro
139 QAFHHFGAPWDVYLGIRLHNEGVWIFMFFNSFIHTIMYTYYGLTAAGYKF  SEQ ID NO27.pro

    ...K.LIT.MQI.QF..GF..VW.Y.N.PC...D....F.W.FNY.YVG.  Consensus #1
            210       220       230       240       250
184 PMPKSLITSMQIIQFNVGFYIVWKYRNIPCYRQDGMRMFGWFFNYFYVGT  SEQ ID NO5.pro
189 -KAKPLITAMQICQFVGGFLLVWDYINVPCFNSDKGKLFSWAFNYAYVGS  SEQ ID NO27.pro

    V..LF..F..Q.....K....A.K..                          Consensus #1
            260       270
234 VLCLFLNFYVQTYIVRKHKG-AKKIQ                          SEQ ID NO5.pro
238 VFLLFCHFFYQDNLATKKSAKAGKQL                          SEQ ID NO27.pro
```

FIG. 16

| Event | Fatty acid composition (wt.%) 16:0 | 18:0 | 18:1 | LA | ALA | EDA | ERA | delta-9 %Elong | LA %Elong | ALA %Elong | Ratio (LA/ALA) %Elong |
|---|---|---|---|---|---|---|---|---|---|---|---|
| '1936-5-2-1 | 18.4 | 2.4 | 17.5 | 21.7 | 4.7 | 28.6 | 6.6 | 57.2 | 56.9 | 58.5 | 1.0 |
| '1936-5-2-2 | 15.2 | 2.1 | 14.3 | 24.6 | 7.0 | 29.1 | 7.6 | 53.8 | 54.2 | 52.2 | 1.0 |
| '1936-5-2-3 | 14.3 | 2.7 | 11.2 | 18.8 | 3.1 | 40.5 | 9.5 | 69.5 | 68.3 | 75.3 | 0.9 |
| '1936-5-2-4 | 16.5 | 2.5 | 5.2 | 50.3 | 24.1 | 0.9 | 0.5 | 1.8 | 1.8 | 2.0 | 0.9 |
| '1936-5-2-5 | 14.7 | 2.8 | 10.5 | 20.5 | 4.1 | 38.9 | 8.5 | 65.7 | 65.4 | 67.2 | 1.0 |
| Average | 15.8 | 2.5 | 11.7 | 27.2 | 8.6 | 27.6 | 6.5 | 49.6 | 49.3 | 51.0 | 1.0 |
| '1936-5-3-1 | 13.3 | 2.7 | 26.1 | 23.8 | 4.9 | 23.9 | 5.4 | 50.5 | 50.2 | 52.4 | 1.0 |
| '1936-5-3-2 | 17.1 | 2.1 | 21.5 | 26.1 | 6.4 | 20.6 | 6.3 | 45.4 | 44.2 | 49.7 | 0.9 |
| '1936-5-3-3 | 15.3 | 2.2 | 11.0 | 28.5 | 6.1 | 30.4 | 6.4 | 51.6 | 51.6 | 51.4 | 1.0 |
| '1936-5-3-4 | 13.2 | 3.0 | 19.2 | 17.7 | 3.6 | 35.7 | 7.7 | 67.1 | 66.8 | 68.2 | 1.0 |
| '1936-5-3-5 | 14.0 | 2.8 | 10.4 | 18.5 | 4.2 | 39.2 | 10.9 | 68.9 | 67.9 | 72.3 | 0.9 |
| Average | 14.6 | 2.6 | 17.6 | 22.9 | 5.0 | 30.0 | 7.3 | 56.7 | 56.2 | 58.8 | 1.0 |
| '1936-6-4-1 | 15.1 | 1.6 | 14.7 | 35.4 | 7.5 | 19.8 | 5.8 | 37.3 | 35.8 | 43.7 | 0.8 |
| '1936-6-4-2 | 12.8 | 2.3 | 21.3 | 16.6 | 2.1 | 38.1 | 6.6 | 70.5 | 69.7 | 75.6 | 0.9 |
| '1936-6-4-3 | 17.7 | 3.0 | 13.2 | 19.8 | 2.8 | 36.9 | 6.7 | 65.9 | 65.2 | 70.4 | 0.9 |
| '1936-6-4-4 | 18.5 | 3.1 | 17.1 | 19.9 | 2.4 | 32.8 | 6.2 | 63.6 | 62.2 | 72.0 | 0.9 |
| '1936-6-4-5 | 16.1 | 2.0 | 17.4 | 25.2 | 4.8 | 28.5 | 6.1 | 53.5 | 53.0 | 56.2 | 0.9 |
| Average | 16.0 | 2.4 | 16.8 | 23.4 | 3.9 | 31.2 | 6.3 | 58.2 | 57.2 | 63.6 | 0.9 |
| '1936-6-16-1 | 15.0 | 1.6 | 13.8 | 27.3 | 4.1 | 30.7 | 7.6 | 54.9 | 52.9 | 64.7 | 0.8 |
| '1936-6-16-2 | 14.6 | 2.2 | 12.0 | 23.2 | 3.0 | 37.2 | 7.8 | 63.2 | 61.6 | 72.6 | 0.8 |
| '1936-6-16-3 | 16.9 | 2.3 | 12.1 | 19.9 | 2.5 | 39.0 | 7.3 | 67.4 | 66.2 | 74.6 | 0.9 |
| '1936-6-16-4 | 15.9 | 1.7 | 13.7 | 27.7 | 4.3 | 29.8 | 6.9 | 53.5 | 51.9 | 61.9 | 0.8 |
| '1936-6-16-5 | 14.5 | 1.5 | 15.1 | 32.0 | 6.0 | 23.5 | 7.4 | 44.9 | 42.4 | 55.5 | 0.8 |
| Average | 15.4 | 1.8 | 13.3 | 26.0 | 4.0 | 32.1 | 7.4 | 56.8 | 55.0 | 65.8 | 0.8 |
| '1936-6-26-1 | 14.4 | 3.4 | 22.3 | 16.3 | 2.2 | 37.0 | 4.4 | 69.1 | 69.4 | 66.8 | 1.0 |
| '1936-6-26-2 | 14.5 | 2.9 | 14.4 | 18.3 | 3.6 | 38.4 | 8.0 | 68.0 | 67.7 | 69.1 | 1.0 |
| '1936-6-26-3 | 19.4 | 3.1 | 5.5 | 14.9 | 2.6 | 44.0 | 10.5 | 75.7 | 74.7 | 80.0 | 0.9 |
| '1936-6-26-4 | 18.6 | 2.7 | 7.8 | 21.4 | 4.3 | 38.0 | 7.2 | 63.7 | 63.9 | 62.8 | 1.0 |
| '1936-6-26-5 | 13.2 | 3.5 | 38.9 | 14.9 | 2.8 | 23.2 | 3.6 | 60.3 | 60.9 | 56.6 | 1.1 |
| Average | 16.0 | 3.1 | 17.8 | 17.2 | 3.1 | 36.1 | 6.7 | 67.4 | 67.3 | 67.1 | 1.0 |

FIG. 20

| Event | Fatty acid composition (wt.%) 16:0 | 18:0 | 18:1 | LA | ALA | EDA | HGLA | ERA | ETA | Total delta-9 %Elong | LA %Elong | ALA %Elong | Ratio (LA/ALA) %Elong |
|---|---|---|---|---|---|---|---|---|---|---|---|---|---|
| 1919-2-2-41 | 16.8 | 3.4 | 10.7 | 17.8 | 1.6 | 19.4 | 26.3 | 0.8 | 3.3 | 72.0 | 72.0 | 72.4 | 1.0 |
| 1919-2-2-42 | 14.7 | 2.4 | 13.6 | 24.3 | 2.6 | 18.7 | 18.9 | 1.3 | 3.2 | 61.0 | 60.8 | 63.2 | 1.0 |
| 1919-2-2-43 | 16.4 | 3.3 | 15.4 | 21.2 | 2.7 | 18.6 | 18.3 | 1.3 | 2.7 | 63.2 | 63.6 | 59.8 | 1.1 |
| 1919-2-2-44 | 15.4 | 2.8 | 16.4 | 22.7 | 3.4 | 18.5 | 16.0 | 1.6 | 3.2 | 60.1 | 60.3 | 58.8 | 1.0 |
| 1919-2-2-45 | 17.0 | 3.6 | 18.8 | 23.6 | 4.6 | 12.3 | 16.4 | 0.6 | 3.1 | 53.6 | 54.8 | 46.2 | 1.2 |
| 1919-2-2-46 | 17.4 | 2.3 | 14.5 | 27.7 | 4.4 | 13.6 | 15.5 | 1.5 | 3.1 | 51.2 | 51.3 | 50.5 | 1.0 |
| Average | 16.3 | 3.0 | 14.9 | 22.9 | 3.2 | 16.9 | 18.6 | 1.2 | 3.1 | 60.2 | 60.5 | 58.5 | 1.0 |
| 1919-4-7-41 | 20.5 | 2.5 | 16.7 | 21.3 | 4.8 | 19.1 | 9.8 | 2.6 | 2.7 | 56.6 | 57.6 | 52.8 | 1.1 |
| 1919-4-7-42 | 23.7 | 3.6 | 10.7 | 18.7 | 3.6 | 26.3 | 5.1 | 6.1 | 2.1 | 64.0 | 62.6 | 69.5 | 0.9 |
| 1919-4-7-43 | 18.7 | 3.0 | 14.4 | 17.6 | 2.8 | 34.9 | 1.8 | 6.1 | 0.7 | 68.1 | 67.6 | 71.0 | 1.0 |
| 1919-4-7-44 | 14.6 | 3.8 | 14.0 | 22.7 | 4.0 | 29.7 | 4.4 | 5.3 | 1.5 | 60.4 | 60.0 | 62.7 | 1.0 |
| 1919-4-7-45 | 19.1 | 2.7 | 10.5 | 20.0 | 4.6 | 19.7 | 15.0 | 4.5 | 3.9 | 63.6 | 63.4 | 64.5 | 1.0 |
| 1919-4-7-46 | 15.3 | 4.4 | 13.0 | 13.6 | 1.6 | 40.5 | 4.9 | 5.1 | 1.6 | 77.4 | 77.0 | 80.6 | 1.0 |
| Average | 18.7 | 3.3 | 13.2 | 19.0 | 3.6 | 28.4 | 6.8 | 5.0 | 2.1 | 65.1 | 64.7 | 66.9 | 1.0 |
| 1919-4-9-41 | 15.4 | 3.0 | 20.9 | 19.2 | 3.0 | 15.5 | 18.7 | 1.0 | 3.3 | 63.5 | 64.0 | 59.6 | 1.1 |
| 1919-4-9-42 | 19.2 | 3.7 | 11.3 | 15.0 | 4.0 | 14.5 | 26.7 | 1.1 | 4.5 | 71.2 | 73.3 | 58.5 | 1.3 |
| 1919-4-9-43 | 12.9 | 4.2 | 25.7 | 21.1 | 2.7 | 14.9 | 14.4 | 1.0 | 3.1 | 58.3 | 58.1 | 60.0 | 1.0 |
| 1919-4-9-44 | 14.7 | 2.6 | 13.8 | 24.0 | 2.4 | 15.7 | 21.9 | 1.2 | 3.8 | 61.7 | 61.0 | 67.4 | 0.9 |
| 1919-4-9-45 | 17.2 | 2.5 | 13.4 | 24.9 | 4.8 | 8.7 | 22.9 | 0.7 | 4.8 | 55.5 | 55.9 | 53.5 | 1.0 |
| 1919-4-9-46 | 17.6 | 2.0 | 14.4 | 21.6 | 2.8 | 13.0 | 23.1 | 1.2 | 4.3 | 63.0 | 62.6 | 66.0 | 0.9 |
| Average | 16.2 | 3.0 | 16.6 | 21.0 | 3.3 | 13.7 | 21.3 | 1.0 | 4.0 | 62.2 | 62.5 | 60.8 | 1.0 |
| 1919-5-5-41 | 20.9 | 2.1 | 14.1 | 18.2 | 2.8 | 15.9 | 19.9 | 2.3 | 4.0 | 66.7 | 66.3 | 69.2 | 1.0 |
| 1919-5-5-42 | 17.4 | 2.6 | 18.0 | 21.3 | 4.5 | 10.0 | 19.8 | 1.6 | 4.9 | 58.4 | 58.3 | 59.1 | 1.0 |
| 1919-5-5-43 | 20.8 | 1.5 | 8.0 | 23.0 | 5.7 | 8.6 | 25.9 | 1.2 | 5.2 | 58.8 | 60.0 | 53.1 | 1.1 |
| 1919-5-5-44 | 23.6 | 4.5 | 9.6 | 9.9 | 0.9 | 22.4 | 23.0 | 2.0 | 4.1 | 82.7 | 82.1 | 87.2 | 0.9 |
| 1919-5-5-45 | 17.3 | 1.8 | 21.0 | 26.1 | 6.3 | 4.1 | 16.0 | 0.8 | 4.6 | 42.5 | 43.4 | 39.7 | 1.1 |
| 1919-5-5-46 | 20.8 | 3.0 | 13.4 | 19.6 | 3.6 | 15.5 | 19.6 | 1.5 | 3.0 | 63.1 | 64.2 | 55.7 | 1.2 |
| Average | 20.1 | 2.6 | 14.0 | 19.7 | 4.3 | 12.8 | 20.7 | 1.6 | 4.3 | 62.0 | 62.4 | 60.7 | 1.0 |
| 1919-6-8-41 | 18.3 | 1.9 | 10.4 | 18.5 | 2.9 | 13.9 | 27.6 | 1.6 | 4.9 | 69.1 | 69.1 | 69.1 | 1.0 |
| 1919-6-8-42 | 19.2 | 2.3 | 13.7 | 17.3 | 2.3 | 29.7 | 7.6 | 5.4 | 2.6 | 69.8 | 68.3 | 77.7 | 0.9 |
| 1919-6-8-43 | 14.7 | 2.5 | 29.6 | 28.0 | 7.5 | 8.0 | 5.2 | 2.0 | 2.5 | 33.3 | 32.0 | 37.5 | 0.9 |
| 1919-6-8-44 | 17.8 | 2.5 | 17.7 | 10.5 | 1.4 | 25.5 | 17.5 | 3.5 | 3.6 | 80.8 | 80.4 | 83.8 | 1.0 |
| 1919-6-8-45 | 17.6 | 2.3 | 14.8 | 15.9 | 2.5 | 29.2 | 9.6 | 5.2 | 2.7 | 71.8 | 71.0 | 75.9 | 0.9 |
| 1919-6-8-46 | 15.6 | 2.5 | 15.0 | 17.9 | 3.4 | 15.4 | 21.8 | 2.4 | 6.1 | 66.3 | 67.6 | 71.7 | 0.9 |
| Average | 17.2 | 2.3 | 16.9 | 18.0 | 3.3 | 20.3 | 14.9 | 3.3 | 3.7 | 65.5 | 64.7 | 69.3 | 0.9 |

FIG. 21

| Event | Fatty acid composition (wt.%) | | | | | | | | |
|---|---|---|---|---|---|---|---|---|---|
| | 16:0 | 18:0 | 18:1 | LA | ALA | 20:0 | 20:1(11) | EDA | ERA |
| wild-type (wt) | 8.4 | 2.9 | 14.6 | 30.6 | 20.3 | 1.8 | 18.7 | 2.2 | 0.5 |
| wt pKR926-1 | 8.0 | 3.0 | 13.6 | 26.2 | 11.0 | 1.4 | 15.5 | 14.6 | 6.6 |
| wt pKR926-2 | 8.1 | 3.3 | 13.5 | 26.0 | 12.4 | 1.6 | 17.1 | 12.3 | 5.7 |
| wt pKR926-3 | 8.6 | 3.0 | 13.7 | 28.1 | 11.2 | 1.5 | 16.3 | 12.4 | 5.2 |
| wt pKR926-4 | 8.3 | 3.0 | 15.1 | 29.0 | 12.5 | 1.5 | 17.8 | 9.2 | 3.6 |
| wt pKR926-5 | 8.2 | 3.1 | 13.7 | 26.5 | 11.5 | 1.5 | 16.0 | 13.4 | 6.0 |
| wt pKR926-6 | 8.4 | 3.2 | 14.0 | 27.2 | 11.3 | 1.5 | 16.4 | 12.7 | 5.4 |
| wt pKR926-7 | 8.3 | 3.1 | 13.8 | 27.0 | 11.2 | 1.5 | 16.3 | 13.2 | 5.5 |
| wt pKR926-8 | 8.9 | 2.9 | 12.4 | 26.5 | 11.8 | 1.4 | 14.7 | 14.7 | 6.7 |
| wt pKR926-9 | 8.1 | 3.2 | 13.5 | 26.1 | 11.9 | 1.5 | 16.2 | 13.3 | 6.1 |
| wt pKR926-10 | 8.4 | 3.2 | 14.3 | 27.7 | 12.0 | 1.5 | 16.6 | 11.4 | 4.9 |
| wt pKR926-11 | 8.8 | 3.1 | 13.3 | 26.3 | 10.8 | 1.5 | 15.1 | 14.7 | 6.3 |
| wt pKR926-12 | 8.3 | 3.1 | 12.8 | 26.8 | 10.8 | 1.4 | 15.7 | 14.7 | 6.3 |
| wt pKR926-13 | 8.9 | 3.0 | 15.3 | 32.6 | 15.6 | 1.7 | 19.4 | 2.8 | 0.8 |
| wt pKR926-14 | 8.1 | 3.0 | 13.8 | 27.4 | 12.1 | 1.6 | 17.6 | 11.5 | 4.9 |
| wt pKR926-15 | 8.3 | 2.7 | 12.7 | 27.6 | 12.5 | 1.4 | 16.1 | 13.0 | 5.8 |
| wt pKR926-16 | 8.3 | 3.0 | 13.8 | 27.7 | 12.9 | 1.6 | 17.7 | 10.4 | 4.6 |
| wt pKR926-17 | 8.0 | 3.1 | 14.5 | 28.3 | 12.8 | 1.6 | 17.6 | 9.9 | 4.2 |
| wt pKR926-18 | 8.4 | 3.1 | 14.2 | 26.7 | 12.3 | 1.5 | 16.5 | 12.0 | 5.3 |
| wt pKR926-19 | 7.7 | 3.1 | 14.3 | 27.0 | 12.6 | 1.7 | 17.9 | 10.9 | 4.9 |
| wt pKR926-20 | 8.4 | 3.0 | 14.0 | 27.3 | 11.9 | 1.4 | 16.4 | 12.2 | 5.2 |
| wt pKR926-21 | 8.4 | 3.1 | 12.8 | 24.8 | 10.0 | 1.4 | 14.8 | 16.9 | 7.7 |
| wt pKR926-22 | 8.0 | 3.0 | 13.8 | 26.6 | 11.0 | 1.5 | 16.1 | 14.0 | 6.0 |

FIG. 22

| Event | Fatty acid composition (wt.%) | | | | | | | | |
|---|---|---|---|---|---|---|---|---|---|
| | 16:0 | 18:0 | 18:1 | LA | ALA | 20:0 | 20:1(11) | EDA | ERA |
| fad3/fae1 (ff) | 8.8 | 3.0 | 29.7 | 56.2 | 1.1 | 0.7 | 0.3 | 0.2 | 0.0 |
| ff pKR926-1 | 8.7 | 3.0 | 22.8 | 42.2 | 0.8 | 0.8 | 1.8 | 19.1 | 0.8 |
| ff pKR926-2 | 9.9 | 3.0 | 28.6 | 55.6 | 1.6 | 0.7 | 0.4 | 0.2 | 0.0 |
| ff pKR926-3 | 9.2 | 3.1 | 22.4 | 45.3 | 1.4 | 0.7 | 0.8 | 16.2 | 0.7 |
| ff pKR926-4 | 8.2 | 2.9 | 27.4 | 48.9 | 2.3 | 0.8 | 2.0 | 7.2 | 0.3 |
| ff pKR926-5 | 10.2 | 3.0 | 20.9 | 45.6 | 2.0 | 0.8 | 0.7 | 15.8 | 0.9 |
| ff pKR926-6 | 8.8 | 2.9 | 22.3 | 46.2 | 1.6 | 0.7 | 1.1 | 15.7 | 0.6 |
| ff pKR926-7 | 8.1 | 2.9 | 25.2 | 42.4 | 0.5 | 0.7 | 1.1 | 18.3 | 0.8 |
| ff pKR926-8 | 9.7 | 3.0 | 23.2 | 45.1 | 1.8 | 0.7 | 0.7 | 15.1 | 0.8 |
| ff pKR926-9 | 8.4 | 3.1 | 23.7 | 40.7 | 0.4 | 0.6 | 1.4 | 20.9 | 0.9 |
| ff pKR926-10 | 9.3 | 3.0 | 25.8 | 47.7 | 1.0 | 0.7 | 0.5 | 11.6 | 0.5 |
| ff pKR926-11 | 9.0 | 3.2 | 26.1 | 45.9 | 1.1 | 0.8 | 0.9 | 12.5 | 0.6 |
| ff pKR926-12 | 8.6 | 3.0 | 28.1 | 43.6 | 1.0 | 0.7 | 0.8 | 13.6 | 0.6 |
| ff pKR926-13 | 8.8 | 3.2 | 26.2 | 45.8 | 0.6 | 0.7 | 0.9 | 13.2 | 0.6 |
| ff pKR926-14 | 8.7 | 2.8 | 23.1 | 42.9 | 1.1 | 0.7 | 1.4 | 18.5 | 0.8 |
| ff pKR926-15 | 8.9 | 3.1 | 21.6 | 41.6 | 0.8 | 0.8 | 1.7 | 20.6 | 0.9 |
| ff pKR926-16 | 8.9 | 3.0 | 24.6 | 44.9 | 1.1 | 0.7 | 0.8 | 15.2 | 0.8 |

FIG. 23

| Event | Fatty acid composition (wt.%) | | | | | | | | | Total delta-9 | LA | ALA | Ratio (LA/ALA) |
|---|---|---|---|---|---|---|---|---|---|---|---|---|---|
| | 16:0 | 18:0 | 18:1 | LA | ALA | 20:0 | 20:1(11) | EDA | ERA | %Elong | %Elong | %Elong | %Elong |
| wild-type (wt) | 8.4 | 2.9 | 14.6 | 30.6 | 20.3 | 1.8 | 18.7 | 2.2 | 0.5 | 5.0 | 6.7 | 2.5 | 2.7 |
| wt pKR926-8-1 | 10.6 | 2.4 | 12.2 | 26.5 | 8.4 | 0.0 | 10.2 | 21.8 | 7.9 | 46.0 | 45.2 | 48.6 | 0.9 |
| wt pKR926-8-2 | 8.6 | 2.7 | 11.1 | 25.1 | 10.5 | 1.0 | 11.3 | 20.1 | 9.6 | 45.5 | 44.4 | 47.9 | 0.9 |
| wt pKR926-8-3 | 7.2 | 3.0 | 10.6 | 23.1 | 10.0 | 1.5 | 14.3 | 20.2 | 10.1 | 47.8 | 46.7 | 50.4 | 0.9 |
| wt pKR926-8-4 | 7.0 | 2.8 | 10.0 | 21.7 | 9.2 | 1.5 | 13.0 | 22.8 | 11.9 | 52.8 | 51.1 | 56.4 | 0.9 |
| wt pKR926-8-5 | 8.4 | 3.2 | 11.8 | 22.9 | 7.2 | 1.5 | 11.7 | 23.3 | 10.0 | 52.5 | 50.4 | 58.0 | 0.9 |
| wt pKR926-8-6 | 8.7 | 3.2 | 14.8 | 32.2 | 17.1 | 1.9 | 19.5 | 2.3 | 0.4 | 5.0 | 6.6 | 2.1 | 3.2 |
| wt pKR926-8-7 | 7.3 | 2.8 | 16.1 | 29.6 | 18.5 | 1.9 | 21.4 | 2.1 | 0.4 | 5.0 | 6.7 | 2.2 | 3.1 |
| wt pKR926-8-8 | 7.9 | 3.2 | 10.8 | 24.1 | 8.5 | 1.5 | 13.5 | 21.2 | 9.4 | 48.4 | 46.8 | 52.5 | 0.9 |
| wt pKR926-8-9 | 7.9 | 3.2 | 11.4 | 24.4 | 7.9 | 1.4 | 13.3 | 21.5 | 9.0 | 48.6 | 46.9 | 53.3 | 0.9 |
| wt pKR926-8-10 | 8.6 | 3.0 | 10.2 | 21.5 | 9.3 | 1.2 | 10.3 | 23.5 | 12.4 | 53.7 | 52.2 | 56.9 | 0.9 |
| fad3/fae1 (ff) | 8.8 | 3.0 | 29.7 | 56.2 | 1.1 | 0.7 | 0.3 | 0.2 | 0.0 | 0.3 | 0.3 | 0.0 | |
| ff pKR926-1-1 | 8.0 | 3.0 | 21.9 | 40.1 | 0.2 | 0.6 | 1.9 | 23.3 | 0.9 | 37.5 | 36.7 | 79.5 | 0.5 |
| ff pKR926-1-2 | 8.3 | 4.1 | 18.8 | 31.1 | 1.1 | 0.7 | 1.6 | 33.1 | 1.3 | 51.7 | 51.6 | 54.1 | 1.0 |
| ff pKR926-1-3 | 7.5 | 3.0 | 23.1 | 40.5 | 0.2 | 0.6 | 1.7 | 22.5 | 0.9 | 36.5 | 35.7 | 81.1 | 0.4 |
| ff pKR926-1-4 | 8.3 | 3.1 | 30.4 | 55.8 | 1.3 | 0.8 | 0.3 | 0.1 | 0.0 | 0.2 | 0.2 | 0.0 | |
| ff pKR926-1-5 | 8.2 | 3.1 | 32.1 | 54.5 | 1.0 | 0.6 | 0.3 | 0.1 | 0.0 | 0.3 | 0.3 | 0.0 | |
| ff pKR926-1-6 | 7.2 | 2.8 | 24.4 | 38.1 | 0.2 | 0.6 | 1.3 | 24.3 | 1.0 | 39.7 | 38.9 | 81.8 | 0.5 |
| ff pKR926-1-7 | 8.1 | 2.8 | 22.6 | 43.1 | 0.2 | 0.6 | 1.5 | 20.2 | 0.9 | 32.8 | 31.9 | 78.4 | 0.4 |
| ff pKR926-1-8 | 9.6 | 2.8 | 28.2 | 57.3 | 1.2 | 0.6 | 0.3 | 0.0 | 0.0 | 0.0 | 0.0 | 0.0 | |
| ff pKR926-1-9 | 9.2 | 2.9 | 21.5 | 41.4 | 0.3 | 0.6 | 1.3 | 21.7 | 1.1 | 35.3 | 34.4 | 77.5 | 0.4 |
| ff pKR926-1-10 | 7.9 | 2.7 | 23.7 | 44.2 | 0.3 | 0.5 | 1.4 | 18.5 | 0.8 | 30.2 | 29.5 | 71.5 | 0.4 |

| Event | Embryos Analyzed | Fatty Acid Composition (wt.%) 16:0 | 18:0 | 18:1 | LA | GLA | ALA | EDA | HGLA | ARA | ERA | JUN | ETA | EPA | DPA | Other | Total delta-9 %Elong |
|---|---|---|---|---|---|---|---|---|---|---|---|---|---|---|---|---|---|
| AFS 4697-6-1 | 9 | 15.5 | 2.0 | 17.2 | 22.7 | 0.1 | 14.9 | 2.7 | 1.6 | 0.3 | 1.3 | 1.6 | 3.3 | 14.8 | 0.2 | 1.9 | 40.7 |
| AFS 4709-6-16 | 10 | 13.8 | 1.9 | 14.8 | 15.6 | 0.0 | 15.1 | 4.2 | 0.5 | 0.1 | 4.6 | 9.9 | 2.7 | 14.5 | 0.2 | 2.1 | 54.5 |
| AFS 4709-6-8 | 10 | 15.8 | 1.8 | 16.2 | 25.3 | 0.1 | 12.5 | 2.9 | 1.3 | 0.2 | 2.0 | 2.1 | 4.1 | 14.3 | 0.1 | 1.4 | 41.7 |
| AFS 4709-5-7 | 10 | 15.3 | 1.7 | 19.6 | 21.3 | 0.0 | 13.7 | 2.0 | 0.5 | 0.0 | 2.2 | 3.9 | 3.1 | 14.0 | 0.1 | 2.5 | 42.6 |
| AFS 4709-8-6 | 10 | 16.3 | 2.7 | 17.3 | 18.3 | 0.0 | 12.2 | 5.2 | 1.1 | 0.1 | 3.4 | 4.3 | 3.2 | 13.8 | 0.5 | 1.8 | 50.8 |
| AFS 4697-6-5 | 10 | 15.7 | 2.4 | 16.1 | 24.5 | 0.0 | 16.5 | 2.2 | 1.7 | 0.3 | 1.1 | 1.4 | 3.0 | 13.7 | 0.1 | 1.3 | 36.3 |
| AFS 4697-7-5 | 10 | 14.4 | 3.1 | 18.4 | 16.8 | 0.0 | 6.1 | 9.6 | 1.7 | 0.3 | 3.5 | 5.4 | 3.6 | 13.7 | 0.4 | 2.9 | 62.5 |
| AFS 4709-5-5 | 10 | 15.9 | 2.0 | 16.3 | 26.4 | 0.0 | 14.3 | 2.0 | 1.4 | 0.1 | 1.4 | 1.2 | 6.0 | 11.8 | 0.1 | 1.1 | 37.0 |
| AFS 4697-7-3 | 10 | 3.1 | 3.1 | 20.5 | 29.4 | 0.1 | 16.0 | 3.5 | 0.8 | 0.0 | 2.7 | 3.0 | 4.3 | 11.6 | 0.2 | 1.5 | 36.7 |
| AFS 4697-1-5 | 10 | 14.3 | 3.0 | 20.9 | 22.8 | 0.0 | 7.8 | 7.4 | 0.9 | 0.1 | 2.8 | 2.0 | 4.4 | 11.5 | 0.2 | 2.0 | 48.8 |

FIG. 25B

| Event | Fatty Acid Composition (wt.%) 16:0 | 18:0 | 18:1 | LA | GLA | ALA | EDA | HGLA | ARA | ERA | JUN | ETA | EPA | DPA | Other | Total delta-9 %Elong |
|---|---|---|---|---|---|---|---|---|---|---|---|---|---|---|---|---|
| 4697-6-1-3-2 | 12.8 | 3.9 | 34.4 | 6.7 | 0.0 | 5.5 | 5.6 | 1.0 | 0.1 | 4.8 | 1.6 | 3.8 | 11.0 | 1.5 | 7.2 | 70.6 |
| 4697-6-1-1-7 | 10.6 | 2.9 | 25.4 | 12.1 | 0.0 | 12.6 | 6.3 | 0.3 | 0.2 | 6.4 | 6.9 | 1.1 | 10.2 | 0.3 | 4.7 | 56.2 |
| 4697-6-1-3-4 | 11.2 | 7.3 | 26.0 | 10.6 | 0.0 | 7.8 | 7.9 | 0.8 | 0.2 | 5.3 | 4.4 | 1.7 | 9.1 | 0.3 | 7.4 | 61.8 |
| 4697-6-1-4-4 | 11.8 | 3.9 | 15.3 | 7.8 | 0.0 | 23.7 | 4.6 | 0.3 | 0.2 | 12.7 | 7.8 | 1.3 | 8.6 | 0.1 | 1.8 | 53.0 |
| 4697-6-1-2-10 | 10.4 | 3.1 | 29.0 | 4.9 | 0.0 | 19.7 | 2.7 | 0.2 | 0.2 | 10.3 | 6.5 | 0.9 | 8.0 | 0.1 | 4.1 | 54.0 |
| 4697-6-1-4-9 | 11.2 | 2.8 | 11.7 | 50.8 | 0.0 | 22.6 | 0.1 | 0.0 | 0.0 | 0.0 | 0.0 | 0.0 | 0.0 | 0.1 | 0.5 | 0.0 |
| 4697-6-5-2-4 | 14.4 | 4.8 | 13.3 | 9.4 | 0.0 | 4.9 | 6.1 | 2.6 | 0.0 | 3.7 | 2.9 | 12.2 | 16.2 | 4.3 | 5.3 | 77.1 |
| 4697-6-5-3-4 | 12.8 | 3.4 | 15.5 | 16.1 | 0.0 | 6.3 | 9.3 | 2.0 | 0.2 | 4.5 | 2.1 | 5.4 | 15.1 | 2.7 | 4.5 | 64.9 |
| 4697-6-5-3-1 | 12.0 | 3.7 | 25.3 | 10.0 | 0.1 | 8.6 | 6.6 | 1.4 | 0.2 | 5.5 | 1.7 | 4.9 | 13.9 | 0.8 | 5.2 | 65.3 |
| 4697-6-5-4-4 | 13.5 | 4.8 | 24.3 | 8.5 | 0.0 | 6.8 | 7.3 | 1.3 | 0.0 | 5.3 | 2.7 | 4.7 | 13.9 | 1.1 | 5.8 | 70.3 |
| 4697-6-5-4-2 | 12.5 | 2.9 | 26.7 | 9.1 | 0.0 | 15.3 | 4.5 | 0.6 | 0.3 | 5.6 | 4.7 | 1.5 | 13.1 | 0.0 | 3.2 | 55.5 |
| 4697-6-5-4-1 | 13.3 | 3.1 | 13.6 | 51.3 | 0.0 | 17.3 | 0.3 | 0.0 | 0.0 | 0.2 | 0.1 | 0.0 | 0.2 | 0.0 | 0.5 | 0.0 |

```
    M...N..................W......E.L........LK..L...G  Consensus #1
              10        20        30        40        50
1   MEVVNEIVSIGQEVLPKVDYAQLWSDASHCEVLYLSIAFVILKFTLGPLG  SEQ ID NO5 Euglena gracilis D9e.pro
1   MALANDAG------------ERIWAAVTDPEILIGTFSYLLLKPLLRNSG  SEQ ID NO27 Isochyrsis galbana D9e.pro

    ..............YN.L....S..SF...A.A...............  Consensus #1
              60        70        80        90       100
51  PKGQSR--MKFVFTNYNLLMSIYSLGSFLSMAYAM---------------  SEQ ID NO5 Euglena gracilis D9e.pro
39  LVDEKKGAYRTSMIWYNVLLALFSALSFYVTATALGWDYGTGAWLRRQTG  SEQ ID NO27 Isochyrsis galbana D9e.pro

    .T...........D...F..T...FY.SK..EY.D...L.L.GK....L  Consensus #1
             110       120       130       140       150
84  YTIGVMSDNCEKAFDNNVFRITTQLFYLSKFLEYIDSFYLPLMGKPLTWL  SEQ ID NO5 Euglena gracilis D9e.pro
89  DTPQPLFQCPSPVWDSKLFTWTAKAFYYSKYVEYLDTAWLVLKGKRVSFL  SEQ ID NO27 Isochyrsis galbana D9e.pro

    Q.FHH.GAP.D..L.....NE.VWIF...N.FIH.IMY.YY.......KF  Consensus #1
             160       170       180       190       200
134 QFFHHLGAPMDMWLFYNYRNEAVWIFVLLNGFIHWIMYGYYWTRLIKLKF  SEQ ID NO5 Euglena gracilis D9e.pro
139 QAFHHFGAPWDVYLGIRLHNEGVWIFMFFNSFIHTIMYTYYGLTAAGYKF  SEQ ID NO27 Isochyrsis galbana D9e.pro

    ...K.LIT.MQI.QF..GF..VW.Y.N.PC...D....F.W.FNY.YVG.  Consensus #1
             210       220       230       240       250
184 PMPKSLITSMQIIQFNVGFYIVWKYRNIPCYRQDGMRMFGWFFNYFYVGT  SEQ ID NO5 Euglena gracilis D9e.pro
189 KA-KPLITAMQICQFVGGFLLVWDYINVPCFNSDKGKLFSWAFNYAYVGS  SEQ ID NO27 Isochyrsis galbana D9e.pro

    V..LF..F..Q.....K.......Q.                          Consensus #1
             260       270
234 VLCLFLNFYVQTYIVRKHKGAKKIQ                           SEQ ID NO5 Euglena gracilis D9e.pro
238 VFLLFCHFFYQDNLATKKSAKAGKQL                          SEQ ID NO27 Isochyrsis galbana D9e.pro
```

FIG. 27

```
        M...............L........W......E.L........LK..L....L.....  Consensus #1
                 10        20        30        40        50        60
  1     M----EVVNEIVSIGQEVLPKVDYAQLWSDASHCEVLYLSIAFVILKFTL--GPLGPKGQ  SEQ ID NO5 Euglena gracilis D9e.pro
  1     MAAVIEVANEFVAITAETLPKVDYQRLWRDIYSCELLYFSIAFVILKFTL--GELSDSGK  SEQ ID NO127 Eutreptiella D9e.pro
  1     MA---------------LANDAGERIWAAVTDPEILIGTFSYLLLKPLLRNSGLVDEKK  SEQ ID NO27 Isochyrsis galbana D9e.pro

        .........YN......S..SF.....A....Y..G...............C.....D.  Consensus #1
                 70        80        90       100       110       120
 55     SRMKFVFTNYNLLMSIYSLGSFLSMAYAM---YTIGVMSD-----------NCEKA-FDN  SEQ ID NO5 Euglena gracilis D9e.pro
 59     KILRVLFKWYNLFMSVFSLVSFLCMGYAI---YTVGLYSN-----------ECDRA-FDN  SEQ ID NO127 Eutreptiella D9e.pro
 45     GAYRTSMIWYNVLLALFSALSFYVTATALGWDYGTGAWLRRQTGDTPQPLFQCPSPVWDS  SEQ ID NO27 Isochyrsis galbana D9e.pro

        ..F......FY.SK..EY.D...L.L..K....LQ.FHH.GAP.D..L......E..WIF  Consensus #1
                130       140       150       160       170       180
100     NVFRITTQLFYLSKFLEYIDSFYLPLMGKPLTWLQFFHHLGAPMDMWLFYNYRNEAVWIF  SEQ ID NO5 Euglena gracilis D9e.pro
104     SLFRFATKVFYYSKFLEYIDSFYLPLMAKPLSFLQFFHHLGAPMDMWLFVQYSGESIWIF  SEQ ID NO127 Eutreptiella D9e.pro
105     KLFTWTAKAFYYSKYVEYLDTAWLVLKGKRVSFLQAFHHFGAPWDVYLGIRLHNEGVWIF  SEQ ID NO27 Isochyrsis galbana D9e.pro

        ...N.FIH..MY.YY........F...K.LIT.MQI.QF..GF..VW.Y...PC...D..  Consensus #1
                190       200       210       220       230       240
160     VLLNGFIHWIMYGYYWTRLIKLKFPMPKSLITSMQIIQFNVGFYIVWKYRNIPCYRQDGM  SEQ ID NO5 Euglena gracilis D9e.pro
164     VFLNGFIHFVMYGYYWTRLMKFNFPMPKQLITAMQITQFNVGFYLVWWYKDIPCYRKDPM  SEQ ID NO127 Eutreptiella D9e.pro
165     MFFNSFIHTIMYTYYGLTAAGYKF-KAKPLITAMQICQFVGGFLLVWDYINVPCFNSDKG  SEQ ID NO27 Isochyrsis galbana D9e.pro

        ....W.FNY.YVG.V..LF..F........K......K..                      Consensus #1
                250       260       270       280
220     RMFGWFFNYFYVGTVLCLFLNFYVQTYIVRKHKGA-KKIQ                      SEQ ID NO5 Euglena gracilis D9e.pro
224     RMLAWIFNYWYVGTVLLLFINFFVKSYVFPKPKTADKKVQ                      SEQ ID NO127 Eutreptiella D9e.pro
224     KLFSWAFNYAYVGSVFLLFCHFFYQDNLATKKSAKAGKQL                      SEQ ID NO27 Isochyrsis galbana D9e.pro
```

FIG. 29

SEQUENCE LISTING

```
<160> NUMBER OF SEQ ID NOS: 136

<210> SEQ ID NO 1
<211> LENGTH: 757
<212> TYPE: DNA
<213> ORGANISM: Euglena gracilis
<220> FEATURE:
<221> NAME/KEY: misc_feature
<222> LOCATION: (677)..(677)
<223> OTHER INFORMATION: n is a, c, g, or t

<400> SEQUENCE: 1

tttttttcg aacacttaat ggaggtggtg aatgaaatag tctcaattgg gcaggaagtt     60

ttacccaaag ttgattatgc ccaactctgg agtgatgcca gtcactgtga ggtgctttac    120

ttgtccatcg catttgtcat cttgaagttc actcttggcc cccttggtcc aaaaggtcag    180

tctcgtatga agtttgtttt caccaattac aaccttctca tgtccattta ttcgttggga    240

tcattcctct caatggcata tgccatgtac accatcggtg ttatgtctga caactgcgag    300

aaggcttttg acaacaacgt cttcaggatc accacgcagt tgttctattt gagcaagttc    360

ctggagtata ttgactcctt ctatttgcca ctgatgggca agcctctgac ctggttgcaa    420

ttcttccatc atttgggggc accgatggat atgtggctgt tctataatta ccgaaatgaa    480

gctgtttgga tttttgtgct gttgaatggt ttcatccact ggatcatgta cggttattat    540

tggaccagat tgatcaagct gaagttcccc atgccaaaat ccctgattac atcaatgcag    600

atcattcaat tcaatgttgg tttctacatt gtctggaagt acaggaacat tccctgttat    660

cgccaagatg ggatgangat gtttggctgg ttcttcaatt acttttatgt tggcacagtc    720

ttgtgtttgt tcttgaattt ctatgtgcaa acgtata                             757


<210> SEQ ID NO 2
<211> LENGTH: 774
<212> TYPE: DNA
<213> ORGANISM: Euglena gracilis
<220> FEATURE:
<221> NAME/KEY: misc_feature
<222> LOCATION: (34)..(34)
<223> OTHER INFORMATION: n is a, c, g, or t
```

<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (218)..(220)
<223> OTHER INFORMATION: n is a, c, g, or t
<220> FEATURE:
<221> NAME/KEY: misc_feature
<222> LOCATION: (707)..(709)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t

<400> SEQUENCE: 2

```
tcaggatcac cacgcagttg ttctatttga gcangttcct ggagtatatt gactccttct     60

atttgccant gatgggcaag cntctgacct ggttgcaatt cttccatcat tngggggcac    120

cgatggatat gtggctgttc tataattacc gaaatgaagc tgtttggatt tttgtgctgt    180

tgaatggttt catccactgg atcatgtacg gttattannn gaccagattg atcaagctga    240

agttccccat gccaaaatcc ctgattacat caatgcagat cattcaattc aatgttggtt    300

tctacattgt ctggaagtac aggaacattc cctgttatcg ccaagatggg atgaggatgt    360

ttggctggtt cttcaattac ttttatgttg gcacagtctt gtgtttgttc ttgaatttct    420

atgtgcaaac gtatatcgtc aggaagcaca agggagccaa aaagattcag tgatatttcc    480

tcctctgcgg tggcctcttt tgacctcccc ttgacaccta taatgtggag gtgtcgggct    540

ctctccgtct caccagcact tgactctgca ggtgctcact tttatttttt acccatcttt    600

gcttgttgac cattcacctc tcccacttcc acatagtcca ttctaactgt tgcagactgc    660

ggtccatttt ttccagagct cccaatgacc atacgcgaca ccttgtnnnc ncccagccca    720

ttgtgcacaa ttcatagtgg catcgttttg ccttgatacg tgtgcatcca gcgg          774
```

<210> SEQ ID NO 3
<211> LENGTH: 1201
<212> TYPE: DNA
<213> ORGANISM: Euglena gracilis
<220> FEATURE:
<221> NAME/KEY: misc_feature
<222> LOCATION: (1134)..(1136)
<223> OTHER INFORMATION: n is a, c, g, or t
<220> FEATURE:
<221> NAME/KEY: misc_feature
<222> LOCATION: (1138)..(1138)
<223> OTHER INFORMATION: n is a, c, g, or t

<400> SEQUENCE: 3

```
gacatggcaa ctatgatttt attttgactg atagtgacct gttcgttgca acaaattgat     60

gagcaatgct tttttataat gccaactttg tacaaaaaag ttggattttt tttcgaacac    120

ttaatggagg tggtgaatga aatagtctca attgggcagg aagttttacc caaagttgat    180

tatgcccaac tctggagtga tgccagtcac tgtgaggtgc tttacttgtc catcgcattt    240

gtcatcttga agttcactct tggccccctt ggtccaaaag gtcagtctcg tatgaagttt    300
```

-continued

```
gttttcacca attacaacct tctcatgtcc atttattcgt tgggatcatt cctctcaatg    360

gcatatgcca tgtacaccat cggtgttatg tctgacaact gcgagaaggc ttttgacaac    420

aacgtcttca ggatcaccac gcagttgttc tatttgagca agttcctgga gtatattgac    480

tccttctatt tgccactgat gggcaagcct ctgacctggt tgcaattctt ccatcatttg    540

ggggcaccga tggatatgtg gctgttctat aattaccgaa atgaagctgt ttggattttt    600

gtgctgttga atggtttcat ccactggatc atgtacggtt attattggac cagattgatc    660

aagctgaagt tccccatgcc aaaatccctg attacatcaa tgcagatcat tcaattcaat    720

gttggtttct acattgtctg gaagtacagg aacattccct gttatcgcca agatgggatg    780

aggatgtttg gctggttctt caattacttt tatgttggca cagtcttgtg tttgttcttg    840

aatttctatg tgcaaacgta tatcgtcagg aagcacaagg gagccaaaaa gattcagtga    900

tatttcctcc tctgcggtgg cctcttttga cctccccttg acacctataa tgtggaggtg    960

tcgggctctc tccgtctcac cagcacttga ctctgcaggt gctcactttt atttttacc   1020

catctttgct tgttgaccat tcacctctcc cacttccaca tagtccattc taactgttgc   1080

agactgcggt ccatttttc cagagctccc aatgaccata cgcgacacct tgtnnncncc    1140

cagcccattg tgcacaattc atagtggcat cgttttgcct tgatacgtgt gcatccagcg   1200

g                                                                   1201


<210> SEQ ID NO 4
<211> LENGTH: 777
<212> TYPE: DNA
<213> ORGANISM: Euglena gracilis

<400> SEQUENCE: 4

atggaggtgg tgaatgaaat agtctcaatt gggcaggaag ttttacccaa agttgattat     60

gcccaactct ggagtgatgc cagtcactgt gaggtgcttt acttgtccat cgcatttgtc    120

atcttgaagt tcactcttgg ccccccttggt ccaaaaggtc agtctcgtat gaagtttgtt    180

ttcaccaatt acaaccttct catgtccatt tattcgttgg gatcattcct ctcaatggca    240

tatgccatgt acaccatcgg tgttatgtct gacaactgcg agaaggcttt tgacaacaac    300

gtcttcagga tcaccacgca gttgttctat ttgagcaagt tcctggagta tattgactcc    360

ttctatttgc cactgatggg caagcctctg acctggttgc aattcttcca tcatttgggg    420

gcaccgatgg atatgtggct gttctataat taccgaaatg aagctgtttg gatttttgtg    480

ctgttgaatg gtttcatcca ctggatcatg tacggttatt attggaccag attgatcaag    540

ctgaagttcc ccatgccaaa atccctgatt acatcaatgc agatcattca attcaatgtt    600

ggtttctaca ttgtctggaa gtacaggaac attccctgtt atcgccaaga tgggatgagg    660

atgtttggct ggttcttcaa ttacttttat gttggcacag tcttgtgttt gttcttgaat    720

ttctatgtgc aaacgtatat cgtcaggaag cacaagggag ccaaaaagat tcagtga       777


<210> SEQ ID NO 5
<211> LENGTH: 258
<212> TYPE: PRT
<213> ORGANISM: Euglena gracilis

<400> SEQUENCE: 5

Met Glu Val Val Asn Glu Ile Val Ser Ile Gly Gln Glu Val Leu Pro
1               5                   10                  15

Lys Val Asp Tyr Ala Gln Leu Trp Ser Asp Ala Ser His Cys Glu Val
            20                  25                  30
```

```
Leu Tyr Leu Ser Ile Ala Phe Val Ile Leu Lys Phe Thr Leu Gly Pro
        35                  40                  45

Leu Gly Pro Lys Gly Gln Ser Arg Met Lys Phe Val Phe Thr Asn Tyr
    50                  55                  60

Asn Leu Leu Met Ser Ile Tyr Ser Leu Gly Ser Phe Leu Ser Met Ala
65                  70                  75                  80

Tyr Ala Met Tyr Thr Ile Gly Val Met Ser Asp Asn Cys Glu Lys Ala
                85                  90                  95

Phe Asp Asn Asn Val Phe Arg Ile Thr Thr Gln Leu Phe Tyr Leu Ser
            100                 105                 110

Lys Phe Leu Glu Tyr Ile Asp Ser Phe Tyr Leu Pro Leu Met Gly Lys
        115                 120                 125

Pro Leu Thr Trp Leu Gln Phe Phe His His Leu Gly Ala Pro Met Asp
    130                 135                 140

Met Trp Leu Phe Tyr Asn Tyr Arg Asn Glu Ala Val Trp Ile Phe Val
145                 150                 155                 160

Leu Leu Asn Gly Phe Ile His Trp Ile Met Tyr Gly Tyr Tyr Trp Thr
                165                 170                 175

Arg Leu Ile Lys Leu Lys Phe Pro Met Pro Lys Ser Leu Ile Thr Ser
            180                 185                 190

Met Gln Ile Ile Gln Phe Asn Val Gly Phe Tyr Ile Val Trp Lys Tyr
        195                 200                 205

Arg Asn Ile Pro Cys Tyr Arg Gln Asp Gly Met Arg Met Phe Gly Trp
    210                 215                 220

Phe Phe Asn Tyr Phe Tyr Val Gly Thr Val Leu Cys Leu Phe Leu Asn
225                 230                 235                 240

Phe Tyr Val Gln Thr Tyr Ile Val Arg Lys His Lys Gly Ala Lys Lys
                245                 250                 255

Ile Gln
```

<210> SEQ ID NO 6
<211> LENGTH: 31
<212> TYPE: DNA
<213> ORGANISM: Artificial Sequence
<220> FEATURE:
<223> OTHER INFORMATION: sequence of the ig-s primer

<400> SEQUENCE: 6
caccatggct ctggccaacg acgctggcga g 31

<210> SEQ ID NO 7
<211> LENGTH: 26
<212> TYPE: DNA
<213> ORGANISM: Artificial Sequence
<220> FEATURE:
<223> OTHER INFORMATION: sequence of the ig-as primer

<400> SEQUENCE: 7
ctaaagctgc ttaccagcct tagcgg 26

<210> SEQ ID NO 8
<211> LENGTH: 30
<212> TYPE: DNA
<213> ORGANISM: Artificial Sequence
<220> FEATURE:
<223> OTHER INFORMATION: sequence of the oEugEL1-1 primer

<400> SEQUENCE: 8
agcggccgca ccatggaggt ggtgaatgaa 30

<210> SEQ ID NO 9
<211> LENGTH: 30
<212> TYPE: DNA
<213> ORGANISM: Artificial Sequence
<220> FEATURE:
<223> OTHER INFORMATION: sequence of the oEugEL1-2 primer

<400> SEQUENCE: 9
tgcggccgct cactgaatct ttttggctcc 30

<210> SEQ ID NO 10
<211> LENGTH: 19
<212> TYPE: DNA
<213> ORGANISM: Artificial Sequence
<220> FEATURE:
<223> OTHER INFORMATION: sequence of the Eg5-1 primer

<400> SEQUENCE: 10
gaaatgaagt caaagcgcc 19

<210> SEQ ID NO 11
<211> LENGTH: 19
<212> TYPE: DNA
<213> ORGANISM: Artificial Sequence
<220> FEATURE:
<223> OTHER INFORMATION: sequence of the Eg3-3 primer

<400> SEQUENCE: 11
ccttatagag ccttccccg 19

<210> SEQ ID NO 12
<211> LENGTH: 19
<212> TYPE: DNA
<213> ORGANISM: Artificial Sequence
<220> FEATURE:
<223> OTHER INFORMATION: sequence of T7

<400> SEQUENCE: 12
ggaaacagct atgaccatg 19

<210> SEQ ID NO 13
<211> LENGTH: 22
<212> TYPE: DNA
<213> ORGANISM: Artificial Sequence
<220> FEATURE:
<223> OTHER INFORMATION: sequence of M13-28Rev

<400> SEQUENCE: 13
gtaatacgac tcactatagg gc 22

<210> SEQ ID NO 14
<211> LENGTH: 19
<212> TYPE: DNA
<213> ORGANISM: Artificial Sequence
<220> FEATURE:
<223> OTHER INFORMATION: sequence of Eg3-2

<400> SEQUENCE: 14
aatgttcatg gtctcatgg 19

<210> SEQ ID NO 15
<211> LENGTH: 19
<212> TYPE: DNA
<213> ORGANISM: Artificial Sequence -continued
<220> FEATURE:
<223> OTHER INFORMATION: sequence of Eg5-2

<400> SEQUENCE: 15
ttggcaatgg tctgcaagg 19

<210> SEQ ID NO 16
<211> LENGTH: 1266
<212> TYPE: DNA
<213> ORGANISM: Euglena gracilis

<400> SEQUENCE: 16
atgaagtcaa agcgccaagc gcttcccctt acaattgatg gaacaacata tgatgtgtct 60
gcctgggtca atttccaccc tggtggtgcg gaaattatag agaattacca aggaagggat 120
gccactgatg ccttcatggt tatgcactct caagaagcct tcgacaagct caagcgcatg 180
cccaaaatca atcccagttc tgagttgcca ccccaggctg cagtgaatga agctcaagag 240
gatttccgga agctccgaga agagttgatc gcaactggca tgtttgatgc ctcccccctc 300
tggtactcat acaaaatcag caccacactg ggccttggag tgctgggtta tttcctgatg 360
gttcagtatc agatgtattt cattggggca gtgttgcttg ggatgcacta tcaacagatg 420
ggctggcttt ctcatgacat ttgccaccac cagactttca agaaccggaa ctggaacaac 480
ctcgtgggac tggtatttgg caatggtctg caaggttttt ccgtgacatg gtggaaggac 540
agacacaatg cacatcattc ggcaaccaat gttcaagggc acgaccctga tattgacaac 600 ctcccccctct tagcctggtc tgaggatgac gtcacacggg cgtcaccgat ttcccgcaag 660
ctcattcagt tccagcagta ctatttcttg gtcatctgta tcttgttgcg gttcatttgg 720
tgtttccaga gcgtgttgac cgtgcgcagt ttgaaggaca gagataacca attctatcgc 780
tctcagtata agaaggaggc cattggcctc gccctgcact ggaccttgaa gaccctgttc 840
cacttattct ttatgcccag catcctcaca tcgctgttgg tgtttttcgt ttcggagctg 900
gttggcggct tcggcattgc gatcgtggtg ttcatgaacc actacccact ggagaagatc 960
ggggactcag tctgggatgg ccatggattc tcggttggcc agatccatga gaccatgaac 1020
attcggcgag ggattatcac agattggttt ttcggaggct tgaattacca gattgagcac 1080
catttgtggc cgaccctccc tcgccacaac ctgacagcgg ttagctacca ggtggaacag 1140
ctgtgccaga agcacaacct gccgtatcgg aacccgctgc cccatgaagg gttggtcatc 1200
ctgctgcgct atctggcggt gttcgcccgg atggcggaga agcaacccgc ggggaaggct 1260
ctataa 1266

<210> SEQ ID NO 17
<211> LENGTH: 421
<212> TYPE: PRT
<213> ORGANISM: Euglena gracilis

<400> SEQUENCE: 17

Met Lys Ser Lys Arg Gln Ala Leu Pro Leu Thr Ile Asp Gly Thr Thr
1 5 10 15

Tyr Asp Val Ser Ala Trp Val Asn Phe His Pro Gly Gly Ala Glu Ile
20 25 30

Ile Glu Asn Tyr Gln Gly Arg Asp Ala Thr Asp Ala Phe Met Val Met
35 40 45

His Ser Gln Glu Ala Phe Asp Lys Leu Lys Arg Met Pro Lys Ile Asn
50 55 60

-continued

Pro Ser Ser Glu Leu Pro Pro Gln Ala Ala Val Asn Glu Ala Gln Glu
65                  70                  75                  80

Asp Phe Arg Lys Leu Arg Glu Glu Leu Ile Ala Thr Gly Met Phe Asp
                85                  90                  95

Ala Ser Pro Leu Trp Tyr Ser Tyr Lys Ile Ser Thr Thr Leu Gly Leu
            100                 105                 110

Gly Val Leu Gly Tyr Phe Leu Met Val Gln Tyr Gln Met Tyr Phe Ile
        115                 120                 125

Gly Ala Val Leu Leu Gly Met His Tyr Gln Gln Met Gly Trp Leu Ser
    130                 135                 140

His Asp Ile Cys His His Gln Thr Phe Lys Asn Arg Asn Trp Asn Asn
145                 150                 155                 160

Leu Val Gly Leu Val Phe Gly Asn Gly Leu Gln Gly Phe Ser Val Thr
                165                 170                 175

Trp Trp Lys Asp Arg His Asn Ala His His Ser Ala Thr Asn Val Gln
            180                 185                 190

Gly His Asp Pro Asp Ile Asp Asn Leu Pro Leu Leu Ala Trp Ser Glu
        195                 200                 205

Asp Asp Val Thr Arg Ala Ser Pro Ile Ser Arg Lys Leu Ile Gln Phe
    210                 215                 220

Gln Gln Tyr Tyr Phe Leu Val Ile Cys Ile Leu Leu Arg Phe Ile Trp
225                 230                 235                 240

Cys Phe Gln Ser Val Leu Thr Val Arg Ser Leu Lys Asp Arg Asp Asn
                245                 250                 255

Gln Phe Tyr Arg Ser Gln Tyr Lys Lys Glu Ala Ile Gly Leu Ala Leu
            260                 265                 270

His Trp Thr Leu Lys Thr Leu Phe His Leu Phe Phe Met Pro Ser Ile
        275                 280                 285

Leu Thr Ser Leu Leu Val Phe Phe Val Ser Glu Leu Val Gly Gly Phe
    290                 295                 300

Gly Ile Ala Ile Val Val Phe Met Asn His Tyr Pro Leu Glu Lys Ile
305                 310                 315                 320

Gly Asp Ser Val Trp Asp Gly His Gly Phe Ser Val Gly Gln Ile His
                325                 330                 335

Glu Thr Met Asn Ile Arg Arg Gly Ile Ile Thr Asp Trp Phe Phe Gly
            340                 345                 350

Gly Leu Asn Tyr Gln Ile Glu His His Leu Trp Pro Thr Leu Pro Arg
        355                 360                 365

His Asn Leu Thr Ala Val Ser Tyr Gln Val Glu Gln Leu Cys Gln Lys
    370                 375                 380

His Asn Leu Pro Tyr Arg Asn Pro Leu Pro His Glu Gly Leu Val Ile
385                 390                 395                 400

Leu Leu Arg Tyr Leu Ala Val Phe Ala Arg Met Ala Glu Lys Gln Pro
                405                 410                 415

Ala Gly Lys Ala Leu
            420

<210> SEQ ID NO 18
<211> LENGTH: 37
<212> TYPE: DNA
<213> ORGANISM: Artificial Sequence
<220> FEATURE:
<223> OTHER INFORMATION: sequence of the Kti cassette 5' end MCS for
      pKR457

<400> SEQUENCE: 18
aagcttgcat gcctgcaggt cgactcgacg tacgtcc 37

<210> SEQ ID NO 19
<211> LENGTH: 282
<212> TYPE: DNA
<213> ORGANISM: Artificial Sequence
<220> FEATURE:
<223> OTHER INFORMATION: sequence of the Kti cassette 3' end MCS for pKR457 including the soy albumin transcription 3' terminator

<400> SEQUENCE: 19
ggtctagagg atccaaggcc gcgaagttaa aagcaatgtt gtcacttgtc gtactaacac 60
atgatgtgat agtttatgct agctagctat aacataagct gtctctgagt gtgttgtata 120
ttaataaaga tcatcactgg tgaatggtga tcgtgtacgt accctactta gtaggcaatg 180
gaagcactta gagtgtgctt tgtgcatggc cttgcctctg ttttgagact tttgtaatgt 240
tttcgagttt aaatctttgc ctttgcgtac gtgggcggat cc 282

<210> SEQ ID NO 20
<211> LENGTH: 32
<212> TYPE: DNA
<213> ORGANISM: Artificial Sequence
<220> FEATURE:
<223> OTHER INFORMATION: sequence of the oSalb-12 primer

<400> SEQUENCE: 20
tttggatcct ctagacgtac gcaaaggcaa ag 32

<210> SEQ ID NO 21
<211> LENGTH: 36
<212> TYPE: DNA
<213> ORGANISM: Artificial Sequence
<220> FEATURE:
<223> OTHER INFORMATION: sequence of the oSalb-13 primer

<400> SEQUENCE: 21
aaaggatcca aggccgcgaa gttaaaagca atgttg 36

<210> SEQ ID NO 22
<211> LENGTH: 69
<212> TYPE: DNA
<213> ORGANISM: Artificial Sequence
<220> FEATURE:
<223> OTHER INFORMATION: sequence of restriction sites added to pKR287 to make pKR767

<400> SEQUENCE: 22
ccatggtcaa tcaatgagac gccaacttct taatctattg agacctgcag gtctagaagg 60
gcggatccc 69

<210> SEQ ID NO 23
<211> LENGTH: 33
<212> TYPE: DNA
<213> ORGANISM: Artificial Sequence
<220> FEATURE:
<223> OTHER INFORMATION: sequence of the oSAlb-9 primer

<400> SEQUENCE: 23
ttctagacgt acgaaaccaa ctgcgtttgg ggc 33

<210> SEQ ID NO 24
<211> LENGTH: 35
<212> TYPE: DNA

<213> ORGANISM: Artificial Sequence
<220> FEATURE:
<223> OTHER INFORMATION: sequence of the oSAlb-2 primer

<400> SEQUENCE: 24
aatctagacg tacgcaaagg caaagattta aactc 35

<210> SEQ ID NO 25
<211> LENGTH: 8165
<212> TYPE: DNA
<213> ORGANISM: Artificial Sequence
<220> FEATURE:
<223> OTHER INFORMATION: sequence of pZUF17

<400> SEQUENCE: 25
gtacgagccg gaagcataaa gtgtaaagcc tggggtgcct aatgagtgag ctaactcaca 60
ttaattgcgt tgcgctcact gcccgctttc cagtcgggaa acctgtcgtg ccagctgcat 120
taatgaatcg gccaacgcgc ggggagaggc ggtttgcgta ttgggcgctc ttccgcttcc 180
tcgctcactg actcgctgcg ctcggtcgtt cggctgcggc gagcggtatc agctcactca 240
aaggcggtaa tacggttatc cacagaatca ggggataacg caggaaagaa catgtgagca 300
aaaggccagc aaaaggccag gaaccgtaaa aaggccgcgt tgctggcgtt tttccatagg 360
ctccgccccc ctgacgagca tcacaaaaat cgacgctcaa gtcagaggtg gcgaaacccg 420
acaggactat aaagatacca ggcgtttccc cctggaagct ccctcgtgcg ctctcctgtt 480
ccgaccctgc cgcttaccgg atacctgtcc gcctttctcc cttcgggaag cgtggcgctt 540
tctcatagct cacgctgtag gtatctcagt tcggtgtagg tcgttcgctc caagctgggc 600
tgtgtgcacg aaccccccgt tcagcccgac cgctgcgcct tatccggtaa ctatcgtctt 660
gagtccaacc cggtaagaca cgacttatcg ccactggcag cagccactgg taacaggatt 720
agcagagcga ggtatgtagg cggtgctaca gagttcttga agtggtggcc taactacggc 780
tacactagaa ggacagtatt tggtatctgc gctctgctga agccagttac cttcggaaaa 840
agagttggta gctcttgatc cggcaaacaa accaccgctg gtagcggtgg tttttttgtt 900
tgcaagcagc agattacgcg cagaaaaaaa ggatctcaag aagatccttt gatcttttct 960
acggggtctg acgctcagtg gaacgaaaac tcacgttaag ggattttggt catgagatta 1020
tcaaaaagga tcttcaccta gatcctttta aattaaaaat gaagttttaa atcaatctaa 1080
agtatatatg agtaaacttg gtctgacagt taccaatgct taatcagtga ggcacctatc 1140
tcagcgatct gtctatttcg ttcatccata gttgcctgac tccccgtcgt gtagataact 1200
acgatacggg agggcttacc atctggcccc agtgctgcaa tgataccgcg agacccacgc 1260
tcaccggctc cagatttatc agcaataaac cagccagccg gaagggccga gcgcagaagt 1320
ggtcctgcaa ctttatccgc ctccatccag tctattaatt gttgccggga agctagagta 1380
agtagttcgc cagttaatag tttgcgcaac gttgttgcca ttgctacagg catcgtggtg 1440
tcacgctcgt cgtttggtat ggcttcattc agctccggtt cccaacgatc aaggcgagtt 1500
acatgatccc ccatgttgtg caaaaaagcg gttagctcct tcggtcctcc gatcgttgtc 1560
agaagtaagt tggccgcagt gttatcactc atggttatgg cagcactgca taattctctt 1620
actgtcatgc catccgtaag atgcttttct gtgactggtg agtactcaac caagtcattc 1680
tgagaatagt gtatgcggcg accgagttgc tcttgcccgg cgtcaatacg ggataatacc 1740
gcgccacata gcagaacttt aaaagtgctc atcattggaa aacgttcttc ggggcgaaaa 1800
ctctcaagga tcttaccgct gttgagatcc agttcgatgt aacccactcg tgcacccaac 1860

-continued

```
tgatcttcag catcttttac tttcaccagc gtttctgggt gagcaaaaac aggaaggcaa   1920
aatgccgcaa aaaagggaat aagggcgaca cggaaatgtt gaatactcat actcttcctt   1980
tttcaatatt attgaagcat ttatcagggt tattgtctca tgagcggata catatttgaa   2040
tgtatttaga aaaataaaca aataggggtt ccgcgcacat ttccccgaaa agtgccacct   2100
gacgcgccct gtagcggcgc attaagcgcg gcgggtgtgg tggttacgcg cagcgtgacc   2160
gctacacttg ccagcgccct agcgcccgct cctttcgctt tcttcccttc ctttctcgcc   2220
acgttcgccg gctttccccg tcaagctcta aatcgggggc tccctttagg gttccgattt   2280
agtgctttac ggcacctcga ccccaaaaaa cttgattagg gtgatggttc acgtagtggg   2340
ccatcgccct gatagacggt ttttcgccct ttgacgttgg agtccacgtt ctttaatagt   2400
ggactcttgt tccaaactgg aacaacactc aaccctatct cggtctattc ttttgattta   2460
taagggattt tgccgatttc ggcctattgg ttaaaaaatg agctgattta acaaaaattt   2520
aacgcgaatt ttaacaaaat attaacgctt acaatttcca ttcgccattc aggctgcgca   2580
actgttggga agggcgatcg gtgcgggcct cttcgctatt acgccagctg gcgaaagggg   2640
gatgtgctgc aaggcgatta agttgggtaa cgccagggtt ttcccagtca cgacgttgta   2700
aaacgacggc cagtgaattg taatacgact cactataggg cgaattgggt accgggcccc   2760
ccctcgaggt cgatggtgtc gataagcttg atatcgaatt catgtcacac aaaccgatct   2820
tcgcctcaag gaaacctaat tctacatccg agagactgcc gagatccagt ctacactgat   2880
taattttcgg gccaataatt taaaaaaatc gtgttatata atattatatg tattatatat   2940
atacatcatg atgatactga cagtcatgtc ccattgctaa atagacagac tccatctgcc   3000
gcctccaact gatgttctca atatttaagg ggtcatctcg cattgtttaa taataaacag   3060
actccatcta ccgcctccaa atgatgttct caaaatatat tgtatgaact tatttttatt   3120
acttagtatt attagacaac ttacttgctt tatgaaaaac acttcctatt taggaaacaa   3180
tttataatgg cagttcgttc atttaacaat ttatgtagaa taaatgttat aaatgcgtat   3240
gggaaatctt aaatatggat agcataaatg atatctgcat tgcctaattc gaaatcaaca   3300
gcaacgaaaa aaatcccttg tacaacataa atagtcatcg agaaatatca actatcaaag   3360
aacagctatt cacacgttac tattgagatt attattggac gagaatcaca cactcaactg   3420
tctttctctc ttctagaaat acaggtacaa gtatgtacta ttctcattgt tcatacttct   3480
agtcatttca tcccacatat tccttggatt tctctccaat gaatgacatt ctatcttgca   3540
aattcaacaa ttataataag atataccaaa gtagcggtat agtggcaatc aaaaagcttc   3600
tctggtgtgc ttctcgtatt tatttttatt ctaatgatcc attaaaggta tatatttatt   3660
tcttgttata taatcctttt gtttattaca tgggctggat acataaaggt attttgattt   3720
aattttttgc ttaaattcaa tccccccctcg ttcagtgtca actgtaatgg taggaaatta   3780
ccatactttt gaagaagcaa aaaaaatgaa agaaaaaaaa aatcgtattt ccaggttaga   3840
cgttccgcag aatctagaat gcggtatgcg gtacattgtt cttcgaacgt aaaagttgcg   3900
ctccctgaga tattgtacat ttttgctttt acaagtacaa gtacatcgta caactatgta   3960
ctactgttga tgcatccaca acagtttgtt ttgttttttt ttgttttttt tttttctaat   4020
gattcattac cgctatgtat acctacttgt acttgtagta agccgggtta ttggcgttca   4080
attaatcata gacttatgaa tctgcacggt gtgcgctgcg agttactttt agcttatgca   4140
tgctacttgg gtgtaatatt gggatctgtt cggaaatcaa cggatgctca atcgatttcg   4200
```

-continued

```
acagtaatta attaagtcat acacaagtca gctttcttcg agcctcatat aagtataagt   4260
agttcaacgt attagcactg tacccagcat ctccgtatcg agaaacacaa caacatgccc   4320
cattggacag atcatgcgga tacacaggtt gtgcagtatc atacatactc gatcagacag   4380
gtcgtctgac catcatacaa gctgaacaag cgctccatac ttgcacgctc tctatataca   4440
cagttaaatt acatatccat agtctaacct ctaacagtta atcttctggt aagcctccca   4500
gccagccttc tggtatcgct tggcctcctc aataggatct cggttctggc cgtacagacc   4560
tcggccgaca attatgatat ccgttccggt agacatgaca tcctcaacag ttcggtactg   4620
ctgtccgaga gcgtctccct tgtcgtcaag acccaccccg gggtcagaa taagccagtc   4680
ctcagagtcg cccttaggtc ggttctgggc aatgaagcca accacaaact cggggtcgga   4740
tcgggcaagc tcaatggtct gcttggagta ctcgccagtg gccagagagc ccttgcaaga   4800
cagctcggcc agcatgagca gacctctggc cagcttctcg ttgggagagg ggactaggaa   4860
ctccttgtac tgggagttct cgtagtcaga gacgtcctcc ttcttctgtt cagagacagt   4920
ttcctcggca ccagctcgca ggccagcaat gattccggtt ccgggtacac cgtgggcgtt   4980
ggtgatatcg gaccactcgg cgattcggtg acaccggtac tggtgcttga cagtgttgcc   5040
aatatctgcg aactttctgt cctcgaacag gaagaaaccg tgcttaagag caagttcctt   5100
gagggggagc acagtgccgg cgtaggtgaa gtcgtcaatg atgtcgatat gggttttgat   5160
catgcacaca taaggtccga ccttatcggc aagctcaatg agctccttgg tggtggtaac   5220
atccagagaa gcacacaggt tggttttctt ggctgccacg agcttgagca ctcgagcggc   5280
aaaggcggac ttgtggacgt tagctcgagc ttcgtaggag ggcattttgg tggtgaagag   5340
gagactgaaa taaatttagt ctgcagaact ttttatcgga accttatctg gggcagtgaa   5400
gtatatgtta tggtaatagt tacgagttag ttgaacttat agatagactg gactatacgg   5460
ctatcggtcc aaattagaaa gaacgtcaat ggctctctgg gcgtcgcctt tgccgacaaa   5520
aatgtgatca tgatgaaagc cagcaatgac gttgcagctg atattgttgt cggccaaccg   5580
cgccgaaaac gcagctgtca gacccacagc ctccaacgaa gaatgtatcg tcaaagtgat   5640
ccaagcacac tcatagttgg agtcgtactc caaaggcggc aatgacgagt cagacagata   5700
ctcgtcgact caggcgacga cggaattcct gcagcccatc tgcagaattc aggagagacc   5760
gggttggcgg cgtatttgtg tcccaaaaaa cagccccaat tgccccggag aagacggcca   5820
ggccgcctag atgacaaatt caacaactca cagctgactt tctgccattg ccactagggg   5880
ggggcctttt tatatggcca agccaagctc tccacgtcgg ttgggctgca cccaacaata   5940
aatgggtagg gttgcaccaa caaagggatg ggatgggggg tagaagatac gaggataacg   6000
gggctcaatg gcacaaataa gaacgaatac tgccattaag actcgtgatc cagcgactga   6060
caccattgca tcatctaagg gcctcaaaac tacctcggaa ctgctgcgct gatctggaca   6120
ccacagaggt tccgagcact ttaggttgca ccaaatgtcc caccaggtgc aggcagaaaa   6180
cgctggaaca gcgtgtacag tttgtcttaa caaaaagtga gggcgctgag gtcgagcagg   6240
gtggtgtgac ttgttatagc ctttagagct gcgaaagcgc gtatggattt ggctcatcag   6300
gccagattga gggtctgtgg acacatgtca tgttagtgta cttcaatcgc cccctggata   6360
tagccccgac aataggccgt ggcctcattt ttttgccttc cgcacatttc cattgctcgg   6420
tacccacacc ttgcttctcc tgcacttgcc aaccttaata ctggtttaca ttgaccaaca   6480
tcttacaagc ggggggcttg tctagggtat atataaacag tggctctccc aatcggttgc   6540
cagtctcttt tttcctttct ttccccacag attcgaaatc taaactacac atcacacaat   6600
```

gcctgttact gacgtcctta agcgaaagtc cggtgtcatc gtcggcgacg atgtccgagc 6660
cgtgagtatc cacgacaaga tcagtgtcga gacgacgcgt tttgtgtaat gacacaatcc 6720
gaaagtcgct agcaacacac actctctaca caaactaacc cagctctcca tggctgagga 6780
taagaccaag gtcgagttcc ctaccctgac tgagctgaag cactctatcc ctaacgcttg 6840
ctttgagtcc aacctcggac tctcgctcta ctacactgcc cgagcgatct tcaacgcatc 6900
tgcctctgct gctctgctct acgctgcccg atctactccc ttcattgccg ataacgttct 6960
gctccacgct ctggtttgcg ccacctacat ctacgtgcag ggtgtcatct tctggggttt 7020
ctttaccgtc ggtcacgact gtggtcactc tgccttctcc cgataccact ccgtcaactt 7080
catcattggc tgcatcatgc actctgccat tctgactccc ttcgagtcct ggcgagtgac 7140
ccaccgacac catcacaaga acactggcaa cattgataag gacgagatct tctaccctca 7200
tcggtccgtc aaggacctcc aggacgtgcg acaatgggtc tacaccctcg gaggtgcttg 7260
gtttgtctac ctgaaggtcg gatatgctcc tcgaaccatg tcccactttg accccctgga 7320
ccctctcctg cttcgacgag cctccgctgt catcgtgtcc ctcggagtct gggctgcctt 7380
cttcgctgcc tacgcctacc tcacatactc gctcggcttt gccgtcatgg gcctctacta 7440
ctatgctcct ctctttgtct ttgcttcgtt cctcgtcatt actaccttct tgcatcacaa 7500
cgacgaagct actccctggt acggtgactc ggagtggacc tacgtcaagg gcaacctgag 7560
ctccgtcgac cgatcgtacg gagctttcgt ggacaacctg tctcaccaca ttggcaccca 7620
ccaggtccat cacttgttcc ctatcattcc ccactacaag ctcaacgaag ccaccaagca 7680
ctttgctgcc gcttaccctc acctcgtgag acgtaacgac gagcccatca ttactgcctt 7740
cttcaagacc gctcacctct ttgtcaacta cggagctgtg cccgagactg ctcagatttt 7800
caccctcaaa gagtctgccg ctgcagccaa ggccaagagc gactaagcgg ccgcaagtgt 7860
ggatggggaa gtgagtgccc ggttctgtgt gcacaattgg caatccaaga tggatggatt 7920
caacacaggg atatagcgag ctacgtggtg gtgcgaggat atagcaacgg atatttatgt 7980
ttgacacttg agaatgtacg atacaagcac tgtccaagta caatactaaa catactgtac 8040
atactcatac tcgtacccgg gcaacggttt cacttgagtg cagtggctag tgctcttact 8100
cgtacagtgt gcaatactgc gtatcatagt ctttgatgta tatcgtattc attcatgtta 8160
gttgc 8165

<210> SEQ ID NO 26
<211> LENGTH: 7879
<212> TYPE: DNA
<213> ORGANISM: Artificial Sequence
<220> FEATURE:
<223> OTHER INFORMATION: sequence of pDMW237

<400> SEQUENCE: 26
ggccgcaagt gtggatgggg aagtgagtgc ccggttctgt gtgcacaatt ggcaatccaa 60
gatggatgga ttcaacacag ggatatagcg agctacgtgg tggtgcgagg atatagcaac 120
ggatatttat gtttgacact tgagaatgta cgatacaagc actgtccaag tacaatacta 180
aacatactgt acatactcat actcgtaccc gggcaacggt ttcacttgag tgcagtggct 240
agtgctctta ctcgtacagt gtgcaatact gcgtatcata gtctttgatg tatatcgtat 300
tcattcatgt tagttgcgta cgagccggaa gcataaagtg taaagcctgg ggtgcctaat 360
gagtgagcta actcacatta attgcgttgc gctcactgcc cgctttccag tcgggaaacc 420

-continued

```
tgtcgtgcca gctgcattaa tgaatcggcc aacgcgcggg gagaggcggt ttgcgtattg    480
ggcgctcttc cgcttcctcg ctcactgact cgctgcgctc ggtcgttcgg ctgcggcgag    540
cggtatcagc tcactcaaag gcggtaatac ggttatccac agaatcaggg gataacgcag    600
gaaagaacat gtgagcaaaa ggccagcaaa aggccaggaa ccgtaaaaag gccgcgttgc    660
tggcgttttt ccataggctc cgcccccctg acgagcatca caaaaatcga cgctcaagtc    720
agaggtggcg aaacccgaca ggactataaa gataccaggc gtttccccct ggaagctccc    780
tcgtgcgctc tcctgttccg accctgccgc ttaccggata cctgtccgcc tttctccctt    840
cgggaagcgt ggcgctttct catagctcac gctgtaggta tctcagttcg gtgtaggtcg    900
ttcgctccaa gctgggctgt gtgcacgaac cccccgttca gcccgaccgc tgcgccttat    960
ccggtaacta tcgtcttgag tccaacccgg taagacacga cttatcgcca ctggcagcag   1020
ccactggtaa caggattagc agagcgaggt atgtaggcgg tgctacagag ttcttgaagt   1080
ggtggcctaa ctacggctac actagaagga cagtatttgg tatctgcgct ctgctgaagc   1140
cagttacctt cggaaaaaga gttggtagct cttgatccgg caaacaaacc accgctggta   1200
gcggtggttt ttttgtttgc aagcagcaga ttacgcgcag aaaaaaagga tctcaagaag   1260
atcctttgat cttttctacg gggtctgacg ctcagtggaa cgaaaactca cgttaaggga   1320
ttttggtcat gagattatca aaaaggatct tcacctagat ccttttaaat taaaaatgaa   1380
gttttaaatc aatctaaagt atatatgagt aaacttggtc tgacagttac caatgcttaa   1440
tcagtgaggc acctatctca gcgatctgtc tatttcgttc atccatagtt gcctgactcc   1500
ccgtcgtgta gataactacg atacgggagg gcttaccatc tggccccagt gctgcaatga   1560
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt gcgcaacgtt gttgccattg   1740
ctacaggcat cgtggtgtca cgctcgtcgt ttggtatggc ttcattcagc tccggttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttccttttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgccctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca agctctaaat cgggggctcc   2580
ctttagggtt ccgatttagt gctttacggc acctcgaccc caaaaaactt gattagggtg   2640
atggttcacg tagtgggcca tcgccctgat agacggtttt tcgccctttg acgttggagt   2700
ccacgttctt taatagtgga ctcttgttcc aaactggaac aacactcaac cctatctcgg   2760
tctattcttt tgatttataa gggattttgc cgatttcggc ctattggtta aaaaatgagc   2820
```

-continued

```
tgatttaaca aaaatttaac gcgaatttta acaaaatatt aacgcttaca atttccattc   2880
gccattcagg ctgcgcaact gttgggaagg gcgatcggtg cgggcctctt cgctattacg   2940
ccagctggcg aaagggggat gtgctgcaag gcgattaagt tgggtaacgc cagggttttc   3000
ccagtcacga cgttgtaaaa cgacggccag tgaattgtaa tacgactcac tatagggcga   3060
attgggtacc gggccccccc tcgaggtcga tggtgtcgat aagcttgata tcgaattcat   3120
gtcacacaaa ccgatcttcg cctcaaggaa acctaattct acatccgaga gactgccgag   3180
atccagtcta cactgattaa ttttcgggcc aataatttaa aaaaatcgtg ttatataata   3240
ttatatgtat tatatatata catcatgatg atactgacag tcatgtccca ttgctaaata   3300
gacagactcc atctgccgcc tccaactgat gttctcaata tttaaggggt catctcgcat   3360
tgtttaataa taaacagact ccatctaccg cctccaaatg atgttctcaa aatatattgt   3420
atgaacttat ttttattact tagtattatt agacaactta cttgctttat gaaaaacact   3480
tcctatttag gaaacaattt ataatggcag ttcgttcatt taacaattta tgtagaataa   3540
atgttataaa tgcgtatggg aaatcttaaa tatggatagc ataaatgata tctgcattgc   3600
ctaattcgaa atcaacagca acgaaaaaaa tcccttgtac aacataaata gtcatcgaga   3660
aatatcaact atcaaagaac agctattcac acgttactat tgagattatt attggacgag   3720
aatcacacac tcaactgtct ttctctcttc tagaaataca ggtacaagta tgtactattc   3780
tcattgttca tacttctagt catttcatcc cacatattcc ttggatttct ctccaatgaa   3840
tgacattcta tcttgcaaat tcaacaatta taataagata taccaaagta gcggtatagt   3900
ggcaatcaaa aagcttctct ggtgtgcttc tcgtatttat ttttattcta atgatccatt   3960
aaaggtatat atttatttct tgttatataa tccttttgtt tattacatgg gctggataca   4020
taaaggtatt ttgatttaat tttttgctta aattcaatcc cccctcgttc agtgtcaact   4080
gtaatggtag gaaattacca tacttttgaa gaagcaaaaa aaatgaaaga aaaaaaaaat   4140
cgtatttcca ggttagacgt tccgcagaat ctagaatgcg gtatgcggta cattgttctt   4200
cgaacgtaaa agttgcgctc cctgagatat tgtacatttt tgcttttaca agtacaagta   4260
catcgtacaa ctatgtacta ctgttgatgc atccacaaca gtttgttttg tttttttttg   4320
tttttttttt ttctaatgat tcattaccgc tatgtatacc tacttgtact tgtagtaagc   4380
cgggttattg gcgttcaatt aatcatagac ttatgaatct gcacggtgtg cgctgcgagt   4440
tacttttagc ttatgcatgc tacttgggtg taatattggg atctgttcgg aaatcaacgg   4500
atgctcaatc gatttcgaca gtaattaatt aagtcataca caagtcagct ttcttcgagc   4560
ctcatataag tataagtagt tcaacgtatt agcactgtac ccagcatctc cgtatcgaga   4620
aacacaacaa catgccccat tggacagatc atgcggatac acaggttgtg cagtatcata   4680
catactcgat cagacaggtc gtctgaccat catacaagct gaacaagcgc tccatacttg   4740
cacgctctct atatacacag ttaaattaca tatccatagt ctaacctcta acagttaatc   4800
ttctggtaag cctcccagcc agccttctgg tatcgcttgg cctcctcaat aggatctcgg   4860
ttctggccgt acagacctcg gccgacaatt atgatatccg ttccggtaga catgacatcc   4920
tcaacagttc ggtactgctg tccgagagcg tctcccttgt cgtcaagacc caccccgggg   4980
gtcagaataa gccagtcctc agagtcgccc ttaggtcggt tctgggcaat gaagccaacc   5040
acaaactcgg ggtcggatcg ggcaagctca atggtctgct tggagtactc gccagtggcc   5100
agagagccct tgcaagacag ctcggccagc atgagcagac ctctggccag cttctcgttg   5160
```

```
ggagagggga ctaggaactc cttgtactgg gagttctcgt agtcagagac gtcctccttc   5220
ttctgttcag agacagtttc ctcggcacca gctcgcaggc cagcaatgat tccggttccg   5280
ggtacaccgt gggcgttggt gatatcggac cactcggcga ttcggtgaca ccggtactgg   5340
tgcttgacag tgttgccaat atctgcgaac tttctgtcct cgaacaggaa gaaaccgtgc   5400
ttaagagcaa gttccttgag ggggagcaca gtgccggcgt aggtgaagtc gtcaatgatg   5460
tcgatatggg ttttgatcat gcacacataa ggtccgacct tatcggcaag ctcaatgagc   5520
tccttggtgg tggtaacatc cagagaagca cacaggttgg ttttcttggc tgccacgagc   5580
ttgagcactc gagcggcaaa ggcggacttg tggacgttag ctcgagcttc gtaggagggc   5640
attttggtgg tgaagaggag actgaaataa atttagtctg cagaactttt tatcggaacc   5700
ttatctgggg cagtgaagta tatgttatgg taatagttac gagttagttg aacttataga   5760
tagactggac tatacggcta tcggtccaaa ttagaaagaa cgtcaatggc tctctgggcg   5820
tcgcctttgc cgacaaaaat gtgatcatga tgaaagccag caatgacgtt gcagctgata   5880
ttgttgtcgg ccaaccgcgc cgaaaacgca gctgtcagac ccacagcctc caacgaagaa   5940
tgtatcgtca aagtgatcca agcacactca tagttggagt cgtactccaa aggcggcaat   6000
gacgagtcag acagatactc gtcgactcag gcgacgacgg aattcctgca gcccatctgc   6060
agaattcagg agagaccggg ttggcggcgt atttgtgtcc caaaaaacag ccccaattgc   6120
cccggagaag acggccaggc cgcctagatg acaaattcaa caactcacag ctgactttct   6180
gccattgcca ctaggggggg gcctttttat atggccaagc caagctctcc acgtcggttg   6240
ggctgcaccc aacaataaat gggtagggtt gcaccaacaa agggatggga tggggggtag   6300
aagatacgag gataacgggg ctcaatggca caaataagaa cgaatactgc cattaagact   6360
cgtgatccag cgactgacac cattgcatca tctaagggcc tcaaaactac ctcggaactg   6420
ctgcgctgat ctggacacca cagaggttcc gagcacttta ggttgcacca aatgtcccac   6480
caggtgcagg cagaaaacgc tggaacagcg tgtacagttt gtcttaacaa aaagtgaggg   6540
cgctgaggtc gagcagggtg gtgtgacttg ttatagcctt tagagctgcg aaagcgcgta   6600
tggatttggc tcatcaggcc agattgaggg tctgtggaca catgtcatgt tagtgtactt   6660
caatcgcccc ctggatatag ccccgacaat aggccgtggc ctcatttttt tgccttccgc   6720
acatttccat tgctcggtac ccacaccttg cttctcctgc acttgccaac cttaatactg   6780
gtttacattg accaacatct tacaagcggg gggcttgtct agggtatata taaacagtgg   6840
ctctcccaat cggttgccag tctctttttt cctttcttc cccacagatt cgaaatctaa   6900
actacacatc acacaatgcc tgttactgac gtccttaagc gaaagtccgg tgtcatcgtc   6960
ggcgacgatg tccgagccgt gagtatccac gacaagatca gtgtcgagac gacgcgtttt   7020
gtgtaatgac acaatccgaa agtcgctagc aacacacact ctctacacaa actaacccag   7080
ctctccatgg ctctggccaa cgacgctggc gagcgaatct gggctgccgt caccgatccc   7140
gaaatcctca ttggcacctt ctcctacctg ctcctgaagc ctctcctgcg aaactctggt   7200
ctcgtggacg agaagaaagg agcctaccga acctccatga tctggtacaa cgtcctcctg   7260
gctctcttct ctgccctgtc cttctacgtg actgccaccg ctctcggctg ggactacggt   7320
actggagcct ggctgcgaag acagaccggt gatactcccc agcctctctt tcagtgtccc   7380
tctcctgtct gggactccaa gctgttcacc tggactgcca aggccttcta ctattctaag   7440
tacgtggagt acctcgacac cgcttggctg gtcctcaagg gcaagcgagt gtcctttctg   7500
caggccttcc atcactttgg agctccctgg gacgtctacc tcggcattcg actgcacaac   7560
```

gagggtgtgt ggatcttcat gttctttaac tcgttcattc acaccatcat gtacacctac 7620
tatggactga ctgccgctgg ctacaagttc aaggccaagc ctctgatcac tgccatgcag 7680
atttgccagt tcgtcggtgg ctttctcctg gtctgggact acatcaacgt tccctgcttc 7740
aactctgaca agggcaagct gttctcctgg gctttcaact acgcctacgt cggatctgtc 7800
tttctcctgt tctgtcactt cttttaccag gacaacctgg ccaccaagaa atccgctaag 7860
gctggtaagc agctttagc 7879

<210> SEQ ID NO 27
<211> LENGTH: 263
<212> TYPE: PRT
<213> ORGANISM: Isochrysis galbana

<400> SEQUENCE: 27

Met Ala Leu Ala Asn Asp Ala Gly Glu Arg Ile Trp Ala Ala Val Thr
1 5 10 15

Asp Pro Glu Ile Leu Ile Gly Thr Phe Ser Tyr Leu Leu Leu Lys Pro
20 25 30

Leu Leu Arg Asn Ser Gly Leu Val Asp Glu Lys Lys Gly Ala Tyr Arg
35 40 45

Thr Ser Met Ile Trp Tyr Asn Val Leu Leu Ala Leu Phe Ser Ala Leu
50 55 60

Ser Phe Tyr Val Thr Ala Thr Ala Leu Gly Trp Asp Tyr Gly Thr Gly
65 70 75 80

Ala Trp Leu Arg Arg Gln Thr Gly Asp Thr Pro Gln Pro Leu Phe Gln
85 90 95

Cys Pro Ser Pro Val Trp Asp Ser Lys Leu Phe Thr Trp Thr Ala Lys
100 105 110

Ala Phe Tyr Tyr Ser Lys Tyr Val Glu Tyr Leu Asp Thr Ala Trp Leu
115 120 125

Val Leu Lys Gly Lys Arg Val Ser Phe Leu Gln Ala Phe His His Phe
130 135 140

Gly Ala Pro Trp Asp Val Tyr Leu Gly Ile Arg Leu His Asn Glu Gly
145 150 155 160

Val Trp Ile Phe Met Phe Phe Asn Ser Phe Ile His Thr Ile Met Tyr
165 170 175

Thr Tyr Tyr Gly Leu Thr Ala Ala Gly Tyr Lys Phe Lys Ala Lys Pro
180 185 190

Leu Ile Thr Ala Met Gln Ile Cys Gln Phe Val Gly Gly Phe Leu Leu
195 200 205

Val Trp Asp Tyr Ile Asn Val Pro Cys Phe Asn Ser Asp Lys Gly Lys
210 215 220

Leu Phe Ser Trp Ala Phe Asn Tyr Ala Tyr Val Gly Ser Val Phe Leu
225 230 235 240

Leu Phe Cys His Phe Phe Tyr Gln Asp Asn Leu Ala Thr Lys Lys Ser
245 250 255

Ala Lys Ala Gly Lys Gln Leu
260

<210> SEQ ID NO 28
<211> LENGTH: 18
<212> TYPE: DNA
<213> ORGANISM: Artificial Sequence
<220> FEATURE:
<223> OTHER INFORMATION: sequence of the M13F universal primer

<400> SEQUENCE: 28
tgtaaaacga cggccagt 18

<210> SEQ ID NO 29
<211> LENGTH: 792
<212> TYPE: DNA
<213> ORGANISM: Isochrysis galbana

<400> SEQUENCE: 29
atggccctcg caaacgacgc gggagagcgc atctgggcgg ctgtgaccga cccggaaatc 60
ctcattggca ccttctcgta cttgctactc aaaccgctgc tccgcaattc cgggctggtg 120
gatgagaaga agggcgcata caggacgtcc atgatctggt acaacgttct gctggcgctc 180
ttctctgcgc tgagcttcta cgtgacggcg accgccctcg gctgggacta tggtacgggc 240
gcgtggctgc gcaggcaaac cggcgacaca ccgcagccgc tcttccagtg cccgtccccg 300
gtttgggact cgaagctctt cacatggacc gccaaggcat tctattactc caagtacgtg 360
gagtacctcg acacggcctg gctggtgctc aagggcaaga gggtctcctt tctccaggcc 420
ttccaccact ttggcgcgcc gtgggatgtg tacctcggca ttcggctgca caacgagggc 480
gtatggatct tcatgttttt caactcgttc attcacacca tcatgtacac ctactacggc 540
ctcaccgccg ccgggtataa gttcaaggcc aagccgctca tcaccgcgat gcagatctgc 600
cagttcgtgg gcggcttcct gttggtctgg gactacatca acgtcccctg cttcaactcg 660
gacaaaggga agttgttcag ctgggctttc aactatgcat acgtcggctc ggtcttcttg 720
ctcttctgcc actttttcta ccaggacaac ttggcaacga agaaatcggc caaggcgggc 780
aagcagctct ag 792

<210> SEQ ID NO 30
<211> LENGTH: 7783
<212> TYPE: DNA
<213> ORGANISM: Artificial Sequence
<220> FEATURE:
<223> OTHER INFORMATION: sequence of pY115

<400> SEQUENCE: 30
catggctctg gccaacgacg ctggcgagcg aatctgggct gccgtcaccg atcccgaaat 60
cctcattggc accttctcct acctgctcct gaagcctctc ctgcgaaact ctggtctcgt 120
ggacgagaag aaaggagcct accgaacctc catgatctgg tacaacgtcc tcctggctct 180
cttctctgcc ctgtccttct acgtgactgc caccgctctc ggctgggact acggtactgg 240
agcctggctg cgaagacaga ccggtgatac tccccagcct ctctttcagt gtccctctcc 300
tgtctgggac tccaagctgt tcacctggac tgccaaggcc ttctactatt ctaagtacgt 360
ggagtacctc gacaccgctt ggctggtcct caagggcaag cgagtgtcct ttctgcaggc 420
cttccatcac tttggagctc cctgggacgt ctacctcggc attcgactgc acaacgaggg 480
tgtgtggatc ttcatgttct ttaactcgtt cattcacacc atcatgtaca cctactatgg 540
actgactgcc gctggctaca agttcaaggc caagcctctg atcactgcca tgcagatttg 600
ccagttcgtc ggtggctttc tcctggtctg ggactacatc aacgttccct gcttcaactc 660
tgacaagggc aagctgttct cctgggcttt caactacgcc tacgtcggat ctgtctttct 720
cctgttctgt cacttctttt accaggacaa cctggccacc aagaaatccg ctaaggctgg 780
taagcagctt tagcggccgc aagtgtggat ggggaagtga gtgcccggtt ctgtgtgcac 840

-continued

```
aattggcaat ccaagatgga tggattcaac acagggatat agcgagctac gtggtggtgc    900
gaggatatag caacggatat ttatgtttga cacttgagaa tgtacgatac aagcactgtc    960
caagtacaat actaaacata ctgtacatac tcatactcgt acccgggcaa cggtttcact   1020
tgagtgcagt ggctagtgct cttactcgta cagtgtgcaa tactgcgtat catagtcttt   1080
gatgtatatc gtattcattc atgttagttg cgtacgagcc ggaagcataa agtgtaaagc   1140
ctggggtgcc taatgagtga gctaactcac attaattgcg ttgcgctcac tgcccgcttt   1200
ccagtcggga aacctgtcgt gccagctgca ttaatgaatc ggccaacgcg cggggagagg   1260
cggtttgcgt attgggcgct cttccgcttc ctcgctcact gactcgctgc gctcggtcgt   1320
tcggctgcgg cgagcggtat cagctcactc aaaggcggta atacggttat ccacagaatc   1380
aggggataac gcaggaaaga acatgtgagc aaaaggccag caaaaggcca ggaaccgtaa   1440
aaaggccgcg ttgctggcgt ttttccatag gctccgcccc cctgacgagc atcacaaaaa   1500
tcgacgctca agtcagaggt ggcgaaaccc gacaggacta taaagatacc aggcgtttcc   1560
ccctggaagc tccctcgtgc gctctcctgt tccgaccctg ccgcttaccg gatacctgtc   1620
cgcctttctc ccttcgggaa gcgtggcgct ttctcatagc tcacgctgta ggtatctcag   1680
ttcggtgtag gtcgttcgct ccaagctggg ctgtgtgcac gaaccccccg ttcagcccga   1740
ccgctgcgcc ttatccggta actatcgtct tgagtccaac ccggtaagac acgacttatc   1800
gccactggca gcagccactg gtaacaggat tagcagagcg aggtatgtag gcggtgctac   1860
agagttcttg aagtggtggc ctaactacgg ctacactaga aggacagtat ttggtatctg   1920
cgctctgctg aagccagtta ccttcggaaa aagagttggt agctcttgat ccggcaaaca   1980
aaccaccgct ggtagcggtg gtttttttgt ttgcaagcag cagattacgc gcagaaaaaa   2040
aggatctcaa gaagatcctt tgatcttttc tacggggtct gacgctcagt ggaacgaaaa   2100
ctcacgttaa gggattttgg tcatgagatt atcaaaaagg atcttcacct agatcctttt   2160
aaattaaaaa tgaagtttta aatcaatcta aagtatatat gagtaaactt ggtctgacag   2220
ttaccaatgc ttaatcagtg aggcacctat ctcagcgatc tgtctatttc gttcatccat   2280
agttgcctga ctccccgtcg tgtagataac tacgatacgg gagggcttac catctggccc   2340
cagtgctgca atgataccgc gagacccacg ctcaccggct ccagatttat cagcaataaa   2400
ccagccagcc ggaagggccg agcgcagaag tggtcctgca actttatccg cctccatcca   2460
gtctattaat tgttgccggg aagctagagt aagtagttcg ccagttaata gtttgcgcaa   2520
cgttgttgcc attgctacag gcatcgtggt gtcacgctcg tcgtttggta tggcttcatt   2580
cagctccggt tcccaacgat caaggcgagt tacatgatcc cccatgttgt gcaaaaaagc   2640
ggttagctcc ttcggtcctc cgatcgttgt cagaagtaag ttggccgcag tgttatcact   2700
catggttatg gcagcactgc ataattctct tactgtcatg ccatccgtaa gatgcttttc   2760
tgtgactggt gagtactcaa ccaagtcatt ctgagaatag tgtatgcggc gaccgagttg   2820
ctcttgcccg gcgtcaatac gggataatac cgcgccacat agcagaactt taaaagtgct   2880
catcattgga aaacgttctt cggggcgaaa actctcaagg atcttaccgc tgttgagatc   2940
cagttcgatg taacccactc gtgcacccaa ctgatcttca gcatctttta ctttcaccag   3000
cgtttctggg tgagcaaaaa caggaaggca aaatgccgca aaaaagggaa taagggcgac   3060
acggaaatgt tgaatactca tactcttcct ttttcaatat tattgaagca tttatcaggg   3120
ttattgtctc atgagcggat acatatttga atgtatttag aaaaataaac aaataggggt   3180
tccgcgcaca tttccccgaa aagtgccacc tgacgcgccc tgtagcggcg cattaagcgc   3240
```

```
ggcgggtgtg gtggttacgc gcagcgtgac cgctacactt gccagcgccc tagcgcccgc   3300
tcctttcgct ttcttccctt cctttctcgc cacgttcgcc ggctttcccc gtcaagctct   3360
aaatcggggg ctccctttag ggttccgatt tagtgcttta cggcacctcg accccaaaaa   3420
acttgattag ggtgatggtt cacgtagtgg gccatcgccc tgatagacgg tttttcgccc   3480
tttgacgttg gagtccacgt tctttaatag tggactcttg ttccaaactg gaacaacact   3540
caaccctatc tcggtctatt cttttgattt ataagggatt ttgccgattt cggcctattg   3600
gttaaaaaat gagctgattt aacaaaaatt taacgcgaat tttaacaaaa tattaacgct   3660
tacaatttcc attcgccatt caggctgcgc aactgttggg aagggcgatc ggtgcgggcc   3720
tcttcgctat tacgccagct ggcgaaaggg ggatgtgctg caaggcgatt aagttgggta   3780
acgccagggt tttcccagtc acgacgttgt aaaacgacgg ccagtgaatt gtaatacgac   3840
tcactatagg gcgaattggg taccgggccc cccctcgagg tcgatggtgt cgataagctt   3900
gatatcgaat tcatgtcaca caaaccgatc ttcgcctcaa ggaaacctaa ttctacatcc   3960
gagagactgc cgagatccag tctacactga ttaattttcg ggccaataat ttaaaaaaat   4020
cgtgttatat aatattatat gtattatata tatacatcat gatgatactg acagtcatgt   4080
cccattgcta aatagacaga ctccatctgc cgcctccaac tgatgttctc aatatttaag   4140
gggtcatctc gcattgttta ataataaaca gactccatct accgcctcca aatgatgttc   4200
tcaaaatata ttgtatgaac ttatttttat tacttagtat tattagacaa cttacttgct   4260
ttatgaaaaa cacttcctat ttaggaaaca atttataatg gcagttcgtt catttaacaa   4320
tttatgtaga ataaatgtta taaatgcgta tgggaaatct taaatatgga tagcataaat   4380
gatatctgca ttgcctaatt cgaaatcaac agcaacgaaa aaaatccctt gtacaacata   4440
aatagtcatc gagaaatatc aactatcaaa gaacagctat tcacacgtta ctattgagat   4500
tattattgga cgagaatcac acactcaact gtctttctct cttctagaaa tacaggtaca   4560
agtatgtact attctcattg ttcatacttc tagtcatttc atcccacata ttccttggat   4620
ttctctccaa tgaatgacat tctatcttgc aaattcaaca attataataa gatataccaa   4680
agtagcggta tagtggcaat caaaaagctt ctctggtgtg cttctcgtat ttatttttat   4740
tctaatgatc cattaaaggt atatatttat ttcttgttat ataatccttt tgtttattac   4800
atgggctgga tacataaagg tattttgatt taatttttg cttaaattca atccccccctc   4860
gttcagtgtc aactgtaatg gtaggaaatt accatacttt tgaagaagca aaaaaaatga   4920
aagaaaaaaa aaatcgtatt tccaggttag acgttccgca gaatctagaa tgcggtatgc   4980
ggtacattgt tcttcgaacg taaaagttgc gctccctgag atattgtaca tttttgcttt   5040
tacaagtaca agtacatcgt acaactatgt actactgttg atgcatccac aacagtttgt   5100
tttgtttttt tttgtttttt ttttttctaa tgattcatta ccgctatgta tacctacttg   5160
tacttgtagt aagccgggtt attggcgttc aattaatcat agacttatga atctgcacgg   5220
tgtgcgctgc gagttacttt tagcttatgc atgctacttg ggtgtaatat tgggatctgt   5280
tcggaaatca acggatgctc aatcgatttc gacagtaatt aattaagtca tacacaagtc   5340
agctttcttc gagcctcata taagtataag tagttcaacg tattagcact gtacccagca   5400
tctccgtatc gagaaacaca acaacatgcc ccattggaca gatcatgcgg atacacaggt   5460
tgtgcagtat catacatact cgatcagaca ggtcgtctga ccatcataca agctgaacaa   5520
gcgctccata cttgcacgct ctctatatac acagttaaat tacatatcca tagtctaacc   5580
```

tctaacagtt aatcttctgg taagcctccc agccagcctt ctggtatcgc ttggcctcct 5640
caataggatc tcggttctgg ccgtacagac ctcggccgac aattatgata tccgttccgg 5700
tagacatgac atcctcaaca gttcggtact gctgtccgag agcgtctccc ttgtcgtcaa 5760
gacccacccc gggggtcaga ataagccagt cctcagagtc gcccttaggt cggttctggg 5820
caatgaagcc aaccacaaac tcggggtcgg atcgggcaag ctcaatggtc tgcttggagt 5880
actcgccagt ggccagagag cccttgcaag acagctcggc cagcatgagc agacctctgg 5940
ccagcttctc gttgggagag ggactagga actccttgta ctgggagttc tcgtagtcag 6000
agacgtcctc cttcttctgt tcagagacag tttcctcggc accagctcgc aggccagcaa 6060
tgattccggt tccgggtaca ccgtgggcgt tggtgatatc ggaccactcg gcgattcggt 6120
gacaccggta ctggtgcttg acagtgttgc caatatctgc gaactttctg tcctcgaaca 6180
ggaagaaacc gtgcttaaga gcaagttcct tgagggggag cacagtgccg gcgtaggtga 6240
agtcgtcaat gatgtcgata tgggttttga tcatgcacac ataaggtccg accttatcgg 6300
caagctcaat gagctccttg gtggtggtaa catccagaga agcacacagg ttggttttct 6360
tggctgccac gagcttgagc actcgagcgg caaaggcgga cttgtggacg ttagctcgag 6420
cttcgtagga gggcattttg gtggtgaaga ggagactgaa ataaatttag tctgcagaac 6480
tttttatcgg aaccttatct ggggcagtga agtatatgtt atggtaatag ttacgagtta 6540
gttgaactta tagatagact ggactatacg gctatcggtc caaattagaa agaacgtcaa 6600
tggctctctg ggcgtcgcct ttgccgacaa aaatgtgatc atgatgaaag ccagcaatga 6660
cgttgcagct gatattgttg tcggccaacc gcgccgaaaa cgcagctgtc agacccacag 6720
cctccaacga agaatgtatc gtcaaagtga tccaagcaca ctcatagttg gagtcgtact 6780
ccaaaggcgg caatgacgag tcagacagat actcgtcgac gtttaaacag tgtacgcaga 6840
tctactatag aggaacattt aaattgcccc ggagaagacg gccaggccgc ctagatgaca 6900
aattcaacaa ctcacagctg actttctgcc attgccacta ggggggggcc tttttatatg 6960
gccaagccaa gctctccacg tcggttgggc tgcacccaac aataaatggg tagggttgca 7020
ccaacaaagg gatgggatgg ggggtagaag atacgaggat aacggggctc aatggcacaa 7080
ataagaacga atactgccat taagactcgt gatccagcga ctgacaccat tgcatcatct 7140
aagggcctca aaactacctc ggaactgctg cgctgatctg gacaccacag aggttccgag 7200
cactttaggt tgcaccaaat gtcccaccag gtgcaggcag aaaacgctgg aacagcgtgt 7260
acagtttgtc ttaacaaaaa gtgagggcgc tgaggtcgag cagggtggtg tgacttgtta 7320
tagcctttag agctgcgaaa gcgcgtatgg atttggctca tcaggccaga ttgagggtct 7380
gtggacacat gtcatgttag tgtacttcaa tcgccccctg gatatagccc cgacaatagg 7440
ccgtggcctc atttttttgc cttccgcaca tttccattgc tcgataccca caccttgctt 7500
ctcctgcact tgccaacctt aatactggtt tacattgacc aacatcttac aagcgggggg 7560
cttgtctagg gtatatataa acagtggctc tcccaatcgg ttgccagtct ctttttttcct 7620 ttctttcccc acagattcga aatctaaact acacatcaca gaattccgag ccgtgagtat 7680
ccacgacaag atcagtgtcg agacgacgcg ttttgtgtaa tgacacaatc cgaaagtcgc 7740
tagcaacaca cactctctac acaaactaac ccagctctgg tac 7783

<210> SEQ ID NO 31
<211> LENGTH: 8704
<212> TYPE: DNA
<213> ORGANISM: Artificial Sequence
<220> FEATURE:
<223> OTHER INFORMATION: sequence of pBY1

<400> SEQUENCE: 31
ggccgcaagt gtggatgggg aagtgagtgc ccggttctgt gtgcacaatt ggcaatccaa 60
gatggatgga ttcaacacag ggatatagcg agctacgtgg tggtgcgagg atatagcaac 120
ggatatttat gtttgacact tgagaatgta cgatacaagc actgtccaag tacaatacta 180
aacatactgt acatactcat actcgtaccc gggcaacggt ttcacttgag tgcagtggct 240
agtgctctta ctcgtacagt gtgcaatact gcgtatcata gtctttgatg tatatcgtat 300
tcattcatgt tagttgcgta cgagccggaa gcataaagtg taaagcctgg ggtgcctaat 360
gagtgagcta actcacatta attgcgttgc gctcactgcc cgctttccag tcgggaaacc 420
tgtcgtgcca gctgcattaa tgaatcggcc aacgcgcggg gagaggcggt ttgcgtattg 480
ggcgctcttc cgcttcctcg ctcactgact cgctgcgctc ggtcgttcgg ctgcggcgag 540
cggtatcagc tcactcaaag gcggtaatac ggttatccac agaatcaggg gataacgcag 600
gaaagaacat gtgagcaaaa ggccagcaaa aggccaggaa ccgtaaaaag gccgcgttgc 660
tggcgttttt ccataggctc cgcccccctg acgagcatca caaaaatcga cgctcaagtc 720
agaggtggcg aaacccgaca ggactataaa gataccaggc gtttccccct ggaagctccc 780
tcgtgcgctc tcctgttccg accctgccgc ttaccggata cctgtccgcc tttctccctt 840
cgggaagcgt ggcgctttct catagctcac gctgtaggta tctcagttcg gtgtaggtcg 900
ttcgctccaa gctgggctgt gtgcacgaac cccccgttca gcccgaccgc tgcgccttat 960
ccggtaacta tcgtcttgag tccaacccgg taagacacga cttatcgcca ctggcagcag 1020
ccactggtaa caggattagc agagcgaggt atgtaggcgg tgctacagag ttcttgaagt 1080
ggtggcctaa ctacggctac actagaagga cagtatttgg tatctgcgct ctgctgaagc 1140
cagttacctt cggaaaaaga gttggtagct cttgatccgg caaacaaacc accgctggta 1200
gcggtggttt ttttgtttgc aagcagcaga ttacgcgcag aaaaaaagga tctcaagaag 1260
atcctttgat cttttctacg gggtctgacg ctcagtggaa cgaaaactca cgttaaggga 1320
ttttggtcat gagattatca aaaaggatct tcacctagat ccttttaaat taaaaatgaa 1380
gttttaaatc aatctaaagt atatatgagt aaacttggtc tgacagttac caatgcttaa 1440
tcagtgaggc acctatctca gcgatctgtc tatttcgttc atccatagtt gcctgactcc 1500
ccgtcgtgta gataactacg atacgggagg gcttaccatc tggccccagt gctgcaatga 1560
taccgcgaga cccacgctca ccggctccag atttatcagc aataaaccag ccagccggaa 1620
gggccgagcg cagaagtggt cctgcaactt tatccgcctc catccagtct attaattgtt 1680
gccgggaagc tagagtaagt agttcgccag ttaatagttt gcgcaacgtt gttgccattg 1740
ctacaggcat cgtggtgtca cgctcgtcgt ttggtatggc ttcattcagc tccggttccc 1800
aacgatcaag gcgagttaca tgatccccca tgttgtgcaa aaaagcggtt agctccttcg 1860
gtcctccgat cgttgtcaga agtaagttgg ccgcagtgtt atcactcatg gttatggcag 1920
cactgcataa ttctcttact gtcatgccat ccgtaagatg cttttctgtg actggtgagt 1980
actcaaccaa gtcattctga gaatagtgta tgcggcgacc gagttgctct tgcccggcgt 2040
caatacggga taataccgcg ccacatagca gaactttaaa agtgctcatc attggaaaac 2100
gttcttcggg gcgaaaactc tcaaggatct taccgctgtt gagatccagt tcgatgtaac 2160
ccactcgtgc acccaactga tcttcagcat cttttacttt caccagcgtt tctgggtgag 2220

```
caaaaacagg aaggcaaaat gccgcaaaaa agggaataag ggcgacacgg aaatgttgaa   2280
tactcatact cttccttttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgccctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca agctctaaat cgggggctcc   2580
ctttagggtt ccgatttagt gctttacggc acctcgaccc caaaaaactt gattagggtg   2640
atggttcacg tagtgggcca tcgccctgat agacggtttt tcgccctttg acgttggagt   2700
ccacgttctt taatagtgga ctcttgttcc aaactggaac aacactcaac cctatctcgg   2760
tctattcttt tgatttataa gggattttgc cgatttcggc ctattggtta aaaaatgagc   2820
tgatttaaca aaaatttaac gcgaatttta acaaaatatt aacgcttaca atttccattc   2880
gccattcagg ctgcgcaact gttgggaagg gcgatcggtg cgggcctctt cgctattacg   2940
ccagctggcg aaagggggat gtgctgcaag gcgattaagt tgggtaacgc cagggttttc   3000
ccagtcacga cgttgtaaaa cgacggccag tgaattgtaa tacgactcac tatagggcga   3060
attgggtacc gggccccccc tcgaggtcga tggtgtcgat aagcttgata tcgaattcat   3120
gtcacacaaa ccgatcttcg cctcaaggaa acctaattct acatccgaga gactgccgag   3180
atccagtcta cactgattaa ttttcgggcc aataatttaa aaaaatcgtg ttatataata   3240
ttatatgtat tatatatata catcatgatg atactgacag tcatgtccca ttgctaaata   3300
gacagactcc atctgccgcc tccaactgat gttctcaata tttaaggggt catctcgcat   3360
tgtttaataa taaacagact ccatctaccg cctccaaatg atgttctcaa aatatattgt   3420
atgaacttat ttttattact tagtattatt agacaactta cttgctttat gaaaaacact   3480
tcctatttag gaaacaattt ataatggcag ttcgttcatt taacaattta tgtagaataa   3540
atgttataaa tgcgtatggg aaatcttaaa tatggatagc ataaatgata tctgcattgc   3600
ctaattcgaa atcaacagca acgaaaaaaa tcccttgtac aacataaata gtcatcgaga   3660
aatatcaact atcaaagaac agctattcac acgttactat tgagattatt attggacgag   3720
aatcacacac tcaactgtct ttctctcttc tagaaataca ggtacaagta tgtactattc   3780
tcattgttca tacttctagt catttcatcc cacatattcc ttggatttct ctccaatgaa   3840
tgacattcta tcttgcaaat tcaacaatta taataagata taccaaagta gcggtatagt   3900
ggcaatcaaa aagcttctct ggtgtgcttc tcgtatttat ttttattcta atgatccatt   3960
aaaggtatat atttatttct tgttatataa tccttttgtt tattacatgg gctggataca   4020
taaaggtatt ttgatttaat tttttgctta aattcaatcc cccctcgttc agtgtcaact   4080
gtaatggtag gaaattacca tacttttgaa gaagcaaaaa aaatgaaaga aaaaaaaaat   4140
cgtatttcca ggttagacgt tccgcagaat ctagaatgcg gtatgcggta cattgttctt   4200
cgaacgtaaa agttgcgctc cctgagatat tgtacatttt tgcttttaca agtacaagta   4260
catcgtacaa ctatgtacta ctgttgatgc atccacaaca gtttgttttg tttttttttg   4320
tttttttttt ttctaatgat tcattaccgc tatgtatacc tacttgtact tgtagtaagc   4380
cgggttattg gcgttcaatt aatcatagac ttatgaatct gcacggtgtg cgctgcgagt   4440
tacttttagc ttatgcatgc tacttgggtg taatattggg atctgttcgg aaatcaacgg   4500
atgctcaatc gatttcgaca gtaattaatt aagtcataca caagtcagct ttcttcgagc   4560
ctcatataag tataagtagt tcaacgtatt agcactgtac ccagcatctc cgtatcgaga   4620
```

```
aacacaacaa catgccccat tggacagatc atgcggatac acaggttgtg cagtatcata   4680
catactcgat cagacaggtc gtctgaccat catacaagct gaacaagcgc tccatacttg   4740
cacgctctct atatacacag ttaaattaca tatccatagt ctaacctcta acagttaatc   4800
ttctggtaag cctcccagcc agccttctgg tatcgcttgg cctcctcaat aggatctcgg   4860
ttctggccgt acagacctcg gccgacaatt atgatatccg ttccggtaga catgacatcc   4920
tcaacagttc ggtactgctg tccgagagcg tctcccttgt cgtcaagacc caccccgggg   4980
gtcagaataa gccagtcctc agagtcgccc ttaggtcggt tctgggcaat gaagccaacc   5040
acaaactcgg ggtcggatcg ggcaagctca atggtctgct tggagtactc gccagtggcc   5100
agagagccct tgcaagacag ctcggccagc atgagcagac ctctggccag cttctcgttg   5160
ggagagggga ctaggaactc cttgtactgg gagttctcgt agtcagagac gtcctccttc   5220
ttctgttcag agacagtttc ctcggcacca gctcgcaggc cagcaatgat tccggttccg   5280
ggtacaccgt gggcgttggt gatatcggac cactcggcga ttcggtgaca ccggtactgg   5340
tgcttgacag tgttgccaat atctgcgaac tttctgtcct cgaacaggaa gaaaccgtgc   5400
ttaagagcaa gttccttgag ggggagcaca gtgccggcgt aggtgaagtc gtcaatgatg   5460
tcgatatggg ttttgatcat gcacacataa ggtccgacct tatcggcaag ctcaatgagc   5520
tccttggtgg tggtaacatc cagagaagca cacaggttgg ttttcttggc tgccacgagc   5580
ttgagcactc gagcggcaaa ggcggacttg tggacgttag ctcgagcttc gtaggagggc   5640
attttggtgg tgaagaggag actgaaataa atttagtctg cagaactttt tatcggaacc   5700
ttatctgggg cagtgaagta tatgttatgg taatagttac gagttagttg aacttataga   5760
tagactggac tatacggcta tcggtccaaa ttagaaagaa cgtcaatggc tctctgggcg   5820
tcgcctttgc cgacaaaaat gtgatcatga tgaaagccag caatgacgtt gcagctgata   5880
ttgttgtcgg ccaaccgcgc cgaaaacgca gctgtcagac ccacagcctc caacgaagaa   5940
tgtatcgtca aagtgatcca agcacactca tagttggagt cgtactccaa aggcggcaat   6000
gacgagtcag acagatactc gtcgacgttt aaacagtgta cgcagatcta ctatagagga   6060
acatttaaat tgccccggag aagacggcca ggccgcctag atgacaaatt caacaactca   6120
cagctgactt tctgccattg ccactagggg ggggcctttt tatatggcca agccaagctc   6180
tccacgtcgg ttgggctgca cccaacaata aatgggtagg gttgcaccaa caaagggatg   6240
ggatgggggg tagaagatac gaggataacg gggctcaatg gcacaaataa gaacgaatac   6300
tgccattaag actcgtgatc cagcgactga caccattgca tcatctaagg gcctcaaaac   6360
tacctcggaa ctgctgcgct gatctggaca ccacagaggt tccgagcact ttaggttgca   6420
ccaaatgtcc caccaggtgc aggcagaaaa cgctggaaca gcgtgtacag tttgtcttaa   6480
caaaaagtga gggcgctgag gtcgagcagg gtggtgtgac ttgttatagc ctttagagct   6540
gcgaaagcgc gtatggattt ggctcatcag gccagattga gggtctgtgg acacatgtca   6600
tgttagtgta cttcaatcgc cccctggata tagccccgac aataggccgt ggcctcattt   6660
ttttgccttc cgcacatttc cattgctcga tacccacacc ttgcttctcc tgcacttgcc   6720
aaccttaata ctggtttaca ttgaccaaca tcttacaagc ggggggcttg tctagggtat   6780
atataaacag tggctctccc aatcggttgc cagtctcttt tttcctttct ttccccacag   6840
attcgaaatc taaactacac atcacagaat tccgagccgt gagtatccac gacaagatca   6900
gtgtcgagac gacgcgtttt gtgtaatgac acaatccgaa agtcgctagc aacacacact   6960
```

-continued

```
ctctacacaa actaacccag ctctggtacc atgatcacaa gtttgtacaa aaaagctgaa   7020

cgagaaacgt aaaatgatat aaatatcaat atattaaatt agattttgca taaaaaacag   7080

actacataat actgtaaaac acaacatatc cagtcatatt ggcggccgca ttaggcaccc   7140

caggctttac actttatgct tccggctcgt ataatgtgtg gattttgagt taggatccgt   7200

cgagattttc aggagctaag gaagctaaaa tggagaaaaa aatcactgga tataccaccg   7260

ttgatatatc ccaatggcat cgtaaagaac attttgaggc atttcagtca gttgctcaat   7320

gtacctataa ccagaccgtt cagctggata ttacggcctt tttaaagacc gtaaagaaaa   7380

ataagcacaa gttttatccg gcctttattc acattcttgc ccgcctgatg aatgctcatc   7440

cggaattccg tatggcaatg aaagacggtg agctggtgat atgggatagt gttcaccctt   7500

gttacaccgt tttccatgag caaactgaaa cgttttcatc gctctggagt gaataccacg   7560

acgatttccg gcagtttcta cacatatatt cgcaagatgt ggcgtgttac ggtgaaaacc   7620

tggcctattt ccctaaaggg tttattgaga atatgttttt cgtctcagcc aatccctggg   7680

tgagtttcac cagttttgat ttaaacgtgg ccaatatgga caacttcttc gcccccgttt   7740

tcaccatggg caaatattat acgcaaggcg acaaggtgct gatgccgctg gcgattcagg   7800

ttcatcatgc cgtttgtgat ggcttccatg tcggcagaat gcttaatgaa ttacaacagt   7860

actgcgatga gtggcagggc ggggcgtaaa cgcgtggatc cggcttacta aaagccagat   7920

aacagtatgc gtatttgcgc gctgattttt gcggtataag aatatatact gatatgtata   7980

cccgaagtat gtcaaaaaga ggtatgctat gaagcagcgt attacagtga cagttgacag   8040

cgacagctat cagttgctca aggcatatat gatgtcaata tctccggtct ggtaagcaca   8100

accatgcaga atgaagcccg tcgtctgcgt gccgaacgct ggaaagcgga aaatcaggaa   8160

gggatggctg aggtcgcccg gtttattgaa atgaacggct cttttgctga cgagaacagg   8220

ggctggtgaa atgcagttta aggtttacac ctataaaaga gagagccgtt atcgtctgtt   8280

tgtggatgta cagagtgata ttattgacac gcccgggcga cggatggtga tccccctggc   8340

cagtgcacgt ctgctgtcag ataaagtctc ccgtgaactt tacccggtgg tgcatatcgg   8400

ggatgaaagc tggcgcatga tgaccaccga tatggccagt gtgccggtct ccgttatcgg   8460

ggaagaagtg gctgatctca gccaccgcga aaatgacatc aaaaacgcca ttaacctgat   8520

gttctgggga atataaatgt caggctccct tatacacagc cagtctgcag gtcgaccata   8580

gtgactggat atgttgtgtt ttacagcatt atgtagtctg tttttatgc aaaatctaat   8640

ttaatatatt gatatttata tcattttacg tttctcgttc agctttcttg tacaaagtgg   8700

tgat                                                                8704
```

<210> SEQ ID NO 32
<211> LENGTH: 8145
<212> TYPE: DNA
<213> ORGANISM: Artificial Sequence
<220> FEATURE:
<223> OTHER INFORMATION: sequence of pBY2
<220> FEATURE:
<221> NAME/KEY: misc_feature
<222> LOCATION: (8028)..(8031)
<223> OTHER INFORMATION: n is a, c, g, or t
<220> FEATURE:
<221> NAME/KEY: misc_feature
<222> LOCATION: (8063)..(8065)
<223> OTHER INFORMATION: n is a, c, g, or t
<220> FEATURE:
<221> NAME/KEY: misc_feature
<222> LOCATION: (8067)..(8069)
<223> OTHER INFORMATION: n is a, c, g, or t
<220> FEATURE:
<221> NAME/KEY: misc_feature
<222> LOCATION: (8071)..(8073)
<223> OTHER INFORMATION: n is a, c, g, or t
<220> FEATURE:
<221> NAME/KEY: misc_feature
<222> LOCATION: (8075)..(8075)
<223> OTHER INFORMATION: n is a, c, g, or t
<220> FEATURE:
<221> NAME/KEY: misc_feature
<222> LOCATION: (8126)..(8135)
<223> OTHER INFORMATION: n is a, c, g, or t

<400> SEQUENCE: 32
cttgtacaaa gtggtgatgg ccgcaagtgt ggatggggaa gtgagtgccc ggttctgtgt 60
gcacaattgg caatccaaga tggatggatt caacacaggg atatagcgag ctacgtggtg 120
gtgcgaggat atagcaacgg atatttatgt ttgacacttg agaatgtacg atacaagcac 180
tgtccaagta caatactaaa catactgtac atactcatac tcgtacccgg gcaacggttt 240
cacttgagtg cagtggctag tgctcttact cgtacagtgt gcaatactgc gtatcatagt 300
ctttgatgta tatcgtattc attcatgtta gttgcgtacg agccggaagc ataaagtgta 360
aagcctgggg tgcctaatga gtgagctaac tcacattaat tgcgttgcgc tcactgcccg 420
ctttccagtc gggaaacctg tcgtgccagc tgcattaatg aatcggccaa cgcgcgggga 480
gaggcggttt gcgtattggg cgctcttccg cttcctcgct cactgactcg ctgcgctcgg 540
tcgttcggct gcggcgagcg gtatcagctc actcaaaggc ggtaatacgg ttatccacag 600
aatcagggga taacgcagga aagaacatgt gagcaaaagg ccagcaaaag gccaggaacc 660
gtaaaaaggc cgcgttgctg gcgtttttcc ataggctccg cccccctgac gagcatcaca 720
aaaatcgacg ctcaagtcag aggtggcgaa acccgacagg actataaaga taccaggcgt 780
ttccccctgg aagctccctc gtgcgctctc ctgttccgac cctgccgctt accggatacc 840
tgtccgcctt tctcccttcg ggaagcgtgg cgctttctca tagctcacgc tgtaggtatc 900
tcagttcggt gtaggtcgtt cgctccaagc tgggctgtgt gcacgaaccc cccgttcagc 960
ccgaccgctg cgccttatcc ggtaactatc gtcttgagtc caacccggta agacacgact 1020
tatcgccact ggcagcagcc actggtaaca ggattagcag agcgaggtat gtaggcggtg 1080
ctacagagtt cttgaagtgg tggcctaact acggctacac tagaaggaca gtatttggta 1140
tctgcgctct gctgaagcca gttaccttcg gaaaaagagt tggtagctct tgatccggca 1200
aacaaaccac cgctggtagc ggtggttttt ttgtttgcaa gcagcagatt acgcgcagaa 1260
aaaaaggatc tcaagaagat cctttgatct tttctacggg gtctgacgct cagtggaacg 1320
aaaactcacg ttaagggatt ttggtcatga gattatcaaa aaggatcttc acctagatcc 1380
ttttaaatta aaaatgaagt tttaaatcaa tctaaagtat atatgagtaa acttggtctg 1440
acagttacca atgcttaatc agtgaggcac ctatctcagc gatctgtcta tttcgttcat 1500
ccatagttgc ctgactcccc gtcgtgtaga taactacgat acgggagggc ttaccatctg 1560
gccccagtgc tgcaatgata ccgcgagacc cacgctcacc ggctccagat ttatcagcaa 1620
taaaccagcc agccggaagg gccgagcgca gaagtggtcc tgcaacttta tccgcctcca 1680
tccagtctat taattgttgc cgggaagcta gagtaagtag ttcgccagtt aatagtttgc 1740
gcaacgttgt tgccattgct acaggcatcg tggtgtcacg ctcgtcgttt ggtatggctt 1800
cattcagctc cggttcccaa cgatcaaggc gagttacatg atcccccatg ttgtgcaaaa 1860
aagcggttag ctccttcggt cctccgatcg ttgtcagaag taagttggcc gcagtgttat 1920

-continued

```
cactcatggt tatggcagca ctgcataatt ctcttactgt catgccatcc gtaagatgct   1980
tttctgtgac tggtgagtac tcaaccaagt cattctgaga atagtgtatg cggcgaccga   2040
gttgctcttg cccggcgtca atacgggata ataccgcgcc acatagcaga actttaaaag   2100
tgctcatcat tggaaaacgt tcttcggggc gaaaactctc aaggatctta ccgctgttga   2160
gatccagttc gatgtaaccc actcgtgcac ccaactgatc ttcagcatct tttactttca   2220
ccagcgtttc tgggtgagca aaaacaggaa ggcaaaatgc cgcaaaaaag ggaataaggg   2280
cgacacggaa atgttgaata ctcatactct tcctttttca atattattga agcatttatc   2340
agggttattg tctcatgagc ggatacatat ttgaatgtat ttagaaaaat aaacaaatag   2400
gggttccgcg cacatttccc cgaaaagtgc cacctgacgc gccctgtagc ggcgcattaa   2460
gcgcggcggg tgtggtggtt acgcgcagcg tgaccgctac acttgccagc gccctagcgc   2520
ccgctccttt cgctttcttc ccttcctttc tcgccacgtt cgccggcttt ccccgtcaag   2580
ctctaaatcg ggggctccct ttagggttcc gatttagtgc tttacggcac ctcgacccca   2640
aaaaacttga ttagggtgat ggttcacgta gtgggccatc gccctgatag acggtttttc   2700
gccctttgac gttggagtcc acgttcttta atagtggact cttgttccaa actggaacaa   2760
cactcaaccc tatctcggtc tattcttttg atttataagg gattttgccg atttcggcct   2820
attggttaaa aaatgagctg atttaacaaa aatttaacgc gaattttaac aaaatattaa   2880
cgcttacaat ttccattcgc cattcaggct gcgcaactgt tgggaagggc gatcggtgcg   2940
ggcctcttcg ctattacgcc agctggcgaa agggggatgt gctgcaaggc gattaagttg   3000
ggtaacgcca gggttttccc agtcacgacg ttgtaaaacg acggccagtg aattgtaata   3060
cgactcacta tagggcgaat tgggtaccgg gccccccctc gaggtcgatg gtgtcgataa   3120
gcttgatatc gaattcatgt cacacaaacc gatcttcgcc tcaaggaaac ctaattctac   3180
atccgagaga ctgccgagat ccagtctaca ctgattaatt ttcgggccaa taatttaaaa   3240
aaatcgtgtt atataatatt atatgtatta tatatataca tcatgatgat actgacagtc   3300
atgtcccatt gctaaataga cagactccat ctgccgcctc caactgatgt tctcaatatt   3360
taaggggtca tctcgcattg tttaataata aacagactcc atctaccgcc tccaaatgat   3420
gttctcaaaa tatattgtat gaacttattt ttattactta gtattattag acaacttact   3480
tgctttatga aaaacacttc ctatttagga aacaatttat aatggcagtt cgttcattta   3540
acaatttatg tagaataaat gttataaatg cgtatgggaa atcttaaata tggatagcat   3600
aaatgatatc tgcattgcct aattcgaaat caacagcaac gaaaaaaatc ccttgtacaa   3660
cataaatagt catcgagaaa tatcaactat caaagaacag ctattcacac gttactattg   3720
agattattat tggacgagaa tcacacactc aactgtcttt ctctcttcta gaaatacagg   3780
tacaagtatg tactattctc attgttcata cttctagtca tttcatccca catattcctt   3840
ggatttctct ccaatgaatg acattctatc ttgcaaattc aacaattata ataagatata   3900
ccaaagtagc ggtatagtgg caatcaaaaa gcttctctgg tgtgcttctc gtatttattt   3960
ttattctaat gatccattaa aggtatatat ttatttcttg ttatataatc cttttgttta   4020
ttacatgggc tggatacata aaggtatttt gatttaattt tttgcttaaa ttcaatcccc   4080
cctcgttcag tgtcaactgt aatggtagga aattaccata cttttgaaga agcaaaaaaa   4140
atgaaagaaa aaaaaaatcg tatttccagg ttagacgttc cgcagaatct agaatgcggt   4200
atgcggtaca ttgttcttcg aacgtaaaag ttgcgctccc tgagatattg tacatttttg   4260
cttttacaag tacaagtaca tcgtacaact atgtactact gttgatgcat ccacaacagt   4320
```

-continued

```
ttgttttgtt tttttttgtt ttttttttt ctaatgattc attaccgcta tgtataccta   4380
cttgtacttg tagtaagccg ggttattggc gttcaattaa tcatagactt atgaatctgc   4440
acggtgtgcg ctgcgagtta cttttagctt atgcatgcta cttgggtgta atattgggat   4500
ctgttcggaa atcaacggat gctcaatcga tttcgacagt aattaattaa gtcatacaca   4560
agtcagcttt cttcgagcct catataagta taagtagttc aacgtattag cactgtaccc   4620
agcatctccg tatcgagaaa cacaacaaca tgccccattg gacagatcat gcggatacac   4680
aggttgtgca gtatcataca tactcgatca gacaggtcgt ctgaccatca tacaagctga   4740
acaagcgctc catacttgca cgctctctat atacacagtt aaattacata tccatagtct   4800
aacctctaac agttaatctt ctggtaagcc tcccagccag ccttctggta tcgcttggcc   4860
tcctcaatag gatctcggtt ctggccgtac agacctcggc cgacaattat gatatccgtt   4920
ccggtagaca tgacatcctc aacagttcgg tactgctgtc cgagagcgtc tcccttgtcg   4980
tcaagaccca ccccgggggt cagaataagc cagtcctcag agtcgccctt aggtcggttc   5040
tgggcaatga agccaaccac aaactcgggg tcggatcggg caagctcaat ggtctgcttg   5100
gagtactcgc cagtggccag agagcccttg caagacagct cggccagcat gagcagacct   5160
ctggccagct tctcgttggg agaggggact aggaactcct tgtactggga gttctcgtag   5220
tcagagacgt cctccttctt ctgttcagag acagtttcct cggcaccagc tcgcaggcca   5280
gcaatgattc cggttccggg tacaccgtgg gcgttggtga tatcggacca ctcggcgatt   5340
cggtgacacc ggtactggtg cttgacagtg ttgccaatat ctgcgaactt tctgtcctcg   5400
aacaggaaga aaccgtgctt aagagcaagt tccttgaggg ggagcacagt gccggcgtag   5460
gtgaagtcgt caatgatgtc gatatgggtt ttgatcatgc acacataagg tccgacctta   5520
tcggcaagct caatgagctc cttggtggtg gtaacatcca gagaagcaca caggttggtt   5580
ttcttggctg ccacgagctt gagcactcga gcggcaaagg cggacttgtg gacgttagct   5640
cgagcttcgt aggagggcat tttggtggtg aagaggagac tgaaataaat ttagtctgca   5700
gaacttttta tcggaacctt atctggggca gtgaagtata tgttatggta atagttacga   5760
gttagttgaa cttatagata gactggacta tacggctatc ggtccaaatt agaaagaacg   5820
tcaatggctc tctgggcgtc gcctttgccg acaaaaatgt gatcatgatg aaagccagca   5880
atgacgttgc agctgatatt gttgtcggcc aaccgcgccg aaaacgcagc tgtcagaccc   5940
acagcctcca acgaagaatg tatcgtcaaa gtgatccaag cacactcata gttggagtcg   6000
tactccaaag gcggcaatga cgagtcagac agatactcgt cgacgtttaa acagtgtacg   6060
cagatctact atagaggaac atttaaattg ccccggagaa gacggccagg ccgcctagat   6120
gacaaattca acaactcaca gctgactttc tgccattgcc actagggggg ggcctttttta  6180
tatggccaag ccaagctctc cacgtcggtt gggctgcacc caacaataaa tgggtagggt   6240
tgcaccaaca aagggatggg atgggggggta gaagatacga ggataacggg gctcaatggc  6300
acaaataaga acgaatactg ccattaagac tcgtgatcca gcgactgaca ccattgcatc   6360
atctaagggc ctcaaaacta cctcggaact gctgcgctga tctggacacc acagaggttc   6420
cgagcacttt aggttgcacc aaatgtccca ccaggtgcag gcagaaaacg ctggaacagc   6480
gtgtacagtt tgtcttaaca aaaagtgagg gcgctgaggt cgagcagggt ggtgtgactt   6540
gttatagcct ttagagctgc gaaagcgcgt atggatttgg ctcatcaggc cagattgagg   6600
gtctgtggac acatgtcatg ttagtgtact tcaatcgccc cctggatata gccccgacaa   6660
```

taggccgtgg cctcattttt ttgccttccg cacatttcca ttgctcgata cccacacctt 6720
gcttctcctg cacttgccaa ccttaatact ggtttacatt gaccaacatc ttacaagcgg 6780
ggggcttgtc tagggtatat ataaacagtg gctctcccaa tcggttgcca gtctcttttt 6840
tcctttcttt ccccacagat tcgaaatcta aactacacat cacagaattc cgagccgtga 6900
gtatccacga caagatcagt gtcgagacga cgcgttttgt gtaatgacac aatccgaaag 6960
tcgctagcaa cacacactct ctacacaaac taacccagct ctggtaccat gatcacaagt 7020
ttgtacaaaa aagttggatt ttttttcgaa cacttaatgg aggtggtgaa tgaaatagtc 7080
tcaattgggc aggaagtttt acccaaagtt gattatgccc aactctggag tgatgccagt 7140
cactgtgagg tgctttactt gtccatcgca tttgtcatct tgaagttcac tcttggcccc 7200
cttggtccaa aaggtcagtc tcgtatgaag tttgttttca ccaattacaa ccttctcatg 7260
tccatttatt cgttgggatc attcctctca atggcatatg ccatgtacac catcggtgtt 7320
atgtctgaca actgcgagaa ggcttttgac aacaacgtct tcaggatcac cacgcagttg 7380
ttctatttga gcaagttcct ggagtatatt gactccttct atttgccact gatgggcaag 7440
cctctgacct ggttgcaatt cttccatcat ttgggggcac cgatggatat gtggctgttc 7500
tataattacc gaaatgaagc tgtttggatt tttgtgctgt tgaatggttt catccactgg 7560
atcatgtacg gttattattg gaccagattg atcaagctga agttccccat gccaaaatcc 7620
ctgattacat caatgcagat cattcaattc aatgttggtt tctacattgt ctggaagtac 7680
aggaacattc cctgttatcg ccaagatggg atgaggatgt ttggctggtt cttcaattac 7740
ttttatgttg gcacagtctt gtgtttgttc ttgaatttct atgtgcaaac gtatatcgtc 7800
aggaagcaca agggagccaa aaagattcag tgatatttcc tcctctgcgg tggcctcttt 7860
tgacctcccc ttgacaccta taatgtggag gtgtcgggct ctctccgtct caccagcact 7920
tgactctgca ggtgctcact tttatttttt acccatcttt gcttgttgac cattcacctc 7980
tcccacttcc acatagtcca ttctaactgt tgcagactgc ggtccatnnn ntccagagct 8040
cccaatgacc atacgcgaca ccnnntnnna nnncngccca ttgtgcacaa ttcatagtgg 8100
catcgttttg ccttgatacg tgtgcnnnnn nnnnnaccca acttt 8145

<210> SEQ ID NO 33
<211> LENGTH: 7877
<212> TYPE: DNA
<213> ORGANISM: Artificial Sequence
<220> FEATURE:
<223> OTHER INFORMATION: sequence of pBY-FAE

<400> SEQUENCE: 33
cttgtacaaa gtggtgatgg ccgcaagtgt ggatggggaa gtgagtgccc ggttctgtgt 60
gcacaattgg caatccaaga tggatggatt caacacaggg atatagcgag ctacgtggtg 120
gtgcgaggat atagcaacgg atatttatgt ttgacacttg agaatgtacg atacaagcac 180
tgtccaagta caatactaaa catactgtac atactcatac tcgtacccgg gcaacggttt 240
cacttgagtg cagtggctag tgctcttact cgtacagtgt gcaatactgc gtatcatagt 300
ctttgatgta tatcgtattc attcatgtta gttgcgtacg agccggaagc ataaagtgta 360
aagcctgggg tgcctaatga gtgagctaac tcacattaat tgcgttgcgc tcactgcccg 420
ctttccagtc gggaaacctg tcgtgccagc tgcattaatg aatcggccaa cgcgcgggga 480
gaggcggttt gcgtattggg cgctcttccg cttcctcgct cactgactcg ctgcgctcgg 540
tcgttcggct gcggcgagcg gtatcagctc actcaaaggc ggtaatacgg ttatccacag 600

-continued

```
aatcagggga taacgcagga aagaacatgt gagcaaaagg ccagcaaaag gccaggaacc    660
gtaaaaaggc cgcgttgctg gcgtttttcc ataggctccg cccccctgac gagcatcaca    720
aaaatcgacg ctcaagtcag aggtggcgaa acccgacagg actataaaga taccaggcgt    780
ttccccctgg aagctccctc gtgcgctctc ctgttccgac cctgccgctt accggatacc    840
tgtccgcctt tctcccttcg ggaagcgtgg cgctttctca tagctcacgc tgtaggtatc    900
tcagttcggt gtaggtcgtt cgctccaagc tgggctgtgt gcacgaaccc cccgttcagc    960
ccgaccgctg cgccttatcc ggtaactatc gtcttgagtc caacccggta agacacgact   1020
tatcgccact ggcagcagcc actggtaaca ggattagcag agcgaggtat gtaggcggtg   1080
ctacagagtt cttgaagtgg tggcctaact acggctacac tagaaggaca gtatttggta   1140
tctgcgctct gctgaagcca gttaccttcg gaaaaagagt tggtagctct tgatccggca   1200
aacaaaccac cgctggtagc ggtggttttt ttgtttgcaa gcagcagatt acgcgcagaa   1260
aaaaaggatc tcaagaagat cctttgatct tttctacggg gtctgacgct cagtggaacg   1320
aaaactcacg ttaagggatt ttggtcatga gattatcaaa aaggatcttc acctagatcc   1380
ttttaaatta aaaatgaagt tttaaatcaa tctaaagtat atatgagtaa acttggtctg   1440
acagttacca atgcttaatc agtgaggcac ctatctcagc gatctgtcta tttcgttcat   1500
ccatagttgc ctgactcccc gtcgtgtaga taactacgat acgggagggc ttaccatctg   1560
gccccagtgc tgcaatgata ccgcgagacc cacgctcacc ggctccagat ttatcagcaa   1620
taaaccagcc agccggaagg gccgagcgca gaagtggtcc tgcaacttta tccgcctcca   1680
tccagtctat taattgttgc cgggaagcta gagtaagtag ttcgccagtt aatagtttgc   1740
gcaacgttgt tgccattgct acaggcatcg tggtgtcacg ctcgtcgttt ggtatggctt   1800
cattcagctc cggttcccaa cgatcaaggc gagttacatg atcccccatg ttgtgcaaaa   1860
aagcggttag ctccttcggt cctccgatcg ttgtcagaag taagttggcc gcagtgttat   1920
cactcatggt tatggcagca ctgcataatt ctcttactgt catgccatcc gtaagatgct   1980
tttctgtgac tggtgagtac tcaaccaagt cattctgaga atagtgtatg cggcgaccga   2040
gttgctcttg cccggcgtca atacgggata ataccgcgcc acatagcaga actttaaaag   2100
tgctcatcat tggaaaacgt tcttcggggc gaaaactctc aaggatctta ccgctgttga   2160
gatccagttc gatgtaaccc actcgtgcac ccaactgatc ttcagcatct tttactttca   2220
ccagcgtttc tgggtgagca aaaacaggaa ggcaaaatgc cgcaaaaaag ggaataaggg   2280
cgacacggaa atgttgaata ctcatactct tcctttttca atattattga agcatttatc   2340
agggttattg tctcatgagc ggatacatat ttgaatgtat ttagaaaaat aaacaaatag   2400
gggttccgcg cacatttccc cgaaaagtgc cacctgacgc gccctgtagc ggcgcattaa   2460
gcgcggcggg tgtggtggtt acgcgcagcg tgaccgctac acttgccagc gccctagcgc   2520
ccgctccttt cgctttcttc ccttcctttc tcgccacgtt cgccggcttt ccccgtcaag   2580
ctctaaatcg ggggctccct ttagggttcc gatttagtgc tttacggcac ctcgacccca   2640
aaaaacttga ttagggtgat ggttcacgta gtgggccatc gccctgatag acggtttttc   2700
gccctttgac gttggagtcc acgttcttta atagtggact cttgttccaa actggaacaa   2760
cactcaaccc tatctcggtc tattcttttg atttataagg gattttgccg atttcggcct   2820
attggttaaa aaatgagctg atttaacaaa aatttaacgc gaattttaac aaaatattaa   2880
cgcttacaat ttccattcgc cattcaggct gcgcaactgt tgggaagggc gatcggtgcg   2940
```

-continued

```
ggcctcttcg ctattacgcc agctggcgaa agggggatgt gctgcaaggc gattaagttg   3000
ggtaacgcca gggttttccc agtcacgacg ttgtaaaacg acggccagtg aattgtaata   3060
cgactcacta tagggcgaat tgggtaccgg gccccccctc gaggtcgatg gtgtcgataa   3120
gcttgatatc gaattcatgt cacacaaacc gatcttcgcc tcaaggaaac ctaattctac   3180
atccgagaga ctgccgagat ccagtctaca ctgattaatt ttcgggccaa taatttaaaa   3240
aaatcgtgtt atataatatt atatgtatta tatatataca tcatgatgat actgacagtc   3300
atgtcccatt gctaaataga cagactccat ctgccgcctc caactgatgt tctcaatatt   3360
taaggggtca tctcgcattg tttaataata aacagactcc atctaccgcc tccaaatgat   3420
gttctcaaaa tatattgtat gaacttattt ttattactta gtattattag acaacttact   3480
tgctttatga aaaacacttc ctatttagga aacaatttat aatggcagtt cgttcattta   3540
acaatttatg tagaataaat gttataaatg cgtatgggaa atcttaaata tggatagcat   3600
aaatgatatc tgcattgcct aattcgaaat caacagcaac gaaaaaaatc ccttgtacaa   3660
cataaatagt catcgagaaa tatcaactat caaagaacag ctattcacac gttactattg   3720
agattattat tggacgagaa tcacacactc aactgtcttt ctctcttcta gaaatacagg   3780
tacaagtatg tactattctc attgttcata cttctagtca tttcatccca catattcctt   3840
ggatttctct ccaatgaatg acattctatc ttgcaaattc aacaattata ataagatata   3900
ccaaagtagc ggtatagtgg caatcaaaaa gcttctctgg tgtgcttctc gtatttattt   3960
ttattctaat gatccattaa aggtatatat ttatttcttg ttatataatc cttttgttta   4020
ttacatgggc tggatacata aaggtatttt gatttaattt tttgcttaaa ttcaatcccc   4080
cctcgttcag tgtcaactgt aatggtagga aattaccata cttttgaaga agcaaaaaaa   4140
atgaaagaaa aaaaaaatcg tatttccagg ttagacgttc cgcagaatct agaatgcggt   4200
atgcggtaca ttgttcttcg aacgtaaaag ttgcgctccc tgagatattg tacatttttg   4260
cttttacaag tacaagtaca tcgtacaact atgtactact gttgatgcat ccacaacagt   4320
ttgttttgtt tttttttgtt tttttttttt ctaatgattc attaccgcta tgtataccta   4380
cttgtacttg tagtaagccg ggttattggc gttcaattaa tcatagactt atgaatctgc   4440
acggtgtgcg ctgcgagtta cttttagctt atgcatgcta cttgggtgta atattgggat   4500
ctgttcggaa atcaacggat gctcaatcga tttcgacagt aattaattaa gtcatacaca   4560
agtcagcttt cttcgagcct catataagta taagtagttc aacgtattag cactgtaccc   4620
agcatctccg tatcgagaaa cacaacaaca tgccccattg gacagatcat gcggatacac   4680
aggttgtgca gtatcataca tactcgatca gacaggtcgt ctgaccatca tacaagctga   4740
acaagcgctc catacttgca cgctctctat atacacagtt aaattacata tccatagtct   4800
aacctctaac agttaatctt ctggtaagcc tcccagccag ccttctggta tcgcttggcc   4860
tcctcaatag gatctcggtt ctggccgtac agacctcggc cgacaattat gatatccgtt   4920
ccggtagaca tgacatcctc aacagttcgg tactgctgtc cgagagcgtc tcccttgtcg   4980
tcaagaccca ccccgggggt cagaataagc cagtcctcag agtcgccctt aggtcggttc   5040
tgggcaatga agccaaccac aaactcgggg tcggatcggg caagctcaat ggtctgcttg   5100
gagtactcgc cagtggccag agagcccttg caagacagct cggccagcat gagcagacct   5160
ctggccagct tctcgttggg agaggggact aggaactcct tgtactggga gttctcgtag   5220
tcagagacgt cctccttctt ctgttcagag acagtttcct cggcaccagc tcgcaggcca   5280
gcaatgattc cggttccggg tacaccgtgg gcgttggtga tatcggacca ctcggcgatt   5340
```

```
cggtgacacc ggtactggtg cttgacagtg ttgccaatat ctgcgaactt tctgtcctcg   5400
aacaggaaga aaccgtgctt aagagcaagt tccttgaggg ggagcacagt gccggcgtag   5460
gtgaagtcgt caatgatgtc gatatgggtt ttgatcatgc acacataagg tccgacctta   5520
tcggcaagct caatgagctc cttggtggtg gtaacatcca gagaagcaca caggttggtt   5580
ttcttggctg ccacgagctt gagcactcga gcggcaaagg cggacttgtg gacgttagct   5640
cgagcttcgt aggagggcat tttggtggtg aagaggagac tgaaataaat ttagtctgca   5700
gaacttttta tcggaacctt atctggggca gtgaagtata tgttatggta atagttacga   5760
gttagttgaa cttatagata gactggacta tacggctatc ggtccaaatt agaaagaacg   5820
tcaatggctc tctgggcgtc gcctttgccg acaaaaatgt gatcatgatg aaagccagca   5880
atgacgttgc agctgatatt gttgtcggcc aaccgcgccg aaaacgcagc tgtcagaccc   5940
acagcctcca acgaagaatg tatcgtcaaa gtgatccaag cacactcata gttggagtcg   6000
tactccaaag gcggcaatga cgagtcagac agatactcgt cgacgtttaa acagtgtacg   6060
cagatctact atagaggaac atttaaattg ccccggagaa gacggccagg ccgcctagat   6120
gacaaattca acaactcaca gctgactttc tgccattgcc actagggggg ggccttttta   6180
tatggccaag ccaagctctc cacgtcggtt gggctgcacc caacaataaa tgggtagggt   6240
tgcaccaaca aagggatggg atgggggta gaagatacga ggataacggg gctcaatggc   6300
acaaataaga acgaatactg ccattaagac tcgtgatcca gcgactgaca ccattgcatc   6360
atctaagggc ctcaaaacta cctcggaact gctgcgctga tctggacacc acagaggttc   6420
cgagcacttt aggttgcacc aaatgtccca ccaggtgcag gcagaaaacg ctggaacagc   6480
gtgtacagtt tgtcttaaca aaaagtgagg gcgctgaggt cgagcagggt ggtgtgactt   6540
gttatagcct ttagagctgc gaaagcgcgt atggatttgg ctcatcaggc cagattgagg   6600
gtctgtggac acatgtcatg ttagtgtact tcaatcgccc cctggatata gccccgacaa   6660
taggccgtgg cctcattttt ttgccttccg cacatttcca ttgctcgata cccacacctt   6720
gcttctcctg cacttgccaa ccttaatact ggtttacatt gaccaacatc ttacaagcgg   6780
ggggcttgtc tagggtatat ataaacagtg gctctcccaa tcggttgcca gtctcttttt   6840
tcctttcttt ccccacagat tcgaaatcta aactacacat cacagaattc cgagccgtga   6900
gtatccacga caagatcagt gtcgagacga cgcgttttgt gtaatgacac aatccgaaag   6960
tcgctagcaa cacacactct ctacacaaac taacccagct ctggtaccat gatcacaagt   7020
ttgtacaaaa aagcaggctc cgcggccgcc cccttcacca tggctctggc caacgacgct   7080
ggcgagcgaa tctgggctgc cgtcaccgat cccgaaatcc tcattggcac cttctcctac   7140
ctgctcctga agcctctcct gcgaaactct ggtctcgtgg acgagaagaa aggagcctac   7200
cgaacctcca tgatctggta caacgtcctc ctggctctct tctctgccct gtccttctac   7260
gtgactgcca ccgctctcgg ctgggactac ggtactggag cctggctgcg aagacagacc   7320
ggtgatactc cccagcctct ctttcagtgt ccctctcctg tctgggactc caagctgttc   7380
acctggactg ccaaggcctt ctactattct aagtacgtgg agtacctcga caccgcttgg   7440
ctggtcctca agggcaagcg agtgtccttt ctgcaggcct tccatcactt tggagctccc   7500
tgggacgtct acctcggcat tcgactgcac aacgagggtg tgtggatctt catgttcttt   7560
aactcgttca ttcacaccat catgtacacc tactatggac tgactgccgc tggctacaag   7620
ttcaaggcca agcctctgat cactgccatg cagatttgcc agttcgtcgg tggctttctc   7680
```

ctggtctggg actacatcaa cgttccctgc ttcaactctg acaagggcaa gctgttctcc 7740
tgggctttca actacgccta cgtcggatct gtctttctcc tgttctgtca cttcttttac 7800
caggacaacc tggccaccaa gaaatccgct aaggctggta agcagcttta gaagggtggg 7860
cgcgccgacc cagcttt 7877

<210> SEQ ID NO 34
<211> LENGTH: 7769
<212> TYPE: DNA
<213> ORGANISM: Artificial Sequence
<220> FEATURE:
<223> OTHER INFORMATION: the sequence of pY120

<400> SEQUENCE: 34
ggccgcaagt gtggatgggg aagtgagtgc ccggttctgt gtgcacaatt ggcaatccaa 60
gatggatgga ttcaacacag ggatatagcg agctacgtgg tggtgcgagg atatagcaac 120
ggatatttat gtttgacact tgagaatgta cgatacaagc actgtccaag tacaatacta 180
aacatactgt acatactcat actcgtaccc gggcaacggt ttcacttgag tgcagtggct 240
agtgctctta ctcgtacagt gtgcaatact gcgtatcata gtctttgatg tatatcgtat 300
tcattcatgt tagttgcgta cgagccggaa gcataaagtg taaagcctgg ggtgcctaat 360
gagtgagcta actcacatta attgcgttgc gctcactgcc cgctttccag tcgggaaacc 420
tgtcgtgcca gctgcattaa tgaatcggcc aacgcgcggg gagaggcggt ttgcgtattg 480
ggcgctcttc cgcttcctcg ctcactgact cgctgcgctc ggtcgttcgg ctgcggcgag 540
cggtatcagc tcactcaaag gcggtaatac ggttatccac agaatcaggg gataacgcag 600
gaaagaacat gtgagcaaaa ggccagcaaa aggccaggaa ccgtaaaaag gccgcgttgc 660
tggcgttttt ccataggctc cgcccccctg acgagcatca caaaaatcga cgctcaagtc 720
agaggtggcg aaacccgaca ggactataaa gataccaggc gtttccccct ggaagctccc 780
tcgtgcgctc tcctgttccg accctgccgc ttaccggata cctgtccgcc tttctccctt 840
cgggaagcgt ggcgctttct catagctcac gctgtaggta tctcagttcg gtgtaggtcg 900
ttcgctccaa gctgggctgt gtgcacgaac cccccgttca gcccgaccgc tgcgccttat 960
ccggtaacta tcgtcttgag tccaacccgg taagacacga cttatcgcca ctggcagcag 1020
ccactggtaa caggattagc agagcgaggt atgtaggcgg tgctacagag ttcttgaagt 1080
ggtggcctaa ctacggctac actagaagga cagtatttgg tatctgcgct ctgctgaagc 1140
cagttacctt cggaaaaaga gttggtagct cttgatccgg caaacaaacc accgctggta 1200
gcggtggttt ttttgtttgc aagcagcaga ttacgcgcag aaaaaaagga tctcaagaag 1260
atcctttgat cttttctacg gggtctgacg ctcagtggaa cgaaaactca cgttaaggga 1320
ttttggtcat gagattatca aaaaggatct tcacctagat ccttttaaat taaaaatgaa 1380
gttttaaatc aatctaaagt atatatgagt aaacttggtc tgacagttac caatgcttaa 1440
tcagtgaggc acctatctca gcgatctgtc tatttcgttc atccatagtt gcctgactcc 1500
ccgtcgtgta gataactacg atacgggagg gcttaccatc tggccccagt gctgcaatga 1560
taccgcgaga cccacgctca ccggctccag atttatcagc aataaaccag ccagccggaa 1620
gggccgagcg cagaagtggt cctgcaactt tatccgcctc catccagtct attaattgtt 1680
gccgggaagc tagagtaagt agttcgccag ttaatagttt gcgcaacgtt gttgccattg 1740
ctacaggcat cgtggtgtca cgctcgtcgt ttggtatggc ttcattcagc tccggttccc 1800
aacgatcaag gcgagttaca tgatccccca tgttgtgcaa aaaagcggtt agctccttcg 1860

```
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttccttttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgccctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca agctctaaat cgggggctcc   2580
ctttagggtt ccgatttagt gctttacggc acctcgaccc caaaaaactt gattagggtg   2640
atggttcacg tagtgggcca tcgccctgat agacggtttt tcgccctttg acgttggagt   2700
ccacgttctt taatagtgga ctcttgttcc aaactggaac aacactcaac cctatctcgg   2760
tctattcttt tgatttataa gggattttgc cgatttcggc ctattggtta aaaaatgagc   2820
tgatttaaca aaaatttaac gcgaatttta acaaaatatt aacgcttaca atttccattc   2880
gccattcagg ctgcgcaact gttgggaagg gcgatcggtg cgggcctctt cgctattacg   2940
ccagctggcg aaagggggat gtgctgcaag gcgattaagt tgggtaacgc cagggttttc   3000
ccagtcacga cgttgtaaaa cgacggccag tgaattgtaa tacgactcac tatagggcga   3060
attgggtacc gggccccccc tcgaggtcga tggtgtcgat aagcttgata tcgaattcat   3120
gtcacacaaa ccgatcttcg cctcaaggaa acctaattct acatccgaga gactgccgag   3180
atccagtcta cactgattaa ttttcgggcc aataatttaa aaaaatcgtg ttatataata   3240
ttatatgtat tatatatata catcatgatg atactgacag tcatgtccca ttgctaaata   3300
gacagactcc atctgccgcc tccaactgat gttctcaata tttaaggggt catctcgcat   3360
tgtttaataa taaacagact ccatctaccg cctccaaatg atgttctcaa aatatattgt   3420
atgaacttat ttttattact tagtattatt agacaactta cttgctttat gaaaaacact   3480
tcctatttag gaaacaattt ataatggcag ttcgttcatt taacaattta tgtagaataa   3540
atgttataaa tgcgtatggg aaatcttaaa tatggatagc ataaatgata tctgcattgc   3600
ctaattcgaa atcaacagca acgaaaaaaa tcccttgtac aacataaata gtcatcgaga   3660
aatatcaact atcaaagaac agctattcac acgttactat tgagattatt attggacgag   3720
aatcacacac tcaactgtct ttctctcttc tagaaataca ggtacaagta tgtactattc   3780
tcattgttca tacttctagt catttcatcc cacatattcc ttggatttct ctccaatgaa   3840
tgacattcta tcttgcaaat tcaacaatta taataagata taccaaagta gcggtatagt   3900
ggcaatcaaa aagcttctct ggtgtgcttc tcgtatttat ttttattcta atgatccatt   3960
aaaggtatat atttatttct tgttatataa tccttttgtt tattacatgg gctggataca   4020
taaaggtatt ttgatttaat tttttgctta aattcaatcc cccctcgttc agtgtcaact   4080
gtaatggtag gaaattacca tacttttgaa gaagcaaaaa aaatgaaaga aaaaaaaaat   4140
cgtatttcca ggttagacgt tccgcagaat ctagaatgcg gtatgcggta cattgttctt   4200
```

```
cgaacgtaaa agttgcgctc cctgagatat tgtacatttt tgcttttaca agtacaagta   4260
catcgtacaa ctatgtacta ctgttgatgc atccacaaca gtttgttttg tttttttttg   4320
tttttttttt ttctaatgat tcattaccgc tatgtatacc tacttgtact tgtagtaagc   4380
cgggttattg gcgttcaatt aatcatagac ttatgaatct gcacggtgtg cgctgcgagt   4440
tacttttagc ttatgcatgc tacttgggtg taatattggg atctgttcgg aaatcaacgg   4500
atgctcaatc gatttcgaca gtaattaatt aagtcataca caagtcagct ttcttcgagc   4560
ctcatataag tataagtagt tcaacgtatt agcactgtac ccagcatctc cgtatcgaga   4620
aacacaacaa catgccccat tggacagatc atgcggatac acaggttgtg cagtatcata   4680
catactcgat cagacaggtc gtctgaccat catacaagct gaacaagcgc tccatacttg   4740
cacgctctct atatacacag ttaaattaca tatccatagt ctaacctcta acagttaatc   4800
ttctggtaag cctcccagcc agccttctgg tatcgcttgg cctcctcaat aggatctcgg   4860
ttctggccgt acagacctcg gccgacaatt atgatatccg ttccggtaga catgacatcc   4920
tcaacagttc ggtactgctg tccgagagcg tctcccttgt cgtcaagacc caccccgggg   4980
gtcagaataa gccagtcctc agagtcgccc ttaggtcggt tctgggcaat gaagccaacc   5040
acaaactcgg ggtcggatcg ggcaagctca atggtctgct tggagtactc gccagtggcc   5100
agagagccct tgcaagacag ctcggccagc atgagcagac ctctggccag cttctcgttg   5160
ggagagggga ctaggaactc cttgtactgg gagttctcgt agtcagagac gtcctccttc   5220
ttctgttcag agacagtttc ctcggcacca gctcgcaggc cagcaatgat tccggttccg   5280
ggtacaccgt gggcgttggt gatatcggac cactcggcga ttcggtgaca ccggtactgg   5340
tgcttgacag tgttgccaat atctgcgaac tttctgtcct cgaacaggaa gaaaccgtgc   5400
ttaagagcaa gttccttgag ggggagcaca gtgccggcgt aggtgaagtc gtcaatgatg   5460
tcgatatggg ttttgatcat gcacacataa ggtccgacct tatcggcaag ctcaatgagc   5520
tccttggtgg tggtaacatc cagagaagca cacaggttgg ttttcttggc tgccacgagc   5580
ttgagcactc gagcggcaaa ggcggacttg tggacgttag ctcgagcttc gtaggagggc   5640
attttggtgg tgaagaggag actgaaataa atttagtctg cagaactttt tatcggaacc   5700
ttatctgggg cagtgaagta tatgttatgg taatagttac gagttagttg aacttataga   5760
tagactggac tatacggcta tcggtccaaa ttagaaagaa cgtcaatggc tctctgggcg   5820
tcgcctttgc cgacaaaaat gtgatcatga tgaaagccag caatgacgtt gcagctgata   5880
ttgttgtcgg ccaaccgcgc cgaaaacgca gctgtcagac ccacagcctc caacgaagaa   5940
tgtatcgtca aagtgatcca agcacactca tagttggagt cgtactccaa aggcggcaat   6000
gacgagtcag acagatactc gtcgacgttt aaacagtgta cgcagatcta ctatagagga   6060
acatttaaat tgccccggag aagacggcca ggccgcctag atgacaaatt caacaactca   6120
cagctgactt tctgccattg ccactagggg ggggcctttt tatatggcca agccaagctc   6180
tccacgtcgg ttgggctgca cccaacaata aatgggtagg gttgcaccaa caaagggatg   6240
ggatgggggg tagaagatac gaggataacg gggctcaatg gcacaaataa gaacgaatac   6300
tgccattaag actcgtgatc cagcgactga caccattgca tcatctaagg gcctcaaaac   6360
tacctcggaa ctgctgcgct gatctggaca ccacagaggt tccgagcact ttaggttgca   6420
ccaaatgtcc caccaggtgc aggcagaaaa cgctggaaca gcgtgtacag tttgtcttaa   6480
caaaaagtga gggcgctgag gtcgagcagg gtggtgtgac ttgttatagc ctttagagct   6540
gcgaaagcgc gtatggattt ggctcatcag gccagattga gggtctgtgg acacatgtca   6600
```

```
tgttagtgta cttcaatcgc cccctggata tagccccgac aataggccgt ggcctcattt   6660

ttttgccttc cgcacatttc cattgctcga tacccacacc ttgcttctcc tgcacttgcc   6720

aaccttaata ctggtttaca ttgaccaaca tcttacaagc ggggggcttg tctagggtat   6780

atataaacag tggctctccc aatcggttgc cagtctcttt tttcctttct ttccccacag   6840

attcgaaatc taaactacac atcacagaat tccgagccgt gagtatccac gacaagatca   6900

gtgtcgagac gacgcgtttt gtgtaatgac acaatccgaa agtcgctagc aacacacact   6960

ctctacacaa actaacccag ctctggtacc atggaggtgg tgaatgaaat agtctcaatt   7020

gggcaggaag ttttacccaa agttgattat gcccaactct ggagtgatgc cagtcactgt   7080

gaggtgcttt acttgtccat cgcatttgtc atcttgaagt tcactcttgg ccccccttggt   7140

ccaaaaggtc agtctcgtat gaagtttgtt ttcaccaatt acaaccttct catgtccatt   7200

tattcgttgg gatcattcct ctcaatggca tatgccatgt acaccatcgg tgttatgtct   7260

gacaactgcg agaaggcttt tgacaacaac gtcttcagga tcaccacgca gttgttctat   7320

ttgagcaagt tcctggagta tattgactcc ttctatttgc cactgatggg caagcctctg   7380

acctggttgc aattcttcca tcatttgggg gcaccgatgg atatgtggct gttctataat   7440

taccgaaatg aagctgtttg gatttttgtg ctgttgaatg gtttcatcca ctggatcatg   7500

tacggttatt attggaccag attgatcaag ctgaagttcc ccatgccaaa atccctgatt   7560

acatcaatgc agatcattca attcaatgtt ggtttctaca ttgtctggaa gtacaggaac   7620

attccctgtt atcgccaaga tgggatgagg atgtttggct ggttcttcaa ttacttttat   7680

gttggcacag tcttgtgttt gttcttgaat ttctatgtgc aaacgtatat cgtcaggaag   7740

cacaagggag ccaaaaagat tcagtgagc                                      7769
```

<210> SEQ ID NO 35
<211> LENGTH: 8306
<212> TYPE: DNA
<213> ORGANISM: Artificial Sequence
<220> FEATURE:
<223> OTHER INFORMATION: the sequence of pY119

<400> SEQUENCE: 35

```
ggccgcaggg cggatccccc gggctgcagg aattcgatat caagcttatc gataccgtcg     60

acctcgaggg ggggcccggt acccaattcg ccctatagtg agtcgtatta cgcgcgctca    120

ctggccgtcg ttttacaacg tcgtgactgg gaaaaccctg gcgttaccca acttaatcgc    180

cttgcagcac atcccccttt cgccagctgg cgtaatagcg aagaggcccg caccgatcgc    240

ccttcccaac agttgcgcag cctgaatggc gaatggcgcg acgcgccctg tagcggcgca    300

ttaagcgcgg cgggtgtggt ggttacgcgc agcgtgaccg ctacacttgc cagcgcccta    360

gcgcccgctc ctttcgcttt cttcccttcc tttctcgcca cgttcgccgg ctttccccgt    420

caagctctaa atcgggggct ccctttaggg ttccgattta gtgctttacg gcacctcgac    480

cccaaaaaac ttgattaggg tgatggttca cgtagtgggc catcgccctg atagacggtt    540

tttcgccctt tgacgttgga gtccacgttc tttaatagtg gactcttgtt ccaaactgga    600

acaacactca accctatctc ggtctattct tttgatttat aagggatttt gccgatttcg    660

gcctattggt taaaaaatga gctgatttaa caaaaattta acgcgaattt taacaaaata    720

ttaacgttta caatttcctg atgcggtatt ttctccttac gcatctgtgc ggtatttcac    780

accgcatatc gacggtcgag gagaacttct agtatatcca catacctaat attattgcct    840
```

```
tattaaaaat ggaatcccaa caattacatc aaaatccaca ttctcttcaa aatcaattgt     900
cctgtacttc cttgttcatg tgtgttcaaa aacgttatat ttataggata attatactct     960
atttctcaac aagtaattgg ttgtttggcc gagcggtcta aggcgcctga ttcaagaaat    1020
atcttgaccg cagttaactg tgggaatact caggtatcgt aagatgcaag agttcgaatc    1080
tcttagcaac cattattttt ttcctcaaca taacgagaac acacaggggc gctatcgcac    1140
agaatcaaat tcgatgactg gaaatttttt gttaatttca gaggtcgcct gacgcatata    1200
ccttttttcaa ctgaaaaatt gggagaaaaa ggaaaggtga gaggccggaa ccggcttttc   1260
atatagaata gagaagcgtt catgactaaa tgcttgcatc acaatacttg aagttgacaa    1320
tattatttaa ggacctattg ttttttccaa taggtggtta gcaatcgtct tactttctaa    1380
cttttcttac cttttacatt tcagcaatat atatatatat ttcaaggata taccattcta    1440
atgtctgccc ctatgtctgc ccctaagaag atcgtcgttt tgccaggtga ccacgttggt    1500
caagaaatca cagccgaagc cattaaggtt cttaaagcta tttctgatgt tcgttccaat    1560
gtcaagttcg atttcgaaaa tcatttaatt ggtggtgctg ctatcgatgc tacaggtgtc    1620
ccacttccag atgaggcgct ggaagcctcc aagaaggttg atgccgtttt gttaggtgct    1680
gtggctggtc ctaaatgggg taccggtagt gttagacctg aacaaggttt actaaaaatc    1740
cgtaaagaac ttcaattgta cgccaactta agaccatgta actttgcatc cgactctctt    1800
ttagacttat ctccaatcaa gccacaattt gctaaaggta ctgacttcgt tgttgtcaga    1860
gaattagtgg gaggtattta ctttggtaag agaaaggaag acgatggtga tggtgtcgct    1920
tgggatagtg aacaatacac cgttccagaa gtgcaaagaa tcacaagaat ggccgctttc    1980
atggccctac aacatgagcc accattgcct atttggtcct tggataaagc taatcttttg    2040
gcctcttcaa gattatggag aaaaactgtg gaggaaacca tcaagaacga attccctaca    2100
ttgaaggttc aacatcaatt gattgattct gccgccatga tcctagttaa gaacccaacc    2160
cacctaaatg gtattataat caccagcaac atgtttggtg atatcatctc cgatgaagcc    2220
tccgttatcc caggttcctt gggtttgttg ccatctgcgt ccttggcctc tttgccagac    2280
aagaacaccg catttggttt gtacgaacca tgccacggtt ctgctccaga tttgccaaag    2340
aataaggttg accctatcgc cactatcttg tctgctgcaa tgatgttgaa attgtcattg    2400
aacttgcctg aagaaggtaa ggccattgaa gatgcagtta aaaaggtttt ggatgcaggt    2460
atcagaactg gtgatttagg tggttccaac agtaccaccg aagtcggtga tgctgtcgcc    2520
gaagaagtta agaaaatcct tgcttaaaaa gattctcttt ttttatgata tttgtacata    2580
aactttataa atgaaattca taatagaaac gacacgaaat tacaaaatgg aatatgttca    2640
tagggtagac gaaactatat acgcaatcta catacattta tcaagaagga gaaaaaggag    2700
gatagtaaag gaatacaggt aagcaaattg atactaatgg ctcaacgtga taaggaaaaa    2760
gaattgcact ttaacattaa tattgacaag gaggagggca ccacacaaaa agttaggtgt    2820
aacagaaaat catgaaacta cgattcctaa tttgatattg gaggattttc tctaaaaaaa    2880
aaaaaataca acaaataaaa aacactcaat gacctgacca tttgatggag tttaagtcaa    2940
taccttcttg aagcatttcc cataatggtg aaagttccct caagaatttt actctgtcag    3000
aaacggcctt acgacgtagt cgatatggtg cactctcagt acaatctgct ctgatgccgc    3060
atagttaagc cagccccgac acccgccaac acccgctgac gcgccctgac gggcttgtct    3120
gctcccggca tccgcttaca gacaagctgt gaccgtctcc gggagctgca tgtgtcagag    3180
gttttcaccg tcatcaccga aacgcgcgag acgaaagggc ctcgtgatac gcctattttt    3240
```

ataggttaat gtcatgataa taatggtttc ttagtatgat ccaatatcaa aggaaatgat 3300
agcattgaag gatgagacta atccaattga ggagtggcag catatagaac agctaaaggg 3360
tagtgctgaa ggaagcatac gataccccgc atggaatggg ataatatcac aggaggtact 3420
agactacctt tcatcctaca taaatagacg catataagta cgcatttaag cataaacacg 3480
cactatgccg ttcttctcat gtatatatat atacaggcaa cacgcagata taggtgcgac 3540
gtgaacagtg agctgtatgt gcgcagctcg cgttgcattt tcggaagcgc tcgttttcgg 3600
aaacgctttg aagttcctat tccgaagttc ctattctcta gaaagtatag gaacttcaga 3660
gcgcttttga aaaccaaaag cgctctgaag acgcactttc aaaaaaccaa aaacgcaccg 3720
gactgtaacg agctactaaa atattgcgaa taccgcttcc acaaacattg ctcaaaagta 3780
tctctttgct atatatctct gtgctatatc cctatataac ctacccatcc acctttcgct 3840
ccttgaactt gcatctaaac tcgacctcta catttttat gtttatctct agtattactc 3900
tttagacaaa aaaattgtag taagaactat tcatagagtg aatcgaaaac aatacgaaaa 3960
tgtaaacatt tcctatacgt agtatataga gacaaaatag aagaaaccgt tcataatttt 4020
ctgaccaatg aagaatcatc aacgctatca ctttctgttc acaaagtatg cgcaatccac 4080
atcggtatag aatataatcg gggatgcctt tatcttgaaa aaatgcaccc gcagcttcgc 4140
tagtaatcag taaacgcggg aagtggagtc aggctttttt tatggaagag aaaatagaca 4200
ccaaagtagc cttcttctaa ccttaacgga cctacagtgc aaaaagttat caagagactg 4260
cattatagag cgcacaaagg agaaaaaaag taatctaaga tgctttgtta gaaaaatagc 4320
gctctcggga tgcatttttg tagaacaaaa aagaagtata gattctttgt tggtaaaata 4380
gcgctctcgc gttgcatttc tgttctgtaa aaatgcagct cagattcttt gtttgaaaaa 4440
ttagcgctct cgcgttgcat ttttgtttta caaaaatgaa gcacagattc ttcgttggta 4500
aaatagcgct ttcgcgttgc atttctgttc tgtaaaaatg cagctcagat tctttgtttg 4560
aaaaattagc gctctcgcgt tgcatttttg ttctacaaaa tgaagcacag atgcttcgtt 4620
caggtggcac ttttcgggga aatgtgcgcg gaacccctat ttgtttattt ttctaaatac 4680
attcaaatat gtatccgctc atgagacaat aaccctgata aatgcttcaa taatattgaa 4740
aaaggaagag tatgagtatt caacatttcc gtgtcgccct tattcccttt tttgcggcat 4800
tttgccttcc tgtttttgct cacccagaaa cgctggtgaa agtaaaagat gctgaagatc 4860
agttgggtgc acgagtgggt tacatcgaac tggatctcaa cagcggtaag atccttgaga 4920
gttttcgccc cgaagaacgt tttccaatga tgagcacttt taaagttctg ctatgtggcg 4980
cggtattatc ccgtattgac gccgggcaag agcaactcgg tcgccgcata cactattctc 5040
agaatgactt ggttgagtac tcaccagtca cagaaaagca tcttacggat ggcatgacag 5100
taagagaatt atgcagtgct gccataacca tgagtgataa cactgcggcc aacttacttc 5160
tgacaacgat cggaggaccg aaggagctaa ccgctttttt gcacaacatg ggggatcatg 5220
taactcgcct tgatcgttgg gaaccggagc tgaatgaagc cataccaaac gacgagcgtg 5280
acaccacgat gcctgtagca atggcaacaa cgttgcgcaa actattaact ggcgaactac 5340
ttactctagc ttcccggcaa caattaatag actggatgga ggcggataaa gttgcaggac 5400
cacttctgcg ctcggccctt ccggctggct ggtttattgc tgataaatct ggagccggtg 5460
agcgtgggtc tcgcggtatc attgcagcac tggggccaga tggtaagccc tcccgtatcg 5520
tagttatcta cacgacgggg agtcaggcaa ctatggatga acgaaataga cagatcgctg 5580

-continued

```
agataggtgc ctcactgatt aagcattggt aactgtcaga ccaagtttac tcatatatac   5640
tttagattga tttaaaactt catttttaat ttaaaaggat ctaggtgaag atcctttttg   5700
ataatctcat gaccaaaatc ccttaacgtg agttttcgtt ccactgagcg tcagaccccg   5760
tagaaaagat caaaggatct tcttgagatc ctttttttct gcgcgtaatc tgctgcttgc   5820
aaacaaaaaa accaccgcta ccagcggtgg tttgtttgcc ggatcaagag ctaccaactc   5880
tttttccgaa ggtaactggc ttcagcagag cgcagatacc aaatactgtc cttctagtgt   5940
agccgtagtt aggccaccac ttcaagaact ctgtagcacc gcctacatac ctcgctctgc   6000
taatcctgtt accagtggct gctgccagtg gcgataagtc gtgtcttacc gggttggact   6060
caagacgata gttaccggat aaggcgcagc ggtcgggctg aacggggggt tcgtgcacac   6120
agcccagctt ggagcgaacg acctacaccg aactgagata cctacagcgt gagctatgag   6180
aaagcgccac gcttcccgaa gggagaaagg cggacaggta tccggtaagc ggcagggtcg   6240
gaacaggaga gcgcacgagg gagcttccag ggggaaacgc ctggtatctt tatagtcctg   6300
tcgggtttcg ccacctctga cttgagcgtc gatttttgtg atgctcgtca ggggggcgga   6360
gcctatggaa aaacgccagc aacgcggcct ttttacggtt cctggccttt tgctggcctt   6420
ttgctcacat gttctttcct gcgttatccc ctgattctgt ggataaccgt attaccgcct   6480
ttgagtgagc tgataccgct cgccgcagcc gaacgaccga gcgcagcgag tcagtgagcg   6540
aggaagcgga agagcgccca atacgcaaac cgcctctccc cgcgcgttgg ccgattcatt   6600
aatgcagctg gcacgacagg tttcccgact ggaaagcggg cagtgagcgc aacgcaatta   6660
atgtgagtta cctcactcat taggcacccc aggctttaca ctttatgctt ccggctccta   6720
tgttgtgtgg aattgtgagc ggataacaat ttcacacagg aaacagctat gaccatgatt   6780
acgccaagcg cgcaattaac cctcactaaa gggaacaaaa gctggagctc caccgcggga   6840
tttcgaaact aagttcttgg tgttttaaaa ctaaaaaaaa gactaactat aaaagtagaa   6900
tttaagaagt ttaagaaata gatttacaga attacaatca atacctaccg tctttatata   6960
cttattagtc aagtagggga ataatttcag ggaactggtt tcaacctttt ttttcagctt   7020
tttccaaatc agagagagca gaaggtaata gaaggtgtaa gaaaatgaga tagatacatg   7080
cgtgggtcaa ttgccttgtg tcatcattta ctccaggcag gttgcatcac tccattgagg   7140
ttgtgcccgt tttttgcctg tttgtgcccc tgttctctgt agttgcgcta agagaatgga   7200
cctatgaact gatggttggt gaagaaaaca atattttggt gctgggattc ttttttttc   7260
tggatgccag cttaaaaagc gggctccatt atatttagtg gatgccagga ataaactgtt   7320
cacccagaca cctacgatgt tatatattct gtgtaacccg ccccctattt tgggcatgta   7380
cgggttacag cagaattaaa aggctaattt tttgactaaa taaagttagg aaaatcacta   7440
ctattaatta tttacgtatt ctttgaaatg gcagtattga taatgataaa ctcgaaatca   7500
ctagtggatc cgcccagcgg ccgcaccatg gaggtggtga atgaaatagt ctcaattggg   7560
caggaagttt tacccaaagt tgattatgcc caactctgga gtgatgccag tcactgtgag   7620
gtgctttact tgtccatcgc atttgtcatc ttgaagttca ctcttggccc ccttggtcca   7680
aaaggtcagt ctcgtatgaa gtttgttttc accaattaca accttctcat gtccatttat   7740
tcgttgggat cattcctctc aatggcatat gccatgtaca ccatcggtgt tatgtctgac   7800
aactgcgaga aggcttttga caacaacgtc ttcaggatca ccacgcagtt gttctatttg   7860
agcaagttcc tggagtatat tgactccttc tatttgccac tgatgggcaa gcctctgacc   7920
tggttgcaat tcttccatca tttgggggca ccgatggata tgtggctgtt ctataattac   7980
```

cgaaatgaag ctgtttggat ttttgtgctg ttgaatggtt tcatccactg gatcatgtac 8040
ggttattatt ggaccagatt gatcaagctg aagttcccca tgccaaaatc cctgattaca 8100
tcaatgcaga tcattcaatt caatgttggt ttctacattg tctggaagta caggaacatt 8160
ccctgttatc gccaagatgg gatgaggatg tttggctggt tcttcaatta cttttatgtt 8220
ggcacagtct tgtgtttgtt cttgaatttc tatgtgcaaa cgtatatcgt caggaagcac 8280
aagggagcca aaaagattca gtgagc 8306

<210> SEQ ID NO 36
<211> LENGTH: 7085
<212> TYPE: DNA
<213> ORGANISM: Artificial Sequence
<220> FEATURE:
<223> OTHER INFORMATION: the sequence of pKR72

<400> SEQUENCE: 36
gtacggatcc gtcgacggcg cgcccgatca tccggatata gttcctcctt tcagcaaaaa 60
acccctcaag acccgtttag aggccccaag gggttatgct agttattgct cagcggtggc 120
agcagccaac tcagcttcct ttcgggcttt gttagcagcc ggatcgatcc aagctgtacc 180
tcactattcc tttgccctcg gacgagtgct ggggcgtcgg tttccactat cggcgagtac 240
ttctacacag ccatcggtcc agacggccgc gcttctgcgg gcgatttgtg tacgcccgac 300
agtcccggct ccggatcgga cgattgcgtc gcatcgaccc tgcgcccaag ctgcatcatc 360
gaaattgccg tcaaccaagc tctgatagag ttggtcaaga ccaatgcgga gcatatacgc 420
ccggagccgc ggcgatcctg caagctccgg atgcctccgc tcgaagtagc gcgtctgctg 480
ctccatacaa gccaaccacg gcctccagaa gaagatgttg gcgacctcgt attgggaatc 540
cccgaacatc gcctcgctcc agtcaatgac cgctgttatg cggccattgt ccgtcaggac 600
attgttggag ccgaaatccg cgtgcacgag gtgccggact tcggggcagt cctcggccca 660
aagcatcagc tcatcgagag cctgcgcgac ggacgcactg acggtgtcgt ccatcacagt 720
ttgccagtga tacacatggg gatcagcaat cgcgcatatg aaatcacgcc atgtagtgta 780
ttgaccgatt ccttgcggtc cgaatgggcc gaacccgctc gtctggctaa gatcggccgc 840
agcgatcgca tccatagcct ccgcgaccgg ctgcagaaca gcgggcagtt cggtttcagg 900
caggtcttgc aacgtgacac cctgtgcacg gcgggagatg caataggtca ggctctcgct 960
gaattcccca atgtcaagca cttccggaat cgggagcgcg gccgatgcaa agtgccgata 1020
aacataacga tctttgtaga aaccatcggc gcagctattt acccgcagga catatccacg 1080
ccctcctaca tcgaagctga aagcacgaga ttcttcgccc tccgagagct gcatcaggtc 1140
ggagacgctg tcgaactttt cgatcagaaa cttctcgaca gacgtcgcgg tgagttcagg 1200
cttttccatg ggtatatctc cttcttaaag ttaaacaaaa ttatttctag agggaaaccg 1260
ttgtggtctc cctatagtga gtcgtattaa tttcgcggga tcgagatcga tccaattcca 1320
atcccacaaa aatctgagct taacagcaca gttgctcctc tcagagcaga atcgggtatt 1380
caacaccctc atatcaacta ctacgttgtg tataacggtc cacatgccgg tatatacgat 1440
gactggggtt gtacaaaggc ggcaacaaac ggcgttcccg gagttgcaca caagaaattt 1500
gccactatta cagaggcaag agcagcagct gacgcgtaca caacaagtca gcaaacagac 1560
aggttgaact tcatccccaa aggagaagct caactcaagc ccaagagctt tgctaaggcc 1620
ctaacaagcc caccaaagca aaaagcccac tggctcacgc taggaaccaa aaggcccagc 1680

-continued

```
agtgatccag ccccaaaaga gatctccttt gccccggaga ttacaatgga cgatttcctc   1740
tatctttacg atctaggaag gaagttcgaa ggtgaaggtg acgacactat gttcaccact   1800
gataatgaga aggttagcct cttcaatttc agaaagaatg ctgacccaca gatggttaga   1860
gaggcctacg cagcaggtct catcaagacg atctacccga gtaacaatct ccaggagatc   1920
aaataccttc ccaagaaggt taaagatgca gtcaaaagat tcaggactaa ttgcatcaag   1980
aacacagaga aagacatatt tctcaagatc agaagtacta ttccagtatg gacgattcaa   2040
ggcttgcttc ataaaccaag gcaagtaata gagattggag tctctaaaaa ggtagttcct   2100
actgaatcta aggccatgca tggagtctaa gattcaaatc gaggatctaa cagaactcgc   2160
cgtgaagact ggcgaacagt tcatacagag tcttttacga ctcaatgaca agaagaaaat   2220
cttcgtcaac atggtggagc acgacactct ggtctactcc aaaaatgtca aagatacagt   2280
ctcagaagac caaagggcta ttgagacttt tcaacaaagg ataatttcgg gaaacctcct   2340
cggattccat tgcccagcta tctgtcactt catcgaaagg acagtagaaa aggaaggtgg   2400
ctcctacaaa tgccatcatt gcgataaagg aaaggctatc attcaagatg cctctgccga   2460
cagtggtccc aaagatggac ccccacccac gaggagcatc gtggaaaaag aagacgttcc   2520
aaccacgtct tcaaagcaag tggattgatg tgacatctcc actgacgtaa gggatgacgc   2580
acaatcccac tatccttcgc aagacccttc ctctatataa ggaagttcat ttcatttgga   2640
gaggacacgc tcgagctcat ttctctatta cttcagccat aacaaaagaa ctcttttctc   2700
ttcttattaa accatgaaaa agcctgaact caccgcgacg tctgtcgaga agtttctgat   2760
cgaaaagttc gacagcgtct ccgacctgat gcagctctcg gagggcgaag aatctcgtgc   2820
tttcagcttc gatgtaggag ggcgtggata tgtcctgcgg gtaaatagct gcgccgatgg   2880
tttctacaaa gatcgttatg tttatcggca ctttgcatcg gccgcgctcc cgattccgga   2940
agtgcttgac attggggaat tcagcgagag cctgacctat tgcatctccc gccgtgcaca   3000
gggtgtcacg ttgcaagacc tgcctgaaac cgaactgccc gctgttctgc agccggtcgc   3060
ggaggccatg gatgcgatcg ctgcggccga tcttagccag acgagcgggt tcggcccatt   3120
cggaccgcaa ggaatcggtc aatacactac atggcgtgat ttcatatgcg cgattgctga   3180
tccccatgtg tatcactggc aaactgtgat ggacgacacc gtcagtgcgt ccgtcgcgca   3240
ggctctcgat gagctgatgc tttgggccga ggactgcccc gaagtccggc acctcgtgca   3300
cgcggatttc ggctccaaca atgtcctgac ggacaatggc cgcataacag cggtcattga   3360
ctggagcgag gcgatgttcg gggattccca atacgaggtc gccaacatct tcttctggag   3420
gccgtggttg gcttgtatgg agcagcagac gcgctacttc gagcggaggc atccggagct   3480
tgcaggatcg ccgcggctcc gggcgtatat gctccgcatt ggtcttgacc aactctatca   3540
gagcttggtt gacggcaatt tcgatgatgc agcttgggcg cagggtcgat gcgacgcaat   3600
cgtccgatcc ggagccggga ctgtcgggcg tacacaaatc gcccgcagaa gcgcggccgt   3660
ctggaccgat ggctgtgtag aagtactcgc cgatagtgga aaccgacgcc ccagcactcg   3720
tccgagggca aaggaatagt gaggtaccta aagaaggagt gcgtcgaagc agatcgttca   3780
aacatttggc aataaagttt cttaagattg aatcctgttg ccggtcttgc gatgattatc   3840
atataatttc tgttgaatta cgttaagcat gtaataatta acatgtaatg catgacgtta   3900
tttatgagat gggtttttat gattagagtc ccgcaattat acatttaata cgcgatagaa   3960
aacaaaatat agcgcgcaaa ctaggataaa ttatcgcgcg cggtgtcatc tatgttacta   4020
gatcgatgtc gaatcgatca acctgcatta atgaatcggc caacgcgcgg ggagaggcgg   4080
```

-continued

```
tttgcgtatt gggcgctctt ccgcttcctc gctcactgac tcgctgcgct cggtcgttcg   4140
gctgcggcga gcggtatcag ctcactcaaa ggcggtaata cggttatcca cagaatcagg   4200
ggataacgca ggaaagaaca tgtgagcaaa aggccagcaa aaggccagga accgtaaaaa   4260
ggccgcgttg ctggcgtttt tccataggct ccgcccccct gacgagcatc acaaaaatcg   4320
acgctcaagt cagaggtggc gaaacccgac aggactataa agataccagg cgtttccccc   4380
tggaagctcc ctcgtgcgct ctcctgttcc gaccctgccg cttaccggat acctgtccgc   4440
ctttctccct tcgggaagcg tggcgctttc tcaatgctca cgctgtaggt atctcagttc   4500
ggtgtaggtc gttcgctcca agctgggctg tgtgcacgaa ccccccgttc agcccgaccg   4560
ctgcgcctta tccggtaact atcgtcttga gtccaacccg gtaagacacg acttatcgcc   4620
actggcagca gccactggta acaggattag cagagcgagg tatgtaggcg gtgctacaga   4680
gttcttgaag tggtggccta actacggcta cactagaagg acagtatttg gtatctgcgc   4740
tctgctgaag ccagttacct tcggaaaaag agttggtagc tcttgatccg gcaaacaaac   4800
caccgctggt agcggtggtt tttttgtttg caagcagcag attacgcgca gaaaaaaagg   4860
atctcaagaa gatcctttga tcttttctac ggggtctgac gctcagtgga acgaaaactc   4920
acgttaaggg attttggtca tgacattaac ctataaaaat aggcgtatca cgaggccctt   4980
tcgtctcgcg cgtttcggtg atgacggtga aaacctctga cacatgcagc tcccggagac   5040
ggtcacagct tgtctgtaag cggatgccgg gagcagacaa gcccgtcagg gcgcgtcagc   5100
gggtgttggc gggtgtcggg gctggcttaa ctatgcggca tcagagcaga ttgtactgag   5160
agtgcaccat atggacatat tgtcgttaga acgcggctac aattaataca taaccttatg   5220
tatcatacac atacgattta ggtgacacta tagaacggcg cgccaagctt gttgaaacat   5280
ccctgaagtg tctcatttta ttttatttat tctttgctga taaaaaaata aaataaaaga   5340
agctaagcac acggtcaacc attgctctac tgctaaaagg gttatgtgta gtgttttact   5400
gcataaatta tgcagcaaac aagacaactc aaattaaaaa atttcctttg cttgtttttt   5460
tgttgtctct gacttgactt tcttgtggaa gttggttgta taaggattgg gacaccattg   5520
tccttcttaa tttaatttta ttctttgctg ataaaaaaaa aaatttcata tagtgttaaa   5580
taataatttg ttaaataacc aaaaagtcaa atatgtttac tctcgtttaa ataattgaga   5640
ttcgtccagc aaggctaaac gattgtatag atttatgaca atatttactt ttttatagat   5700
aaatgttata ttataataaa tttatataca tatattatat gttatttatt attattttaa   5760
atccttcaat attttatcaa accaactcat aatttttttt ttatctgtaa gaagcaataa   5820
aattaaatag acccacttta aggatgatcc aacctttata cagagtaaga gagttcaaat   5880
agtacccttt catatacata tcaactaaaa tattagaaat atcatggatc aaaccttata   5940
aagacattaa ataagtggat aagtataata tataaatggg tagtatataa tatataaatg   6000
gatacaaact tctctcttta taattgttat gtctccttaa catcctaata taatacataa   6060
gtgggtaata tataatatat aaatggagac aaacttcttc cattataatt gttatgtctt   6120
cttaacactt atgtctcgtt cacaatgcta aggttagaat tgtttagaaa gtcttatagt   6180
acacatttgt ttttgtacta tttgaagcat tccataagcc gtcacgattc agatgattta   6240
taataataag aggaaattta tcatagaaca ataaggtgca tagatagagt gttaatatat   6300
cataacatcc tttgtttatt catagaagaa gtgagatgga gctcagttat tatactgtta   6360
catggtcgga tacaatattc catgctctcc atgagctctt acacctacat gcattttagt   6420
```

```
tcatacttgc ggccgcagta tatcttaaat tctttaatac ggtgtactag gatattgaac   6480

tggttcttga tgatgaaaac ctgggccgag attgcagcta tttatagtca taggtcttgt   6540

taacatgcat ggacatttgg ccacggggtg gcatgcagtt tgacgggtgt tgaaataaac   6600

aaaaatgagg tggcggaaga gaatacgagt ttgaggttgg gttagaaaca acaaatgtga   6660

gggctcatga tgggttgagt tggtgaatgt tttgggctgc tcgattgaca cctttgtgag   6720

tacgtgttgt tgtgcatggc ttttggggtc cagttttttt ttcttgacgc ggcgatcctg   6780

atcagctagt ggataagtga tgtccactgt gtgtgattgc gtttttgttt gaattttatg   6840

aacttagaca ttgctatgca aaggatactc tcattgtgtt ttgtcttctt ttgttccttg   6900

gctttttctt atgatccaag agactagtca gtgttgtggc attcgagact accaagatta   6960

attatgatgg gggaaggata agtaactgat tagtacggac tgttaccaaa ttaattaata   7020

agcggcaaat gaagggcatg gatcaaaagc ttggatctcc tgcaggatct ggccggccgg   7080

atctc                                                               7085
```

<210> SEQ ID NO 37
<211> LENGTH: 7873
<212> TYPE: DNA
<213> ORGANISM: Artificial Sequence
<220> FEATURE:
<223> OTHER INFORMATION: the sequence of pKR912

<400> SEQUENCE: 37

```
ggccgcaagt atgaactaaa atgcatgtag gtgtaagagc tcatggagag catggaatat     60

tgtatccgac catgtaacag tataataact gagctccatc tcacttcttc tatgaataaa    120

caaaggatgt tatgatatat taacactcta tctatgcacc ttattgttct atgataaatt    180

tcctcttatt attataaatc atctgaatcg tgacggctta tggaatgctt caaatagtac    240

aaaaacaaat gtgtactata agactttcta aacaattcta accttagcat tgtgaacgag    300

acataagtgt taagaagaca taacaattat aatggaagaa gtttgtctcc atttatatat    360

tatatattac ccacttatgt attatattag gatgttaagg agacataaca attataaaga    420

gagaagtttg tatccattta tatattatat actacccatt tatatattat acttatccac    480

ttatttaatg tctttataag gtttgatcca tgatatttct aatattttag ttgatatgta    540

tatgaaaggg tactatttga actctcttac tctgtataaa ggttggatca tccttaaagt    600

gggtctattt aattttattg cttcttacag ataaaaaaaa aattatgagt tggtttgata    660

aaatattgaa ggatttaaaa taataataaa taacatataa tatatgtata taaatttatt    720

ataatataac atttatctat aaaaaagtaa atattgtcat aaatctatac aatcgtttag    780

ccttgctgga cgaatctcaa ttatttaaac gagagtaaac atatttgact ttttggttat    840

ttaacaaatt attatttaac actatatgaa attttttttt ttatcagcaa agaataaaat    900

taaattaaga aggacaatgg tgtcccaatc cttatacaac caacttccac aagaaagtca    960

agtcagagac aacaaaaaaa caagcaaagg aaattttttta atttgagttg tcttgtttgc   1020

tgcataattt atgcagtaaa acactacaca taacccttt agcagtagag caatggttga   1080

ccgtgtgctt agcttctttt attttatttt tttatcagca aagaataaat aaaataaaat   1140

gagacacttc agggatgttt caacaagctt ggcgcgccgt tctatagtgt cacctaaatc   1200

gtatgtgtat gatacataag gttatgtatt aattgtagcc gcgttctaac gacaatatgt   1260

ccatatggtg cactctcagt acaatctgct ctgatgccgc atagttaagc cagccccgac   1320

acccgccaac acccgctgac gcgccctgac gggcttgtct gctcccggca tccgcttaca   1380
```

```
gacaagctgt gaccgtctcc gggagctgca tgtgtcagag gttttcaccg tcatcaccga   1440
aacgcgcgag acgaaagggc ctcgtgatac gcctattttt ataggttaat gtcatgacca   1500
aaatccctta acgtgagttt tcgttccact gagcgtcaga ccccgtagaa aagatcaaag   1560
gatcttcttg agatcctttt tttctgcgcg taatctgctg cttgcaaaca aaaaaaccac   1620
cgctaccagc ggtggtttgt ttgccggatc aagagctacc aactcttttt ccgaaggtaa   1680
ctggcttcag cagagcgcag ataccaaata ctgtccttct agtgtagccg tagttaggcc   1740
accacttcaa gaactctgta gcaccgccta catacctcgc tctgctaatc ctgttaccag   1800
tggctgctgc cagtggcgat aagtcgtgtc ttaccgggtt ggactcaaga cgatagttac   1860
cggataaggc gcagcggtcg ggctgaacgg ggggttcgtg cacacagccc agcttggagc   1920
gaacgaccta caccgaactg agatacctac agcgtgagca ttgagaaagc gccacgcttc   1980
ccgaagggag aaaggcggac aggtatccgg taagcggcag ggtcggaaca ggagagcgca   2040
cgagggagct tccaggggga aacgcctggt atctttatag tcctgtcggg tttcgccacc   2100
tctgacttga gcgtcgattt ttgtgatgct cgtcaggggg gcggagccta tggaaaaacg   2160
ccagcaacgc ggccttttta cggttcctgg ccttttgctg gccttttgct cacatgttct   2220
ttcctgcgtt atcccctgat tctgtggata accgtattac cgcctttgag tgagctgata   2280
ccgctcgccg cagccgaacg accgagcgca gcgagtcagt gagcgaggaa gcggaagagc   2340
gcccaatacg caaaccgcct ctccccgcgc gttggccgat tcattaatgc aggttgatcg   2400
attcgacatc gatctagtaa catagatgac accgcgcgcg ataatttatc ctagtttgcg   2460
cgctatattt tgttttctat cgcgtattaa atgtataatt gcgggactct aatcataaaa   2520
acccatctca taaataacgt catgcattac atgttaatta ttacatgctt aacgtaattc   2580
aacagaaatt atatgataat catcgcaaga ccggcaacag gattcaatct taagaaactt   2640
tattgccaaa tgtttgaacg atctgcttcg acgcactcct tctttaggta cctcactatt   2700
cctttgccct cggacgagtg ctggggcgtc ggtttccact atcggcgagt acttctacac   2760
agccatcggt ccagacggcc gcgcttctgc gggcgatttg tgtacgcccg acagtcccgg   2820
ctccggatcg gacgattgcg tcgcatcgac cctgcgccca agctgcatca tcgaaattgc   2880
cgtcaaccaa gctctgatag agttggtcaa gaccaatgcg gagcatatac gcccggagcc   2940
gcggcgatcc tgcaagctcc ggatgcctcc gctcgaagta gcgcgtctgc tgctccatac   3000
aagccaacca cggcctccag aagaagatgt tggcgacctc gtattgggaa tccccgaaca   3060
tcgcctcgct ccagtcaatg accgctgtta tgcggccatt gtccgtcagg acattgttgg   3120
agccgaaatc cgcgtgcacg aggtgccgga cttcggggca gtcctcggcc caaagcatca   3180
gctcatcgag agcctgcgcg acggacgcac tgacggtgtc gtccatcaca gtttgccagt   3240
gatacacatg gggatcagca atcgcgcata tgaaatcacg ccatgtagtg tattgaccga   3300
ttccttgcgg tccgaatggg ccgaacccgc tcgtctggct aagatcggcc gcagcgatcg   3360
catccatggc ctccgcgacc ggctgcagaa cagcgggcag ttcggtttca ggcaggtctt   3420
gcaacgtgac accctgtgca cggcgggaga tgcaataggt caggctctcg ctgaattccc   3480
caatgtcaag cacttccgga atcgggagcg cggccgatgc aaagtgccga taaacataac   3540
gatctttgta gaaaccatcg gcgcagctat ttacccgcag gacatatcca cgccctccta   3600
catcgaagct gaaagcacga gattcttcgc cctccgagag ctgcatcagg tcggagacgc   3660
tgtcgaactt ttcgatcaga aacttctcga cagacgtcgc ggtgagttca ggctttttca   3720
```

-continued

```
tggtttaata agaagagaaa agagttcttt tgttatggct gaagtaatag agaaatgagc   3780
tcgagcgtgt cctctccaaa tgaaatgaac ttccttatat agaggaaggg tcttgcgaag   3840
gatagtggga ttgtgcgtca tcccttacgt cagtggagat gtcacatcaa tccacttgct   3900
ttgaagacgt ggttggaacg tcttcttttt ccacgatgct cctcgtgggt gggggtccat   3960
ctttgggacc actgtcggca gaggcatctt gaatgatagc ctttccttta tcgcaatgat   4020
ggcatttgta ggagccacct tccttttcta ctgtcctttc gatgaagtga cagatagctg   4080
ggcaatggaa tccgaggagg tttcccgaaa ttatcctttg ttgaaaagtc tcaatagccc   4140
tttggtcttc tgagactgta tctttgacat ttttggagta gaccagagtg tcgtgctcca   4200
ccatgttgac gaagattttc ttcttgtcat tgagtcgtaa aagactctgt atgaactgtt   4260
cgccagtctt cacggcgagt tctgttagat cctcgatttg aatcttagac tccatgcatg   4320
gccttagatt cagtaggaac taccttttta gagactccaa tctctattac ttgccttggt   4380
ttatgaagca agccttgaat cgtccatact ggaatagtac ttctgatctt gagaaatatg   4440
tctttctctg tgttcttgat gcaattagtc ctgaatcttt tgactgcatc tttaaccttc   4500
ttgggaaggt atttgatctc ctggagattg ttactcgggt agatcgtctt gatgagacct   4560
gctgcgtagg cctctctaac catctgtggg tcagcattct ttctgaaatt gaagaggcta   4620
accttctcat tatcagtggt gaacatagtg tcgtcacctt caccttcgaa cttccttcct   4680
agatcgtaaa gatagaggaa atcgtccatt gtaatctccg gggcaaagga gatctctttt   4740
ggggctggat cactgctggg ccttttggtt cctagcgtga gccagtgggc tttttgcttt   4800
ggtgggcttg ttagggcctt agcaaagctc ttgggcttga gttgagcttc tcctttgggg   4860
atgaagttca acctgtctgt ttgctgactt gttgtgtacg cgtcagctgc tgctcttgcc   4920
tctgtaatag tggcaaattt cttgtgtgca actccgggaa cgccgtttgt tgccgccttt   4980
gtacaacccc agtcatcgta tataccggca tgtggaccgt tatacacaac gtagtagttg   5040
atatgagggt gttgaatacc cgattctgct ctgagaggag caactgtgct gttaagctca   5100
gatttttgtg ggattggaat tggatcgatc tcgatcccgc gaaattaata cgactcacta   5160
tagggagacc acaacggttt ccctctagaa ataattttgt ttaactttaa gaaggagata   5220
tacccatgga aaagcctgaa ctcaccgcga cgtctgtcga gaagtttctg atcgaaaagt   5280
tcgacagcgt ctccgacctg atgcagctct cggagggcga agaatctcgt gctttcagct   5340
tcgatgtagg agggcgtgga tatgtcctgc gggtaaatag ctgcgccgat ggtttctaca   5400
aagatcgtta tgtttatcgg cactttgcat cggccgcgct cccgattccg gaagtgcttg   5460
acattgggga attcagcgag agcctgacct attgcatctc ccgccgtgca cagggtgtca   5520
cgttgcaaga cctgcctgaa accgaactgc ccgctgttct gcagccggtc gcggaggcta   5580
tggatgcgat cgctgcggcc gatcttagcc agacgagcgg gttcggccca ttcggaccgc   5640
aaggaatcgg tcaatacact acatggcgtg atttcatatg cgcgattgct gatccccatg   5700
tgtatcactg gcaaactgtg atggacgaca ccgtcagtgc gtccgtcgcg caggctctcg   5760
atgagctgat gctttgggcc gaggactgcc ccgaagtccg gcacctcgtg cacgcggatt   5820
tcggctccaa caatgtcctg acggacaatg gccgcataac agcggtcatt gactggagcg   5880
aggcgatgtt cggggattcc caatacgagg tcgccaacat cttcttctgg aggccgtggt   5940
tggcttgtat ggagcagcag acgcgctact tcgagcggag gcatccggag cttgcaggat   6000
cgccgcggct ccgggcgtat atgctccgca ttggtcttga ccaactctat cagagcttgg   6060
ttgacggcaa tttcgatgat gcagcttggg cgcagggtcg atgcgacgca atcgtccgat   6120
```

```
ccggagccgg gactgtcggg cgtacacaaa tcgcccgcag aagcgcggcc gtctggaccg   6180

atggctgtgt agaagtactc gccgatagtg gaaaccgacg ccccagcact cgtccgaggg   6240

caaaggaata gtgaggtaca gcttggatcg atccggctgc taacaaagcc cgaaaggaag   6300

ctgagttggc tgctgccacc gctgagcaat aactagcata accccttggg gcctctaaac   6360

gggtcttgag gggttttttg ctgaaaggag gaactatatc cggatgatcg ggcgcgccgt   6420

cgacggatcc gtacgagatc cggccggcca gatcctgcag gagatccaag cttttgatcc   6480

atgcccttca tttgccgctt attaattaat ttggtaacag tccgtactaa tcagttactt   6540

atccttcccc catcataatt aatcttggta gtctcgaatg ccacaacact gactagtctc   6600

ttggatcata agaaaaagcc aaggaacaaa agaagacaaa acacaatgag agtatccttt   6660

gcatagcaat gtctaagttc ataaaattca aacaaaaacg caatcacaca cagtggacat   6720

cacttatcca ctagctgatc aggatcgccg cgtcaagaaa aaaaaactgg accccaaaag   6780

ccatgcacaa caacacgtac tcacaaaggt gtcaatcgag cagcccaaaa cattcaccaa   6840

ctcaacccat catgagccct cacatttgtt gtttctaacc caacctcaaa ctcgtattct   6900

cttccgccac ctcatttttg tttatttcaa cacccgtcaa actgcatgcc accccgtggc   6960

caaatgtcca tgcatgttaa caagacctat gactataaat agctgcaatc tcggcccagg   7020

ttttcatcat caagaaccag ttcaatatcc tagtacaccg tattaaagaa tttaagatat   7080

actgcggccg caccatggag gtggtgaatg aaatagtctc aattgggcag gaagttttac   7140

ccaaagttga ttatgcccaa ctctggagtg atgccagtca ctgtgaggtg ctttacttgt   7200

ccatcgcatt tgtcatcttg aagttcactc ttggcccccct tggtccaaaa ggtcagtctc   7260

gtatgaagtt tgttttcacc aattacaacc ttctcatgtc catttattcg ttgggatcat   7320

tcctctcaat ggcatatgcc atgtacacca tcggtgttat gtctgacaac tgcgagaagg   7380

cttttgacaa caacgtcttc aggatcacca cgcagttgtt ctatttgagc aagttcctgg   7440

agtatattga ctccttctat ttgccactga tgggcaagcc tctgacctgg ttgcaattct   7500

tccatcattt gggggcaccg atggatatgt ggctgttcta taattaccga aatgaagctg   7560

tttggatttt tgtgctgttg aatggtttca tccactggat catgtacggt tattattgga   7620

ccagattgat caagctgaag ttccccatgc caaaatccct gattacatca atgcagatca   7680

ttcaattcaa tgttggtttc tacattgtct ggaagtacag gaacattccc tgttatcgcc   7740

aagatgggat gaggatgttt ggctggttct tcaattactt ttatgttggc acagtcttgt   7800

gtttgttctt gaatttctat gtgcaaacgt atatcgtcag gaagcacaag ggagccaaaa   7860

agattcagtg agc                                                      7873
```

<210> SEQ ID NO 38
<211> LENGTH: 2540
<212> TYPE: DNA
<213> ORGANISM: Artificial Sequence
<220> FEATURE:
<223> OTHER INFORMATION: the sequence of pKS102

<400> SEQUENCE: 38

```
cgatcatccg gatatagttc ctcctttcag caaaaaaccc ctcaagaccc gtttagaggc     60

cccaaggggt tatgctagtt attgctcagc ggtggcagca gccaactcag cttcctttcg    120

ggctttgtta gcagccggat cgatccaagc tgtacctcac tattcctttg ccctcggacg    180

agtgctgggg cgtcggtttc cactatcggc gagtacttct acacagccat cggtccagac    240
```

-continued

```
ggccgcgctt ctgcgggcga tttgtgtacg cccgacagtc ccggctccgg atcggacgat    300
tgcgtcgcat cgaccctgcg cccaagctgc atcatcgaaa ttgccgtcaa ccaagctctg    360
atagagttgg tcaagaccaa tgcggagcat atacgcccgg agccgcggcg atcctgcaag    420
ctccggatgc ctccgctcga agtagcgcgt ctgctgctcc atacaagcca accacggcct    480
ccagaagaag atgttggcga cctcgtattg ggaatccccg aacatcgcct cgctccagtc    540
aatgaccgct gttatgcggc cattgtccgt caggacattg ttggagccga aatccgcgtg    600
cacgaggtgc cggacttcgg ggcagtcctc ggcccaaagc atcagctcat cgagagcctg    660
cgcgacggac gcactgacgg tgtcgtccat cacagtttgc cagtgataca catggggatc    720
agcaatcgcg catatgaaat cacgccatgt agtgtattga ccgattcctt gcggtccgaa    780
tgggccgaac ccgctcgtct ggctaagatc ggccgcagcg atcgcatcca tagcctccgc    840
gaccggctgc agaacagcgg gcagttcggt ttcaggcagg tcttgcaacg tgacaccctg    900
tgcacggcgg gagatgcaat aggtcaggct ctcgctgaat tccccaatgt caagcacttc    960
cggaatcggg agcgcggccg atgcaaagtg ccgataaaca taacgatctt tgtagaaacc   1020
atcggcgcag ctatttaccc gcaggacata tccacgccct cctacatcga agctgaaagc   1080
acgagattct tcgccctccg agagctgcat caggtcggag acgctgtcga acttttcgat   1140
cagaaacttc tcgacagacg tcgcggtgag ttcaggcttt tccatgggta tatctccttc   1200
ttaaagttaa acaaaattat ttctagaggg aaaccgttgt ggtctcccta tagtgagtcg   1260
tattaatttc gcgggatcga gatctgatca acctgcatta atgaatcggc caacgcgcgg   1320
ggagaggcgg tttgcgtatt gggcgctctt ccgcttcctc gctcactgac tcgctgcgct   1380
cggtcgttcg gctgcggcga gcggtatcag ctcactcaaa ggcggtaata cggttatcca   1440
cagaatcagg ggataacgca ggaaagaaca tgtgagcaaa aggccagcaa aaggccagga   1500
accgtaaaaa ggccgcgttg ctggcgtttt tccataggct ccgcccccct gacgagcatc   1560
acaaaaatcg acgctcaagt cagaggtggc gaaacccgac aggactataa agataccagg   1620
cgtttccccc tggaagctcc ctcgtgcgct ctcctgttcc gaccctgccg cttaccggat   1680
acctgtccgc ctttctccct tcgggaagcg tggcgctttc tcaatgctca cgctgtaggt   1740
atctcagttc ggtgtaggtc gttcgctcca agctgggctg tgtgcacgaa ccccccgttc   1800
agcccgaccg ctgcgcctta tccggtaact atcgtcttga gtccaacccg gtaagacacg   1860
acttatcgcc actggcagca gccactggta acaggattag cagagcgagg tatgtaggcg   1920
gtgctacaga gttcttgaag tggtggccta actacggcta cactagaagg acagtatttg   1980
gtatctgcgc tctgctgaag ccagttacct tcggaaaaag agttggtagc tcttgatccg   2040
gcaaacaaac caccgctggt agcggtggtt tttttgtttg caagcagcag attacgcgca   2100
gaaaaaaagg atctcaagaa gatcctttga tcttttctac ggggtctgac gctcagtgga   2160
acgaaaactc acgttaaggg attttggtca tgacattaac ctataaaaat aggcgtatca   2220
cgaggccctt tcgtctcgcg cgtttcggtg atgacggtga aaacctctga cacatgcagc   2280
tcccggagac ggtcacagct tgtctgtaag cggatgccgg gagcagacaa gcccgtcagg   2340
gcgcgtcagc gggtgttggc gggtgtcggg gctggcttaa ctatgcggca tcagagcaga   2400
ttgtactgag agtgcaccat atggacatat tgtcgttaga acgcggctac aattaataca   2460
taaccttatg tatcatacac atacgattta ggtgacacta tagaacggcg cgccaagctt   2520
ggatccgtcg acggcgcgcc                                               2540
```

<210> SEQ ID NO 39
<211> LENGTH: 4359
<212> TYPE: DNA
<213> ORGANISM: Artificial Sequence
<220> FEATURE:
<223> OTHER INFORMATION: the sequence of pKR197

<400> SEQUENCE: 39
cgcgcccgat catccggata tagttcctcc tttcagcaaa aaacccctca agacccgttt 60
agaggcccca aggggttatg ctagttattg ctcagcggtg gcagcagcca actcagcttc 120
ctttcgggct ttgttagcag ccggatcgat ccaagctgta cctcactatt cctttgccct 180
cggacgagtg ctggggcgtc ggtttccact atcggcgagt acttctacac agccatcggt 240
ccagacggcc gcgcttctgc gggcgatttg tgtacgcccg acagtcccgg ctccggatcg 300
gacgattgcg tcgcatcgac cctgcgccca agctgcatca tcgaaattgc cgtcaaccaa 360
gctctgatag agttggtcaa gaccaatgcg gagcatatac gcccggagcc gcggcgatcc 420
tgcaagctcc ggatgcctcc gctcgaagta gcgcgtctgc tgctccatac aagccaacca 480
cggcctccag aagaagatgt tggcgacctc gtattgggaa tccccgaaca tcgcctcgct 540
ccagtcaatg accgctgtta tgcggccatt gtccgtcagg acattgttgg agccgaaatc 600
cgcgtgcacg aggtgccgga cttcggggca gtcctcggcc caaagcatca gctcatcgag 660
agcctgcgcg acggacgcac tgacggtgtc gtccatcaca gtttgccagt gatacacatg 720
gggatcagca atcgcgcata tgaaatcacg ccatgtagtg tattgaccga ttccttgcgg 780
tccgaatggg ccgaacccgc tcgtctggct aagatcggcc gcagcgatcg catccatagc 840
ctccgcgacc ggctgcagaa cagcgggcag ttcggtttca ggcaggtctt gcaacgtgac 900
accctgtgca cggcgggaga tgcaataggt caggctctcg ctgaattccc caatgtcaag 960
cacttccgga atcgggagcg cggccgatgc aaagtgccga taaacataac gatctttgta 1020
gaaaccatcg gcgcagctat ttacccgcag gacatatcca cgccctccta catcgaagct 1080
gaaagcacga gattcttcgc cctccgagag ctgcatcagg tcggagacgc tgtcgaactt 1140
ttcgatcaga aacttctcga cagacgtcgc ggtgagttca ggctttttca tgggtatatc 1200
tccttcttaa agttaaacaa aattatttct agagggaaac cgttgtggtc tccctatagt 1260
gagtcgtatt aatttcgcgg gatcgagatc tgatcaacct gcattaatga atcggccaac 1320
gcgcggggag aggcggtttg cgtattgggc gctcttccgc ttcctcgctc actgactcgc 1380
tgcgctcggt cgttcggctg cggcgagcgg tatcagctca ctcaaaggcg gtaatacggt 1440
tatccacaga atcaggggat aacgcaggaa agaacatgtg agcaaaaggc cagcaaaagg 1500
ccaggaaccg taaaaaggcc gcgttgctgg cgtttttcca taggctccgc ccccctgacg 1560
agcatcacaa aaatcgacgc tcaagtcaga ggtggcgaaa cccgacagga ctataaagat 1620
accaggcgtt tccccctgga agctccctcg tgcgctctcc tgttccgacc ctgccgctta 1680
ccggatacct gtccgccttt ctcccttcgg gaagcgtggc gctttctcaa tgctcacgct 1740
gtaggtatct cagttcggtg taggtcgttc gctccaagct gggctgtgtg cacgaacccc 1800
ccgttcagcc cgaccgctgc gccttatccg gtaactatcg tcttgagtcc aacccggtaa 1860
gacacgactt atcgccactg gcagcagcca ctggtaacag gattagcaga gcgaggtatg 1920
taggcggtgc tacagagttc ttgaagtggt ggcctaacta cggctacact agaaggacag 1980
tatttggtat ctgcgctctg ctgaagccag ttaccttcgg aaaaagagtt ggtagctctt 2040
gatccggcaa acaaaccacc gctggtagcg gtggtttttt tgtttgcaag cagcagatta 2100

-continued

```
cgcgcagaaa aaaaggatct caagaagatc ctttgatctt ttctacgggg tctgacgctc   2160
agtggaacga aaactcacgt taagggattt tggtcatgac attaacctat aaaaataggc   2220
gtatcacgag gccctttcgt ctcgcgcgtt tcggtgatga cggtgaaaac ctctgacaca   2280
tgcagctccc ggagacggtc acagcttgtc tgtaagcgga tgccgggagc agacaagccc   2340
gtcagggcgc gtcagcgggt gttggcgggt gtcggggctg gcttaactat gcggcatcag   2400
agcagattgt actgagagtg caccatatgg acatattgtc gttagaacgc ggctacaatt   2460
aatacataac cttatgtatc atacacatac gatttaggtg acactataga acggcgcgcc   2520
aagcttgttg aaacatccct gaagtgtctc attttatttt atttattctt tgctgataaa   2580
aaaataaaat aaaagaagct aagcacacgg tcaaccattg ctctactgct aaaagggtta   2640
tgtgtagtgt tttactgcat aaattatgca gcaaacaaga caactcaaat taaaaaattt   2700
cctttgcttg tttttttgtt gtctctgact tgactttctt gtggaagttg gttgtataag   2760
gattgggaca ccattgtcct tcttaattta attttattct ttgctgataa aaaaaaaaat   2820
ttcatatagt gttaaataat aatttgttaa ataaccaaaa agtcaaatat gtttactctc   2880
gtttaaataa ttgagattcg tccagcaagg ctaaacgatt gtatagattt atgacaatat   2940
ttactttttt atagataaat gttatattat aataaattta tatacatata ttatatgtta   3000
tttattatta ttttaaatcc ttcaatattt tatcaaacca actcataatt ttttttttat   3060
ctgtaagaag caataaaatt aaatagaccc actttaagga tgatccaacc tttatacaga   3120
gtaagagagt tcaaatagta ccctttcata tacatatcaa ctaaaatatt agaaatatca   3180
tggatcaaac cttataaaga cattaaataa gtggataagt ataatatata aatgggtagt   3240
atataatata taaatggata caaacttctc tctttataat tgttatgtct ccttaacatc   3300
ctaatataat acataagtgg gtaatatata atatataaat ggagacaaac ttcttccatt   3360
ataattgtta tgtcttctta acacttatgt ctcgttcaca atgctaaggt tagaattgtt   3420
tagaaagtct tatagtacac atttgttttt gtactatttg aagcattcca taagccgtca   3480
cgattcagat gatttataat aataagagga aatttatcat agaacaataa ggtgcataga   3540
tagagtgtta atatatcata acatcctttg tttattcata gaagaagtga gatggagctc   3600
agttattata ctgttacatg gtcggataca atattccatg ctctccatga gctcttacac   3660
ctacatgcat tttagttcat acttgcggcc gcagtatatc ttaaattctt taatacggtg   3720
tactaggata ttgaactggt tcttgatgat gaaaacctgg gccgagattg cagctattta   3780
tagtcatagg tcttgttaac atgcatggac atttggccac ggggtggcat gcagtttgac   3840
gggtgttgaa ataaacaaaa atgaggtggc ggaagagaat acgagtttga ggttgggtta   3900
gaaacaacaa atgtgagggc tcatgatggg ttgagttggt gaatgttttg ggctgctcga   3960
ttgacacctt tgtgagtacg tgttgttgtg catggctttt ggggtccagt tttttttttct   4020
tgacgcggcg atcctgatca gctagtggat aagtgatgtc cactgtgtgt gattgcgttt   4080
ttgtttgaat tttatgaact tagacattgc tatgcaaagg atactctcat tgtgttttgt   4140
cttcttttgt tccttggctt tttcttatga tccaagagac tagtcagtgt tgtggcattc   4200
gagactacca agattaatta tgatgggggga aggataagta actgattagt acggactgtt   4260
accaaattaa ttaataagcg gcaaatgaag ggcatggatc aaaagcttgg atctcctgca   4320
ggatctggcc ggccggatct cgtacggatc cgtcgacgg                          4359
```

<210> SEQ ID NO 40
<211> LENGTH: 5147

<212> TYPE: DNA
<213> ORGANISM: Artificial Sequence
<220> FEATURE:
<223> OTHER INFORMATION: the sequence of pKR911

<400> SEQUENCE: 40
ggccgcaagt atgaactaaa atgcatgtag gtgtaagagc tcatggagag catggaatat 60
tgtatccgac catgtaacag tataataact gagctccatc tcacttcttc tatgaataaa 120
caaaggatgt tatgatatat taacactcta tctatgcacc ttattgttct atgataaatt 180
tcctcttatt attataaatc atctgaatcg tgacggctta tggaatgctt caaatagtac 240
aaaaacaaat gtgtactata agactttcta aacaattcta accttagcat tgtgaacgag 300
acataagtgt taagaagaca taacaattat aatggaagaa gtttgtctcc atttatatat 360
tatatattac ccacttatgt attatattag gatgttaagg agacataaca attataaaga 420
gagaagtttg tatccattta tatattatat actacccatt tatatattat acttatccac 480
ttatttaatg tctttataag gtttgatcca tgatatttct aatattttag ttgatatgta 540
tatgaaaggg tactatttga actctcttac tctgtataaa ggttggatca tccttaaagt 600
gggtctattt aattttattg cttcttacag ataaaaaaaa aattatgagt tggtttgata 660
aaatattgaa ggatttaaaa taataataaa taacatataa tatatgtata taaatttatt 720
ataatataac atttatctat aaaaaagtaa atattgtcat aaatctatac aatcgtttag 780
ccttgctgga cgaatctcaa ttatttaaac gagagtaaac atatttgact ttttggttat 840
ttaacaaatt attatttaac actatatgaa attttttttt ttatcagcaa agaataaaat 900
taaattaaga aggacaatgg tgtcccaatc cttatacaac caacttccac aagaaagtca 960
agtcagagac aacaaaaaaa caagcaaagg aaattttttta atttgagttg tcttgtttgc 1020
tgcataattt atgcagtaaa acactacaca taaccctttt agcagtagag caatggttga 1080
ccgtgtgctt agcttctttt attttatttt tttatcagca aagaataaat aaaataaaat 1140
gagacacttc agggatgttt caacaagctt ggcgcgccgt tctatagtgt cacctaaatc 1200
gtatgtgtat gatacataag gttatgtatt aattgtagcc gcgttctaac gacaatatgt 1260
ccatatggtg cactctcagt acaatctgct ctgatgccgc atagttaagc cagccccgac 1320
acccgccaac acccgctgac gcgccctgac gggcttgtct gctcccggca tccgcttaca 1380
gacaagctgt gaccgtctcc gggagctgca tgtgtcagag gttttcaccg tcatcaccga 1440
aacgcgcgag acgaaagggc ctcgtgatac gcctattttt ataggttaat gtcatgacca 1500
aaatccctta acgtgagttt tcgttccact gagcgtcaga ccccgtagaa aagatcaaag 1560
gatcttcttg agatcctttt tttctgcgcg taatctgctg cttgcaaaca aaaaaaccac 1620
cgctaccagc ggtggtttgt ttgccggatc aagagctacc aactcttttt ccgaaggtaa 1680
ctggcttcag cagagcgcag ataccaaata ctgtccttct agtgtagccg tagttaggcc 1740
accacttcaa gaactctgta gcaccgccta catacctcgc tctgctaatc ctgttaccag 1800
tggctgctgc cagtggcgat aagtcgtgtc ttaccgggtt ggactcaaga cgatagttac 1860
cggataaggc gcagcggtcg ggctgaacgg ggggttcgtg cacacagccc agcttggagc 1920
gaacgaccta caccgaactg agatacctac agcgtgagca ttgagaaagc gccacgcttc 1980
ccgaagggag aaaggcggac aggtatccgg taagcggcag ggtcggaaca ggagagcgca 2040
cgagggagct tccaggggga aacgcctggt atctttatag tcctgtcggg tttcgccacc 2100
tctgacttga gcgtcgattt ttgtgatgct cgtcaggggg gcggagccta tggaaaaacg 2160

-continued

```
ccagcaacgc ggccttttta cggttcctgg ccttttgctg gccttttgct cacatgttct   2220
ttcctgcgtt atcccctgat tctgtggata accgtattac cgcctttgag tgagctgata   2280
ccgctcgccg cagccgaacg accgagcgca gcgagtcagt gagcgaggaa gcggaagagc   2340
gcccaatacg caaaccgcct ctccccgcgc gttggccgat tcattaatgc aggttgatca   2400
gatctcgatc ccgcgaaatt aatacgactc actataggga gaccacaacg gtttccctct   2460
agaaataatt ttgtttaact ttaagaagga gatataccca tggaaaagcc tgaactcacc   2520
gcgacgtctg tcgagaagtt tctgatcgaa aagttcgaca gcgtctccga cctgatgcag   2580
ctctcggagg gcgaagaatc tcgtgctttc agcttcgatg taggagggcg tggatatgtc   2640
ctgcgggtaa atagctgcgc cgatggtttc tacaaagatc gttatgttta tcggcacttt   2700
gcatcggccg cgctcccgat tccggaagtg cttgacattg gggaattcag cgagagcctg   2760
acctattgca tctcccgccg tgcacagggt gtcacgttgc aagacctgcc tgaaaccgaa   2820
ctgcccgctg ttctgcagcc ggtcgcggag gctatggatg cgatcgctgc ggccgatctt   2880
agccagacga gcgggttcgg cccattcgga ccgcaaggaa tcggtcaata cactacatgg   2940
cgtgatttca tatgcgcgat tgctgatccc catgtgtatc actggcaaac tgtgatggac   3000
gacaccgtca gtgcgtccgt cgcgcaggct ctcgatgagc tgatgctttg ggccgaggac   3060
tgccccgaag tccggcacct cgtgcacgcg gatttcggct ccaacaatgt cctgacggac   3120
aatggccgca taacagcggt cattgactgg agcgaggcga tgttcgggga ttcccaatac   3180
gaggtcgcca acatcttctt ctggaggccg tggttggctt gtatggagca gcagacgcgc   3240
tacttcgagc ggaggcatcc ggagcttgca ggatcgccgc ggctccgggc gtatatgctc   3300
cgcattggtc ttgaccaact ctatcagagc ttggttgacg gcaatttcga tgatgcagct   3360
tgggcgcagg gtcgatgcga cgcaatcgtc cgatccggag ccgggactgt cgggcgtaca   3420
caaatcgccc gcagaagcgc ggccgtctgg accgatggct gtgtagaagt actcgccgat   3480
agtggaaacc gacgccccag cactcgtccg agggcaaagg aatagtgagg tacagcttgg   3540
atcgatccgg ctgctaacaa agcccgaaag gaagctgagt tggctgctgc caccgctgag   3600
caataactag cataacccct tggggcctct aaacgggtct tgaggggttt tttgctgaaa   3660
ggaggaacta tatccggatg atcgggcgcg ccgtcgacgg atccgtacga gatccggccg   3720
gccagatcct gcaggagatc caagcttttg atccatgccc ttcatttgcc gcttattaat   3780
taatttggta acagtccgta ctaatcagtt acttatcctt cccccatcat aattaatctt   3840
ggtagtctcg aatgccacaa cactgactag tctcttggat cataagaaaa agccaaggaa   3900
caaaagaaga caaaacacaa tgagagtatc ctttgcatag caatgtctaa gttcataaaa   3960
ttcaaacaaa aacgcaatca cacacagtgg acatcactta tccactagct gatcaggatc   4020
gccgcgtcaa gaaaaaaaaa ctggacccca aaagccatgc acaacaacac gtactcacaa   4080
aggtgtcaat cgagcagccc aaaacattca ccaactcaac ccatcatgag ccctcacatt   4140
tgttgtttct aacccaacct caaactcgta ttctcttccg ccacctcatt tttgtttatt   4200
tcaacacccg tcaaactgca tgccaccccg tggccaaatg tccatgcatg ttaacaagac   4260
ctatgactat aaatagctgc aatctcggcc caggttttca tcatcaagaa ccagttcaat   4320
atcctagtac accgtattaa agaatttaag atatactgcg gccgcaccat ggaggtggtg   4380
aatgaaatag tctcaattgg gcaggaagtt ttacccaaag ttgattatgc ccaactctgg   4440
agtgatgcca gtcactgtga ggtgctttac ttgtccatcg catttgtcat cttgaagttc   4500
actcttggcc cccttggtcc aaaaggtcag tctcgtatga agtttgtttt caccaattac   4560
```

```
aaccttctca tgtccattta ttcgttggga tcattcctct caatggcata tgccatgtac   4620

accatcggtg ttatgtctga caactgcgag aaggcttttg acaacaacgt cttcaggatc   4680

accacgcagt tgttctattt gagcaagttc ctggagtata ttgactcctt ctatttgcca   4740

ctgatgggca agcctctgac ctggttgcaa ttcttccatc atttgggggc accgatggat   4800

atgtggctgt tctataatta ccgaaatgaa gctgtttgga tttttgtgct gttgaatggt   4860

ttcatccact ggatcatgta cggttattat tggaccagat tgatcaagct gaagttcccc   4920

atgccaaaat ccctgattac atcaatgcag atcattcaat tcaatgttgg tttctacatt   4980

gtctggaagt acaggaacat tccctgttat cgccaagatg ggatgaggat gtttggctgg   5040

ttcttcaatt acttttatgt tggcacagtc ttgtgtttgt tcttgaattt ctatgtgcaa   5100

acgtatatcg tcaggaagca caagggagcc aaaaagattc agtgagc                5147
```

```
<210> SEQ ID NO 41
<211> LENGTH: 4826
<212> TYPE: DNA
<213> ORGANISM: Artificial Sequence
<220> FEATURE:
<223> OTHER INFORMATION: the sequence of pKS121
<220> FEATURE:
<221> NAME/KEY: misc_feature
<222> LOCATION: (3711)..(3711)
<223> OTHER INFORMATION: n is a, c, g, or t

<400> SEQUENCE: 41
```

```
tcgacggcgc gcccgatcat ccggatatag ttcctccttt cagcaaaaaa cccctcaaga     60

cccgtttaga ggccccaagg ggttatgcta gttattgctc agcggtggca gcagccaact    120

cagcttcctt tcgggctttg ttagcagccg gatcgatcca agctgtacct cactattcct    180

ttgccctcgg acgagtgctg gggcgtcggt ttccactatc ggcgagtact tctacacagc    240

catcggtcca gacggccgcg cttctgcggg cgatttgtgt acgcccgaca gtcccggctc    300

cggatcggac gattgcgtcg catcgaccct gcgcccaagc tgcatcatcg aaattgccgt    360

caaccaagct ctgatagagt tggtcaagac caatgcggag catatacgcc cggagccgcg    420

gcgatcctgc aagctccgga tgcctccgct cgaagtagcg cgtctgctgc tccatacaag    480

ccaaccacgg cctccagaag aagatgttgg cgacctcgta ttgggaatcc ccgaacatcg    540

cctcgctcca gtcaatgacc gctgttatgc ggccattgtc cgtcaggaca ttgttggagc    600

cgaaatccgc gtgcacgagg tgccggactt cggggcagtc ctcggcccaa agcatcagct    660

catcgagagc ctgcgcgacg gacgcactga cggtgtcgtc catcacagtt tgccagtgat    720

acacatgggg atcagcaatc gcgcatatga aatcacgcca tgtagtgtat tgaccgattc    780

cttgcggtcc gaatgggccg aacccgctcg tctggctaag atcggccgca gcgatcgcat    840

ccatagcctc cgcgaccggc tgcagaacag cgggcagttc ggtttcaggc aggtcttgca    900

acgtgacacc ctgtgcacgg cgggagatgc aataggtcag gctctcgctg aattccccaa    960

tgtcaagcac ttccggaatc gggagcgcgg ccgatgcaaa gtgccgataa acataacgat   1020

ctttgtagaa accatcggcg cagctattta cccgcaggac atatccacgc cctcctacat   1080

cgaagctgaa agcacgagat tcttcgccct ccgagagctg catcaggtcg gagacgctgt   1140

cgaacttttc gatcagaaac ttctcgacag acgtcgcggt gagttcaggc ttttccatgg   1200

gtatatctcc ttcttaaagt taaacaaaat tatttctaga gggaaaccgt tgtggtctcc   1260

ctatagtgag tcgtattaat ttcgcgggat cgagatctga tcaacctgca ttaatgaatc   1320
```

-continued

```
ggccaacgcg cggggagagg cggtttgcgt attgggcgct cttccgcttc ctcgctcact   1380
gactcgctgc gctcggtcgt tcggctgcgg cgagcggtat cagctcactc aaaggcggta   1440
atacggttat ccacagaatc aggggataac gcaggaaaga acatgtgagc aaaaggccag   1500
caaaaggcca ggaaccgtaa aaaggccgcg ttgctggcgt ttttccatag gctccgcccc   1560
cctgacgagc atcacaaaaa tcgacgctca agtcagaggt ggcgaaaccc gacaggacta   1620
taaagatacc aggcgtttcc ccctggaagc tccctcgtgc gctctcctgt tccgaccctg   1680
ccgcttaccg gatacctgtc cgcctttctc ccttcgggaa gcgtggcgct ttctcaatgc   1740
tcacgctgta ggtatctcag ttcggtgtag gtcgttcgct ccaagctggg ctgtgtgcac   1800
gaaccccccg ttcagcccga ccgctgcgcc ttatccggta actatcgtct tgagtccaac   1860
ccggtaagac acgacttatc gccactggca gcagccactg gtaacaggat tagcagagcg   1920
aggtatgtag gcggtgctac agagttcttg aagtggtggc ctaactacgg ctacactaga   1980
aggacagtat ttggtatctg cgctctgctg aagccagtta ccttcggaaa aagagttggt   2040
agctcttgat ccggcaaaca aaccaccgct ggtagcggtg gtttttttgt ttgcaagcag   2100
cagattacgc gcagaaaaaa aggatctcaa gaagatcctt tgatcttttc tacggggtct   2160
gacgctcagt ggaacgaaaa ctcacgttaa gggattttgg tcatgacatt aacctataaa   2220
aataggcgta tcacgaggcc ctttcgtctc gcgcgtttcg gtgatgacgg tgaaaacctc   2280
tgacacatgc agctcccgga gacggtcaca gcttgtctgt aagcggatgc cgggagcaga   2340
caagcccgtc agggcgcgtc agcgggtgtt ggcgggtgtc ggggctggct taactatgcg   2400
gcatcagagc agattgtact gagagtgcac catatggaca tattgtcgtt agaacgcggc   2460
tacaattaat acataacctt atgtatcata cacatacgat ttaggtgaca ctatagaacg   2520
gcgcgccaag cttggatcct cgaagagaag ggttaataac acatttttta acatttttaa   2580
cacaaatttt agttatttaa aaatttatta aaaaatttaa aataagaaga ggaactcttt   2640
aaataaatct aacttacaaa atttatgatt tttaataagt tttcaccaat aaaaaatgtc   2700
ataaaaatat gttaaaaagt atattatcaa tattctcttt atgataaata aaaagaaaaa   2760
aaaaataaaa gttaagtgaa aatgagattg aagtgacttt aggtgtgtat aaatatatca   2820
accccgccaa caatttattt aatccaaata tattgaagta tattattcca tagcctttat   2880
ttatttatat atttattata taaaagcttt atttgttcta ggttgttcat gaaatatttt   2940
tttggtttta tctccgttgt aagaaaatca tgtgctttgt gtcgccactc actattgcag   3000
ctttttcatg cattggtcag attgacggtt gattgtattt ttgtttttta tggttttgtg   3060
ttatgactta agtcttcatc tctttatctc ttcatcaggt ttgatggtta cctaatatgg   3120
tccatgggta catgcatggt taaattaggt ggccaacttt gttgtgaacg atagaatttt   3180
ttttatatta agtaaactat ttttatatta tgaaataata ataaaaaaaa tattttatca   3240
ttattaacaa aatcatatta gttaatttgt taactctata ataaaagaaa tactgtaaca   3300
ttcacattac atggtaacat ctttccaccc tttcatttgt tttttgtttg atgacttttt   3360
ttcttgttta aatttatttc ccttctttta aatttggaat acattatcat catatataaa   3420
ctaaaatact aaaaacagga ttacacaaat gataaataat aacacaaata tttataaatc   3480
tagctgcaat atatttaaac tagctatatc gatattgtaa aataaaacta gctgcattga   3540
tactgataaa aaaatatcat gtgctttctg gactgatgat gcagtatact tttgacattg   3600
cctttatttt atttttcaga aaagctttct tagttctggg ttcttcatta tttgtttccc   3660
atctccattg tgaattgaat catttgcttc gtgtcacaaa tacaatttag ntaggtacat   3720
```

```
gcattggtca gattcacggt ttattatgtc atgacttaag ttcatggtag tacattacct   3780
gccacgcatg cattatattg gttagatttg ataggcaaat ttggttgtca acaatataaa   3840
tataaataat gtttttatat tacgaaataa cagtgatcaa aacaaacagt tttatcttta   3900
ttaacaagat tttgtttttg tttgatgacg ttttttaatg tttacgcttt ccccccttctt   3960
ttgaatttag aacactttat catcataaaa tcaaatacta aaaaaattac atatttcata   4020
aataataaca caaatatttt taaaaaatct gaaataataa tgaacaatat tacatattat   4080
cacgaaaatt cattaataaa aatattatat aaataaaatg taatagtagt tatatgtagg   4140
aaaaaagtac tgcacgcata atatatacaa aaagattaaa atgaactatt ataaataata   4200
acactaaatt aatggtgaat catatcaaaa taatgaaaaa gtaaataaaa tttgtaatta   4260
acttctatat gtattacaca cacaaataat aaataatagt aaaaaaaatt atgataaata   4320
tttaccatct cataagatat ttaaaataat gataaaaata tagattattt tttatgcaac   4380
tagctagcca aaaagagaac acgggtatat ataaaaagag tacctttaaa ttctactgta   4440
cttcctttat tcctgacgtt tttatatcaa gtggacatac gtgaagattt taattatcag   4500
tctaaatatt tcattagcac ttaatacttt tctgttttat tcctatccta taagtagtcc   4560
cgattctccc aacattgctt attcacacaa ctaactaaga aagtcttcca tagcccccca   4620
agcggccgcg acacaagtgt gagagtacta aataaatgct ttggttgtac gaaatcatta   4680
cactaaataa aataatcaaa gcttatatat gccttccgct aaggccgaat gcaaagaaat   4740
tggttctttc tcgttatctt ttgccacttt tactagtacg tattaattac tacttaatca   4800
tctttgttta cggctcatta tatccg                                        4826
```

<210> SEQ ID NO 42
<211> LENGTH: 5252
<212> TYPE: DNA
<213> ORGANISM: Artificial Sequence
<220> FEATURE:
<223> OTHER INFORMATION: the sequence of pKR457
<220> FEATURE:
<221> NAME/KEY: misc_feature
<222> LOCATION: (3872)..(3872)
<223> OTHER INFORMATION: n is a, c, g, or t

<400> SEQUENCE: 42

```
gtacgtgggc ggatccccccg ggctgcagga attcactggc cgtcgtttta caacgtcgtg    60
actgggaaaa ccctggcgtt acccaactta atcgccttgc agcacatccc cctttcgcca   120
gctggcgtaa tagcgaagag gcccgcaccg atcgcccttc ccaacagttg cgcagcctga   180
atggcgaatg gcgcctgatg cggtattttc tccttacgca tctgtgcggt atttcacacc   240
gcatatggtg cactctcagt acaatctgct ctgatgccgc atagttaagc cagccccgac   300
acccgccaac acccgctgac gcgccctgac gggcttgtct gctcccggca tccgcttaca   360
gacaagctgt gaccgtctcc gggagctgca tgtgtcagag gttttcaccg tcatcaccga   420
aacgcgcgag acgaaagggc ctcgtgatac gcctattttt ataggttaat gtcatgataa   480
taatggtttc ttagacgtca ggtggcactt ttcggggaaa tgtgcgcgga acccctattt   540
gtttattttt ctaaatacat tcaaatatgt atccgctcat gagacaataa ccctgataaa   600
tgcttcaata atattgaaaa aggaagagta tgagtattca acatttccgt gtcgccctta   660
ttcccttttt tgcggcattt tgccttcctg tttttgctca cccagaaacg ctggtgaaag   720
taaaagatgc tgaagatcag ttgggtgcac gagtgggtta catcgaactg gatctcaaca   780
```

-continued

```
gcggtaagat ccttgagagt tttcgccccg aagaacgttt tccaatgatg agcactttta    840
aagttctgct atgtggcgcg gtattatccc gtattgacgc cgggcaagag caactcggtc    900
gccgcataca ctattctcag aatgacttgg ttgagtactc accagtcaca gaaaagcatc    960
ttacggatgg catgacagta agagaattat gcagtgctgc cataaccatg agtgataaca   1020
ctgcggccaa cttacttctg acaacgatcg gaggaccgaa ggagctaacc gcttttttgc   1080
acaacatggg ggatcatgta actcgccttg atcgttggga accggagctg aatgaagcca   1140
taccaaacga cgagcgtgac accacgatgc ctgtagcaat ggcaacaacg ttgcgcaaac   1200
tattaactgg cgaactactt actctagctt cccggcaaca attaatagac tggatggagg   1260
cggataaagt tgcaggacca cttctgcgct cggcccttcc ggctggctgg tttattgctg   1320
ataaatctgg agccggtgag cgtgggtctc gcggtatcat tgcagcactg gggccagatg   1380
gtaagccctc ccgtatcgta gttatctaca cgacggggag tcaggcaact atggatgaac   1440
gaaatagaca gatcgctgag ataggtgcct cactgattaa gcattggtaa ctgtcagacc   1500
aagtttactc atatatactt tagattgatt taaaacttca tttttaattt aaaaggatct   1560
aggtgaagat cctttttgat aatctcatga ccaaaatccc ttaacgtgag ttttcgttcc   1620
actgagcgtc agaccccgta gaaaagatca aaggatcttc ttgagatcct ttttttctgc   1680
gcgtaatctg ctgcttgcaa acaaaaaaac caccgctacc agcggtggtt tgtttgccgg   1740
atcaagagct accaactctt tttccgaagg taactggctt cagcagagcg cagataccaa   1800
atactgtcct tctagtgtag ccgtagttag gccaccactt caagaactct gtagcaccgc   1860
ctacatacct cgctctgcta atcctgttac cagtggctgc tgccagtggc gataagtcgt   1920
gtcttaccgg gttggactca agacgatagt taccggataa ggcgcagcgg tcgggctgaa   1980
cggggggttc gtgcacacag cccagcttgg agcgaacgac ctacaccgaa ctgagatacc   2040
tacagcgtga gctatgagaa agcgccacgc ttcccgaagg gagaaaggcg gacaggtatc   2100
cggtaagcgg cagggtcgga acaggagagc gcacgaggga gcttccaggg ggaaacgcct   2160
ggtatcttta tagtcctgtc gggtttcgcc acctctgact tgagcgtcga tttttgtgat   2220
gctcgtcagg ggggcggagc ctatggaaaa acgccagcaa cgcggccttt ttacggttcc   2280
tggccttttg ctggcctttt gctcacatgt tctttcctgc gttatcccct gattctgtgg   2340
ataaccgtat taccgccttt gagtgagctg ataccgctcg ccgcagccga acgaccgagc   2400
gcagcgagtc agtgagcgag gaagcggaag agcgcccaat acgcaaaccg cctctccccg   2460
cgcgttggcc gattcattaa tgcagctggc acgacaggtt tcccgactgg aaagcgggca   2520
gtgagcgcaa cgcaattaat gtgagttagc tcactcatta ggcaccccag gctttacact   2580
ttatgcttcc ggctcgtatg ttgtgtggaa ttgtgagcgg ataacaattt cacacaggaa   2640
acagctatga ccatgattac gccaagcttg catgcctgca ggtcgactcg acgtacgtcc   2700
tcgaagagaa gggttaataa cacatttttt aacattttta acacaaattt tagttattta   2760
aaaatttatt aaaaaattta aaataagaag aggaactctt taaataaatc taacttacaa   2820
aatttatgat ttttaataag ttttcaccaa taaaaaatgt cataaaaata tgttaaaaag   2880
tatattatca atattctctt tatgataaat aaaaagaaaa aaaaaataaa agttaagtga   2940
aaatgagatt gaagtgactt taggtgtgta taaatatatc aaccccgcca acaatttatt   3000
taatccaaat atattgaagt atattattcc atagccttta tttatttata tatttattat   3060
ataaaagctt tatttgttct aggttgttca tgaaatattt ttttggtttt atctccgttg   3120
taagaaaatc atgtgctttg tgtcgccact cactattgca gctttttcat gcattggtca   3180
```

```
gattgacggt tgattgtatt tttgtttttt atggttttgt gttatgactt aagtcttcat   3240
ctctttatct cttcatcagg tttgatggtt acctaatatg gtccatgggt acatgcatgg   3300
ttaaattagg tggccaactt tgttgtgaac gatagaattt tttttatatt aagtaaacta   3360
tttttatatt atgaaataat aataaaaaaa atattttatc attattaaca aaatcatatt   3420
agttaatttg ttaactctat aataaaagaa atactgtaac attcacatta catggtaaca   3480
tctttccacc ctttcatttg ttttttgttt gatgactttt tttcttgttt aaatttattt   3540
cccttctttt aaatttggaa tacattatca tcatatataa actaaaatac taaaaacagg   3600
attacacaaa tgataaataa taacacaaat atttataaat ctagctgcaa tatatttaaa   3660
ctagctatat cgatattgta aaataaaact agctgcattg atactgataa aaaaatatca   3720
tgtgctttct ggactgatga tgcagtatac ttttgacatt gcctttattt tatttttcag   3780
aaaagctttc ttagttctgg gttcttcatt atttgtttcc catctccatt gtgaattgaa   3840
tcatttgctt cgtgtcacaa atacaattta gntaggtaca tgcattggtc agattcacgg   3900
tttattatgt catgacttaa gttcatggta gtacattacc tgccacgcat gcattatatt   3960
ggttagattt gataggcaaa tttggttgtc aacaatataa atataaataa tgtttttata   4020
ttacgaaata acagtgatca aaacaaacag ttttatcttt attaacaaga ttttgttttt   4080
gtttgatgac gtttttttaat gtttacgctt tcccccttct tttgaattta gaacacttta   4140
tcatcataaa atcaaatact aaaaaaatta catatttcat aaataataac acaaatattt   4200
ttaaaaaatc tgaaataata atgaacaata ttacatatta tcacgaaaat tcattaataa   4260
aaatattata taaataaaat gtaatagtag ttatatgtag gaaaaaagta ctgcacgcat   4320
aatatataca aaaagattaa aatgaactat tataaataat aacactaaat taatggtgaa   4380
tcatatcaaa ataatgaaaa agtaaataaa atttgtaatt aacttctata tgtattacac   4440
acacaaataa taaataatag taaaaaaaat tatgataaat atttaccatc tcataagata   4500
tttaaaataa tgataaaaat atagattatt ttttatgcaa ctagctagcc aaaaagagaa   4560
cacgggtata tataaaaaga gtacctttaa attctactgt acttccttta ttcctgacgt   4620
ttttatatca agtggacata cgtgaagatt ttaattatca gtctaaatat ttcattagca   4680
cttaatactt ttctgtttta ttcctatcct ataagtagtc ccgattctcc caacattgct   4740
tattcacaca actaactaag aaagtcttcc atagcccccc aagcggccgc gacacaagtg   4800
tgagagtact aaataaatgc tttggttgta cgaaatcatt acactaaata aaataatcaa   4860
agcttatata tgccttccgc taaggccgaa tgcaaagaaa ttggttcttt ctcgttatct   4920
tttgccactt ttactagtac gtattaatta ctacttaatc atctttgttt acggctcatt   4980
atatccggtc tagaggatcc aaggccgcga agttaaaagc aatgttgtca cttgtcgtac   5040
taacacatga tgtgatagtt tatgctagct agctataaca taagctgtct ctgagtgtgt   5100
tgtatattaa taaagatcat cactggtgaa tggtgatcgt gtacgtaccc tacttagtag   5160
gcaatggaag cacttagagt gtgctttgtg catggccttg cctctgtttt gagacttttg   5220
taatgttttc gagtttaaat ctttgccttt gc                                 5252
```

<210> SEQ ID NO 43
<211> LENGTH: 6559
<212> TYPE: DNA
<213> ORGANISM: Artificial Sequence
<220> FEATURE:
<223> OTHER INFORMATION: the sequence of pKR680
<220> FEATURE:

<221> NAME/KEY: misc_feature
<222> LOCATION: (4340)..(4340)
<223> OTHER INFORMATION: n is a, c, g, or t

<400> SEQUENCE: 43

```
ggccgcgaca caagtgtgag agtactaaat aaatgctttg gttgtacgaa atcattacac     60
taaataaaat aatcaaagct tatatatgcc ttccgctaag gccgaatgca aagaaattgg    120
ttctttctcg ttatcttttg ccacttttac tagtacgtat taattactac ttaatcatct    180
ttgtttacgg ctcattatat ccggtctaga ggatccaagg ccgcgaagtt aaaagcaatg    240
ttgtcacttg tcgtactaac acatgatgtg atagtttatg ctagctagct ataacataag    300
ctgtctctga gtgtgttgta tattaataaa gatcatcact ggtgaatggt gatcgtgtac    360
gtaccctact tagtaggcaa tggaagcact tagagtgtgc tttgtgcatg gccttgcctc    420
tgttttgaga cttttgtaat gttttcgagt ttaaatcttt gcctttgcgt acgtgggcgg    480
atcccccggg ctgcaggaat tcactggccg tcgttttaca acgtcgtgac tgggaaaacc    540
ctggcgttac ccaacttaat cgccttgcag cacatccccc tttcgccagc tggcgtaata    600
gcgaagaggc ccgcaccgat cgcccttccc aacagttgcg cagcctgaat ggcgaatggc    660
gcctgatgcg gtattttctc cttacgcatc tgtgcggtat ttcacaccgc atatggtgca    720
ctctcagtac aatctgctct gatgccgcat agttaagcca gccccgacac ccgccaacac    780
ccgctgacgc gccctgacgg gcttgtctgc tcccggcatc cgcttacaga caagctgtga    840
ccgtctccgg gagctgcatg tgtcagaggt tttcaccgtc atcaccgaaa cgcgcgagac    900
gaaagggcct cgtgatacgc ctatttttat aggttaatgt catgataata atggtttctt    960
agacgtcagg tggcactttt cggggaaatg tgcgcggaac ccctatttgt ttatttttct   1020
aaatacattc aaatatgtat ccgctcatga gacaataacc ctgataaatg cttcaataat   1080
attgaaaaag gaagagtatg agtattcaac atttccgtgt cgcccttatt cccttttttg   1140
cggcattttg ccttcctgtt tttgctcacc cagaaacgct ggtgaaagta aaagatgctg   1200
aagatcagtt gggtgcacga gtgggttaca tcgaactgga tctcaacagc ggtaagatcc   1260
ttgagagttt tcgccccgaa gaacgttttc caatgatgag cacttttaaa gttctgctat   1320
gtggcgcggt attatcccgt attgacgccg ggcaagagca actcggtcgc cgcatacact   1380
attctcagaa tgacttggtt gagtactcac cagtcacaga aaagcatctt acggatggca   1440
tgacagtaag agaattatgc agtgctgcca taaccatgag tgataacact gcggccaact   1500
tacttctgac aacgatcgga ggaccgaagg agctaaccgc ttttttgcac aacatggggg   1560
atcatgtaac tcgccttgat cgttgggaac cggagctgaa tgaagccata ccaaacgacg   1620
agcgtgacac cacgatgcct gtagcaatgg caacaacgtt gcgcaaacta ttaactggcg   1680
aactacttac tctagcttcc cggcaacaat taatagactg gatggaggcg gataaagttg   1740
caggaccact tctgcgctcg gcccttccgg ctggctggtt tattgctgat aaatctggag   1800
ccggtgagcg tgggtctcgc ggtatcattg cagcactggg gccagatggt aagccctccc   1860
gtatcgtagt tatctacacg acggggagtc aggcaactat ggatgaacga aatagacaga   1920
tcgctgagat aggtgcctca ctgattaagc attggtaact gtcagaccaa gtttactcat   1980
atatacttta gattgattta aaacttcatt tttaatttaa aaggatctag gtgaagatcc   2040
tttttgataa tctcatgacc aaaatccctt aacgtgagtt ttcgttccac tgagcgtcag   2100
accccgtaga aaagatcaaa ggatcttctt gagatccttt ttttctgcgc gtaatctgct   2160
gcttgcaaac aaaaaaacca ccgctaccag cggtggtttg tttgccggat caagagctac   2220
```

caactctttt tccgaaggta actggcttca gcagagcgca gataccaaat actgtccttc 2280
tagtgtagcc gtagttaggc caccacttca agaactctgt agcaccgcct acatacctcg 2340
ctctgctaat cctgttacca gtggctgctg ccagtggcga taagtcgtgt cttaccgggt 2400
tggactcaag acgatagtta ccggataagg cgcagcggtc gggctgaacg gggggttcgt 2460
gcacacagcc cagcttggag cgaacgacct acaccgaact gagataccta cagcgtgagc 2520
tatgagaaag cgccacgctt cccgaaggga gaaaggcgga caggtatccg gtaagcggca 2580
gggtcggaac aggagagcgc acgagggagc ttccaggggg aaacgcctgg tatctttata 2640
gtcctgtcgg gtttcgccac ctctgacttg agcgtcgatt tttgtgatgc tcgtcagggg 2700
ggcggagcct atggaaaaac gccagcaacg cggccttttt acggttcctg gccttttgct 2760
ggccttttgc tcacatgttc tttcctgcgt tatcccctga ttctgtggat aaccgtatta 2820
ccgcctttga gtgagctgat accgctcgcc gcagccgaac gaccgagcgc agcgagtcag 2880
tgagcgagga agcggaagag cgcccaatac gcaaaccgcc tctccccgcg cgttggccga 2940
ttcattaatg cagctggcac gacaggtttc ccgactggaa agcgggcagt gagcgcaacg 3000
caattaatgt gagttagctc actcattagg caccccaggc tttacacttt atgcttccgg 3060
ctcgtatgtt gtgtggaatt gtgagcggat aacaatttca cacaggaaac agctatgacc 3120
atgattacgc caagcttgca tgcctgcagg tcgactcgac gtacgtcctc gaagagaagg 3180
gttaataaca catttttaa catttttaac acaaatttta gttatttaaa aatttattaa 3240
aaaatttaaa ataagaagag gaactcttta aataaatcta acttacaaaa tttatgattt 3300
ttaataagtt ttcaccaata aaaaatgtca taaaaatatg ttaaaaagta tattatcaat 3360
attctcttta tgataaataa aaagaaaaaa aaaataaaag ttaagtgaaa atgagattga 3420
agtgacttta ggtgtgtata aatatatcaa ccccgccaac aatttattta atccaaatat 3480
attgaagtat attattccat agcctttatt tatttatata tttattatat aaaagcttta 3540
tttgttctag gttgttcatg aaatattttt ttggttttat ctccgttgta agaaaatcat 3600
gtgctttgtg tcgccactca ctattgcagc tttttcatgc attggtcaga ttgacggttg 3660
attgtatttt tgttttttat ggttttgtgt tatgacttaa gtcttcatct ctttatctct 3720
tcatcaggtt tgatggttac ctaatatggt ccatgggtac atgcatggtt aaattaggtg 3780
gccaactttg ttgtgaacga tagaattttt tttatattaa gtaaactatt tttatattat 3840
gaaataataa taaaaaaaat attttatcat tattaacaaa atcatattag ttaatttgtt 3900
aactctataa taaaagaaat actgtaacat tcacattaca tggtaacatc tttccaccct 3960
ttcatttgtt ttttgtttga tgactttttt tcttgtttaa atttatttcc cttcttttaa 4020
atttggaata cattatcatc atatataaac taaaatacta aaaacaggat tacacaaatg 4080
ataaataata acacaaatat ttataaatct agctgcaata tatttaaact agctatatcg 4140
atattgtaaa ataaaactag ctgcattgat actgataaaa aaatatcatg tgctttctgg 4200
actgatgatg cagtatactt ttgacattgc ctttatttta tttttcagaa aagctttctt 4260
agttctgggt tcttcattat ttgtttccca tctccattgt gaattgaatc atttgcttcg 4320
tgtcacaaat acaatttagn taggtacatg cattggtcag attcacggtt tattatgtca 4380
tgacttaagt tcatggtagt acattacctg ccacgcatgc attatattgg ttagatttga 4440
taggcaaatt tggttgtcaa caatataaat ataaataatg tttttatatt acgaaataac 4500
agtgatcaaa acaaacagtt ttatctttat taacaagatt ttgtttttgt ttgatgacgt 4560

-continued

```
tttttaatgt ttacgctttc cccttctttt tgaatttaga acactttatc atcataaaat   4620

caaatactaa aaaaattaca tatttcataa ataataacac aaatattttt aaaaaatctg   4680

aaataataat gaacaatatt acatattatc acgaaaattc attaataaaa atattatata   4740

aataaaatgt aatagtagtt atatgtagga aaaaagtact gcacgcataa tatatacaaa   4800

aagattaaaa tgaactatta taaataataa cactaaatta atggtgaatc atatcaaaat   4860

aatgaaaaag taaataaaat ttgtaattaa cttctatatg tattacacac acaaataata   4920

aataatagta aaaaaaatta tgataaatat ttaccatctc ataagatatt taaaataatg   4980

ataaaaatat agattatttt ttatgcaact agctagccaa aaagagaaca cgggtatata   5040

taaaaagagt acctttaaat tctactgtac ttcctttatt cctgacgttt ttatatcaag   5100

tggacatacg tgaagatttt aattatcagt ctaaatattt cattagcact taatactttt   5160

ctgttttatt cctatcctat aagtagtccc gattctccca acattgctta ttcacacaac   5220

taactaagaa agtcttccat agccccccaa gcggccgcgg gaattcgatt gaaatgaagt   5280

caaagcgcca agcgcttccc cttacaattg atggaacaac atatgatgtg tctgcctggg   5340

tcaatttcca ccctggtggt gcggaaatta tagagaatta ccaaggaagg gatgccactg   5400

atgccttcat ggttatgcac tctcaagaag ccttcgacaa gctcaagcgc atgcccaaaa   5460

tcaatcccag ttctgagttg ccaccccagg ctgcagtgaa tgaagctcaa gaggatttcc   5520

ggaagctccg agaagagttg atcgcaactg gcatgtttga tgcctccccc ctctggtact   5580

catacaaaat cagcaccaca ctgggccttg gagtgctggg ttatttcctg atggttcagt   5640

atcagatgta tttcattggg gcagtgttgc ttgggatgca ctatcaacag atgggctggc   5700

tttctcatga catttgccac caccagactt tcaagaaccg gaactggaac aacctcgtgg   5760

gactggtatt tggcaatggt ctgcaaggtt tttccgtgac atggtggaag gacagacaca   5820

atgcacatca ttcggcaacc aatgttcaag ggcacgaccc tgatattgac aacctccccc   5880

tcttagcctg gtctgaggat gacgtcacac gggcgtcacc gatttcccgc aagctcattc   5940

agttccagca gtactatttc ttggtcatct gtatcttgtt gcggttcatt tggtgtttcc   6000

agagcgtgtt gaccgtgcgc agtttgaagg acagagataa ccaattctat cgctctcagt   6060

ataagaagga ggccattggc ctcgccctgc actggacctt gaagaccctg ttccacttat   6120

tctttatgcc cagcatcctc acatcgctgt tggtgttttt cgtttcggag ctggttggcg   6180

gcttcggcat tgcgatcgtg gtgttcatga accactaccc actggagaag atcgggggact  6240

cagtctggga tggccatgga ttctcggttg gccagatcca tgagaccatg aacattcggc   6300

gagggattat cacagattgg tttttcggag gcttgaatta ccagattgag caccatttgt   6360

ggccgaccct ccctcgccac aacctgacag cggttagcta ccaggtggaa cagctgtgcc   6420

agaagcacaa cctgccgtat cggaacccgc tgccccatga agggttggtc atcctgctgc   6480

gctatctggc ggtgttcgcc cggatggcgg agaagcaacc cgcggggaag gctctataag   6540

gaatcactag tgaattcgc                                                6559
```

<210> SEQ ID NO 44
<211> LENGTH: 9014
<212> TYPE: DNA
<213> ORGANISM: Artificial Sequence
<220> FEATURE:
<223> OTHER INFORMATION: the sequence of pKR913
<220> FEATURE:
<221> NAME/KEY: misc_feature
<222> LOCATION: (7839)..(7839)
<223> OTHER INFORMATION: n is a, c, g, or t

<400> SEQUENCE: 44
gtacgagatc cggccggcca gatcctgcag gagatccaag cttttgatcc atgcccttca 60
tttgccgctt attaattaat ttggtaacag tccgtactaa tcagttactt atccttcccc 120
catcataatt aatcttggta gtctcgaatg ccacaacact gactagtctc ttggatcata 180
agaaaaagcc aaggaacaaa agaagacaaa acacaatgag agtatccttt gcatagcaat 240
gtctaagttc ataaaattca aacaaaaacg caatcacaca cagtggacat cacttatcca 300
ctagctgatc aggatcgccg cgtcaagaaa aaaaaactgg accccaaaag ccatgcacaa 360
caacacgtac tcacaaaggt gtcaatcgag cagcccaaaa cattcaccaa ctcaacccat 420
catgagccct cacatttgtt gtttctaacc caacctcaaa ctcgtattct cttccgccac 480
ctcatttttg tttatttcaa cacccgtcaa actgcatgcc accccgtggc caaatgtcca 540
tgcatgttaa caagacctat gactataaat agctgcaatc tcggcccagg ttttcatcat 600
caagaaccag ttcaatatcc tagtacaccg tattaaagaa tttaagatat actgcggccg 660
caccatggag gtggtgaatg aaatagtctc aattgggcag gaagttttac ccaaagttga 720
ttatgcccaa ctctggagtg atgccagtca ctgtgaggtg ctttacttgt ccatcgcatt 780
tgtcatcttg aagttcactc ttggcccct tggtccaaaa ggtcagtctc gtatgaagtt 840
tgttttcacc aattacaacc ttctcatgtc catttattcg ttgggatcat tcctctcaat 900
ggcatatgcc atgtacacca tcggtgttat gtctgacaac tgcgagaagg cttttgacaa 960
caacgtcttc aggatcacca cgcagttgtt ctatttgagc aagttcctgg agtatattga 1020
ctccttctat ttgccactga tgggcaagcc tctgacctgg ttgcaattct tccatcattt 1080
gggggcaccg atggatatgt ggctgttcta taattaccga aatgaagctg tttggatttt 1140
tgtgctgttg aatggtttca tccactggat catgtacggt tattattgga ccagattgat 1200
caagctgaag ttccccatgc caaaatccct gattacatca atgcagatca ttcaattcaa 1260
tgttggtttc tacattgtct ggaagtacag gaacattccc tgttatcgcc aagatgggat 1320
gaggatgttt ggctggttct tcaattactt ttatgttggc acagtcttgt gtttgttctt 1380
gaatttctat gtgcaaacgt atatcgtcag gaagcacaag ggagccaaaa agattcagtg 1440
agcggccgca agtatgaact aaaatgcatg taggtgtaag agctcatgga gagcatggaa 1500
tattgtatcc gaccatgtaa cagtataata actgagctcc atctcacttc ttctatgaat 1560
aaacaaagga tgttatgata tattaacact ctatctatgc accttattgt tctatgataa 1620
atttcctctt attattataa atcatctgaa tcgtgacggc ttatggaatg cttcaaatag 1680
tacaaaaaca aatgtgtact ataagacttt ctaaacaatt ctaaccttag cattgtgaac 1740
gagacataag tgttaagaag acataacaat tataatggaa gaagtttgtc tccatttata 1800
tattatatat tacccactta tgtattatat taggatgtta aggagacata acaattataa 1860
agagagaagt ttgtatccat ttatatatta tatactaccc atttatatat tatacttatc 1920
cacttattta atgtctttat aaggtttgat ccatgatatt tctaatattt tagttgatat 1980
gtatatgaaa gggtactatt tgaactctct tactctgtat aaaggttgga tcatccttaa 2040
agtgggtcta tttaatttta ttgcttctta cagataaaaa aaaaattatg agttggtttg 2100
ataaaatatt gaaggattta aaataataat aaataacata taatatatgt atataaattt 2160
attataatat aacatttatc tataaaaaag taaatattgt cataaatcta tacaatcgtt 2220
tagccttgct ggacgaatct caattattta aacgagagta aacatatttg actttttggt 2280

-continued

```
tatttaacaa attattattt aacactatat gaaatttttt tttttatcag caaagaataa   2340
aattaaatta agaaggacaa tggtgtccca atccttatac aaccaacttc cacaagaaag   2400
tcaagtcaga gacaacaaaa aaacaagcaa aggaaatttt ttaatttgag ttgtcttgtt   2460
tgctgcataa tttatgcagt aaaacactac acataaccct tttagcagta gagcaatggt   2520
tgaccgtgtg cttagcttct tttattttat tttttttatca gcaaagaata aataaaataa  2580
aatgagacac ttcagggatg tttcaacaag cttggcgcgc cgttctatag tgtcacctaa   2640
atcgtatgtg tatgatacat aaggttatgt attaattgta gccgcgttct aacgacaata   2700
tgtccatatg gtgcactctc agtacaatct gctctgatgc cgcatagtta agccagcccc   2760
gacacccgcc aacacccgct gacgcgccct gacgggcttg tctgctcccg gcatccgctt   2820
acagacaagc tgtgaccgtc tccgggagct gcatgtgtca gaggttttca ccgtcatcac   2880
cgaaacgcgc gagacgaaag ggcctcgtga tacgcctatt tttataggtt aatgtcatga   2940
ccaaaatccc ttaacgtgag ttttcgttcc actgagcgtc agaccccgta gaaaagatca   3000
aaggatcttc ttgagatcct ttttttctgc gcgtaatctg ctgcttgcaa acaaaaaaac   3060
caccgctacc agcggtggtt tgtttgccgg atcaagagct accaactctt tttccgaagg   3120
taactggctt cagcagagcg cagataccaa atactgtcct tctagtgtag ccgtagttag   3180
gccaccactt caagaactct gtagcaccgc ctacatacct cgctctgcta atcctgttac   3240
cagtggctgc tgccagtggc gataagtcgt gtcttaccgg gttggactca agacgatagt   3300
taccggataa ggcgcagcgg tcgggctgaa cggggggttc gtgcacacag cccagcttgg   3360
agcgaacgac ctacaccgaa ctgagatacc tacagcgtga gcattgagaa agcgccacgc   3420
ttcccgaagg gagaaaggcg gacaggtatc cggtaagcgg cagggtcgga acaggagagc   3480
gcacgaggga gcttccaggg ggaaacgcct ggtatcttta tagtcctgtc gggtttcgcc   3540
acctctgact tgagcgtcga tttttgtgat gctcgtcagg ggggcggagc ctatggaaaa   3600
acgccagcaa cgcggccttt ttacggttcc tggccttttg ctggcctttt gctcacatgt   3660
tctttcctgc gttatcccct gattctgtgg ataaccgtat taccgccttt gagtgagctg   3720
ataccgctcg ccgcagccga acgaccgagc gcagcgagtc agtgagcgag gaagcggaag   3780
agcgcccaat acgcaaaccg cctctccccg cgcgttggcc gattcattaa tgcaggttga   3840
tcagatctcg atcccgcgaa attaatacga ctcactatag ggagaccaca acggtttccc   3900
tctagaaata attttgttta actttaagaa ggagatatac ccatggaaaa gcctgaactc   3960
accgcgacgt ctgtcgagaa gtttctgatc gaaaagttcg acagcgtctc cgacctgatg   3020
cagctctcgg agggcgaaga atctcgtgct ttcagcttcg atgtaggagg gcgtggatat   4080
gtcctgcggg taaatagctg cgccgatggt ttctacaaag atcgttatgt ttatcggcac   4140
tttgcatcgg ccgcgctccc gattccggaa gtgcttgaca ttggggaatt cagcgagagc   4200
ctgacctatt gcatctcccg ccgtgcacag ggtgtcacgt tgcaagacct gcctgaaacc   4260
gaactgcccg ctgttctgca gccggtcgcg gaggctatgg atgcgatcgc tgcggccgat   4320
cttagccaga cgagcgggtt cggcccattc ggaccgcaag gaatcggtca atacactaca   4380
tggcgtgatt tcatatgcgc gattgctgat ccccatgtgt atcactggca aactgtgatg   4440
gacgacaccg tcagtgcgtc cgtcgcgcag gctctcgatg agctgatgct ttgggccgag   4500
gactgccccg aagtccggca cctcgtgcac gcggatttcg gctccaacaa tgtcctgacg   4560
gacaatggcc gcataacagc ggtcattgac tggagcgagg cgatgttcgg ggattcccaa   4620
tacgaggtcg ccaacatctt cttctggagg ccgtggttgg cttgtatgga gcagcagacg   4680
```

-continued

```
cgctacttcg agcggaggca tccggagctt gcaggatcgc cgcggctccg ggcgtatatg   4740
ctccgcattg gtcttgacca actctatcag agcttggttg acggcaattt cgatgatgca   4800
gcttgggcgc agggtcgatg cgacgcaatc gtccgatccg gagccgggac tgtcgggcgt   4860
acacaaatcg cccgcagaag cgcggccgtc tggaccgatg gctgtgtaga agtactcgcc   4920
gatagtggaa accgacgccc cagcactcgt ccgagggcaa aggaatagtg aggtacagct   4980
tggatcgatc cggctgctaa caaagcccga aaggaagctg agttggctgc tgccaccgct   5040
gagcaataac tagcataacc ccttggggcc tctaaacggg tcttgagggg ttttttgctg   5100
aaaggaggaa ctatatccgg atgatcgggc gcgccgtcga cggatccgta cgcaaaggca   5160
aagatttaaa ctcgaaaaca ttacaaaagt ctcaaaacag aggcaaggcc atgcacaaag   5220
cacactctaa gtgcttccat tgcctactaa gtagggtacg tacacgatca ccattcacca   5280
gtgatgatct ttattaatat acaacacact cagagacagc ttatgttata gctagctagc   5340
ataaactatc acatcatgtg ttagtacgac aagtgacaac attgctttta acttcgcggc   5400
cttggatcct ctagaccgga tataatgagc cgtaaacaaa gatgattaag tagtaattaa   5460
tacgtactag taaaagtggc aaaagataac gagaaagaac caatttcttt gcattcggcc   5520
ttagcggaag gcatatataa gctttgatta ttttatttag tgtaatgatt tcgtacaacc   5580
aaagcattta tttagtactc tcacacttgt gtcgcggccg cgaattcact agtgattcct   5640
tatagagcct tccccgcggg ttgcttctcc gccatccggg cgaacaccgc cagatagcgc   5700
agcaggatga ccaacccttc atggggcagc gggttccgat acggcaggtt gtgcttctgg   5760
cacagctgtt ccacctggta gctaaccgct gtcaggttgt ggcgagggag ggtcggccac   5820
aaatggtgct caatctggta attcaagcct ccgaaaaacc aatctgtgat aatccctcgc   5880
cgaatgttca tggtctcatg gatctggcca accgagaatc catggccatc ccagactgag   5940
tccccgatct tctccagtgg gtagtggttc atgaacacca cgatcgcaat gccgaagccg   6000
ccaaccagct ccgaaacgaa aaacaccaac agcgatgtga ggatgctggg cataaagaat   6060
aagtggaaca gggtcttcaa ggtccagtgc agggcgaggc caatggcctc cttcttatac   6120
tgagagcgat agaattggtt atctctgtcc ttcaaactgc gcacggtcaa cacgctctgg   6180
aaacaccaaa tgaaccgcaa caagatacag atgaccaaga aatagtactg ctggaactga   6240
atgagcttgc gggaaatcgg tgacgcccgt gtgacgtcat cctcagacca ggctaagagg   6300
gggaggttgt caatatcagg gtcgtgccct tgaacattgg ttgccgaatg atgtgcattg   6360
tgtctgtcct tccaccatgt cacggaaaaa ccttgcagac cattgccaaa taccagtccc   6420
acgaggttgt tccagttccg gttcttgaaa gtctggtggt ggcaaatgtc atgagaaagc   6480
cagcccatct gttgatagtg catcccaagc aacactgccc caatgaaata catctgatac   6540
tgaaccatca ggaaataacc cagcactcca aggcccagtg tggtgctgat tttgtatgag   6600
taccagaggg gggaggcatc aaacatgcca gttgcgatca actcttctcg gagcttccgg   6660
aaatcctctt gagcttcatt cactgcagcc tggggtggca actcagaact gggattgatt   6720
ttgggcatgc gcttgagctt gtcgaaggct tcttgagagt gcataaccat gaaggcatca   6780
gtggcatccc ttccttggta attctctata atttccgcac caccagggtg gaaattgacc   6840
caggcagaca catcatatgt tgttccatca attgtaaggg gaagcgcttg gcgctttgac   6900
ttcatttcaa tcgaattccc gcggccgctt ggggggctat ggaagacttt cttagttagt   6960
tgtgtgaata agcaatgttg ggagaatcgg gactacttat aggataggaa taaaacagaa   7020
```

```
aagtattaag tgctaatgaa atatttagac tgataattaa aatcttcacg tatgtccact   7080

tgatataaaa acgtcaggaa taaaggaagt acagtagaat ttaaaggtac tctttttata   7140

tatacccgtg ttctcttttt ggctagctag ttgcataaaa aataatctat atttttatca   7200

ttattttaaa tatcttatga gatggtaaat atttatcata attttttttta ctattattta   7260

ttatttgtgt gtgtaataca tatagaagtt aattacaaat tttatttact ttttcattat   7320

tttgatatga ttcaccatta atttagtgtt attatttata atagttcatt ttaatctttt   7380

tgtatatatt atgcgtgcag tactttttttc ctacatataa ctactattac attttattta   7440

tataatattt ttattaatga attttcgtga taatatgtaa tattgttcat tattatttca   7500

gatttttttaa aaatatttgt gttattattt atgaaatatg taattttttt agtatttgat   7560

tttatgatga taaagtgttc taaattcaaa agaaggggga aagcgtaaac attaaaaaac   7620

gtcatcaaac aaaaacaaaa tcttgttaat aaagataaaa ctgtttgttt tgatcactgt   7680

tatttcgtaa tataaaaaca ttatttatat ttatattgtt gacaaccaaa tttgcctatc   7740

aaatctaacc aatataatgc atgcgtggca ggtaatgtac taccatgaac ttaagtcatg   7800

acataataaa ccgtgaatct gaccaatgca tgtacctanc taaattgtat ttgtgacacg   7860

aagcaaatga ttcaattcac aatggagatg ggaaacaaat aatgaagaac ccagaactaa   7920

gaaagctttt ctgaaaaata aaataaaggc aatgtcaaaa gtatactgca tcatcagtcc   7980

agaaagcaca tgatattttt ttatcagtat caatgcagct agttttattt tacaatatcg   8040

atatagctag tttaaatata ttgcagctag atttataaat atttgtgtta ttatttatca   8100

tttgtgtaat cctgttttta gtattttagt ttatatatga tgataatgta ttccaaattt   8160

aaaagaaggg aaataaattt aaacaagaaa aaaagtcatc aaacaaaaaa caaatgaaag   8220

ggtggaaaga tgttaccatg taatgtgaat gttacagtat ttcttttatt atagagttaa   8280

caaattaact aatatgattt tgttaataat gataaaatat tttttttatt attatttcat   8340

aatataaaaa tagtttactt aatataaaaa aaattctatc gttcacaaca aagttggcca   8400

cctaatttaa ccatgcatgt acccatggac catattaggt aaccatcaaa cctgatgaag   8460

agataaagag atgaagactt aagtcataac acaaaaccat aaaaaacaaa aatacaatca   8520

accgtcaatc tgaccaatgc atgaaaaagc tgcaatagtg agtggcgaca caaagcacat   8580

gattttctta caacggagat aaaaccaaaa aaatatttca tgaacaacct agaacaaata   8640

aagcttttat ataataaata tataaataaa taaaggctat ggaataatat acttcaatat   8700

atttggatta aataaattgt tggcggggtt gatatattta tacacaccta aagtcacttc   8760

aatctcattt tcacttaact tttatttttt ttttcttttt atttatcata aagagaatat   8820

tgataaatata ctttttaaca tatttttatg acatttttta ttggtgaaaa cttattaaaa   8880

atcataaatt ttgtaagtta gatttattta aagagttcct cttcttattt taaatttttt   8940

aataaatttt taaataacta aaatttgtgt taaaaatgtt aaaaaatgtg ttattaaccc   9000

ttctcttcga ggac                                                      9014
```

<210> SEQ ID NO 45
<211> LENGTH: 5561
<212> TYPE: DNA
<213> ORGANISM: Artificial Sequence
<220> FEATURE:
<223> OTHER INFORMATION: the sequence of pKR767

<400> SEQUENCE: 45

```
catggtcaat caatgagacg ccaacttctt aatctattga gacctgcagg tctagaaggg     60
```

-continued

```
cggatccccg ggtaccgagc tcgaattcac tggccgtcgt tttacaacgt cgtgactggg    120
aaaaccctgg cgttacccaa cttaatcgcc ttgcagcaca tccccctttc gccagctggc    180
gtaatagcga agaggcccgc accgatcgcc cttcccaaca gttgcgcagc ctgaatggcg    240
aatggcgcct gatgcggtat tttctcctta cgcatctgtg cggtatttca caccgcatat    300
ggtgcactct cagtacaatc tgctctgatg ccgcatagtt aagccagccc cgacacccgc    360
caacacccgc tgacgcgccc tgacgggctt gtctgctccc ggcatccgct tacagacaag    420
ctgtgaccgt ctccgggagc tgcatgtgtc agaggttttc accgtcatca ccgaaacgcg    480
cgagacgaaa gggcctcgtg atacgcctat ttttataggt taatgtcatg ataataatgg    540
tttcttagac gtcaggtggc acttttcggg gaaatgtgcg cggaacccct atttgtttat    600
ttttctaaat acattcaaat atgtatccgc tcatgagaca ataaccctga taaatgcttc    660
aataatattg aaaaaggaag agtatgagta ttcaacattt ccgtgtcgcc cttattccct    720
tttttgcggc attttgcctt cctgtttttg ctcacccaga aacgctggtg aaagtaaaag    780
atgctgaaga tcagttgggt gcacgagtgg gttacatcga actggatctc aacagcggta    840
agatccttga gagttttcgc cccgaagaac gttttccaat gatgagcact tttaaagttc    900
tgctatgtgg cgcggtatta tcccgtattg acgccgggca agagcaactc ggtcgccgca    960
tacactattc tcagaatgac ttggttgagt actcaccagt cacagaaaag catcttacgg   1020
atggcatgac agtaagagaa ttatgcagtg ctgccataac catgagtgat aacactgcgg   1080
ccaacttact tctgacaacg atcggaggac cgaaggagct aaccgctttt ttgcacaaca   1140
tgggggatca tgtaactcgc cttgatcgtt gggaaccgga gctgaatgaa gccataccaa   1200
acgacgagcg tgacaccacg atgcctgtag caatggcaac aacgttgcgc aaactattaa   1260
ctggcgaact acttactcta gcttcccggc aacaattaat agactggatg gaggcggata   1320
aagttgcagg accacttctg cgctcggccc ttccggctgg ctggtttatt gctgataaat   1380
ctggagccgg tgagcgtggg tctcgcggta tcattgcagc actggggcca gatggtaagc   1440
cctcccgtat cgtagttatc tacacgacgg ggagtcaggc aactatggat gaacgaaata   1500
gacagatcgc tgagataggt gcctcactga ttaagcattg gtaactgtca gaccaagttt   1560
actcatatat actttagatt gatttaaaac ttcattttta atttaaaagg atctaggtga   1620
agatcctttt tgataatctc atgaccaaaa tcccttaacg tgagttttcg ttccactgag   1680
cgtcagaccc cgtagaaaag atcaaaggat cttcttgaga tccttttttt ctgcgcgtaa   1740
tctgctgctt gcaaacaaaa aaaccaccgc taccagcggt ggtttgtttg ccggatcaag   1800
agctaccaac tctttttccg aaggtaactg gcttcagcag agcgcagata ccaaatactg   1860
tccttctagt gtagccgtag ttaggccacc acttcaagaa ctctgtagca ccgcctacat   1920
acctcgctct gctaatcctg ttaccagtgg ctgctgccag tggcgataag tcgtgtctta   1980
ccgggttgga ctcaagacga tagttaccgg ataaggcgca gcggtcgggc tgaacggggg   2040
gttcgtgcac acagcccagc ttggagcgaa cgacctacac cgaactgaga tacctacagc   2100
gtgagctatg agaaagcgcc acgcttcccg aagggagaaa ggcggacagg tatccggtaa   2160
gcggcagggt cggaacagga gagcgcacga gggagcttcc agggggaaac gcctggtatc   2220
tttatagtcc tgtcgggttt cgccacctct gacttgagcg tcgatttttg tgatgctcgt   2280
caggggggcg gagcctatgg aaaaacgcca gcaacgcggc ctttttacgg ttcctggcct   2340
tttgctggcc ttttgctcac atgttctttc ctgcgttatc ccctgattct gtggataacc   2400
```

-continued

```
gtattaccgc ctttgagtga gctgataccg ctcgccgcag ccgaacgacc gagcgcagcg   2460
agtcagtgag cgaggaagcg gaagagcgcc caatacgcaa accgcctctc cccgcgcgtt   2520
ggccgattca ttaatgcagc tggcacgaca ggtttcccga ctggaaagcg ggcagtgagc   2580
gcaacgcaat taatgtgagt tagctcactc attaggcacc ccaggcttta cactttatgc   2640
ttccggctcg tatgttgtgt ggaattgtga gcggataaca atttcacaca ggaaacagct   2700
atgaccatga ttacgccaag cttgcatgcc tgcaggctag cctaagtacg tactcaaaat   2760
gccaacaaat aaaaaaaaag ttgctttaat aatgccaaaa caaattaata aaacacttac   2820
aacaccggat ttttttaat taaaatgtgc catttaggat aaatagttaa tatttttaat   2880
aattatttaa aaagccgtat ctactaaaat gatttttatt tggttgaaaa tattaatatg   2940
tttaaatcaa cacaatctat caaaattaaa ctaaaaaaaa aataagtgta cgtggttaac   3000
attagtacag taatataaga ggaaaatgag aaattaagaa attgaaagcg agtctaattt   3060
ttaaattatg aacctgcata tataaaagga aagaaagaat ccaggaagaa aagaaatgaa   3120
accatgcatg gtcccctcgt catcacgagt ttctgccatt tgcaatagaa acactgaaac   3180
acctttctct ttgtcactta attgagatgc cgaagccacc tcacaccatg aacttcatga   3240
ggtgtagcac ccaaggcttc catagccatg catactgaag aatgtctcaa gctcagcacc   3300
ctacttctgt gacgtgtccc tcattcacct tcctctcttc cctataaata accacgcctc   3360
aggttctccg cttcacaact caaacattct ctccattggt ccttaaacac tcatcagtca   3420
tcaccgcggc cgcatgggaa cggaccaagg aaaaaccttc acctgggaag agctggcggc   3480
ccataacacc aaggacgacc tactcttggc catccgcggc agggtgtacg atgtcacaaa   3540
gttcttgagc cgccatcctg gtggagtgga cactctcctg ctcggagctg gccgagatgt   3600
tactccggtc tttgagatgt atcacgcgtt tggggctgca gatgccatta tgaagaagta   3660
ctatgtcggt acactggtct cgaatgagct gcccatcttc ccggagccaa cggtgttcca   3720
caaaaccatc aagacgagag tcgagggcta ctttacggat cggaacattg atcccaagaa   3780
tagaccagag atctggggac gatacgctct tatctttgga tccttgatcg cttcctacta   3840
cgcgcagctc tttgtgcctt tcgttgtcga acgcacatgg cttcaggtgg tgtttgcaat   3900
catcatggga tttgcgtgcg cacaagtcgg actcaaccct cttcatgatg cgtctcactt   3960
ttcagtgacc cacaacccca ctgtctggaa gattctggga gccacgcacg actttttcaa   4020
cggagcatcg tacctggtgt ggatgtacca acatatgctc ggccatcacc cctacaccaa   4080
cattgctgga gcagatcccg acgtgtcgac gtctgagccc gatgttcgtc gtatcaagcc   4140
caaccaaaag tggtttgtca accacatcaa ccagcacatg tttgttcctt tcctgtacgg   4200
actgctggcg ttcaaggtgc gcattcagga catcaacatt ttgtactttg tcaagaccaa   4260
tgacgctatt cgtgtcaatc ccatctcgac atggcacact gtgatgttct ggggcggcaa   4320
ggctttcttt gtctggtatc gcctgattgt tcccctgcag tatctgcccc tgggcaaggt   4380
gctgctcttg ttcacggtcg cggacatggt gtcgtcttac tggctggcgc tgaccttcca   4440
ggcgaaccac gttgttgagg aagttcagtg gccgttgcct gacgagaacg ggatcatcca   4500
aaaggactgg gcagctatgc aggtcgagac tacgcaggat tacgcacacg attcgcacct   4560
ctggaccagc atcactggca gcttgaacta ccaggctgtg caccatctgt tccccaacgt   4620
gtcgcagcac cattatcccg atattctggc catcatcaag aacacctgca gcgagtacaa   4680
ggttccatac cttgtcaagg atacgttttg gcaagcattt gcttcacatt tggagcactt   4740
gcgtgttctt ggactccgtc ccaaggaaga gtaggcggcc gcatttcgca ccaaatcaat   4800
```

gaaagtaata atgaaaagtc tgaataagaa tacttaggct tagatgcctt tgttacttgt 4860
gtaaaataac ttgagtcatg tacctttggc ggaaacagaa taaataaaag gtgaaattcc 4920
aatgctctat gtataagtta gtaatactta atgtgttcta cggttgtttc aatatcatca 4980
aactctaatt gaaactttag aaccacaaat ctcaatcttt tcttaatgaa atgaaaaatc 5040
ttaattgtac catgtttatg ttaaacacct tacaattggt tggagaggag gaccaaccga 5100
tgggacaaca ttgggagaaa gagattcaat ggagatttgg ataggagaac aacattcttt 5160
ttcacttcaa tacaagatga gtgcaacact aaggatatgt atgagacttt cagaagctac 5220
gacaacatag atgagtgagg tggtgattcc tagcaagaaa gacattagag gaagccaaaa 5280
tcgaacaagg aagacatcaa gggcaagaga caggaccatc catctcagga aaaggagctt 5340
tgggatagtc cgagaagttg tacaagaaat tttttggagg gtgagtgatg cattgctggt 5400
gactttaact caatcaaaat tgagaaagaa agaaaaggga gggggctcac atgtgaatag 5460
aagggaaacg ggagaatttt acagttttga tctaatgggc atcccagcta gtggtaacat 5520
attcaccatg tttaaccttc acgtacgtct agaggatccc c 5561

<210> SEQ ID NO 46
<211> LENGTH: 8671
<212> TYPE: DNA
<213> ORGANISM: Artificial Sequence
<220> FEATURE:
<223> OTHER INFORMATION: the sequence of pKR328

<400> SEQUENCE: 46
ggatctggcc ggccggatct cgtacggatc cgtcgacggc gcgcccgatc atccggatat 60
agttcctcct ttcagcaaaa aacccctcaa gacccgttta gaggccccaa ggggttatgc 120
tagttattgc tcagcggtgg cagcagccaa ctcagcttcc tttcgggctt tgttagcagc 180
cggatcgatc caagctgtac ctcactattc ctttgccctc ggacgagtgc tggggcgtcg 240
gtttccacta tcggcgagta cttctacaca gccatcggtc cagacggccg cgcttctgcg 300
ggcgatttgt gtacgcccga cagtcccggc tccggatcgg acgattgcgt cgcatcgacc 360
ctgcgcccaa gctgcatcat cgaaattgcc gtcaaccaag ctctgataga gttggtcaag 420
accaatgcgg agcatatacg cccggagccg cggcgatcct gcaagctccg gatgcctccg 480
ctcgaagtag cgcgtctgct gctccataca agccaaccac ggcctccaga agaagatgtt 540
ggcgacctcg tattgggaat ccccgaacat cgcctcgctc cagtcaatga ccgctgttat 600
gcggccattg tccgtcagga cattgttgga gccgaaatcc gcgtgcacga ggtgccggac 660
ttcggggcag tcctcggccc aaagcatcag ctcatcgaga gcctgcgcga cggacgcact 720
gacggtgtcg tccatcacag tttgccagtg atacacatgg ggatcagcaa tcgcgcatat 780
gaaatcacgc catgtagtgt attgaccgat tccttgcggt ccgaatgggc cgaacccgct 840
cgtctggcta agatcggccg cagcgatcgc atccatagcc tccgcgaccg gctgcagaac 900
agcgggcagt tcggtttcag gcaggtcttg caacgtgaca ccctgtgcac ggcgggagat 960
gcaataggtc aggctctcgc tgaattcccc aatgtcaagc acttccggaa tcgggagcgc 1020
ggccgatgca aagtgccgat aaacataacg atctttgtag aaaccatcgg cgcagctatt 1080
tacccgcagg acatatccac gccctcctac atcgaagctg aaagcacgag attcttcgcc 1140
ctccgagagc tgcatcaggt cggagacgct gtcgaacttt tcgatcagaa acttctcgac 1200
agacgtcgcg gtgagttcag gcttttccat gggtatatct ccttcttaaa gttaaacaaa 1260

-continued

```
attatttcta gagggaaacc gttgtggtct ccctatagtg agtcgtatta atttcgcggg   1320
atcgagatcg atccaattcc aatcccacaa aaatctgagc ttaacagcac agttgctcct   1380
ctcagagcag aatcgggtat tcaacaccct catatcaact actacgttgt gtataacggt   1440
ccacatgccg gtatatacga tgactggggt tgtacaaagg cggcaacaaa cggcgttccc   1500
ggagttgcac acaagaaatt tgccactatt acagaggcaa gagcagcagc tgacgcgtac   1560
acaacaagtc agcaaacaga caggttgaac ttcatcccca aaggagaagc tcaactcaag   1620
cccaagagct ttgctaaggc cctaacaagc ccaccaaagc aaaaagccca ctggctcacg   1680
ctaggaacca aaaggcccag cagtgatcca gccccaaaag agatctcctt tgccccggag   1740
attacaatgg acgatttcct ctatctttac gatctaggaa ggaagttcga aggtgaaggt   1800
gacgacacta tgttcaccac tgataatgag aaggttagcc tcttcaattt cagaaagaat   1860
gctgacccac agatggttag agaggcctac gcagcaggtc tcatcaagac gatctacccg   1920
agtaacaatc tccaggagat caaatacctt cccaagaagg ttaaagatgc agtcaaaaga   1980
ttcaggacta attgcatcaa gaacacagag aaagacatat ttctcaagat cagaagtact   2040
attccagtat ggacgattca aggcttgctt cataaaccaa ggcaagtaat agagattgga   2100
gtctctaaaa aggtagttcc tactgaatct aaggccatgc atggagtcta agattcaaat   2160
cgaggatcta acagaactcg ccgtgaagac tggcgaacag ttcatacaga gtcttttacg   2220
actcaatgac aagaagaaaa tcttcgtcaa catggtggag cacgacactc tggtctactc   2280
caaaaatgtc aaagatacag tctcagaaga ccaaagggct attgagactt ttcaacaaag   2340
gataatttcg ggaaacctcc tcggattcca ttgcccagct atctgtcact tcatcgaaag   2400
gacagtagaa aaggaaggtg gctcctacaa atgccatcat tgcgataaag gaaaggctat   2460
cattcaagat gcctctgccg acagtggtcc caaagatgga cccccaccca cgaggagcat   2520
cgtggaaaaa gaagacgttc caaccacgtc ttcaaagcaa gtggattgat gtgacatctc   2580
cactgacgta agggatgacg cacaatccca ctatccttcg caagaccctt cctctatata   2640
aggaagttca tttcatttgg agaggacacg ctcgagctca tttctctatt acttcagcca   2700
taacaaaaga actcttttct cttcttatta aaccatgaaa aagcctgaac tcaccgcgac   2760
gtctgtcgag aagtttctga tcgaaaagtt cgacagcgtc tccgacctga tgcagctctc   2820
ggagggcgaa gaatctcgtg ctttcagctt cgatgtagga gggcgtggat atgtcctgcg   2880
ggtaaatagc tgcgccgatg gtttctacaa agatcgttat gtttatcggc actttgcatc   2940
ggccgcgctc ccgattccgg aagtgcttga cattggggaa ttcagcgaga gcctgaccta   3000
ttgcatctcc cgccgtgcac agggtgtcac gttgcaagac ctgcctgaaa ccgaactgcc   3060
cgctgttctg cagccggtcg cggaggccat ggatgcgatc gctgcggccg atcttagcca   3120
gacgagcggg ttcggcccat tcggaccgca aggaatcggt caatacacta catggcgtga   3180
tttcatatgc gcgattgctg atccccatgt gtatcactgg caaactgtga tggacgacac   3240
cgtcagtgcg tccgtcgcgc aggctctcga tgagctgatg ctttgggccg aggactgccc   3300
cgaagtccgg cacctcgtgc acgcggattt cggctccaac aatgtcctga cggacaatgg   3360
ccgcataaca gcggtcattg actggagcga ggcgatgttc ggggattccc aatacgaggt   3420
cgccaacatc ttcttctgga ggccgtggtt ggcttgtatg gagcagcaga cgcgctactt   3480
cgagcggagg catccggagc ttgcaggatc gccgcggctc cgggcgtata tgctccgcat   3540
tggtcttgac caactctatc agagcttggt tgacggcaat ttcgatgatg cagcttgggc   3600
gcagggtcga tgcgacgcaa tcgtccgatc cggagccggg actgtcgggc gtacacaaat   3660
```

-continued cgcccgcaga agcgcggccg tctggaccga tggctgtgta gaagtactcg ccgatagtgg 3720
aaaccgacgc cccagcactc gtccgagggc aaaggaatag tgaggtacct aaagaaggag 3780
tgcgtcgaag cagatcgttc aaacatttgg caataaagtt tcttaagatt gaatcctgtt 3840
gccggtcttg cgatgattat catataattt ctgttgaatt acgttaagca tgtaataatt 3900
aacatgtaat gcatgacgtt atttatgaga tgggttttta tgattagagt cccgcaatta 3960
tacatttaat acgcgataga aaacaaaata tagcgcgcaa actaggataa attatcgcgc 4020
gcggtgtcat ctatgttact agatcgatgt cgaatcgatc aacctgcatt aatgaatcgg 4080
ccaacgcgcg gggagaggcg gtttgcgtat tgggcgctct tccgcttcct cgctcactga 4140
ctcgctgcgc tcggtcgttc ggctgcggcg agcggtatca gctcactcaa aggcggtaat 4200
acggttatcc acagaatcag gggataacgc aggaaagaac atgtgagcaa aaggccagca 4260
aaaggccagg aaccgtaaaa aggccgcgtt gctggcgttt ttccataggc tccgcccccc 4320
tgacgagcat cacaaaaatc gacgctcaag tcagaggtgg cgaaacccga caggactata 4380
aagataccag gcgtttcccc ctggaagctc cctcgtgcgc tctcctgttc cgaccctgcc 4440
gcttaccgga tacctgtccg cctttctccc ttcgggaagc gtggcgcttt ctcaatgctc 4500
acgctgtagg tatctcagtt cggtgtaggt cgttcgctcc aagctgggct gtgtgcacga 4560
accccccgtt cagcccgacc gctgcgcctt atccggtaac tatcgtcttg agtccaaccc 4620
ggtaagacac gacttatcgc cactggcagc agccactggt aacaggatta gcagagcgag 4680
gtatgtaggc ggtgctacag agttcttgaa gtggtggcct aactacggct acactagaag 4740
gacagtattt ggtatctgcg ctctgctgaa gccagttacc ttcggaaaaa gagttggtag 4800
ctcttgatcc ggcaaacaaa ccaccgctgg tagcggtggt ttttttgttt gcaagcagca 4860
gattacgcgc agaaaaaaag gatctcaaga agatcctttg atcttttcta cggggtctga 4920
cgctcagtgg aacgaaaact cacgttaagg gattttggtc atgacattaa cctataaaaa 4980
taggcgtatc acgaggccct ttcgtctcgc gcgtttcggt gatgacggtg aaaacctctg 5040
acacatgcag ctcccggaga cggtcacagc ttgtctgtaa gcggatgccg ggagcagaca 5100
agcccgtcag ggcgcgtcag cgggtgttgg cgggtgtcgg ggctggctta actatgcggc 5160
atcagagcag attgtactga gagtgcacca tatggacata ttgtcgttag aacgcggcta 5220
caattaatac ataaccttat gtatcataca catacgattt aggtgacact atagaacggc 5280
gcgccaagct tggatctcct gcagcccggg ggatccgccc acgtacggta ccatctgcta 5340
atattttaaa tcacatgcaa gagaggaggc atggttccat tttctacctt cacattattt 5400
gagaaaaacg aacttgttct gtgttttatt tttgcccttc acattagtac aacgtggaag 5460
actcatggtt acacagaatc atacataagt acaatgcttg tccctaagaa aacaagcact 5520
cgttgtattg aacctttacg gctcatgcgg ccgcgaattc actagtgatt gaattcgcgg 5580
ccgcttagtc cgacttggcc ttggcggccg cggccgactc tttgagcgtg aagatctgcg 5640
ccgtctcggg cacagcgccg tagttgacaa agaggtgcgc ggtcttgaag aaggccgtga 5700
tgatgggctc gtcgttcctg cgcacgaggt gcgggtacgc ggccgcaaag tgcttggtgg 5760
cttcgttgag cttgtagtgc ggaatgatcg ggaacaagtg gtggacctgg tgcgtgccaa 5820
tgtggtggct caggttgtcc acgaacgcgc cgtacgagcg gtcgacgctc gagaggttgc 5880
ccttgacgta cgtccactcc gagtcgccgt accacggcgt cgcttcgtcg ttgtggtgca 5940
agaaggtcgt aatgacgagg aacgaagcaa agacaaagag cggcgcatag tagtagaggc 6000

```
ccatgacggc aaagccgagc gagtatgtga ggtacgcgta cgcggcgaag aaggcggccc   6060
agacgccgag cgacacgatg acggccgacg cgcggcgaag gaggagcggg tcccacgggt   6120
caaagtggct catcgtgcgc ggggcatacc cgaccttcaa gtagacaaac cacgcaccgc   6180
cgagcgtgta gacccattgg cgcacgtcct ggaggtcctt gaccgaccgg tgcgggtaaa   6240
agatctcgtc cttatcaatg ttgcccgtgt tcttgtggtg gtggcggtgc gtcacgcgcc   6300
agctctcgaa cggcgtcaaa atcgcagagt gcatgatgca gccgatgata aagttgacgc   6360
tgtggtagcg cgagaaggcc gagtggccgc agtcgtggcc gaccgtgaag aagccccaga   6420
agatgacgcc ctgcacgtag atgtaggtgg cgcaaacgag cgcgtggagc agaacgttat   6480
cggcaatgaa cggcgtcgag cgcgccgcgt agagcagcgc cgccgaggcc gacgcgttga   6540
agatcgcgcg ggccgtgtag tagagcgaga ggccgaggtt cgactcaaag cacgcgttcg   6600
ggatcgagtg cttgagctcc gtgagcgtcg ggaactcgac cttcgtctta tcctcagtca   6660
tgcggccgct gaagtattgc ttcttagtta acctttcctt tctctctcag ctatgtgaat   6720
tcattttgct ttcgtcacaa tttatatagt gaaattggat ctttggagtt aacgccttca   6780
caggattatc gtgttagaac aatgcttttt catgttctaa ttagtagtac attacaaatg   6840
tgcactctat tcaataagca tcttttggca cgttaataaa tcatgtgaaa aaaaaatact   6900
actatttcaa agaaagtgtt gtaaaaagaa acggaaagag agctggcttc agttgttgag   6960
acttgtttgc tagtaaaaat ggtgtgaaga gtgattcatg gtgaggtggt ttttcgtccc   7020
tttctgtttg catgaaaaac aaatggcaag agatgacgta ggattccttc ccttaacgat   7080
tatctgtttt taatttcaaa tatacatata ggaatttatg aattactaag gttgtaaaat   7140
atgctggtca tttatttatg gctaaaatat tttttttct cgtaaatata aaaatattta   7200
aaatttattt ttatcatatt ttttatcctt ataaaattat gtgtacaacc tatataaaaa   7260
aatatcatat ttaatattga ttatatgttt aatcaatata aaaaatcatt atcatatatt   7320
tagatttatt cgaatataca tctaaacaaa aaataacata ttttaatttt atgaagaaaa   7380
aaaaatattt tatcctttat ttatttaaga ttaattaata gttatgtatt gtggaaagac   7440
ttttacacat gcaatagata tactgaatca attagatgcc aatgctgagt tggaaatcac   7500
ttgaggaggg gaggagactt gccaatgctt ttcagtttca tttaaatgat ttagtggagg   7560
agatagagta gtgataaagg catgccccaa ttttggagtg tatatatgag tggaaataag   7620
agagggatag agagaaaaaa taaagagagt aaaaataatt aatgtgaaat gatatgataa   7680
aaaaataaag aaagagataa agagaaaaat gaaatgagag atagatgaaa tagagagtag   7740
atacatgttt gtttaggttt tttttaggaa ataacacatt tttttctcat cacttattac   7800
tcactgtcaa tttcctctct ttcaatcata atgatatgat ttgtttaaca aaaatgtgaa   7860
aaaacatata aagtaaaata tttttataaa ttgataaata aaaatttaca aaatttattt   7920
cttattaaat tgaatagaaa atgaaagaaa agaaaagaaa aagtatatat aaaatgatat   7980
agctttaaaa agaataaatt tttcatatca gtcttttttt aataatttag aaatatttaa   8040
gtatatagca aaaatataat gtactttaca tatgcataaa taataatttg aaaatagaac   8100
taatagaata gagaaaaaag taatataata attaactata tgaaaattta gaagggacaa   8160
tatttttaat taagaatata aacaatattt cttttcatgt aatgagggac ggatgtacgg   8220
ggccagtgtt ggagtcaaag ccaaaatagt cacggggaaa ttaatgcact gcatgactat   8280
tcgaaaaaat tcactagcct tacttagatg ttagattaat agctaggggg tgcagataat   8340
tttgaaaggc atgaaaaaca ttaatttgta cattgcaagc ttttgatgac aagctttgca   8400
```

attgttcaca ctaccttatg ccatttataa atagagtgat tggcatatga aggaaatcat 8460
gagagtcgaa gcgaaaaaca aagcttgaga gtgtaggaaa aatacagttt ttttggtaaa 8520
aatacagtat ttgaatagga gcgaaaaata tcctttcaaa atgatccttt tctttttttt 8580
tttttttctt gttgttcttg gtcagttatt caaaggaaaa gggattgaaa taaaaacttg 8640
catgtgggat cgtacgtcga gtcgacctgc a 8671

<210> SEQ ID NO 47
<211> LENGTH: 9892
<212> TYPE: DNA
<213> ORGANISM: Artificial Sequence
<220> FEATURE:
<223> OTHER INFORMATION: the sequence of pKR886

<400> SEQUENCE: 47
ggtcgactcg acgtacgtct agaggatccg tcgacggcgc gcccgatcat ccggatatag 60
ttcctccttt cagcaaaaaa cccctcaaga cccgtttaga ggccccaagg ggttatgcta 120
gttattgctc agcggtggca gcagccaact cagcttcctt tcgggctttg ttagcagccg 180
gatcgatcca agctgtacct cactattcct ttgccctcgg acgagtgctg gggcgtcggt 240
ttccactatc ggcgagtact tctacacagc catcggtcca gacggccgcg cttctgcggg 300
cgatttgtgt acgcccgaca gtcccggctc cggatcggac gattgcgtcg catcgaccct 360
gcgcccaagc tgcatcatcg aaattgccgt caaccaagct ctgatagagt tggtcaagac 420
caatgcggag catatacgcc cggagccgcg gcgatcctgc aagctccgga tgcctccgct 480
cgaagtagcg cgtctgctgc tccatacaag ccaaccacgg cctccagaag aagatgttgg 540
cgacctcgta ttgggaatcc ccgaacatcg cctcgctcca gtcaatgacc gctgttatgc 600
ggccattgtc cgtcaggaca ttgttggagc cgaaatccgc gtgcacgagg tgccggactt 660
cggggcagtc ctcggcccaa agcatcagct catcgagagc ctgcgcgacg gacgcactga 720
cggtgtcgtc catcacagtt tgccagtgat acacatgggg atcagcaatc gcgcatatga 780
aatcacgcca tgtagtgtat tgaccgattc cttgcggtcc gaatgggccg aacccgctcg 840
tctggctaag atcggccgca gcgatcgcat ccatagcctc cgcgaccggc tgcagaacag 900
cgggcagttc ggtttcaggc aggtcttgca acgtgacacc ctgtgcacgg cgggagatgc 960
aataggtcag gctctcgctg aattccccaa tgtcaagcac ttccggaatc gggagcgcgg 1020
ccgatgcaaa gtgccgataa acataacgat ctttgtagaa accatcggcg cagctattta 1080
cccgcaggac atatccacgc cctcctacat cgaagctgaa agcacgagat tcttcgccct 1140
ccgagagctg catcaggtcg gagacgctgt cgaacttttc gatcagaaac ttctcgacag 1200
acgtcgcggt gagttcaggc ttttccatgg gtatatctcc ttcttaaagt taaacaaaat 1260
tatttctaga gggaaaccgt tgtggtctcc ctatagtgag tcgtattaat ttcgcgggat 1320
cgagatctga tcaacctgca ttaatgaatc ggccaacgcg cggggagagg cggtttgcgt 1380
attgggcgct cttccgcttc ctcgctcact gactcgctgc gctcggtcgt tcggctgcgg 1440
cgagcggtat cagctcactc aaaggcggta atacggttat ccacagaatc aggggataac 1500
gcaggaaaga acatgtgagc aaaaggccag caaaaggcca ggaaccgtaa aaaggccgcg 1560
ttgctggcgt ttttccatag gctccgcccc cctgacgagc atcacaaaaa tcgacgctca 1620
agtcagaggt ggcgaaaccc gacaggacta taaagatacc aggcgtttcc ccctggaagc 1680
tccctcgtgc gctctcctgt tccgaccctg ccgcttaccg gatacctgtc cgcctttctc 1740

-continued

```
ccttcgggaa gcgtggcgct ttctcaatgc tcacgctgta ggtatctcag ttcggtgtag   1800
gtcgttcgct ccaagctggg ctgtgtgcac gaaccccccg ttcagcccga ccgctgcgcc   1860
ttatccggta actatcgtct tgagtccaac ccggtaagac acgacttatc gccactggca   1920
gcagccactg gtaacaggat tagcagagcg aggtatgtag gcggtgctac agagttcttg   1980
aagtggtggc ctaactacgg ctacactaga aggacagtat ttggtatctg cgctctgctg   2040
aagccagtta ccttcggaaa aagagttggt agctcttgat ccggcaaaca aaccaccgct   2100
ggtagcggtg gtttttttgt ttgcaagcag cagattacgc gcagaaaaaa aggatctcaa   2160
gaagatcctt tgatcttttc tacggggtct gacgctcagt ggaacgaaaa ctcacgttaa   2220
gggattttgg tcatgacatt aacctataaa aataggcgta tcacgaggcc ctttcgtctc   2280
gcgcgtttcg gtgatgacgg tgaaaacctc tgacacatgc agctcccgga gacggtcaca   2340
gcttgtctgt aagcggatgc cgggagcaga caagcccgtc agggcgcgtc agcgggtgtt   2400
ggcgggtgtc ggggctggct taactatgcg gcatcagagc agattgtact gagagtgcac   2460
catatggaca tattgtcgtt agaacgcggc tacaattaat acataacctt atgtatcata   2520
cacatacgat ttaggtgaca ctatagaacg gcgcgccaag ctgggtctag aactagaaac   2580
gtgatgccac ttgttattga agtcgattac agcatctatt ctgttttact atttataact   2640
ttgccatttc tgacttttga aaactatctc tggatttcgg tatcgctttg tgaagatcga   2700
gcaaaagaga cgttttgtgg acgcaatggt ccaaatccgt tctacatgaa caaattggtc   2760
acaatttcca ctaaaagtaa ataaatggca agttaaaaaa ggaatatgca ttttactgat   2820
tgcctaggtg agctccaaga gaagttgaat ctacacgtct accaaccgct aaaaaaagaa   2880
aaacattgat atgtaacctg attccattag cttttgactt cttcaacaga ttctctactt   2940
agatttctaa cagaaatatt attactagca catcattttc agtctcacta cagcaaaaaa   3000
tccaacggca caatacagac aacaggagat atcagactac agagatagat agatgctact   3060
gcatgtagta agttaaataa aaggaaaata aaatgtcttg ctaccaaaac tactacagac   3120
tatgatgctc accacaggcc aaatcctgca actaggacag cattatctta tatatattgt   3180
acaaaaacaag catcaaggaa catttggtct aggcaatcag tacctcgttc taccatcacc   3240
ctcagttatc acatccttga aggatccatt actgggaatc atcggcaaca catgctcctg   3300
atggggcaca atgacatcaa gaaggtaggg gccaggggtg tccaacattc tctgaattgc   3360
cgctctaagc tcttccttct tcgtcactcg cgctgccggt atcccacaag catcagcaaa   3420
cttgagcatg tttgggaata tctcgctctc gctagacgga tctccaagat aggtgtgagc   3480
tctattggac ttgtagaacc tatcctccaa ctgaaccacc atacccaaat gctgattgtt   3540
caacaacaat atcttaactg ggagattctc cactcttata gtggccaact cctgaacatt   3600
catgatgaaa ctaccatccc catcaatgtc aaccacaaca gccccagggt tagcaacagc   3660
agcaccaata gccgcaggca atccaaaacc catggctcca agacccccctg aggtcaacca   3720
ctgcctcggt ctcttgtact tgtaaaactg cgcagcccac atttgatgct gcccaacccc   3780
agtactaaca atagcatctc cattagtcaa ctcatcaaga acctcgatag catgctgcgg   3840
agaaatcgcg tcctggaatg tcttgtaacc caatggaaac ttgtgtttct gcacattaat   3900
ctcttctctc caacctccaa gatcaaactt accctccact cctttctcct ccaaaatcat   3960
attaattccc ttcaaggcca acttcaaatc cgcgcaaacc gacacgtgcg cctgcttgtt   4020
cttcccaatc tcggcagaat caatatcaat gtgaacaatc ttagccctac tagcaaaagc   4080
ctcaagcttc ccagtaacac ggtcatcaaa ccttacccca aaggcaagca acaaatcact   4140
```

-continued

```
attgtcaaca gcatagttag cataaacagt accatgcata cccagcatct gaagggaata   4200
ttcatcacca ataggaaaag ttccaagacc cattaaagtg ctagcaacgg gaataccagt   4260
gagttcaaca aagcgcctca attcagcact ggaattcaaa ctgccaccgc cgacgtagag   4320
aacgggcttt tgggcctcca tgatgagtct gacaatgtgt tccaattggg cctcggcggg   4380
gggcctgggc agcctggcga ggtaaccggg gaggttaacg ggctcgtccc aattaggcac   4440
ggcgagttgc tgctgaacgt ctttgggaat gtcgatgagg accggaccgg ggcggccgga   4500
ggtggcgacg aagaaagcct cggcgacgac gcgggggatg tcgtcgacgt cgaggatgag   4560
gtagttgtgc ttcgtgatgg atctgctcac ctccacgatc ggggtttctt ggaaggcgtc   4620
ggtgccgatc atccggcggg cgacctggcc ggtgatggcg acgactggga cgctgtccat   4680
taaagcgtcg gcgaggccgc tcacgaggtt ggtggcgccg gggccggagg tggcaatgca   4740
gacgccgggg aggccggagg aacgcgcgta gccttcggcg gcgaagacgc cgccctgctc   4800
gtggcgcggg agcacgttgc ggatggcggc ggagcgcgtg agcgcctggt ggatctccat   4860
cgacgcaccg ccggggtacg cgaacaccgt cgtcacgccc tgcctctcca gcgcctccac   4920
aaggatgtcc gcgcccttgc gaggttcgcc ggaggcgaac cgtgacacga agggctccgt   4980
ggtcggcgct tccttggtga agggcgccgc cgtggggggt ttggagatgg aacatttgat   5040
tttgagagcg tggttgggtt tggtgagggt ttgatgagag agagggaggg tggatctagt   5100
aatgcgtttg gggaaggtgg ggtgtgaaga ggaagaagag aatcgggtgg ttctggaagc   5160
ggtggccgcc attgtgttgt gtggcatggt tatacttcaa aaactgcaca acaagcctag   5220
agttagtacc taaacagtaa atttacaaca gagagcaaag acacatgcaa aaatttcagc   5280
cataaaaaaa gttataatag aatttaaagc aaaagtttca ttttttaaac atatatacaa   5340
acaaactgga tttgaaggaa gggattaatt cccctgctca aagtttgaat tcctattgtg   5400
acctatactc gaataaaatt gaagcctaag gaatgtatga gaaacaagaa aacaaaacaa   5460
aactacagac aaacaagtac aattacaaaa ttcgctaaaa ttctgtaatc accaaacccc   5520
atctcagtca gcacaaggcc caaggtttat tttgaaataa aaaaaaagtg attttatttc   5580
tcataagcta aaagaaagaa aggcaattat gaaatgattt cgactagatc tgaaagtcca   5640
acgcgtattc cgcagatatt aaagaaagag tagagtttca catggatcct agatggaccc   5700
agttgaggaa aaagcaaggc aaagcaaacc agaagtgcaa gatccgaaat tgaaccacgg   5760
aatctaggat ttggtagagg gagaagaaaa gtaccttgag aggtagaaga gaagagaaga   5820
gcagagagat atatgaacga gtgtgtcttg gtctcaactc tgaagcgata cgagtttaga   5880
ggggagcatt gagttccaat ttatagggaa accgggtggc aggggtgagt taatgacgga   5940
aaagccccta agtaacgaga ttggattgtg ggttagattc aaccgtttgc atccgcggct   6000
tagattgggg aagtcagagt gaatctcaac cgttgactga gttgaaaatt gaatgtagca   6060
accaattgag ccaaccccag cctttgccct ttgattttga tttgtttgtt gcatactttt   6120
tatttgtctt ctggttctga ctctctttct ctcgtttcaa tgccaggttg cctactccca   6180
caccactcac aagaagattc tactgttagt attaaatatt ttttaatgta ttaaatgatg   6240
aatgcttttg taaacagaac aagactatgt ctaataagtg tcttgcaaca ttttttaaga   6300
aattaaaaaa aatatattta ttatcaaaat caaatgtatg aaaaatcatg aataatataa   6360
ttttatacat ttttttaaaa aatcttttaa tttcttaatt aatatcttaa aaataatgat   6420
taatatttaa cccaaaataa ttagtatgat tggtaaggaa gatatccatg ttatgtttgg   6480
```

```
atgtgagttt gatctagagc aaagcttact agagtcgacc tgcaggtcga ctcgacgtac   6540
gatcccacat gcaagttttt atttcaatcc cttttccttt gaataactga ccaagaacaa   6600
caagaaaaaa aaaaaaaaag aaaaggatca ttttgaaagg atatttttcg ctcctattca   6660
aatactgtat ttttaccaaa aaaactgtat ttttcctaca ctctcaagct ttgtttttcg   6720
cttcgactct catgatttcc ttcatatgcc aatcactcta tttataaatg gcataaggta   6780
gtgtgaacaa ttgcaaagct tgtcatcaaa agcttgcaat gtacaaatta atgtttttca   6840
tgcctttcaa aattatctgc accccctagc tattaatcta acatctaagt aaggctagtg   6900
aatttttcg aatagtcatg cagtgcatta atttccccgt gactattttg gctttgactc   6960
caacactggc cccgtacatc cgtccctcat tacatgaaaa gaaatattgt ttatattctt   7020
aattaaaaat attgtccctt ctaaattttc atatagttaa ttattatatt acttttttct   7080
ctattctatt agttctattt tcaaattatt atttatgcat atgtaaagta cattatattt   7140
ttgctatata cttaaatatt tctaaattat taaaaaaaga ctgatatgaa aaatttattc   7200
tttttaaagc tatatcattt tatatatact ttttcttttc ttttctttca ttttctattc   7260
aatttaataa gaaataaatt ttgtaaattt ttatttatca atttataaaa atattttact   7320
ttatatgttt tttcacattt ttgttaaaca aatcatatca ttatgattga aagagaggaa   7380
attgacagtg agtaataagt gatgagaaaa aaatgtgtta tttcctaaaa aaaacctaaa   7440
caaacatgta tctactctct atttcatcta tctctcattt cattttctc tttatctctt   7500
tctttatttt tttatcatat catttcacat taattatttt tactctcttt attttttctc   7560
tctatccctc tcttatttcc actcatatat acactccaaa attggggcat gcctttatca   7620
ctactctatc tcctccacta aatcatttaa atgaaactga aaagcattgg caagtctcct   7680
cccctcctca agtgatttcc aactcagcat tggcatctaa ttgattcagt atatctattg   7740
catgtgtaaa agtctttcca caatacataa ctattaatta atcttaaata aataaaggat   7800
aaaatatttt tttttcttca taaaattaaa atatgttatt ttttgtttag atgtatattc   7860
gaataaatct aaatatatga taatgatttt ttatattgat taaacatata atcaatatta   7920
aatatgatat ttttttatat aggttgtaca cataatttta taaggataaa aaatatgata   7980
aaaataaatt ttaaatattt ttatatttac gagaaaaaaa aatattttag ccataaataa   8040
atgaccagca tattttacaa ccttagtaat tcataaattc ctatatgtat atttgaaatt   8100
aaaaacagat aatcgttaag ggaaggaatc ctacgtcatc tcttgccatt tgtttttcat   8160
gcaaacagaa agggacgaaa aaccacctca ccatgaatca ctcttcacac catttttact   8220
agcaaacaag tctcaacaac tgaagccagc tctctttccg tttcttttta caacactttc   8280
tttgaaatag tagtattttt ttttcacatg atttattaac gtgccaaaag atgcttattg   8340
aatagagtgc acatttgtaa tgtactacta attagaacat gaaaaagcat tgttctaaca   8400
cgataatcct gtgaaggcgt taactccaaa gatccaattt cactatataa attgtgacga   8460
aagcaaaatg aattcacata gctgagagag aaaggaaagg ttaactaaga agcaatactt   8520
cagcggccgc atgactgagg ataagacgaa ggtcgagttc ccgacgctca cggagctcaa   8580
gcactcgatc ccgaacgcgt gctttgagtc gaacctcggc ctctcgctct actacacggc   8640
ccgcgcgatc ttcaacgcgt cggcctcggc ggcgctgctc tacgcggcgc gctcgacgcc   8700
gttcattgcc gataacgttc tgctccacgc gctcgtttgc gccacctaca tctacgtgca   8760
gggcgtcatc ttctggggct tcttcacggt cggccacgac tgcggccact cggccttctc   8820
gcgctaccac agcgtcaact ttatcatcgg ctgcatcatg cactctgcga ttttgacgcc   8880
```

```
gttcgagagc tggcgcgtga cgcaccgcca ccaccacaag aacacgggca acattgataa   8940
ggacgagatc ttttacccgc accggtcggt caaggacctc caggacgtgc gccaatgggt   9000
ctacacgctc ggcggtgcgt ggtttgtcta cttgaaggtc gggtatgccc cgcgcacgat   9060
gagccacttt gacccgtggg acccgctcct ccttcgccgc gcgtcggccg tcatcgtgtc   9120
gctcggcgtc tgggccgcct tcttcgccgc gtacgcgtac ctcacatact cgctcggctt   9180
tgccgtcatg ggcctctact actatgcgcc gctctttgtc tttgcttcgt tcctcgtcat   9240
tacgaccttc ttgcaccaca acgacgaagc gacgccgtgg tacggcgact cggagtggac   9300
gtacgtcaag ggcaacctct cgagcgtcga ccgctcgtac ggcgcgttcg tggacaacct   9360
gagccaccac attggcacgc accaggtcca ccacttgttc ccgatcattc cgcactacaa   9420
gctcaacgaa gccaccaagc actttgcggc cgcgtacccg cacctcgtgc gcaggaacga   9480
cgagcccatc atcacggcct tcttcaagac cgcgcacctc tttgtcaact acggcgctgt   9540
gcccgagacg gcgcagatct tcacgctcaa agagtcggcc gcggccgcca aggccaagtc   9600
ggactaagcg gccgcgaatt caatcactag tgaattcgcg gccgcatgag ccgtaaaggt   9660
tcaatacaac gagtgcttgt ttcttaggg acaagcattg tacttatgta tgattctgtg    9720
taaccatgag tcttccacgt tgtactaatg tgaagggcaa aaataaaaca cagaacaagt   9780
tcgtttttct caaataatgt gaaggtagaa aatggaacca tgcctcctct cttgcatgtg   9840
atttaaaata ttagcagatg gtaccgtacg tgggcggatc ccccgggctg ca           9892
```

<210> SEQ ID NO 48
<211> LENGTH: 9892
<212> TYPE: DNA
<213> ORGANISM: Artificial Sequence
<220> FEATURE:
<223> OTHER INFORMATION: the sequence of pKR886r

<400> SEQUENCE: 48

```
ggtcgactcg acgtacgtct agaggatccg tcgacggcgc gcccgatcat ccggatatag     60
ttcctccttt cagcaaaaaa cccctcaaga cccgtttaga ggccccaagg ggttatgcta    120
gttattgctc agcggtggca gcagccaact cagcttcctt tcgggctttg ttagcagccg    180
gatcgatcca agctgtacct cactattcct ttgccctcgg acgagtgctg gggcgtcggt    240
ttccactatc ggcgagtact tctacacagc catcggtcca gacggccgcg cttctgcggg    300
cgatttgtgt acgcccgaca gtcccggctc cggatcggac gattgcgtcg catcgaccct    360
gcgcccaagc tgcatcatcg aaattgccgt caaccaagct ctgatagagt tggtcaagac    420
caatgcggag catatacgcc cggagccgcg gcgatcctgc aagctccgga tgcctccgct    480
cgaagtagcg cgtctgctgc tccatacaag ccaaccacgg cctccagaag aagatgttgg    540
cgacctcgta ttgggaatcc ccgaacatcg cctcgctcca gtcaatgacc gctgttatgc    600
ggccattgtc cgtcaggaca ttgttggagc cgaaatccgc gtgcacgagg tgccggactt    660
cggggcagtc ctcggcccaa agcatcagct catcgagagc ctgcgcgacg gacgcactga    720
cggtgtcgtc catcacagtt tgccagtgat acacatgggg atcagcaatc gcgcatatga    780
aatcacgcca tgtagtgtat tgaccgattc cttgcggtcc gaatgggccg aacccgctcg    840
tctggctaag atcggccgca gcgatcgcat ccatagcctc cgcgaccggc tgcagaacag    900
cgggcagttc ggtttcaggc aggtcttgca acgtgacacc ctgtgcacgg cgggagatgc    960
aataggtcag gctctcgctg aattccccaa tgtcaagcac ttccggaatc gggagcgcgg   1020
```

-continued

```
ccgatgcaaa gtgccgataa acataacgat ctttgtagaa accatcggcg cagctattta   1080
cccgcaggac atatccacgc cctcctacat cgaagctgaa agcacgagat tcttcgccct   1140
ccgagagctg catcaggtcg gagacgctgt cgaacttttc gatcagaaac ttctcgacag   1200
acgtcgcggt gagttcaggc ttttccatgg gtatatctcc ttcttaaagt taaacaaaat   1260
tatttctaga gggaaaccgt tgtggtctcc ctatagtgag tcgtattaat ttcgcgggat   1320
cgagatctga tcaacctgca ttaatgaatc ggccaacgcg cggggagagg cggtttgcgt   1380
attgggcgct cttccgcttc ctcgctcact gactcgctgc gctcggtcgt tcggctgcgg   1440
cgagcggtat cagctcactc aaaggcggta atacggttat ccacagaatc aggggataac   1500
gcaggaaaga acatgtgagc aaaaggccag caaaaggcca ggaaccgtaa aaaggccgcg   1560
ttgctggcgt ttttccatag gctccgcccc cctgacgagc atcacaaaaa tcgacgctca   1620
agtcagaggt ggcgaaaccc gacaggacta taaagatacc aggcgtttcc ccctggaagc   1680
tccctcgtgc gctctcctgt tccgaccctg ccgcttaccg gatacctgtc cgcctttctc   1740
ccttcgggaa gcgtggcgct ttctcaatgc tcacgctgta ggtatctcag ttcggtgtag   1800
gtcgttcgct ccaagctggg ctgtgtgcac gaaccccccg ttcagcccga ccgctgcgcc   1860
ttatccggta actatcgtct tgagtccaac ccggtaagac acgacttatc gccactggca   1920
gcagccactg gtaacaggat tagcagagcg aggtatgtag gcggtgctac agagttcttg   1980
aagtggtggc ctaactacgg ctacactaga aggacagtat ttggtatctg cgctctgctg   2040
aagccagtta ccttcggaaa aagagttggt agctcttgat ccggcaaaca aaccaccgct   2100
ggtagcggtg gtttttttgt ttgcaagcag cagattacgc gcagaaaaaa aggatctcaa   2160
gaagatcctt tgatcttttc tacggggtct gacgctcagt ggaacgaaaa ctcacgttaa   2220
gggattttgg tcatgacatt aacctataaa aataggcgta tcacgaggcc ctttcgtctc   2280
gcgcgtttcg gtgatgacgg tgaaaacctc tgacacatgc agctcccgga gacggtcaca   2340
gcttgtctgt aagcggatgc cgggagcaga caagcccgtc agggcgcgtc agcgggtgtt   2400
ggcgggtgtc ggggctggct taactatgcg gcatcagagc agattgtact gagagtgcac   2460
catatggaca tattgtcgtt agaacgcggc tacaattaat acataacctt atgtatcata   2520
cacatacgat ttaggtgaca ctatagaacg gcgcgccaag ctgggtctag aactagaaac   2580
gtgatgccac ttgttattga agtcgattac agcatctatt ctgttttact atttataact   2640
ttgccatttc tgacttttga aaactatctc tggatttcgg tatcgctttg tgaagatcga   2700
gcaaaagaga cgttttgtgg acgcaatggt ccaaatccgt tctacatgaa caaattggtc   2760
acaatttcca ctaaaagtaa ataaatggca agttaaaaaa ggaatatgca ttttactgat   2820
tgcctaggtg agctccaaga gaagttgaat ctacacgtct accaaccgct aaaaaaagaa   2880
aaacattgat atgtaacctg attccattag cttttgactt cttcaacaga ttctctactt   2940
agatttctaa cagaaatatt attactagca catcattttc agtctcacta cagcaaaaaa   3000
tccaacggca caatacagac aacaggagat atcagactac agagatagat agatgctact   3060
gcatgtagta agttaaataa aaggaaaata aaatgtcttg ctaccaaaac tactacagac   3120
tatgatgctc accacaggcc aaatcctgca actaggacag cattatctta tatatattgt   3180
acaaaacaag catcaaggaa catttggtct aggcaatcag tacctcgttc taccatcacc   3240
ctcagttatc acatccttga aggatccatt actgggaatc atcggcaaca catgctcctg   3300
atggggcaca atgacatcaa gaaggtaggg gccaggggtg tccaacattc tctgaattgc   3360
cgctctaagc tcttccttct tcgtcactcg cgctgccggt atcccacaag catcagcaaa   3420
```

```
cttgagcatg tttgggaata tctcgctctc gctagacgga tctccaagat aggtgtgagc   3480
tctattggac ttgtagaacc tatcctccaa ctgaaccacc atacccaaat gctgattgtt   3540
caacaacaat atcttaactg ggagattctc cactcttata gtggccaact cctgaacatt   3600
catgatgaaa ctaccatccc catcaatgtc aaccacaaca gccccagggt tagcaacagc   3660
agcaccaata gccgcaggca atccaaaacc catggctcca agaccccctg aggtcaacca   3720
ctgcctcggt ctcttgtact tgtaaaactg cgcagcccac atttgatgct gcccaacccc   3780
agtactaaca atagcatctc cattagtcaa ctcatcaaga acctcgatag catgctgcgg   3840
agaaatcgcg tcctggaatg tcttgtaacc caatggaaac ttgtgtttct gcacattaat   3900
ctcttctctc caacctccaa gatcaaactt accctccact cctttctcct ccaaaatcat   3960
attaattccc ttcaaggcca acttcaaatc cgcgcaaacc gacacgtgcg cctgcttgtt   4020
cttcccaatc tcggcagaat caatatcaat gtgaacaatc ttagccctac tagcaaaagc   4080
ctcaagcttc ccagtaacac ggtcatcaaa ccttacccca aaggcaagca acaaatcact   4140
attgtcaaca gcatagttag cataaacagt accatgcata cccagcatct gaagggaata   4200
ttcatcacca ataggaaaag ttccaagacc cattaaagtg ctagcaacgg gaataccagt   4260
gagttcaaca aagcgcctca attcagcact ggaattcaaa ctgccaccgc cgacgtagag   4320
aacgggcttt tgggcctcca tgatgagtct gacaatgtgt tccaattggg cctcggcggg   4380
gggcctgggc agcctggcga ggtaaccggg gaggttaacg ggctcgtccc aattaggcac   4440
ggcgagttgc tgctgaacgt ctttgggaat gtcgatgagg accggaccgg ggcggccgga   4500
ggtggcgacg aagaaagcct cggcgacgac gcgggggatg tcgtcgacgt cgaggatgag   4560
gtagttgtgc ttcgtgatgg atctgctcac ctccacgatc ggggtttctt ggaaggcgtc   4620
ggtgccgatc atccggcggg cgacctggcc ggtgatggcg acgactggga cgctgtccat   4680
taaagcgtcg gcgaggccgc tcacgaggtt ggtggcgccg gggccggagg tggcaatgca   4740
gacgccgggg aggccggagg aacgcgcgta gccttcggcg gcgaagacgc cgccctgctc   4800
gtggcgcggg agcacgttgc ggatggcggc ggagcgcgtg agcgcctggt ggatctccat   4860
cgacgcaccg ccggggtacg cgaacaccgt cgtcacgccc tgcctctcca gcgcctccac   4920
aaggatgtcc gcgcccttgc gaggttcgcc ggaggcgaac cgtgacacga agggctccgt   4980
ggtcggcgct tccttggtga agggcgccgc cgtggggggt ttggagatgg aacatttgat   5040
tttgagagcg tggttgggtt tggtgagggt ttgatgagag agagggaggg tggatctagt   5100
aatgcgtttg gggaaggtgg ggtgtgaaga ggaagaagag aatcgggtgg ttctggaagc   5160
ggtggccgcc attgtgttgt gtggcatggt tatacttcaa aaactgcaca acaagcctag   5220
agttagtacc taaacagtaa atttacaaca gagagcaaag acacatgcaa aaatttcagc   5280
cataaaaaaa gttataatag aatttaaagc aaaagtttca ttttttaaac atatatacaa   5340
acaaactgga tttgaaggaa gggattaatt cccctgctca aagtttgaat tcctattgtg   5400
acctatactc gaataaaatt gaagcctaag gaatgtatga gaaacaagaa aacaaaacaa   5460
aactacagac aaacaagtac aattacaaaa ttcgctaaaa ttctgtaatc accaaacccc   5520
atctcagtca gcacaaggcc caaggtttat tttgaaataa aaaaaaagtg attttatttc   5580
tcataagcta aaagaaagaa aggcaattat gaaatgattt cgactagatc tgaaagtcca   5640
acgcgtattc cgcagatatt aaagaaagag tagagtttca catggatcct agatggaccc   5700
agttgaggaa aaagcaaggc aaagcaaacc agaagtgcaa gatccgaaat tgaaccacgg   5760
```

-continued

```
aatctaggat ttggtagagg gagaagaaaa gtaccttgag aggtagaaga gaagagaaga   5820
gcagagagat atatgaacga gtgtgtcttg gtctcaactc tgaagcgata cgagtttaga   5880
ggggagcatt gagttccaat ttatagggaa accgggtggc aggggtgagt taatgacgga   5940
aaagcccccta agtaacgaga ttggattgtg ggttagattc aaccgtttgc atccgcggct   6000
tagattgggg aagtcagagt gaatctcaac cgttgactga gttgaaaatt gaatgtagca   6060
accaattgag ccaaccccag cctttgccct ttgattttga tttgtttgtt gcatactttt   6120
tatttgtctt ctggttctga ctctctttct ctcgtttcaa tgccaggttg cctactccca   6180
caccactcac aagaagattc tactgttagt attaaatatt ttttaatgta ttaaatgatg   6240
aatgcttttg taaacagaac aagactatgt ctaataagtg tcttgcaaca ttttttaaga   6300
aattaaaaaa aatatattta ttatcaaaat caaatgtatg aaaaatcatg aataatataa   6360
ttttatacat ttttttaaaa aatcttttaa tttcttaatt aatatcttaa aaataatgat   6420
taatatttaa cccaaaataa ttagtatgat tggtaaggaa gatatccatg ttatgtttgg   6480
atgtgagttt gatctagagc aaagcttact agagtcgacc tgcagcccgg gggatccgcc   6540
cacgtacggt accatctgct aatattttaa atcacatgca agagaggagg catggttcca   6600
ttttctacct tcacattatt tgagaaaaac gaacttgttc tgtgttttat ttttgccctt   6660
cacattagta caacgtggaa gactcatggt tacacagaat catacataag tacaatgctt   6720
gtccctaaga aaacaagcac tcgttgtatt gaacctttac ggctcatgcg gccgcgaatt   6780
cactagtgat tgaattcgcg gccgcttagt ccgacttggc cttggcggcc gcggccgact   6840
ctttgagcgt gaagatctgc gccgtctcgg gcacagcgcc gtagttgaca aagaggtgcg   6900
cggtcttgaa gaaggccgtg atgatgggct cgtcgttcct gcgcacgagg tgcgggtacg   6960
cggccgcaaa gtgcttggtg gcttcgttga gcttgtagtg cggaatgatc gggaacaagt   7020
ggtggacctg gtgcgtgcca atgtggtggc tcaggttgtc cacgaacgcg ccgtacgagc   7080
ggtcgacgct cgagaggttg cccttgacgt acgtccactc cgagtcgccg taccacggcg   7140
tcgcttcgtc gttgtggtgc aagaaggtcg taatgacgag gaacgaagca aagacaaaga   7200
gcggcgcata gtagtagagg cccatgacgg caaagccgag cgagtatgtg aggtacgcgt   7260
acgcggcgaa gaaggcggcc cagacgccga gcgacacgat gacggccgac gcgcggcgaa   7320
ggaggagcgg gtcccacggg tcaaagtggc tcatcgtgcg cggggcatac ccgaccttca   7380
agtagacaaa ccacgcaccg ccgagcgtgt agacccattg gcgcacgtcc tggaggtcct   7440
tgaccgaccg gtgcgggtaa aagatctcgt ccttatcaat gttgcccgtg ttcttgtggt   7500
ggtggcggtg cgtcacgcgc cagctctcga acggcgtcaa aatcgcagag tgcatgatgc   7560
agccgatgat aaagttgacg ctgtggtagc gcgagaaggc cgagtggccg cagtcgtggc   7620
cgaccgtgaa gaagccccag aagatgacgc cctgcacgta gatgtaggtg gcgcaaacga   7680
gcgcgtggag cagaacgtta tcggcaatga acggcgtcga gcgcgccgcg tagagcagcg   7740
ccgccgaggc cgacgcgttg aagatcgcgc gggccgtgta gtagagcgag aggccgaggt   7800
tcgactcaaa gcacgcgttc gggatcgagt gcttgagctc cgtgagcgtc gggaactcga   7860
ccttcgtctt atcctcagtc atgcggccgc tgaagtattg cttcttagtt aacctttcct   7920
ttctctctca gctatgtgaa ttcattttgc tttcgtcaca atttatatag tgaaattgga   7980
tctttggagt taacgccttc acaggattat cgtgttagaa caatgctttt tcatgttcta   8040
attagtagta cattacaaat gtgcactcta ttcaataagc atcttttggc acgttaataa   8100
atcatgtgaa aaaaaaatac tactatttca aagaaagtgt tgtaaaaaga aacggaaaga   8160
```

```
gagctggctt cagttgttga gacttgtttg ctagtaaaaa tggtgtgaag agtgattcat   8220

ggtgaggtgg tttttcgtcc ctttctgttt gcatgaaaaa caaatggcaa gagatgacgt   8280

aggattcctt cccttaacga ttatctgttt ttaatttcaa atatacatat aggaatttat   8340

gaattactaa ggttgtaaaa tatgctggtc atttatttat ggctaaaata tttttttttc   8400

tcgtaaatat aaaaatattt aaaatttatt tttatcatat tttttatcct tataaaatta   8460

tgtgtacaac ctatataaaa aaatatcata tttaatattg attatatgtt taatcaatat   8520

aaaaaatcat tatcatatat ttagatttat tcgaatatac atctaaacaa aaaataacat   8580

attttaattt tatgaagaaa aaaaaatatt ttatccttta tttatttaag attaattaat   8640

agttatgtat tgtggaaaga cttttacaca tgcaatagat atactgaatc aattagatgc   8700

caatgctgag ttggaaatca cttgaggagg ggaggagact tgccaatgct tttcagtttc   8760

atttaaatga tttagtggag gagatagagt agtgataaag gcatgcccca attttggagt   8820

gtatatatga gtggaaataa gagagggata gagagaaaaa ataaagagag taaaaataat   8880

taatgtgaaa tgatatgata aaaaaataaa gaaagagata aagagaaaaa tgaaatgaga   8940

gatagatgaa atagagagta gatacatgtt tgtttaggtt ttttttagga aataacacat   9000

tttttctca tcacttatta ctcactgtca atttcctctc tttcaatcat aatgatatga   9060

tttgtttaac aaaaatgtga aaaaacatat aaagtaaaat atttttataa attgataaat   9120

aaaaatttac aaaatttatt tcttattaaa ttgaatagaa aatgaaagaa aagaaaagaa   9180

aaagtatata taaaatgata tagctttaaa aagaataaat ttttcatatc agtctttttt   9240

taataattta gaaatattta agtatatagc aaaaatataa tgtactttac atatgcataa   9300

ataataattt gaaaatagaa ctaatagaat agagaaaaaa gtaatataat aattaactat   9360

atgaaaattt agaagggaca atatttttaa ttaagaatat aaacaatatt tcttttcatg   9420

taatgaggga cggatgtacg gggccagtgt tggagtcaaa gccaaaatag tcacggggaa   9480

attaatgcac tgcatgacta ttcgaaaaaa ttcactagcc ttacttagat gttagattaa   9540

tagctagggg gtgcagataa ttttgaaagg catgaaaaac attaatttgt acattgcaag   9600

cttttgatga caagctttgc aattgttcac actaccttat gccatttata aatagagtga   9660

ttggcatatg aaggaaatca tgagagtcga agcgaaaaac aaagcttgag agtgtaggaa   9720

aaatacagtt tttttggtaa aaatacagta tttgaatagg agcgaaaaat atcctttcaa   9780

aatgatcctt ttcttttttt tttttttct tgttgttctt ggtcagttat tcaaaggaaa   9840

agggattgaa ataaaaactt gcatgtggga tcgtacgtcg agtcgacctg ca           9892
```

<210> SEQ ID NO 49
<211> LENGTH: 6021
<212> TYPE: DNA
<213> ORGANISM: Artificial Sequence
<220> FEATURE:
<223> OTHER INFORMATION: the sequence of pKR271

<400> SEQUENCE: 49

```
ggccgcgaat tcaatcacta gtgaattcgc ggccgcatga gccgtaaagg ttcaatacaa     60

cgagtgcttg ttttcttagg gacaagcatt gtacttatgt atgattctgt gtaaccatga    120

gtcttccacg ttgtactaat gtgaagggca aaaataaaac acagaacaag ttcgtttttc    180

tcaaataatg tgaaggtaga aaatggaacc atgcctcctc tcttgcatgt gatttaaaat    240

attagcagat ggtaccgtac gtgggcggat cccccgggct gcaggaattc actggccgtc    300
```

-continued

```
gttttacaac gtcgtgactg ggaaaaccct ggcgttaccc aacttaatcg ccttgcagca    360
catccccctt tcgccagctg gcgtaatagc gaagaggccc gcaccgatcg cccttcccaa    420
cagttgcgca gcctgaatgg cgaatggcgc ctgatgcggt attttctcct tacgcatctg    480
tgcggtattt cacaccgcat atggtgcact ctcagtacaa tctgctctga tgccgcatag    540
ttaagccagc cccgacaccc gccaacaccc gctgacgcgc cctgacgggc ttgtctgctc    600
ccggcatccg cttacagaca agctgtgacc gtctccggga gctgcatgtg tcagaggttt    660
tcaccgtcat caccgaaacg cgcgagacga aagggcctcg tgatacgcct atttttatag    720
gttaatgtca tgataataat ggtttcttag acgtcaggtg gcacttttcg gggaaatgtg    780
cgcggaaccc ctatttgttt atttttctaa atacattcaa atatgtatcc gctcatgaga    840
caataaccct gataaatgct tcaataatat tgaaaaagga agagtatgag tattcaacat    900
ttccgtgtcg cccttattcc cttttttgcg gcattttgcc ttcctgtttt tgctcaccca    960
gaaacgctgg tgaaagtaaa agatgctgaa gatcagttgg gtgcacgagt gggttacatc   1020
gaactggatc tcaacagcgg taagatcctt gagagttttc gccccgaaga acgttttcca   1080
atgatgagca cttttaaagt tctgctatgt ggcgcggtat tatcccgtat tgacgccggg   1140
caagagcaac tcggtcgccg catacactat tctcagaatg acttggttga gtactcacca   1200
gtcacagaaa agcatcttac ggatggcatg acagtaagag aattatgcag tgctgccata   1260
accatgagtg ataacactgc ggccaactta cttctgacaa cgatcggagg accgaaggag   1320
ctaaccgctt ttttgcacaa catgggggat catgtaactc gccttgatcg ttgggaaccg   1380
gagctgaatg aagccatacc aaacgacgag cgtgacacca cgatgcctgt agcaatggca   1440
acaacgttgc gcaaactatt aactggcgaa ctacttactc tagcttcccg gcaacaatta   1500
atagactgga tggaggcgga taaagttgca ggaccacttc tgcgctcggc ccttccggct   1560
ggctggttta ttgctgataa atctggagcc ggtgagcgtg ggtctcgcgg tatcattgca   1620
gcactggggc cagatggtaa gccctcccgt atcgtagtta tctacacgac ggggagtcag   1680
gcaactatgg atgaacgaaa tagacagatc gctgagatag gtgcctcact gattaagcat   1740
tggtaactgt cagaccaagt ttactcatat atactttaga ttgatttaaa acttcatttt   1800
taatttaaaa ggatctaggt gaagatcctt tttgataatc tcatgaccaa aatcccttaa   1860
cgtgagtttt cgttccactg agcgtcagac cccgtagaaa agatcaaagg atcttcttga   1920
gatccttttt ttctgcgcgt aatctgctgc ttgcaaacaa aaaaaccacc gctaccagcg   1980
gtggtttgtt tgccggatca agagctacca actctttttc cgaaggtaac tggcttcagc   2040
agagcgcaga taccaaatac tgtccttcta gtgtagccgt agttaggcca ccacttcaag   2100
aactctgtag caccgcctac atacctcgct ctgctaatcc tgttaccagt ggctgctgcc   2160
agtggcgata agtcgtgtct taccgggttg gactcaagac gatagttacc ggataaggcg   2220
cagcggtcgg gctgaacggg gggttcgtgc acacagccca gcttggagcg aacgacctac   2280
accgaactga gatacctaca gcgtgagcta tgagaaagcg ccacgcttcc cgaagggaga   2340
aaggcggaca ggtatccggt aagcggcagg gtcggaacag gagagcgcac gagggagctt   2400
ccagggggaa acgcctggta tctttatagt cctgtcgggt ttcgccacct ctgacttgag   2460
cgtcgatttt tgtgatgctc gtcagggggg cggagcctat ggaaaaacgc cagcaacgcg   2520
gcctttttac ggttcctggc cttttgctgg ccttttgctc acatgttctt tcctgcgtta   2580
tcccctgatt ctgtggataa ccgtattacc gcctttgagt gagctgatac cgctcgccgc   2640
agccgaacga ccgagcgcag cgagtcagtg agcgaggaag cggaagagcg cccaatacgc   2700
```

-continued

```
aaaccgcctc tccccgcgcg ttggccgatt cattaatgca gctggcacga caggtttccc   2760
gactggaaag cgggcagtga gcgcaacgca attaatgtga gttagctcac tcattaggca   2820
ccccaggctt tacactttat gcttccggct cgtatgttgt gtggaattgt gagcggataa   2880
caatttcaca caggaaacag ctatgaccat gattacgcca agcttgcatg cctgcaggtc   2940
gactcgacgt acgatcccac atgcaagttt ttatttcaat cccttttcct ttgaataact   3000
gaccaagaac aacaagaaaa aaaaaaaaaa agaaaaggat cattttgaaa ggatattttt   3060
cgctcctatt caaatactgt atttttacca aaaaaactgt atttttccta cactctcaag   3120
ctttgttttt cgcttcgact ctcatgattt ccttcatatg ccaatcactc tatttataaa   3180
tggcataagg tagtgtgaac aattgcaaag cttgtcatca aaagcttgca atgtacaaat   3240
taatgttttt catgcctttc aaaattatct gcacccccta gctattaatc taacatctaa   3300
gtaaggctag tgaatttttt cgaatagtca tgcagtgcat taatttcccc gtgactattt   3360
tggctttgac tccaacactg gccccgtaca tccgtccctc attacatgaa aagaaatatt   3420
gtttatattc ttaattaaaa atattgtccc ttctaaattt tcatatagtt aattattata   3480
ttactttttt ctctattcta ttagttctat tttcaaatta ttatttatgc atatgtaaag   3540
tacattatat ttttgctata tacttaaata tttctaaatt attaaaaaaa gactgatatg   3600
aaaaatttat tctttttaaa gctatatcat tttatatata ctttttcttt tcttttcttt   3660
cattttctat tcaatttaat aagaaataaa ttttgtaaat ttttatttat caatttataa   3720
aaatatttta ctttatatgt tttttcacat ttttgttaaa caaatcatat cattatgatt   3780
gaaagagagg aaattgacag tgagtaataa gtgatgagaa aaaaatgtgt tatttcctaa   3840
aaaaaaccta aacaaacatg tatctactct ctatttcatc tatctctcat ttcatttttc   3900
tctttatctc tttctttatt tttttatcat atcatttcac attaattatt tttactctct   3960
ttatttttttc tctctatccc tctcttattt ccactcatat atacactcca aaattggggc   4020
atgcctttat cactactcta tctcctccac taaatcattt aaatgaaact gaaaagcatt   4080
ggcaagtctc ctcccctcct caagtgattt ccaactcagc attggcatct aattgattca   4140
gtatatctat tgcatgtgta aaagtctttc cacaatacat aactattaat taatcttaaa   4200
taaataaagg ataaaatatt ttttttttctt cataaaatta aaatatgtta tttttttgttt   4260
agatgtatat tcgaataaat ctaaatatat gataatgatt ttttatattg attaaacata   4320
taatcaatat taaatatgat atttttttat ataggttgta cacataattt tataaggata   4380
aaaaatatga taaaaataaa ttttaaatat ttttatattt acgagaaaaa aaaatatttt   4440
agccataaat aaatgaccag catattttac aaccttagta attcataaat tcctatatgt   4500
atatttgaaa ttaaaaacag ataatcgtta agggaaggaa tcctacgtca tctcttgcca   4560
tttgtttttc atgcaaacag aaagggacga aaaaccacct caccatgaat cactcttcac   4620
accattttta ctagcaaaca agtctcaaca actgaagcca gctctctttc cgtttctttt   4680
tacaacactt tctttgaaat agtagtattt tttttcaca tgatttatta acgtgccaaa   4740
agatgcttat tgaatagagt gcacatttgt aatgtactac taattagaac atgaaaaagc   4800
attgttctaa cacgataatc ctgtgaaggc gttaactcca aagatccaat ttcactatat   4860
aaattgtgac gaaagcaaaa tgaattcaca tagctgagag agaaaggaaa ggttaactaa   4920
gaagcaatac ttcagcggcc gcatgactga ggataagacg aaggtcgagt tcccgacgct   4980
cacggagctc aagcactcga tcccgaacgc gtgctttgag tcgaacctcg gcctctcgct   5040
```

```
ctactacacg gcccgcgcga tcttcaacgc gtcggcctcg gcggcgctgc tctacgcggc   5100

gcgctcgacg ccgttcattg ccgataacgt tctgctccac gcgctcgttt gcgccaccta   5160

catctacgtg cagggcgtca tcttctgggg cttcttcacg gtcggccacg actgcggcca   5220

ctcggccttc tcgcgctacc acagcgtcaa ctttatcatc ggctgcatca tgcactctgc   5280

gattttgacg ccgttcgaga gctggcgcgt gacgcaccgc caccaccaca agaacacggg   5340

caacattgat aaggacgaga tcttttaccc gcaccggtcg gtcaaggacc tccaggacgt   5400

gcgccaatgg gtctacacgc tcggcggtgc gtggtttgtc tacttgaagg tcgggtatgc   5460

cccgcgcacg atgagccact ttgacccgtg ggacccgctc ctccttcgcc gcgcgtcggc   5520

cgtcatcgtg tcgctcggcg tctgggccgc cttcttcgcc gcgtacgcgt acctcacata   5580

ctcgctcggc tttgccgtca tgggcctcta ctactatgcg ccgctctttg tctttgcttc   5640

gttcctcgtc attacgacct tcttgcacca caacgacgaa gcgacgccgt ggtacggcga   5700

ctcggagtgg acgtacgtca agggcaacct ctcgagcgtc gaccgctcgt acggcgcgtt   5760

cgtggacaac ctgagccacc acattggcac gcaccaggtc caccacttgt tcccgatcat   5820

tccgcactac aagctcaacg aagccaccaa gcactttgcg gccgcgtacc cgcacctcgt   5880

gcgcaggaac gacgagccca tcatcacggc cttcttcaag accgcgcacc tctttgtcaa   5940

ctacggcgct gtgcccgaga cggcgcagat cttcacgctc aaagagtcgg ccgcggccgc   6000

caaggccaag tcggactaag c                                             6021
```

<210> SEQ ID NO 50
<211> LENGTH: 6524
<212> TYPE: DNA
<213> ORGANISM: Artificial Sequence
<220> FEATURE:
<223> OTHER INFORMATION: the sequence of pKR226

<400> SEQUENCE: 50

```
gtacgtctag aggatccgtc gacggcgcgc ccgatcatcc ggatatagtt cctcctttca     60

gcaaaaaacc cctcaagacc cgtttagagg ccccaagggg ttatgctagt tattgctcag    120

cggtggcagc agccaactca gcttcctttc gggctttgtt agcagccgga tcgatccaag    180

ctgtacctca ctattccttt gccctcggac gagtgctggg gcgtcggttt ccactatcgg    240

cgagtacttc tacacagcca tcggtccaga cggccgcgct tctgcgggcg atttgtgtac    300

gcccgacagt cccggctccg gatcggacga ttgcgtcgca tcgaccctgc gcccaagctg    360

catcatcgaa attgccgtca accaagctct gatagagttg gtcaagacca atgcggagca    420

tatacgcccg gagccgcggc gatcctgcaa gctccggatg cctccgctcg aagtagcgcg    480

tctgctgctc catacaagcc aaccacggcc tccagaagaa gatgttggcg acctcgtatt    540

gggaatcccc gaacatcgcc tcgctccagt caatgaccgc tgttatgcgg ccattgtccg    600

tcaggacatt gttggagccg aaatccgcgt gcacgaggtg ccggacttcg gggcagtcct    660

cggcccaaag catcagctca tcgagagcct gcgcgacgga cgcactgacg gtgtcgtcca    720

tcacagtttg ccagtgatac acatggggat cagcaatcgc gcatatgaaa tcacgccatg    780

tagtgtattg accgattcct tgcggtccga atgggccgaa cccgctcgtc tggctaagat    840

cggccgcagc gatcgcatcc atagcctccg cgaccggctg cagaacagcg ggcagttcgg    900

tttcaggcag gtcttgcaac gtgacaccct gtgcacggcg ggagatgcaa taggtcaggc    960

tctcgctgaa ttccccaatg tcaagcactt ccggaatcgg gagcgcggcc gatgcaaagt   1020

gccgataaac ataacgatct ttgtagaaac catcggcgca gctatttacc cgcaggacat   1080
```

```
atccacgccc tcctacatcg aagctgaaag cacgagattc ttcgccctcc gagagctgca   1140
tcaggtcgga gacgctgtcg aacttttcga tcagaaactt ctcgacagac gtcgcggtga   1200
gttcaggctt ttccatgggt atatctcctt cttaaagtta aacaaaatta tttctagagg   1260
gaaaccgttg tggtctccct atagtgagtc gtattaattt cgcgggatcg agatctgatc   1320
aacctgcatt aatgaatcgg ccaacgcgcg gggagaggcg gtttgcgtat tgggcgctct   1380
tccgcttcct cgctcactga ctcgctgcgc tcggtcgttc ggctgcggcg agcggtatca   1440
gctcactcaa aggcggtaat acggttatcc acagaatcag gggataacgc aggaaagaac   1500
atgtgagcaa aaggccagca aaaggccagg aaccgtaaaa aggccgcgtt gctggcgttt   1560
ttccataggc tccgcccccc tgacgagcat cacaaaaatc gacgctcaag tcagaggtgg   1620
cgaaacccga caggactata aagataccag gcgtttcccc ctggaagctc cctcgtgcgc   1680
tctcctgttc cgaccctgcc gcttaccgga tacctgtccg cctttctccc ttcgggaagc   1740
gtggcgcttt ctcaatgctc acgctgtagg tatctcagtt cggtgtaggt cgttcgctcc   1800
aagctgggct gtgtgcacga accccccgtt cagcccgacc gctgcgcctt atccggtaac   1860
tatcgtcttg agtccaaccc ggtaagacac gacttatcgc cactggcagc agccactggt   1920
aacaggatta gcagagcgag gtatgtaggc ggtgctacag agttcttgaa gtggtggcct   1980
aactacggct acactagaag gacagtattt ggtatctgcg ctctgctgaa gccagttacc   2040
ttcggaaaaa gagttggtag ctcttgatcc ggcaaacaaa ccaccgctgg tagcggtggt   2100
tttttgttt gcaagcagca gattacgcgc agaaaaaaag gatctcaaga agatcctttg   2160
atcttttcta cggggtctga cgctcagtgg aacgaaaact cacgttaagg gattttggtc   2220
atgacattaa cctataaaaa taggcgtatc acgaggccct ttcgtctcgc gcgtttcggt   2280
gatgacggtg aaaacctctg acacatgcag ctcccggaga cggtcacagc ttgtctgtaa   2340
gcggatgccg ggagcagaca agcccgtcag ggcgcgtcag cgggtgttgg cgggtgtcgg   2400
ggctggctta actatgcggc atcagagcag attgtactga gagtgcacca tatggacata   2460
ttgtcgttag aacgcggcta caattaatac ataaccttat gtatcataca catacgattt   2520
aggtgacact atagaacggc gcgccaagct gggtctagaa ctagaaacgt gatgccactt   2580
gttattgaag tcgattacag catctattct gttttactat ttataacttt gccatttctg   2640
acttttgaaa actatctctg gatttcggta tcgctttgtg aagatcgagc aaaagagacg   2700
ttttgtggac gcaatggtcc aaatccgttc tacatgaaca aattggtcac aatttccact   2760
aaaagtaaat aaatggcaag ttaaaaaagg aatatgcatt ttactgattg cctaggtgag   2820
ctccaagaga agttgaatct acacgtctac caaccgctaa aaaaagaaaa acattgatat   2880
gtaacctgat tccattagct tttgacttct tcaacagatt ctctacttag atttctaaca   2940
gaaatattat tactagcaca tcattttcag tctcactaca gcaaaaaatc caacggcaca   3000
atacagacaa caggagatat cagactacag agatagatag atgctactgc atgtagtaag   3060
ttaaataaaa ggaaaataaa atgtcttgct accaaaacta ctacagacta tgatgctcac   3120
cacaggccaa atcctgcaac taggacagca ttatcttata tatattgtac aaaacaagca   3180
tcaaggaaca tttggtctag gcaatcagta cctcgttcta ccatcaccct cagttatcac   3240
atccttgaag gatccattac tgggaatcat cggcaacaca tgctcctgat ggggcacaat   3300
gacatcaaga aggtaggggc caggggtgtc caacattctc tgaattgccg ctctaagctc   3360
ttccttcttc gtcactcgcg ctgccggtat cccacaagca tcagcaaact tgagcatgtt   3420
```

-continued

```
tgggaatatc tcgctctcgc tagacggatc tccaagatag gtgtgagctc tattggactt   3480
gtagaaccta tcctccaact gaaccaccat acccaaatgc tgattgttca acaacaatat   3540
cttaactggg agattctcca ctcttatagt ggccaactcc tgaacattca tgatgaaact   3600
accatcccca tcaatgtcaa ccacaacagc cccagggtta gcaacagcag caccaatagc   3660
cgcaggcaat ccaaaaccca tggctccaag accccctgag gtcaaccact gcctcggtct   3720
cttgtacttg taaaactgcg cagcccacat ttgatgctgc ccaaccccag tactaacaat   3780
agcatctcca ttagtcaact catcaagaac ctcgatagca tgctgcggag aaatcgcgtc   3840
ctggaatgtc ttgtaaccca atggaaactt gtgtttctgc acattaatct cttctctcca   3900
acctccaaga tcaaacttac cctccactcc tttctcctcc aaaatcatat taattccctt   3960
caaggccaac ttcaaatccg cgcaaaccga cacgtgcgcc tgcttgttct tcccaatctc   4020
ggcagaatca atatcaatgt gaacaatctt agccctacta gcaaaagcct caagcttccc   4080
agtaacacgg tcatcaaacc ttaccccaaa ggcaagcaac aaatcactat tgtcaacagc   4140
atagttagca taaacagtac catgcatacc cagcatctga agggaatatt catcaccaat   4200
aggaaaagtt ccaagaccca ttaaagtgct agcaacggga ataccagtga gttcaacaaa   4260
gcgcctcaat tcagcactgg aattcaaact gccaccgccg acgtagagaa cgggcttttg   4320
ggcctccatg atgagtctga caatgtgttc caattgggcc tcggcggggg gcctgggcag   4380
cctggcgagg taaccgggga ggttaacggg ctcgtcccaa ttaggcacgg cgagttgctg   4440
ctgaacgtct ttgggaatgt cgatgaggac cggaccgggg cggccggagg tggcgacgaa   4500
gaaagcctcg gcgacgacgc gggggatgtc gtcgacgtcg aggatgaggt agttgtgctt   4560
cgtgatggat ctgctcacct ccacgatcgg ggtttcttgg aaggcgtcgg tgccgatcat   4620
ccggcgggcg acctggccgg tgatggcgac gactgggacg ctgtccatta aagcgtcggc   4680
gaggccgctc acgaggttgg tggcgccggg gccggaggtg gcaatgcaga cgccggggag   4740
gccggaggaa cgcgcgtagc cttcggcggc gaagacgccg ccctgctcgt ggcgcgggag   4800
cacgttgcgg atggcggcgg agcgcgtgag cgcctggtgg atctccatcg acgcaccgcc   4860
ggggtacgcg aacaccgtcg tcacgccctg cctctccagc gcctccacaa ggatgtccgc   4920
gcccttgcga ggttcgccgg aggcgaaccg tgacacgaag ggctccgtgg tcggcgcttc   4980
cttggtgaag ggcgccgccg tggggggttt ggagatggaa catttgattt tgagagcgtg   5040
gttgggtttg gtgagggttt gatgagagag agggagggtg gatctagtaa tgcgtttggg   5100
gaaggtgggg tgtgaagagg aagaagagaa tcgggtggtt ctggaagcgg tggccgccat   5160
tgtgttgtgt ggcatggtta tacttcaaaa actgcacaac aagcctagag ttagtaccta   5220
aacagtaaat ttacaacaga gagcaaagac acatgcaaaa atttcagcca taaaaaaagt   5280
tataatagaa tttaaagcaa aagtttcatt ttttaaacat atatacaaac aaactggatt   5340
tgaaggaagg gattaattcc cctgctcaaa gtttgaattc ctattgtgac ctatactcga   5400
ataaaattga agcctaagga atgtatgaga aacaagaaaa caaaacaaaa ctacagacaa   5460
acaagtacaa ttacaaaatt cgctaaaatt ctgtaatcac caaaccccat ctcagtcagc   5520
acaaggccca aggtttattt tgaaataaaa aaaaagtgat tttatttctc ataagctaaa   5580
agaaagaaag gcaattatga aatgatttcg actagatctg aaagtccaac gcgtattccg   5640
cagatattaa agaaagagta gagtttcaca tggatcctag atggacccag ttgaggaaaa   5700
agcaaggcaa agcaaaccag aagtgcaaga tccgaaattg aaccacggaa tctaggattt   5760
ggtagaggga gaagaaaagt accttgagag gtagaagaga agagaagagc agagagatat   5820
```

```
atgaacgagt gtgtcttggt ctcaactctg aagcgatacg agtttagagg ggagcattga   5880
gttccaattt atagggaaac cgggtggcag gggtgagtta atgacggaaa agcccctaag   5940
taacgagatt ggattgtggg ttagattcaa ccgtttgcat ccgcggctta gattggggaa   6000
gtcagagtga atctcaaccg ttgactgagt tgaaaattga atgtagcaac caattgagcc   6060
aaccccagcc tttgcccttt gattttgatt tgtttgttgc atacttttta tttgtcttct   6120
ggttctgact ctctttctct cgtttcaatg ccaggttgcc tactcccaca ccactcacaa   6180
gaagattcta ctgttagtat taaatatttt ttaatgtatt aaatgatgaa tgcttttgta   6240
aacagaacaa gactatgtct aataagtgtc ttgcaacatt ttttaagaaa ttaaaaaaaa   6300
tatatttatt atcaaaatca aatgtatgaa aaatcatgaa taatataatt ttatacattt   6360
ttttaaaaaa tcttttaatt tcttaattaa tatcttaaaa ataatgatta atatttaacc   6420
caaaataatt agtatgattg gtaaggaaga tatccatgtt atgtttggat gtgagtttga   6480
tctagagcaa agcttactag agtcgacctg caggtcgact cgac                    6524
```

<210> SEQ ID NO 51
<211> LENGTH: 13514
<212> TYPE: DNA
<213> ORGANISM: Artificial Sequence
<220> FEATURE:
<223> OTHER INFORMATION: the sequence of pKR275
<220> FEATURE:
<221> NAME/KEY: misc_feature
<222> LOCATION: (1192)..(1192)
<223> OTHER INFORMATION: n is a, c, g, or t
<220> FEATURE:
<221> NAME/KEY: misc_feature
<222> LOCATION: (2675)..(2675)
<223> OTHER INFORMATION: n is a, c, g, or t

<400> SEQUENCE: 51

```
ggtcgactcg acgtacgtcc tcgaagagaa gggttaataa cacatttttt aacattttta     60
acacaaattt tagttattta aaaatttatt aaaaaattta aaataagaag aggaactctt    120
taaataaatc taacttacaa aatttatgat ttttaataag ttttcaccaa taaaaaatgt    180
cataaaaata tgttaaaaag tatattatca atattctctt tatgataaat aaaaagaaaa    240
aaaaaataaa agttaagtga aaatgagatt gaagtgactt taggtgtgta taaatatatc    300
aaccccgcca acaatttatt taatccaaat atattgaagt atattattcc atagccttta    360
tttatttata tatttattat ataaaagctt tatttgttct aggttgttca tgaaatattt    420
ttttggtttt atctccgttg taagaaaatc atgtgctttg tgtcgccact cactattgca    480
gctttttcat gcattggtca gattgacggt tgattgtatt tttgtttttt atggttttgt    540
gttatgactt aagtcttcat ctctttatct cttcatcagg tttgatggtt acctaatatg    600
gtccatgggt acatgcatgg ttaaattagg tggccaactt tgttgtgaac gatagaattt    660
tttttatatt aagtaaacta tttttatatt atgaaataat aataaaaaaa atattttatc    720
attattaaca aaatcatatt agttaatttg ttaactctat aataaaagaa atactgtaac    780
attcacatta catggtaaca tctttccacc ctttcatttg ttttttgttt gatgactttt    840
tttcttgttt aaatttattt cccttctttt aaatttggaa tacattatca tcatatataa    900
actaaaatac taaaaacagg attacacaaa tgataaataa taacacaaat atttataaat    960
ctagctgcaa tatatttaaa ctagctatat cgatattgta aaataaaact agctgcattg   1020
atactgataa aaaaatatca tgtgctttct ggactgatga tgcagtatac ttttgacatt   1080
```

-continued

```
gcctttattt tatttttcag aaaagctttc ttagttctgg gttcttcatt atttgtttcc   1140
catctccatt gtgaattgaa tcatttgctt cgtgtcacaa atacaattta gntaggtaca   1200
tgcattggtc agattcacgg tttattatgt catgacttaa gttcatggta gtacattacc   1260
tgccacgcat gcattatatt ggttagattt gataggcaaa tttggttgtc aacaatataa   1320
atataaataa tgtttttata ttacgaaata acagtgatca aaacaaacag ttttatcttt   1380
attaacaaga ttttgttttt gtttgatgac gtttttttaat gtttacgctt tcccccttct   1440
tttgaattta gaacacttta tcatcataaa atcaaatact aaaaaaatta catatttcat   1500
aaataataac acaaatattt ttaaaaaatc tgaaataata atgaacaata ttacatatta   1560
tcacgaaaat tcattaataa aaatattata taaataaaat gtaatagtag ttatatgtag   1620
gaaaaaagta ctgcacgcat aatatataca aaaagattaa aatgaactat tataaataat   1680
aacactaaat taatggtgaa tcatatcaaa ataatgaaaa agtaaataaa atttgtaatt   1740
aacttctata tgtattacac acacaaataa taaataatag taaaaaaaat tatgataaat   1800
atttaccatc tcataagata tttaaaataa tgataaaaat atagattatt ttttatgcaa   1860
ctagctagcc aaaaagagaa cacgggtata tataaaaaga gtacctttaa attctactgt   1920
acttccttta ttcctgacgt ttttatatca agtggacata cgtgaagatt ttaattatca   1980
gtctaaatat ttcattagca cttaatactt ttctgtttta ttcctatcct ataagtagtc   2040
ccgattctcc caacattgct tattcacaca actaactaag aaagtcttcc atagcccccc   2100
aagcggccgc ctctctctct ctctcttctc tctttctctc cccctctctc cggcgatggt   2160
tgttgctatg gaccaacgca ccaatgtgaa cggagatccc ggcgccggag accggaagaa   2220
agaagaaagg tttgatccga gtgcacaacc accgttcaag atcggagata taagggcggc   2280
gattcctaag cactgttggg ttaagagtcc tttgagatca atgagttacg tcgtcagaga   2340
cattatcgcc gtcgcggctt tggccatcgc tgccgtgtat gttgatagct ggttcctttg   2400
gcctctttat tgggccgccc aaggaacact tttctgggcc atctttgttc tcggccacga   2460
ctgtggacat gggagtttct cagacattcc tctactgaat agtgtggttg gtcacattct   2520
tcattctttc atcctcgttc cttaccatgg ttggagaata agccaccgga cacaccacca   2580
gaaccatggc catgttgaaa acgacgagtc atgggttccg ttaccagaaa gggtgtacaa   2640
gaaattgccc cacagtactc ggatgctcag atacnctgtc cctctcccca tgctcgcata   2700
tcctctctat ttgtgctaca gaagtcctgg aaaagaagga tcacatttta acccatacag   2760
tagtttattt gctccaagcg agagaaagct tattgcaact tcaactactt gttggtccat   2820
aatgttcgtc agtcttatcg ctctatcttt cgtcttcggt ccactcgcgg ttcttaaagt   2880
ctacggtgta ccgtacatta tctttgtgat gtggttggat gctgtcacgt atttgcatca   2940
tcatggtcac gatgagaagt tgccttggta tagaggcaag gaatggagtt atctacgtgg   3000
aggattaaca acaattgata gagattacgg aatctttaac aacattcatc acgacattgg   3060
aactcacgtg atccatcatc tcttcccaca aatccctcac tatcacttgg tcgacgccac   3120
gaaagcagct aaacatgtgt tgggaagata ctacagagaa ccaaagacgt caggagcaat   3180
accgatccac ttggtggaga gtttggtcgc aagtattaag aaagatcatt acgtcagcga   3240
cactggtgat attgtcttct acgagacaga tccagatctc tacgtttacg cttctgacaa   3300
atctaaaatc aattaatctc catttgttta gctctattag gaataaacca gcccactttt   3360
aaaattttta tttcttgttg tttttaagtt aaaagtgtac tcgtgaaact cttttttttt   3420
tctttttttt tattaatgta tttacattac aaggcgtaaa gcggccgcga cacaagtgtg   3480
```

-continued

```
agagtactaa ataaatgctt tggttgtacg aaatcattac actaaataaa ataatcaaag   3540
cttatatatg ccttccgcta aggccgaatg caaagaaatt ggttctttct cgttatcttt   3600
tgccactttt actagtacgt attaattact acttaatcat ctttgtttac ggctcattat   3660
atccgtacgt ctagaggatc cgtcgacggc gcgcccgatc atccggatat agttcctcct   3720
ttcagcaaaa aacccctcaa gacccgttta gaggccccaa ggggttatgc tagttattgc   3780
tcagcggtgg cagcagccaa ctcagcttcc tttcgggctt tgttagcagc cggatcgatc   3840
caagctgtac ctcactattc ctttgccctc ggacgagtgc tggggcgtcg gtttccacta   3900
tcggcgagta cttctacaca gccatcggtc cagacggccg cgcttctgcg ggcgatttgt   3960
gtacgcccga cagtcccggc tccggatcgg acgattgcgt cgcatcgacc ctgcgcccaa   4020
gctgcatcat cgaaattgcc gtcaaccaag ctctgataga gttggtcaag accaatgcgg   4080
agcatatacg cccggagccg cggcgatcct gcaagctccg gatgcctccg ctcgaagtag   4140
cgcgtctgct gctccataca agccaaccac ggcctccaga agaagatgtt ggcgacctcg   4200
tattgggaat ccccgaacat cgcctcgctc cagtcaatga ccgctgttat gcggccattg   4260
tccgtcagga cattgttgga gccgaaatcc gcgtgcacga ggtgccggac ttcggggcag   4320
tcctcggccc aaagcatcag ctcatcgaga gcctgcgcga cggacgcact gacggtgtcg   4380
tccatcacag tttgccagtg atacacatgg ggatcagcaa tcgcgcatat gaaatcacgc   4440
catgtagtgt attgaccgat tccttgcggt ccgaatgggc cgaacccgct cgtctggcta   4500
agatcggccg cagcgatcgc atccatagcc tccgcgaccg gctgcagaac agcgggcagt   4560
tcggtttcag gcaggtcttg caacgtgaca ccctgtgcac ggcgggagat gcaataggtc   4620
aggctctcgc tgaattcccc aatgtcaagc acttccggaa tcgggagcgc ggccgatgca   4680
aagtgccgat aaacataacg atctttgtag aaaccatcgg cgcagctatt tacccgcagg   4740
acatatccac gccctcctac atcgaagctg aaagcacgag attcttcgcc ctccgagagc   4800
tgcatcaggt cggagacgct gtcgaacttt tcgatcagaa acttctcgac agacgtcgcg   4860
gtgagttcag gcttttccat gggtatatct ccttcttaaa gttaaacaaa attatttcta   4920
gagggaaacc gttgtggtct ccctatagtg agtcgtatta atttcgcggg atcgagatct   4980
gatcaacctg cattaatgaa tcggccaacg cgcggggaga ggcggtttgc gtattgggcg   5040
ctcttccgct tcctcgctca ctgactcgct gcgctcggtc gttcggctgc ggcgagcggt   5100
atcagctcac tcaaaggcgg taatacggtt atccacagaa tcaggggata acgcaggaaa   5160
gaacatgtga gcaaaaggcc agcaaaaggc caggaaccgt aaaaaggccg cgttgctggc   5220
gtttttccat aggctccgcc cccctgacga gcatcacaaa aatcgacgct caagtcagag   5280
gtggcgaaac ccgacaggac tataaagata ccaggcgttt ccccctggaa gctccctcgt   5340
gcgctctcct gttccgaccc tgccgcttac cggatacctg tccgcctttc tcccttcggg   5400
aagcgtggcg ctttctcaat gctcacgctg taggtatctc agttcggtgt aggtcgttcg   5460
ctccaagctg ggctgtgtgc acgaaccccc cgttcagccc gaccgctgcg ccttatccgg   5520
taactatcgt cttgagtcca acccggtaag acacgactta tcgccactgg cagcagccac   5580
tggtaacagg attagcagag cgaggtatgt aggcggtgct acagagttct tgaagtggtg   5640
gcctaactac ggctacacta gaaggacagt atttggtatc tgcgctctgc tgaagccagt   5700
taccttcgga aaaagagttg gtagctcttg atccggcaaa caaaccaccg ctggtagcgg   5760
tggttttttt gtttgcaagc agcagattac gcgcagaaaa aaaggatctc aagaagatcc   5820
```

tttgatcttt tctacggggt ctgacgctca gtggaacgaa aactcacgtt aagggatttt 5880
ggtcatgaca ttaacctata aaaataggcg tatcacgagg ccctttcgtc tcgcgcgttt 5940
cggtgatgac ggtgaaaacc tctgacacat gcagctcccg gagacggtca cagcttgtct 6000
gtaagcggat gccgggagca gacaagcccg tcagggcgcg tcagcgggtg ttggcgggtg 6060
tcggggctgg cttaactatg cggcatcaga gcagattgta ctgagagtgc accatatgga 6120
catattgtcg ttagaacgcg gctacaatta atacataacc ttatgtatca tacacatacg 6180
atttaggtga cactatagaa cggcgcgcca agctgggtct agaactagaa acgtgatgcc 6240
acttgttatt gaagtcgatt acagcatcta ttctgtttta ctatttataa ctttgccatt 6300
tctgactttt gaaaactatc tctggatttc ggtatcgctt tgtgaagatc gagcaaaaga 6360
gacgttttgt ggacgcaatg gtccaaatcc gttctacatg aacaaattgg tcacaatttc 6420
cactaaaagt aaataaatgg caagttaaaa aaggaatatg cattttactg attgcctagg 6480
tgagctccaa gagaagttga atctacacgt ctaccaaccg ctaaaaaaag aaaaacattg 6540
atatgtaacc tgattccatt agcttttgac ttcttcaaca gattctctac ttagatttct 6600
aacagaaata ttattactag cacatcattt tcagtctcac tacagcaaaa aatccaacgg 6660
cacaatacag acaacaggag atatcagact acagagatag atagatgcta ctgcatgtag 6720
taagttaaat aaaaggaaaa taaaatgtct tgctaccaaa actactacag actatgatgc 6780
tcaccacagg ccaaatcctg caactaggac agcattatct tatatatatt gtacaaaaca 6840
agcatcaagg aacatttggt ctaggcaatc agtacctcgt tctaccatca ccctcagtta 6900
tcacatcctt gaaggatcca ttactgggaa tcatcggcaa cacatgctcc tgatggggca 6960
caatgacatc aagaaggtag gggccagggg tgtccaacat tctctgaatt gccgctctaa 7020
gctcttcctt cttcgtcact cgcgctgccg gtatcccaca agcatcagca aacttgagca 7080
tgtttgggaa tatctcgctc tcgctagacg gatctccaag ataggtgtga gctctattgg 7140
acttgtagaa cctatcctcc aactgaacca ccatacccaa atgctgattg ttcaacaaca 7200
atatcttaac tgggagattc tccactctta tagtggccaa ctcctgaaca ttcatgatga 7260
aactaccatc cccatcaatg tcaaccacaa cagccccagg gttagcaaca gcagcaccaa 7320
tagccgcagg caatccaaaa cccatggctc caagaccccc tgaggtcaac cactgcctcg 7380
gtctcttgta cttgtaaaac tgcgcagccc acatttgatg ctgcccaacc ccagtactaa 7440
caatagcatc tccattagtc aactcatcaa gaacctcgat agcatgctgc ggagaaatcg 7500
cgtcctggaa tgtcttgtaa cccaatggaa acttgtgttt ctgcacatta atctcttctc 7560
tccaacctcc aagatcaaac ttaccctcca ctcctttctc ctccaaaatc atattaattc 7620
ccttcaaggc caacttcaaa tccgcgcaaa ccgacacgtg cgcctgcttg ttcttcccaa 7680
tctcggcaga atcaatatca atgtgaacaa tcttagccct actagcaaaa gcctcaagct 7740
tcccagtaac acggtcatca aaccttaccc caaaggcaag caacaaatca ctattgtcaa 7800
cagcatagtt agcataaaca gtaccatgca tacccagcat ctgaagggaa tattcatcac 7860
caataggaaa agttccaaga cccattaaag tgctagcaac gggaatacca gtgagttcaa 7920
caaagcgcct caattcagca ctggaattca aactgccacc gccgacgtag agaacgggct 7980
tttgggcctc catgatgagt ctgacaatgt gttccaattg ggcctcggcg gggggcctgg 8040
gcagcctggc gaggtaaccg gggaggttaa cgggctcgtc ccaattaggc acggcgagtt 8100
gctgctgaac gtctttggga atgtcgatga ggaccggacc ggggcggccg gaggtggcga 8160
cgaagaaagc ctcggcgacg acgcggggga tgtcgtcgac gtcgaggatg aggtagttgt 8220

```
gcttcgtgat ggatctgctc acctccacga tcggggtttc ttggaaggcg tcggtgccga   8280
tcatccggcg ggcgacctgg ccggtgatgg cgacgactgg gacgctgtcc attaaagcgt   8340
cggcgaggcc gctcacgagg ttggtggcgc cggggccgga ggtggcaatg cagacgccgg   8400
ggaggccgga ggaacgcgcg tagccttcgg cggcgaagac gccgccctgc tcgtggcgcg   8460
ggagcacgtt gcggatggcg gcggagcgcg tgagcgcctg gtggatctcc atcgacgcac   8520
cgccggggta cgcgaacacc gtcgtcacgc cctgcctctc cagcgcctcc acaaggatgt   8580
ccgcgccctt gcgaggttcg ccggaggcga accgtgacac gaagggctcc gtggtcggcg   8640
cttccttggt gaagggcgcc gccgtggggg gtttggagat ggaacatttg attttgagag   8700
cgtggttggg tttggtgagg gtttgatgag agagagggag ggtggatcta gtaatgcgtt   8760
tggggaaggt ggggtgtgaa gaggaagaag agaatcgggt ggttctggaa gcggtggccg   8820
ccattgtgtt gtgtggcatg gttatacttc aaaaactgca caacaagcct agagttagta   8880
cctaaacagt aaatttacaa cagagagcaa agacacatgc aaaaatttca gccataaaaa   8940
aagttataat agaatttaaa gcaaaagttt catttttttaa acatatatac aaacaaactg   9000
gatttgaagg aagggattaa ttcccctgct caaagtttga attcctattg tgacctatac   9060
tcgaataaaa ttgaagccta aggaatgtat gagaaacaag aaaacaaaac aaaactacag   9120
acaaacaagt acaattacaa aattcgctaa aattctgtaa tcaccaaacc ccatctcagt   9180
cagcacaagg cccaaggttt attttgaaat aaaaaaaaag tgattttatt tctcataagc   9240
taaaagaaag aaaggcaatt atgaaatgat ttcgactaga tctgaaagtc caacgcgtat   9300
tccgcagata ttaaagaaag agtagagttt cacatggatc ctagatggac ccagttgagg   9360
aaaaagcaag gcaaagcaaa ccagaagtgc aagatccgaa attgaaccac ggaatctagg   9420
atttggtaga gggagaagaa aagtaccttg agaggtagaa gagaagagaa gagcagagag   9480
atatatgaac gagtgtgtct tggtctcaac tctgaagcga tacgagttta gaggggagca   9540
ttgagttcca atttataggg aaaccgggtg gcaggggtga gttaatgacg gaaaagcccc   9600
taagtaacga gattggattg tgggttagat tcaaccgttt gcatccgcgg cttagattgg   9660
ggaagtcaga gtgaatctca accgttgact gagttgaaaa ttgaatgtag caaccaattg   9720
agccaacccc agcctttgcc ctttgatttt gatttgtttg ttgcatactt tttatttgtc   9780
ttctggttct gactctcttt ctctcgtttc aatgccaggt tgcctactcc cacaccactc   9840
acaagaagat tctactgtta gtattaaata ttttttaatg tattaaatga tgaatgcttt   9900
tgtaaacaga acaagactat gtctaataag tgtcttgcaa catttttttaa gaaattaaaa   9960
aaaatatatt tattatcaaa atcaaatgta tgaaaaatca tgaataatat aattttatac  10020
atttttttaa aaaatctttt aatttcttaa ttaatatctt aaaaataatg attaatattt  10080
aacccaaaat aattagtatg attggtaagg aagatatcca tgttatgttt ggatgtgagt  10140
ttgatctaga gcaaagctta ctagagtcga cctgcaggtc gactcgacgt acgatcccac  10200
atgcaagttt ttatttcaat ccccttttcct ttgaataact gaccaagaac aacaagaaaa  10260
aaaaaaaaaa agaaaaggat cattttgaaa ggatattttt cgctcctatt caaatactgt  10320
atttttacca aaaaaactgt atttttccta cactctcaag ctttgttttt cgcttcgact  10380
ctcatgattt ccttcatatg ccaatcactc tatttataaa tggcataagg tagtgtgaac  10440
aattgcaaag cttgtcatca aaagcttgca atgtacaaat taatgttttt catgcctttc  10500
aaaattatct gcacccccta gctattaatc taacatctaa gtaaggctag tgaatttttt  10560
```

```
cgaatagtca tgcagtgcat taatttcccc gtgactattt tggctttgac tccaacactg  10620
gccccgtaca tccgtccctc attacatgaa aagaaatatt gtttatattc ttaattaaaa  10680
atattgtccc ttctaaattt tcatatagtt aattattata ttactttttt ctctattcta  10740
ttagttctat tttcaaatta ttatttatgc atatgtaaag tacattatat ttttgctata  10800
tacttaaata tttctaaatt attaaaaaaa gactgatatg aaaaatttat tctttttaaa  10860
gctatatcat tttatatata ctttttcttt tcttttcttt cattttctat tcaatttaat  10920
aagaaataaa ttttgtaaat ttttatttat caatttataa aaatatttta ctttatatgt  10980
tttttcacat ttttgttaaa caaatcatat cattatgatt gaaagagagg aaattgacag  11040
tgagtaataa gtgatgagaa aaaaatgtgt tatttcctaa aaaaaaccta aacaaacatg  11100
tatctactct ctatttcatc tatctctcat ttcatttttc tctttatctc tttctttatt  11160
tttttatcat atcatttcac attaattatt tttactctct ttattttttc tctctatccc  11220
tctcttattt ccactcatat atacactcca aaattggggc atgcctttat cactactcta  11280
tctcctccac taaatcattt aaatgaaact gaaaagcatt ggcaagtctc ctcccctcct  11340
caagtgattt ccaactcagc attggcatct aattgattca gtatatctat tgcatgtgta  11400
aaagtctttc cacaatacat aactattaat taatcttaaa taaataaagg ataaaatatt  11460
ttttttttctt cataaaatta aaatatgtta tttttttgttt agatgtatat tcgaataaat  11520
ctaaatatat gataatgatt ttttatattg attaaacata taatcaatat taaatatgat  11580
atttttttat ataggttgta cacataattt tataaggata aaaaatatga taaaaataaa  11640
ttttaaatat ttttatattt acgagaaaaa aaaatatttt agccataaat aaatgaccag  11700
catattttac aaccttagta attcataaat tcctatatgt atatttgaaa ttaaaaacag  11760
ataatcgtta agggaaggaa tcctacgtca tctcttgcca tttgtttttc atgcaaacag  11820
aaagggacga aaaaccacct caccatgaat cactcttcac accattttta ctagcaaaca  11880
agtctcaaca actgaagcca gctctctttc cgtttctttt tacaacactt tctttgaaat  11940
agtagtattt ttttttcaca tgatttatta acgtgccaaa agatgcttat tgaatagagt  12000
gcacatttgt aatgtactac taattagaac atgaaaaagc attgttctaa cacgataatc  12060
ctgtgaaggc gttaactcca aagatccaat ttcactatat aaattgtgac gaaagcaaaa  12120
tgaattcaca tagctgagag agaaaggaaa ggttaactaa gaagcaatac ttcagcggcc  12180
gcatgactga ggataagacg aaggtcgagt tcccgacgct cacggagctc aagcactcga  12240
tcccgaacgc gtgctttgag tcgaacctcg gcctctcgct ctactacacg gcccgcgcga  12300
tcttcaacgc gtcggcctcg gcggcgctgc tctacgcggc gcgctcgacg ccgttcattg  12360
ccgataacgt tctgctccac gcgctcgttt gcgccaccta catctacgtg cagggcgtca  12420
tcttctgggg cttcttcacg gtcggccacg actgcggcca ctcggccttc tcgcgctacc  12480
acagcgtcaa ctttatcatc ggctgcatca tgcactctgc gattttgacg ccgttcgaga  12540
gctggcgcgt gacgcaccgc caccaccaca agaacacggg caacattgat aaggacgaga  12600
tcttttaccc gcaccggtcg gtcaaggacc tccaggacgt gcgccaatgg gtctacacgc  12660
tcggcggtgc gtggtttgtc tacttgaagg tcgggtatgc cccgcgcacg atgagccact  12720
ttgacccgtg ggacccgctc ctccttcgcc gcgcgtcggc cgtcatcgtg tcgctcggcg  12780
tctgggccgc cttcttcgcc gcgtacgcgt acctcacata ctcgctcggc tttgccgtca  12840
tgggcctcta ctactatgcg ccgctctttg tctttgcttc gttcctcgtc attacgacct  12900
tcttgcacca caacgacgaa gcgacgccgt ggtacggcga ctcggagtgg acgtacgtca  12960
```

```
agggcaacct ctcgagcgtc gaccgctcgt acggcgcgtt cgtggacaac ctgagccacc  13020

acattggcac gcaccaggtc caccacttgt tcccgatcat tccgcactac aagctcaacg  13080

aagccaccaa gcactttgcg gccgcgtacc cgcacctcgt gcgcaggaac gacgagccca  13140

tcatcacggc cttcttcaag accgcgcacc tctttgtcaa ctacggcgct gtgcccgaga  13200

cggcgcagat cttcacgctc aaagagtcgg ccgcggccgc caaggccaag tcggactaag  13260

cggccgcatg agccgtaaag gttcaataca acgagtgctt gttttcttag ggacaagcat  13320

tgtacttatg tatgattctg tgtaaccatg agtcttccac gttgtactaa tgtgaagggc  13380

aaaaataaaa cacagaacaa gttcgttttt ctcaaataat gtgaaggtag aaaatggaac  13440

catgcctcct ctcttgcatg tgatttaaaa tattagcaga tggtaccgta cgtgggcgga  13500

tccccgggc tgca                                                    13514
```

<210> SEQ ID NO 52
<211> LENGTH: 12323
<212> TYPE: DNA
<213> ORGANISM: Artificial Sequence
<220> FEATURE:
<223> OTHER INFORMATION: the sequence of pKR329
<220> FEATURE:
<221> NAME/KEY: misc_feature
<222> LOCATION: (1201)..(1201)
<223> OTHER INFORMATION: n is a, c, g, or t
<220> FEATURE:
<221> NAME/KEY: misc_feature
<222> LOCATION: (2684)..(2684)
<223> OTHER INFORMATION: n is a, c, g, or t

<400> SEQUENCE: 52

```
ggatctggcc ggccggatct cgtacgtcct cgaagagaag ggttaataac acattttta     60

acatttttaa cacaaatttt agttatttaa aaatttatta aaaaatttaa aataagaaga    120

ggaactcttt aaataaatct aacttacaaa atttatgatt tttaataagt tttcaccaat    180

aaaaaatgtc ataaaaatat gttaaaaagt atattatcaa tattctcttt atgataaata    240

aaaagaaaaa aaaaataaaa gttaagtgaa aatgagattg aagtgacttt aggtgtgtat    300

aaatatatca accccgccaa caatttattt aatccaaata tattgaagta tattattcca    360

tagcctttat ttatttatat atttattata taaaagcttt atttgttcta ggttgttcat    420

gaaatatttt tttggtttta tctccgttgt aagaaaatca tgtgctttgt gtcgccactc    480

actattgcag ctttttcatg cattggtcag attgacggtt gattgtattt ttgtttttta    540

tggttttgtg ttatgactta agtcttcatc tctttatctc ttcatcaggt ttgatggtta    600

cctaatatgg tccatgggta catgcatggt taaattaggt ggccaacttt gttgtgaacg    660

atagaatttt ttttatatta agtaaactat ttttatatta tgaaataata ataaaaaaaa    720

tattttatca ttattaacaa aatcatatta gttaatttgt taactctata ataaaagaaa    780

tactgtaaca ttcacattac atggtaacat ctttccaccc tttcatttgt tttttgtttg    840

atgacttttt ttcttgttta aatttatttc ccttctttta aatttggaat acattatcat    900

catatataaa ctaaaatact aaaaacagga ttacacaaat gataaataat aacacaaata    960

tttataaatc tagctgcaat atatttaaac tagctatatc gatattgtaa aataaaacta   1020

gctgcattga tactgataaa aaaatatcat gtgctttctg gactgatgat gcagtatact   1080

tttgacattg cctttatttt atttttcaga aaagctttct tagttctggg ttcttcatta   1140

tttgtttccc atctccattg tgaattgaat catttgcttc gtgtcacaaa tacaatttag   1200
```

```
ntaggtacat gcattggtca gattcacggt ttattatgtc atgacttaag ttcatggtag   1260
tacattacct gccacgcatg cattatattg gttagatttg ataggcaaat ttggttgtca   1320
acaatataaa tataaataat gtttttatat tacgaaataa cagtgatcaa aacaaacagt   1380
tttatcttta ttaacaagat tttgtttttg tttgatgacg ttttttaatg tttacgcttt   1440
ccccttcttt ttgaatttag aacactttat catcataaaa tcaaatacta aaaaaattac   1500
atatttcata aataataaca caaatatttt taaaaaatct gaaataataa tgaacaatat   1560
tacatattat cacgaaaatt cattaataaa aatattatat aaataaaatg taatagtagt   1620
tatatgtagg aaaaaagtac tgcacgcata atatatacaa aaagattaaa atgaactatt   1680
ataaataata acactaaatt aatggtgaat catatcaaaa taatgaaaaa gtaaataaaa   1740
tttgtaatta acttctatat gtattacaca cacaaataat aaataatagt aaaaaaaatt   1800
atgataaata tttaccatct cataagatat ttaaaataat gataaaaata tagattattt   1860
tttatgcaac tagctagcca aaaagagaac acgggtatat ataaaaagag tacctttaaa   1920
ttctactgta cttcctttat tcctgacgtt tttatatcaa gtggacatac gtgaagattt   1980
taattatcag tctaaatatt tcattagcac ttaatacttt tctgttttat tcctatccta   2040
taagtagtcc cgattctccc aacattgctt attcacacaa ctaactaaga aagtcttcca   2100
tagcccccca agcggccgcc tctctctctc tctcttctct ctttctctcc ccctctctcc   2160
ggcgatggtt gttgctatgg accaacgcac caatgtgaac ggagatcccg gcgccggaga   2220
ccggaagaaa gaagaaaggt ttgatccgag tgcacaacca ccgttcaaga tcggagatat   2280
aagggcggcg attcctaagc actgttgggt taagagtcct ttgagatcaa tgagttacgt   2340
cgtcagagac attatcgccg tcgcggcttt ggccatcgct gccgtgtatg ttgatagctg   2400
gttcctttgg cctctttatt gggccgccca aggaacactt ttctgggcca tctttgttct   2460
cggccacgac tgtggacatg ggagtttctc agacattcct ctactgaata gtgtggttgg   2520
tcacattctt cattctttca tcctcgttcc ttaccatggt tggagaataa gccaccggac   2580
acaccaccag aaccatggcc atgttgaaaa cgacgagtca tgggttccgt taccagaaag   2640
ggtgtacaag aaattgcccc acagtactcg gatgctcaga tacnctgtcc ctctccccat   2700
gctcgcatat cctctctatt tgtgctacag aagtcctgga aaagaaggat cacattttaa   2760
cccatacagt agtttatttg ctccaagcga gagaaagctt attgcaactt caactacttg   2820
ttggtccata atgttcgtca gtcttatcgc tctatctttc gtcttcggtc cactcgcggt   2880
tcttaaagtc tacggtgtac cgtacattat ctttgtgatg tggttggatg ctgtcacgta   2940
tttgcatcat catggtcacg atgagaagtt gccttggtat agaggcaagg aatggagtta   3000
tctacgtgga ggattaacaa caattgatag agattacgga atctttaaca acattcatca   3060
cgacattgga actcacgtga tccatcatct cttcccacaa atccctcact atcacttggt   3120
cgacgccacg aaagcagcta aacatgtgtt gggaagatac tacagagaac caaagacgtc   3180
aggagcaata ccgatccact tggtggagag tttggtcgca agtattaaga aagatcatta   3240
cgtcagcgac actggtgata ttgtcttcta cgagacagat ccagatctct acgtttacgc   3300
ttctgacaaa tctaaaatca attaatctcc atttgtttag ctctattagg aataaaccag   3360
cccactttta aaatttttat ttcttgttgt ttttaagtta aaagtgtact cgtgaaactc   3420
ttttttttt cttttttttt attaatgtat ttacattaca aggcgtaaag cggccgcgac   3480
acaagtgtga gagtactaaa taaatgcttt ggttgtacga aatcattaca ctaaataaaa   3540
taatcaaagc ttatatatgc cttccgctaa ggccgaatgc aaagaaattg gttctttctc   3600
```

-continued

```
gttatctttt gccactttta ctagtacgta ttaattacta cttaatcatc tttgtttacg   3660
gctcattata tccgtacgga tccgtcgacg gcgcgcccga tcatccggat atagttcctc   3720
ctttcagcaa aaaacccctc aagacccgtt tagaggcccc aaggggttat gctagttatt   3780
gctcagcggt ggcagcagcc aactcagctt cctttcgggc tttgttagca gccggatcga   3840
tccaagctgt acctcactat tcctttgccc tcggacgagt gctggggcgt cggtttccac   3900
tatcggcgag tacttctaca cagccatcgg tccagacggc cgcgcttctg cgggcgattt   3960
gtgtacgccc gacagtcccg gctccggatc ggacgattgc gtcgcatcga ccctgcgccc   4020
aagctgcatc atcgaaattg ccgtcaacca agctctgata gagttggtca agaccaatgc   4080
ggagcatata cgcccggagc cgcggcgatc ctgcaagctc cggatgcctc cgctcgaagt   4140
agcgcgtctg ctgctccata caagccaacc acggcctcca gaagaagatg ttggcgacct   4200
cgtattggga atccccgaac atcgcctcgc tccagtcaat gaccgctgtt atgcggccat   4260
tgtccgtcag gacattgttg gagccgaaat ccgcgtgcac gaggtgccgg acttcggggc   4320
agtcctcggc ccaaagcatc agctcatcga gagcctgcgc gacggacgca ctgacggtgt   4380
cgtccatcac agtttgccag tgatacacat ggggatcagc aatcgcgcat atgaaatcac   4440
gccatgtagt gtattgaccg attccttgcg gtccgaatgg gccgaacccg ctcgtctggc   4500
taagatcggc cgcagcgatc gcatccatag cctccgcgac cggctgcaga acagcgggca   4560
gttcggtttc aggcaggtct tgcaacgtga caccctgtgc acggcgggag atgcaatagg   4620
tcaggctctc gctgaattcc ccaatgtcaa gcacttccgg aatcgggagc gcggccgatg   4680
caaagtgccg ataaacataa cgatctttgt agaaaccatc ggcgcagcta tttacccgca   4740
ggacatatcc acgccctcct acatcgaagc tgaaagcacg agattcttcg ccctccgaga   4800
gctgcatcag gtcggagacg ctgtcgaact tttcgatcag aaacttctcg acagacgtcg   4860
cggtgagttc aggcttttcc atgggtatat ctccttctta aagttaaaca aaattatttc   4920
tagagggaaa ccgttgtggt ctccctatag tgagtcgtat taatttcgcg ggatcgagat   4980
cgatccaatt ccaatcccac aaaaatctga gcttaacagc acagttgctc ctctcagagc   5040
agaatcgggt attcaacacc ctcatatcaa ctactacgtt gtgtataacg gtccacatgc   5100
cggtatatac gatgactggg gttgtacaaa ggcggcaaca aacggcgttc ccggagttgc   5160
acacaagaaa tttgccacta ttacagaggc aagagcagca gctgacgcgt acacaacaag   5220
tcagcaaaca gacaggttga acttcatccc caaaggagaa gctcaactca agcccaagag   5280
ctttgctaag gccctaacaa gcccaccaaa gcaaaaagcc cactggctca cgctaggaac   5340
caaaaggccc agcagtgatc cagccccaaa agagatctcc tttgccccgg agattacaat   5400
ggacgatttc ctctatcttt acgatctagg aaggaagttc gaaggtgaag gtgacgacac   5460
tatgttcacc actgataatg agaaggttag cctcttcaat ttcagaaaga atgctgaccc   5520
acagatggtt agagaggcct acgcagcagg tctcatcaag acgatctacc cgagtaacaa   5580
tctccaggag atcaaatacc ttcccaagaa ggttaaagat gcagtcaaaa gattcaggac   5640
taattgcatc aagaacacag agaaagacat atttctcaag atcagaagta ctattccagt   5700
atggacgatt caaggcttgc ttcataaacc aaggcaagta atagagattg gagtctctaa   5760
aaaggtagtt cctactgaat ctaaggccat gcatggagtc taagattcaa atcgaggatc   5820
taacagaact cgccgtgaag actggcgaac agttcataca gagtctttta cgactcaatg   5880
acaagaagaa aatcttcgtc aacatggtgg agcacgacac tctggtctac tccaaaaatg   5940
```

-continued

```
tcaaagatac agtctcagaa gaccaaaggg ctattgagac ttttcaacaa aggataattt   6000
cgggaaacct cctcggattc cattgcccag ctatctgtca cttcatcgaa aggacagtag   6060
aaaaggaagg tggctcctac aaatgccatc attgcgataa aggaaaggct atcattcaag   6120
atgcctctgc cgacagtggt cccaaagatg gacccccacc cacgaggagc atcgtggaaa   6180
aagaagacgt tccaaccacg tcttcaaagc aagtggattg atgtgacatc tccactgacg   6240
taagggatga cgcacaatcc cactatcctt cgcaagaccc ttcctctata taaggaagtt   6300
catttcattt ggagaggaca cgctcgagct catttctcta ttacttcagc cataacaaaa   6360
gaactctttt ctcttcttat taaaccatga aaaagcctga actcaccgcg acgtctgtcg   6420
agaagtttct gatcgaaaag ttcgacagcg tctccgacct gatgcagctc tcggagggcg   6480
aagaatctcg tgctttcagc ttcgatgtag gagggcgtgg atatgtcctg cgggtaaata   6540
gctgcgccga tggtttctac aaagatcgtt atgtttatcg gcactttgca tcggccgcgc   6600
tcccgattcc ggaagtgctt gacattgggg aattcagcga gagcctgacc tattgcatct   6660
cccgccgtgc acagggtgtc acgttgcaag acctgcctga aaccgaactg cccgctgttc   6720
tgcagccggt cgcggaggcc atggatgcga tcgctgcggc cgatcttagc cagacgagcg   6780
ggttcggccc attcggaccg caaggaatcg gtcaatacac tacatggcgt gatttcatat   6840
gcgcgattgc tgatccccat gtgtatcact ggcaaactgt gatggacgac accgtcagtg   6900
cgtccgtcgc gcaggctctc gatgagctga tgctttgggc cgaggactgc cccgaagtcc   6960
ggcacctcgt gcacgcggat ttcggctcca acaatgtcct gacggacaat ggccgcataa   7020
cagcggtcat tgactggagc gaggcgatgt tcggggattc ccaatacgag gtcgccaaca   7080
tcttcttctg gaggccgtgg ttggcttgta tggagcagca gacgcgctac ttcgagcgga   7140
ggcatccgga gcttgcagga tcgccgcggc tccgggcgta tatgctccgc attggtcttg   7200
accaactcta tcagagcttg gttgacggca atttcgatga tgcagcttgg gcgcagggtc   7260
gatgcgacgc aatcgtccga tccggagccg ggactgtcgg gcgtacacaa atcgcccgca   7320
gaagcgcggc cgtctggacc gatggctgtg tagaagtact cgccgatagt ggaaaccgac   7380
gccccagcac tcgtccgagg gcaaaggaat agtgaggtac ctaaagaagg agtgcgtcga   7440
agcagatcgt tcaaacattt ggcaataaag tttcttaaga ttgaatcctg ttgccggtct   7500
tgcgatgatt atcatataat ttctgttgaa ttacgttaag catgtaataa ttaacatgta   7560
atgcatgacg ttatttatga gatgggtttt tatgattaga gtcccgcaat tatacattta   7620
atacgcgata gaaaacaaaa tatagcgcgc aaactaggat aaattatcgc gcgcggtgtc   7680
atctatgtta ctagatcgat gtcgaatcga tcaacctgca ttaatgaatc ggccaacgcg   7740
cggggagagg cggtttgcgt attgggcgct cttccgcttc ctcgctcact gactcgctgc   7800
gctcggtcgt tcggctgcgg cgagcggtat cagctcactc aaaggcggta atacggttat   7860
ccacagaatc aggggataac gcaggaaaga acatgtgagc aaaaggccag caaaaggcca   7920
ggaaccgtaa aaaggccgcg ttgctggcgt ttttccatag gctccgcccc cctgacgagc   7980
atcacaaaaa tcgacgctca agtcagaggt ggcgaaaccc gacaggacta taaagatacc   8040
aggcgtttcc ccctggaagc tccctcgtgc gctctcctgt tccgaccctg ccgcttaccg   8100
gatacctgtc cgcctttctc ccttcgggaa gcgtggcgct ttctcaatgc tcacgctgta   8160
ggtatctcag ttcggtgtag gtcgttcgct ccaagctggg ctgtgtgcac gaaccccccg   8220
ttcagcccga ccgctgcgcc ttatccggta actatcgtct tgagtccaac ccggtaagac   8280
acgacttatc gccactggca gcagccactg gtaacaggat tagcagagcg aggtatgtag   8340
```

-continued

```
gcggtgctac agagttcttg aagtggtggc ctaactacgg ctacactaga aggacagtat   8400
ttggtatctg cgctctgctg aagccagtta ccttcggaaa aagagttggt agctcttgat   8460
ccggcaaaca aaccaccgct ggtagcggtg gtttttttgt ttgcaagcag cagattacgc   8520
gcagaaaaaa aggatctcaa gaagatcctt tgatcttttc tacggggtct gacgctcagt   8580
ggaacgaaaa ctcacgttaa gggattttgg tcatgacatt aacctataaa aataggcgta   8640
tcacgaggcc ctttcgtctc gcgcgtttcg gtgatgacgg tgaaaacctc tgacacatgc   8700
agctcccgga gacggtcaca gcttgtctgt aagcggatgc cgggagcaga caagcccgtc   8760
agggcgcgtc agcgggtgtt ggcgggtgtc ggggctggct taactatgcg gcatcagagc   8820
agattgtact gagagtgcac catatggaca tattgtcgtt agaacgcggc tacaattaat   8880
acataacctt atgtatcata cacatacgat ttaggtgaca ctatagaacg gcgcgccaag   8940
cttggatctc ctgcagcccg ggggatccgc ccacgtacgg taccatctgc taatatttta   9000
aatcacatgc aagagaggag gcatggttcc attttctacc ttcacattat ttgagaaaaa   9060
cgaacttgtt ctgtgtttta tttttgccct tcacattagt acaacgtgga agactcatgg   9120
ttacacagaa tcatacataa gtacaatgct tgtccctaag aaaacaagca ctcgttgtat   9180
tgaaccttta cggctcatgc ggccgcgaat tcactagtga ttgaattcgc ggccgcttag   9240
tccgacttgg ccttggcggc cgcggccgac tctttgagcg tgaagatctg cgccgtctcg   9300
ggcacagcgc cgtagttgac aaagaggtgc gcggtcttga agaaggccgt gatgatgggc   9360
tcgtcgttcc tgcgcacgag gtgcgggtac gcggccgcaa agtgcttggt ggcttcgttg   9420
agcttgtagt gcggaatgat cgggaacaag tggtggacct ggtgcgtgcc aatgtggtgg   9480
ctcaggttgt ccacgaacgc gccgtacgag cggtcgacgc tcgagaggtt gcccttgacg   9540
tacgtccact ccgagtcgcc gtaccacggc gtcgcttcgt cgttgtggtg caagaaggtc   9600
gtaatgacga ggaacgaagc aaagacaaag agcggcgcat agtagtagag gcccatgacg   9660
gcaaagccga gcgagtatgt gaggtacgcg tacgcggcga agaaggcggc ccagacgccg   9720
agcgacacga tgacggccga cgcgcggcga aggaggagcg ggtcccacgg gtcaaagtgg   9780
ctcatcgtgc gcggggcata cccgaccttc aagtagacaa accacgcacc gccgagcgtg   9840
tagacccatt ggcgcacgtc ctggaggtcc ttgaccgacc ggtgcgggta aaagatctcg   9900
tccttatcaa tgttgcccgt gttcttgtgg tggtggcggt gcgtcacgcg ccagctctcg   9960
aacggcgtca aaatcgcaga gtgcatgatg cagccgatga taaagttgac gctgtggtag  10020
cgcgagaagg ccgagtggcc gcagtcgtgg ccgaccgtga agaagcccca gaagatgacg  10080
ccctgcacgt agatgtaggt ggcgcaaacg agcgcgtgga gcagaacgtt atcggcaatg  10140
aacggcgtcg agcgcgccgc gtagagcagc gccgccgagg ccgacgcgtt gaagatcgcg  10200
cgggccgtgt agtagagcga gaggccgagg ttcgactcaa agcacgcgtt cgggatcgag  10260
tgcttgagct ccgtgagcgt cgggaactcg accttcgtct tatcctcagt catgcggccg  10320
ctgaagtatt gcttcttagt taacctttcc tttctctctc agctatgtga attcattttg  10380
ctttcgtcac aatttatata gtgaaattgg atctttggag ttaacgcctt cacaggatta  10440
tcgtgttaga acaatgcttt ttcatgttct aattagtagt acattacaaa tgtgcactct  10500
attcaataag catcttttgg cacgttaata aatcatgtga aaaaaaaata ctactatttc  10560
aaagaaagtg ttgtaaaaag aaacggaaag agagctggct tcagttgttg agacttgttt  10620
gctagtaaaa atggtgtgaa gagtgattca tggtgaggtg gtttttcgtc cctttctgtt  10680
```

```
tgcatgaaaa acaaatggca agagatgacg taggattcct tcccttaacg attatctgtt  10740

tttaatttca aatatacata taggaattta tgaattacta aggttgtaaa atatgctggt  10800

catttattta tggctaaaat atttttttt ctcgtaaata taaaaatatt taaaatttat  10860

ttttatcata ttttttatcc ttataaaatt atgtgtacaa cctatataaa aaaatatcat  10920

atttaatatt gattatatgt ttaatcaata taaaaaatca ttatcatata tttagattta  10980

ttcgaatata catctaaaca aaaaataaca tattttaatt ttatgaagaa aaaaaaatat  11040

tttatccttt atttatttaa gattaattaa tagttatgta ttgtggaaag acttttacac  11100

atgcaataga tatactgaat caattagatg ccaatgctga gttggaaatc acttgaggag  11160

gggaggagac ttgccaatgc ttttcagttt catttaaatg atttagtgga ggagatagag  11220

tagtgataaa ggcatgcccc aattttggag tgtatatatg agtggaaata agagagggat  11280

agagagaaaa aataaagaga gtaaaaataa ttaatgtgaa atgatatgat aaaaaaataa  11340

agaaagagat aaagagaaaa atgaaatgag agatagatga aatagagagt agatacatgt  11400

ttgtttaggt tttttttagg aaataacaca tttttttctc atcacttatt actcactgtc  11460

aatttcctct ctttcaatca taatgatatg atttgtttaa caaaaatgtg aaaaaacata  11520

taaagtaaaa tatttttata aattgataaa taaaaattta caaaatttat ttcttattaa  11580

attgaataga aaatgaaaga aaagaaaaga aaaagtatat ataaaatgat atagctttaa  11640

aaagaataaa tttttcatat cagtcttttt ttaataattt agaaatattt aagtatatag  11700

caaaaatata atgtacttta catatgcata aataataatt tgaaaataga actaatagaa  11760

tagagaaaaa agtaatataa taattaacta tatgaaaatt tagaagggac aatattttta  11820

attaagaata taaacaatat ttcttttcat gtaatgaggg acggatgtac ggggccagtg  11880

ttggagtcaa agccaaaata gtcacgggga aattaatgca ctgcatgact attcgaaaaa  11940

attcactagc cttacttaga tgttagatta atagctaggg ggtgcagata attttgaaag  12000

gcatgaaaaa cattaatttg tacattgcaa gcttttgatg acaagctttg caattgttca  12060

cactacctta tgccatttat aaatagagtg attggcatat gaaggaaatc atgagagtcg  12120

aagcgaaaaa caaagcttga gagtgtagga aaaatacagt ttttttggta aaaatacagt  12180

atttgaatag gagcgaaaaa tatcctttca aaatgatcct tttctttttt tttttttttc  12240

ttgttgttct tggtcagtta ttcaaaggaa aagggattga aataaaaact tgcatgtggg  12300

atcgtacgtc gagtcgacct gca                                          12323
```

<210> SEQ ID NO 53
<211> LENGTH: 12456
<212> TYPE: DNA
<213> ORGANISM: Artificial Sequence
<220> FEATURE:
<223> OTHER INFORMATION: the sequence of pKR585
<220> FEATURE:
<221> NAME/KEY: misc_feature
<222> LOCATION: (1201)..(1201)
<223> OTHER INFORMATION: n is a, c, g, or t

<400> SEQUENCE: 53

```
ggatctggcc ggccggatct cgtacgtcct cgaagagaag ggttaataac acatttttta     60

acatttttaa cacaaatttt agttatttaa aaatttatta aaaaatttaa aataagaaga    120

ggaactcttt aaataaatct aacttacaaa atttatgatt tttaataagt tttcaccaat    180

aaaaaatgtc ataaaaatat gttaaaaagt atattatcaa tattctcttt atgataaata    240

aaaagaaaaa aaaaataaaa gttaagtgaa aatgagattg aagtgacttt aggtgtgtat    300
```

```
aaatatatca accccgccaa caatttattt aatccaaata tattgaagta tattattcca    360
tagcctttat ttatttatat atttattata taaaagcttt atttgttcta ggttgttcat    420
gaaatatttt tttggtttta tctccgttgt aagaaaatca tgtgctttgt gtcgccactc    480
actattgcag ctttttcatg cattggtcag attgacggtt gattgtattt ttgtttttta    540
tggttttgtg ttatgactta agtcttcatc tctttatctc ttcatcaggt ttgatggtta    600
cctaatatgg tccatgggta catgcatggt taaattaggt ggccaacttt gttgtgaacg    660
atagaatttt ttttatatta agtaaactat ttttatatta tgaaataata ataaaaaaaa    720
tattttatca ttattaacaa aatcatatta gttaatttgt taactctata ataaaagaaa    780
tactgtaaca ttcacattac atggtaacat ctttccaccc tttcatttgt tttttgtttg    840
atgacttttt ttcttgttta aatttatttc ccttctttta aatttggaat acattatcat    900
catatataaa ctaaaatact aaaaacagga ttacacaaat gataaataat aacacaaata    960
tttataaatc tagctgcaat atatttaaac tagctatatc gatattgtaa aataaaacta   1020
gctgcattga tactgataaa aaaatatcat gtgctttctg gactgatgat gcagtatact   1080
tttgacattg cctttatttt atttttcaga aaagctttct tagttctggg ttcttcatta   1140
tttgtttccc atctccattg tgaattgaat catttgcttc gtgtcacaaa tacaatttag   1200
ntaggtacat gcattggtca gattcacggt ttattatgtc atgacttaag ttcatggtag   1260
tacattacct gccacgcatg cattatattg gttagatttg ataggcaaat ttggttgtca   1320
acaatataaa tataaataat gtttttatat tacgaaataa cagtgatcaa aacaaacagt   1380
tttatcttta ttaacaagat tttgtttttg tttgatgacg ttttttaatg tttacgcttt   1440
ccccccttctt ttgaatttag aacactttat catcataaaa tcaaatacta aaaaaattac   1500
atatttcata aataataaca caaatatttt taaaaaatct gaaataataa tgaacaatat   1560
tacatattat cacgaaaatt cattaataaa aatattatat aaataaaatg taatagtagt   1620
tatatgtagg aaaaaagtac tgcacgcata atatatacaa aaagattaaa atgaactatt   1680
ataaataata acactaaatt aatggtgaat catatcaaaa taatgaaaaa gtaaataaaa   1740
tttgtaatta acttctatat gtattacaca cacaaataat aaataatagt aaaaaaaatt   1800
atgataaata tttaccatct cataagatat ttaaaataat gataaaaata tagattattt   1860
tttatgcaac tagctagcca aaaagagaac acgggtatat ataaaaagag tacctttaaa   1920
ttctactgta cttcctttat tcctgacgtt tttatatcaa gtggacatac gtgaagattt   1980
taattatcag tctaaatatt tcattagcac ttaatacttt tctgttttat tcctatccta   2040
taagtagtcc cgattctccc aacattgctt attcacacaa ctaactaaga aagtcttcca   2100
tagccccccca agcggccgca caatggcgac tcgacagcga actgccacca ctgttgtggt   2160
cgaggacctt cccaaggtca ctcttgaggc caagtctgaa cctgtgttcc ccgatatcaa   2220
gaccatcaag gatgccattc ccgcgcactg cttccagccc tcgctcgtca cctcattcta   2280
ctacgtcttc cgcgattttg ccatggtctc tgccctcgtc tgggctgctc tcacctacat   2340
ccccagcatc cccgaccaga ccctccgcgt cgcagcttgg atggtctacg gcttcgtcca   2400
gggtctgttc tgcaccggtg tctggattct cggccatgag tgcggccacg gtgctttctc   2460
tctccacgga aaggtcaaca atgtgaccgg ctggttcctc cactcgttcc tcctcgtccc   2520
ctacttcagc tggaagtact ctcaccaccg ccaccaccgc ttcaccggcc acatggatct   2580
cgacatggct ttcgtcccca agactgagcc caagccctcc aagtcgctca tgattgctgg   2640
```

-continued

```
cattgacgtc gccgagcttg ttgaggacac ccccgctgct cagatggtca agctcatctt   2700
ccaccagctt ttcggatggc aggcgtacct cttcttcaac gctagctctg gcaagggcag   2760
caagcagtgg gagcccaaga ctggcctctc caagtggttc cgagtcagtc acttcgagcc   2820
taccagcgct gtcttccgcc ccaacgaggc catcttcatc ctcatctccg atatcggtct   2880
tgctctaatg ggaactgctc tgtactttgc ttccaagcaa gttggtgttt cgaccattct   2940
cttcctctac cttgttccct acctgtgggt tcaccactgg ctcgttgcca ttacctacct   3000
ccaccaccac cacaccgagc tccctcacta caccgctgag ggctggacct acgtcaaggg   3060
agctctcgcc actgtcgacc gtgagtttgg cttcatcgga aagcacctct tccacggtat   3120
cattgagaag cacgttgttc accatctctt ccctaagatc cccttctaca aggctgacga   3180
ggccaccgag gccatcaagc ccgtcattgg cgaccactac tgccacgacg accgaagctt   3240
cctgggccag ctgtggacca tcttcggcac gctcaagtac gtcgagcacg accctgcccg   3300
acccggtgcc atgcgatgga acaaggacta ggctaggcgg ccgcgacaca agtgtgagag   3360
tactaaataa atgctttggt tgtacgaaat cattacacta aataaaataa tcaaagctta   3420
tatatgcctt ccgctaaggc cgaatgcaaa gaaattggtt ctttctcgtt atcttttgcc   3480
acttttacta gtacgtatta attactactt aatcatcttt gtttacggct cattatatcc   3540
ggtctagagg atccaaggcc gcgaagttaa aagcaatgtt gtcacttgtc gtactaacac   3600
atgatgtgat agtttatgct agctagctat aacataagct gtctctgagt gtgttgtata   3660
ttaataaaga tcatcactgg tgaatggtga tcgtgtacgt accctactta gtaggcaatg   3720
gaagcactta gagtgtgctt tgtgcatggc cttgcctctg ttttgagact tttgtaatgt   3780
tttcgagttt aaatctttgc ctttgcgtac ggatccgtcg acggcgcgcc cgatcatccg   3840
gatatagttc ctcctttcag caaaaaaccc ctcaagaccc gtttagaggc cccaaggggt   3900
tatgctagtt attgctcagc ggtggcagca gccaactcag cttcctttcg ggctttgtta   3960
gcagccggat cgatccaagc tgtacctcac tattcctttg ccctcggacg agtgctgggg   4020
cgtcggtttc cactatcggc gagtacttct acacagccat cggtccagac ggccgcgctt   4080
ctgcgggcga tttgtgtacg cccgacagtc ccggctccgg atcggacgat tgcgtcgcat   4140
cgaccctgcg cccaagctgc atcatcgaaa ttgccgtcaa ccaagctctg atagagttgg   4200
tcaagaccaa tgcggagcat atacgcccgg agccgcggcg atcctgcaag ctccggatgc   4260
ctccgctcga agtagcgcgt ctgctgctcc atacaagcca accacggcct ccagaagaag   4320
atgttggcga cctcgtattg ggaatccccg aacatcgcct cgctccagtc aatgaccgct   4380
gttatgcggc cattgtccgt caggacattg ttggagccga aatccgcgtg cacgaggtgc   4440
cggacttcgg ggcagtcctc ggcccaaagc atcagctcat cgagagcctg cgcgacggac   4500
gcactgacgg tgtcgtccat cacagtttgc cagtgataca catggggatc agcaatcgcg   4560
catatgaaat cacgccatgt agtgtattga ccgattcctt gcggtccgaa tgggccgaac   4620
ccgctcgtct ggctaagatc ggccgcagcg atcgcatcca tagcctccgc gaccggctgc   4680
agaacagcgg gcagttcggt ttcaggcagg tcttgcaacg tgacaccctg tgcacggcgg   4740
gagatgcaat aggtcaggct ctcgctgaat tccccaatgt caagcacttc cggaatcggg   4800
agcgcggccg atgcaaagtg ccgataaaca taacgatctt tgtagaaacc atcggcgcag   4860
ctatttaccc gcaggacata tccacgccct cctacatcga agctgaaagc acgagattct   4920
tcgccctccg agagctgcat caggtcggag acgctgtcga acttttcgat cagaaacttc   4980
tcgacagacg tcgcggtgag ttcaggcttt tccatgggta tatctccttc ttaaagttaa   5040
```

-continued

```
acaaaattat ttctagaggg aaaccgttgt ggtctcccta tagtgagtcg tattaatttc   5100
gcgggatcga gatcgatcca attccaatcc cacaaaaatc tgagcttaac agcacagttg   5160
ctcctctcag agcagaatcg ggtattcaac accctcatat caactactac gttgtgtata   5220
acggtccaca tgccggtata tacgatgact ggggttgtac aaaggcggca acaaacggcg   5280
ttcccggagt tgcacacaag aaatttgcca ctattacaga ggcaagagca gcagctgacg   5340
cgtacacaac aagtcagcaa acagacaggt tgaacttcat ccccaaagga gaagctcaac   5400
tcaagcccaa gagctttgct aaggccctaa caagcccacc aaagcaaaaa gcccactggc   5460
tcacgctagg aaccaaaagg cccagcagtg atccagcccc aaaagagatc tcctttgccc   5520
cggagattac aatggacgat ttcctctatc tttacgatct aggaaggaag ttcgaaggtg   5580
aaggtgacga cactatgttc accactgata atgagaaggt tagcctcttc aatttcagaa   5640
agaatgctga cccacagatg gttagagagg cctacgcagc aggtctcatc aagacgatct   5700
acccgagtaa caatctccag gagatcaaat accttcccaa gaaggttaaa gatgcagtca   5760
aaagattcag gactaattgc atcaagaaca cagagaaaga catatttctc aagatcagaa   5820
gtactattcc agtatggacg attcaaggct tgcttcataa accaaggcaa gtaatagaga   5880
ttggagtctc taaaaaggta gttcctactg aatctaaggc catgcatgga gtctaagatt   5940
caaatcgagg atctaacaga actcgccgtg aagactggcg aacagttcat acagagtctt   6000
ttacgactca atgacaagaa gaaaatcttc gtcaacatgg tggagcacga cactctggtc   6060
tactccaaaa atgtcaaaga tacagtctca gaagaccaaa gggctattga gacttttcaa   6120
caaaggataa tttcgggaaa cctcctcgga ttccattgcc cagctatctg tcacttcatc   6180
gaaaggacag tagaaaagga aggtggctcc tacaaatgcc atcattgcga taaaggaaag   6240
gctatcattc aagatgcctc tgccgacagt ggtcccaaag atggaccccc acccacgagg   6300
agcatcgtgg aaaaagaaga cgttccaacc acgtcttcaa agcaagtgga ttgatgtgac   6360
atctccactg acgtaaggga tgacgcacaa tcccactatc cttcgcaaga cccttcctct   6420
atataaggaa gttcatttca tttggagagg acacgctcga gctcatttct ctattacttc   6480
agccataaca aaagaactct ttctcttctt tattaaacca tgaaaaagcc tgaactcacc   6540
gcgacgtctg tcgagaagtt tctgatcgaa aagttcgaca gcgtctccga cctgatgcag   6600
ctctcggagg gcgaagaatc tcgtgctttc agcttcgatg taggagggcg tggatatgtc   6660
ctgcgggtaa atagctgcgc cgatggtttc tacaaagatc gttatgttta tcggcacttt   6720
gcatcggccg cgctcccgat tccggaagtg cttgacattg gggaattcag cgagagcctg   6780
acctattgca tctcccgccg tgcacagggt gtcacgttgc aagacctgcc tgaaaccgaa   6840
ctgcccgctg ttctgcagcc ggtcgcggag gccatggatg cgatcgctgc ggccgatctt   6900
agccagacga gcgggttcgg cccattcgga ccgcaaggaa tcggtcaata cactacatgg   6960
cgtgatttca tatgcgcgat tgctgatccc catgtgtatc actggcaaac tgtgatggac   7020
gacaccgtca gtgcgtccgt cgcgcaggct ctcgatgagc tgatgctttg ggccgaggac   7080
tgccccgaag tccggcacct cgtgcacgcg gatttcggct ccaacaatgt cctgacggac   7140
aatggccgca taacagcggt cattgactgg agcgaggcga tgttcgggga ttcccaatac   7200
gaggtcgcca acatcttctt ctggaggccg tggttggctt gtatggagca gcagacgcgc   7260
tacttcgagc ggaggcatcc ggagcttgca ggatcgccgc ggctccgggc gtatatgctc   7320
cgcattggtc ttgaccaact ctatcagagc ttggttgacg gcaatttcga tgatgcagct   7380
```

-continued

```
tgggcgcagg gtcgatgcga cgcaatcgtc cgatccggag ccgggactgt cgggcgtaca   7440
caaatcgccc gcagaagcgc ggccgtctgg accgatggct gtgtagaagt actcgccgat   7500
agtggaaacc gacgccccag cactcgtccg agggcaaagg aatagtgagg tacctaaaga   7560
aggagtgcgt cgaagcagat cgttcaaaca tttggcaata aagtttctta agattgaatc   7620
ctgttgccgg tcttgcgatg attatcatat aatttctgtt gaattacgtt aagcatgtaa   7680
taattaacat gtaatgcatg acgttattta tgagatgggt ttttatgatt agagtcccgc   7740
aattatacat ttaatacgcg atagaaaaca aaatatagcg cgcaaactag gataaattat   7800
cgcgcgcggt gtcatctatg ttactagatc gatgtcgaat cgatcaacct gcattaatga   7860
atcggccaac gcgcggggag aggcggtttg cgtattgggc gctcttccgc ttcctcgctc   7920
actgactcgc tgcgctcggt cgttcggctg cggcgagcgg tatcagctca ctcaaaggcg   7980
gtaatacggt tatccacaga atcaggggat aacgcaggaa agaacatgtg agcaaaaggc   8040
cagcaaaagg ccaggaaccg taaaaaggcc gcgttgctgg cgtttttcca taggctccgc   8100
ccccctgacg agcatcacaa aaatcgacgc tcaagtcaga ggtggcgaaa cccgacagga   8160
ctataaagat accaggcgtt tccccctgga agctccctcg tgcgctctcc tgttccgacc   8220
ctgccgctta ccggatacct gtccgccttt ctcccttcgg gaagcgtggc gctttctcaa   8280
tgctcacgct gtaggtatct cagttcggtg taggtcgttc gctccaagct gggctgtgtg   8340
cacgaacccc ccgttcagcc cgaccgctgc gccttatccg gtaactatcg tcttgagtcc   8400
aacccggtaa gacacgactt atcgccactg gcagcagcca ctggtaacag gattagcaga   8460
gcgaggtatg taggcggtgc tacagagttc ttgaagtggt ggcctaacta cggctacact   8520
agaaggacag tatttggtat ctgcgctctg ctgaagccag ttaccttcgg aaaaagagtt   8580
ggtagctctt gatccggcaa acaaaccacc gctggtagcg gtggtttttt tgtttgcaag   8640
cagcagatta cgcgcagaaa aaaaggatct caagaagatc ctttgatctt ttctacgggg   8700
tctgacgctc agtggaacga aaactcacgt taagggattt tggtcatgac attaacctat   8760
aaaaataggc gtatcacgag gccctttcgt ctcgcgcgtt tcggtgatga cggtgaaaac   8820
ctctgacaca tgcagctccc ggagacggtc acagcttgtc tgtaagcgga tgccgggagc   8880
agacaagccc gtcagggcgc gtcagcgggt gttggcgggt gtcggggctg gcttaactat   8940
gcggcatcag agcagattgt actgagagtg caccatatgg acatattgtc gttagaacgc   9000
ggctacaatt aatacataac cttatgtatc atacacatac gatttaggtg acactataga   9060
acggcgcgcc aagcttggat ctcctgcagc ccgggggatc cgcccacgta cggtaccatc   9120
tgctaatatt ttaaatcaca tgcaagagag gaggcatggt tccattttct accttcacat   9180
tatttgagaa aaacgaactt gttctgtgtt ttattttttgc ccttcacatt agtacaacgt   9240
ggaagactca tggttacaca gaatcataca taagtacaat gcttgtccct aagaaaacaa   9300
gcactcgttg tattgaacct ttacggctca tgcggccgcg aattcactag tgattgaatt   9360
cgcggccgct tagtccgact tggccttggc ggccgcggcc gactctttga gcgtgaagat   9420
ctgcgccgtc tcgggcacag cgccgtagtt gacaaagagg tgcgcggtct tgaagaaggc   9480
cgtgatgatg ggctcgtcgt tcctgcgcac gaggtgcggg tacgcggccg caaagtgctt   9540
ggtggcttcg ttgagcttgt agtgcggaat gatcgggaac aagtggtgga cctggtgcgt   9600
gccaatgtgg tggctcaggt tgtccacgaa cgcgccgtac gagcggtcga cgctcgagag   9660
gttgcccttg acgtacgtcc actccgagtc gccgtaccac ggcgtcgctt cgtcgttgtg   9720
gtgcaagaag gtcgtaatga cgaggaacga agcaaagaca aagagcggcg catagtagta   9780
```

gaggcccatg acggcaaagc cgagcgagta tgtgaggtac gcgtacgcgg cgaagaaggc 9840
ggcccagacg ccgagcgaca cgatgacggc cgacgcgcgg cgaaggagga gcgggtccca 9900
cgggtcaaag tggctcatcg tgcgcggggc atacccgacc ttcaagtaga caaaccacgc 9960
accgccgagc gtgtagaccc attggcgcac gtcctggagg tccttgaccg accggtgcgg 10020
gtaaaagatc tcgtccttat caatgttgcc cgtgttcttg tggtggtggc ggtgcgtcac 10080
gcgccagctc tcgaacggcg tcaaaatcgc agagtgcatg atgcagccga tgataaagtt 10140
gacgctgtgg tagcgcgaga aggccgagtg gccgcagtcg tggccgaccg tgaagaagcc 10200
ccagaagatg acgccctgca cgtagatgta ggtggcgcaa acgagcgcgt ggagcagaac 10260
gttatcggca atgaacggcg tcgagcgcgc cgcgtagagc agcgccgccg aggccgacgc 10320
gttgaagatc gcgcgggccg tgtagtagag cgagaggccg aggttcgact caaagcacgc 10380
gttcgggatc gagtgcttga gctccgtgag cgtcgggaac tcgaccttcg tcttatcctc 10440
agtcatgcgg ccgctgaagt attgcttctt agttaacctt tcctttctct ctcagctatg 10500
tgaattcatt ttgctttcgt cacaatttat atagtgaaat tggatctttg gagttaacgc 10560
cttcacagga ttatcgtgtt agaacaatgc tttttcatgt tctaattagt agtacattac 10620
aaatgtgcac tctattcaat aagcatcttt tggcacgtta ataaatcatg tgaaaaaaaa 10680
atactactat ttcaaagaaa gtgttgtaaa aagaaacgga aagagagctg gcttcagttg 10740
ttgagacttg tttgctagta aaaatggtgt gaagagtgat tcatggtgag gtggtttttc 10800
gtccctttct gtttgcatga aaaacaaatg gcaagagatg acgtaggatt ccttccctta 10860
acgattatct gtttttaatt tcaaatatac atataggaat ttatgaatta ctaaggttgt 10920
aaaatatgct ggtcatttat ttatggctaa aatatttttt tttctcgtaa atataaaaat 10980
atttaaaatt tatttttatc atattttta tccttataaa attatgtgta caacctatat 11040
aaaaaaatat catatttaat attgattata tgtttaatca atataaaaaa tcattatcat 11100
atatttagat ttattcgaat atacatctaa acaaaaaata acatatttta attttatgaa 11160
gaaaaaaaaa tattttatcc tttatttatt taagattaat taatagttat gtattgtgga 11220
aagactttta cacatgcaat agatatactg aatcaattag atgccaatgc tgagttggaa 11280
atcacttgag gaggggagga gacttgccaa tgcttttcag tttcatttaa atgatttagt 11340
ggaggagata gagtagtgat aaaggcatgc cccaattttg gagtgtatat atgagtggaa 11400
ataagagagg gatagagaga aaaaataaag agagtaaaaa taattaatgt gaaatgatat 11460
gataaaaaaa taaagaaaga gataaagaga aaaatgaaat gagagataga tgaaatagag 11520
agtagataca tgtttgttta ggttttttt aggaaataac acattttttt ctcatcactt 11580
attactcact gtcaatttcc tctctttcaa tcataatgat atgatttgtt taacaaaaat 11640
gtgaaaaaac atataaagta aaatattttt ataaattgat aaataaaaat ttacaaaatt 11700
tatttcttat taaattgaat agaaaatgaa agaaaagaaa agaaaaagta tatataaaat 11760
gatatagctt taaaaagaat aaatttttca tatcagtctt tttttaataa tttagaaata 11820
tttaagtata tagcaaaaat ataatgtact ttacatatgc ataaataata atttgaaaat 11880
agaactaata gaatagagaa aaaagtaata taataattaa ctatatgaaa atttagaagg 11940
gacaatattt ttaattaaga atataaacaa tatttctttt catgtaatga gggacggatg 12000
tacggggcca gtgttggagt caaagccaaa atagtcacgg ggaaattaat gcactgcatg 12060
actattcgaa aaaattcact agccttactt agatgttaga ttaatagcta gggggtgcag 12120

```
ataattttga aaggcatgaa aaacattaat ttgtacattg caagcttttg atgacaagct  12180

ttgcaattgt tcacactacc ttatgccatt tataaataga gtgattggca tatgaaggaa  12240

atcatgagag tcgaagcgaa aaacaaagct tgagagtgta ggaaaaaatac agttttttttg  12300

gtaaaaatac agtatttgaa taggagcgaa aaatatcctt tcaaaatgat ccttttcttt  12360

ttttttttt ttcttgttgt tcttggtcag ttattcaaag gaaaagggat tgaaataaaa  12420

acttgcatgt gggatcgtac gtcgagtcga cctgca                          12456
```

<210> SEQ ID NO 54
<211> LENGTH: 9088
<212> TYPE: DNA
<213> ORGANISM: Artificial Sequence
<220> FEATURE:
<223> OTHER INFORMATION: the sequence of pKR578
<220> FEATURE:
<221> NAME/KEY: misc_feature
<222> LOCATION: (6951)..(6951)
<223> OTHER INFORMATION: n is a, c, g, or t

<400> SEQUENCE: 54

```
ggccgcgaca caagtgtgag agtactaaat aaatgctttg gttgtacgaa atcattacac     60

taaataaaat aatcaaagct tatatatgcc ttccgctaag gccgaatgca aagaaattgg    120

ttctttctcg ttatcttttg ccacttttac tagtacgtat taattactac ttaatcatct    180

ttgtttacgg ctcattatat ccggtctaga ggatccaagg ccgcgaagtt aaaagcaatg    240

ttgtcacttg tcgtactaac acatgatgtg atagtttatg ctagctagct ataacataag    300

ctgtctctga gtgtgttgta tattaataaa gatcatcact ggtgaatggt gatcgtgtac    360

gtaccctact tagtaggcaa tggaagcact tagagtgtgc tttgtgcatg gccttgcctc    420

tgttttgaga cttttgtaat gttttcgagt ttaaatcttt gcctttgcgt acggatccgt    480

cgacggcgcg cccgatcatc cggatatagt tcctcctttc agcaaaaaac ccctcaagac    540

ccgtttagag gccccaaggg gttatgctag ttattgctca gcggtggcag cagccaactc    600

agcttccttt cgggctttgt tagcagccgg atcgatccaa gctgtacctc actattcctt    660

tgccctcgga cgagtgctgg ggcgtcggtt tccactatcg gcgagtactt ctacacagcc    720

atcggtccag acggccgcgc ttctgcgggc gatttgtgta cgcccgacag tcccggctcc    780

ggatcggacg attgcgtcgc atcgaccctg cgcccaagct gcatcatcga aattgccgtc    840

aaccaagctc tgatagagtt ggtcaagacc aatgcggagc atatacgccc ggagccgcgg    900

cgatcctgca agctccggat gcctccgctc gaagtagcgc gtctgctgct ccatacaagc    960

caaccacggc ctccagaaga agatgttggc gacctcgtat tgggaatccc cgaacatcgc   1020

ctcgctccag tcaatgaccg ctgttatgcg gccattgtcc gtcaggacat tgttggagcc   1080

gaaatccgcg tgcacgaggt gccggacttc ggggcagtcc tcggcccaaa gcatcagctc   1140

atcgagagcc tgcgcgacgg acgcactgac ggtgtcgtcc atcacagttt gccagtgata   1200

cacatgggga tcagcaatcg cgcatatgaa atcacgccat gtagtgtatt gaccgattcc   1260

ttgcggtccg aatgggccga acccgctcgt ctggctaaga tcggccgcag cgatcgcatc   1320

catagcctcc gcgaccggct gcagaacagc gggcagttcg gtttcaggca ggtcttgcaa   1380

cgtgacaccc tgtgcacggc gggagatgca ataggtcagg ctctcgctga attccccaat   1440

gtcaagcact tccggaatcg ggagcgcggc cgatgcaaag tgccgataaa cataacgatc   1500

tttgtagaaa ccatcggcgc agctatttac ccgcaggaca tatccacgcc ctcctacatc   1560

gaagctgaaa gcacgagatt cttcgccctc cgagagctgc atcaggtcgg agacgctgtc   1620
```

```
gaacttttcg atcagaaact tctcgacaga cgtcgcggtg agttcaggct tttccatggg   1680
tatatctcct tcttaaagtt aaacaaaatt atttctagag ggaaaccgtt gtggtctccc   1740
tatagtgagt cgtattaatt tcgcgggatc gagatcgatc caattccaat cccacaaaaa   1800
tctgagctta acagcacagt tgctcctctc agagcagaat cgggtattca acaccctcat   1860
atcaactact acgttgtgta taacggtcca catgccggta tatacgatga ctggggttgt   1920
acaaaggcgg caacaaacgg cgttcccgga gttgcacaca agaaatttgc cactattaca   1980
gaggcaagag cagcagctga cgcgtacaca acaagtcagc aaacagacag gttgaacttc   2040
atccccaaag gagaagctca actcaagccc aagagctttg ctaaggccct aacaagccca   2100
ccaaagcaaa aagcccactg gctcacgcta ggaaccaaaa ggcccagcag tgatccagcc   2160
ccaaaagaga tctcctttgc cccggagatt acaatggacg atttcctcta tctttacgat   2220
ctaggaagga agttcgaagg tgaaggtgac gacactatgt tcaccactga taatgagaag   2280
gttagcctct tcaatttcag aaagaatgct gacccacaga tggttagaga ggcctacgca   2340
gcaggtctca tcaagacgat ctacccgagt aacaatctcc aggagatcaa ataccttccc   2400
aagaaggtta aagatgcagt caaaagattc aggactaatt gcatcaagaa cacagagaaa   2460
gacatatttc tcaagatcag aagtactatt ccagtatgga cgattcaagg cttgcttcat   2520
aaaccaaggc aagtaataga gattggagtc tctaaaaagg tagttcctac tgaatctaag   2580
gccatgcatg gagtctaaga ttcaaatcga ggatctaaca gaactcgccg tgaagactgg   2640
cgaacagttc atacagagtc ttttacgact caatgacaag aagaaaatct tcgtcaacat   2700
ggtggagcac gacactctgg tctactccaa aaatgtcaaa gatacagtct cagaagacca   2760
aagggctatt gagacttttc aacaaaggat aatttcggga aacctcctcg gattccattg   2820
cccagctatc tgtcacttca tcgaaaggac agtagaaaag gaaggtggct cctacaaatg   2880
ccatcattgc gataaaggaa aggctatcat tcaagatgcc tctgccgaca gtggtcccaa   2940
agatggaccc ccacccacga ggagcatcgt ggaaaaagaa gacgttccaa ccacgtcttc   3000
aaagcaagtg gattgatgtg acatctccac tgacgtaagg gatgacgcac aatcccacta   3060
tccttcgcaa gacccttcct ctatataagg aagttcattt catttggaga ggacacgctc   3120
gagctcattt ctctattact tcagccataa caaaagaact cttttctctt cttattaaac   3180
catgaaaaag cctgaactca ccgcgacgtc tgtcgagaag tttctgatcg aaaagttcga   3240
cagcgtctcc gacctgatgc agctctcgga gggcgaagaa tctcgtgctt tcagcttcga   3300
tgtaggaggg cgtggatatg tcctgcgggt aaatagctgc gccgatggtt tctacaaaga   3360
tcgttatgtt tatcggcact ttgcatcggc cgcgctcccg attccggaag tgcttgacat   3420
tggggaattc agcgagagcc tgacctattg catctcccgc cgtgcacagg gtgtcacgtt   3480
gcaagacctg cctgaaaccg aactgcccgc tgttctgcag ccggtcgcgg aggccatgga   3540
tgcgatcgct gcggccgatc ttagccagac gagcgggttc ggcccattcg gaccgcaagg   3600
aatcggtcaa tacactacat ggcgtgattt catatgcgcg attgctgatc cccatgtgta   3660
tcactggcaa actgtgatgg acgacaccgt cagtgcgtcc gtcgcgcagg ctctcgatga   3720
gctgatgctt tgggccgagg actgccccga agtccggcac ctcgtgcacg cggatttcgg   3780
ctccaacaat gtcctgacgg acaatggccg cataacagcg gtcattgact ggagcgaggc   3840
gatgttcggg gattcccaat acgaggtcgc caacatcttc ttctggaggc cgtggttggc   3900
ttgtatggag cagcagacgc gctacttcga gcggaggcat ccggagcttg caggatcgcc   3960
```

-continued

```
gcggctccgg gcgtatatgc tccgcattgg tcttgaccaa ctctatcaga gcttggttga   4020
cggcaatttc gatgatgcag cttgggcgca gggtcgatgc gacgcaatcg tccgatccgg   4080
agccgggact gtcgggcgta cacaaatcgc ccgcagaagc gcggccgtct ggaccgatgg   4140
ctgtgtagaa gtactcgccg atagtggaaa ccgacgcccc agcactcgtc cgagggcaaa   4200
ggaatagtga ggtacctaaa gaaggagtgc gtcgaagcag atcgttcaaa catttggcaa   4260
taaagtttct taagattgaa tcctgttgcc ggtcttgcga tgattatcat ataatttctg   4320
ttgaattacg ttaagcatgt aataattaac atgtaatgca tgacgttatt tatgagatgg   4380
gtttttatga ttagagtccc gcaattatac atttaatacg cgatagaaaa caaaatatag   4440
cgcgcaaact aggataaatt atcgcgcgcg gtgtcatcta tgttactaga tcgatgtcga   4500
atcgatcaac ctgcattaat gaatcggcca acgcgcgggg agaggcggtt tgcgtattgg   4560
gcgctcttcc gcttcctcgc tcactgactc gctgcgctcg gtcgttcggc tgcggcgagc   4620
ggtatcagct cactcaaagg cggtaatacg gttatccaca gaatcagggg ataacgcagg   4680
aaagaacatg tgagcaaaag gccagcaaaa ggccaggaac cgtaaaaagg ccgcgttgct   4740
ggcgtttttc cataggctcc gcccccctga cgagcatcac aaaaatcgac gctcaagtca   4800
gaggtggcga aacccgacag gactataaag ataccaggcg tttccccctg gaagctccct   4860
cgtgcgctct cctgttccga ccctgccgct taccggatac ctgtccgcct ttctcccttc   4920
gggaagcgtg gcgctttctc aatgctcacg ctgtaggtat ctcagttcgg tgtaggtcgt   4980
tcgctccaag ctgggctgtg tgcacgaacc ccccgttcag cccgaccgct gcgccttatc   5040
cggtaactat cgtcttgagt ccaacccggt aagacacgac ttatcgccac tggcagcagc   5100
cactggtaac aggattagca gagcgaggta tgtaggcggt gctacagagt tcttgaagtg   5160
gtggcctaac tacggctaca ctagaaggac agtatttggt atctgcgctc tgctgaagcc   5220
agttaccttc ggaaaaagag ttggtagctc ttgatccggc aaacaaacca ccgctggtag   5280
cggtggtttt tttgtttgca agcagcagat tacgcgcaga aaaaaaggat ctcaagaaga   5340
tcctttgatc ttttctacgg ggtctgacgc tcagtggaac gaaaactcac gttaagggat   5400
tttggtcatg acattaacct ataaaaatag gcgtatcacg aggccctttc gtctcgcgcg   5460
tttcggtgat gacggtgaaa acctctgaca catgcagctc ccggagacgg tcacagcttg   5520
tctgtaagcg gatgccggga gcagacaagc ccgtcagggc gcgtcagcgg gtgttggcgg   5580
gtgtcggggc tggcttaact atgcggcatc agagcagatt gtactgagag tgcaccatat   5640
ggacatattg tcgttagaac gcggctacaa ttaatacata accttatgta tcatacacat   5700
acgatttagg tgacactata gaacggcgcg ccaagcttgg atctcctgca ggatctggcc   5760
ggccggatct cgtacgtcct cgaagagaag ggttaataac acatttttta acatttttaa   5820
cacaaatttt agttatttaa aaatttatta aaaaatttaa aataagaaga ggaactcttt   5880
aaataaatct aacttacaaa atttatgatt tttaataagt tttcaccaat aaaaaatgtc   5940
ataaaaatat gttaaaaagt atattatcaa tattctcttt atgataaata aaaagaaaaa   6000
aaaaataaaa gttaagtgaa aatgagattg aagtgacttt aggtgtgtat aaatatatca   6060
accccgccaa caatttattt aatccaaata tattgaagta tattattcca tagcctttat   6120
ttatttatat atttattata taaaagcttt atttgttcta ggttgttcat gaaatatttt   6180
tttggtttta tctccgttgt aagaaaatca tgtgctttgt gtcgccactc actattgcag   6240
ctttttcatg cattggtcag attgacggtt gattgtattt ttgtttttta tggttttgtg   6300
ttatgactta agtcttcatc tctttatctc ttcatcaggt ttgatggtta cctaatatgg   6360
```

```
tccatgggta catgcatggt taaattaggt ggccaacttt gttgtgaacg atagaatttt   6420
ttttatatta agtaaactat ttttatatta tgaaataata ataaaaaaaa tattttatca   6480
ttattaacaa aatcatatta gttaatttgt taactctata ataaaagaaa tactgtaaca   6540
ttcacattac atggtaacat ctttccaccc tttcatttgt tttttgtttg atgacttttt   6600
ttcttgttta aatttatttc ccttctttta aatttggaat acattatcat catatataaa   6660
ctaaaatact aaaaacagga ttacacaaat gataaataat aacacaaata tttataaatc   6720
tagctgcaat atatttaaac tagctatatc gatattgtaa aataaaacta gctgcattga   6780
tactgataaa aaaatatcat gtgctttctg gactgatgat gcagtatact tttgacattg   6840
cctttatttt atttttcaga aaagctttct tagttctggg ttcttcatta tttgtttccc   6900
atctccattg tgaattgaat catttgcttc gtgtcacaaa tacaatttag ntaggtacat   6960
gcattggtca gattcacggt ttattatgtc atgacttaag ttcatggtag tacattacct   7020
gccacgcatg cattatattg gttagatttg ataggcaaat ttggttgtca acaatataaa   7080
tataaataat gtttttatat tacgaaataa cagtgatcaa aacaaacagt tttatcttta   7140
ttaacaagat tttgtttttg tttgatgacg ttttttaatg tttacgcttt ccccccttctt   7200
ttgaatttag aacactttat catcataaaa tcaaatacta aaaaaattac atatttcata   7260
aataataaca caaatatttt taaaaaatct gaaataataa tgaacaatat tacatattat   7320
cacgaaaatt cattaataaa aatattatat aaataaaatg taatagtagt tatatgtagg   7380
aaaaaagtac tgcacgcata atatatacaa aaagattaaa atgaactatt ataaataata   7440
acactaaatt aatggtgaat catatcaaaa taatgaaaaa gtaaataaaa tttgtaatta   7500
acttctatat gtattacaca cacaaataat aaataatagt aaaaaaaatt atgataaata   7560
tttaccatct cataagatat ttaaaataat gataaaaata tagattattt tttatgcaac   7620
tagctagcca aaaagagaac acgggtatat ataaaaagag tacctttaaa ttctactgta   7680
cttcctttat tcctgacgtt tttatatcaa gtggacatac gtgaagattt taattatcag   7740
tctaaatatt tcattagcac ttaatacttt tctgttttat tcctatccta taagtagtcc   7800
cgattctccc aacattgctt attcacacaa ctaactaaga aagtcttcca tagcccccca   7860
agcggccgca caatggcgac tcgacagcga actgccacca ctgttgtggt cgaggacctt   7920
cccaaggtca ctcttgaggc caagtctgaa cctgtgttcc ccgatatcaa gaccatcaag   7980
gatgccattc ccgcgcactg cttccagccc tcgctcgtca cctcattcta ctacgtcttc   8040
cgcgattttg ccatggtctc tgccctcgtc tgggctgctc tcacctacat ccccagcatc   8100
cccgaccaga ccctccgcgt cgcagcttgg atggtctacg gcttcgtcca gggtctgttc   8160
tgcaccggtg tctggattct cggccatgag tgcggccacg gtgctttctc tctccacgga   8220
aaggtcaaca atgtgaccgg ctggttcctc cactcgttcc tcctcgtccc ctacttcagc   8280
tggaagtact ctcaccaccg ccaccaccgc ttcaccggcc acatggatct cgacatggct   8340
ttcgtcccca agactgagcc caagccctcc aagtcgctca tgattgctgg cattgacgtc   8400
gccgagcttg ttgaggacac ccccgctgct cagatggtca agctcatctt ccaccagctt   8460
ttcggatggc aggcgtacct cttcttcaac gctagctctg gcaagggcag caagcagtgg   8520
gagcccaaga ctggcctctc caagtggttc cgagtcagtc acttcgagcc taccagcgct   8580
gtcttccgcc ccaacgaggc catcttcatc ctcatctccg atatcggtct tgctctaatg   8640
ggaactgctc tgtactttgc ttccaagcaa gttggtgttt cgaccattct cttcctctac   8700
```

-continued

```
cttgttccct acctgtgggt tcaccactgg ctcgttgcca ttacctacct ccaccaccac   8760

cacaccgagc tccctcacta caccgctgag ggctggacct acgtcaaggg agctctcgcc   8820

actgtcgacc gtgagtttgg cttcatcgga aagcacctct tccacggtat cattgagaag   8880

cacgttgttc accatctctt ccctaagatc cccttctaca aggctgacga ggccaccgag   8940

gccatcaagc ccgtcattgg cgaccactac tgccacgacg accgaagctt cctgggccag   9000

ctgtggacca tcttcggcac gctcaagtac gtcgagcacg accctgcccg acccggtgcc   9060

atgcgatgga acaaggacta ggctaggc                                      9088
```

<210> SEQ ID NO 55
<211> LENGTH: 10309
<212> TYPE: DNA
<213> ORGANISM: Artificial Sequence
<220> FEATURE:
<223> OTHER INFORMATION: the sequence of pKR667
<220> FEATURE:
<221> NAME/KEY: misc_feature
<222> LOCATION: (7704)..(7704)
<223> OTHER INFORMATION: n is a, c, g, or t

<400> SEQUENCE: 55

```
gtacgtctag aggatccgtc gacggcgcgc ccgatcatcc ggatatagtt cctcctttca     60

gcaaaaaacc cctcaagacc cgtttagagg ccccaagggg ttatgctagt tattgctcag    120

cggtggcagc agccaactca gcttcctttc gggctttgtt agcagccgga tcgatccaag    180

ctgtacctca ctattccttt gccctcggac gagtgctggg gcgtcggttt ccactatcgg    240

cgagtacttc tacacagcca tcggtccaga cggccgcgct tctgcgggcg atttgtgtac    300

gcccgacagt cccggctccg gatcggacga ttgcgtcgca tcgaccctgc gcccaagctg    360

catcatcgaa attgccgtca accaagctct gatagagttg gtcaagacca atgcggagca    420

tatacgcccg gagccgcggc gatcctgcaa gctccggatg cctccgctcg aagtagcgcg    480

tctgctgctc catacaagcc aaccacggcc tccagaagaa gatgttggcg acctcgtatt    540

gggaatcccc gaacatcgcc tcgctccagt caatgaccgc tgttatgcgg ccattgtccg    600

tcaggacatt gttggagccg aaatccgcgt gcacgaggtg ccggacttcg gggcagtcct    660

cggcccaaag catcagctca tcgagagcct gcgcgacgga cgcactgacg gtgtcgtcca    720

tcacagtttg ccagtgatac acatggggat cagcaatcgc gcatatgaaa tcacgccatg    780

tagtgtattg accgattcct tgcggtccga atgggccgaa cccgctcgtc tggctaagat    840

cggccgcagc gatcgcatcc atagcctccg cgaccggctg cagaacagcg ggcagttcgg    900

tttcaggcag gtcttgcaac gtgacaccct gtgcacggcg ggagatgcaa taggtcaggc    960

tctcgctgaa ttccccaatg tcaagcactt ccggaatcgg gagcgcggcc gatgcaaagt   1020

gccgataaac ataacgatct ttgtagaaac catcggcgca gctatttacc cgcaggacat   1080

atccacgccc tcctacatcg aagctgaaag cacgagattc ttcgccctcc gagagctgca   1140

tcaggtcgga gacgctgtcg aacttttcga tcagaaactt ctcgacagac gtcgcggtga   1200

gttcaggctt ttccatgggt atatctcctt cttaaagtta aacaaaatta tttctagagg   1260

gaaaccgttg tggtctccct atagtgagtc gtattaattt cgcgggatcg agatctgatc   1320

aacctgcatt aatgaatcgg ccaacgcgcg gggagaggcg gtttgcgtat tgggcgctct   1380

tccgcttcct cgctcactga ctcgctgcgc tcggtcgttc ggctgcggcg agcggtatca   1440

gctcactcaa aggcggtaat acggttatcc acagaatcag gggataacgc aggaaagaac   1500

atgtgagcaa aaggccagca aaaggccagg aaccgtaaaa aggccgcgtt gctggcgttt   1560
```

```
ttccataggc tccgcccccc tgacgagcat cacaaaaatc gacgctcaag tcagaggtgg   1620
cgaaacccga caggactata aagataccag gcgtttcccc ctggaagctc cctcgtgcgc   1680
tctcctgttc cgaccctgcc gcttaccgga tacctgtccg cctttctccc ttcgggaagc   1740
gtggcgcttt ctcaatgctc acgctgtagg tatctcagtt cggtgtaggt cgttcgctcc   1800
aagctgggct gtgtgcacga accccccgtt cagcccgacc gctgcgcctt atccggtaac   1860
tatcgtcttg agtccaaccc ggtaagacac gacttatcgc cactggcagc agccactggt   1920
aacaggatta gcagagcgag gtatgtaggc ggtgctacag agttcttgaa gtggtggcct   1980
aactacggct acactagaag gacagtattt ggtatctgcg ctctgctgaa gccagttacc   2040
ttcggaaaaa gagttggtag ctcttgatcc ggcaaacaaa ccaccgctgg tagcggtggt   2100
tttttgttt gcaagcagca gattacgcgc agaaaaaaag gatctcaaga agatcctttg   2160
atcttttcta cggggtctga cgctcagtgg aacgaaaact cacgttaagg gattttggtc   2220
atgacattaa cctataaaaa taggcgtatc acgaggccct ttcgtctcgc gcgtttcggt   2280
gatgacggtg aaaacctctg acacatgcag ctcccggaga cggtcacagc ttgtctgtaa   2340
gcggatgccg ggagcagaca agcccgtcag ggcgcgtcag cgggtgttgg cgggtgtcgg   2400
ggctggctta actatgcggc atcagagcag attgtactga gagtgcacca tatggacata   2460
ttgtcgttag aacgcggcta caattaatac ataaccttat gtatcataca catacgattt   2520
aggtgacact atagaacggc gcgccaagct gggtctagaa ctagaaacgt gatgccactt   2580
gttattgaag tcgattacag catctattct gttttactat ttataacttt gccatttctg   2640
acttttgaaa actatctctg gatttcggta tcgctttgtg aagatcgagc aaaagagacg   2700
ttttgtggac gcaatggtcc aaatccgttc tacatgaaca aattggtcac aatttccact   2760
aaaagtaaat aaatggcaag ttaaaaaagg aatatgcatt ttactgattg cctaggtgag   2820
ctccaagaga agttgaatct acacgtctac caaccgctaa aaaaagaaaa acattgatat   2880
gtaacctgat tccattagct tttgacttct tcaacagatt ctctacttag atttctaaca   2940
gaaatattat tactagcaca tcattttcag tctcactaca gcaaaaaatc caacggcaca   3000
atacagacaa caggagatat cagactacag agatagatag atgctactgc atgtagtaag   3060
ttaaataaaa ggaaaataaa atgtcttgct accaaaacta ctacagacta tgatgctcac   3120
cacaggccaa atcctgcaac taggacagca ttatcttata tatattgtac aaaacaagca   3180
tcaaggaaca tttggtctag gcaatcagta cctcgttcta ccatcaccct cagttatcac   3240
atccttgaag gatccattac tgggaatcat cggcaacaca tgctcctgat ggggcacaat   3300
gacatcaaga aggtaggggc caggggtgtc caacattctc tgaattgccg ctctaagctc   3360
ttccttcttc gtcactcgcg ctgccggtat cccacaagca tcagcaaact tgagcatgtt   3420
tgggaatatc tcgctctcgc tagacggatc tccaagatag gtgtgagctc tattggactt   3480
gtagaaccta tcctccaact gaaccaccat acccaaatgc tgattgttca acaacaatat   3540
cttaactggg agattctcca ctcttatagt ggccaactcc tgaacattca tgatgaaact   3600
accatcccca tcaatgtcaa ccacaacagc cccagggtta gcaacagcag caccaatagc   3660
cgcaggcaat ccaaaaccca tggctccaag acccccctgag gtcaaccact gcctcggtct   3720
cttgtacttg taaaactgcg cagcccacat ttgatgctgc ccaaccccag tactaacaat   3780
agcatctcca ttagtcaact catcaagaac ctcgatagca tgctgcggag aaatcgcgtc   3840
ctggaatgtc ttgtaaccca atggaaactt gtgtttctgc acattaatct cttctctcca   3900
```

-continued

```
acctccaaga tcaaacttac cctccactcc tttctcctcc aaaatcatat taattccctt   3960
caaggccaac ttcaaatccg cgcaaaccga cacgtgcgcc tgcttgttct tcccaatctc   4020
ggcagaatca atatcaatgt gaacaatctt agccctacta gcaaaagcct caagcttccc   4080
agtaacacgg tcatcaaacc ttaccccaaa ggcaagcaac aaatcactat tgtcaacagc   4140
atagttagca taaacagtac catgcatacc cagcatctga agggaatatt catcaccaat   4200
aggaaaagtt ccaagaccca ttaaagtgct agcaacggga ataccagtga gttcaacaaa   4260
gcgcctcaat tcagcactgg aattcaaact gccaccgccg acgtagagaa cgggcttttg   4320
ggcctccatg atgagtctga caatgtgttc caattgggcc tcggcggggg gcctgggcag   4380
cctggcgagg taaccgggga ggttaacggg ctcgtcccaa ttaggcacgg cgagttgctg   4440
ctgaacgtct ttgggaatgt cgatgaggac cggaccgggg cggccggagg tggcgacgaa   4500
gaaagcctcg gcgacgacgc gggggatgtc gtcgacgtcg aggatgaggt agttgtgctt   4560
cgtgatggat ctgctcacct ccacgatcgg ggtttcttgg aaggcgtcgg tgccgatcat   4620
ccggcgggcg acctggccgg tgatggcgac gactgggacg ctgtccatta aagcgtcggc   4680
gaggccgctc acgaggttgg tggcgccggg gccggaggtg gcaatgcaga cgccggggag   4740
gccggaggaa cgcgcgtagc cttcggcggc gaagacgccg ccctgctcgt ggcgcgggag   4800
cacgttgcgg atggcggcgg agcgcgtgag cgcctggtgg atctccatcg acgcaccgcc   4860
ggggtacgcg aacaccgtcg tcacgccctg cctctccagc gcctccacaa ggatgtccgc   4920
gcccttgcga ggttcgccgg aggcgaaccg tgacacgaag ggctccgtgg tcggcgcttc   4980
cttggtgaag ggcgccgccg tggggggttt ggagatggaa catttgattt tgagagcgtg   5040
gttgggtttg gtgagggttt gatgagagag agggagggtg gatctagtaa tgcgtttggg   5100
gaaggtgggg tgtgaagagg aagaagagaa tcgggtggtt ctggaagcgg tggccgccat   5160
tgtgttgtgt ggcatggtta tacttcaaaa actgcacaac aagcctagag ttagtaccta   5220
aacagtaaat ttacaacaga gagcaaagac acatgcaaaa atttcagcca taaaaaaagt   5280
tataatagaa tttaaagcaa aagtttcatt ttttaaacat atatacaaac aaactggatt   5340
tgaaggaagg gattaattcc cctgctcaaa gtttgaattc ctattgtgac ctatactcga   5400
ataaaattga agcctaagga atgtatgaga aacaagaaaa caaaacaaaa ctacagacaa   5460
acaagtacaa ttacaaaatt cgctaaaatt ctgtaatcac caaaccccat ctcagtcagc   5520
acaaggccca aggtttattt tgaaataaaa aaaaagtgat tttatttctc ataagctaaa   5580
agaaagaaag gcaattatga aatgatttcg actagatctg aaagtccaac gcgtattccg   5640
cagatattaa agaaagagta gagtttcaca tggatcctag atggacccag ttgaggaaaa   5700
agcaaggcaa agcaaaccag aagtgcaaga tccgaaattg aaccacggaa tctaggattt   5760
ggtagaggga gaagaaaagt accttgagag gtagaagaga agagaagagc agagagatat   5820
atgaacgagt gtgtcttggt ctcaactctg aagcgatacg agtttagagg ggagcattga   5880
gttccaattt atagggaaac cgggtggcag gggtgagtta atgacggaaa agcccctaag   5940
taacgagatt ggattgtggg ttagattcaa ccgtttgcat ccgcggctta gattggggaa   6000
gtcagagtga atctcaaccg ttgactgagt tgaaaattga atgtagcaac caattgagcc   6060
aaccccagcc tttgcccttt gattttgatt tgtttgttgc atactttttta tttgtcttct  6120
ggttctgact ctctttctct cgtttcaatg ccaggttgcc tactcccaca ccactcacaa   6180
gaagattcta ctgttagtat taaatatttt ttaatgtatt aaatgatgaa tgcttttgta   6240
aacagaacaa gactatgtct aataagtgtc ttgcaacatt ttttaagaaa ttaaaaaaaa   6300
```

```
tatatttatt atcaaaatca aatgtatgaa aaatcatgaa taatataatt ttatacattt   6360
ttttaaaaaa tcttttaatt tcttaattaa tatcttaaaa ataatgatta atatttaacc   6420
caaaataatt agtatgattg gtaaggaaga tatccatgtt atgtttggat gtgagtttga   6480
tctagagcaa agcttactag agtcgacctg caggtcgact cgacgtacgt cctcgaagag   6540
aagggttaat aacacatttt ttaacatttt taacacaaat tttagttatt taaaaattta   6600
ttaaaaaatt taaaataaga agaggaactc tttaaataaa tctaacttac aaaatttatg   6660
atttttaata agttttcacc aataaaaaat gtcataaaaa tatgttaaaa agtatattat   6720
caatattctc tttatgataa ataaaaagaa aaaaaaaata aaagttaagt gaaaatgaga   6780
ttgaagtgac tttaggtgtg tataaatata tcaaccccgc caacaattta tttaatccaa   6840
atatattgaa gtatattatt ccatagcctt tatttattta tatatttatt atataaaagc   6900
tttatttgtt ctaggttgtt catgaaatat ttttttggtt ttatctccgt tgtaagaaaa   6960
tcatgtgctt tgtgtcgcca ctcactattg cagctttttc atgcattggt cagattgacg   7020
gttgattgta tttttgtttt ttatggtttt gtgttatgac ttaagtcttc atctctttat   7080
ctcttcatca ggtttgatgg ttacctaata tggtccatgg gtacatgcat ggttaaatta   7140
ggtggccaac tttgttgtga acgatagaat tttttttata ttaagtaaac tatttttata   7200
ttatgaaata ataataaaaa aaatatttta tcattattaa caaaatcata ttagttaatt   7260
tgttaactct ataataaaag aaatactgta acattcacat tacatggtaa catctttcca   7320
ccctttcatt tgtttttttgt ttgatgactt tttttcttgt ttaaatttat ttcccttctt   7380
ttaaatttgg aatacattat catcatatat aaactaaaat actaaaaaca ggattacaca   7440
aatgataaat aataacacaa atatttataa atctagctgc aatatattta aactagctat   7500
atcgatattg taaaataaaa ctagctgcat tgatactgat aaaaaaatat catgtgcttt   7560
ctggactgat gatgcagtat acttttgaca ttgcctttat tttatttttc agaaaagctt   7620
tcttagttct gggttcttca ttatttgttt cccatctcca ttgtgaattg aatcatttgc   7680
ttcgtgtcac aaatacaatt tagntaggta catgcattgg tcagattcac ggtttattat   7740
gtcatgactt aagttcatgg tagtacatta cctgccacgc atgcattata ttggttagat   7800
ttgataggca aatttggttg tcaacaatat aaatataaat aatgttttta tattacgaaa   7860
taacagtgat caaaacaaac agttttatct ttattaacaa gattttgttt ttgtttgatg   7920
acgtttttta atgtttacgc tttccccctt cttttgaatt tagaacactt tatcatcata   7980
aaatcaaata ctaaaaaaat tacatatttc ataaataata acacaaatat ttttaaaaaa   8040
tctgaaataa taatgaacaa tattacatat tatcacgaaa attcattaat aaaaatatta   8100
tataaataaa atgtaatagt agttatatgt aggaaaaaag tactgcacgc ataatatata   8160
caaaaagatt aaaatgaact attataaata ataacactaa attaatggtg aatcatatca   8220
aaataatgaa aaagtaaata aaatttgtaa ttaacttcta tatgtattac acacacaaat   8280
aataaataat agtaaaaaaa attatgataa atatttacca tctcataaga tatttaaaat   8340
aatgataaaa atatagatta ttttttatgc aactagctag ccaaaaagag aacacgggta   8400
tatataaaaa gagtaccttt aaattctact gtacttcctt tattcctgac gtttttatat   8460
caagtggaca tacgtgaaga ttttaattat cagtctaaat atttcattag cacttaatac   8520
ttttctgttt tattcctatc ctataagtag tcccgattct cccaacattg cttattcaca   8580
caactaacta agaaagtctt ccatagcccc ccaagcggcc gcacaatggc gactcgacag   8640
```

-continued

```
cgaactgcca ccactgttgt ggtcgaggac cttcccaagg tcactcttga ggccaagtct   8700

gaacctgtgt tccccgatat caagaccatc aaggatgcca ttcccgcgca ctgcttccag   8760

ccctcgctcg tcacctcatt ctactacgtc ttccgcgatt ttgccatggt ctctgccctc   8820

gtctgggctg ctctcaccta catccccagc atccccgacc agaccctccg cgtcgcagct   8880

tggatggtct acggcttcgt ccagggtctg ttctgcaccg gtgtctggat tctcggccat   8940

gagtgcggcc acggtgcttt ctctctccac ggaaaggtca acaatgtgac cggctggttc   9000

ctccactcgt tcctcctcgt cccctacttc agctggaagt actctcacca ccgccaccac   9060

cgcttcaccg gccacatgga tctcgacatg gctttcgtcc ccaagactga gcccaagccc   9120

tccaagtcgc tcatgattgc tggcattgac gtcgccgagc ttgttgagga cacccccgct   9180

gctcagatgg tcaagctcat cttccaccag cttttcggat ggcaggcgta cctcttcttc   9240

aacgctagct ctggcaaggg cagcaagcag tgggagccca agactggcct ctccaagtgg   9300

ttccgagtca gtcacttcga gcctaccagc gctgtcttcc gccccaacga ggccatcttc   9360

atcctcatct ccgatatcgg tcttgctcta atgggaactg ctctgtactt tgcttccaag   9420

caagttggtg tttcgaccat tctcttcctc taccttgttc cctacctgtg ggttcaccac   9480

tggctcgttg ccattaccta cctccaccac caccacaccg agctccctca ctacaccgct   9540

gagggctgga cctacgtcaa gggagctctc gccactgtcg accgtgagtt tggcttcatc   9600

ggaaagcacc tcttccacgg tatcattgag aagcacgttg ttcaccatct cttccctaag   9660

atccccttct acaaggctga cgaggccacc gaggccatca agcccgtcat tggcgaccac   9720

tactgccacg acgaccgaag cttcctgggc cagctgtgga ccatcttcgg cacgctcaag   9780

tacgtcgagc acgaccctgc ccgacccggt gccatgcgat ggaacaagga ctaggctagg   9840

cggccgcgac acaagtgtga gagtactaaa taaatgcttt ggttgtacga aatcattaca   9900

ctaaataaaa taatcaaagc ttatatatgc cttccgctaa ggccgaatgc aaagaaattg   9960

gttctttctc gttatctttt gccactttta ctagtacgta ttaattacta cttaatcatc  10020

tttgtttacg gctcattata tccggtctag aggatccaag gccgcgaagt taaaagcaat  10080

gttgtcactt gtcgtactaa cacatgatgt gatagtttat gctagctagc tataacataa  10140

gctgtctctg agtgtgttgt atattaataa agatcatcac tggtgaatgg tgatcgtgta  10200

cgtaccctac ttagtaggca atggaagcac ttagagtgtg ctttgtgcat ggccttgcct  10260

ctgttttgag acttttgtaa tgttttcgag tttaaatctt tgcctttgc             10309
```

<210> SEQ ID NO 56
<211> LENGTH: 12403
<212> TYPE: DNA
<213> ORGANISM: Artificial Sequence
<220> FEATURE:
<223> OTHER INFORMATION: the sequence of pKR873

<400> SEQUENCE: 56

```
ggtcgactcg acgtacgaaa ccaactgcgt ttggggctcc agattaaacg acgccgtttc     60

gttcctttcg cttcacggct taacgatgtc gtttctgtct gtgcccaaaa aataaaggca    120

tttgttattt gcaccagata tttactaagt gcaccctagt ttgacaagta ggcgataatt    180

acaaatagat gcggtgcaaa taataaattt tgaaggaaat aattacaaaa gaacagaact    240

tatatttact ttattttaaa aaactaaaat gaaagaacaa aaaaagtaaa aaatacaaaa    300

aatgtgcttt aaccactttc attatttgtt acagaaagta tgattctact caaattgatc    360

tgttgtatct ggtgctgcct tgtcacactg gcgatttcaa tcccctaaag atatggtgca    420
```

```
aactgcgaag tgatcaatat ctgctcggtt aatttagatt aattaataat attcaacgtg    480
atgtaccaaa aaaagacaat tttttgctcc attgacaaat taaacctcat caaggtaatt    540
tccaaaccta taagcaaaaa aatttcacat taattggccc gcaatcctat tagtcttatt    600
atactagagt aggaaaaaaa acaattacac aacttgtctt attattctct atgctaatga    660
atatttttcc cttttgttag aaatcagtgt ttcctaattt attgagtatt aattccactc    720
accgcatata tttaccgttg aataagaaaa ttttacacat aattcttttt aagataaata    780
atttttttat actagatctt atatgattac gtgaagccaa gtgggttata ctaatgatat    840
ataatgtttg atagtaatca gtttataaac caaatgcatg gaaatgttac gtggaagcac    900
gtaaattaac aagcattgaa gcaaatgcag ccaccgcacc aaaaccaccc cacttcactt    960
ccacgtacca tattccatgc aactacaaca ccctaaaact tcaataaatg cccccacctt   1020
cacttcactt cacccatcaa tagcaagcgg ccgcacaatg gcgactcgac agcgaactgc   1080
caccactgtt gtggtcgagg accttcccaa ggtcactctt gaggccaagt ctgaacctgt   1140
gttccccgat atcaagacca tcaaggatgc cattcccgcg cactgcttcc agccctcgct   1200
cgtcacctca ttctactacg tcttccgcga ttttgccatg gtctctgccc tcgtctgggc   1260
tgctctcacc tacatcccca gcatccccga ccagaccctc cgcgtcgcag cttggatggt   1320
ctacggcttc gtccagggtc tgttctgcac cggtgtctgg attctcggcc atgagtgcgg   1380
ccacggtgct ttctctctcc acggaaaggt caacaatgtg accggctggt tcctccactc   1440
gttcctcctc gtcccctact tcagctggaa gtactctcac caccgccacc accgcttcac   1500
cggccacatg gatctcgaca tggctttcgt ccccaagact gagcccaagc cctccaagtc   1560
gctcatgatt gctggcattg acgtcgccga gcttgttgag gacacccccg ctgctcagat   1620
ggtcaagctc atcttccacc agcttttcgg atggcaggcg tacctcttct tcaacgctag   1680
ctctggcaag ggcagcaagc agtgggagcc caagactggc ctctccaagt ggttccgagt   1740
cagtcacttc gagcctacca gcgctgtctt ccgccccaac gaggccatct tcatcctcat   1800
ctccgatatc ggtcttgctc taatgggaac tgctctgtac tttgcttcca agcaagttgg   1860
tgtttcgacc attctcttcc tctaccttgt tccctacctg tgggttcacc actggctcgt   1920
tgccattacc tacctccacc accaccacac cgagctccct cactacaccg ctgagggctg   1980
gacctacgtc aagggagctc tcgccactgt cgaccgtgag tttggcttca tcggaaagca   2040
cctcttccac ggtatcattg agaagcacgt tgttcaccat ctcttcccta agatcccctt   2100
ctacaaggct gacgaggcca ccgaggccat caagcccgtc attggcgacc actactgcca   2160
cgacgaccga agcttcctgg gccagctgtg gaccatcttc ggcacgctca agtacgtcga   2220
gcacgaccct gcccgacccg gtgccatgcg atggaacaag gactaggcta ggcggccgcg   2280
aagttaaaag caatgttgtc acttgtcgta ctaacacatg atgtgatagt ttatgctagc   2340
tagctataac ataagctgtc tctgagtgtg ttgtatatta ataaagatca tcactggtga   2400
atggtgatcg tgtacgtacc ctacttagta ggcaatggaa gcacttagag tgtgctttgt   2460
gcatggcctt gcctctgttt tgagactttt gtaatgtttt cgagtttaaa tctttgcctt   2520
tgcgtacgtc tagaggatcc gtcgacggcg cgcccgatca tccggatata gttcctcctt   2580
tcagcaaaaa acccctcaag acccgtttag aggccccaag gggttatgct agttattgct   2640
cagcggtggc agcagccaac tcagcttcct ttcgggcttt gttagcagcc ggatcgatcc   2700
aagctgtacc tcactattcc tttgccctcg gacgagtgct ggggcgtcgg tttccactat   2760
```

```
cggcgagtac ttctacacag ccatcggtcc agacggccgc gcttctgcgg gcgatttgtg   2820
tacgcccgac agtcccggct ccggatcgga cgattgcgtc gcatcgaccc tgcgcccaag   2880
ctgcatcatc gaaattgccg tcaaccaagc tctgatagag ttggtcaaga ccaatgcgga   2940
gcatatacgc ccggagccgc ggcgatcctg caagctccgg atgcctccgc tcgaagtagc   3000
gcgtctgctg ctccatacaa gccaaccacg gcctccagaa gaagatgttg gcgacctcgt   3060
attgggaatc cccgaacatc gcctcgctcc agtcaatgac cgctgttatg cggccattgt   3120
ccgtcaggac attgttggag ccgaaatccg cgtgcacgag gtgccggact tcggggcagt   3180
cctcggccca aagcatcagc tcatcgagag cctgcgcgac ggacgcactg acggtgtcgt   3240
ccatcacagt ttgccagtga tacacatggg gatcagcaat cgcgcatatg aaatcacgcc   3300
atgtagtgta ttgaccgatt ccttgcggtc cgaatgggcc gaacccgctc gtctggctaa   3360
gatcggccgc agcgatcgca tccatagcct ccgcgaccgg ctgcagaaca gcgggcagtt   3420
cggtttcagg caggtcttgc aacgtgacac cctgtgcacg gcgggagatg caataggtca   3480
ggctctcgct gaattcccca atgtcaagca cttccggaat cgggagcgcg gccgatgcaa   3540
agtgccgata aacataacga tctttgtaga aaccatcggc gcagctattt acccgcagga   3600
catatccacg ccctcctaca tcgaagctga aagcacgaga ttcttcgccc tccgagagct   3660
gcatcaggtc ggagacgctg tcgaactttt cgatcagaaa cttctcgaca gacgtcgcgg   3720
tgagttcagg cttttccatg ggtatatctc cttcttaaag ttaaacaaaa ttatttctag   3780
agggaaaccg ttgtggtctc cctatagtga gtcgtattaa tttcgcggga tcgagatctg   3840
atcaacctgc attaatgaat cggccaacgc gcggggagag gcggtttgcg tattgggcgc   3900
tcttccgctt cctcgctcac tgactcgctg cgctcggtcg ttcggctgcg gcgagcggta   3960
tcagctcact caaaggcggt aatacggtta tccacagaat caggggataa cgcaggaaag   4020
aacatgtgag caaaaggcca gcaaaaggcc aggaaccgta aaaaggccgc gttgctggcg   4080
tttttccata ggctccgccc ccctgacgag catcacaaaa atcgacgctc aagtcagagg   4140
tggcgaaacc cgacaggact ataaagatac caggcgtttc cccctggaag ctccctcgtg   4200
cgctctcctg ttccgaccct gccgcttacc ggatacctgt ccgcctttct cccttcggga   4260
agcgtggcgc tttctcaatg ctcacgctgt aggtatctca gttcggtgta ggtcgttcgc   4320
tccaagctgg gctgtgtgca cgaacccccc gttcagcccg accgctgcgc cttatccggt   4380
aactatcgtc ttgagtccaa cccggtaaga cacgacttat cgccactggc agcagccact   4440
ggtaacagga ttagcagagc gaggtatgta ggcggtgcta cagagttctt gaagtggtgg   4500
cctaactacg gctacactag aaggacagta tttggtatct gcgctctgct gaagccagtt   4560
accttcggaa aaagagttgg tagctcttga tccggcaaac aaaccaccgc tggtagcggt   4620
ggtttttttg tttgcaagca gcagattacg cgcagaaaaa aaggatctca agaagatcct   4680
ttgatctttt ctacggggtc tgacgctcag tggaacgaaa actcacgtta agggattttg   4740
gtcatgacat taacctataa aaataggcgt atcacgaggc cctttcgtct cgcgcgtttc   4800
ggtgatgacg gtgaaaacct ctgacacatg cagctcccgg agacggtcac agcttgtctg   4860
taagcggatg ccgggagcag acaagcccgt cagggcgcgt cagcgggtgt tggcgggtgt   4920
cggggctggc ttaactatgc ggcatcagag cagattgtac tgagagtgca ccatatggac   4980
atattgtcgt tagaacgcgg ctacaattaa tacataacct tatgtatcat acacatacga   5040
tttaggtgac actatagaac ggcgcgccaa gctgggtcta gaactagaaa cgtgatgcca   5100
cttgttattg aagtcgatta cagcatctat tctgttttac tatttataac tttgccattt   5160
```

ctgacttttg aaaactatct ctggatttcg gtatcgcttt gtgaagatcg agcaaaagag 5220
acgttttgtg gacgcaatgg tccaaatccg ttctacatga acaaattggt cacaatttcc 5280
actaaaagta aataaatggc aagttaaaaa aggaatatgc attttactga ttgcctaggt 5340
gagctccaag agaagttgaa tctacacgtc taccaaccgc taaaaaaaga aaaacattga 5400
tatgtaacct gattccatta gcttttgact tcttcaacag attctctact tagatttcta 5460
acagaaatat tattactagc acatcatttt cagtctcact acagcaaaaa atccaacggc 5520
acaatacaga caacaggaga tatcagacta cagagataga tagatgctac tgcatgtagt 5580
aagttaaata aaaggaaaat aaaatgtctt gctaccaaaa ctactacaga ctatgatgct 5640
caccacaggc caaatcctgc aactaggaca gcattatctt atatatattg tacaaaacaa 5700
gcatcaagga acatttggtc taggcaatca gtacctcgtt ctaccatcac cctcagttat 5760
cacatccttg aaggatccat tactgggaat catcggcaac acatgctcct gatggggcac 5820
aatgacatca agaaggtagg ggccaggggt gtccaacatt ctctgaattg ccgctctaag 5880
ctcttccttc ttcgtcactc gcgctgccgg tatcccacaa gcatcagcaa acttgagcat 5940
gtttgggaat atctcgctct cgctagacgg atctccaaga taggtgtgag ctctattgga 6000
cttgtagaac ctatcctcca actgaaccac catacccaaa tgctgattgt tcaacaacaa 6060
tatcttaact gggagattct ccactcttat agtggccaac tcctgaacat tcatgatgaa 6120
actaccatcc ccatcaatgt caaccacaac agccccaggg ttagcaacag cagcaccaat 6180
agccgcaggc aatccaaaac ccatggctcc aagaccccct gaggtcaacc actgcctcgg 6240
tctcttgtac ttgtaaaact gcgcagccca catttgatgc tgcccaaccc cagtactaac 6300
aatagcatct ccattagtca actcatcaag aacctcgata gcatgctgcg gagaaatcgc 6360
gtcctggaat gtcttgtaac ccaatggaaa cttgtgtttc tgcacattaa tctcttctct 6420
ccaacctcca agatcaaact taccctccac tcctttctcc tccaaaatca tattaattcc 6480
cttcaaggcc aacttcaaat ccgcgcaaac cgacacgtgc gcctgcttgt tcttcccaat 6540
ctcggcagaa tcaatatcaa tgtgaacaat cttagcccta ctagcaaaag cctcaagctt 6600
cccagtaaca cggtcatcaa accttacccc aaaggcaagc aacaaatcac tattgtcaac 6660
agcatagtta gcataaacag taccatgcat acccagcatc tgaagggaat attcatcacc 6720
aataggaaaa gttccaagac ccattaaagt gctagcaacg ggaataccag tgagttcaac 6780
aaagcgcctc aattcagcac tggaattcaa actgccaccg ccgacgtaga gaacgggctt 6840
ttgggcctcc atgatgagtc tgacaatgtg ttccaattgg gcctcggcgg ggggcctggg 6900
cagcctggcg aggtaaccgg ggaggttaac gggctcgtcc caattaggca cggcgagttg 6960
ctgctgaacg tctttgggaa tgtcgatgag gaccggaccg gggcggccgg aggtggcgac 7020
gaagaaagcc tcggcgacga cgcgggggat gtcgtcgacg tcgaggatga ggtagttgtg 7080
cttcgtgatg gatctgctca cctccacgat cggggtttct tggaaggcgt cggtgccgat 7140
catccggcgg gcgacctggc cggtgatggc gacgactggg acgctgtcca ttaaagcgtc 7200
ggcgaggccg ctcacgaggt tggtggcgcc ggggccggag gtggcaatgc agacgccggg 7260
gaggccggag gaacgcgcgt agccttcggc ggcgaagacg ccgccctgct cgtggcgcgg 7320
gagcacgttg cggatggcgg cggagcgcgt gagcgcctgg tggatctcca tcgacgcacc 7380
gccggggtac gcgaacaccg tcgtcacgcc ctgcctctcc agcgcctcca caaggatgtc 7440
cgcgcccttg cgaggttcgc cggaggcgaa ccgtgacacg aagggctccg tggtcggcgc 7500

-continued

```
ttccttggtg aagggcgccg ccgtgggggg tttggagatg gaacatttga ttttgagagc   7560
gtggttgggt ttggtgaggg tttgatgaga gagagggagg gtggatctag taatgcgttt   7620
ggggaaggtg gggtgtgaag aggaagaaga gaatcgggtg gttctggaag cggtggccgc   7680
cattgtgttg tgtggcatgg ttatacttca aaaactgcac aacaagccta gagttagtac   7740
ctaaacagta aatttacaac agagagcaaa gacacatgca aaaatttcag ccataaaaaa   7800
agttataata gaatttaaag caaaagtttc atttttttaaa catatataca aacaaactgg   7860
atttgaagga agggattaat tcccctgctc aaagtttgaa ttcctattgt gacctatact   7920
cgaataaaat tgaagcctaa ggaatgtatg agaaacaaga aaacaaaaca aaactacaga   7980
caaacaagta caattacaaa attcgctaaa attctgtaat caccaaaccc catctcagtc   8040
agcacaaggc ccaaggttta ttttgaaata aaaaaaaagt gattttattt ctcataagct   8100
aaaagaaaga aaggcaatta tgaaatgatt tcgactagat ctgaaagtcc aacgcgtatt   8160
ccgcagatat taaagaaaga gtagagtttc acatggatcc tagatggacc cagttgagga   8220
aaaagcaagg caaagcaaac cagaagtgca agatccgaaa ttgaaccacg gaatctagga   8280
tttggtagag ggagaagaaa agtaccttga gaggtagaag agaagagaag agcagagaga   8340
tatatgaacg agtgtgtctt ggtctcaact ctgaagcgat acgagtttag aggggagcat   8400
tgagttccaa tttatagga aaccgggtgg caggggtgag ttaatgacgg aaaagcccct   8460
aagtaacgag attggattgt gggttagatt caaccgtttg catccgcggc ttagattggg   8520
gaagtcagag tgaatctcaa ccgttgactg agttgaaaat tgaatgtagc aaccaattga   8580
gccaacccca gcctttgccc tttgattttg atttgtttgt tgcatacttt ttatttgtct   8640
tctggttctg actctctttc tctcgtttca atgccaggtt gcctactccc acaccactca   8700
caagaagatt ctactgttag tattaaatat tttttaatgt attaaatgat gaatgctttt   8760
gtaaacagaa caagactatg tctaataagt gtcttgcaac attttttaag aaattaaaaa   8820
aaatatattt attatcaaaa tcaaatgtat gaaaaatcat gaataatata attttataca   8880
tttttttaaa aaatctttta atttcttaat taatatctta aaaataatga ttaatattta   8940
acccaaaata attagtatga ttggtaagga agatatccat gttatgtttg gatgtgagtt   9000
tgatctagag caaagcttac tagagtcgac ctgcagcccg gggatccgc ccacgtacgg   9060
taccatctgc taatatttta aatcacatgc aagagaggag gcatggttcc attttctacc   9120
ttcacattat ttgagaaaaa cgaacttgtt ctgtgtttta tttttgccct tcacattagt   9180
acaacgtgga agactcatgg ttacacagaa tcatacataa gtacaatgct tgtccctaag   9240
aaaacaagca ctcgttgtat tgaacctta cggctcatgc ggccgcgaat tcactagtga   9300
ttgaattcgc ggccgcttag tccgacttgg ccttggcggc cgcggccgac tctttgagcg   9360
tgaagatctg cgccgtctcg ggcacagcgc cgtagttgac aaagaggtgc gcggtcttga   9420
agaaggccgt gatgatgggc tcgtcgttcc tgcgcacgag gtgcgggtac gcggccgcaa   9480
agtgcttggt ggcttcgttg agcttgtagt gcggaatgat cgggaacaag tggtggacct   9540
ggtgcgtgcc aatgtggtgg ctcaggttgt ccacgaacgc gccgtacgag cggtcgacgc   9600
tcgagaggtt gcccttgacg tacgtccact ccgagtcgcc gtaccacggc gtcgcttcgt   9660
cgttgtggtg caagaaggtc gtaatgacga ggaacgaagc aaagacaaag agcggcgcat   9720
agtagtagag gcccatgacg gcaaagccga gcgagtatgt gaggtacgcg tacgcggcga   9780
agaaggcggc ccagacgccg agcgacacga tgacggccga cgcgcggcga aggaggagcg   9840
ggtcccacgg gtcaaagtgg ctcatcgtgc gcggggcata cccgaccttc aagtagacaa   9900
```

-continued

```
accacgcacc gccgagcgtg tagacccatt ggcgcacgtc ctggaggtcc ttgaccgacc   9960
ggtgcgggta aaagatctcg tccttatcaa tgttgcccgt gttcttgtgg tggtggcggt  10020
gcgtcacgcg ccagctctcg aacggcgtca aaatcgcaga gtgcatgatg cagccgatga  10080
taaagttgac gctgtggtag cgcgagaagg ccgagtggcc gcagtcgtgg ccgaccgtga  10140
agaagcccca gaagatgacg ccctgcacgt agatgtaggt ggcgcaaacg agcgcgtgga  10200
gcagaacgtt atcggcaatg aacggcgtcg agcgcgccgc gtagagcagc gccgccgagg  10260
ccgacgcgtt gaagatcgcg cgggccgtgt agtagagcga gaggccgagg ttcgactcaa  10320
agcacgcgtt cgggatcgag tgcttgagct ccgtgagcgt cgggaactcg accttcgtct  10380
tatcctcagt catgcggccg ctgaagtatt gcttcttagt taacctttcc tttctctctc  10440
agctatgtga attcattttg ctttcgtcac aatttatata gtgaaattgg atctttggag  10500
ttaacgcctt cacaggatta tcgtgttaga acaatgcttt ttcatgttct aattagtagt  10560
acattacaaa tgtgcactct attcaataag catcttttgg cacgttaata aatcatgtga  10620
aaaaaaaata ctactatttc aaagaaagtg ttgtaaaaag aaacggaaag agagctggct  10680
tcagttgttg agacttgttt gctagtaaaa atggtgtgaa gagtgattca tggtgaggtg  10740
gtttttcgtc cctttctgtt tgcatgaaaa acaaatggca agagatgacg taggattcct  10800
tcccttaacg attatctgtt tttaatttca aatatacata taggaattta tgaattacta  10860
aggttgtaaa atatgctggt catttattta tggctaaaat attttttttt ctcgtaaata  10920
taaaaatatt taaaatttat ttttatcata tttttatcc ttataaaatt atgtgtacaa  10980
cctatataaa aaaatatcat atttaatatt gattatatgt ttaatcaata taaaaaatca  11040
ttatcatata tttagattta ttcgaatata catctaaaca aaaaataaca tattttaatt  11100
ttatgaagaa aaaaaaatat tttatccttt atttatttaa gattaattaa tagttatgta  11160
ttgtggaaag acttttacac atgcaataga tatactgaat caattagatg ccaatgctga  11220
gttggaaatc acttgaggag gggaggagac ttgccaatgc ttttcagttt catttaaatg  11280
atttagtgga ggagatagag tagtgataaa ggcatgcccc aattttggag tgtatatatg  11340
agtggaaata agagagggat agagagaaaa aataaagaga gtaaaaataa ttaatgtgaa  11400
atgatatgat aaaaaaataa agaaagagat aaagagaaaa atgaaatgag agatagatga  11460
aatagagagt agatacatgt ttgtttaggt ttttttagg aaataacaca tttttttctc  11520
atcacttatt actcactgtc aatttcctct ctttcaatca taatgatatg atttgtttaa  11580
caaaaatgtg aaaaaacata taaagtaaaa tatttttata aattgataaa taaaaattta  11640
caaaatttat ttcttattaa attgaataga aaatgaaaga aaagaaaaga aaaagtatat  11700
ataaaatgat atagctttaa aaagaataaa tttttcatat cagtcttttt ttaataattt  11760
agaaatattt aagtatatag caaaaatata atgtacttta catatgcata aataataatt  11820
tgaaaataga actaatagaa tagagaaaaa agtaatataa taattaacta tatgaaaatt  11880
tagaagggac aatattttta attaagaata taaacaatat ttcttttcat gtaatgaggg  11940
acggatgtac ggggccagtg ttggagtcaa agccaaaata gtcacgggga aattaatgca  12000
ctgcatgact attcgaaaaa attcactagc cttacttaga tgttagatta atagctaggg  12060
ggtgcagata attttgaaag gcatgaaaaa cattaatttg tacattgcaa gcttttgatg  12120
acaagctttg caattgttca cactacctta tgccatttat aaatagagtg attggcatat  12180
gaaggaaatc atgagagtcg aagcgaaaaa caaagcttga gagtgtagga aaaatacagt  12240
```

tttttggta aaaatacagt atttgaatag gagcgaaaaa tatcctttca aaatgatcct 12300 tttcttttt ttttttttc ttgttgttct tggtcagtta ttcaaaggaa aagggattga 12360
aataaaaact tgcatgtggg atcgtacgtc gagtcgacct gca 12403

<210> SEQ ID NO 57
<211> LENGTH: 3983
<212> TYPE: DNA
<213> ORGANISM: Artificial Sequence
<220> FEATURE:
<223> OTHER INFORMATION: the sequence of pKR132

<400> SEQUENCE: 57
ctagagtcga cctgcaggca tgcaagcttg gcgtaatcat ggtcatagct gtttcctgtg 60
tgaaattgtt atccgctcac aattccacac aacatacgag ccggaagcat aaagtgtaaa 120
gcctggggtg cctaatgagt gagctaactc acattaattg cgttgcgctc actgcccgct 180
ttccagtcgg gaaacctgtc gtgccagctg cattaatgaa tcggccaacg cgcggggaga 240
ggcggtttgc gtattgggcg ctcttccgct tcctcgctca ctgactcgct gcgctcggtc 300
gttcggctgc ggcgagcggt atcagctcac tcaaaggcgg taatacggtt atccacagaa 360
tcaggggata acgcaggaaa gaacatgtga gcaaaaggcc agcaaaaggc caggaaccgt 420
aaaaaggccg cgttgctggc gtttttccat aggctccgcc cccctgacga gcatcacaaa 480
aatcgacgct caagtcagag gtggcgaaac ccgacaggac tataaagata ccaggcgttt 540
ccccctggaa gctccctcgt gcgctctcct gttccgaccc tgccgcttac cggatacctg 600
tccgcctttc tcccttcggg aagcgtggcg ctttctcata gctcacgctg taggtatctc 660
agttcggtgt aggtcgttcg ctccaagctg ggctgtgtgc acgaaccccc cgttcagccc 720
gaccgctgcg ccttatccgg taactatcgt cttgagtcca acccggtaag acacgactta 780
tcgccactgg cagcagccac tggtaacagg attagcagag cgaggtatgt aggcggtgct 840
acagagttct tgaagtggtg gcctaactac ggctacacta gaaggacagt atttggtatc 900
tgcgctctgc tgaagccagt taccttcgga aaaagagttg gtagctcttg atccggcaaa 960
caaaccaccg ctggtagcgg tggttttttt gtttgcaagc agcagattac gcgcagaaaa 1020
aaaggatctc aagaagatcc tttgatcttt tctacggggt ctgacgctca gtggaacgaa 1080
aactcacgtt aagggatttt ggtcatgaga ttatcaaaaa ggatcttcac ctagatcctt 1140
ttaaattaaa aatgaagttt taaatcaatc taaagtatat atgagtaaac ttggtctgac 1200
agttaccaat gcttaatcag tgaggcacct atctcagcga tctgtctatt tcgttcatcc 1260
atagttgcct gactccccgt cgtgtagata actacgatac gggagggctt accatctggc 1320
cccagtgctg caatgatacc gcgagaccca cgctcaccgg ctccagattt atcagcaata 1380
aaccagccag ccggaagggc cgagcgcaga agtggtcctg caactttatc cgcctccatc 1440
cagtctatta attgttgccg ggaagctaga gtaagtagtt cgccagttaa tagtttgcgc 1500
aacgttgttg ccattgctac aggcatcgtg gtgtcacgct cgtcgtttgg tatggcttca 1560
ttcagctccg gttcccaacg atcaaggcga gttacatgat cccccatgtt gtgcaaaaaa 1620
gcggttagct ccttcggtcc tccgatcgtt gtcagaagta agttggccgc agtgttatca 1680
ctcatggtta tggcagcact gcataattct cttactgtca tgccatccgt aagatgcttt 1740
tctgtgactg gtgagtactc aaccaagtca ttctgagaat agtgtatgcg gcgaccgagt 1800
tgctcttgcc cggcgtcaat acgggataat accgcgccac atagcagaac tttaaaagtg 1860
ctcatcattg gaaaacgttc ttcggggcga aaactctcaa ggatcttacc gctgttgaga 1920

-continued

```
tccagttcga tgtaacccac tcgtgcaccc aactgatctt cagcatcttt tactttcacc   1980
agcgtttctg ggtgagcaaa aacaggaagg caaaatgccg caaaaaaggg aataagggcg   2040
acacggaaat gttgaatact catactcttc ctttttcaat attattgaag catttatcag   2100
ggttattgtc tcatgagcgg atacatattt gaatgtattt agaaaaataa acaaataggg   2160
gttccgcgca catttccccg aaaagtgcca cctgacgtct aagaaaccat tattatcatg   2220
acattaacct ataaaaatag gcgtatcacg aggccctttc gtctcgcgcg tttcggtgat   2280
gacggtgaaa acctctgaca catgcagctc ccggagacgg tcacagcttg tctgtaagcg   2340
gatgccggga gcagacaagc ccgtcagggc gcgtcagcgg gtgttggcgg gtgtcggggc   2400
tggcttaact atgcggcatc agagcagatt gtactgagag tgcaccatat gcggtgtgaa   2460
ataccgcaca gatgcgtaag gagaaaatac cgcatcaggc gccattcgcc attcaggctg   2520
cgcaactgtt gggaagggcg atcggtgcgg gcctcttcgc tattacgcca gctggcgaaa   2580
gggggatgtg ctgcaaggcg attaagttgg gtaacgccag ggttttccca gtcacgacgt   2640
tgtaaaacga cggccagtga attcgagctc ggtacccggg gatcctctag acctgcaggc   2700
caactgcgtt tggggctcca gattaaacga cgccgtttcg ttcctttcgc ttcacggctt   2760
aacgatgtcg tttctgtctg tgcccaaaaa ataaaggcat ttgttatttg caccagatat   2820
ttactaagtg caccctagtt tgacaagtag gcgataatta caaatagatg cggtgcaaat   2880
aataaatttt gaaggaaata attacaaaag aacagaactt atatttactt tattttaaaa   2940
aactaaaatg aaagaacaaa aaaagtaaaa aatacaaaaa atgtgcttta accactttca   3000
ttatttgtta cagaaagtat gattctactc aaattgatct gttgtatctg gtgctgcctt   3060
gtcacactgg cgatttcaat cccctaaaga tatggtgcaa actgcgaagt gatcaatatc   3120
tgctcggtta atttagatta attaataata ttcaacgtga tgtaccaaaa aaagacaatt   3180
ttttgctcca ttgacaaatt aaacctcatc aaggtaattt ccaaacctat aagcaaaaaa   3240
atttcacatt aattggcccg caatcctatt agtcttatta tactagagta ggaaaaaaaa   3300
caattacaca acttgtctta ttattctcta tgctaatgaa tatttttccc ttttgttaga   3360
aatcagtgtt tcctaattta ttgagtatta attccactca ccgcatatat ttaccgttga   3420
ataagaaaat tttacacata attcttttta agataaataa ttttttttata ctagatctta   3480
tatgattacg tgaagccaag tgggttatac taatgatata taatgtttga tagtaatcag   3540
tttataaacc aaatgcatgg aaatgttacg tggaagcacg taaattaaca agcattgaag   3600
caaatgcagc caccgcacca aaaccacccc acttcacttc cacgtaccat attccatgca   3660
actacaacac cctaaaactt caataaatgc ccccaccttc acttcacttc acccatcaat   3720
agcaagcggc cgcgaagtta aaagcaatgt tgtcacttgt cgtactaaca catgatgtga   3780
tagtttatgc tagctagcta taacataagc tgtctctgag tgtgttgtat attaataaag   3840
atcatcactg gtgaatggtg atcgtgtacg taccctactt agtaggcaat ggaagcactt   3900
agagtgtgct ttgtgcatgg ccttgcctct gttttgagac ttttgtaatg ttttcgagtt   3960
taaatctttg cctttgcgta cgt                                           3983
```

<210> SEQ ID NO 58
<211> LENGTH: 4268
<212> TYPE: DNA
<213> ORGANISM: Artificial Sequence
<220> FEATURE:
<223> OTHER INFORMATION: the sequence of pKR160

<400> SEQUENCE: 58
aatctagacg tacgcaaagg caaagattta aactcgaaaa cattacaaaa gtctcaaaac 60
agaggcaagg ccatgcacaa agcacactct aagtgcttcc attgcctact aagtagggta 120
cgtacacgat caccattcac cagtgatgat ctttattaat atacaacaca ctcagagaca 180
gcttatgtta tagctagcta gcataaacta tcacatcatg tgttagtacg acaagtgaca 240
acattgcttt taacttcgcg gccgcttgct attgatgggt gaagtgaagt gaaggtgggg 300
gcatttattg aagttttagg gtgttgtagt tgcatggaat atggtacgtg gaagtgaagt 360
ggggtggttt tggtgcggtg gctgcatttg cttcaatgct tgttaattta cgtgcttcca 420
cgtaacattt ccatgcattt ggtttataaa ctgattacta tcaaacatta tatatcatta 480
gtataaccca cttggcttca cgtaatcata taagatctag tataaaaaaa ttatttatct 540
taaaaagaat tatgtgtaaa attttcttat tcaacggtaa atatatgcgg tgagtggaat 600
taatactcaa taaattagga aacactgatt tctaacaaaa gggaaaaata ttcattagca 660
tagagaataa taagacaagt tgtgtaattg ttttttttcc tactctagta taataagact 720
aataggattg cgggccaatt aatgtgaaat ttttttgctt ataggtttgg aaattacctt 780
gatgaggttt aatttgtcaa tggagcaaaa aattgtcttt ttttggtaca tcacgttgaa 840
tattattaat taatctaaat taaccgagca gatattgatc acttcgcagt ttgcaccata 900
tctttagggg attgaaatcg ccagtgtgac aaggcagcac cagatacaac agatcaattt 960
gagtagaatc atactttctg taacaaataa tgaaagtggt taaagcacat tttttgtatt 1020
ttttactttt tttgttcttt cattttagtt ttttaaaata aagtaaatat aagttctgtt 1080
cttttgtaat tatttccttc aaaatttatt atttgcaccg catctatttg taattatcgc 1140
ctacttgtca aactagggtg cacttagtaa atatctggtg caaataacaa atgcctttat 1200
tttttgggca cagacagaaa cgacatcgtt aagccgtgaa gcgaaaggaa cgaaacggcg 1260
tcgtttaatc tggagcccca aacgcagttg gtttcgtacg tctagaaggg ctagagcggc 1320
cgccaccgcg gtggagctcc agcttttgtt ccctttagtg agggttaatt gcgcgcttgg 1380
cgtaatcatg gtcatagctg tttcctgtgt gaaattgtta tccgctcaca attccacaca 1440
acatacgagc cggaagcata aagtgtaaag cctggggtgc ctaatgagtg agctaactca 1500
cattaattgc gttgcgctca ctgcccgctt tccagtcggg aaacctgtcg tgccagctgc 1560
attaatgaat cggccaacgc gcggggagag gcggtttgcg tattgggcgc tcttccgctt 1620
cctcgctcac tgactcgctg cgctcggtcg ttcggctgcg gcgagcggta tcagctcact 1680
caaaggcggt aatacggtta tccacagaat caggggataa cgcaggaaag aacatgtgag 1740
caaaaggcca gcaaaaggcc aggaaccgta aaaaggccgc gttgctggcg tttttccata 1800
ggctccgccc ccctgacgag catcacaaaa atcgacgctc aagtcagagg tggcgaaacc 1860
cgacaggact ataaagatac caggcgtttc cccctggaag ctccctcgtg cgctctcctg 1920
ttccgaccct gccgcttacc ggatacctgt ccgcctttct cccttcggga agcgtggcgc 1980
tttctcatag ctcacgctgt aggtatctca gttcggtgta ggtcgttcgc tccaagctgg 2040
gctgtgtgca cgaacccccc gttcagcccg accgctgcgc cttatccggt aactatcgtc 2100
ttgagtccaa cccggtaaga cacgacttat cgccactggc agcagccact ggtaacagga 2160
ttagcagagc gaggtatgta ggcggtgcta cagagttctt gaagtggtgg cctaactacg 2220
gctacactag aaggacagta tttggtatct gcgctctgct gaagccagtt accttcggaa 2280
aaagagttgg tagctcttga tccggcaaac aaaccaccgc tggtagcggt ggtttttttg 2340

-continued

```
tttgcaagca gcagattacg cgcagaaaaa aaggatctca agaagatcct ttgatctttt   2400

ctacggggtc tgacgctcag tggaacgaaa actcacgtta agggattttg gtcatgagat   2460

tatcaaaaag gatcttcacc tagatccttt taaattaaaa atgaagtttt aaatcaatct   2520

aaagtatata tgagtaaact tggtctgaca gttaccaatg cttaatcagt gaggcaccta   2580

tctcagcgat ctgtctattt cgttcatcca tagttgcctg actccccgtc gtgtagataa   2640

ctacgatacg ggagggctta ccatctggcc ccagtgctgc aatgataccg cgagacccac   2700

gctcaccggc tccagattta tcagcaataa accagccagc cggaagggcc gagcgcagaa   2760

gtggtcctgc aactttatcc gcctccatcc agtctattaa ttgttgccgg gaagctagag   2820

taagtagttc gccagttaat agtttgcgca acgttgttgc cattgctaca ggcatcgtgg   2880

tgtcacgctc gtcgtttggt atggcttcat tcagctccgg ttcccaacga tcaaggcgag   2940

ttacatgatc ccccatgttg tgcaaaaaag cggttagctc cttcggtcct ccgatcgttg   3000

tcagaagtaa gttggccgca gtgttatcac tcatggttat ggcagcactg cataattctc   3060

ttactgtcat gccatccgta agatgctttt ctgtgactgg tgagtactca accaagtcat   3120

tctgagaata gtgtatgcgg cgaccgagtt gctcttgccc ggcgtcaata cgggataata   3180

ccgcgccaca tagcagaact ttaaaagtgc tcatcattgg aaaacgttct tcggggcgaa   3240

aactctcaag gatcttaccg ctgttgagat ccagttcgat gtaacccact cgtgcaccca   3300

actgatcttc agcatctttt actttcacca gcgtttctgg gtgagcaaaa acaggaaggc   3360

aaaatgccgc aaaaaaggga ataagggcga cacggaaatg ttgaatactc atactcttcc   3420

tttttcaata ttattgaagc atttatcagg gttattgtct catgagcgga tacatatttg   3480

aatgtattta gaaaaataaa caaatagggg ttccgcgcac atttccccga aaagtgccac   3540

ctaaattgta agcgttaata ttttgttaaa attcgcgtta aatttttgtt aaatcagctc   3600

attttttaac caataggccg aaatcggcaa aatcccttat aaatcaaaag aatagaccga   3660

gatagggttg agtgttgttc cagtttggaa caagagtcca ctattaaaga acgtggactc   3720

caacgtcaaa gggcgaaaaa ccgtctatca gggcgatggc ccactacgtg aaccatcacc   3780

ctaatcaagt tttttggggt cgaggtgccg taaagcacta aatcggaacc ctaaagggag   3840

cccccgattt agagcttgac ggggaaagcc ggcgaacgtg gcgagaaagg aagggaagaa   3900

agcgaaagga gcgggcgcta gggcgctggc aagtgtagcg gtcacgctgc gcgtaaccac   3960

cacacccgcc gcgcttaatg cgccgctaca gggcgcgtcc cattcgccat tcaggctgcg   4020

caactgttgg gaagggcgat cggtgcgggc ctcttcgcta ttacgccagc tggcgaaagg   4080

gggatgtgct gcaaggcgat taagttgggt aacgccaggg ttttcccagt cacgacgttg   4140

taaaacgacg gccagtgagc gcgcgtaata cgactcacta tagggcgaat tgggtaccgg   4200

gccccccctc gaggtcgacg gtatcgataa gcttgatatc gaattcctgc agcccggggg   4260

atccgccc                                                            4268
```

<210> SEQ ID NO 59
<211> LENGTH: 4990
<212> TYPE: DNA
<213> ORGANISM: Artificial Sequence
<220> FEATURE:
<223> OTHER INFORMATION: the sequence of pKR124
<220> FEATURE:
<221> NAME/KEY: misc_feature
<222> LOCATION: (1186)..(1186)
<223> OTHER INFORMATION: n is a, c, g, or t

<400> SEQUENCE: 59

```
ctagacgtac gtcctcgaag agaagggtta ataacacatt ttttaacatt tttaacacaa      60
attttagtta tttaaaaatt tattaaaaaa tttaaaataa gaagaggaac tctttaaata     120
aatctaactt acaaaattta tgatttttaa taagttttca ccaataaaaa atgtcataaa     180
aatatgttaa aaagtatatt atcaatattc tctttatgat aaataaaaag aaaaaaaaaa     240
taaaagttaa gtgaaaatga gattgaagtg actttaggtg tgtataaata tatcaacccc     300
gccaacaatt tatttaatcc aaatatattg aagtatatta ttccatagcc tttatttatt     360
tatatattta ttatataaaa gctttatttg ttctaggttg ttcatgaaat atttttttgg     420
ttttatctcc gttgtaagaa aatcatgtgc tttgtgtcgc cactcactat tgcagctttt     480
tcatgcattg gtcagattga cggttgattg tatttttgtt ttttatggtt ttgtgttatg     540
acttaagtct tcatctcttt atctcttcat caggtttgat ggttacctaa tatggtccat     600
gggtacatgc atggttaaat taggtggcca actttgttgt gaacgataga atttttttta     660
tattaagtaa actattttta tattatgaaa taataataaa aaaaatattt tatcattatt     720
aacaaaatca tattagttaa tttgttaact ctataataaa agaaatactg taacattcac     780
attacatggt aacatctttc caccctttca tttgtttttt gtttgatgac tttttttctt     840
gtttaaattt atttcccttc ttttaaattt ggaatacatt atcatcatat ataaactaaa     900
atactaaaaa caggattaca caaatgataa ataataacac aaatatttat aaatctagct     960
gcaatatatt taaactagct atatcgatat tgtaaaataa aactagctgc attgatactg    1020
ataaaaaaat atcatgtgct ttctggactg atgatgcagt atacttttga cattgccttt    1080
atttatttt tcagaaaagc tttcttagtt ctgggttctt cattatttgt ttcccatctc    1140
cattgtgaat tgaatcattt gcttcgtgtc acaaatacaa tttagntagg tacatgcatt    1200
ggtcagattc acggtttatt atgtcatgac ttaagttcat ggtagtacat tacctgccac    1260
gcatgcatta tattggttag atttgatagg caaatttggt tgtcaacaat ataaatataa    1320
ataatgtttt tatattacga aataacagtg atcaaaacaa acagttttat ctttattaac    1380
aagattttgt ttttgtttga tgacgttttt taatgtttac gctttccccc ttcttttgaa    1440
tttagaacac tttatcatca taaaatcaaa tactaaaaaa attacatatt tcataaataa    1500
taacacaaat atttttaaaa aatctgaaat aataatgaac aatattacat attatcacga    1560
aaattcatta ataaaaatat tatataaata aaatgtaata gtagttatat gtaggaaaaa    1620
agtactgcac gcataatata tacaaaaaga ttaaaatgaa ctattataaa taataacact    1680
aaattaatgg tgaatcatat caaaataatg aaaaagtaaa taaaatttgt aattaacttc    1740
tatatgtatt acacacacaa ataataaata atagtaaaaa aaattatgat aaatatttac    1800
catctcataa gatatttaaa ataatgataa aaatatagat tattttttat gcaactagct    1860
agccaaaaag agaacacggg tatatataaa aagagtacct ttaaattcta ctgtacttcc    1920
tttattcctg acgtttttat atcaagtgga catacgtgaa gattttaatt atcagtctaa    1980
atatttcatt agcacttaat acttttctgt tttattccta tcctataagt agtcccgatt    2040
ctcccaacat tgcttattca cacaactaac taagaaagtc ttccatagcc ccccaagcgg    2100
ccgcgacaca agtgtgagag tactaaataa atgctttggt tgtacgaaat cattacacta    2160
aataaaataa tcaaagctta tatatgcctt ccgctaaggc cgaatgcaaa gaaattggtt    2220
ctttctcgtt atcttttgcc acttttacta gtacgtatta attactactt aatcatcttt    2280
gtttacggct cattatatcc gtacgtcgag tcgacctgca ggcatgcaag cttggcgtaa    2340
```

```
tcatggtcat agctgtttcc tgtgtgaaat tgttatccgc tcacaattcc acacaacata   2400
cgagccggaa gcataaagtg taaagcctgg ggtgcctaat gagtgagcta actcacatta   2460
attgcgttgc gctcactgcc cgctttccag tcgggaaacc tgtcgtgcca gctgcattaa   2520
tgaatcggcc aacgcgcggg gagaggcggt ttgcgtattg ggcgctcttc cgcttcctcg   2580
ctcactgact cgctgcgctc ggtcgttcgg ctgcggcgag cggtatcagc tcactcaaag   2640
gcggtaatac ggttatccac agaatcaggg gataacgcag gaaagaacat gtgagcaaaa   2700
ggccagcaaa aggccaggaa ccgtaaaaag gccgcgttgc tggcgttttt ccataggctc   2760
cgcccccctg acgagcatca caaaaatcga cgctcaagtc agaggtggcg aaacccgaca   2820
ggactataaa gataccaggc gtttccccct ggaagctccc tcgtgcgctc tcctgttccg   2880
accctgccgc ttaccggata cctgtccgcc tttctccctt cgggaagcgt ggcgctttct   2940
catagctcac gctgtaggta tctcagttcg gtgtaggtcg ttcgctccaa gctgggctgt   3000
gtgcacgaac cccccgttca gcccgaccgc tgcgccttat ccggtaacta tcgtcttgag   3060
tccaacccgg taagacacga cttatcgcca ctggcagcag ccactggtaa caggattagc   3120
agagcgaggt atgtaggcgg tgctacagag ttcttgaagt ggtggcctaa ctacggctac   3180
actagaagga cagtatttgg tatctgcgct ctgctgaagc cagttacctt cggaaaaaga   3240
gttggtagct cttgatccgg caaacaaacc accgctggta gcggtggttt ttttgtttgc   3300
aagcagcaga ttacgcgcag aaaaaaagga tctcaagaag atcctttgat cttttctacg   3360
gggtctgacg ctcagtggaa cgaaaactca cgttaaggga ttttggtcat gagattatca   3420
aaaaggatct tcacctagat ccttttaaat taaaaatgaa gttttaaatc aatctaaagt   3480
atatatgagt aaacttggtc tgacagttac caatgcttaa tcagtgaggc acctatctca   3540
gcgatctgtc tatttcgttc atccatagtt gcctgactcc ccgtcgtgta gataactacg   3600
atacgggagg gcttaccatc tggccccagt gctgcaatga taccgcgaga cccacgctca   3660
ccggctccag atttatcagc aataaaccag ccagccggaa gggccgagcg cagaagtggt   3720
cctgcaactt tatccgcctc catccagtct attaattgtt gccgggaagc tagagtaagt   3780
agttcgccag ttaatagttt gcgcaacgtt gttgccattg ctacaggcat cgtggtgtca   3840
cgctcgtcgt ttggtatggc ttcattcagc tccggttccc aacgatcaag gcgagttaca   3900
tgatccccca tgttgtgcaa aaaagcggtt agctccttcg gtcctccgat cgttgtcaga   3960
agtaagttgg ccgcagtgtt atcactcatg gttatggcag cactgcataa ttctcttact   4020
gtcatgccat ccgtaagatg cttttctgtg actggtgagt actcaaccaa gtcattctga   4080
gaatagtgta tgcggcgacc gagttgctct tgcccggcgt caatacggga taataccgcg   4140
ccacatagca gaactttaaa agtgctcatc attggaaaac gttcttcggg gcgaaaactc   4200
tcaaggatct taccgctgtt gagatccagt tcgatgtaac ccactcgtgc acccaactga   4260
tcttcagcat cttttacttt caccagcgtt tctgggtgag caaaaacagg aaggcaaaat   4320
gccgcaaaaa agggaataag ggcgacacgg aaatgttgaa tactcatact cttccttttt   4380
caatattatt gaagcattta tcagggttat tgtctcatga gcggatacat atttgaatgt   4440
atttagaaaa ataaacaaat aggggttccg cgcacatttc cccgaaaagt gccacctgac   4500
gtctaagaaa ccattattat catgacatta acctataaaa ataggcgtat cacgaggccc   4560
tttcgtctcg cgcgtttcgg tgatgacggt gaaaacctct gacacatgca gctcccggag   4620
acggtcacag cttgtctgta agcggatgcc gggagcagac aagcccgtca gggcgcgtca   4680
```

gcgggtgttg gcgggtgtcg gggctggctt aactatgcgg catcagagca gattgtactg 4740
agagtgcacc atatgcggtg tgaaataccg cacagatgcg taaggagaaa ataccgcatc 4800
aggcgccatt cgccattcag gctgcgcaac tgttgggaag ggcgatcggt gcgggcctct 4860
tcgctattac gccagctggc gaaaggggga tgtgctgcaa ggcgattaag ttgggtaacg 4920
ccagggtttt cccagtcacg acgttgtaaa acgacggcca gtgaattcga gctcggtacc 4980
cggggatcct 4990

<210> SEQ ID NO 60
<211> LENGTH: 3982
<212> TYPE: DNA
<213> ORGANISM: Artificial Sequence
<220> FEATURE:
<223> OTHER INFORMATION: the sequence of pKR163

<400> SEQUENCE: 60
gtacgaaacc aactgcgttt ggggctccag attaaacgac gccgtttcgt tcctttcgct 60
tcacggctta acgatgtcgt ttctgtctgt gcccaaaaaa taaaggcatt tgttatttgc 120
accagatatt tactaagtgc accctagttt gacaagtagg cgataattac aaatagatgc 180
ggtgcaaata ataaattttg aaggaaataa ttacaaaaga acagaactta tatttacttt 240
attttaaaaa actaaaatga aagaacaaaa aaagtaaaaa atacaaaaaa tgtgctttaa 300
ccactttcat tatttgttac agaaagtatg attctactca aattgatctg ttgtatctgg 360
tgctgccttg tcacactggc gatttcaatc ccctaaagat atggtgcaaa ctgcgaagtg 420
atcaatatct gctcggttaa tttagattaa ttaataatat tcaacgtgat gtaccaaaaa 480
aagacaattt tttgctccat tgacaaatta aacctcatca aggtaatttc caaacctata 540
agcaaaaaaa tttcacatta attggcccgc aatcctatta gtcttattat actagagtag 600
gaaaaaaaac aattacacaa cttgtcttat tattctctat gctaatgaat atttttccct 660
tttgttagaa atcagtgttt cctaatttat tgagtattaa ttccactcac cgcatatatt 720
taccgttgaa taagaaaatt ttacacataa ttctttttaa gataaataat tttttatac 780 tagatcttat atgattacgt gaagccaagt gggttatact aatgatatat aatgtttgat 840
agtaatcagt ttataaacca aatgcatgga aatgttacgt ggaagcacgt aaattaacaa 900
gcattgaagc aaatgcagcc accgcaccaa aaccacccca cttcacttcc acgtaccata 960
ttccatgcaa ctacaacacc ctaaaacttc aataaatgcc cccaccttca cttcacttca 1020
cccatcaata gcaagcggcc gcgaagttaa aagcaatgtt gtcacttgtc gtactaacac 1080
atgatgtgat agtttatgct agctagctat aacataagct gtctctgagt gtgttgtata 1140
ttaataaaga tcatcactgg tgaatggtga tcgtgtacgt accctactta gtaggcaatg 1200
gaagcactta gagtgtgctt tgtgcatggc cttgcctctg ttttgagact tttgtaatgt 1260
tttcgagttt aaatctttgc ctttgcgtac gtcgagtcga cctgcaggca tgcaagcttg 1320
gcgtaatcat ggtcatagct gtttcctgtg tgaaattgtt atccgctcac aattccacac 1380
aacatacgag ccggaagcat aaagtgtaaa gcctggggtg cctaatgagt gagctaactc 1440
acattaattg cgttgcgctc actgcccgct ttccagtcgg gaaacctgtc gtgccagctg 1500
cattaatgaa tcggccaacg cgcggggaga ggcggtttgc gtattgggcg ctcttccgct 1560
tcctcgctca ctgactcgct gcgctcggtc gttcggctgc ggcgagcggt atcagctcac 1620
tcaaaggcgg taatacggtt atccacagaa tcaggggata acgcaggaaa gaacatgtga 1680
gcaaaaggcc agcaaaaggc caggaaccgt aaaaaggccg cgttgctggc gtttttccat 1740

```
aggctccgcc cccctgacga gcatcacaaa aatcgacgct caagtcagag gtggcgaaac   1800
ccgacaggac tataaagata ccaggcgttt ccccctggaa gctccctcgt gcgctctcct   1860
gttccgaccc tgccgcttac cggatacctg tccgcctttc tcccttcggg aagcgtggcg   1920
ctttctcata gctcacgctg taggtatctc agttcggtgt aggtcgttcg ctccaagctg   1980
ggctgtgtgc acgaaccccc cgttcagccc gaccgctgcg ccttatccgg taactatcgt   2040
cttgagtcca acccggtaag acacgactta tcgccactgg cagcagccac tggtaacagg   2100
attagcagag cgaggtatgt aggcggtgct acagagttct tgaagtggtg gcctaactac   2160
ggctacacta gaaggacagt atttggtatc tgcgctctgc tgaagccagt taccttcgga   2220
aaaagagttg gtagctcttg atccggcaaa caaaccaccg ctggtagcgg tggttttttt   2280
gtttgcaagc agcagattac gcgcagaaaa aaaggatctc aagaagatcc tttgatcttt   2340
tctacggggt ctgacgctca gtggaacgaa aactcacgtt aagggatttt ggtcatgaga   2400
ttatcaaaaa ggatcttcac ctagatcctt ttaaattaaa aatgaagttt taaatcaatc   2460
taaagtatat atgagtaaac ttggtctgac agttaccaat gcttaatcag tgaggcacct   2520
atctcagcga tctgtctatt tcgttcatcc atagttgcct gactccccgt cgtgtagata   2580
actacgatac gggagggctt accatctggc cccagtgctg caatgatacc gcgagaccca   2640
cgctcaccgg ctccagattt atcagcaata aaccagccag ccggaagggc cgagcgcaga   2700
agtggtcctg caactttatc cgcctccatc cagtctatta attgttgccg ggaagctaga   2760
gtaagtagtt cgccagttaa tagtttgcgc aacgttgttg ccattgctac aggcatcgtg   2820
gtgtcacgct cgtcgtttgg tatggcttca ttcagctccg gttcccaacg atcaaggcga   2880
gttacatgat cccccatgtt gtgcaaaaaa gcggttagct ccttcggtcc tccgatcgtt   2940
gtcagaagta agttggccgc agtgttatca ctcatggtta tggcagcact gcataattct   3000
cttactgtca tgccatccgt aagatgcttt tctgtgactg gtgagtactc aaccaagtca   3060
ttctgagaat agtgtatgcg gcgaccgagt tgctcttgcc cggcgtcaat acgggataat   3120
accgcgccac atagcagaac tttaaaagtg ctcatcattg gaaaacgttc ttcggggcga   3180
aaactctcaa ggatcttacc gctgttgaga tccagttcga tgtaacccac tcgtgcaccc   3240
aactgatctt cagcatcttt tactttcacc agcgtttctg ggtgagcaaa aacaggaagg   3300
caaaatgccg caaaaaaggg aataagggcg acacggaaat gttgaatact catactcttc   3360
ctttttcaat attattgaag catttatcag ggttattgtc tcatgagcgg atacatattt   3420
gaatgtattt agaaaaataa acaaataggg gttccgcgca catttccccg aaaagtgcca   3480
cctgacgtct aagaaaccat tattatcatg acattaacct ataaaaatag gcgtatcacg   3540
aggccctttc gtctcgcgcg tttcggtgat gacggtgaaa acctctgaca catgcagctc   3600
ccggagacgg tcacagcttg tctgtaagcg gatgccggga gcagacaagc ccgtcagggc   3660
gcgtcagcgg gtgttggcgg gtgtcggggc tggcttaact atgcggcatc agagcagatt   3720
gtactgagag tgcaccatat gcggtgtgaa ataccgcaca gatgcgtaag gagaaaatac   3780
cgcatcaggc gccattcgcc attcaggctg cgcaactgtt gggaagggcg atcggtgcgg   3840
gcctcttcgc tattacgcca gctggcgaaa gggggatgtg ctgcaaggcg attaagttgg   3900
gtaacgccag ggttttccca gtcacgacgt tgtaaaacga cggccagtga attcgagctc   3960
ggtacccggg gatcctctag ac                                            3982
```

<210> SEQ ID NO 61

<211> LENGTH: 8878
<212> TYPE: DNA
<213> ORGANISM: Artificial Sequence
<220> FEATURE:
<223> OTHER INFORMATION: the sequence of pY34

<400> SEQUENCE: 61
ggccgcacag gccgcacaat ggcgactcga cagcgaactg ccaccactgt tgtggtcgag 60
gaccttccca aggtcactct tgaggccaag tctgaacctg tgttccccga tatcaagacc 120
atcaaggatg ccattcccgc gcactgcttc cagccctcgc tcgtcacctc attctactac 180
gtcttccgcg attttgccat ggtctctgcc ctcgtctggg ctgctctcac ctacatcccc 240
agcatccccg accagaccct ccgcgtcgca gcttggatgg tctacggctt cgtccagggt 300
ctgttctgca ccggtgtctg gattctcggc catgagtgcg gccacggtgc tttctctctc 360
cacggaaagg tcaacaatgt gaccggctgg ttcctccact cgttcctcct cgtcccctac 420
ttcagctgga agtactctca ccaccgccac caccgcttca ccggccacat ggatctcgac 480
atggctttcg tccccaagac tgagcccaag ccctccaagt cgctcatgat tgctggcatt 540
gacgtcgccg agcttgttga ggacaccccc gctgctcaga tggtcaagct catcttccac 600
cagcttttcg gatggcaggc gtacctcttc ttcaacgcta gctctggcaa gggcagcaag 660
cagtgggagc ccaagactgg cctctccaag tggttccgag tcagtcactt cgagcctacc 720
agcgctgtct tccgccccaa cgaggccatc ttcatcctca tctccgatat cggtcttgct 780
ctaatgggaa ctgctctgta ctttgcttcc aagcaagttg gtgtttcgac cattctcttc 840
ctctaccttg ttccctacct gtgggttcac cactggctcg ttgccattac ctacctccac 900
caccaccaca ccgagctccc tcactacacc gctgagggct ggacctacgt caagggagct 960
ctcgccactg tcgaccgtga gtttggcttc atcggaaagc acctcttcca cggtatcatt 1020
gagaagcacg ttgttcacca tctcttccct aagatcccct tctacaaggc tgacgaggcc 1080
accgaggcca tcaagcccgt cattggcgac cactactgcc acgacgaccg aagcttcctg 1140
ggccagctgt ggaccatctt cggcacgctc aagtacgtcg agcacgaccc tgcccgaccc 1200
ggtgccatgc gatggaacaa ggactaggct aggcggccgc caccgcggcc cgagattccg 1260
gcctcttcgg ccgccaagcg acccgggtgg acgtctagag gtacctagca attaacagat 1320
agtttgccgg tgataattct cttaacctcc cacactcctt tgacataacg atttatgtaa 1380
cgaaactgaa atttgaccag atattgtgtc cgcggtggag ctccagcttt tgttcccttt 1440
agtgagggtt aatttcgagc ttggcgtaat catggtcata gctgtttcct gtgtgaaatt 1500
gttatccgct cacaattcca cacaacgtac gagccggaag cataaagtgt aaagcctggg 1560
gtgcctaatg agtgagctaa ctcacattaa ttgcgttgcg ctcactgccc gctttccagt 1620
cgggaaacct gtcgtgccag ctgcattaat gaatcggcca acgcgcgggg agaggcggtt 1680
tgcgtattgg gcgctcttcc gcttcctcgc tcactgactc gctgcgctcg gtcgttcggc 1740
tgcggcgagc ggtatcagct cactcaaagg cggtaatacg gttatccaca gaatcagggg 1800
ataacgcagg aaagaacatg tgagcaaaag gccagcaaaa ggccaggaac cgtaaaaagg 1860
ccgcgttgct ggcgtttttc cataggctcc gcccccctga cgagcatcac aaaaatcgac 1920
gctcaagtca gaggtggcga aacccgacag gactataaag ataccaggcg tttccccctg 1980
gaagctccct cgtgcgctct cctgttccga ccctgccgct taccggatac ctgtccgcct 2040
ttctcccttc gggaagcgtg gcgctttctc atagctcacg ctgtaggtat ctcagttcgg 2100
tgtaggtcgt tcgctccaag ctgggctgtg tgcacgaacc ccccgttcag cccgaccgct 2160

-continued gcgccttatc cggtaactat cgtcttgagt ccaacccggt aagacacgac ttatcgccac 2220
tggcagcagc cactggtaac aggattagca gagcgaggta tgtaggcggt gctacagagt 2280
tcttgaagtg gtggcctaac tacggctaca ctagaaggac agtatttggt atctgcgctc 2340
tgctgaagcc agttaccttc ggaaaaagag ttggtagctc ttgatccggc aaacaaacca 2400
ccgctggtag cggtggtttt tttgtttgca agcagcagat tacgcgcaga aaaaaaggat 2460
ctcaagaaga tcctttgatc ttttctacgg ggtctgacgc tcagtggaac gaaaactcac 2520
gttaagggat tttggtcatg agattatcaa aaaggatctt cacctagatc cttttaaatt 2580
aaaaatgaag ttttaaatca atctaaagta tatatgagta aacttggtct gacagttacc 2640
aatgcttaat cagtgaggca cctatctcag cgatctgtct atttcgttca tccatagttg 2700
cctgactccc cgtcgtgtag ataactacga tacgggaggg cttaccatct ggccccagtg 2760
ctgcaatgat accgcgagac ccacgctcac cggctccaga tttatcagca ataaaccagc 2820
cagccggaag ggccgagcgc agaagtggtc ctgcaacttt atccgcctcc atccagtcta 2880
ttaattgttg ccgggaagct agagtaagta gttcgccagt taatagtttg cgcaacgttg 2940
ttgccattgc tacaggcatc gtggtgtcac gctcgtcgtt tggtatggct tcattcagct 3000
ccggttccca acgatcaagg cgagttacat gatcccccat gttgtgcaaa aaagcggtta 3060
gctccttcgg tcctccgatc gttgtcagaa gtaagttggc cgcagtgtta tcactcatgg 3120
ttatggcagc actgcataat tctcttactg tcatgccatc cgtaagatgc ttttctgtga 3180
ctggtgagta ctcaaccaag tcattctgag aatagtgtat gcggcgaccg agttgctctt 3240
gcccggcgtc aatacgggat aataccgcgc cacatagcag aactttaaaa gtgctcatca 3300
ttggaaaacg ttcttcgggg cgaaaactct caaggatctt accgctgttg agatccagtt 3360
cgatgtaacc cactcgtgca cccaactgat cttcagcatc ttttactttc accagcgttt 3420
ctgggtgagc aaaaacagga aggcaaaatg ccgcaaaaaa gggaataagg gcgacacgga 3480
aatgttgaat actcatactc ttcctttttc aatattattg aagcatttat cagggttatt 3540
gtctcatgag cggatacata tttgaatgta tttagaaaaa taaacaaata ggggttccgc 3600
gcacatttcc ccgaaaagtg ccacctgacg cgccctgtag cggcgcatta agcgcggcgg 3660
gtgtggtggt tacgcgcagc gtgaccgcta cacttgccag cgccctagcg cccgctcctt 3720
tcgctttctt cccttccttt ctcgccacgt tcgccggctt tccccgtcaa gctctaaatc 3780
gggggctccc tttagggttc cgatttagtg ctttacggca cctcgacccc aaaaaacttg 3840
attagggtga tggttcacgt agtgggccat cgccctgata gacggttttt cgccctttga 3900
cgttggagtc cacgttcttt aatagtggac tcttgttcca aactggaaca acactcaacc 3960
ctatctcggt ctattctttt gatttataag ggattttgcc gatttcggcc tattggttaa 4020
aaaatgagct gatttaacaa aaatttaacg cgaattttaa caaaatatta acgcttacaa 4080
tttccattcg ccattcaggc tgcgcaactg ttgggaaggg cgatcggtgc gggcctcttc 4140
gctattacgc cagctggcga aagggggatg tgctgcaagg cgattaagtt gggtaacgcc 4200
agggttttcc cagtcacgac gttgtaaaac gacggccagt gaattgtaat acgactcact 4260
atagggcgaa ttgggtaccg ggccccccct cgaggtcgat ggtgtcgata agcttgatat 4320
cgaattcatg tcacacaaac cgatcttcgc ctcaaggaaa cctaattcta catccgagag 4380
actgccgaga tccagtctac actgattaat tttcgggcca ataatttaaa aaaatcgtgt 4440
tatataatat tatatgtatt atatatatac atcatgatga tactgacagt catgtcccat 4500

-continued

```
tgctaaatag acagactcca tctgccgcct ccaactgatg ttctcaatat ttaaggggtc   4560
atctcgcatt gtttaataat aaacagactc catctaccgc ctccaaatga tgttctcaaa   4620
atatattgta tgaacttatt tttattactt agtattatta gacaacttac ttgctttatg   4680
aaaaacactt cctatttagg aaacaattta taatggcagt tcgttcattt aacaatttat   4740
gtagaataaa tgttataaat gcgtatggga aatcttaaat atggatagca taaatgatat   4800
ctgcattgcc taattcgaaa tcaacagcaa cgaaaaaaat cccttgtaca acataaatag   4860
tcatcgagaa atatcaacta tcaaagaaca gctattcaca cgttactatt gagattatta   4920
ttggacgaga atcacacact caactgtctt tctctcttct agaaatacag gtacaagtat   4980
gtactattct cattgttcat acttctagtc atttcatccc acatattcct tggatttctc   5040
tccaatgaat gacattctat cttgcaaatt caacaattat aataagatat accaaagtag   5100
cggtatagtg gcaatcaaaa agcttctctg gtgtgcttct cgtatttatt tttattctaa   5160
tgatccatta aaggtatata tttatttctt gttatataat ccttttgttt attacatggg   5220
ctggatacat aaaggtattt tgatttaatt ttttgcttaa attcaatccc ccctcgttca   5280
gtgtcaactg taatggtagg aaattaccat acttttgaag aagcaaaaaa aatgaaagaa   5340
aaaaaaaatc gtatttccag gttagacgtt ccgcagaatc tagaatgcgg tatgcggtac   5400
attgttcttc gaacgtaaaa gttgcgctcc ctgagatatt gtacattttt gcttttacaa   5460
gtacaagtac atcgtacaac tatgtactac tgttgatgca tccacaacag tttgttttgt   5520
tttttttgt tttttttttt tctaatgatt cattaccgct atgtatacct acttgtactt   5580
gtagtaagcc gggttattgg cgttcaatta atcatagact tatgaatctg cacggtgtgc   5640
gctgcgagtt acttttagct tatgcatgct acttgggtgt aatattggga tctgttcgga   5700
aatcaacgga tgctcaaccg atttcgacag taataatttg aatcgaatcg gagcctaaaa   5760
tgaacccgag tatatctcat aaaattctcg gtgagaggtc tgtgactgtc agtacaaggt   5820
gccttcatta tgccctcaac cttaccatac ctcactgaat gtagtgtacc tctaaaaatg   5880
aaatacagtg ccaaaagcca aggcactgag ctcgtctaac ggacttgata tacaaccaat   5940
taaaacaaat gaaaagaaat acagttcttt gtatcatttg taacaattac cctgtacaaa   6000
ctaaggtatt gaaatcccac aatattccca aagtccaccc ctttccaaat tgtcatgcct   6060
acaactcata taccaagcac taacctacca aacaccacta aaaccccaca aaatatatct   6120
taccgaatat acagtaacaa gctaccacca cactcgttgg gtgcagtcgc cagcttaaag   6180
atatctatcc acatcagcca caactccctt cctttaataa accgactaca cccttggcta   6240
ttgaggttat gagtgaatat actgtagaca agacactttc aagaagactg tttccaaaac   6300
gtaccactgt cctccactac aaacacaccc aatctgcttc ttctagtcaa ggttgctaca   6360
ccggtaaatt ataaatcatc atttcattag cagggcaggg ccctttttat agagtcttat   6420
acactagcgg accctgccgg tagaccaacc cgcaggcgcg tcagtttgct ccttccatca   6480
atgcgtcgta gaaacgactt actccttctt gagcagctcc ttgaccttgt tggcaacaag   6540
tctccgacct cggaggtgga ggaagagcct ccgatatcgg cggtagtgat accagcctcg   6600
acggactcct tgacggcagc ctcaacagcg tcaccggcgg gcttcatgtt aagagagaac   6660
ttgagcatca tggcggcaga cagaatggtg gcaatggggt tgaccttctg cttgccgaga   6720
tcgggggcag atccgtgaca gggctcgtac agaccgaacg cctcgttggt gtcgggcaga   6780
gaagccagag aggcggaggg cagcagaccc agagaaccgg ggatgacgga ggcctcgtcg   6840
gagatgatat cgccaaacat gttggtggtg atgatgatac cattcatctt ggagggctgc   6900
```

ttgatgagga tcatggcggc cgagtcgatc agctggtggt tgagctcgag ctgggggaat 6960
tcgtccttga ggactcgagt gacagtcttt cgccaaagtc gagaggaggc cagcacgttg 7020
gccttgtcaa gagaccacac gggaagaggg gggttgtgct gaagggccag gaaggcggcc 7080
attcgggcaa ttcgctcaac ctcaggaacg gagtaggtct cggtgtcgga agcgacgcca 7140
gatccgtcat cctcctttcg ctctccaaag tagatacctc cgacgagctc tcggacaatg 7200
atgaagtcgg tgccctcaac gtttcggatg ggggagagat cggcgagctt gggcgacagc 7260
agctggcagg gtcgcaggtt ggcgtacagg ttcaggtcct ttcgcagctt gaggagaccc 7320
tgctcgggtc gcacgtcggt tcgtccgtcg ggagtggtcc atacggtgtt ggcagcgcct 7380
ccgacagcac cgagcataat agagtcagcc tttcggcaga tgtcgagagt agcgtcggtg 7440
atgggctcgc cctccttctc aatggcagct cctccaatga gtcggtcctc aaacacaaac 7500
tcggtgccgg aggcctcagc aacagacttg agcaccttga cggcctcggc aatcacctcg 7560
gggccacaga agtcgccgcc gagaagaaca atcttcttgg agtcagtctt ggtcttctta 7620
gtttcgggtt ccattgtgga tgtgtgtggt tgtatgtgtg atgtggtgtg tggagtgaaa 7680
atctgtggct ggcaaacgct cttgtatata tacgcacttt tgcccgtgct atgtggaaga 7740
ctaaacctcc gaagattgtg actcaggtag tgcggtatcg gctagggacc caaaccttgt 7800
cgatgccgat agcgctatcg aacgtacccc agccggccgg gagtatgtcg gaggggacat 7860
acgagatcgt caagggtttg tggccaactg gtatttaaat gatgtcgacg cagtaggatg 7920
tcctgcacgg gtctttttgt ggggtgtgga gaaaggggtg cttggagatg gaagccggta 7980
gaaccgggct gcttgtgctt ggagatggaa gccggtagaa ccgggctgct tgggggatt 8040 tggggccgct gggctccaaa gaggggtagg catttcgttg gggttacgta attgcggcat 8100
ttgggtcctg cgcgcatgtc ccattggtca gaattagtcc ggataggaga cttatcagcc 8160
aatcacagcg ccggatccac ctgtaggttg ggttgggtgg gagcacccct ccacagagta 8220
gagtcaaaca gcagcagcaa catgatagtt gggggtgtgc gtgttaaagg aaaaaaaaga 8280
agcttgggtt atattcccgc tctatttaga ggttgcggga tagacgccga cggagggcaa 8340
tggcgccatg gaaccttgcg gatatcgata cgccgcggcg gactgcgtcc gaaccagctc 8400
cagcagcgtt ttttccgggc cattgagccg actgcgaccc cgccaacgtg tcttggccca 8460
cgcactcatg tcatgttggt gttgggaggc cactttttaa gtagcacaag gcacctagct 8520
cgcagcaagg tgtccgaacc aaagaagcgg ctgcagtggt gcaaacgggg cggaaacggc 8580
gggaaaaagc cacgggggca cgaattgagg cacgccctcg aatttgagac gagtcacggc 8640
cccattcgcc cgcgcaatgg ctcgccaacg cccggtcttt tgcaccacat caggttaccc 8700
caagccaaac ctttgtgtta aaaagcttaa catattatac cgaacgtagg tttgggcggg 8760
cttgctccgt ctgtccaagg caacatttat ataagggtct gcatcgccgg ctcaattgaa 8820 tctttttct tcttctcttc tctatattca ttcttgaatt aaacacacat caatccgc 8878

<210> SEQ ID NO 62
<211> LENGTH: 5207
<212> TYPE: DNA
<213> ORGANISM: Artificial Sequence
<220> FEATURE:
<223> OTHER INFORMATION: the sequence of pKR863

<400> SEQUENCE: 62
ggccgcgaag ttaaaagcaa tgttgtcact tgtcgtacta acacatgatg tgatagttta 60

```
tgctagctag ctataacata agctgtctct gagtgtgttg tatattaata aagatcatca    120
ctggtgaatg gtgatcgtgt acgtacccta cttagtaggc aatggaagca cttagagtgt    180
gctttgtgca tggccttgcc tctgttttga gacttttgta atgttttcga gtttaaatct    240
ttgcctttgc gtacgtcgag tcgacctgca ggcatgcaag cttggcgtaa tcatggtcat    300
agctgtttcc tgtgtgaaat tgttatccgc tcacaattcc acacaacata cgagccggaa    360
gcataaagtg taaagcctgg ggtgcctaat gagtgagcta actcacatta attgcgttgc    420
gctcactgcc cgctttccag tcgggaaacc tgtcgtgcca gctgcattaa tgaatcggcc    480
aacgcgcggg gagaggcggt ttgcgtattg ggcgctcttc cgcttcctcg ctcactgact    540
cgctgcgctc ggtcgttcgg ctgcggcgag cggtatcagc tcactcaaag gcggtaatac    600
ggttatccac agaatcaggg gataacgcag gaaagaacat gtgagcaaaa ggccagcaaa    660
aggccaggaa ccgtaaaaag gccgcgttgc tggcgttttt ccataggctc cgcccccctg    720
acgagcatca caaaaatcga cgctcaagtc agaggtggcg aaacccgaca ggactataaa    780
gataccaggc gtttccccct ggaagctccc tcgtgcgctc tcctgttccg accctgccgc    840
ttaccggata cctgtccgcc tttctccctt cgggaagcgt ggcgctttct catagctcac    900
gctgtaggta tctcagttcg gtgtaggtcg ttcgctccaa gctgggctgt gtgcacgaac    960
cccccgttca gcccgaccgc tgcgccttat ccggtaacta tcgtcttgag tccaacccgg   1020
taagacacga cttatcgcca ctggcagcag ccactggtaa caggattagc agagcgaggt   1080
atgtaggcgg tgctacagag ttcttgaagt ggtggcctaa ctacggctac actagaagga   1140
cagtatttgg tatctgcgct ctgctgaagc cagttacctt cggaaaaaga gttggtagct   1200
cttgatccgg caaacaaacc accgctggta gcggtggttt ttttgtttgc aagcagcaga   1260
ttacgcgcag aaaaaaagga tctcaagaag atcctttgat cttttctacg gggtctgacg   1320
ctcagtggaa cgaaaactca cgttaaggga ttttggtcat gagattatca aaaaggatct   1380
tcacctagat ccttttaaat taaaaatgaa gttttaaatc aatctaaagt atatatgagt   1440
aaacttggtc tgacagttac caatgcttaa tcagtgaggc acctatctca gcgatctgtc   1500
tatttcgttc atccatagtt gcctgactcc ccgtcgtgta gataactacg atacgggagg   1560
gcttaccatc tggccccagt gctgcaatga taccgcgaga cccacgctca ccggctccag   1620
atttatcagc aataaaccag ccagccggaa gggccgagcg cagaagtggt cctgcaactt   1680
tatccgcctc catccagtct attaattgtt gccgggaagc tagagtaagt agttcgccag   1740
ttaatagttt gcgcaacgtt gttgccattg ctacaggcat cgtggtgtca cgctcgtcgt   1800
ttggtatggc ttcattcagc tccggttccc aacgatcaag gcgagttaca tgatccccca   1860
tgttgtgcaa aaaagcggtt agctccttcg gtcctccgat cgttgtcaga agtaagttgg   1920
ccgcagtgtt atcactcatg gttatggcag cactgcataa ttctcttact gtcatgccat   1980
ccgtaagatg cttttctgtg actggtgagt actcaaccaa gtcattctga gaatagtgta   2040
tgcggcgacc gagttgctct tgcccggcgt caatacggga taataccgcg ccacatagca   2100
gaactttaaa agtgctcatc attggaaaac gttcttcggg gcgaaaactc tcaaggatct   2160
taccgctgtt gagatccagt tcgatgtaac ccactcgtgc acccaactga tcttcagcat   2220
cttttacttt caccagcgtt tctgggtgag caaaaacagg aaggcaaaat gccgcaaaaa   2280
agggaataag ggcgacacgg aaatgttgaa tactcatact cttccttttt caatattatt   2340
gaagcattta tcagggttat tgtctcatga gcggatacat atttgaatgt atttagaaaa   2400
ataaacaaat aggggttccg cgcacatttc cccgaaaagt gccacctgac gtctaagaaa   2460
```

```
ccattattat catgacatta acctataaaa ataggcgtat cacgaggccc tttcgtctcg   2520
cgcgtttcgg tgatgacggt gaaaacctct gacacatgca gctcccggag acggtcacag   2580
cttgtctgta agcggatgcc gggagcagac aagcccgtca gggcgcgtca gcgggtgttg   2640
gcgggtgtcg gggctggctt aactatgcgg catcagagca gattgtactg agagtgcacc   2700
atatgcggtg tgaaataccg cacagatgcg taaggagaaa ataccgcatc aggcgccatt   2760
cgccattcag gctgcgcaac tgttgggaag ggcgatcggt gcgggcctct tcgctattac   2820
gccagctggc gaaaggggga tgtgctgcaa ggcgattaag ttgggtaacg ccagggtttt   2880
cccagtcacg acgttgtaaa acgacggcca gtgaattcga gctcggtacc cggggatcct   2940
ctagacgtac gaaaccaact gcgtttgggg ctccagatta aacgacgccg tttcgttcct   3000
ttcgcttcac ggcttaacga tgtcgtttct gtctgtgccc aaaaaataaa ggcatttgtt   3060
atttgcacca gatatttact aagtgcaccc tagtttgaca agtaggcgat aattacaaat   3120
agatgcggtg caaataataa attttgaagg aaataattac aaaagaacag aacttatatt   3180
tactttattt taaaaaacta aaatgaaaga acaaaaaaag taaaaaatac aaaaaatgtg   3240
ctttaaccac tttcattatt tgttacagaa agtatgattc tactcaaatt gatctgttgt   3300
atctggtgct gccttgtcac actggcgatt tcaatcccct aaagatatgg tgcaaactgc   3360
gaagtgatca atatctgctc ggttaattta gattaattaa taatattcaa cgtgatgtac   3420
caaaaaaaga caatttttg ctccattgac aaattaaacc tcatcaaggt aatttccaaa   3480
cctataagca aaaaaatttc acattaattg gcccgcaatc ctattagtct tattatacta   3540
gagtaggaaa aaaaacaatt acacaacttg tcttattatt ctctatgcta atgaatattt   3600
ttccctttg ttagaaatca gtgtttccta atttattgag tattaattcc actcaccgca   3660
tatatttacc gttgaataag aaaattttac acataattct ttttaagata aataattttt   3720
ttatactaga tcttatatga ttacgtgaag ccaagtgggt tatactaatg atatataatg   3780
tttgatagta atcagtttat aaaccaaatg catggaaatg ttacgtggaa gcacgtaaat   3840
taacaagcat tgaagcaaat gcagccaccg caccaaaacc accccacttc acttccacgt   3900
accatattcc atgcaactac aacaccctaa aacttcaata aatgccccca ccttcacttc   3960
acttcaccca tcaatagcaa gcggccgcac aatggcgact cgacagcgaa ctgccaccac   4020
tgttgtggtc gaggaccttc ccaaggtcac tcttgaggcc aagtctgaac ctgtgttccc   4080
cgatatcaag accatcaagg atgccattcc cgcgcactgc ttccagccct cgctcgtcac   4140
ctcattctac tacgtcttcc gcgattttgc catggtctct gccctcgtct gggctgctct   4200
cacctacatc cccagcatcc ccgaccagac cctccgcgtc gcagcttgga tggtctacgg   4260
cttcgtccag ggtctgttct gcaccggtgt ctggattctc ggccatgagt gcggccacgg   4320
tgctttctct ctccacggaa aggtcaacaa tgtgaccggc tggttcctcc actcgttcct   4380
cctcgtcccc tacttcagct ggaagtactc tcaccaccgc caccaccgct tcaccggcca   4440
catggatctc gacatggctt tcgtccccaa gactgagccc aagccctcca agtcgctcat   4500
gattgctggc attgacgtcg ccgagcttgt tgaggacacc cccgctgctc agatggtcaa   4560
gctcatcttc caccagcttt tcggatggca ggcgtacctc ttcttcaacg ctagctctgg   4620
caagggcagc aagcagtggg agcccaagac tggcctctcc aagtggttcc gagtcagtca   4680
cttcgagcct accagcgctg tcttccgccc caacgaggcc atcttcatcc tcatctccga   4740
tatcggtctt gctctaatgg gaactgctct gtactttgct tccaagcaag ttggtgtttc   4800
```

```
gaccattctc ttcctctacc ttgttcccta cctgtgggtt caccactggc tcgttgccat   4860
tacctacctc caccaccacc acaccgagct ccctcactac accgctgagg gctggaccta   4920
cgtcaaggga gctctcgcca ctgtcgaccg tgagtttggc ttcatcggaa agcacctctt   4980
ccacggtatc attgagaagc acgttgttca ccatctcttc cctaagatcc ccttctacaa   5040
ggctgacgag gccaccgagg ccatcaagcc cgtcattggc gaccactact gccacgacga   5100
ccgaagcttc ctgggccagc tgtggaccat cttcggcacg ctcaagtacg tcgagcacga   5160
ccctgcccga cccggtgcca tgcgatggaa caaggactag gctaggc                  5207
```

<210> SEQ ID NO 63
<211> LENGTH: 9035
<212> TYPE: DNA
<213> ORGANISM: Artificial Sequence
<220> FEATURE:
<223> OTHER INFORMATION: the sequence of pKR88=69

<400> SEQUENCE: 63

```
gtacgtctag aggatccgtc gacggcgcgc ccgatcatcc ggatatagtt cctcctttca     60
gcaaaaaacc cctcaagacc cgtttagagg ccccaagggg ttatgctagt tattgctcag    120
cggtggcagc agccaactca gcttcctttc gggctttgtt agcagccgga tcgatccaag    180
ctgtacctca ctattccttt gccctcggac gagtgctggg gcgtcggttt ccactatcgg    240
cgagtacttc tacacagcca tcggtccaga cggccgcgct tctgcgggcg atttgtgtac    300
gcccgacagt cccggctccg gatcggacga ttgcgtcgca tcgaccctgc gcccaagctg    360
catcatcgaa attgccgtca accaagctct gatagagttg gtcaagacca atgcggagca    420
tatacgcccg gagccgcggc gatcctgcaa gctccggatg cctccgctcg aagtagcgcg    480
tctgctgctc catacaagcc aaccacggcc tccagaagaa gatgttggcg acctcgtatt    540
gggaatcccc gaacatcgcc tcgctccagt caatgaccgc tgttatgcgg ccattgtccg    600
tcaggacatt gttggagccg aaatccgcgt gcacgaggtg ccggacttcg gggcagtcct    660
cggcccaaag catcagctca tcgagagcct gcgcgacgga cgcactgacg gtgtcgtcca    720
tcacagtttg ccagtgatac acatggggat cagcaatcgc gcatatgaaa tcacgccatg    780
tagtgtattg accgattcct tgcggtccga atgggccgaa cccgctcgtc tggctaagat    840
cggccgcagc gatcgcatcc atagcctccg cgaccggctg cagaacagcg ggcagttcgg    900
tttcaggcag gtcttgcaac gtgacaccct gtgcacggcg ggagatgcaa taggtcaggc    960
tctcgctgaa ttccccaatg tcaagcactt ccggaatcgg gagcgcggcc gatgcaaagt   1020
gccgataaac ataacgatct ttgtagaaac catcggcgca gctatttacc cgcaggacat   1080
atccacgccc tcctacatcg aagctgaaag cacgagattc ttcgccctcc gagagctgca   1140
tcaggtcgga gacgctgtcg aacttttcga tcagaaactt ctcgacagac gtcgcggtga   1200
gttcaggctt ttccatgggt atatctcctt cttaaagtta aacaaaatta tttctagagg   1260
gaaaccgttg tggtctccct atagtgagtc gtattaattt cgcgggatcg agatctgatc   1320
aacctgcatt aatgaatcgg ccaacgcgcg gggagaggcg gtttgcgtat tgggcgctct   1380
tccgcttcct cgctcactga ctcgctgcgc tcggtcgttc ggctgcggcg agcggtatca   1440
gctcactcaa aggcggtaat acggttatcc acagaatcag gggataacgc aggaaagaac   1500
atgtgagcaa aaggccagca aaaggccagg aaccgtaaaa aggccgcgtt gctggcgttt   1560
ttccataggc tccgcccccc tgacgagcat cacaaaaatc gacgctcaag tcagaggtgg   1620
cgaaacccga caggactata aagataccag gcgtttcccc ctggaagctc cctcgtgcgc   1680
```

tctcctgttc cgaccctgcc gcttaccgga tacctgtccg cctttctccc ttcgggaagc 1740
gtggcgcttt ctcaatgctc acgctgtagg tatctcagtt cggtgtaggt cgttcgctcc 1800
aagctgggct gtgtgcacga accccccgtt cagcccgacc gctgcgcctt atccggtaac 1860
tatcgtcttg agtccaaccc ggtaagacac gacttatcgc cactggcagc agccactggt 1920
aacaggatta gcagagcgag gtatgtaggc ggtgctacag agttcttgaa gtggtggcct 1980
aactacggct acactagaag gacagtattt ggtatctgcg ctctgctgaa gccagttacc 2040
ttcggaaaaa gagttggtag ctcttgatcc ggcaaacaaa ccaccgctgg tagcggtggt 2100
tttttgttt gcaagcagca gattacgcgc agaaaaaaag gatctcaaga agatcctttg 2160
atcttttcta cggggtctga cgctcagtgg aacgaaaact cacgttaagg gattttggtc 2220
atgacattaa cctataaaaa taggcgtatc acgaggccct ttcgtctcgc gcgtttcggt 2280
gatgacggtg aaaacctctg acacatgcag ctcccggaga cggtcacagc ttgtctgtaa 2340
gcggatgccg ggagcagaca agcccgtcag ggcgcgtcag cgggtgttgg cgggtgtcgg 2400
ggctggctta actatgcggc atcagagcag attgtactga gagtgcacca tatggacata 2460
ttgtcgttag aacgcggcta caattaatac ataaccttat gtatcataca catacgattt 2520
aggtgacact atagaacggc gcgccaagct gggtctagaa ctagaaacgt gatgccactt 2580
gttattgaag tcgattacag catctattct gttttactat ttataacttt gccatttctg 2640
acttttgaaa actatctctg gatttcggta tcgctttgtg aagatcgagc aaaagagacg 2700
ttttgtggac gcaatggtcc aaatccgttc tacatgaaca aattggtcac aatttccact 2760
aaaagtaaat aaatggcaag ttaaaaaagg aatatgcatt ttactgattg cctaggtgag 2820
ctccaagaga agttgaatct acacgtctac caaccgctaa aaaaagaaaa acattgatat 2880
gtaacctgat tccattagct tttgacttct tcaacagatt ctctacttag atttctaaca 2940
gaaatattat tactagcaca tcattttcag tctcactaca gcaaaaaatc caacggcaca 3000
atacagacaa caggagatat cagactacag agatagatag atgctactgc atgtagtaag 3060
ttaaataaaa ggaaaataaa atgtcttgct accaaaacta ctacagacta tgatgctcac 3120
cacaggccaa atcctgcaac taggacagca ttatcttata tatattgtac aaaacaagca 3180
tcaaggaaca tttggtctag gcaatcagta cctcgttcta ccatcaccct cagttatcac 3240
atccttgaag gatccattac tgggaatcat cggcaacaca tgctcctgat ggggcacaat 3300
gacatcaaga aggtaggggc caggggtgtc caacattctc tgaattgccg ctctaagctc 3360
ttccttcttc gtcactcgcg ctgccggtat cccacaagca tcagcaaact tgagcatgtt 3420
tgggaatatc tcgctctcgc tagacggatc tccaagatag gtgtgagctc tattggactt 3480
gtagaaccta tcctccaact gaaccaccat acccaaatgc tgattgttca acaacaatat 3540
cttaactggg agattctcca ctcttatagt ggccaactcc tgaacattca tgatgaaact 3600
accatcccca tcaatgtcaa ccacaacagc cccagggtta gcaacagcag caccaatagc 3660
cgcaggcaat ccaaaaccca tggctccaag accccctgag gtcaaccact gcctcggtct 3720
cttgtacttg taaaactgcg cagcccacat ttgatgctgc ccaaccccag tactaacaat 3780
agcatctcca ttagtcaact catcaagaac ctcgatagca tgctgcggag aaatcgcgtc 3840
ctggaatgtc ttgtaaccca atggaaactt gtgtttctgc acattaatct cttctctcca 3900
acctccaaga tcaaacttac cctccactcc tttctcctcc aaaatcatat taattccctt 3960
caaggccaac ttcaaatccg cgcaaaccga cacgtgcgcc tgcttgttct tcccaatctc 4020

-continued

```
ggcagaatca atatcaatgt gaacaatctt agccctacta gcaaaagcct caagcttccc   4080
agtaacacgg tcatcaaacc ttaccccaaa ggcaagcaac aaatcactat tgtcaacagc   4140
atagttagca taaacagtac catgcatacc cagcatctga agggaatatt catcaccaat   4200
aggaaaagtt ccaagaccca ttaaagtgct agcaacggga ataccagtga gttcaacaaa   4260
gcgcctcaat tcagcactgg aattcaaact gccaccgccg acgtagagaa cgggcttttg   4320
ggcctccatg atgagtctga caatgtgttc caattgggcc tcggcggggg gcctgggcag   4380
cctggcgagg taaccgggga ggttaacggg ctcgtcccaa ttaggcacgg cgagttgctg   4440
ctgaacgtct ttgggaatgt cgatgaggac cggaccgggg cggccggagg tggcgacgaa   4500
gaaagcctcg gcgacgacgc gggggatgtc gtcgacgtcg aggatgaggt agttgtgctt   4560
cgtgatggat ctgctcacct ccacgatcgg ggtttcttgg aaggcgtcgg tgccgatcat   4620
ccggcgggcg acctggccgg tgatggcgac gactgggacg ctgtccatta aagcgtcggc   4680
gaggccgctc acgaggttgg tggcgccggg gccggaggtg gcaatgcaga cgccggggag   4740
gccggaggaa cgcgcgtagc cttcggcggc gaagacgccg ccctgctcgt ggcgcgggag   4800
cacgttgcgg atggcggcgg agcgcgtgag cgcctggtgg atctccatcg acgcaccgcc   4860
ggggtacgcg aacaccgtcg tcacgccctg cctctccagc gcctccacaa ggatgtccgc   4920
gcccttgcga ggttcgccgg aggcgaaccg tgacacgaag ggctccgtgg tcggcgcttc   4980
cttggtgaag ggcgccgccg tggggggttt ggagatggaa catttgattt tgagagcgtg   5040
gttgggtttg gtgagggttt gatgagagag agggagggtg gatctagtaa tgcgtttggg   5100
gaaggtgggg tgtgaagagg aagaagagaa tcgggtggtt ctggaagcgg tggccgccat   5160
tgtgttgtgt ggcatggtta tacttcaaaa actgcacaac aagcctagag ttagtaccta   5220
aacagtaaat ttacaacaga gagcaaagac acatgcaaaa atttcagcca taaaaaaagt   5280
tataatagaa tttaaagcaa aagtttcatt ttttaaacat atatacaaac aaactggatt   5340
tgaaggaagg gattaattcc cctgctcaaa gtttgaattc ctattgtgac ctatactcga   5400
ataaaattga agcctaagga atgtatgaga aacaagaaaa caaaacaaaa ctacagacaa   5460
acaagtacaa ttacaaaatt cgctaaaatt ctgtaatcac caaaccccat ctcagtcagc   5520
acaaggccca aggtttattt tgaaataaaa aaaaagtgat tttatttctc ataagctaaa   5580
agaaagaaag gcaattatga aatgatttcg actagatctg aaagtccaac gcgtattccg   5640
cagatattaa agaaagagta gagtttcaca tggatcctag atggacccag ttgaggaaaa   5700
agcaaggcaa agcaaaccag aagtgcaaga tccgaaattg aaccacggaa tctaggattt   5760
ggtagaggga gaagaaaagt accttgagag gtagaagaga agagaagagc agagagatat   5820
atgaacgagt gtgtcttggt ctcaactctg aagcgatacg agtttagagg ggagcattga   5880
gttccaattt atagggaaac cgggtggcag gggtgagtta atgacggaaa agcccctaag   5940
taacgagatt ggattgtggg ttagattcaa ccgtttgcat ccgcggctta gattggggaa   6000
gtcagagtga atctcaaccg ttgactgagt tgaaaattga atgtagcaac caattgagcc   6060
aaccccagcc tttgcccttt gattttgatt tgtttgttgc atactttta tttgtcttct   6120
ggttctgact ctctttctct cgtttcaatg ccaggttgcc tactcccaca ccactcacaa   6180
gaagattcta ctgttagtat taaatatttt ttaatgtatt aaatgatgaa tgcttttgta   6240
aacagaacaa gactatgtct aataagtgtc ttgcaacatt ttttaagaaa ttaaaaaaaa   6300
tatatttatt atcaaaatca aatgtatgaa aaatcatgaa taatataatt ttatacattt   6360
ttttaaaaaa tcttttaatt tcttaattaa tatcttaaaa ataatgatta atatttaacc   6420
```

```
caaaataatt agtatgattg gtaaggaaga tatccatgtt atgtttggat gtgagtttga   6480
tctagagcaa agcttactag agtcgacctg caggtcgact cgacgtacga aaccaactgc   6540
gtttggggct ccagattaaa cgacgccgtt tcgttccttt cgcttcacgg cttaacgatg   6600
tcgtttctgt ctgtgcccaa aaaataaagg catttgttat ttgcaccaga tatttactaa   6660
gtgcacccta gtttgacaag taggcgataa ttacaaatag atgcggtgca aataataaat   6720
tttgaaggaa ataattacaa aagaacagaa cttatattta ctttatttta aaaaactaaa   6780
atgaaagaac aaaaaaagta aaaaatacaa aaaatgtgct ttaaccactt tcattatttg   6840
ttacagaaag tatgattcta ctcaaattga tctgttgtat ctggtgctgc cttgtcacac   6900
tggcgatttc aatcccctaa agatatggtg caaactgcga agtgatcaat atctgctcgg   6960
ttaatttaga ttaattaata atattcaacg tgatgtacca aaaaaagaca attttttgct   7020
ccattgacaa attaaacctc atcaaggtaa tttccaaacc tataagcaaa aaaatttcac   7080
attaattggc ccgcaatcct attagtctta ttatactaga gtaggaaaaa aaacaattac   7140
acaacttgtc ttattattct ctatgctaat gaatattttt cccttttgtt agaaatcagt   7200
gtttcctaat ttattgagta ttaattccac tcaccgcata tatttaccgt tgaataagaa   7260
aattttacac ataattcttt ttaagataaa taattttttt atactagatc ttatatgatt   7320
acgtgaagcc aagtgggtta tactaatgat atataatgtt tgatagtaat cagtttataa   7380
accaaatgca tggaaatgtt acgtggaagc acgtaaatta acaagcattg aagcaaatgc   7440
agccaccgca ccaaaaccac ccccacttcac ttccacgtac catattccat gcaactacaa   7500
caccctaaaa cttcaataaa tgcccccacc ttcacttcac ttcacccatc aatagcaagc   7560
ggccgcacaa tggcgactcg acagcgaact gccaccactg ttgtggtcga ggaccttccc   7620
aaggtcactc ttgaggccaa gtctgaacct gtgttccccg atatcaagac catcaaggat   7680
gccattcccg cgcactgctt ccagccctcg ctcgtcacct cattctacta cgtcttccgc   7740
gattttgcca tggtctctgc cctcgtctgg gctgctctca cctacatccc cagcatcccc   7800
gaccagaccc tccgcgtcgc agcttggatg gtctacggct tcgtccaggg tctgttctgc   7860
accggtgtct ggattctcgg ccatgagtgc ggccacggtg ctttctctct ccacggaaag   7920
gtcaacaatg tgaccggctg gttcctccac tcgttcctcc tcgtccccta cttcagctgg   7980
aagtactctc accaccgcca ccaccgcttc accggccaca tggatctcga catggctttc   8040
gtccccaaga ctgagcccaa gccctccaag tcgctcatga ttgctggcat tgacgtcgcc   8100
gagcttgttg aggacacccc cgctgctcag atggtcaagc tcatcttcca ccagcttttc   8160
ggatggcagg cgtacctctt cttcaacgct agctctggca agggcagcaa gcagtgggag   8220
cccaagactg gcctctccaa gtggttccga gtcagtcact tcgagcctac cagcgctgtc   8280
ttccgcccca acgaggccat cttcatcctc atctccgata tcggtcttgc tctaatggga   8340
actgctctgt actttgcttc caagcaagtt ggtgtttcga ccattctctt cctctacctt   8400
gttccctacc tgtgggttca ccactggctc gttgccatta cctacctcca ccaccaccac   8460
accgagctcc ctcactacac cgctgagggc tggacctacg tcaagggagc tctcgccact   8520
gtcgaccgtg agtttggctt catcggaaag cacctcttcc acggtatcat tgagaagcac   8580
gttgttcacc atctcttccc taagatcccc ttctacaagg ctgacgaggc caccgaggcc   8640
atcaagcccg tcattggcga ccactactgc cacgacgacc gaagcttcct gggccagctg   8700
tggaccatct tcggcacgct caagtacgtc gagcacgacc ctgcccgacc cggtgccatg   8760
```

```
cgatggaaca aggactaggc taggcggccg cgaagttaaa agcaatgttg tcacttgtcg   8820

tactaacaca tgatgtgata gtttatgcta gctagctata acataagctg tctctgagtg   8880

tgttgtatat taataaagat catcactggt gaatggtgat cgtgtacgta ccctacttag   8940

taggcaatgg aagcacttag agtgtgcttt gtgcatggcc ttgcctctgt tttgagactt   9000

ttgtaatgtt ttcgagttta aatctttgcc tttgc                              9035


<210> SEQ ID NO 64
<211> LENGTH: 5108
<212> TYPE: DNA
<213> ORGANISM: Artificial Sequence
<220> FEATURE:
<223> OTHER INFORMATION: the sequence of pKR270

<400> SEQUENCE: 64

ggccgcattt cgcaccaaat caatgaaagt aataatgaaa agtctgaata agaatactta     60

ggcttagatg cctttgttac ttgtgtaaaa taacttgagt catgtacctt tggcggaaac    120

agaataaata aaaggtgaaa ttccaatgct ctatgtataa gttagtaata cttaatgtgt    180

tctacggttg tttcaatatc atcaaactct aattgaaact ttagaaccac aaatctcaat    240

cttttcttaa tgaaatgaaa aatcttaatt gtaccatgtt tatgttaaac accttacaat    300

tggttggaga ggaggaccaa ccgatgggac aacattggga gaaagagatt caatggagat    360

ttggatagga gaacaacatt ctttttcact tcaatacaag atgagtgcaa cactaaggat    420

atgtatgaga ctttcagaag ctacgacaac atagatgagt gaggtggtga ttcctagcaa    480

gaaagacatt agaggaagcc aaaatcgaac aaggaagaca tcaagggcaa gagacaggac    540

catccatctc aggaaaagga gctttgggat agtccgagaa gttgtacaag aaatttttg     600

gagggtgagt gatgcattgc tggtgacttt aactcaatca aaattgagaa agaaagaaaa    660

gggagggggc tcacatgtga atagaaggga aacgggagaa ttttacagtt ttgatctaat    720

gggcatccca gctagtggta acatattcac catgtttaac cttcacgtac gtctagagga    780

tccccgggta ccgagctcga attcactggc cgtcgtttta caacgtcgtg actgggaaaa    840

ccctggcgtt acccaactta atcgccttgc agcacatccc cctttcgcca gctggcgtaa    900

tagcgaagag gcccgcaccg atcgcccttc ccaacagttg cgcagcctga atggcgaatg    960

gcgcctgatg cggtattttc tccttacgca tctgtgcggt atttcacacc gcatatggtg   1020

cactctcagt acaatctgct ctgatgccgc atagttaagc cagccccgac acccgccaac   1080

acccgctgac gcgccctgac gggcttgtct gctcccggca tccgcttaca gacaagctgt   1140

gaccgtctcc gggagctgca tgtgtcagag gttttcaccg tcatcaccga aacgcgcgag   1200

acgaaagggc ctcgtgatac gcctattttt ataggttaat gtcatgataa taatggtttc   1260

ttagacgtca ggtggcactt ttcggggaaa tgtgcgcgga acccctattt gtttattttt   1320

ctaaatacat tcaaatatgt atccgctcat gagacaataa ccctgataaa tgcttcaata   1380

atattgaaaa aggaagagta tgagtattca acatttccgt gtcgccctta ttcccttttt   1440

tgcggcattt tgccttcctg tttttgctca cccagaaacg ctggtgaaag taaaagatgc   1500

tgaagatcag ttgggtgcac gagtgggtta catcgaactg gatctcaaca gcggtaagat   1560

ccttgagagt tttcgccccg aagaacgttt tccaatgatg agcactttta aagttctgct   1620

atgtggcgcg gtattatccc gtattgacgc cgggcaagag caactcggtc gccgcataca   1680

ctattctcag aatgacttgg ttgagtactc accagtcaca gaaaagcatc ttacggatgg   1740

catgacagta agagaattat gcagtgctgc cataaccatg agtgataaca ctgcggccaa   1800
```

-continued

```
cttacttctg acaacgatcg gaggaccgaa ggagctaacc gctttttttgc acaacatggg   1860
ggatcatgta actcgccttg atcgttggga accggagctg aatgaagcca taccaaacga   1920
cgagcgtgac accacgatgc ctgtagcaat ggcaacaacg ttgcgcaaac tattaactgg   1980
cgaactactt actctagctt cccggcaaca attaatagac tggatggagg cggataaagt   2040
tgcaggacca cttctgcgct cggcccttcc ggctggctgg tttattgctg ataaatctgg   2100
agccggtgag cgtgggtctc gcggtatcat tgcagcactg gggccagatg gtaagccctc   2160
ccgtatcgta gttatctaca cgacggggag tcaggcaact atggatgaac gaaatagaca   2220
gatcgctgag ataggtgcct cactgattaa gcattggtaa ctgtcagacc aagtttactc   2280
atatatactt tagattgatt taaaacttca tttttaattt aaaaggatct aggtgaagat   2340
cctttttgat aatctcatga ccaaaatccc ttaacgtgag ttttcgttcc actgagcgtc   2400
agaccccgta gaaaagatca aaggatcttc ttgagatcct ttttttctgc gcgtaatctg   2460
ctgcttgcaa acaaaaaaac caccgctacc agcggtggtt tgtttgccgg atcaagagct   2520
accaactctt tttccgaagg taactggctt cagcagagcg cagataccaa atactgtcct   2580
tctagtgtag ccgtagttag gccaccactt caagaactct gtagcaccgc ctacatacct   2640
cgctctgcta atcctgttac cagtggctgc tgccagtggc gataagtcgt gtcttaccgg   2700
gttggactca agacgatagt taccggataa ggcgcagcgg tcgggctgaa cggggggttc   2760
gtgcacacag cccagcttgg agcgaacgac ctacaccgaa ctgagatacc tacagcgtga   2820
gctatgagaa agcgccacgc ttcccgaagg gagaaaggcg gacaggtatc cggtaagcgg   2880
cagggtcgga acaggagagc gcacgaggga gcttccaggg ggaaacgcct ggtatcttta   2940
tagtcctgtc gggtttcgcc acctctgact tgagcgtcga tttttgtgat gctcgtcagg   3000
ggggcggagc ctatggaaaa acgccagcaa cgcggccttt ttacggttcc tggccttttg   3060
ctggcctttt gctcacatgt tctttcctgc gttatcccct gattctgtgg ataaccgtat   3120
taccgccttt gagtgagctg ataccgctcg ccgcagccga acgaccgagc gcagcgagtc   3180
agtgagcgag gaagcggaag agcgcccaat acgcaaaccg cctctccccg cgcgttggcc   3240
gattcattaa tgcagctggc acgacaggtt tcccgactgg aaagcgggca gtgagcgcaa   3300
cgcaattaat gtgagttagc tcactcatta ggcaccccag gctttacact ttatgcttcc   3360
ggctcgtatg ttgtgtggaa ttgtgagcgg ataacaattt cacacaggaa acagctatga   3420
ccatgattac gccaagcttg catgcctgca ggctagccta agtacgtact caaaatgcca   3480
acaaataaaa aaaaagttgc tttaataatg ccaaaacaaa ttaataaaac acttacaaca   3540
ccggattttt tttaattaaa atgtgccatt taggataaat agttaatatt tttaataatt   3600
atttaaaaag ccgtatctac taaaatgatt tttatttggt tgaaaatatt aatatgttta   3660
aatcaacaca atctatcaaa attaaactaa aaaaaaaata agtgtacgtg gttaacatta   3720
gtacagtaat ataagaggaa aatgagaaat taagaaattg aaagcgagtc taatttttaa   3780
attatgaacc tgcatatata aaaggaaaga aagaatccag gaagaaaaga aatgaaacca   3840
tgcatggtcc cctcgtcatc acgagtttct gccatttgca atagaaacac tgaaacacct   3900
ttctctttgt cacttaattg agatgccgaa gccacctcac accatgaact tcatgaggtg   3960
tagcacccaa ggcttccata gccatgcata ctgaagaatg tctcaagctc agcaccctac   4020
ttctgtgacg tgtccctcat tcaccttcct ctcttcccta taaataacca cgcctcaggt   4080
tctccgcttc acaactcaaa cattctctcc attggtcctt aaacactcat cagtcatcac   4140
```

-continued

```
cgcggccgca tggagtcgat tgcgccattc ctcccatcaa agatgccgca agatctgttt   4200

atggaccttg ccaccgctat cggtgtccgg gccgcgccct atgtcgatcc tctcgaggcc   4260

gcgctggtgg cccaggccga gaagtacatc cccacgattg tccatcacac gcgtgggttc   4320

ctggtcgcgg tggagtcgcc tttggcccgt gagctgccgt tgatgaaccc gttccacgtg   4380

ctgttgatcg tgctcgctta tttggtcacg gtctttgtgg gcatgcagat catgaagaac   4440

tttgagcggt tcgaggtcaa gacgttttcg ctcctgcaca acttttgtct ggtctcgatc   4500

agcgcctaca tgtgcggtgg gatcctgtac gaggcttatc aggccaacta tggactgttt   4560

gagaacgctg ctgatcatac cttcaagggt cttcctatgg ccaagatgat ctggctcttc   4620

tacttctcca agatcatgga gtttgtcgac accatgatca tggtcctcaa gaagaacaac   4680

cgccagatct ccttcttgca cgtttaccac cacagctcca tcttcaccat ctggtggttg   4740

gtcacctttg ttgcacccaa cggtgaagcc tacttctctg ctgcgttgaa ctcgttcatc   4800

catgtgatca tgtacggcta ctacttcttg tcggccttgg gcttcaagca ggtgtcgttc   4860

atcaagttct acatcacgcg ctcgcagatg acacagttct gcatgatgtc ggtccagtct   4920

tcctgggaca tgtacgccat gaaggtcctt ggccgccccg gatacccctt cttcatcacg   4980

gctctgcttt ggttctacat gtggaccatg ctcggtctct tctacaactt ttacagaaag   5040

aacgccaagt tggccaagca ggccaaggcc gacgctgcca aggagaaggc aaggaagttg   5100

cagtaagc                                                            5108
```

<210> SEQ ID NO 65
<211> LENGTH: 792
<212> TYPE: DNA
<213> ORGANISM: Artificial Sequence
<220> FEATURE:
<223> OTHER INFORMATION: IgD9e: synthetic delta-9 elongase derived from Isochrysis galbana codon-optimized for expression in Yarrowia lipolytica

<400> SEQUENCE: 65

```
atggctctgg ccaacgacgc tggcgagcga atctgggctg ccgtcaccga tcccgaaatc     60

ctcattggca ccttctccta cctgctcctg aagcctctcc tgcgaaactc tggtctcgtg    120

gacgagaaga aaggagccta ccgaacctcc atgatctggt acaacgtcct cctggctctc    180

ttctctgccc tgtccttcta cgtgactgcc accgctctcg gctgggacta cggtactgga    240

gcctggctgc gaagacagac cggtgatact ccccagcctc tctttcagtg tccctctcct    300

gtctgggact ccaagctgtt cacctggact gccaaggcct tctactattc taagtacgtg    360

gagtacctcg acaccgcttg gctggtcctc aagggcaagc gagtgtcctt tctgcaggcc    420

ttccatcact ttggagctcc ctgggacgtc tacctcggca ttcgactgca caacgagggt    480

gtgtggatct tcatgttctt taactcgttc attcacacca tcatgtacac ctactatgga    540

ctgactgccg ctggctacaa gttcaaggcc aagcctctga tcactgccat gcagatttgc    600

cagttcgtcg gtggctttct cctggtctgg gactacatca acgttccctg cttcaactct    660

gacaagggca agctgttctc ctgggctttc aactacgcct acgtcggatc tgtctttctc    720

ctgttctgtc acttctttta ccaggacaac ctggccacca agaaatccgc taaggctggt    780

aagcagcttt ag                                                        792
```

<210> SEQ ID NO 66
<211> LENGTH: 101
<212> TYPE: DNA
<213> ORGANISM: Artificial Sequence
<220> FEATURE:
<223> OTHER INFORMATION: primer IL3-1A

<400> SEQUENCE: 66
gccaacgacg ctggcgagcg aatctgggct gccgtcaccg atcccgaaat cctcattggc 60
accttctcct acctgctcct gaagcctctc ctgcgaaact c 101

<210> SEQ ID NO 67
<211> LENGTH: 101
<212> TYPE: DNA
<213> ORGANISM: Artificial Sequence
<220> FEATURE:
<223> OTHER INFORMATION: primer IL3-1B

<400> SEQUENCE: 67
accagagttt cgcaggagag gcttcaggag caggtaggag aaggtgccaa tgaggatttc 60
gggatcggtg acggcagccc agattcgctc gccagcgtcg t 101

<210> SEQ ID NO 68
<211> LENGTH: 100
<212> TYPE: DNA
<213> ORGANISM: Artificial Sequence
<220> FEATURE:
<223> OTHER INFORMATION: primer IL3-2A

<400> SEQUENCE: 68
tggtctcgtg gacgagaaga aaggagccta ccgaacctcc atgatctggt acaacgtcct 60
cctggctctc ttctctgccc tgtccttcta cgtgactgcc 100

<210> SEQ ID NO 69
<211> LENGTH: 100
<212> TYPE: DNA
<213> ORGANISM: Artificial Sequence
<220> FEATURE:
<223> OTHER INFORMATION: primer IL3-2B

<400> SEQUENCE: 69
cggtggcagt cacgtagaag gacagggcag agaagagagc caggaggacg ttgtaccaga 60
tcatggaggt tcggtaggct cctttcttct cgtccacgag 100

<210> SEQ ID NO 70
<211> LENGTH: 100
<212> TYPE: DNA
<213> ORGANISM: Artificial Sequence
<220> FEATURE:
<223> OTHER INFORMATION: primer IL3-3A

<400> SEQUENCE: 70
accgctctcg gctgggacta cggtactgga gcctggctgc gaagacagac cggtgatact 60
ccccagcctc tctttcagtg tccctctcct gtctgggact 100

<210> SEQ ID NO 71
<211> LENGTH: 100
<212> TYPE: DNA
<213> ORGANISM: Artificial Sequence
<220> FEATURE:
<223> OTHER INFORMATION: primer IL3-3B

<400> SEQUENCE: 71
ttggagtccc agacaggaga gggacactga aagagaggct ggggagtatc accggtctgt 60
cttcgcagcc aggctccagt accgtagtcc cagccgagag 100

<210> SEQ ID NO 72
<211> LENGTH: 100
<212> TYPE: DNA
<213> ORGANISM: Artificial Sequence
<220> FEATURE:
<223> OTHER INFORMATION: primer IL3-4A

<400> SEQUENCE: 72
ccaagctgtt cacctggact gccaaggcct tctactattc taagtacgtg gagtacctcg 60
acaccgcttg gctggtcctc aagggcaagc gagtgtcctt 100

<210> SEQ ID NO 73
<211> LENGTH: 100
<212> TYPE: DNA
<213> ORGANISM: Artificial Sequence
<220> FEATURE:
<223> OTHER INFORMATION: primer IL3-4B

<400> SEQUENCE: 73
cagaaaggac actcgcttgc ccttgaggac cagccaagcg gtgtcgaggt actccacgta 60
cttagaatag tagaaggcct tggcagtcca ggtgaacagc 100

<210> SEQ ID NO 74
<211> LENGTH: 89
<212> TYPE: DNA
<213> ORGANISM: Artificial Sequence
<220> FEATURE:
<223> OTHER INFORMATION: primer IL3-5A

<400> SEQUENCE: 74
ttccatcact ttggagctcc ctgggacgtc tacctcggca ttcgactgca caacgagggt 60
gtgtggatct tcatgttctt taactcgtt 89

<210> SEQ ID NO 75
<211> LENGTH: 89
<212> TYPE: DNA
<213> ORGANISM: Artificial Sequence
<220> FEATURE:
<223> OTHER INFORMATION: primer IL3-5B

<400> SEQUENCE: 75
aatgaacgag ttaaagaaca tgaagatcca cacaccctcg ttgtgcagtc gaatgccgag 60
gtagacgtcc cagggagctc caaagtgat 89

<210> SEQ ID NO 76
<211> LENGTH: 91
<212> TYPE: DNA
<213> ORGANISM: Artificial Sequence
<220> FEATURE:
<223> OTHER INFORMATION: primer IL3-6A

<400> SEQUENCE: 76
cattcacacc atcatgtaca cctactatgg actgactgcc gctggctaca agttcaaggc 60
caagcctctg atcactgcca tgcagatttg c 91

<210> SEQ ID NO 77
<211> LENGTH: 91
<212> TYPE: DNA
<213> ORGANISM: Artificial Sequence
<220> FEATURE:
<223> OTHER INFORMATION: primer IL3-6B

<400> SEQUENCE: 77
actggcaaat ctgcatggca gtgatcagag gcttggcctt gaacttgtag ccagcggcag 60
tcagtccata gtaggtgtac atgatggtgt g 91

<210> SEQ ID NO 78
<211> LENGTH: 94
<212> TYPE: DNA
<213> ORGANISM: Artificial Sequence
<220> FEATURE:
<223> OTHER INFORMATION: primer IL3-7A

<400> SEQUENCE: 78
cagttcgtcg gtggctttct cctggtctgg gactacatca acgttccctg cttcaactct 60
gacaagggca agctgttctc ctgggctttc aact 94

<210> SEQ ID NO 79
<211> LENGTH: 94
<212> TYPE: DNA
<213> ORGANISM: Artificial Sequence
<220> FEATURE:
<223> OTHER INFORMATION: primer IL3-7B

<400> SEQUENCE: 79
gcgtagttga aagcccagga gaacagcttg cccttgtcag agttgaagca gggaacgttg 60
atgtagtccc agaccaggag aaagccaccg acga 94

<210> SEQ ID NO 80
<211> LENGTH: 91
<212> TYPE: DNA
<213> ORGANISM: Artificial Sequence
<220> FEATURE:
<223> OTHER INFORMATION: primer IL3-8A

<400> SEQUENCE: 80
acgcctacgt cggatctgtc tttctcctgt tctgtcactt cttttaccag gacaacctgg 60
ccaccaagaa atccgctaag gctggtaagc a 91

<210> SEQ ID NO 81
<211> LENGTH: 91
<212> TYPE: DNA
<213> ORGANISM: Artificial Sequence
<220> FEATURE:
<223> OTHER INFORMATION: primer IL3-8B

<400> SEQUENCE: 81
aagctgctta ccagccttag cggatttctt ggtggccagg ttgtcctggt aaaagaagtg 60
acagaacagg agaaagacag atccgacgta g 91

<210> SEQ ID NO 82
<211> LENGTH: 41
<212> TYPE: DNA
<213> ORGANISM: Artificial Sequence
<220> FEATURE:
<223> OTHER INFORMATION: primer IL3-1F

<400> SEQUENCE: 82
tttccatggc tctggccaac gacgctggcg agcgaatctg g 41

<210> SEQ ID NO 83
<211> LENGTH: 36
<212> TYPE: DNA
<213> ORGANISM: Artificial Sequence
<220> FEATURE:

<223> OTHER INFORMATION: Primer IL3-4R

<400> SEQUENCE: 83
tttctgcaga aaggacactc gcttgccctt gaggac 36

<210> SEQ ID NO 84
<211> LENGTH: 41
<212> TYPE: DNA
<213> ORGANISM: Artificial Sequence
<220> FEATURE:
<223> OTHER INFORMATION: primer IL3-5F

<400> SEQUENCE: 84
tttctgcagg ccttccatca ctttggagct ccctgggacg t 41

<210> SEQ ID NO 85
<211> LENGTH: 42
<212> TYPE: DNA
<213> ORGANISM: Artificial Sequence
<220> FEATURE:
<223> OTHER INFORMATION: primer IL3-8R

<400> SEQUENCE: 85
tttgcggccg ctaaagctgc ttaccagcct tagcggattt ct 42

<210> SEQ ID NO 86
<211> LENGTH: 417
<212> TYPE: DNA
<213> ORGANISM: Artificial Sequence
<220> FEATURE:
<223> OTHER INFORMATION: 417 bp NcoI/PstI fragment pT9(1-4)

<400> SEQUENCE: 86
catggctctg gccaacgacg ctggcgagcg aatctgggct gccgtcaccg atcccgaaat 60
cctcattggc accttctcct acctgctcct gaagcctctc ctgcgaaact ctggtctcgt 120
ggacgagaag aaaggagcct accgaacctc catgatctgg tacaacgtcc tcctggctct 180
cttctctgcc ctgtccttct acgtgactgc caccgctctc ggctgggact acggtactgg 240
agcctggctg cgaagacaga ccggtgatac tccccagcct ctctttcagt gtccctctcc 300
tgtctgggac tccaagctgt tcacctggac tgccaaggcc ttctactatt ctaagtacgt 360
ggagtacctc gacaccgctt ggctggtcct caagggcaag cgagtgtcct ttctgca 417

<210> SEQ ID NO 87
<211> LENGTH: 377
<212> TYPE: DNA
<213> ORGANISM: Artificial Sequence
<220> FEATURE:
<223> OTHER INFORMATION: 377 bp PstI/Not1 fragment pT9(5-8)

<400> SEQUENCE: 87
ggccttccat cactttggag ctccctggga cgtctacctc ggcattcgac tgcacaacga 60
gggtgtgtgg atcttcatgt tctttaactc gttcattcac accatcatgt acacctacta 120
tggactgact gccgctggct acaagttcaa ggccaagcct ctgatcactg ccatgcagat 180
ttgccagttc gtcggtggct ttctcctggt ctgggactac atcaacgttc cctgcttcaa 240
ctctgacaag ggcaagctgt tctcctgggc tttcaactac gcctacgtcg gatctgtctt 300
tctcctgttc tgtcacttct tttaccagga caacctggcc accaagaaat ccgctaaggc 360
tggtaagcag ctttagc 377

<210> SEQ ID NO 88
<211> LENGTH: 1341
<212> TYPE: DNA
<213> ORGANISM: Mortierella alpina

<400> SEQUENCE: 88
atgggaacgg accaaggaaa aaccttcacc tgggaagagc tggcggccca taacaccaag 60
gacgacctac tcttggccat ccgcggcagg gtgtacgatg tcacaaagtt cttgagccgc 120
catcctggtg gagtggacac tctcctgctc ggagctggcc gagatgttac tccggtcttt 180
gagatgtatc acgcgtttgg ggctgcagat gccattatga agaagtacta tgtcggtaca 240
ctggtctcga atgagctgcc catcttcccg gagccaacgg tgttccacaa aaccatcaag 300
acgagagtcg agggctactt tacggatcgg aacattgatc ccaagaatag accagagatc 360
tggggacgat acgctcttat ctttggatcc ttgatcgctt cctactacgc gcagctcttt 420
gtgcctttcg ttgtcgaacg cacatggctt caggtggtgt ttgcaatcat catgggattt 480
gcgtgcgcac aagtcggact caaccctctt catgatgcgt ctcacttttc agtgacccac 540
aaccccactg tctggaagat tctgggagcc acgcacgact tttcaacgg agcatcgtac 600 ctggtgtgga tgtaccaaca tatgctcggc catcacccct acaccaacat tgctggagca 660
gatcccgacg tgtcgacgtc tgagcccgat gttcgtcgta tcaagcccaa ccaaaagtgg 720
tttgtcaacc acatcaacca gcacatgttt gttcctttcc tgtacggact gctggcgttc 780
aaggtgcgca ttcaggacat caacattttg tactttgtca agaccaatga cgctattcgt 840
gtcaatccca tctcgacatg gcacactgtg atgttctggg gcggcaaggc tttctttgtc 900
tggtatcgcc tgattgttcc cctgcagtat ctgcccctgg gcaaggtgct gctcttgttc 960
acggtcgcgg acatggtgtc gtcttactgg ctggcgctga ccttccaggc gaaccacgtt 1020
gttgaggaag ttcagtggcc gttgcctgac gagaacggga tcatccaaaa ggactgggca 1080
gctatgcagg tcgagactac gcaggattac gcacacgatt cgcacctctg gaccagcatc 1140
actggcagct tgaactacca ggctgtgcac catctgttcc ccaacgtgtc gcagcaccat 1200
tatcccgata ttctggccat catcaagaac acctgcagcg agtacaaggt tccatacctt 1260
gtcaaggata cgttttggca agcatttgct tcacatttgg agcacttgcg tgttcttgga 1320
ctccgtccca aggaagagta g 1341

<210> SEQ ID NO 89
<211> LENGTH: 9472
<212> TYPE: DNA
<213> ORGANISM: Artificial Sequence
<220> FEATURE:
<223> OTHER INFORMATION: sequence of pDMW263

<400> SEQUENCE: 89
catggcatgg atggtacgtc ctgtagaaac cccaacccgt gaaatcaaaa aactcgacgg 60
cctgtgggca ttcagtctgg atcgcgaaaa ctgtggaatt gatcagcgtt ggtgggaaag 120
cgcgttacaa gaaagccggg caattgctgt gccaggcagt tttaacgatc agttcgccga 180
tgcagatatt cgtaattatg cgggcaacgt ctggtatcag cgcgaagtct ttataccgaa 240
aggttgggca ggccagcgta tcgtgctgcg tttcgatgcg gtcactcatt acggcaaagt 300
gtgggtcaat aatcaggaag tgatggagca tcagggcggc tatacgccat ttgaagccga 360
tgtcacgccg tatgttattg ccgggaaaag tgtacgtatc accgtttgtg tgaacaacga 420
actgaactgg cagactatcc cgccgggaat ggtgattacc gacgaaaacg gcaagaaaaa 480

```
gcagtcttac ttccatgatt tctttaacta tgccgggatc catcgcagcg taatgctcta    540
caccacgccg aacacctggg tggacgatat caccgtggtg acgcatgtcg cgcaagactg    600
taaccacgcg tctgttgact ggcaggtggt ggccaatggt gatgtcagcg ttgaactgcg    660
tgatgcggat caacaggtgg ttgcaactgg acaaggcact agcgggactt tgcaagtggt    720
gaatccgcac ctctggcaac cgggtgaagg ttatctctat gaactgtgcg tcacagccaa    780
aagccagaca gagtgtgata tctacccgct tcgcgtcggc atccggtcag tggcagtgaa    840
gggcgaacag ttcctgatta accacaaacc gttctacttt actggctttg gtcgtcatga    900
agatgcggac ttacgtggca aaggattcga taacgtgctg atggtgcacg accacgcatt    960
aatggactgg attggggcca actcctaccg tacctcgcat tacccttacg ctgaagagat   1020
gctcgactgg gcagatgaac atggcatcgt ggtgattgat gaaactgctg ctgtcggctt   1080
taacctctct ttaggcattg gtttcgaagc gggcaacaag ccgaaagaac tgtacagcga   1140
agaggcagtc aacggggaaa ctcagcaagc gcacttacag gcgattaaag agctgatagc   1200
gcgtgacaaa aaccacccaa gcgtggtgat gtggagtatt gccaacgaac cggatacccg   1260
tccgcaagtg cacgggaata tttcgccact ggcggaagca acgcgtaaac tcgacccgac   1320
gcgtccgatc acctgcgtca atgtaatgtt ctgcgacgct cacaccgata ccatcagcga   1380
tctctttgat gtgctgtgcc tgaaccgtta ttacggatgg tatgtccaaa gcggcgattt   1440
ggaaacggca gagaaggtac tggaaaaaga acttctggcc tggcaggaga aactgcatca   1500
gccgattatc atcaccgaat acggcgtgga tacgttagcc gggctgcact caatgtacac   1560
cgacatgtgg agtgaagagt atcagtgtgc atggctggat atgtatcacc gcgtctttga   1620
tcgcgtcagc gccgtcgtcg gtgaacaggt atggaatttc gccgattttg cgacctcgca   1680
aggcatattg cgcgttggcg gtaacaagaa agggatcttc actcgcgacc gcaaaccgaa   1740
gtcggcggct tttctgctgc aaaaacgctg gactggcatg aacttcggtg aaaaaccgca   1800
gcagggaggc aaacaatgat taattaacta gagcggccgc caccgcggcc cgagattccg   1860
gcctcttcgg ccgccaagcg acccgggtgg acgtctagag gtacctagca attaacagat   1920
agtttgccgg tgataattct cttaacctcc cacactcctt tgacataacg atttatgtaa   1980
cgaaactgaa atttgaccag atattgtgtc cgcggtggag ctccagcttt tgttcccttt   2040
agtgagggtt aatttcgagc ttggcgtaat catggtcata gctgtttcct gtgtgaaatt   2100
gttatccgct cacaattcca cacaacatac gagccggaag cataaagtgt aaagcctggg   2160
gtgcctaatg agtgagctaa ctcacattaa ttgcgttgcg ctcactgccc gctttccagt   2220
cgggaaacct gtcgtgccag ctgcattaat gaatcggcca acgcgcgggg agaggcggtt   2280
tgcgtattgg gcgctcttcc gcttcctcgc tcactgactc gctgcgctcg gtcgttcggc   2340
tgcggcgagc ggtatcagct cactcaaagg cggtaatacg gttatccaca gaatcagggg   2400
ataacgcagg aaagaacatg tgagcaaaag gccagcaaaa ggccaggaac cgtaaaaagg   2460
ccgcgttgct ggcgtttttc cataggctcc gcccccctga cgagcatcac aaaaatcgac   2520
gctcaagtca gaggtggcga aacccgacag gactataaag ataccaggcg tttccccctg   2580
gaagctccct cgtgcgctct cctgttccga ccctgccgct taccggatac ctgtccgcct   2640
ttctcccttc gggaagcgtg gcgctttctc atagctcacg ctgtaggtat ctcagttcgg   2700
tgtaggtcgt tcgctccaag ctgggctgtg tgcacgaacc ccccgttcag cccgaccgct   2760
gcgccttatc cggtaactat cgtcttgagt ccaacccggt aagacacgac ttatcgccac   2820
tggcagcagc cactggtaac aggattagca gagcgaggta tgtaggcggt gctacagagt   2880
```

```
tcttgaagtg gtggcctaac tacggctaca ctagaaggac agtatttggt atctgcgctc   2940
tgctgaagcc agttaccttc ggaaaaagag ttggtagctc ttgatccggc aaacaaacca   3000
ccgctggtag cggtggtttt tttgtttgca agcagcagat tacgcgcaga aaaaaaggat   3060
ctcaagaaga tcctttgatc ttttctacgg ggtctgacgc tcagtggaac gaaaactcac   3120
gttaagggat tttggtcatg agattatcaa aaaggatctt cacctagatc cttttaaatt   3180
aaaaatgaag ttttaaatca atctaaagta tatatgagta aacttggtct gacagttacc   3240
aatgcttaat cagtgaggca cctatctcag cgatctgtct atttcgttca tccatagttg   3300
cctgactccc cgtcgtgtag ataactacga tacgggaggg cttaccatct ggccccagtg   3360
ctgcaatgat accgcgagac ccacgctcac cggctccaga tttatcagca ataaaccagc   3420
cagccggaag ggccgagcgc agaagtggtc ctgcaacttt atccgcctcc atccagtcta   3480
ttaattgttg ccgggaagct agagtaagta gttcgccagt taatagtttg cgcaacgttg   3540
ttgccattgc tacaggcatc gtggtgtcac gctcgtcgtt tggtatggct tcattcagct   3600
ccggttccca acgatcaagg cgagttacat gatcccccat gttgtgcaaa aaagcggtta   3660
gctccttcgg tcctccgatc gttgtcagaa gtaagttggc cgcagtgtta tcactcatgg   3720
ttatggcagc actgcataat tctcttactg tcatgccatc cgtaagatgc ttttctgtga   3780
ctggtgagta ctcaaccaag tcattctgag aatagtgtat gcggcgaccg agttgctctt   3840
gcccggcgtc aatacgggat aataccgcgc cacatagcag aactttaaaa gtgctcatca   3900
ttggaaaacg ttcttcgggg cgaaaactct caaggatctt accgctgttg agatccagtt   3960
cgatgtaacc cactcgtgca cccaactgat cttcagcatc ttttactttc accagcgttt   4020
ctgggtgagc aaaaacagga aggcaaaatg ccgcaaaaaa gggaataagg gcgacacgga   4080
aatgttgaat actcatactc ttcctttttc aatattattg aagcatttat cagggttatt   4140
gtctcatgag cggatacata tttgaatgta tttagaaaaa taaacaaata ggggttccgc   4200
gcacatttcc ccgaaaagtg ccacctgacg cgccctgtag cggcgcatta agcgcggcgg   4260
gtgtggtggt tacgcgcagc gtgaccgcta cacttgccag cgccctagcg cccgctcctt   4320
tcgctttctt cccttccttt ctcgccacgt tcgccggctt tccccgtcaa gctctaaatc   4380
gggggctccc tttagggttc cgatttagtg ctttacggca cctcgacccc aaaaaacttg   4440
attagggtga tggttcacgt agtgggccat cgccctgata gacggttttt cgccctttga   4500
cgttggagtc cacgttcttt aatagtggac tcttgttcca aactggaaca acactcaacc   4560
ctatctcggt ctattctttt gatttataag ggattttgcc gatttcggcc tattggttaa   4620
aaaatgagct gatttaacaa aaatttaacg cgaattttaa caaaatatta acgcttacaa   4680
tttccattcg ccattcaggc tgcgcaactg ttgggaaggg cgatcggtgc gggcctcttc   4740
gctattacgc cagctggcga aagggggatg tgctgcaagg cgattaagtt gggtaacgcc   4800
agggttttcc cagtcacgac gttgtaaaac gacggccagt gaattgtaat acgactcact   4860
atagggcgaa ttgggtaccg ggcccccccct cgaggtcgat ggtgtcgata agcttgatat   4920
cgaattcatg tcacacaaac cgatcttcgc ctcaaggaaa cctaattcta catccgagag   4980
actgccgaga tccagtctac actgattaat tttcgggcca ataatttaaa aaaatcgtgt   5040
tatataatat tatatgtatt atatatatac atcatgatga tactgacagt catgtcccat   5100
tgctaaatag acagactcca tctgccgcct ccaactgatg ttctcaatat ttaaggggtc   5160
atctcgcatt gtttaataat aaacagactc catctaccgc ctccaaatga tgttctcaaa   5220
```

```
atatattgta tgaacttatt tttattactt agtattatta gacaacttac ttgctttatg   5280
aaaaacactt cctatttagg aaacaattta taatggcagt tcgttcattt aacaatttat   5340
gtagaataaa tgttataaat gcgtatggga aatcttaaat atggatagca taaatgatat   5400
ctgcattgcc taattcgaaa tcaacagcaa cgaaaaaaat cccttgtaca acataaatag   5460
tcatcgagaa atatcaacta tcaaagaaca gctattcaca cgttactatt gagattatta   5520
ttggacgaga atcacacact caactgtctt tctctcttct agaaatacag gtacaagtat   5580
gtactattct cattgttcat acttctagtc atttcatccc acatattcct tggatttctc   5640
tccaatgaat gacattctat cttgcaaatt caacaattat aataagatat accaaagtag   5700
cggtatagtg gcaatcaaaa agcttctctg gtgtgcttct cgtatttatt tttattctaa   5760
tgatccatta aaggtatata tttatttctt gttatataat ccttttgttt attacatggg   5820
ctggatacat aaaggtattt tgatttaatt ttttgcttaa attcaatccc ccctcgttca   5880
gtgtcaactg taatggtagg aaattaccat acttttgaag aagcaaaaaa aatgaaagaa   5940
aaaaaaaatc gtatttccag gttagacgtt ccgcagaatc tagaatgcgg tatgcggtac   6000
attgttcttc gaacgtaaaa gttgcgctcc ctgagatatt gtacattttt gcttttacaa   6060
gtacaagtac atcgtacaac tatgtactac tgttgatgca tccacaacag tttgttttgt   6120
tttttttgt ttttttttt tctaatgatt cattaccgct atgtatacct acttgtactt   6180
gtagtaagcc gggttattgg cgttcaatta atcatagact tatgaatctg cacggtgtgc   6240
gctgcgagtt acttttagct tatgcatgct acttgggtgt aatattggga tctgttcgga   6300
aatcaacgga tgctcaaccg atttcgacag taataatttg aatcgaatcg gagcctaaaa   6360
tgaacccgag tatatctcat aaaattctcg gtgagaggtc tgtgactgtc agtacaaggt   6420
gccttcatta tgccctcaac cttaccatac ctcactgaat gtagtgtacc tctaaaaatg   6480
aaatacagtg ccaaaagcca aggcactgag ctcgtctaac ggacttgata tacaaccaat   6540
taaaacaaat gaaaagaaat acagttcttt gtatcatttg taacaattac cctgtacaaa   6600
ctaaggtatt gaaatcccac aatattccca aagtccaccc ctttccaaat tgtcatgcct   6660
acaactcata taccaagcac taacctacca aacaccacta aaaccccaca aaatatatct   6720
taccgaatat acagtaacaa gctaccacca cactcgttgg gtgcagtcgc cagcttaaag   6780
atatctatcc acatcagcca caactccctt cctttaataa accgactaca cccttggcta   6840
ttgaggttat gagtgaatat actgtagaca agacactttc aagaagactg tttccaaaac   6900
gtaccactgt cctccactac aaacacaccc aatctgcttc ttctagtcaa ggttgctaca   6960
ccggtaaatt ataaatcatc atttcattag cagggcaggg cccttttat agagtcttat   7020
acactagcgg accctgccgg tagaccaacc cgcaggcgcg tcagtttgct ccttccatca   7080
atgcgtcgta gaaacgactt actccttctt gagcagctcc ttgaccttgt tggcaacaag   7140
tctccgacct cggaggtgga ggaagagcct ccgatatcgg cggtagtgat accagcctcg   7200
acggactcct tgacggcagc ctcaacagcg tcaccggcgg gcttcatgtt aagagagaac   7260
ttgagcatca tggcggcaga cagaatggtg gcaatggggt tgaccttctg cttgccgaga   7320
tcgggggcag atccgtgaca gggctcgtac agaccgaacg cctcgttggt gtcgggcaga   7380
gaagccagag aggcggaggg cagcagaccc agagaaccgg ggatgacgga ggcctcgtcg   7440
gagatgatat cgccaaacat gttggtggtg atgatgatac cattcatctt ggagggctgc   7500
ttgatgagga tcatggcggc cgagtcgatc agctggtggt tgagctcgag ctgggggaat   7560
tcgtccttga ggactcgagt gacagtcttt cgccaaagtc gagaggaggc cagcacgttg   7620
```

```
gccttgtcaa gagaccacac gggaagaggg gggttgtgct gaagggccag gaaggcggcc   7680

attcgggcaa ttcgctcaac ctcaggaacg gagtaggtct cggtgtcgga agcgacgcca   7740

gatccgtcat cctcctttcg ctctccaaag tagatacctc cgacgagctc tcggacaatg   7800

atgaagtcgg tgccctcaac gtttcggatg ggggagagat cggcgagctt gggcgacagc   7860

agctggcagg gtcgcaggtt ggcgtacagg ttcaggtcct ttcgcagctt gaggagaccc   7920

tgctcgggtc gcacgtcggt tcgtccgtcg ggagtggtcc atacggtgtt ggcagcgcct   7980

ccgacagcac cgagcataat agagtcagcc tttcggcaga tgtcgagagt agcgtcggtg   8040

atgggctcgc cctccttctc aatggcagct cctccaatga gtcggtcctc aaacacaaac   8100

tcggtgccgg aggcctcagc aacagacttg agcaccttga cggcctcggc aatcacctcg   8160

gggccacaga agtcgccgcc gagaagaaca atcttcttgg agtcagtctt ggtcttctta   8220

gtttcgggtt ccattgtgga tgtgtgtggt tgtatgtgtg atgtggtgtg tggagtgaaa   8280

atctgtggct ggcaaacgct cttgtatata tacgcacttt tgcccgtgct atgtggaaga   8340

ctaaacctcc gaagattgtg actcaggtag tgcggtatcg gctagggacc caaaccttgt   8400

cgatgccgat agcgctatcg aacgtacccc agccggccgg gagtatgtcg gaggggacat   8460

acgagatcgt caagggtttg tggccaactg gtaaataaat gatgtcgacg tttaaacagt   8520

gtacgcagat ctactataga ggaacattta aattgccccg gagaagacgg ccaggccgcc   8580

tagatgacaa attcaacaac tcacagctga ctttctgcca ttgccactag gggggggcct   8640

ttttatatgg ccaagccaag ctctccacgt cggttgggct gcacccaaca ataaatgggt   8700

agggttgcac caacaaaggg atgggatggg gggtagaaga tacgaggata acggggctca   8760

atggcacaaa taagaacgaa tactgccatt aagactcgtg atccagcgac tgacaccatt   8820

gcatcatcta agggcctcaa aactacctcg gaactgctgc gctgatctgg acaccacaga   8880

ggttccgagc actttaggtt gcaccaaatg tcccaccagg tgcaggcaga aaacgctgga   8940

acagcgtgta cagtttgtct taacaaaaag tgagggcgct gaggtcgagc agggtggtgt   9000

gacttgttat agcctttaga gctgcgaaag cgcgtatgga tttggctcat caggccagat   9060

tgagggtctg tggacacatg tcatgttagt gtacttcaat cgccccctgg atatagcccc   9120

gacaataggc cgtggcctca tttttttgcc ttccgcacat ttccattgct cgatacccac   9180

accttgcttc tcctgcactt gccaacctta atactggttt acattgacca acatcttaca   9240

agcggggggc ttgtctaggg tatatataaa cagtggctct cccaatcggt tgccagtctc   9300

tttttccctt tctttcccca cagattcgaa atctaaacta cacatcacag aattccgagc   9360

cgtgagtatc cacgacaaga tcagtgtcga gacgacgcgt tttgtgtaat gacacaatcc   9420

gaaagtcgct agcaacacac actctctaca caaactaacc cagctctggt ac           9472
```

<210> SEQ ID NO 90
<211> LENGTH: 777
<212> TYPE: DNA
<213> ORGANISM: Artificial Sequence
<220> FEATURE:
<223> OTHER INFORMATION: synthetic delta-9 elongase derived from Euglena gracilis codon-optimized for expression in Yarrowia lipolytica

<400> SEQUENCE: 90

```
atggaggtcg tgaacgaaat cgtctccatt ggccaggagg ttcttcccaa ggtcgactat     60

gctcagctct ggtctgatgc ctcgcactgc gaggtgctgt acctctccat cgccttcgtc    120

atcctgaagt tcacccttgg tcctctcgga cccaagggtc agtctcgaat gaagtttgtg    180
```

ttcaccaact acaacctgct catgtccatc tactcgctgg gctccttcct ctctatggcc 240
tacgccatgt acaccattgg tgtcatgtcc gacaactgcg agaaggcttt cgacaacaat 300
gtcttccgaa tcaccactca gctgttctac ctcagcaagt tcctcgagta cattgactcc 360
ttctatctgc ccctcatggg caagcctctg acctggttgc agttctttca ccatctcgga 420
gctcctatgg acatgtggct gttctacaac taccgaaacg aagccgtttg gatctttgtg 480
ctgctcaacg gcttcattca ctggatcatg tacggctact attggacccg actgatcaag 540
ctcaagttcc ctatgcccaa gtccctgatt acttctatgc agatcattca gttcaacgtt 600
ggcttctaca tcgtctggaa gtaccggaac attccctgct accgacaaga tggaatgaga 660
atgtttggct ggtttttcaa ctacttctac gttggtactg tcctgtgtct gttcctcaac 720
ttctacgtgc agacctacat cgtccgaaag cacaagggag ccaaaaagat tcagtga 777

<210> SEQ ID NO 91
<211> LENGTH: 11740
<212> TYPE: DNA
<213> ORGANISM: Artificial Sequence
<220> FEATURE:
<223> OTHER INFORMATION: sequence of pKR920
<220> FEATURE:
<221> NAME/KEY: misc_feature
<222> LOCATION: (10565)..(10565)
<223> OTHER INFORMATION: n is a, c, g, or t

<400> SEQUENCE: 91
gtacgagatc cggccggcca gatcctgcag gagatccaag cttttgatcc atgcccttca 60
tttgccgctt attaattaat ttggtaacag tccgtactaa tcagttactt atccttcccc 120
catcataatt aatcttggta gtctcgaatg ccacaacact gactagtctc ttggatcata 180
agaaaaagcc aaggaacaaa agaagacaaa acacaatgag agtatccttt gcatagcaat 240
gtctaagttc ataaaattca aacaaaaacg caatcacaca cagtggacat cacttatcca 300
ctagctgatc aggatcgccg cgtcaagaaa aaaaaactgg accccaaaag ccatgcacaa 360
caacacgtac tcacaaaggt gtcaatcgag cagcccaaaa cattcaccaa ctcaacccat 420
catgagccct cacatttgtt gtttctaacc caacctcaaa ctcgtattct cttccgccac 480
ctcatttttg tttatttcaa cacccgtcaa actgcatgcc accccgtggc caaatgtcca 540
tgcatgttaa caagacctat gactataaat agctgcaatc tcggcccagg ttttcatcat 600
caagaaccag ttcaatatcc tagtacaccg tattaaagaa tttaagatat actgcggccg 660
caccatggag gtggtgaatg aaatagtctc aattgggcag gaagttttac ccaaagttga 720
ttatgcccaa ctctggagtg atgccagtca ctgtgaggtg ctttacttgt ccatcgcatt 780
tgtcatcttg aagttcactc ttggcccct tggtccaaaa ggtcagtctc gtatgaagtt 840
tgttttcacc aattacaacc ttctcatgtc catttattcg ttgggatcat tcctctcaat 900
ggcatatgcc atgtacacca tcggtgttat gtctgacaac tgcgagaagg cttttgacaa 960
caacgtcttc aggatcacca cgcagttgtt ctatttgagc aagttcctgg agtatattga 1020
ctccttctat ttgccactga tgggcaagcc tctgacctgg ttgcaattct tccatcattt 1080
gggggcaccg atggatatgt ggctgttcta taattaccga aatgaagctg tttggatttt 1140
tgtgctgttg aatggtttca tccactggat catgtacggt tattattgga ccagattgat 1200
caagctgaag ttccccatgc caaaatccct gattacatca atgcagatca ttcaattcaa 1260
tgttggtttc tacattgtct ggaagtacag gaacattccc tgttatcgcc aagatgggat 1320

-continued

```
gaggatgttt ggctggttct tcaattactt ttatgttggc acagtcttgt gtttgttctt   1380
gaatttctat gtgcaaacgt atatcgtcag gaagcacaag ggagccaaaa agattcagtg   1440
agcggccgca agtatgaact aaaatgcatg taggtgtaag agctcatgga gagcatggaa   1500
tattgtatcc gaccatgtaa cagtataata actgagctcc atctcacttc ttctatgaat   1560
aaacaaagga tgttatgata tattaacact ctatctatgc accttattgt tctatgataa   1620
atttcctctt attattataa atcatctgaa tcgtgacggc ttatggaatg cttcaaatag   1680
tacaaaaaca aatgtgtact ataagacttt ctaaacaatt ctaaccttag cattgtgaac   1740
gagacataag tgttaagaag acataacaat tataatggaa gaagtttgtc tccatttata   1800
tattatatat tacccactta tgtattatat taggatgtta aggagacata acaattataa   1860
agagagaagt ttgtatccat ttatatatta tatactaccc atttatatat tatacttatc   1920
cacttattta atgtctttat aaggtttgat ccatgatatt tctaatattt tagttgatat   1980
gtatatgaaa gggtactatt tgaactctct tactctgtat aaaggttgga tcatccttaa   2040
agtgggtcta tttaatttta ttgcttctta cagataaaaa aaaaattatg agttggtttg   2100
ataaaatatt gaaggattta aaataataat aaataacata taatatatgt atataaattt   2160
attataatat aacatttatc tataaaaaag taaatattgt cataaatcta tacaatcgtt   2220
tagccttgct ggacgaatct caattattta aacgagagta aacatatttg actttttggt   2280
tatttaacaa attattattt aacactatat gaaatttttt tttttatcag caaagaataa   2340
aattaaatta agaaggacaa tggtgtccca atccttatac aaccaacttc cacaagaaag   2400
tcaagtcaga gacaacaaaa aaacaagcaa aggaaatttt ttaatttgag ttgtcttgtt   2460
tgctgcataa tttatgcagt aaaacactac acataaccct tttagcagta gagcaatggt   2520
tgaccgtgtg cttagcttct tttattttat ttttttatca gcaaagaata aataaaataa   2580
aatgagacac ttcagggatg tttcaacaag cttggcgcgc cgttctatag tgtcacctaa   2640
atcgtatgtg tatgatacat aaggttatgt attaattgta gccgcgttct aacgacaata   2700
tgtccatatg gtgcactctc agtacaatct gctctgatgc cgcatagtta agccagcccc   2760
gacacccgcc aacacccgct gacgcgccct gacgggcttg tctgctcccg gcatccgctt   2820
acagacaagc tgtgaccgtc tccgggagct gcatgtgtca gaggttttca ccgtcatcac   2880
cgaaacgcgc gagacgaaag ggcctcgtga tacgcctatt tttataggtt aatgtcatga   2940
ccaaaatccc ttaacgtgag ttttcgttcc actgagcgtc agaccccgta gaaaagatca   3000
aaggatcttc ttgagatcct ttttttctgc gcgtaatctg ctgcttgcaa acaaaaaaac   3060
caccgctacc agcggtggtt tgtttgccgg atcaagagct accaactctt tttccgaagg   3120
taactggctt cagcagagcg cagataccaa atactgtcct tctagtgtag ccgtagttag   3180
gccaccactt caagaactct gtagcaccgc ctacatacct cgctctgcta atcctgttac   3240
cagtggctgc tgccagtggc gataagtcgt gtcttaccgg gttggactca agacgatagt   3300
taccggataa ggcgcagcgg tcgggctgaa cggggggttc gtgcacacag cccagcttgg   3360
agcgaacgac ctacaccgaa ctgagatacc tacagcgtga gcattgagaa agcgccacgc   3420
ttcccgaagg gagaaaggcg gacaggtatc cggtaagcgg cagggtcgga acaggagagc   3480
gcacgaggga gcttccaggg ggaaacgcct ggtatcttta tagtcctgtc gggtttcgcc   3540
acctctgact tgagcgtcga tttttgtgat gctcgtcagg ggggcggagc ctatggaaaa   3600
acgccagcaa cgcggccttt ttacggttcc tggccttttg ctggcctttt gctcacatgt   3660
tctttcctgc gttatcccct gattctgtgg ataaccgtat taccgccttt gagtgagctg   3720
```

```
ataccgctcg ccgcagccga acgaccgagc gcagcgagtc agtgagcgag gaagcggaag   3780
agcgcccaat acgcaaaccg cctctccccg cgcgttggcc gattcattaa tgcaggttga   3840
tcgattcgac atcgatctag taacatagat gacaccgcgc gcgataattt atcctagttt   3900
gcgcgctata ttttgttttc tatcgcgtat taaatgtata attgcgggac tctaatcata   3960
aaaacccatc tcataaataa cgtcatgcat tacatgttaa ttattacatg cttaacgtaa   4020
ttcaacagaa attatatgat aatcatcgca agaccggcaa caggattcaa tcttaagaaa   4080
ctttattgcc aaatgtttga acgatctgct tcgacgcact ccttctttag gtacctcact   4140
attcctttgc cctcggacga gtgctggggc gtcggtttcc actatcggcg agtacttcta   4200
cacagccatc ggtccagacg gccgcgcttc tgcgggcgat ttgtgtacgc ccgacagtcc   4260
cggctccgga tcggacgatt gcgtcgcatc gaccctgcgc ccaagctgca tcatcgaaat   4320
tgccgtcaac caagctctga tagagttggt caagaccaat gcggagcata tacgcccgga   4380
gccgcggcga tcctgcaagc tccggatgcc tccgctcgaa gtagcgcgtc tgctgctcca   4440
tacaagccaa ccacggcctc cagaagaaga tgttggcgac ctcgtattgg gaatccccga   4500
acatcgcctc gctccagtca atgaccgctg ttatgcggcc attgtccgtc aggacattgt   4560
tggagccgaa atccgcgtgc acgaggtgcc ggacttcggg gcagtcctcg gcccaaagca   4620
tcagctcatc gagagcctgc gcgacggacg cactgacggt gtcgtccatc acagtttgcc   4680
agtgatacac atggggatca gcaatcgcgc atatgaaatc acgccatgta gtgtattgac   4740
cgattccttg cggtccgaat gggccgaacc cgctcgtctg gctaagatcg gccgcagcga   4800
tcgcatccat ggcctccgcg accggctgca gaacagcggg cagttcggtt tcaggcaggt   4860
cttgcaacgt gacaccctgt gcacggcggg agatgcaata ggtcaggctc tcgctgaatt   4920
ccccaatgtc aagcacttcc ggaatcggga gcgcggccga tgcaaagtgc cgataaacat   4980
aacgatcttt gtagaaacca tcggcgcagc tatttacccg caggacatat ccacgccctc   5040
ctacatcgaa gctgaaagca cgagattctt cgccctccga gagctgcatc aggtcggaga   5100
cgctgtcgaa cttttcgatc agaaacttct cgacagacgt cgcggtgagt tcaggctttt   5160
tcatggttta ataagaagag aaaagagttc ttttgttatg gctgaagtaa tagagaaatg   5220
agctcgagcg tgtcctctcc aaatgaaatg aacttcctta tatagaggaa gggtcttgcg   5280
aaggatagtg ggattgtgcg tcatccctta cgtcagtgga gatgtcacat caatccactt   5340
gctttgaaga cgtggttgga acgtcttctt tttccacgat gctcctcgtg ggtgggggtc   5400
catctttggg accactgtcg gcagaggcat cttgaatgat agcctttcct ttatcgcaat   5460
gatggcattt gtaggagcca ccttcctttt ctactgtcct ttcgatgaag tgacagatag   5520
ctgggcaatg gaatccgagg aggtttcccg aaattatcct ttgttgaaaa gtctcaatag   5580
ccctttggtc ttctgagact gtatctttga catttttgga gtagaccaga gtgtcgtgct   5640
ccaccatgtt gacgaagatt ttcttcttgt cattgagtcg taaaagactc tgtatgaact   5700
gttcgccagt cttcacggcg agttctgtta gatcctcgat ttgaatctta gactccatgc   5760
atggccttag attcagtagg aactaccttt ttagagactc caatctctat tacttgcctt   5820
ggtttatgaa gcaagccttg aatcgtccat actggaatag tacttctgat cttgagaaat   5880
atgtctttct ctgtgttctt gatgcaatta gtcctgaatc ttttgactgc atctttaacc   5940
ttcttgggaa ggtatttgat ctcctggaga ttgttactcg ggtagatcgt cttgatgaga   6000
cctgctgcgt aggcctctct aaccatctgt gggtcagcat tctttctgaa attgaagagg   6060
```

-continued

```
ctaaccttct cattatcagt ggtgaacata gtgtcgtcac cttcaccttc gaacttcctt   6120
cctagatcgt aaagatagag gaaatcgtcc attgtaatct ccggggcaaa ggagatctct   6180
tttggggctg gatcactgct gggccttttg gttcctagcg tgagccagtg ggctttttgc   6240
tttggtgggc ttgttagggc cttagcaaag ctcttgggct tgagttgagc ttctcctttg   6300
gggatgaagt tcaacctgtc tgtttgctga cttgttgtgt acgcgtcagc tgctgctctt   6360
gcctctgtaa tagtggcaaa tttcttgtgt gcaactccgg gaacgccgtt tgttgccgcc   6420
tttgtacaac cccagtcatc gtatataccg gcatgtggac cgttatacac aacgtagtag   6480
ttgatatgag ggtgttgaat acccgattct gctctgagag gagcaactgt gctgttaagc   6540
tcagattttt gtgggattgg aattggatcg atctcgatcc cgcgaaatta atacgactca   6600
ctatagggag accacaacgg tttccctcta gaaataattt tgtttaactt taagaaggag   6660
atatacccat ggaaaagcct gaactcaccg cgacgtctgt cgagaagttt ctgatcgaaa   6720
agttcgacag cgtctccgac ctgatgcagc tctcggaggg cgaagaatct cgtgctttca   6780
gcttcgatgt aggagggcgt ggatatgtcc tgcgggtaaa tagctgcgcc gatggtttct   6840
acaaagatcg ttatgtttat cggcactttg catcggccgc gctcccgatt ccggaagtgc   6900
ttgacattgg ggaattcagc gagagcctga cctattgcat ctcccgccgt gcacagggtg   6960
tcacgttgca agacctgcct gaaaccgaac tgcccgctgt tctgcagccg gtcgcggagg   7020
ctatggatgc gatcgctgcg gccgatctta gccagacgag cgggttcggc ccattcggac   7080
cgcaaggaat cggtcaatac actacatggc gtgatttcat atgcgcgatt gctgatcccc   7140
atgtgtatca ctggcaaact gtgatggacg acaccgtcag tgcgtccgtc gcgcaggctc   7200
tcgatgagct gatgctttgg gccgaggact gccccgaagt ccggcacctc gtgcacgcgg   7260
atttcggctc caacaatgtc ctgacggaca atggccgcat aacagcggtc attgactgga   7320
gcgaggcgat gttcggggat tcccaatacg aggtcgccaa catcttcttc tggaggccgt   7380
ggttggcttg tatggagcag cagacgcgct acttcgagcg gaggcatccg gagcttgcag   7440
gatcgccgcg gctccgggcg tatatgctcc gcattggtct tgaccaactc tatcagagct   7500
tggttgacgg caatttcgat gatgcagctt gggcgcaggg tcgatgcgac gcaatcgtcc   7560
gatccggagc cgggactgtc gggcgtacac aaatcgcccg cagaagcgcg gccgtctgga   7620
ccgatggctg tgtagaagta ctcgccgata gtggaaaccg acgccccagc actcgtccga   7680
gggcaaagga atagtgaggt acagcttgga tcgatccggc tgctaacaaa gcccgaaagg   7740
aagctgagtt ggctgctgcc accgctgagc aataactagc ataacccctt ggggcctcta   7800
aacgggtctt gaggggtttt ttgctgaaag gaggaactat atccggatga tcgggcgcgc   7860
cgtcgacgga tccgtacgca aaggcaaaga tttaaactcg aaaacattac aaaagtctca   7920
aaacagaggc aaggccatgc acaaagcaca ctctaagtgc ttccattgcc tactaagtag   7980
ggtacgtaca cgatcaccat tcaccagtga tgatctttat taatatacaa cacactcaga   8040
gacagcttat gttatagcta gctagcataa actatcacat catgtgttag tacgacaagt   8100
gacaacattg cttttaactt cgcggccttg gatcctctag accggatata atgagccgta   8160
aacaaagatg attaagtagt aattaatacg tactagtaaa agtggcaaaa gataacgaga   8220
aagaaccaat ttctttgcat tcggccttag cggaaggcat atataagctt tgattatttt   8280
atttagtgta atgatttcgt acaaccaaag catttattta gtactctcac acttgtgtcg   8340
cggccgcgaa ttcactagtg attccttata gagccttccc cgcgggttgc ttctccgcca   8400
tccgggcgaa caccgccaga tagcgcagca ggatgaccaa cccttcatgg ggcagcgggt   8460
```

-continued

```
tccgatacgg caggttgtgc ttctggcaca gctgttccac ctggtagcta accgctgtca   8520
ggttgtggcg agggagggtc ggccacaaat ggtgctcaat ctggtaattc aagcctccga   8580
aaaaccaatc tgtgataatc cctcgccgaa tgttcatggt ctcatggatc tggccaaccg   8640
agaatccatg gccatcccag actgagtccc cgatcttctc cagtgggtag tggttcatga   8700
acaccacgat cgcaatgccg aagccgccaa ccagctccga aacgaaaaac accaacagcg   8760
atgtgaggat gctgggcata aagaataagt ggaacagggt cttcaaggtc cagtgcaggg   8820
cgaggccaat ggcctccttc ttatactgag agcgatagaa ttggttatct ctgtccttca   8880
aactgcgcac ggtcaacacg ctctggaaac accaaatgaa ccgcaacaag atacagatga   8940
ccaagaaata gtactgctgg aactgaatga gcttgcggga aatcggtgac gcccgtgtga   9000
cgtcatcctc agaccaggct aagaggggga ggttgtcaat atcagggtcg tgcccttgaa   9060
cattggttgc cgaatgatgt gcattgtgtc tgtccttcca ccatgtcacg gaaaaacctt   9120
gcagaccatt gccaaatacc agtcccacga ggttgttcca gttccggttc ttgaaagtct   9180
ggtggtggca aatgtcatga gaaagccagc ccatctgttg atagtgcatc ccaagcaaca   9240
ctgccccaat gaaatacatc tgatactgaa ccatcaggaa ataacccagc actccaaggc   9300
ccagtgtggt gctgatttg tatgagtacc agaggggga ggcatcaaac atgccagttg    9360
cgatcaactc ttctcggagc ttccggaaat cctcttgagc ttcattcact gcagcctggg   9420
gtggcaactc agaactggga ttgattttgg gcatgcgctt gagcttgtcg aaggcttctt   9480
gagagtgcat aaccatgaag gcatcagtgg catcccttcc ttggtaattc tctataattt   9540
ccgcaccacc agggtggaaa ttgacccagg cagacacatc atatgttgtt ccatcaattg   9600
taaggggaag cgcttggcgc tttgacttca tttcaatcga attcccgcgg ccgcttgggg   9660
ggctatggaa gactttctta gttagttgtg tgaataagca atgttgggag aatcgggact   9720
acttatagga taggaataaa acagaaaagt attaagtgct aatgaaatat ttagactgat   9780
aattaaaatc ttcacgtatg tccacttgat ataaaaacgt caggaataaa ggaagtacag   9840
tagaatttaa aggtactctt tttatatata cccgtgttct ctttttggct agctagttgc   9900
ataaaaaata atctatattt ttatcattat tttaaatatc ttatgagatg gtaaatattt   9960
atcataattt tttttactat tatttattat ttgtgtgtgt aatacatata gaagttaatt  10020
acaaatttta tttacttttt cattattttg atatgattca ccattaattt agtgttatta  10080
tttataatag ttcattttaa tctttttgta tatattatgc gtgcagtact tttttcctac  10140
atataactac tattacattt tatttatata atatttttat taatgaattt tcgtgataat  10200
atgtaatatt gttcattatt atttcagatt ttttaaaaat atttgtgtta ttatttatga  10260
aatatgtaat ttttttagta tttgatttta tgatgataaa gtgttctaaa ttcaaaagaa  10320
gggggaaagc gtaaacatta aaaaacgtca tcaaacaaaa acaaaatctt gttaataaag  10380
ataaaactgt ttgttttgat cactgttatt tcgtaatata aaaacattat ttatatttat  10440
attgttgaca accaaatttg cctatcaaat ctaaccaata taatgcatgc gtggcaggta  10500
atgtactacc atgaacttaa gtcatgacat aataaaccgt gaatctgacc aatgcatgta  10560
cctanctaaa ttgtatttgt gacacgaagc aaatgattca attcacaatg gagatgggaa  10620
acaaataatg aagaacccag aactaagaaa gcttttctga aaaataaaat aaaggcaatg  10680
tcaaaagtat actgcatcat cagtccagaa agcacatgat atttttttat cagtatcaat  10740
gcagctagtt ttattttaca atatcgatat agctagttta aatatattgc agctagattt  10800
```

-continued

```
ataaatattt gtgttattat ttatcatttg tgtaatcctg tttttagtat tttagtttat  10860

atatgatgat aatgtattcc aaatttaaaa gaagggaaat aaatttaaac aagaaaaaaa  10920

gtcatcaaac aaaaaacaaa tgaaagggtg gaaagatgtt accatgtaat gtgaatgtta  10980

cagtatttct tttattatag agttaacaaa ttaactaata tgattttgtt aataatgata  11040

aaatattttt tttattatta tttcataata taaaaatagt ttacttaata taaaaaaaat  11100

tctatcgttc acaacaaagt tggccaccta atttaaccat gcatgtaccc atggaccata  11160

ttaggtaacc atcaaacctg atgaagagat aaagagatga agacttaagt cataacacaa  11220

aaccataaaa aacaaaaata caatcaaccg tcaatctgac caatgcatga aaaagctgca  11280

atagtgagtg gcgacacaaa gcacatgatt ttcttacaac ggagataaaa ccaaaaaaat  11340

atttcatgaa caacctagaa caaataaagc ttttatataa taaatatata aataaataaa  11400

ggctatggaa taatatactt caatatattt ggattaaata aattgttggc ggggttgata  11460

tatttataca cacctaaagt cacttcaatc tcattttcac ttaactttta ttttttttt  11520

ctttttattt atcataaaga gaatattgat aatatacttt ttaacatatt tttatgacat  11580

tttttattgg tgaaaactta ttaaaaatca taaattttgt aagttagatt tatttaaaga  11640

gttcctcttc ttattttaaa ttttttaata aatttttaaa taactaaaat ttgtgttaaa  11700

aatgttaaaa aatgtgttat taacccttct cttcgaggac                        11740
```

<210> SEQ ID NO 92
<211> LENGTH: 1098
<212> TYPE: DNA
<213> ORGANISM: Artificial Sequence
<220> FEATURE:
<223> OTHER INFORMATION: sequence of fragment cal a24-4

<400> SEQUENCE: 92

```
aggatcctgc aggcagccaa gaaggttttg gagcgagttc caatctcaaa accgccattc    60

gaatacaatg atctgaagaa agcagtacca ccacattgtt tttcacgacc actttcccga   120

tccttgtatt tcctctttca cgacattatt gtaacatgta tccttttcta cgtagcatca   180

aactacattc atatgctccc tcgtttcctt tcctgcatcg tatggcctgt ttactggatc   240

tcccaaggag tttttctcgg cagattgtgg atgatcggcc acgaatgcgg tcatcatagc   300

ttcagtaatt accgttgggt cgacgataca gtcggttttc taatccatac ggccaccctc   360

actccctatt tttccttcaa atatagccac cgtaatcacc atgcacacac caattccatg   420

gaatacgacg aggttcatat cccgaaacgc aaatcagaag ctctctactt tgaatttctg   480

ggcaacaacc caatcggctt aatgatcacc atgctatgta aactgacttt cggatatgca   540

gcttacatta tgttcaatta cacaggtaag aagcacaaat ctgggggctt agcgagccac   600

ttctacccac aaagccctct ctttaacgac agcgaacgta accatgtttt gttctctgac   660

atcgggattt gcatcgtctt gtacgcgtgt taccgtattg tgacggtcac aggggcaatg   720

ccggcatttt atgtgtacgg tattccttgg gttataatga gtgctattct ctttgcagca   780

acttatttac aacacactca tccttcaatc cctcattatg atacaacgga gtggaactgg   840

cttagagggg ctttatcgac aattgataga gatttagggt tcttcaacat gaacaaaaca   900

cattatcatg ttatccacca tttgtttcct gtcattccgg aataccatgc acaagaggca   960

accgaggcca tcaagcccat cttaggtcaa tattacaagt atgatggtac tccgtttcta  1020

aaggccttgt ggagagaaat gaaggagtgt atttatgtag aatccgatga aggtcagaag  1080

aaacctgcag gagatctt                                                1098
```

<210> SEQ ID NO 93
<211> LENGTH: 30
<212> TYPE: DNA
<213> ORGANISM: Artificial Sequence
<220> FEATURE:
<223> OTHER INFORMATION: sequence of the oCal-15 primer

<400> SEQUENCE: 93
aggatcctgc aggcagccaa gaaggttttg 30

<210> SEQ ID NO 94
<211> LENGTH: 29
<212> TYPE: DNA
<213> ORGANISM: Artificial Sequence
<220> FEATURE:
<223> OTHER INFORMATION: sequence of the oCal-6 primer

<400> SEQUENCE: 94
aagatctcct gcaggtttct tctgacctc 29

<210> SEQ ID NO 95
<211> LENGTH: 8138
<212> TYPE: DNA
<213> ORGANISM: Artificial Sequence
<220> FEATURE:
<223> OTHER INFORMATION: sequence of pKR53B

<400> SEQUENCE: 95
gatccgtcga cggcgcgccc gatcatccgg atatagttcc tcctttcagc aaaaaacccc 60
tcaagacccg tttagaggcc ccaaggggtt atgctagtta ttgctcagcg gtggcagcag 120
ccaactcagc ttcctttcgg gctttgttag cagccggatc gatccaagct gtacctcact 180
attcctttgc cctcggacga gtgctggggc gtcggtttcc actatcggcg agtacttcta 240
cacagccatc ggtccagacg gccgcgcttc tgcgggcgat ttgtgtacgc ccgacagtcc 300
cggctccgga tcggacgatt gcgtcgcatc gaccctgcgc ccaagctgca tcatcgaaat 360
tgccgtcaac caagctctga tagagttggt caagaccaat gcggagcata tacgcccgga 420
gccgcggcga tcctgcaagc tccggatgcc tccgctcgaa gtagcgcgtc tgctgctcca 480
tacaagccaa ccacggcctc cagaagaaga tgttggcgac ctcgtattgg gaatccccga 540
acatcgcctc gctccagtca atgaccgctg ttatgcggcc attgtccgtc aggacattgt 600
tggagccgaa atccgcgtgc acgaggtgcc ggacttcggg gcagtcctcg gcccaaagca 660
tcagctcatc gagagcctgc gcgacggacg cactgacggt gtcgtccatc acagtttgcc 720
agtgatacac atggggatca gcaatcgcgc atatgaaatc acgccatgta gtgtattgac 780
cgattccttg cggtccgaat gggccgaacc cgctcgtctg gctaagatcg gccgcagcga 840
tcgcatccat agcctccgcg accggctgca gaacagcggg cagttcggtt tcaggcaggt 900
cttgcaacgt gacaccctgt gcacggcggg agatgcaata ggtcaggctc tcgctgaatt 960
ccccaatgtc aagcacttcc ggaatcggga gcgcggccga tgcaaagtgc cgataaacat 1020
aacgatcttt gtagaaacca tcggcgcagc tatttacccg caggacatat ccacgccctc 1080
ctacatcgaa gctgaaagca cgagattctt cgccctccga gagctgcatc aggtcggaga 1140
cgctgtcgaa cttttcgatc agaaacttct cgacagacgt cgcggtgagt tcaggctttt 1200
ccatgggtat atctccttct taaagttaaa caaaattatt tctagaggga aaccgttgtg 1260
gtctccctat agtgagtcgt attaatttcg cgggatcgag atcgatccaa ttccaatccc 1320

```
acaaaaatct gagcttaaca gcacagttgc tcctctcaga gcagaatcgg gtattcaaca   1380
ccctcatatc aactactacg ttgtgtataa cggtccacat gccggtatat acgatgactg   1440
gggttgtaca aaggcggcaa caaacggcgt tcccggagtt gcacacaaga aatttgccac   1500
tattacagag gcaagagcag cagctgacgc gtacacaaca agtcagcaaa cagacaggtt   1560
gaacttcatc cccaaaggag aagctcaact caagcccaag agctttgcta aggccctaac   1620
aagcccacca aagcaaaaag cccactggct cacgctagga accaaaaggc ccagcagtga   1680
tccagcccca aaagagatct cctttgcccc ggagattaca atggacgatt tcctctatct   1740
ttacgatcta ggaaggaagt tcgaaggtga aggtgacgac actatgttca ccactgataa   1800
tgagaaggtt agcctcttca atttcagaaa gaatgctgac ccacagatgg ttagagaggc   1860
ctacgcagca ggtctcatca agacgatcta cccgagtaac aatctccagg agatcaaata   1920
ccttcccaag aaggttaaag atgcagtcaa aagattcagg actaattgca tcaagaacac   1980
agagaaagac atatttctca agatcagaag tactattcca gtatggacga ttcaaggctt   2040
gcttcataaa ccaaggcaag taatagagat tggagtctct aaaaaggtag ttcctactga   2100
atctaaggcc atgcatggag tctaagattc aaatcgagga tctaacagaa ctcgccgtga   2160
agactggcga acagttcata cagagtcttt tacgactcaa tgacaagaag aaaatcttcg   2220
tcaacatggt ggagcacgac actctggtct actccaaaaa tgtcaaagat acagtctcag   2280
aagaccaaag ggctattgag acttttcaac aaaggataat ttcgggaaac ctcctcggat   2340
tccattgccc agctatctgt cacttcatcg aaaggacagt agaaaaggaa ggtggctcct   2400
acaaatgcca tcattgcgat aaaggaaagg ctatcattca agatgcctct gccgacagtg   2460
gtcccaaaga tggaccccca cccacgagga gcatcgtgga aaaagaagac gttccaacca   2520
cgtcttcaaa gcaagtggat tgatgtgaca tctccactga cgtaagggat gacgcacaat   2580
cccactatcc ttcgcaagac ccttcctcta tataaggaag ttcatttcat ttggagagga   2640
cacgctcgag ctcatttctc tattacttca gccataacaa aagaactctt ttctcttctt   2700
attaaaccat gaaaaagcct gaactcaccg cgacgtctgt cgagaagttt ctgatcgaaa   2760
agttcgacag cgtctccgac ctgatgcagc tctcggaggg cgaagaatct cgtgctttca   2820
gcttcgatgt aggagggcgt ggatatgtcc tgcgggtaaa tagctgcgcc gatggtttct   2880
acaaagatcg ttatgtttat cggcactttg catcggccgc gctcccgatt ccggaagtgc   2940
ttgacattgg ggaattcagc gagagcctga cctattgcat ctcccgccgt gcacagggtg   3000
tcacgttgca agacctgcct gaaaccgaac tgcccgctgt tctgcagccg gtcgcggagg   3060
ccatggatgc gatcgctgcg gccgatctta gccagacgag cgggttcggc ccattcggac   3120
cgcaaggaat cggtcaatac actacatggc gtgatttcat atgcgcgatt gctgatcccc   3180
atgtgtatca ctggcaaact gtgatggacg acaccgtcag tgcgtccgtc gcgcaggctc   3240
tcgatgagct gatgctttgg gccgaggact gccccgaagt ccggcacctc gtgcacgcgg   3300
atttcggctc caacaatgtc ctgacggaca atggccgcat aacagcggtc attgactgga   3360
gcgaggcgat gttcggggat tcccaatacg aggtcgccaa catcttcttc tggaggccgt   3420
ggttggcttg tatggagcag cagacgcgct acttcgagcg gaggcatccg gagcttgcag   3480
gatcgccgcg gctccgggcg tatatgctcc gcattggtct tgaccaactc tatcagagct   3540
tggttgacgg caatttcgat gatgcagctt gggcgcaggg tcgatgcgac gcaatcgtcc   3600
gatccggagc cgggactgtc gggcgtacac aaatcgcccg cagaagcgcg gccgtctgga   3660
ccgatggctg tgtagaagta ctcgccgata gtggaaaccg acgccccagc actcgtccga   3720
```

gggcaaagga atagtgaggt acctaaagaa ggagtgcgtc gaagcagatc gttcaaacat 3780
ttggcaataa agtttcttaa gattgaatcc tgttgccggt cttgcgatga ttatcatata 3840
atttctgttg aattacgtta agcatgtaat aattaacatg taatgcatga cgttatttat 3900
gagatgggtt tttatgatta gagtcccgca attatacatt taatacgcga tagaaaacaa 3960
aatatagcgc gcaaactagg ataaattatc gcgcgcggtg tcatctatgt tactagatcg 4020
atgtcgaatc gatcaacctg cattaatgaa tcggccaacg cgcggggaga ggcggtttgc 4080
gtattgggcg ctcttccgct tcctcgctca ctgactcgct gcgctcggtc gttcggctgc 4140
ggcgagcggt atcagctcac tcaaaggcgg taatacggtt atccacagaa tcaggggata 4200
acgcaggaaa gaacatgtga gcaaaaggcc agcaaaaggc caggaaccgt aaaaaggccg 4260
cgttgctggc gtttttccat aggctccgcc cccctgacga gcatcacaaa aatcgacgct 4320
caagtcagag gtggcgaaac ccgacaggac tataaagata ccaggcgttt ccccctggaa 4380
gctccctcgt gcgctctcct gttccgaccc tgccgcttac cggatacctg tccgcctttc 4440
tcccttcggg aagcgtggcg ctttctcaat gctcacgctg taggtatctc agttcggtgt 4500
aggtcgttcg ctccaagctg ggctgtgtgc acgaaccccc cgttcagccc gaccgctgcg 4560
ccttatccgg taactatcgt cttgagtcca acccggtaag acacgactta tcgccactgg 4620
cagcagccac tggtaacagg attagcagag cgaggtatgt aggcggtgct acagagttct 4680
tgaagtggtg gcctaactac ggctacacta gaaggacagt atttggtatc tgcgctctgc 4740
tgaagccagt taccttcgga aaaagagttg gtagctcttg atccggcaaa caaaccaccg 4800
ctggtagcgg tggttttttt gtttgcaagc agcagattac gcgcagaaaa aaaggatctc 4860
aagaagatcc tttgatcttt tctacggggt ctgacgctca gtggaacgaa aactcacgtt 4920
aagggatttt ggtcatgaca ttaacctata aaaataggcg tatcacgagg ccctttcgtc 4980
tcgcgcgttt cggtgatgac ggtgaaaacc tctgacacat gcagctcccg gagacggtca 5040
cagcttgtct gtaagcggat gccgggagca gacaagcccg tcagggcgcg tcagcgggtg 5100
ttggcgggtg tcggggctgg cttaactatg cggcatcaga gcagattgta ctgagagtgc 5160
accatatgga catattgtcg ttagaacgcg gctacaatta atacataacc ttatgtatca 5220
tacacatacg atttaggtga cactatagaa cggcgcgcca agcttttgat ccatgccctt 5280
catttgccgc ttattaatta atttggtaac agtccgtact aatcagttac ttatccttcc 5340
cccatcataa ttaatcttgg tagtctcgaa tgccacaaca ctgactagtc tcttggatca 5400
taagaaaaag ccaaggaaca aaagaagaca aaacacaatg agagtatcct ttgcatagca 5460
atgtctaagt tcataaaatt caaacaaaaa cgcaatcaca cacagtggac atcacttatc 5520
cactagctga tcaggatcgc cgcgtcaaga aaaaaaaact ggaccccaaa agccatgcac 5580
aacaacacgt actcacaaag gtgtcaatcg agcagcccaa aacattcacc aactcaaccc 5640
atcatgagcc ctcacatttg ttgtttctaa cccaacctca aactcgtatt ctcttccgcc 5700
acctcatttt tgtttatttc aacacccgtc aaactgcatg ccaccccgtg gccaaatgtc 5760
catgcatgtt aacaagacct atgactataa atagctgcaa tctcggccca ggttttcatc 5820
atcaagaacc agttcaatat cctagtacac cgtattaaag aatttaagat atactgcggc 5880
cgcaagtatg aactaaaatg catgtaggtg taagagctca tggagagcat ggaatattgt 5940
atccgaccat gtaacagtat aataactgag ctccatctca cttcttctat gaataaacaa 6000
aggatgttat gatatattaa cactctatct atgcacctta ttgttctatg ataaatttcc 6060

```
tcttattatt ataaatcatc tgaatcgtga cggcttatgg aatgcttcaa atagtacaaa   6120
aacaaatgtg tactataaga ctttctaaac aattctaacc ttagcattgt gaacgagaca   6180
taagtgttaa gaagacataa caattataat ggaagaagtt tgtctccatt tatatattat   6240
atattaccca cttatgtatt atattaggat gttaaggaga cataacaatt ataaagagag   6300
aagtttgtat ccatttatat attatatact acccatttat atattatact tatccactta   6360
tttaatgtct ttataaggtt tgatccatga tatttctaat attttagttg atatgtatat   6420
gaaagggtac tatttgaact ctcttactct gtataaaggt tggatcatcc ttaaagtggg   6480
tctatttaat tttattgctt cttacagata aaaaaaaaat tatgagttgg tttgataaaa   6540
tattgaagga tttaaaataa taataaataa catataatat atgtatataa atttattata   6600
atataacatt tatctataaa aaagtaaata ttgtcataaa tctatacaat cgtttagcct   6660
tgctggacga atctcaatta tttaaacgag agtaaacata tttgactttt tggttattta   6720
acaaattatt atttaacact atatgaaatt ttttttttta tcagcaaaga ataaaattaa   6780
attaagaagg acaatggtgt cccaatcctt atacaaccaa cttccacaag aaagtcaagt   6840
cagagacaac aaaaaaacaa gcaaaggaaa ttttttaatt tgagttgtct tgtttgctgc   6900
ataatttatg cagtaaaaca ctacacataa cccttttagc agtagagcaa tggttgaccg   6960
tgtgcttagc ttcttttatt ttattttttt atcagcaaag aataaataaa ataaaatgag   7020
acacttcagg gatgtttcaa caagcttgga tctcctgcag gtttcttctg accttcatcg   7080
gattctacat aaatacactc cttcatttct ctccacaagg cctttagaaa cggagtacca   7140
tcatacttgt aatattgacc taagatgggc ttgatggcct cggttgcctc ttgtgcatgg   7200
tattccggaa tgacaggaaa caaatggtgg ataacatgat aatgtgtttt gttcatgttg   7260
aagaacccta aatctctatc aattgtcgat aaagcccctc taagccagtt ccactccgtt   7320
gtatcataat gagggattga aggatgagtg tgttgtaaat aagttgctgc aaagagaata   7380
gcactcatta taacccaagg aataccgtac acataaaatg ccggcattgc ccctgtgacc   7440
gtcacaatac ggtaacacgc gtacaagacg atgcaaatcc cgatgtcaga gaacaaaaca   7500
tggttacgtt cgctgtcgtt aaagagaggg ctttgtgggt agaagtggct cgctaagccc   7560
ccagatttgt gcttcttacc tgtgtaattg aacataatgt aagctgcata tccgaaagtc   7620
agtttacata gcatggtgat cattaagccg attgggttgt tgcccagaaa ttcaaagtag   7680
agagcttctg atttgcgttt cgggatatga acctcgtcgt attccatgga attggtgtgt   7740
gcatggtgat tacggtggct atatttgaag gaaaaatagg gagtgagggt ggccgtatgg   7800
attagaaaac cgactgtatc gtcgacccaa cggtaattac tgaagctatg atgaccgcat   7860
tcgtggccga tcatccacaa tctgccgaga aaaactcctt gggagatcca gtaaacaggc   7920
catacgatgc aggaaaggaa acgagggagc atatgaatgt agtttgatgc tacgtagaaa   7980
aggatacatg ttacaataat gtcgtgaaag aggaaataca aggatcggga aagtggtcgt   8040
gaaaaacaat gtggtggtac tgctttcttc agatcattgt attcgaatgg cggttttgag   8100
attggaactc gctccaaaac cttcttggct gcctgcag                           8138
```

<210> SEQ ID NO 96
<211> LENGTH: 7085
<212> TYPE: DNA
<213> ORGANISM: Artificial Sequence
<220> FEATURE:
<223> OTHER INFORMATION: sequence of pKR85

<400> SEQUENCE: 96

```
cgcgccaagc ttttgatcca tgcccttcat ttgccgctta ttaattaatt tggtaacagt     60
ccgtactaat cagttactta tccttccccc atcataatta atcttggtag tctcgaatgc    120
cacaacactg actagtctct tggatcataa gaaaaagcca aggaacaaaa gaagacaaaa    180
cacaatgaga gtatcctttg catagcaatg tctaagttca taaaattcaa acaaaaacgc    240
aatcacacac agtggacatc acttatccac tagctgatca ggatcgccgc gtcaagaaaa    300
aaaaactgga ccccaaaagc catgcacaac aacacgtact cacaaaggtg tcaatcgagc    360
agcccaaaac attcaccaac tcaacccatc atgagccctc acatttgttg tttctaaccc    420
aacctcaaac tcgtattctc ttccgccacc tcatttttgt ttatttcaac acccgtcaaa    480
ctgcatgcca ccccgtggcc aaatgtccat gcatgttaac aagacctatg actataaata    540
gctgcaatct cggcccaggt tttcatcatc aagaaccagt tcaatatcct agtacaccgt    600
attaaagaat ttaagatata ctgcggccgc aagtatgaac taaaatgcat gtaggtgtaa    660
gagctcatgg agagcatgga atattgtatc cgaccatgta acagtataat aactgagctc    720
catctcactt cttctatgaa taaacaaagg atgttatgat atattaacac tctatctatg    780
caccttattg ttctatgata aatttcctct tattattata aatcatctga atcgtgacgg    840
cttatggaat gcttcaaata gtacaaaaac aaatgtgtac tataagactt tctaaacaat    900
tctaacctta gcattgtgaa cgagacataa gtgttaagaa gacataacaa ttataatgga    960
agaagtttgt ctccatttat atattatata ttacccactt atgtattata ttaggatgtt   1020
aaggagacat aacaattata aagagagaag tttgtatcca tttatatatt atatactacc   1080
catttatata ttatacttat ccacttattt aatgtcttta taaggtttga tccatgatat   1140
ttctaatatt ttagttgata tgtatatgaa agggtactat ttgaactctc ttactctgta   1200
taaaggttgg atcatcctta aagtgggtct atttaatttt attgcttctt acagataaaa   1260
aaaaaattat gagttggttt gataaaatat tgaaggattt aaaataataa taaataacat   1320
ataatatatg tatataaatt tattataata taacatttat ctataaaaaa gtaaatattg   1380
tcataaatct atacaatcgt ttagccttgc tggacgaatc tcaattattt aaacgagagt   1440
aaacatattt gactttttgg ttatttaaca aattattatt taacactata tgaaattttt   1500
tttttatca gcaaagaata aaattaaatt aagaaggaca atggtgtccc aatccttata    1560
caaccaactt ccacaagaaa gtcaagtcag agacaacaaa aaaacaagca aaggaaattt   1620
tttaatttga gttgtcttgt ttgctgcata atttatgcag taaaacacta cacataaccc   1680
ttttagcagt agagcaatgg ttgaccgtgt gcttagcttc ttttatttta ttttttttatc  1740
agcaaagaat aaataaaata aaatgagaca cttcagggat gtttcaacaa gcttggatct   1800
cctgcaggat ctggccggcc ggatctcgta cggatccgtc gacggcgcgc ccgatcatcc   1860
ggatatagtt cctcctttca gcaaaaaacc cctcaagacc cgtttagagg ccccaagggg   1920
ttatgctagt tattgctcag cggtggcagc agccaactca gcttcctttc gggctttgtt   1980
agcagccgga tcgatccaag ctgtacctca ctattccttt gccctcggac gagtgctggg   2040
gcgtcggttt ccactatcgg cgagtacttc tacacagcca tcggtccaga cggccgcgct   2100
tctgcgggcg atttgtgtac gcccgacagt cccggctccg gatcggacga ttgcgtcgca   2160
tcgaccctgc gcccaagctg catcatcgaa attgccgtca accaagctct gatagagttg   2220
gtcaagacca atgcggagca tatacgcccg gagccgcggc gatcctgcaa gctccggatg   2280
cctccgctcg aagtagcgcg tctgctgctc catacaagcc aaccacggcc tccagaagaa   2340
```

gatgttggcg acctcgtatt gggaatcccc gaacatcgcc tcgctccagt caatgaccgc 2400
tgttatgcgg ccattgtccg tcaggacatt gttggagccg aaatccgcgt gcacgaggtg 2460
ccggacttcg gggcagtcct cggcccaaag catcagctca tcgagagcct gcgcgacgga 2520
cgcactgacg gtgtcgtcca tcacagtttg ccagtgatac acatggggat cagcaatcgc 2580
gcatatgaaa tcacgccatg tagtgtattg accgattcct tgcggtccga atgggccgaa 2640
cccgctcgtc tggctaagat cggccgcagc gatcgcatcc atagcctccg cgaccggctg 2700
cagaacagcg ggcagttcgg tttcaggcag gtcttgcaac gtgacaccct gtgcacggcg 2760
ggagatgcaa taggtcaggc tctcgctgaa ttccccaatg tcaagcactt ccggaatcgg 2820
gagcgcggcc gatgcaaagt gccgataaac ataacgatct ttgtagaaac catcggcgca 2880
gctatttacc cgcaggacat atccacgccc tcctacatcg aagctgaaag cacgagattc 2940
ttcgccctcc gagagctgca tcaggtcgga gacgctgtcg aacttttcga tcagaaactt 3000
ctcgacagac gtcgcggtga gttcaggctt ttccatgggt atatctcctt cttaaagtta 3060
aacaaaatta tttctagagg gaaaccgttg tggtctccct atagtgagtc gtattaattt 3120
cgcgggatcg agatcgatcc aattccaatc ccacaaaaat ctgagcttaa cagcacagtt 3180
gctcctctca gagcagaatc gggtattcaa caccctcata tcaactacta cgttgtgtat 3240
aacggtccac atgccggtat atacgatgac tggggttgta caaaggcggc aacaaacggc 3300
gttcccggag ttgcacacaa gaaatttgcc actattacag aggcaagagc agcagctgac 3360
gcgtacacaa caagtcagca aacagacagg ttgaacttca tccccaaagg agaagctcaa 3420
ctcaagccca agagctttgc taaggcccta acaagcccac caaagcaaaa agcccactgg 3480
ctcacgctag gaaccaaaag gcccagcagt gatccagccc caaaagagat ctcctttgcc 3540
ccggagatta caatggacga tttcctctat ctttacgatc taggaaggaa gttcgaaggt 3600
gaaggtgacg acactatgtt caccactgat aatgagaagg ttagcctctt caatttcaga 3660
aagaatgctg acccacagat ggttagagag gcctacgcag caggtctcat caagacgatc 3720
tacccgagta acaatctcca ggagatcaaa taccttccca agaaggttaa agatgcagtc 3780
aaaagattca ggactaattg catcaagaac acagagaaag acatatttct caagatcaga 3840
agtactattc cagtatggac gattcaaggc ttgcttcata aaccaaggca agtaatagag 3900
attggagtct ctaaaaaggt agttcctact gaatctaagg ccatgcatgg agtctaagat 3960
tcaaatcgag gatctaacag aactcgccgt gaagactggc gaacagttca tacagagtct 4020
tttacgactc aatgacaaga agaaaatctt cgtcaacatg gtggagcacg acactctggt 4080
ctactccaaa aatgtcaaag atacagtctc agaagaccaa agggctattg agacttttca 4140
acaaaggata atttcgggaa acctcctcgg attccattgc ccagctatct gtcacttcat 4200
cgaaaggaca gtagaaaagg aaggtggctc ctacaaatgc catcattgcg ataaaggaaa 4260
ggctatcatt caagatgcct ctgccgacag tggtcccaaa gatggacccc cacccacgag 4320
gagcatcgtg gaaaaagaag acgttccaac cacgtcttca aagcaagtgg attgatgtga 4380
catctccact gacgtaaggg atgacgcaca atcccactat ccttcgcaag acccttcctc 4440
tatataagga agttcatttc atttggagag gacacgctcg agctcatttc tctattactt 4500
cagccataac aaaagaactc ttttctcttc ttattaaacc atgaaaaagc ctgaactcac 4560
cgcgacgtct gtcgagaagt ttctgatcga aaagttcgac agcgtctccg acctgatgca 4620
gctctcggag ggcgaagaat ctcgtgcttt cagcttcgat gtaggagggc gtggatatgt 4680
cctgcgggta aatagctgcg ccgatggttt ctacaaagat cgttatgttt atcggcactt 4740

```
tgcatcggcc gcgctcccga ttccggaagt gcttgacatt ggggaattca gcgagagcct   4800
gacctattgc atctcccgcc gtgcacaggg tgtcacgttg caagacctgc ctgaaaccga   4860
actgcccgct gttctgcagc cggtcgcgga ggccatggat gcgatcgctg cggccgatct   4920
tagccagacg agcgggttcg gcccattcgg accgcaagga atcggtcaat acactacatg   4980
gcgtgatttc atatgcgcga ttgctgatcc ccatgtgtat cactggcaaa ctgtgatgga   5040
cgacaccgtc agtgcgtccg tcgcgcaggc tctcgatgag ctgatgcttt gggccgagga   5100
ctgccccgaa gtccggcacc tcgtgcacgc ggatttcggc tccaacaatg tcctgacgga   5160
caatggccgc ataacagcgg tcattgactg gagcgaggcg atgttcgggg attcccaata   5220
cgaggtcgcc aacatcttct tctggaggcc gtggttggct tgtatggagc agcagacgcg   5280
ctacttcgag cggaggcatc cggagcttgc aggatcgccg cggctccggg cgtatatgct   5340
ccgcattggt cttgaccaac tctatcagag cttggttgac ggcaatttcg atgatgcagc   5400
ttgggcgcag ggtcgatgcg acgcaatcgt ccgatccgga gccgggactg tcgggcgtac   5460
acaaatcgcc cgcagaagcg cggccgtctg gaccgatggc tgtgtagaag tactcgccga   5520
tagtggaaac cgacgcccca gcactcgtcc gagggcaaag gaatagtgag gtacctaaag   5580
aaggagtgcg tcgaagcaga tcgttcaaac atttggcaat aaagtttctt aagattgaat   5640
cctgttgccg gtcttgcgat gattatcata taatttctgt tgaattacgt taagcatgta   5700
ataattaaca tgtaatgcat gacgttattt atgagatggg tttttatgat tagagtcccg   5760
caattataca tttaatacgc gatagaaaac aaaatatagc gcgcaaacta ggataaatta   5820
tcgcgcgcgg tgtcatctat gttactagat cgatgtcgaa tcgatcaacc tgcattaatg   5880
aatcggccaa cgcgcgggga gaggcggttt gcgtattggg cgctcttccg cttcctcgct   5940
cactgactcg ctgcgctcgg tcgttcggct gcggcgagcg gtatcagctc actcaaaggc   6000
ggtaatacgg ttatccacag aatcagggga taacgcagga aagaacatgt gagcaaaagg   6060
ccagcaaaag gccaggaacc gtaaaaaggc cgcgttgctg gcgtttttcc ataggctccg   6120
cccccctgac gagcatcaca aaaatcgacg ctcaagtcag aggtggcgaa acccgacagg   6180
actataaaga taccaggcgt ttccccctgg aagctccctc gtgcgctctc ctgttccgac   6240
cctgccgctt accggatacc tgtccgcctt tctcccttcg ggaagcgtgg cgctttctca   6300
atgctcacgc tgtaggtatc tcagttcggt gtaggtcgtt cgctccaagc tgggctgtgt   6360
gcacgaaccc cccgttcagc ccgaccgctg cgccttatcc ggtaactatc gtcttgagtc   6420
caacccggta agacacgact tatcgccact ggcagcagcc actggtaaca ggattagcag   6480
agcgaggtat gtaggcggtg ctacagagtt cttgaagtgg tggcctaact acggctacac   6540
tagaaggaca gtatttggta tctgcgctct gctgaagcca gttaccttcg gaaaaagagt   6600
tggtagctct tgatccggca aacaaaccac cgctggtagc ggtggttttt ttgtttgcaa   6660
gcagcagatt acgcgcagaa aaaaaggatc tcaagaagat cctttgatct tttctacggg   6720
gtctgacgct cagtggaacg aaaactcacg ttaagggatt ttggtcatga cattaaccta   6780
taaaaatagg cgtatcacga ggccctttcg tctcgcgcgt ttcggtgatg acggtgaaaa   6840
cctctgacac atgcagctcc cggagacggt cacagcttgt ctgtaagcgg atgccgggag   6900
cagacaagcc cgtcagggcg cgtcagcggg tgttggcggg tgtcggggct ggcttaacta   6960
tgcggcatca gagcagattg tactgagagt gcaccatatg gacatattgt cgttagaacg   7020
cggctacaat taatacataa ccttatgtat catacacata cgatttaggt gacactatag   7080
```

aacgg 7085

<210> SEQ ID NO 97
<211> LENGTH: 22
<212> TYPE: DNA
<213> ORGANISM: Artificial Sequence
<220> FEATURE:
<223> OTHER INFORMATION: sequence of the oKR85-1 primer

<400> SEQUENCE: 97
actcgaggcg cgccgtcgac gg 22

<210> SEQ ID NO 98
<211> LENGTH: 18
<212> TYPE: DNA
<213> ORGANISM: Artificial Sequence
<220> FEATURE:
<223> OTHER INFORMATION: sequence of the oKR85-2 primer

<400> SEQUENCE: 98
aagatctggc gcgccaag 18

<210> SEQ ID NO 99
<211> LENGTH: 4827
<212> TYPE: DNA
<213> ORGANISM: Artificial Sequence
<220> FEATURE:
<223> OTHER INFORMATION: sequence of pPCR85

<400> SEQUENCE: 99
actcgaggcg cgccgtcgac ggatccgtac gagatccggc cggccagatc ctgcaggaga 60
tccaagcttg ttgaaacatc cctgaagtgt ctcattttat tttatttatt ctttgctgat 120
aaaaaaataa aataaaagaa gctaagcaca cggtcaacca ttgctctact gctaaaaggg 180
ttatgtgtag tgttttactg cataaattat gcagcaaaca agacaactca aattaaaaaa 240
tttcctttgc ttgttttttt gttgtctctg acttgacttt cttgtggaag ttggttgtat 300
aaggattggg acaccattgt ccttcttaat ttaattttat tctttgctga taaaaaaaaa 360
aatttcatat agtgttaaat aataatttgt taaataacca aaaagtcaaa tatgtttact 420
ctcgtttaaa taattgagat tcgtccagca aggctaaacg attgtataga tttatgacaa 480
tatttacttt tttatagata aatgttatat tataataaat ttatatacat atattatatg 540
ttatttatta ttattttaaa tccttcaata ttttatcaaa ccaactcata attttttttt 600
tatctgtaag aagcaataaa attaaataga cccactttaa ggatgatcca acctttatac 660
agagtaagag agttcaaata gtaccctttc atatacatat caactaaaat attagaaata 720
tcatggatca aaccttataa agacattaaa taagtggata agtataatat ataaatgggt 780
agtatataat atataaatgg atacaaactt ctctctttat aattgttatg tctccttaac 840
atcctaatat aatacataag tgggtaatat ataatatata aatggagaca aacttcttcc 900
attataattg ttatgtcttc ttaacactta tgtctcgttc acaatgctaa ggttagaatt 960
gtttagaaag tcttatagta cacatttgtt tttgtactat ttgaagcatt ccataagccg 1020
tcacgattca gatgatttat aataataaga ggaaatttat catagaacaa taaggtgcat 1080
agatagagtg ttaatatatc ataacatcct ttgtttattc atagaagaag tgagatggag 1140
ctcagttatt atactgttac atggtcggat acaatattcc atgctctcca tgagctctta 1200
cacctacatg cattttagtt catacttgcg gccgcagtat atcttaaatt ctttaatacg 1260
gtgtactagg atattgaact ggttcttgat gatgaaaacc tgggccgaga ttgcagctat 1320
ttatagtcat aggtcttgtt aacatgcatg gacatttggc cacggggtgg catgcagttt 1380
gacgggtgtt gaaataaaca aaaatgaggt ggcggaagag aatacgagtt tgaggttggg 1440
ttagaaacaa caaatgtgag ggctcatgat gggttgagtt ggtgaatgtt ttgggctgct 1500
cgattgacac ctttgtgagt acgtgttgtt gtgcatggct tttggggtcc agttttttt 1560
tcttgacgcg gcgatcctga tcagctagtg gataagtgat gtccactgtg tgtgattgcg 1620
tttttgtttg aattttatga acttagacat tgctatgcaa aggatactct cattgtgttt 1680
tgtcttcttt tgttccttgg ctttttctta tgatccaaga gactagtcag tgttgtggca 1740
ttcgagacta ccaagattaa ttatgatggg ggaaggataa gtaactgatt agtacggact 1800
gttaccaaat taattaataa gcggcaaatg aagggcatgg atcaaaagct tggcgcgcca 1860
gatcttgggc tagagcggcc gccaccgcgg tggagctcca gcttttgttc cctttagtga 1920
gggttaattg cgcgcttggc gtaatcatgg tcatagctgt ttcctgtgtg aaattgttat 1980
ccgctcacaa ttccacacaa catacgagcc ggaagcataa agtgtaaagc ctggggtgcc 2040
taatgagtga gctaactcac attaattgcg ttgcgctcac tgcccgcttt ccagtcggga 2100
aacctgtcgt gccagctgca ttaatgaatc ggccaacgcg cggggagagg cggtttgcgt 2160
attgggcgct cttccgcttc ctcgctcact gactcgctgc gctcggtcgt tcggctgcgg 2220
cgagcggtat cagctcactc aaaggcggta atacggttat ccacagaatc aggggataac 2280
gcaggaaaga acatgtgagc aaaaggccag caaaaggcca ggaaccgtaa aaaggccgcg 2340
ttgctggcgt ttttccatag gctccgcccc cctgacgagc atcacaaaaa tcgacgctca 2400
agtcagaggt ggcgaaaccc gacaggacta taaagatacc aggcgtttcc ccctggaagc 2460
tccctcgtgc gctctcctgt tccgaccctg ccgcttaccg gatacctgtc cgcctttctc 2520
ccttcgggaa gcgtggcgct ttctcatagc tcacgctgta ggtatctcag ttcggtgtag 2580
gtcgttcgct ccaagctggg ctgtgtgcac gaaccccccg ttcagcccga ccgctgcgcc 2640
ttatccggta actatcgtct tgagtccaac ccggtaagac acgacttatc gccactggca 2700
gcagccactg gtaacaggat tagcagagcg aggtatgtag gcggtgctac agagttcttg 2760
aagtggtggc ctaactacgg ctacactaga aggacagtat ttggtatctg cgctctgctg 2820
aagccagtta ccttcggaaa aagagttggt agctcttgat ccggcaaaca aaccaccgct 2880
ggtagcggtg gtttttttgt ttgcaagcag cagattacgc gcagaaaaaa aggatctcaa 2940
gaagatcctt tgatcttttc tacggggtct gacgctcagt ggaacgaaaa ctcacgttaa 3000
gggattttgg tcatgagatt atcaaaaagg atcttcacct agatcctttt aaattaaaaa 3060
tgaagtttta aatcaatcta aagtatatat gagtaaactt ggtctgacag ttaccaatgc 3120
ttaatcagtg aggcacctat ctcagcgatc tgtctatttc gttcatccat agttgcctga 3180
ctccccgtcg tgtagataac tacgatacgg gagggcttac catctggccc cagtgctgca 3240
atgataccgc gagacccacg ctcaccggct ccagatttat cagcaataaa ccagccagcc 3300
ggaagggccg agcgcagaag tggtcctgca actttatccg cctccatcca gtctattaat 3360
tgttgccggg aagctagagt aagtagttcg ccagttaata gtttgcgcaa cgttgttgcc 3420
attgctacag gcatcgtggt gtcacgctcg tcgtttggta tggcttcatt cagctccggt 3480
tcccaacgat caaggcgagt tacatgatcc cccatgttgt gcaaaaaagc ggttagctcc 3540
ttcggtcctc cgatcgttgt cagaagtaag ttggccgcag tgttatcact catggttatg 3600
gcagcactgc ataattctct tactgtcatg ccatccgtaa gatgcttttc tgtgactggt 3660
gagtactcaa ccaagtcatt ctgagaatag tgtatgcggc gaccgagttg ctcttgcccg 3720
gcgtcaatac gggataatac cgcgccacat agcagaactt taaaagtgct catcattgga 3780
aaacgttctt cggggcgaaa actctcaagg atcttaccgc tgttgagatc cagttcgatg 3840
taacccactc gtgcacccaa ctgatcttca gcatctttta ctttcaccag cgtttctggg 3900
tgagcaaaaa caggaaggca aaatgccgca aaaaagggaa taagggcgac acggaaatgt 3960
tgaatactca tactcttcct ttttcaatat tattgaagca tttatcaggg ttattgtctc 4020
atgagcggat acatatttga atgtatttag aaaaataaac aaataggggt tccgcgcaca 4080
tttccccgaa aagtgccacc taaattgtaa gcgttaatat tttgttaaaa ttcgcgttaa 4140
atttttgtta aatcagctca ttttttaacc aataggccga aatcggcaaa atcccttata 4200
aatcaaaaga atagaccgag atagggttga gtgttgttcc agtttggaac aagagtccac 4260
tattaaagaa cgtggactcc aacgtcaaag ggcgaaaaac cgtctatcag ggcgatggcc 4320
cactacgtga accatcaccc taatcaagtt ttttggggtc gaggtgccgt aaagcactaa 4380
atcggaaccc taaagggagc ccccgattta gagcttgacg gggaaagccg gcgaacgtgg 4440
cgagaaagga agggaagaaa gcgaaaggag cgggcgctag ggcgctggca agtgtagcgg 4500
tcacgctgcg cgtaaccacc acacccgccg cgcttaatgc gccgctacag ggcgcgtccc 4560
attcgccatt caggctgcgc aactgttggg aagggcgatc ggtgcgggcc tcttcgctat 4620
tacgccagct ggcgaaaggg ggatgtgctg caaggcgatt aagttgggta acgccagggt 4680
tttcccagtc acgacgttgt aaaacgacgg ccagtgagcg cgcgtaatac gactcactat 4740
agggcgaatt gggtaccggg ccccccctcg aggtcgacgg tatcgataag cttgatatcg 4800
aattcctgca gcccggggga tccgccc 4827

<210> SEQ ID NO 100
<211> LENGTH: 15114
<212> TYPE: DNA
<213> ORGANISM: Artificial Sequence
<220> FEATURE:
<223> OTHER INFORMATION: sequence of pKR91

<400> SEQUENCE: 100
gatctggcgc gccaagcttt tgatccatgc ccttcatttg ccgcttatta attaatttgg 60
taacagtccg tactaatcag ttacttatcc ttcccccatc ataattaatc ttggtagtct 120
cgaatgccac aacactgact agtctcttgg atcataagaa aaagccaagg aacaaaagaa 180
gacaaaacac aatgagagta tcctttgcat agcaatgtct aagttcataa aattcaaaca 240
aaaacgcaat cacacacagt ggacatcact tatccactag ctgatcagga tcgccgcgtc 300
aagaaaaaaa aactggaccc caaaagccat gcacaacaac acgtactcac aaaggtgtca 360
atcgagcagc ccaaaacatt caccaactca acccatcatg agccctcaca tttgttgttt 420
ctaacccaac ctcaaactcg tattctcttc cgccacctca tttttgttta tttcaacacc 480
cgtcaaactg catgccaccc cgtggccaaa tgtccatgca tgttaacaag acctatgact 540
ataaatagct gcaatctcgg cccaggtttt catcatcaag aaccagttca atatcctagt 600
acaccgtatt aaagaattta agatatactg cggccgcaag tatgaactaa aatgcatgta 660
ggtgtaagag ctcatggaga gcatggaata ttgtatccga ccatgtaaca gtataataac 720
tgagctccat ctcacttctt ctatgaataa acaaaggatg ttatgatata ttaacactct 780
atctatgcac cttattgttc tatgataaat ttcctcttat tattataaat catctgaatc 840
gtgacggctt atggaatgct tcaaatagta caaaaacaaa tgtgtactat aagactttct 900

```
aaacaattct aaccttagca ttgtgaacga gacataagtg ttaagaagac ataacaatta    960
taatggaaga agtttgtctc catttatata ttatatatta cccacttatg tattatatta   1020
ggatgttaag gagacataac aattataaag agagaagttt gtatccattt atatattata   1080
tactacccat ttatatatta tacttatcca cttatttaat gtctttataa ggtttgatcc   1140
atgatatttc taatatttta gttgatatgt atatgaaagg gtactatttg aactctctta   1200
ctctgtataa aggttggatc atccttaaag tgggtctatt taattttatt gcttcttaca   1260
gataaaaaaa aaattatgag ttggtttgat aaaatattga aggatttaaa ataataataa   1320
ataacatata atatatgtat ataaatttat tataatataa catttatcta taaaaaagta   1380
aatattgtca taaatctata caatcgttta gccttgctgg acgaatctca attatttaaa   1440
cgagagtaaa catatttgac tttttggtta tttaacaaat tattatttaa cactatatga   1500
aatttttttt tttatcagca aagaataaaa ttaaattaag aaggacaatg gtgtcccaat   1560
ccttatacaa ccaacttcca caagaaagtc aagtcagaga caacaaaaaa acaagcaaag   1620
gaaatttttt aatttgagtt gtcttgtttg ctgcataatt tatgcagtaa aacactacac   1680
ataacccttt tagcagtaga gcaatggttg accgtgtgct tagcttcttt tattttattt   1740
ttttatcagc aaagaataaa taaaataaaa tgagacactt cagggatgtt tcaacaagct   1800
tggatctcct gcaggatctg gccggccgga tctcgtacgg atccgtcgac ggcgcgcctc   1860
gagtgggcgg atcccccggg ctgcaggaat tcactggccg tcgttttaca acgtcgtgac   1920
tgggaaaacc ctggcgttac ccaacttaat cgccttgcag cacatccccc tttcgccagc   1980
tggcgtaata gcgaagaggc ccgcaccgat cgcccttccc aacagttgcg cagcctgaat   2040
ggcgaatgga tcgatccatc gcgatgtacc ttttgttagt cagcctctcg attgctcatc   2100
gtcattacac agtaccgaag tttgatcgat ctagtaacat agatgacacc gcgcgcgata   2160
atttatccta gtttgcgcgc tatattttgt tttctatcgc gtattaaatg tataattgcg   2220
ggactctaat cataaaaacc catctcataa ataacgtcat gcattacatg ttaattatta   2280
catgcttaac gtaattcaac agaaattata tgataatcat cgcaagaccg gcaacaggat   2340
tcaatcttaa gaaactttat tgccaaatgt ttgaacgatc tgcttcgacg cactccttct   2400
ttactccacc atctcgtcct tattgaaaac gtgggtagca ccaaaacgaa tcaagtcgct   2460
ggaactgaag ttaccaatca cgctggatga tttgccagtt ggattaatct tgcctttccc   2520
cgcatgaata atattgatga atgcatgcgt gaggggtagt tcgatgttgg caatagctgc   2580
aattgccgcg acatcctcca acgagcataa ttcttcagaa aaatagcgat gttccatgtt   2640
gtcagggcat gcatgatgca cgttatgagg tgacggtgct aggcagtatt ccctcaaagt   2700
ttcatagtca gtatcatatt catcattgca ttcctgcaag agagaattga gacgcaatcc   2760
acacgctgcg gcaaccttcc ggcgttcgtg gtctatttgc tcttggacgt tgcaaacgta   2820
agtgttggat cgatccgggg tgggcgaaga actccagcat gagatccccg cgctggagga   2880
tcatccagcc ggcgtcccgg aaaacgattc cgaagcccaa cctttcatag aaggcggcgg   2940
tggaatcgaa atctcgtgat ggcaggttgg gcgtcgcttg gtcggtcatt tcgaacccca   3000
gagtcccgct cagaagaact cgtcaagaag gcgatagaag gcgatgcgct gcgaatcggg   3060
agcggcgata ccgtaaagca cgaggaagcg gtcagcccat tcgccgccaa gctcttcagc   3120
aatatcacgg gtagccaacg ctatgtcctg atagcggtcc gccacaccca gccggccaca   3180
gtcgatgaat ccagaaaagc ggccattttc caccatgata ttcggcaagc aggcatcgcc   3240
```

-continued

```
atgggtcacg acgagatcct cgccgtcggg catgcgcgcc ttgagcctgg cgaacagttc   3300
ggctggcgcg agcccctgat gctcttcgtc cagatcatcc tgatcgacaa gaccggcttc   3360
catccgagta cgtgctcgct cgatgcgatg tttcgcttgg tggtcgaatg ggcaggtagc   3420
cggatcaagc gtatgcagcc gccgcattgc atcagccatg atggatactt tctcggcagg   3480
agcaaggtga gatgacagga gatcctgccc cggcacttcg cccaatagca gccagtccct   3540
tcccgcttca gtgacaacgt cgagcacagc tgcgcaagga acgcccgtcg tggccagcca   3600
cgatagccgc gctgcctcgt cctgcagttc attcagggca ccggacaggt cggtcttgac   3660
aaaaagaacc gggcgcccct gcgctgacag ccggaacacg gcggcatcag agcagccgat   3720
tgtctgttgt gcccagtcat agccgaatag cctctccacc caagcggccg gagaacctgc   3780
gtgcaatcca tcttgttcaa tcatgcgaaa cgatccccgc aagcttggag actggtgatt   3840
tcagcgtgtc ctctccaaat gaaatgaact tccttatata gaggaagggt cttgcgaagg   3900
atagtgggat tgtgcgtcat cccttacgtc agtggagata tcacatcaat ccacttgctt   3960
tgaagacgtg gttggaacgt cttctttttc cacgatgctc ctcgtgggtg ggggtccatc   4020
tttgggacca ctgtcggcag aggcatcttc aacgatggcc tttcctttat cgcaatgatg   4080
gcatttgtag gagccacctt ccttttccac tatcttcaca ataaagtgac agatagctgg   4140
gcaatggaat ccgaggaggt ttccggatat taccctttgt tgaaaagtct caattgccct   4200
ttggtcttct gagactgtat ctttgatatt tttggagtag acaagcgtgt cgtgctccac   4260
catgttgacg aagattttct tcttgtcatt gagtcgtaag agactctgta tgaactgttc   4320
gccagtcttt acggcgagtt ctgttaggtc ctctatttga atctttgact ccatggcctt   4380
tgattcagtg ggaactacct ttttagagac tccaatctct attacttgcc ttggtttgtg   4440
aagcaagcct tgaatcgtcc atactggaat agtacttctg atcttgagaa atatatcttt   4500
ctctgtgttc ttgatgcagt tagtcctgaa tcttttgact gcatctttaa ccttcttggg   4560
aaggtatttg atctcctgga gattattgct cgggtagatc gtcttgatga gacctgctgc   4620
gtaagcctct ctaaccatct gtgggttagc attctttctg aaattgaaaa ggctaatctt   4680
ctcattatca gtggtgaaca tggtatcgtc accttctccg tcgaacttcc tgactagatc   4740
gtagagatag aggaagtcgt ccattgtgat ctctggggca aaggagatct gaattaattc   4800
gatatggtgg atttatcaca aatgggaccc gccgccgaca gaggtgtgat gttaggccag   4860
gactttgaaa atttgcgcaa ctatcgtata gtggccgaca aattgacgcc gagttgacag   4920
actgcctagc atttgagtga attatgtgag gtaatgggct acactgaatt ggtagctcaa   4980
actgtcagta tttatgtata tgagtgtata ttttcgcata atctcagacc aatctgaaga   5040
tgaaatgggt atctgggaat ggcgaaatca aggcatcgat cgtgaagttt ctcatctaag   5100
cccccatttg gacgtgaatg tagacacgtc gaaataaaga tttccgaatt agaataattt   5160
gtttattgct ttcgcctata aatacgacgg atcgtaattt gtcgttttat caaaatgtac   5220
tttcatttta taataacgct gcggacatct acatttttga attgaaaaaa aattggtaat   5280
tactctttct ttttctccat attgaccatc atactcattg ctgatccatg tagatttccc   5340
ggacatgaag ccatttacaa ttgaatatat cctgccgccg ctgccgcttt gcacccggtg   5400
gagcttgcat gttggtttct acgcagaact gagccggtta ggcagataat ttccattgag   5460
aactgagcca tgtgcacctt ccccccaaca cggtgagcga cggggcaacg gagtgatcca   5520
catgggactt ttaaacatca tccgtcggat ggcgttgcga gagaagcagt cgatccgtga   5580
gatcagccga cgcaccgggc aggcgcgcaa cacgatcgca aagtatttga acgcaggtac   5640
```

-continued

```
aatcgagccg acgttcacgc ggaacgacca agcaagctag ctttaatgcg gtagtttatc   5700
acagttaaat tgctaacgca gtcaggcacc gtgtatgaaa tctaacaatg cgctcatcgt   5760
catcctcggc accgtcaccc tggatgctgt aggcataggc ttggttatgc cggtactgcc   5820
gggcctcttg cgggatatcg tccattccga cagcatcgcc agtcactatg gcgtgctgct   5880
agcgctatat gcgttgatgc aatttctatg cgcacccgtt ctcggagcac tgtccgaccg   5940
ctttggccgc cgcccagtcc tgctcgcttc gctacttgga gccactatcg actacgcgat   6000
catggcgacc acacccgtcc tgtggtccaa cccctccgct gctatagtgc agtcggcttc   6060
tgacgttcag tgcagccgtc ttctgaaaac gacatgtcgc acaagtccta agttacgcga   6120
caggctgccg ccctgccctt ttcctggcgt tttcttgtcg cgtgttttag tcgcataaag   6180
tagaatactt gcgactagaa ccggagacat tacgccatga acaagagcgc cgccgctggc   6240
ctgctgggct atgcccgcgt cagcaccgac gaccaggact tgaccaacca acgggccgaa   6300
ctgcacgcgg ccggctgcac caagctgttt tccgagaaga tcaccggcac caggcgcgac   6360
cgcccggagc tggccaggat gcttgaccac ctacgccctg gcgacgttgt gacagtgacc   6420
aggctagacc gcctggcccg cagcacccgc gacctactgg acattgccga gcgcatccag   6480
gaggccggcg cgggcctgcg tagcctggca gagccgtggg ccgacaccac cacgccggcc   6540
ggccgcatgg tgttgaccgt gttcgccggc attgccgagt tcgagcgttc cctaatcatc   6600
gaccgcaccc ggagcgggcg cgaggccgcc aaggcccgag gcgtgaagtt tggcccccgc   6660
cctaccctca ccccggcaca gatcgcgcac gcccgcgagc tgatcgacca ggaaggccgc   6720
accgtgaaag aggcggctgc actgcttggc gtgcatcgct cgaccctgta ccgcgcactt   6780
gagcgcagcg aggaagtgac gcccaccgag gccaggcggc gcggtgcctt ccgtgaggac   6840
gcattgaccg aggccgacgc cctggcggcc gccgagaatg aacgccaaga ggaacaagca   6900
tgaaaccgca ccaggacggc caggacgaac cgtttttcat taccgaagag atcgaggcgg   6960
agatgatcgc ggccgggtac gtgttcgagc cgcccgcgca cgtctcaacc gtgcggctgc   7020
atgaaatcct ggccggtttg tctgatgcca agctggcggc ctggccggcc agcttggccg   7080
ctgaagaaac cgagcgccgc cgtctaaaaa ggtgatgtgt atttgagtaa aacagcttgc   7140
gtcatgcggt cgctgcgtat atgatgcgat gagtaaataa acaaatacgc aagggaacgc   7200
atgaagttat cgctgtactt aaccagaaag gcgggtcagg caagacgacc atcgcaaccc   7260
atctagcccg cgccctgcaa ctcgccgggg ccgatgttct gttagtcgat tccgatcccc   7320
agggcagtgc ccgcgattgg gcggccgtgc gggaagatca accgctaacc gttgtcggca   7380
tcgaccgccc gacgattgac cgcgacgtga aggccatcgg ccggcgcgac ttcgtagtga   7440
tcgacggagc gccccaggcg gcggacttgg ctgtgtccgc gatcaaggca gccgacttcg   7500
tgctgattcc ggtgcagcca agcccttacg acatatgggc caccgccgac ctggtggagc   7560
tggttaagca gcgcattgag gtcacggatg gaaggctaca agcggccttt gtcgtgtcgc   7620
gggcgatcaa aggcacgcgc atcggcggtg aggttgccga ggcgctggcc gggtacgagc   7680
tgcccattct tgagtcccgt atcacgcagc gcgtgagcta cccaggcact gccgccgccg   7740
gcacaaccgt tcttgaatca gaacccgagg gcgacgctgc ccgcgaggtc caggcgctgg   7800
ccgctgaaat taaatcaaaa ctcatttgag ttaatgaggt aaagagaaaa tgagcaaaag   7860
cacaaacacg ctaagtgccg gccgtccgag cgcacgcagc agcaaggctg caacgttggc   7920
cagcctggca gacacgccag ccatgaagcg ggtcaacttt cagttgccgg cggaggatca   7980
```

-continued

```
caccaagctg aagatgtacg cggtacgcca aggcaagacc attaccgagc tgctatctga   8040
atacatcgcg cagctaccag agtaaatgag caaatgaata aatgagtaga tgaattttag   8100
cggctaaagg aggcggcatg gaaaatcaag aacaaccagg caccgacgcc gtggaatgcc   8160
ccatgtgtgg aggaacgggc ggttggccag gcgtaagcgg ctgggttgtc tgccggccct   8220
gcaatggcac tggaaccccc aagcccgagg aatcggcgtg agcggtcgca aaccatccgg   8280
cccggtacaa atcggcgcgg cgctgggtga tgacctggtg gagaagttga aggccgcgca   8340
ggccgcccag cggcaacgca tcgaggcaga agcacgcccc ggtgaatcgt ggcaagcggc   8400
cgctgatcga atccgcaaag aatcccggca accgccggca gccggtgcgc cgtcgattag   8460
gaagccgccc aagggcgacg agcaaccaga tttttttcgtt ccgatgctct atgacgtggg   8520
cacccgcgat agtcgcagca tcatggacgt ggccgttttc cgtctgtcga agcgtgaccg   8580
acgagctggc gaggtgatcc gctacgagct tccagacggg cacgtagagg tttccgcagg   8640
gccggccggc atggccagtg tgtgggatta cgacctggta ctgatggcgg tttcccatct   8700
aaccgaatcc atgaaccgat accgggaagg gaagggagac aagcccggcc gcgtgttccg   8760
tccacacgtt gcggacgtac tcaagttctg ccggcgagcc gatggcggaa agcagaaaga   8820
cgacctggta gaaacctgca ttcggttaaa caccacgcac gttgccatgc agcgtacgaa   8880
gaaggccaag aacggccgcc tggtgacggt atccgagggt gaagccttga ttagccgcta   8940
caagatcgta aagagcgaaa ccgggcggcc ggagtacatc gagatcgagc tagctgattg   9000
gatgtaccgc gagatcacag aaggcaagaa cccggacgtg ctgacggttc accccgatta   9060
ctttttgatc gatcccggca tcggccgttt tctctaccgc ctggcacgcc gcgccgcagg   9120
caaggcagaa gccagatggt tgttcaagac gatctacgaa cgcagtggca gcgccggaga   9180
gttcaagaag ttctgtttca ccgtgcgcaa gctgatcggg tcaaatgacc tgccggagta   9240
cgatttgaag gaggaggcgg ggcaggctgg cccgatccta gtcatgcgct accgcaacct   9300
gatcgagggc gaagcatccg ccggttccta atgtacggag cagatgctag ggcaaattgc   9360
cctagcaggg gaaaaaggtc gaaaaggtct ctttcctgtg gatagcacgt acattgggaa   9420
cccaaagccg tacattggga accggaaccc gtacattggg aacccaaagc cgtacattgg   9480
gaaccggtca cacatgtaag tgactgatat aaaagagaaa aaaggcgatt tttccgccta   9540
aaactcttta aaacttatta aaactcttaa aacccgcctg gcctgtgcat aactgtctgg   9600
ccagcgcaca gccgaagagc tgcaaaaagc gcctaccctt cggtcgctgc gctccctacg   9660
ccccgccgct tcgcgtcggc ctatcgcggc cgctggccgc tcaaaaatgg ctggcctacg   9720
gccaggcaat ctaccagggc gcggacaagc cgcgccgtcg ccactcgacc gccggcgccc   9780
acatcaaggc accctgcctc gcgcgtttcg gtgatgacgg tgaaaacctc tgacacatgc   9840
agctcccgga gacggtcaca gcttgtctgt aagcggatgc cgggagcaga caagcccgtc   9900
agggcgcgtc agcgggtgtt ggcgggtgtc ggggcgcagc catgacccag tcacgtagcg   9960
atagcggagt gtatactggc ttaactatgc ggcatcagag cagattgtac tgagagtgca  10020
ccatatgcgg tgtgaaatac cgcacagatg cgtaaggaga aaataccgca tcaggcgctc  10080
ttccgcttcc tcgctcactg actcgctgcg ctcggtcgtt cggctgcggc gagcggtatc  10140
agctcactca aaggcggtaa tacggttatc cacagaatca ggggataacg caggaaagaa  10200
catgtgagca aaaggccagc aaaaggccag gaaccgtaaa aaggccgcgt tgctggcgtt  10260
tttccatagg ctccgccccc ctgacgagca tcacaaaaat cgacgctcaa gtcagaggtg  10320
gcgaaacccg acaggactat aaagatacca ggcgtttccc cctggaagct ccctcgtgcg  10380
```

```
ctctcctgtt ccgaccctgc cgcttaccgg atacctgtcc gcctttctcc cttcgggaag  10440
cgtggcgctt tctcatagct cacgctgtag gtatctcagt tcggtgtagg tcgttcgctc  10500
caagctgggc tgtgtgcacg aaccccccgt tcagcccgac cgctgcgcct tatccggtaa  10560
ctatcgtctt gagtccaacc cggtaagaca cgacttatcg ccactggcag cagccactgg  10620
taacaggatt agcagagcga ggtatgtagg cggtgctaca gagttcttga agtggtggcc  10680
taactacggc tacactagaa ggacagtatt tggtatctgc gctctgctga agccagttac  10740
cttcggaaaa agagttggta gctcttgatc cggcaaacaa accaccgctg gtagcggtgg  10800
tttttttgtt tgcaagcagc agattacgcg cagaaaaaaa ggatctcaag aagatccttt  10860
gatcttttct acggggtctg acgctcagtg gaacgaaaac tcacgttaag ggattttggt  10920
catgagatta tcaaaaagga tcttcaccta gatcctttta aattaaaaat gaagttttaa  10980
atcaatctaa agtatatatg agtaaacttg gtctgacagt taccaatgct taatcagtga  11040
ggcacctatc tcagcgatct gtctatttcg ttcatccata gttgcctgac tccccgtcgt  11100
gtagataact acgatacggg agggcttacc atctggcccc agtgctgcaa tgataccgcg  11160
agacccacgc tcaccggctc cagatttatc agcaataaac cagccagccg gaagggccga  11220
gcgcagaagt ggtcctgcaa ctttatccgc ctccatccag tctattaatt gttgccggga  11280
agctagagta agtagttcgc cagttaatag tttgcgcaac gttgttgcca ttgctacagg  11340
catcgtggtg tcacgctcgt cgtttggtat ggcttcattc agctccggtt cccaacgatc  11400
aaggcgagtt acatgatccc ccatgttgtg caaaaaagcg gttagctcct tcggtcctcc  11460
gatcgttgtc agaagtaagt tggccgcagt gttatcactc atggttatgg cagcactgca  11520
taattctctt actgtcatgc catccgtaag atgcttttct gtgactggtg agtactcaac  11580
caagtcattc tgagaatagt gtatgcggcg accgagttgc tcttgcccgg cgtcaacacg  11640
ggataatacc gcgccacata gcagaacttt aaaagtgctc atcattggaa aagacctgca  11700
gggggggggg ggcgctgagg tctgcctcgt gaagaaggtg ttgctgactc ataccaggcc  11760
tgaatcgccc catcatccag ccagaaagtg agggagccac ggttgatgag agctttgttg  11820
taggtggacc agttggtgat tttgaacttt tgctttgcca cggaacggtc tgcgttgtcg  11880
ggaagatgcg tgatctgatc cttcaactca gcaaaagttc gatttattca acaaagccgc  11940
cgtcccgtca agtcagcgta atgctctgcc agtgttacaa ccaattaacc aattctgatt  12000
agaaaaactc atcgagcatc aaatgaaact gcaatttatt catatcagga ttatcaatac  12060
catatttttg aaaaagccgt ttctgtaatg aaggagaaaa ctcaccgagg cagttccata  12120
ggatggcaag atcctggtat cggtctgcga ttccgactcg tccaacatca atacaaccta  12180
ttaatttccc ctcgtcaaaa ataaggttat caagtgagaa atcaccatga gtgacgactg  12240
aatccggtga gaatggcaaa agcttatgca tttctttcca gacttgttca acaggccagc  12300
cattacgctc gtcatcaaaa tcactcgcat caaccaaacc gttattcatt cgtgattgcg  12360
cctgagcgag acgaaatacg cgatcgctgt taaaaggaca attacaaaca ggaatcgaat  12420
gcaaccggcg caggaacact gccagcgcat caacaatatt ttcacctgaa tcaggatatt  12480
cttctaatac ctggaatgct gttttcccgg ggatcgcagt ggtgagtaac catgcatcat  12540
caggagtacg gataaaatgc ttgatggtcg gaagaggcat aaattccgtc agccagttta  12600
gtctgaccat ctcatctgta acatcattgg caacgctacc tttgccatgt ttcagaaaca  12660
actctggcgc atcgggcttc ccatacaatc gatagattgt cgcacctgat tgcccgacat  12720
```

```
tatcgcgagc ccatttatac ccatataaat cagcatccat gttggaattt aatcgcggcc  12780
tcgagcaaga cgtttcccgt tgaatatggc tcataacacc ccttgtatta ctgtttatgt  12840
aagcagacag ttttattgtt catgatgata tatttttatc ttgtgcaatg taacatcaga  12900
gattttgaga cacaacgtgg ctttcccccc ccccctgca ggtcaattcg gtcgatatgg  12960
ctattacgaa gaaggctcgt gcgcggagtc ccgtgaactt tcccacgcaa caagtgaacc  13020
gcaccgggtt tgccggaggc catttcgtta aaatgcgcag ccatggctgc ttcgtccagc  13080
atggcgtaat actgatcctc gtcttcggct ggcggtatat tgccgatggg cttcaaaagc  13140
cgccgtggtt gaaccagtct atccattcca aggtagcgaa ctcgaccgct tcgaagctcc  13200
tccatggtcc acgccgatga atgacctcgg ccttgtaaag accgttgatc gcttctgcga  13260
gggcgttgtc gtgctgtcgc cgacgcttcc gatagatggc tcgatacctg cttctgccaa  13320
ccgctcggaa tagcgaaagg acacgtattg aacaccgcga tccgagtgat gcactaggcc  13380
gccatgagcg ggacgccgat catgatgagc ctcctcgagg gcatcgagga caaagcctgc  13440
atgtgctgtc cggctcgccc gccatccgac aatgcgacgg gcgaagacgt cgatcacgaa  13500
ggccacgtag acgaagccct cccaagtggc gacataagta cggacatgcg caaaggcttt  13560
cccggtttgt cgctgatggt gcaagagacg ctgaagcgcg atccgatgcg caggcatctg  13620
ttcgtcttcc gcggtcgtgg cggtggcctg atcaaggtca ctcgccgaag agctgcatga  13680
ttggctcgaa accgagcggg ggaaattgtc gcgcagttct cccgtcgccg aggcgataaa  13740
ttacatgctc aagcgatggg atggcattac gtcattcctc gatgacggcc cgatttgcct  13800
gacgaacaat gctgccgaac gaacgctcag aggctatgta ctcggcagga agtcatggct  13860
gtttgccgga tcggatcgtt gtgctgaacg tgcggcgttc atggcgacac tgatcatgag  13920
cgccaagctc aataacatcg atccgcaggc ctggcttgcc gacgtccgcg ccgaccttgc  13980
ggacgctccg atcagcaggc ttgagcaaca gctgccgtgg aactggacat ccaagacact  14040
gagtgctcag gcggcctgac ctgcggcctt caccggatac ttaccccatt atcgcagatt  14100
gcgatgaagc atcagcgtca ttcagcaatc ttgccaaagt atgcaggctc gcgagaatcg  14160
acgtgcgaaa ccggctggtt gcgccaaaga tccgcttgcg gagcggtcga acattcatgc  14220
tgggacttca agaggtcgag tagaggaaga accggaaagg ttgcaccgga aaatatgcgt  14280
tcctttggag agcgcctcat ggacgtgaac aaatcgcccg gaccaaggat gccacggata  14340
caaaagctcg cgaagctcgg tcccgtgggt gttctgtcgt ctcgttgtac aacgaaatcc  14400
attcccattc cgcgctcaag atggcttccc ctcggcagtt catcagggct aaatcaatct  14460
agccgacttg tccggtgaaa tgggctgcac tccaacagaa acaatcaaac aaacatacac  14520
agcgacttat tcacacgagc tcaaattaca acggtatata tcctgccagt cagcatcatc  14580
acaccaaaag ttaggcccga atagtttgaa attagaaagc tcgcaattga ggtctacagg  14640
ccaaattcgc tcttagccgt acaatattac tcaccggtgc gatgcccccc atcgtaggtg  14700
aaggtggaaa ttaatgatcc atcttgagac cacaggccca caacagctac cagtttcctc  14760
aagggtccac caaaaacgta agcgcttacg tacatggtcg ataagaaaag gcaatttgta  14820
gatgttaaca tccaacgtcg ctttcaggga tcgatccaat acgcaaaccg cctctccccg  14880
cgcgttggcc gattcattaa tgcagctggc acgacaggtt tcccgactgg aaagcgggca  14940
gtgagcgcaa cgcaattaat gtgagttagc tcactcatta ggcaccccag gctttacact  15000
ttatgcttcc ggctcgtatg ttgtgtggaa ttgtgagcgg ataacaattt cacacaggaa  15060
acagctatga ccatgattac gccaagcttg catgcctgca ggtcgactct agag        15114
```

<210> SEQ ID NO 101
<211> LENGTH: 13268
<212> TYPE: DNA
<213> ORGANISM: Artificial Sequence
<220> FEATURE:
<223> OTHER INFORMATION: sequence of pKR92

<400> SEQUENCE: 101
cgcgcctcga gtgggcggat cccccgggct gcaggaattc actggccgtc gttttacaac 60
gtcgtgactg ggaaaaccct ggcgttaccc aacttaatcg ccttgcagca catcccctt 120 tcgccagctg gcgtaatagc gaagaggccc gcaccgatcg cccttcccaa cagttgcgca 180
gcctgaatgg cgaatggatc gatccatcgc gatgtacctt ttgttagtca gcctctcgat 240
tgctcatcgt cattacacag taccgaagtt tgatcgatct agtaacatag atgacaccgc 300
gcgcgataat ttatcctagt ttgcgcgcta tattttgttt tctatcgcgt attaaatgta 360
taattgcggg actctaatca taaaaaccca tctcataaat aacgtcatgc attacatgtt 420
aattattaca tgcttaacgt aattcaacag aaattatatg ataatcatcg caagaccggc 480
aacaggattc aatcttaaga aactttattg ccaaatgttt gaacgatctg cttcgacgca 540
ctccttcttt actccaccat ctcgtcctta ttgaaaacgt gggtagcacc aaaacgaatc 600
aagtcgctgg aactgaagtt accaatcacg ctggatgatt tgccagttgg attaatcttg 660
cctttccccg catgaataat attgatgaat gcatgcgtga ggggtagttc gatgttggca 720
atagctgcaa ttgccgcgac atcctccaac gagcataatt cttcagaaaa atagcgatgt 780
tccatgttgt cagggcatgc atgatgcacg ttatgaggtg acggtgctag gcagtattcc 840
ctcaaagttt catagtcagt atcatattca tcattgcatt cctgcaagag agaattgaga 900
cgcaatccac acgctgcggc aaccttccgg cgttcgtggt ctatttgctc ttggacgttg 960
caaacgtaag tgttggatcg atccggggtg ggcgaagaac tccagcatga gatccccgcg 1020
ctggaggatc atccagccgg cgtcccggaa aacgattccg aagcccaacc tttcatagaa 1080
ggcggcggtg gaatcgaaat ctcgtgatgg caggttgggc gtcgcttggt cggtcatttc 1140
gaaccccaga gtcccgctca gaagaactcg tcaagaaggc gatagaaggc gatgcgctgc 1200
gaatcgggag cggcgatacc gtaaagcacg aggaagcggt cagcccattc gccgccaagc 1260
tcttcagcaa tatcacgggt agccaacgct atgtcctgat agcggtccgc cacacccagc 1320
cggccacagt cgatgaatcc agaaaagcgg ccattttcca ccatgatatt cggcaagcag 1380
gcatcgccat gggtcacgac gagatcctcg ccgtcgggca tgcgcgcctt gagcctggcg 1440
aacagttcgg ctggcgcgag cccctgatgc tcttcgtcca gatcatcctg atcgacaaga 1500
ccggcttcca tccgagtacg tgctcgctcg atgcgatgtt tcgcttggtg gtcgaatggg 1560
caggtagccg gatcaagcgt atgcagccgc cgcattgcat cagccatgat ggatactttc 1620
tcggcaggag caaggtgaga tgacaggaga tcctgccccg gcacttcgcc caatagcagc 1680
cagtcccttc ccgcttcagt gacaacgtcg agcacagctg cgcaaggaac gcccgtcgtg 1740
gccagccacg atagccgcgc tgcctcgtcc tgcagttcat tcagggcacc ggacaggtcg 1800
gtcttgacaa aaagaaccgg gcgcccctgc gctgacagcc ggaacacggc ggcatcagag 1860
cagccgattg tctgttgtgc ccagtcatag ccgaatagcc tctccaccca agcggccgga 1920
gaacctgcgt gcaatccatc ttgttcaatc atgcgaaacg atccccgcaa gcttggagac 1980
tggtgatttc agcgtgtcct ctccaaatga aatgaacttc cttatataga ggaagggtct 2040

-continued

```
tgcgaaggat agtgggattg tgcgtcatcc cttacgtcag tggagatatc acatcaatcc   2100
acttgctttg aagacgtggt tggaacgtct tctttttcca cgatgctcct cgtgggtggg   2160
ggtccatctt tgggaccact gtcggcagag gcatcttcaa cgatggcctt tcctttatcg   2220
caatgatggc atttgtagga gccaccttcc ttttccacta tcttcacaat aaagtgacag   2280
atagctgggc aatggaatcc gaggaggttt ccggatatta ccctttgttg aaaagtctca   2340
attgcccttt ggtcttctga gactgtatct ttgatatttt tggagtagac aagcgtgtcg   2400
tgctccacca tgttgacgaa gattttcttc ttgtcattga gtcgtaagag actctgtatg   2460
aactgttcgc cagtctttac ggcgagttct gttaggtcct ctatttgaat ctttgactcc   2520
atggcctttg attcagtggg aactaccttt ttagagactc caatctctat tacttgcctt   2580
ggtttgtgaa gcaagccttg aatcgtccat actggaatag tacttctgat cttgagaaat   2640
atatctttct ctgtgttctt gatgcagtta gtcctgaatc ttttgactgc atctttaacc   2700
ttcttgggaa ggtatttgat ctcctggaga ttattgctcg ggtagatcgt cttgatgaga   2760
cctgctgcgt aagcctctct aaccatctgt gggttagcat tctttctgaa attgaaaagg   2820
ctaatcttct cattatcagt ggtgaacatg gtatcgtcac cttctccgtc gaacttcctg   2880
actagatcgt agagatagag gaagtcgtcc attgtgatct ctggggcaaa ggagtctgaa   2940
ttaattcgat atggtggatt tatcacaaat gggacccgcc gccgacagag gtgtgatgtt   3000
aggccaggac tttgaaaatt tgcgcaacta tcgtatagtg gccgacaaat tgacgccgag   3060
ttgacagact gcctagcatt tgagtgaatt atgtgaggta atgggctaca ctgaattggt   3120
agctcaaact gtcagtattt atgtatatga gtgtatattt tcgcataatc tcagaccaat   3180
ctgaagatga aatgggtatc tgggaatggc gaaatcaagg catcgatcgt gaagtttctc   3240
atctaagccc ccatttggac gtgaatgtag acacgtcgaa ataaagattt ccgaattaga   3300
ataatttgtt tattgctttc gcctataaat acgacggatc gtaatttgtc gttttatcaa   3360
aatgtacttt cattttataa taacgctgcg gacatctaca tttttgaatt gaaaaaaaat   3420
tggtaattac tctttctttt tctccatatt gaccatcata ctcattgctg atccatgtag   3480
atttcccgga catgaagcca tttacaattg aatatatcct gccgccgctg ccgctttgca   3540
cccggtggag cttgcatgtt ggtttctacg cagaactgag ccggttaggc agataatttc   3600
cattgagaac tgagccatgt gcaccttccc cccaacacgg tgagcgacgg ggcaacggag   3660
tgatccacat gggactttta aacatcatcc gtcggatggc gttgcgagag aagcagtcga   3720
tccgtgagat cagccgacgc accgggcagg cgcgcaacac gatcgcaaag tatttgaacg   3780
caggtacaat cgagccgacg ttcacgcgga acgaccaagc aagctagctt taatgcggta   3840
gtttatcaca gttaaattgc taacgcagtc aggcaccgtg tatgaaatct aacaatgcgc   3900
tcatcgtcat cctcggcacc gtcaccctgg atgctgtagg cataggcttg gttatgccgg   3960
tactgccggg cctcttgcgg gatatcgtcc attccgacag catcgccagt cactatggcg   4020
tgctgctagc gctatatgcg ttgatgcaat ttctatgcgc acccgttctc ggagcactgt   4080
ccgaccgctt tggccgccgc ccagtcctgc tcgcttcgct acttggagcc actatcgact   4140
acgcgatcat ggcgaccaca cccgtcctgt ggtccaaccc ctccgctgct atagtgcagt   4200
cggcttctga cgttcagtgc agccgtcttc tgaaaacgac atgtcgcaca agtcctaagt   4260
tacgcgacag gctgccgccc tgccctttc ctggcgtttt cttgtcgcgt gttttagtcg   4320
cataaagtag aatacttgcg actagaaccg gagacattac gccatgaaca agagcgccgc   4380
cgctggcctg ctgggctatg cccgcgtcag caccgacgac caggacttga ccaaccaacg   4440
```

ggccgaactg cacgcggccg gctgcaccaa gctgttttcc gagaagatca ccggcaccag 4500
gcgcgaccgc ccggagctgg ccaggatgct tgaccaccta cgccctggcg acgttgtgac 4560
agtgaccagg ctagaccgcc tggcccgcag cacccgcgac ctactggaca ttgccgagcg 4620
catccaggag gccggcgcgg gcctgcgtag cctggcagag ccgtgggccg acaccaccac 4680
gccggccggc cgcatggtgt tgaccgtgtt cgccggcatt gccgagttcg agcgttccct 4740
aatcatcgac cgcacccgga gcgggcgcga ggccgccaag gcccgaggcg tgaagtttgg 4800
cccccgccct accctcaccc cggcacagat cgcgcacgcc cgcgagctga tcgaccagga 4860
aggccgcacc gtgaaagagg cggctgcact gcttggcgtg catcgctcga ccctgtaccg 4920
cgcacttgag cgcagcgagg aagtgacgcc caccgaggcc aggcggcgcg gtgccttccg 4980
tgaggacgca ttgaccgagg ccgacgccct ggcggccgcc gagaatgaac gccaagagga 5040
acaagcatga aaccgcacca ggacggccag gacgaaccgt ttttcattac cgaagagatc 5100
gaggcggaga tgatcgcggc cgggtacgtg ttcgagccgc ccgcgcacgt ctcaaccgtg 5160
cggctgcatg aaatcctggc cggtttgtct gatgccaagc tggcggcctg gccggccagc 5220
ttggccgctg aagaaaccga gcgccgccgt ctaaaaaggt gatgtgtatt tgagtaaaac 5280
agcttgcgtc atgcggtcgc tgcgtatatg atgcgatgag taaataaaca aatacgcaag 5340
ggaacgcatg aagttatcgc tgtacttaac cagaaaggcg ggtcaggcaa gacgaccatc 5400
gcaacccatc tagcccgcgc cctgcaactc gccggggccg atgttctgtt agtcgattcc 5460
gatccccagg gcagtgcccg cgattgggcg gccgtgcggg aagatcaacc gctaaccgtt 5520
gtcggcatcg accgcccgac gattgaccgc gacgtgaagg ccatcggccg gcgcgacttc 5580
gtagtgatcg acggagcgcc ccaggcggcg gacttggctg tgtccgcgat caaggcagcc 5640
gacttcgtgc tgattccggt gcagccaagc ccttacgaca tatgggccac cgccgacctg 5700
gtggagctgg ttaagcagcg cattgaggtc acggatggaa ggctacaagc ggcctttgtc 5760
gtgtcgcggg cgatcaaagg cacgcgcatc ggcggtgagg ttgccgaggc gctggccggg 5820
tacgagctgc ccattcttga gtcccgtatc acgcagcgcg tgagctaccc aggcactgcc 5880
gccgccggca caaccgttct tgaatcagaa cccgagggcg acgctgcccg cgaggtccag 5940
gcgctggccg ctgaaattaa atcaaaactc atttgagtta atgaggtaaa gagaaaatga 6000
gcaaaagcac aaacacgcta agtgccggcc gtccgagcgc acgcagcagc aaggctgcaa 6060
cgttggccag cctggcagac acgccagcca tgaagcgggt caactttcag ttgccggcgg 6120
aggatcacac caagctgaag atgtacgcgg tacgccaagg caagaccatt accgagctgc 6180
tatctgaata catcgcgcag ctaccagagt aaatgagcaa atgaataaat gagtagatga 6240
attttagcgg ctaaaggagg cggcatggaa aatcaagaac aaccaggcac cgacgccgtg 6300
gaatgcccca tgtgtggagg aacgggcggt tggccaggcg taagcggctg ggttgtctgc 6360
cggccctgca atggcactgg aaccccaag cccgaggaat cggcgtgagc ggtcgcaaac 6420
catccggccc ggtacaaatc ggcgcggcgc tgggtgatga cctggtggag aagttgaagg 6480
ccgcgcaggc cgcccagcgg caacgcatcg aggcagaagc acgccccggt gaatcgtggc 6540
aagcggccgc tgatcgaatc cgcaaagaat cccggcaacc gccggcagcc ggtgcgccgt 6600
cgattaggaa gccgcccaag ggcgacgagc aaccagattt tttcgttccg atgctctatg 6660
acgtgggcac ccgcgatagt cgcagcatca tggacgtggc cgttttccgt ctgtcgaagc 6720
gtgaccgacg agctggcgag gtgatccgct acgagcttcc agacgggcac gtagaggttt 6780

-continued

```
ccgcagggcc ggccggcatg gccagtgtgt gggattacga cctggtactg atggcggttt   6840
cccatctaac cgaatccatg aaccgatacc gggaagggaa gggagacaag cccggccgcg   6900
tgttccgtcc acacgttgcg gacgtactca agttctgccg gcgagccgat ggcggaaagc   6960
agaaagacga cctggtagaa acctgcattc ggttaaacac cacgcacgtt gccatgcagc   7020
gtacgaagaa ggccaagaac ggccgcctgg tgacggtatc cgagggtgaa gccttgatta   7080
gccgctacaa gatcgtaaag agcgaaaccg ggcggccgga gtacatcgag atcgagctag   7140
ctgattggat gtaccgcgag atcacagaag gcaagaaccc ggacgtgctg acggttcacc   7200
ccgattactt tttgatcgat cccggcatcg gccgttttct ctaccgcctg gcacgccgcg   7260
ccgcaggcaa ggcagaagcc agatggttgt tcaagacgat ctacgaacgc agtggcagcg   7320
ccggagagtt caagaagttc tgtttcaccg tgcgcaagct gatcgggtca aatgacctgc   7380
cggagtacga tttgaaggag gaggcggggc aggctggccc gatcctagtc atgcgctacc   7440
gcaacctgat cgagggcgaa gcatccgccg gttcctaatg tacggagcag atgctagggc   7500
aaattgccct agcaggggaa aaaggtcgaa aaggtctctt tcctgtggat agcacgtaca   7560
ttgggaaccc aaagccgtac attgggaacc ggaacccgta cattgggaac ccaaagccgt   7620
acattgggaa ccggtcacac atgtaagtga ctgatataaa agagaaaaaa ggcgattttt   7680
ccgcctaaaa ctctttaaaa cttattaaaa ctcttaaaac ccgcctggcc tgtgcataac   7740
tgtctggcca gcgcacagcc gaagagctgc aaaaagcgcc tacccttcgg tcgctgcgct   7800
ccctacgccc cgccgcttcg cgtcggccta tcgcggccgc tggccgctca aaaatggctg   7860
gcctacggcc aggcaatcta ccagggcgcg gacaagccgc gccgtcgcca ctcgaccgcc   7920
ggcgcccaca tcaaggcacc ctgcctcgcg cgtttcggtg atgacggtga aaacctctga   7980
cacatgcagc tcccggagac ggtcacagct tgtctgtaag cggatgccgg gagcagacaa   8040
gcccgtcagg gcgcgtcagc gggtgttggc gggtgtcggg gcgcagccat gacccagtca   8100
cgtagcgata gcggagtgta tactggctta actatgcggc atcagagcag attgtactga   8160
gagtgcacca tatgcggtgt gaaataccgc acagatgcgt aaggagaaaa taccgcatca   8220
ggcgctcttc cgcttcctcg ctcactgact cgctgcgctc ggtcgttcgg ctgcggcgag   8280
cggtatcagc tcactcaaag gcggtaatac ggttatccac agaatcaggg gataacgcag   8340
gaaagaacat gtgagcaaaa ggccagcaaa aggccaggaa ccgtaaaaag gccgcgttgc   8400
tggcgttttt ccataggctc cgcccccctg acgagcatca caaaaatcga cgctcaagtc   8460
agaggtggcg aaacccgaca ggactataaa gataccaggc gtttccccct ggaagctccc   8520
tcgtgcgctc tcctgttccg accctgccgc ttaccggata cctgtccgcc tttctccctt   8580
cgggaagcgt ggcgctttct catagctcac gctgtaggta tctcagttcg gtgtaggtcg   8640
ttcgctccaa gctgggctgt gtgcacgaac cccccgttca gcccgaccgc tgcgccttat   8700
ccggtaacta tcgtcttgag tccaacccgg taagacacga cttatcgcca ctggcagcag   8760
ccactggtaa caggattagc agagcgaggt atgtaggcgg tgctacagag ttcttgaagt   8820
ggtggcctaa ctacggctac actagaagga cagtatttgg tatctgcgct ctgctgaagc   8880
cagttacctt cggaaaaaga gttggtagct cttgatccgg caaacaaacc accgctggta   8940
gcggtggttt ttttgtttgc aagcagcaga ttacgcgcag aaaaaaagga tctcaagaag   9000
atcctttgat cttttctacg gggtctgacg ctcagtggaa cgaaaactca cgttaaggga   9060
ttttggtcat gagattatca aaaaggatct tcacctagat ccttttaaat taaaaatgaa   9120
gttttaaatc aatctaaagt atatatgagt aaacttggtc tgacagttac caatgcttaa   9180
```

-continued

```
tcagtgaggc acctatctca gcgatctgtc tatttcgttc atccatagtt gcctgactcc   9240
ccgtcgtgta gataactacg atacgggagg gcttaccatc tggccccagt gctgcaatga   9300
taccgcgaga cccacgctca ccggctccag atttatcagc aataaaccag ccagccggaa   9360
gggccgagcg cagaagtggt cctgcaactt tatccgcctc catccagtct attaattgtt   9420
gccgggaagc tagagtaagt agttcgccag ttaatagttt gcgcaacgtt gttgccattg   9480
ctacaggcat cgtggtgtca cgctcgtcgt ttggtatggc ttcattcagc tccggttccc   9540
aacgatcaag gcgagttaca tgatccccca tgttgtgcaa aaaagcggtt agctccttcg   9600
gtcctccgat cgttgtcaga agtaagttgg ccgcagtgtt atcactcatg gttatggcag   9660
cactgcataa ttctcttact gtcatgccat ccgtaagatg cttttctgtg actggtgagt   9720
actcaaccaa gtcattctga gaatagtgta tgcggcgacc gagttgctct tgcccggcgt   9780
caacacggga taataccgcg ccacatagca gaactttaaa agtgctcatc attggaaaag   9840
acctgcaggg gggggggggc gctgaggtct gcctcgtgaa gaaggtgttg ctgactcata   9900
ccaggcctga atcgccccat catccagcca gaaagtgagg gagccacggt tgatgagagc   9960
tttgttgtag gtggaccagt tggtgatttt gaacttttgc tttgccacgg aacggtctgc  10020
gttgtcggga agatgcgtga tctgatcctt caactcagca aaagttcgat ttattcaaca  10080
aagccgccgt cccgtcaagt cagcgtaatg ctctgccagt gttacaacca attaaccaat  10140
tctgattaga aaaactcatc gagcatcaaa tgaaactgca atttattcat atcaggatta  10200
tcaataccat atttttgaaa aagccgtttc tgtaatgaag gagaaaactc accgaggcag  10260
ttccatagga tggcaagatc ctggtatcgg tctgcgattc cgactcgtcc aacatcaata  10320
caacctatta atttcccctc gtcaaaaata aggttatcaa gtgagaaatc accatgagtg  10380
acgactgaat ccggtgagaa tggcaaaagc ttatgcattt ctttccagac ttgttcaaca  10440
ggccagccat tacgctcgtc atcaaaatca ctcgcatcaa ccaaaccgtt attcattcgt  10500
gattgcgcct gagcgagacg aaatacgcga tcgctgttaa aaggacaatt acaaacagga  10560
atcgaatgca accggcgcag gaacactgcc agcgcatcaa caatattttc acctgaatca  10620
ggatattctt ctaatacctg gaatgctgtt ttcccgggga tcgcagtggt gagtaaccat  10680
gcatcatcag gagtacggat aaaatgcttg atggtcggaa gaggcataaa ttccgtcagc  10740
cagtttagtc tgaccatctc atctgtaaca tcattggcaa cgctaccttt gccatgtttc  10800
agaaacaact ctggcgcatc gggcttccca tacaatcgat agattgtcgc acctgattgc  10860
ccgacattat cgcgagccca tttataccca tataaatcag catccatgtt ggaatttaat  10920
cgcggcctcg agcaagacgt ttcccgttga atatggctca taacacccct tgtattactg  10980
tttatgtaag cagacagttt tattgttcat gatgatatat ttttatcttg tgcaatgtaa  11040
catcagagat tttgagacac aacgtggctt tccccccccc ccctgcaggt caattcggtc  11100
gatatggcta ttacgaagaa ggctcgtgcg cggagtcccg tgaactttcc cacgcaacaa  11160
gtgaaccgca ccgggtttgc cggaggccat ttcgttaaaa tgcgcagcca tggctgcttc  11220
gtccagcatg gcgtaatact gatcctcgtc ttcggctggc ggtatattgc cgatgggctt  11280
caaaagccgc cgtggttgaa ccagtctatc cattccaagg tagcgaactc gaccgcttcg  11340
aagctcctcc atggtccacg ccgatgaatg acctcggcct tgtaaagacc gttgatcgct  11400
tctgcgaggg cgttgtcgtg ctgtcgccga cgcttccgat agatggctcg atacctgctt  11460
ctgccaaccg ctcggaatag cgaaaggaca cgtattgaac accgcgatcc gagtgatgca  11520
```

```
ctaggccgcc atgagcggga cgccgatcat gatgagcctc ctcgagggca tcgaggacaa  11580
agcctgcatg tgctgtccgg ctcgcccgcc atccgacaat gcgacgggcg aagacgtcga  11640
tcacgaaggc cacgtagacg aagccctccc aagtggcgac ataagtacgg acatgcgcaa  11700
aggctttccc ggtttgtcgc tgatggtgca agagacgctg aagcgcgatc cgatgcgcag  11760
gcatctgttc gtcttccgcg gtcgtggcgg tggcctgatc aaggtcactc gccgaagagc  11820
tgcatgattg gctcgaaacc gagcggggga aattgtcgcg cagttctccc gtcgccgagg  11880
cgataaatta catgctcaag cgatgggatg gcattacgtc attcctcgat gacggcccga  11940
tttgcctgac gaacaatgct gccgaacgaa cgctcagagg ctatgtactc ggcaggaagt  12000
catggctgtt tgccggatcg gatcgttgtg ctgaacgtgc ggcgttcatg gcgacactga  12060
tcatgagcgc caagctcaat aacatcgatc cgcaggcctg gcttgccgac gtccgcgccg  12120
accttgcgga cgctccgatc agcaggcttg agcaacagct gccgtggaac tggacatcca  12180
agacactgag tgctcaggcg gcctgacctg cggccttcac cggatactta ccccattatc  12240
gcagattgcg atgaagcatc agcgtcattc agcaatcttg ccaaagtatg caggctcgcg  12300
agaatcgacg tgcgaaaccg gctggttgcg ccaaagatcc gcttgcggag cggtcgaaca  12360
ttcatgctgg gacttcaaga ggtcgagtag aggaagaacc ggaaaggttg caccggaaaa  12420
tatgcgttcc tttggagagc gcctcatgga cgtgaacaaa tcgcccggac caaggatgcc  12480
acggatacaa aagctcgcga agctcggtcc cgtgggtgtt ctgtcgtctc gttgtacaac  12540
gaaatccatt cccattccgc gctcaagatg gcttcccctc ggcagttcat cagggctaaa  12600
tcaatctagc cgacttgtcc ggtgaaatgg gctgcactcc aacagaaaca atcaaacaaa  12660
catacacagc gacttattca cacgagctca aattacaacg gtatatatcc tgccagtcag  12720
catcatcaca ccaaaagtta ggcccgaata gtttgaaatt agaaagctcg caattgaggt  12780
ctacaggcca aattcgctct tagccgtaca atattactca ccggtgcgat gcccccccatc  12840
gtaggtgaag gtggaaatta atgatccatc ttgagaccac aggcccacaa cagctaccag  12900
tttcctcaag ggtccaccaa aaacgtaagc gcttacgtac atggtcgata agaaaaggca  12960
atttgtagat gttaacatcc aacgtcgctt tcagggatcg atccaatacg caaaccgcct  13020
ctccccgcgc gttggccgat tcattaatgc agctggcacg acaggtttcc cgactggaaa  13080
gcgggcagtg agcgcaacgc aattaatgtg agttagctca ctcattaggc accccaggct  13140
ttacacttta tgcttccggc tcgtatgttg tgtggaattg tgagcggata acaatttcac  13200
acaggaaaca gctatgacca tgattacgcc aagcttgcat gcctgcaggt cgactctaga  13260
ggatctgg                                                           13268
```

```
<210> SEQ ID NO 102
<211> LENGTH: 15901
<212> TYPE: DNA
<213> ORGANISM: Artificial Sequence
<220> FEATURE:
<223> OTHER INFORMATION: sequence of pKR926

<400> SEQUENCE: 102
```

```
cgcgcctcga gtgggcggat cccccgggct gcaggaattc actggccgtc gttttacaac     60
gtcgtgactg ggaaaaccct ggcgttaccc aacttaatcg ccttgcagca catccccctt    120
tcgccagctg gcgtaatagc gaagaggccc gcaccgatcg cccttcccaa cagttgcgca    180
gcctgaatgg cgaatggatc gatccatcgc gatgtacctt ttgttagtca gcctctcgat    240
tgctcatcgt cattacacag taccgaagtt tgatcgatct agtaacatag atgacaccgc    300
```

-continued

```
gcgcgataat ttatcctagt ttgcgcgcta tattttgttt tctatcgcgt attaaatgta    360
taattgcggg actctaatca taaaaaccca tctcataaat aacgtcatgc attacatgtt    420
aattattaca tgcttaacgt aattcaacag aaattatatg ataatcatcg caagaccggc    480
aacaggattc aatcttaaga aactttattg ccaaatgttt gaacgatctg cttcgacgca    540
ctccttcttt actccaccat ctcgtcctta ttgaaaacgt gggtagcacc aaaacgaatc    600
aagtcgctgg aactgaagtt accaatcacg ctggatgatt tgccagttgg attaatcttg    660
cctttccccg catgaataat attgatgaat gcatgcgtga ggggtagttc gatgttggca    720
atagctgcaa ttgccgcgac atcctccaac gagcataatt cttcagaaaa atagcgatgt    780
tccatgttgt cagggcatgc atgatgcacg ttatgaggtg acggtgctag gcagtattcc    840
ctcaaagttt catagtcagt atcatattca tcattgcatt cctgcaagag agaattgaga    900
cgcaatccac acgctgcggc aaccttccgg cgttcgtggt ctatttgctc ttggacgttg    960
caaacgtaag tgttggatcg atccggggtg ggcgaagaac tccagcatga gatccccgcg   1020
ctggaggatc atccagccgg cgtcccggaa aacgattccg aagcccaacc tttcatagaa   1080
ggcggcggtg gaatcgaaat ctcgtgatgg caggttgggc gtcgcttggt cggtcatttc   1140
gaaccccaga gtcccgctca gaagaactcg tcaagaaggc gatagaaggc gatgcgctgc   1200
gaatcgggag cggcgatacc gtaaagcacg aggaagcggt cagcccattc gccgccaagc   1260
tcttcagcaa tatcacgggt agccaacgct atgtcctgat agcggtccgc cacacccagc   1320
cggccacagt cgatgaatcc agaaaagcgg ccattttcca ccatgatatt cggcaagcag   1380
gcatcgccat gggtcacgac gagatcctcg ccgtcgggca tgcgcgcctt gagcctggcg   1440
aacagttcgg ctggcgcgag cccctgatgc tcttcgtcca gatcatcctg atcgacaaga   1500
ccggcttcca tccgagtacg tgctcgctcg atgcgatgtt tcgcttggtg gtcgaatggg   1560
caggtagccg gatcaagcgt atgcagccgc cgcattgcat cagccatgat ggatactttc   1620
tcggcaggag caaggtgaga tgacaggaga tcctgccccg gcacttcgcc caatagcagc   1680
cagtcccttc ccgcttcagt gacaacgtcg agcacagctg cgcaaggaac gcccgtcgtg   1740
gccagccacg atagccgcgc tgcctcgtcc tgcagttcat tcagggcacc ggacaggtcg   1800
gtcttgacaa aaagaaccgg gcgcccctgc gctgacagcc ggaacacggc ggcatcagag   1860
cagccgattg tctgttgtgc ccagtcatag ccgaatagcc tctccaccca agcggccgga   1920
gaacctgcgt gcaatccatc ttgttcaatc atgcgaaacg atccccgcaa gcttggagac   1980
tggtgatttc agcgtgtcct ctccaaatga aatgaacttc cttatataga ggaagggtct   2040
tgcgaaggat agtgggattg tgcgtcatcc cttacgtcag tggagatatc acatcaatcc   2100
acttgctttg aagacgtggt tggaacgtct tctttttcca cgatgctcct cgtgggtggg   2160
ggtccatctt tgggaccact gtcggcagag gcatcttcaa cgatggcctt tcctttatcg   2220
caatgatggc atttgtagga gccaccttcc ttttccacta tcttcacaat aaagtgacag   2280
atagctgggc aatggaatcc gaggaggttt ccggatatta ccctttgttg aaaagtctca   2340
attgcccttt ggtcttctga gactgtatct ttgatatttt tggagtagac aagcgtgtcg   2400
tgctccacca tgttgacgaa gattttcttc ttgtcattga gtcgtaagag actctgtatg   2460
aactgttcgc cagtctttac ggcgagttct gttaggtcct ctatttgaat ctttgactcc   2520
atggcctttg attcagtggg aactaccttt ttagagactc caatctctat tacttgcctt   2580
ggtttgtgaa gcaagccttg aatcgtccat actggaatag tacttctgat cttgagaaat   2640
```

-continued

```
atatctttct ctgtgttctt gatgcagtta gtcctgaatc ttttgactgc atctttaacc   2700
ttcttgggaa ggtatttgat ctcctggaga ttattgctcg ggtagatcgt cttgatgaga   2760
cctgctgcgt aagcctctct aaccatctgt gggttagcat tctttctgaa attgaaaagg   2820
ctaatcttct cattatcagt ggtgaacatg gtatcgtcac cttctccgtc gaacttcctg   2880
actagatcgt agagatagag gaagtcgtcc attgtgatct ctggggcaaa ggagtctgaa   2940
ttaattcgat atggtggatt tatcacaaat gggacccgcc gccgacagag gtgtgatgtt   3000
aggccaggac tttgaaaatt tgcgcaacta tcgtatagtg gccgacaaat tgacgccgag   3060
ttgacagact gcctagcatt tgagtgaatt atgtgaggta atgggctaca ctgaattggt   3120
agctcaaact gtcagtattt atgtatatga gtgtatattt tcgcataatc tcagaccaat   3180
ctgaagatga aatgggtatc tgggaatggc gaaatcaagg catcgatcgt gaagtttctc   3240
atctaagccc ccatttggac gtgaatgtag acacgtcgaa ataaagattt ccgaattaga   3300
ataatttgtt tattgctttc gcctataaat acgacggatc gtaatttgtc gttttatcaa   3360
aatgtacttt cattttataa taacgctgcg gacatctaca tttttgaatt gaaaaaaaat   3420
tggtaattac tctttctttt tctccatatt gaccatcata ctcattgctg atccatgtag   3480
atttcccgga catgaagcca tttacaattg aatatatcct gccgccgctg ccgctttgca   3540
cccggtggag cttgcatgtt ggtttctacg cagaactgag ccggttaggc agataatttc   3600
cattgagaac tgagccatgt gcaccttccc cccaacacgg tgagcgacgg ggcaacggag   3660
tgatccacat gggactttta aacatcatcc gtcggatggc gttgcgagag aagcagtcga   3720
tccgtgagat cagccgacgc accgggcagg cgcgcaacac gatcgcaaag tatttgaacg   3780
caggtacaat cgagccgacg ttcacgcgga acgaccaagc aagctagctt taatgcggta   3840
gtttatcaca gttaaattgc taacgcagtc aggcaccgtg tatgaaatct aacaatgcgc   3900
tcatcgtcat cctcggcacc gtcaccctgg atgctgtagg cataggcttg gttatgccgg   3960
tactgccggg cctcttgcgg gatatcgtcc attccgacag catcgccagt cactatggcg   4020
tgctgctagc gctatatgcg ttgatgcaat ttctatgcgc acccgttctc ggagcactgt   4080
ccgaccgctt tggccgccgc ccagtcctgc tcgcttcgct acttggagcc actatcgact   4140
acgcgatcat ggcgaccaca cccgtcctgt ggtccaaccc ctccgctgct atagtgcagt   4200
cggcttctga cgttcagtgc agccgtcttc tgaaaacgac atgtcgcaca agtcctaagt   4260
tacgcgacag gctgccgccc tgcccttttc ctggcgtttt cttgtcgcgt gttttagtcg   4320
cataaagtag aatacttgcg actagaaccg gagacattac gccatgaaca agagcgccgc   4380
cgctggcctg ctgggctatg cccgcgtcag caccgacgac caggacttga ccaaccaacg   4440
ggccgaactg cacgcggccg gctgcaccaa gctgttttcc gagaagatca ccggcaccag   4500
gcgcgaccgc ccggagctgg ccaggatgct tgaccaccta cgccctggcg acgttgtgac   4560
agtgaccagg ctagaccgcc tggcccgcag cacccgcgac ctactggaca ttgccgagcg   4620
catccaggag gccggcgcgg gcctgcgtag cctggcagag ccgtgggccg acaccaccac   4680
gccggccggc cgcatggtgt tgaccgtgtt cgccggcatt gccgagttcg agcgttccct   4740
aatcatcgac cgcacccgga gcgggcgcga ggccgccaag gcccgaggcg tgaagtttgg   4800
cccccgccct accctcaccc cggcacagat cgcgcacgcc cgcgagctga tcgaccagga   4860
aggccgcacc gtgaaagagg cggctgcact gcttggcgtg catcgctcga ccctgtaccg   4920
cgcacttgag cgcagcgagg aagtgacgcc caccgaggcc aggcggcgcg gtgccttccg   4980
tgaggacgca ttgaccgagg ccgacgccct ggcggccgcc gagaatgaac gccaagagga   5040
```

```
acaagcatga aaccgcacca ggacggccag gacgaaccgt ttttcattac cgaagagatc   5100
gaggcggaga tgatcgcggc cgggtacgtg ttcgagccgc ccgcgcacgt ctcaaccgtg   5160
cggctgcatg aaatcctggc cggtttgtct gatgccaagc tggcggcctg gccggccagc   5220
ttggccgctg aagaaaccga gcgccgccgt ctaaaaaggt gatgtgtatt tgagtaaaac   5280
agcttgcgtc atgcggtcgc tgcgtatatg atgcgatgag taaataaaca aatacgcaag   5340
ggaacgcatg aagttatcgc tgtacttaac cagaaaggcg ggtcaggcaa gacgaccatc   5400
gcaacccatc tagcccgcgc cctgcaactc gccggggccg atgttctgtt agtcgattcc   5460
gatccccagg gcagtgcccg cgattgggcg gccgtgcggg aagatcaacc gctaaccgtt   5520
gtcggcatcg accgcccgac gattgaccgc gacgtgaagg ccatcggccg gcgcgacttc   5580
gtagtgatcg acggagcgcc ccaggcggcg gacttggctg tgtccgcgat caaggcagcc   5640
gacttcgtgc tgattccggt gcagccaagc ccttacgaca tatgggccac cgccgacctg   5700
gtggagctgg ttaagcagcg cattgaggtc acggatggaa ggctacaagc ggcctttgtc   5760
gtgtcgcggg cgatcaaagg cacgcgcatc ggcggtgagg ttgccgaggc gctggccggg   5820
tacgagctgc ccattcttga gtcccgtatc acgcagcgcg tgagctaccc aggcactgcc   5880
gccgccggca caaccgttct tgaatcagaa cccgagggcg acgctgcccg cgaggtccag   5940
gcgctggccg ctgaaattaa atcaaaactc atttgagtta atgaggtaaa gagaaaatga   6000
gcaaaagcac aaacacgcta agtgccggcc gtccgagcgc acgcagcagc aaggctgcaa   6060
cgttggccag cctggcagac acgccagcca tgaagcgggt caactttcag ttgccggcgg   6120
aggatcacac caagctgaag atgtacgcgg tacgccaagg caagaccatt accgagctgc   6180
tatctgaata catcgcgcag ctaccagagt aaatgagcaa atgaataaat gagtagatga   6240
attttagcgg ctaaaggagg cggcatggaa aatcaagaac aaccaggcac cgacgccgtg   6300
gaatgcccca tgtgtggagg aacgggcggt tggccaggcg taagcggctg ggttgtctgc   6360
cggccctgca atggcactgg aacccccaag cccgaggaat cggcgtgagc ggtcgcaaac   6420
catccggccc ggtacaaatc ggcgcggcgc tgggtgatga cctggtggag aagttgaagg   6480
ccgcgcaggc cgcccagcgg caacgcatcg aggcagaagc acgccccggt gaatcgtggc   6540
aagcggccgc tgatcgaatc cgcaaagaat cccggcaacc gccggcagcc ggtgcgccgt   6600
cgattaggaa gccgcccaag ggcgacgagc aaccagattt tttcgttccg atgctctatg   6660
acgtgggcac ccgcgatagt cgcagcatca tggacgtggc cgttttccgt ctgtcgaagc   6720
gtgaccgacg agctggcgag gtgatccgct acgagcttcc agacgggcac gtagaggttt   6780
ccgcagggcc ggccggcatg gccagtgtgt gggattacga cctggtactg atggcggttt   6840
cccatctaac cgaatccatg aaccgatacc gggaagggaa gggagacaag cccggccgcg   6900
tgttccgtcc acacgttgcg gacgtactca agttctgccg gcgagccgat ggcggaaagc   6960
agaaagacga cctggtagaa acctgcattc ggttaaacac cacgcacgtt gccatgcagc   7020
gtacgaagaa ggccaagaac ggccgcctgg tgacggtatc cgagggtgaa gccttgatta   7080
gccgctacaa gatcgtaaag agcgaaaccg ggcggccgga gtacatcgag atcgagctag   7140
ctgattggat gtaccgcgag atcacagaag gcaagaaccc ggacgtgctg acggttcacc   7200
ccgattactt tttgatcgat cccggcatcg gccgttttct ctaccgcctg gcacgccgcg   7260
ccgcaggcaa ggcagaagcc agatggttgt tcaagacgat ctacgaacgc agtggcagcg   7320
ccggagagtt caagaagttc tgtttcaccg tgcgcaagct gatcgggtca aatgacctgc   7380
```

-continued

```
cggagtacga tttgaaggag gaggcggggc aggctggccc gatcctagtc atgcgctacc   7440
gcaacctgat cgagggcgaa gcatccgccg gttcctaatg tacggagcag atgctagggc   7500
aaattgccct agcaggggaa aaaggtcgaa aaggtctctt tcctgtggat agcacgtaca   7560
ttgggaaccc aaagccgtac attgggaacc ggaacccgta cattgggaac ccaaagccgt   7620
acattgggaa ccggtcacac atgtaagtga ctgatataaa agagaaaaaa ggcgattttt   7680
ccgcctaaaa ctctttaaaa cttattaaaa ctcttaaaac ccgcctggcc tgtgcataac   7740
tgtctggcca gcgcacagcc gaagagctgc aaaaagcgcc tacccttcgg tcgctgcgct   7800
ccctacgccc cgccgcttcg cgtcggccta tcgcggccgc tggccgctca aaaatggctg   7860
gcctacggcc aggcaatcta ccagggcgcg gacaagccgc gccgtcgcca ctcgaccgcc   7920
ggcgcccaca tcaaggcacc ctgcctcgcg cgtttcggtg atgacggtga aaacctctga   7980
cacatgcagc tcccggagac ggtcacagct tgtctgtaag cggatgccgg gagcagacaa   8040
gcccgtcagg gcgcgtcagc gggtgttggc gggtgtcggg gcgcagccat gacccagtca   8100
cgtagcgata gcggagtgta tactggctta actatgcggc atcagagcag attgtactga   8160
gagtgcacca tatgcggtgt gaaataccgc acagatgcgt aaggagaaaa taccgcatca   8220
ggcgctcttc cgcttcctcg ctcactgact cgctgcgctc ggtcgttcgg ctgcggcgag   8280
cggtatcagc tcactcaaag gcggtaatac ggttatccac agaatcaggg gataacgcag   8340
gaaagaacat gtgagcaaaa ggccagcaaa aggccaggaa ccgtaaaaag gccgcgttgc   8400
tggcgttttt ccataggctc cgcccccctg acgagcatca caaaaatcga cgctcaagtc   8460
agaggtggcg aaacccgaca ggactataaa gataccaggc gtttccccct ggaagctccc   8520
tcgtgcgctc tcctgttccg accctgccgc ttaccggata cctgtccgcc tttctccctt   8580
cgggaagcgt ggcgctttct catagctcac gctgtaggta tctcagttcg gtgtaggtcg   8640
ttcgctccaa gctgggctgt gtgcacgaac cccccgttca gcccgaccgc tgcgccttat   8700
ccggtaacta tcgtcttgag tccaacccgg taagacacga cttatcgcca ctggcagcag   8760
ccactggtaa caggattagc agagcgaggt atgtaggcgg tgctacagag ttcttgaagt   8820
ggtggcctaa ctacggctac actagaagga cagtatttgg tatctgcgct ctgctgaagc   8880
cagttacctt cggaaaaaga gttggtagct cttgatccgg caaacaaacc accgctggta   8940
gcggtggttt ttttgtttgc aagcagcaga ttacgcgcag aaaaaaagga tctcaagaag   9000
atcctttgat cttttctacg gggtctgacg ctcagtggaa cgaaaactca cgttaaggga   9060
ttttggtcat gagattatca aaaaggatct tcacctagat ccttttaaat taaaaatgaa   9120
gttttaaatc aatctaaagt atatatgagt aaacttggtc tgacagttac caatgcttaa   9180
tcagtgaggc acctatctca gcgatctgtc tatttcgttc atccatagtt gcctgactcc   9240
ccgtcgtgta gataactacg atacgggagg gcttaccatc tggccccagt gctgcaatga   9300
taccgcgaga cccacgctca ccggctccag atttatcagc aataaaccag ccagccggaa   9360
gggccgagcg cagaagtggt cctgcaactt tatccgcctc catccagtct attaattgtt   9420
gccgggaagc tagagtaagt agttcgccag ttaatagttt gcgcaacgtt gttgccattg   9480
ctacaggcat cgtggtgtca cgctcgtcgt ttggtatggc ttcattcagc tccggttccc   9540
aacgatcaag gcgagttaca tgatccccca tgttgtgcaa aaaagcggtt agctccttcg   9600
gtcctccgat cgttgtcaga agtaagttgg ccgcagtgtt atcactcatg gttatggcag   9660
cactgcataa ttctcttact gtcatgccat ccgtaagatg cttttctgtg actggtgagt   9720
actcaaccaa gtcattctga gaatagtgta tgcggcgacc gagttgctct tgcccggcgt   9780
```

```
caacacggga taataccgcg ccacatagca gaactttaaa agtgctcatc attggaaaag   9840
acctgcaggg gggggggggc gctgaggtct gcctcgtgaa gaaggtgttg ctgactcata   9900
ccaggcctga atcgccccat catccagcca gaaagtgagg gagccacggt tgatgagagc   9960
tttgttgtag gtggaccagt tggtgatttt gaacttttgc tttgccacgg aacggtctgc  10020
gttgtcggga agatgcgtga tctgatcctt caactcagca aaagttcgat ttattcaaca  10080
aagccgccgt cccgtcaagt cagcgtaatg ctctgccagt gttacaacca attaaccaat  10140
tctgattaga aaaactcatc gagcatcaaa tgaaactgca atttattcat atcaggatta  10200
tcaataccat atttttgaaa aagccgtttc tgtaatgaag gagaaaactc accgaggcag  10260
ttccatagga tggcaagatc ctggtatcgg tctgcgattc cgactcgtcc aacatcaata  10320
caacctatta atttcccctc gtcaaaaata aggttatcaa gtgagaaatc accatgagtg  10380
acgactgaat ccggtgagaa tggcaaaagc ttatgcattt ctttccagac ttgttcaaca  10440
ggccagccat tacgctcgtc atcaaaatca ctcgcatcaa ccaaaccgtt attcattcgt  10500
gattgcgcct gagcgagacg aaatacgcga tcgctgttaa aaggacaatt acaaacagga  10560
atcgaatgca accggcgcag gaacactgcc agcgcatcaa caatattttc acctgaatca  10620
ggatattctt ctaatacctg gaatgctgtt ttcccgggga tcgcagtggt gagtaaccat  10680
gcatcatcag gagtacggat aaaatgcttg atggtcggaa gaggcataaa ttccgtcagc  10740
cagtttagtc tgaccatctc atctgtaaca tcattggcaa cgctaccttt gccatgtttc  10800
agaaacaact ctggcgcatc gggcttccca tacaatcgat agattgtcgc acctgattgc  10860
ccgacattat cgcgagccca tttataccca tataaatcag catccatgtt ggaatttaat  10920
cgcggcctcg agcaagacgt ttcccgttga atatggctca taacacccct tgtattactg  10980
tttatgtaag cagacagttt tattgttcat gatgatatat ttttatcttg tgcaatgtaa  11040
catcagagat tttgagacac aacgtggctt tccccccccc ccctgcaggt caattcggtc  11100
gatatggcta ttacgaagaa ggctcgtgcg cggagtcccg tgaactttcc cacgcaacaa  11160
gtgaaccgca ccgggtttgc cggaggccat ttcgttaaaa tgcgcagcca tggctgcttc  11220
gtccagcatg gcgtaatact gatcctcgtc ttcggctggc ggtatattgc cgatgggctt  11280
caaaagccgc cgtggttgaa ccagtctatc cattccaagg tagcgaactc gaccgcttcg  11340
aagctcctcc atggtccacg ccgatgaatg acctcggcct tgtaaagacc gttgatcgct  11400
tctgcgaggg cgttgtcgtg ctgtcgccga cgcttccgat agatggctcg atacctgctt  11460
ctgccaaccg ctcggaatag cgaaaggaca cgtattgaac accgcgatcc gagtgatgca  11520
ctaggccgcc atgagcggga cgccgatcat gatgagcctc ctcgagggca tcgaggacaa  11580
agcctgcatg tgctgtccgg ctcgcccgcc atccgacaat gcgacgggcg aagacgtcga  11640
tcacgaaggc cacgtagacg aagccctccc aagtggcgac ataagtacgg acatgcgcaa  11700
aggctttccc ggtttgtcgc tgatggtgca agagacgctg aagcgcgatc cgatgcgcag  11760
gcatctgttc gtcttccgcg gtcgtggcgg tggcctgatc aaggtcactc gccgaagagc  11820
tgcatgattg gctcgaaacc gagcggggga aattgtcgcg cagttctccc gtcgccgagg  11880
cgataaatta catgctcaag cgatgggatg gcattacgtc attcctcgat gacggcccga  11940
tttgcctgac gaacaatgct gccgaacgaa cgctcagagg ctatgtactc ggcaggaagt  12000
catggctgtt tgccggatcg gatcgttgtg ctgaacgtgc ggcgttcatg gcgacactga  12060
tcatgagcgc caagctcaat aacatcgatc cgcaggcctg gcttgccgac gtccgcgccg  12120
```

-continued

```
accttgcgga cgctccgatc agcaggcttg agcaacagct gccgtggaac tggacatcca  12180
agacactgag tgctcaggcg gcctgacctg cggccttcac cggatactta ccccattatc  12240
gcagattgcg atgaagcatc agcgtcattc agcaatcttg ccaaagtatg caggctcgcg  12300
agaatcgacg tgcgaaaccg gctggttgcg ccaaagatcc gcttgcggag cggtcgaaca  12360
ttcatgctgg gacttcaaga ggtcgagtag aggaagaacc ggaaaggttg caccggaaaa  12420
tatgcgttcc tttggagagc gcctcatgga cgtgaacaaa tcgcccggac caaggatgcc  12480
acggatacaa aagctcgcga agctcggtcc cgtgggtgtt ctgtcgtctc gttgtacaac  12540
gaaatccatt cccattccgc gctcaagatg gcttcccctc ggcagttcat cagggctaaa  12600
tcaatctagc cgacttgtcc ggtgaaatgg gctgcactcc aacagaaaca atcaaacaaa  12660
catacacagc gacttattca cacgagctca aattacaacg gtatatatcc tgccagtcag  12720
catcatcaca ccaaaagtta ggcccgaata gtttgaaatt agaaagctcg caattgaggt  12780
ctacaggcca aattcgctct tagccgtaca atattactca ccggtgcgat gccccccatc  12840
gtaggtgaag gtggaaatta atgatccatc ttgagaccac aggcccacaa cagctaccag  12900
tttcctcaag ggtccaccaa aaacgtaagc gcttacgtac atggtcgata agaaaaggca  12960
atttgtagat gttaacatcc aacgtcgctt tcagggatcg atccaatacg caaaccgcct  13020
ctccccgcgc gttggccgat tcattaatgc agctggcacg acaggtttcc cgactggaaa  13080
gcgggcagtg agcgcaacgc aattaatgtg agttagctca ctcattaggc accccaggct  13140
ttacacttta tgcttccggc tcgtatgttg tgtggaattg tgagcggata acaatttcac  13200
acaggaaaca gctatgacca tgattacgcc aagcttgcat gcctgcaggt cgactctaga  13260
ggatctggcg cgccaagctt gttgaaacat ccctgaagtg tctcatttta ttttatttat  13320
tctttgctga taaaaaaata aaataaaaga agctaagcac acggtcaacc attgctctac  13380
tgctaaaagg gttatgtgta gtgttttact gcataaatta tgcagcaaac aagacaactc  13440
aaattaaaaa atttcctttg cttgtttttt tgttgtctct gacttgactt tcttgtggaa  13500
gttggttgta taaggattgg gacaccattg tccttcttaa tttaatttta ttctttgctg  13560
ataaaaaaaa aaatttcata tagtgttaaa taataatttg ttaaataacc aaaaagtcaa  13620
atatgtttac tctcgtttaa ataattgaga ttcgtccagc aaggctaaac gattgtatag  13680
atttatgaca atatttactt ttttatagat aaatgttata ttataataaa tttatataca  13740
tatattatat gttatttatt attattttaa atccttcaat attttatcaa accaactcat  13800
aatttttttt ttatctgtaa gaagcaataa aattaaatag acccacttta aggatgatcc  13860
aacctttata cagagtaaga gagttcaaat agtacccttt catatacata tcaactaaaa  13920
tattagaaat atcatggatc aaaccttata aagacattaa ataagtggat aagtataata  13980
tataaatggg tagtatataa tatataaatg gatacaaact tctctcttta taattgttat  14040
gtctccttaa catcctaata taatacataa gtgggtaata tataatatat aaatggagac  14100
aaacttcttc cattataatt gttatgtctt cttaacactt atgtctcgtt cacaatgcta  14160
aggttagaat tgtttagaaa gtcttatagt acacatttgt ttttgtacta tttgaagcat  14220
tccataagcc gtcacgattc agatgattta taataataag aggaaattta tcatagaaca  14280
ataaggtgca tagatagagt gttaatatat cataacatcc tttgtttatt catagaagaa  14340
gtgagatgga gctcagttat tatactgtta catggtcgga tacaatattc catgctctcc  14400
atgagctctt acacctacat gcattttagt tcatacttgc ggccgctcac tgaatctttt  14460
tggctccctt gtgcttcctg acgatatacg tttgcacata gaaattcaag aacaaacaca  14520
```

agactgtgcc aacataaaag taattgaaga accagccaaa catcctcatc ccatcttggc 14580
gataacaggg aatgttcctg tacttccaga caatgtagaa accaacattg aattgaatga 14640
tctgcattga tgtaatcagg gattttggca tggggaactt cagcttgatc aatctggtcc 14700
aataataacc gtacatgatc cagtggatga aaccattcaa cagcacaaaa atccaaacag 14760
cttcatttcg gtaattatag aacagccaca tatccatcgg tgcccccaaa tgatggaaga 14820
attgcaacca ggtcagaggc ttgcccatca gtggcaaata gaaggagtca atatactcca 14880
ggaacttgct caaatagaac aactgcgtgg tgatcctgaa gacgttgttg tcaaaagcct 14940
tctcgcagtt gtcagacata acaccgatgg tgtacatggc atatgccatt gagaggaatg 15000
atcccaacga ataaatggac atgagaaggt tgtaattggt gaaaacaaac ttcatacgag 15060
actgaccttt tggaccaagg gggccaagag tgaacttcaa gatgacaaat gcgatggaca 15120
agtaaagcac ctcacagtga ctggcatcac tccagagttg ggcataatca actttgggta 15180
aaacttcctg cccaattgag actatttcat tcaccacctc catggtgcgg ccgcagtata 15240
tcttaaattc tttaatacgg tgtactagga tattgaactg gttcttgatg atgaaaacct 15300
gggccgagat tgcagctatt tatagtcata ggtcttgtta acatgcatgg acatttggcc 15360
acggggtggc atgcagtttg acgggtgttg aaataaacaa aaatgaggtg gcggaagaga 15420
atacgagttt gaggttgggt tagaaacaac aaatgtgagg gctcatgatg ggttgagttg 15480
gtgaatgttt tgggctgctc gattgacacc tttgtgagta cgtgttgttg tgcatggctt 15540
ttggggtcca gttttttttt cttgacgcgg cgatcctgat cagctagtgg ataagtgatg 15600
tccactgtgt gtgattgcgt tttgtttga attttatgaa cttagacatt gctatgcaaa 15660
ggatactctc attgtgtttt gtcttctttt gttccttggc tttttcttat gatccaagag 15720
actagtcagt gttgtggcat tcgagactac caagattaat tatgatgggg gaaggataag 15780
taactgatta gtacggactg ttaccaaatt aattaataag cggcaaatga agggcatgga 15840
tcaaaagctt ggatctcctg caggatctgg ccggccggat ctcgtacgga tccgtcgacg 15900
g 15901

<210> SEQ ID NO 103
<211> LENGTH: 5561
<212> TYPE: DNA
<213> ORGANISM: Artificial Sequence
<220> FEATURE:
<223> OTHER INFORMATION: sequence of pKR767

<400> SEQUENCE: 103
catggtcaat caatgagacg ccaacttctt aatctattga gacctgcagg tctagaaggg 60
cggatccccg ggtaccgagc tcgaattcac tggccgtcgt tttacaacgt cgtgactggg 120
aaaaccctgg cgttacccaa cttaatcgcc ttgcagcaca tccccctttc gccagctggc 180
gtaatagcga agaggcccgc accgatcgcc cttcccaaca gttgcgcagc ctgaatggcg 240
aatggcgcct gatgcggtat tttctcctta cgcatctgtg cggtatttca caccgcatat 300
ggtgcactct cagtacaatc tgctctgatg ccgcatagtt aagccagccc cgacacccgc 360
caacacccgc tgacgcgccc tgacgggctt gtctgctccc ggcatccgct tacagacaag 420
ctgtgaccgt ctccgggagc tgcatgtgtc agaggttttc accgtcatca ccgaaacgcg 480
cgagacgaaa gggcctcgtg atacgcctat ttttataggt taatgtcatg ataataatgg 540
tttcttagac gtcaggtggc acttttcggg gaaatgtgcg cggaacccct atttgtttat 600

-continued

```
ttttctaaat acattcaaat atgtatccgc tcatgagaca ataaccctga taaatgcttc    660
aataatattg aaaaaggaag agtatgagta ttcaacattt ccgtgtcgcc cttattccct    720
tttttgcggc attttgcctt cctgtttttg ctcacccaga aacgctggtg aaagtaaaag    780
atgctgaaga tcagttgggt gcacgagtgg gttacatcga actggatctc aacagcggta    840
agatccttga gagttttcgc cccgaagaac gttttccaat gatgagcact tttaaagttc    900
tgctatgtgg cgcggtatta tcccgtattg acgccgggca agagcaactc ggtcgccgca    960
tacactattc tcagaatgac ttggttgagt actcaccagt cacagaaaag catcttacgg   1020
atggcatgac agtaagagaa ttatgcagtg ctgccataac catgagtgat aacactgcgg   1080
ccaacttact tctgacaacg atcggaggac cgaaggagct aaccgctttt ttgcacaaca   1140
tgggggatca tgtaactcgc cttgatcgtt gggaaccgga gctgaatgaa gccataccaa   1200
acgacgagcg tgacaccacg atgcctgtag caatggcaac aacgttgcgc aaactattaa   1260
ctggcgaact acttactcta gcttcccggc aacaattaat agactggatg gaggcggata   1320
aagttgcagg accacttctg cgctcggccc ttccggctgg ctggtttatt gctgataaat   1380
ctggagccgg tgagcgtggg tctcgcggta tcattgcagc actggggcca gatggtaagc   1440
cctcccgtat cgtagttatc tacacgacgg ggagtcaggc aactatggat gaacgaaata   1500
gacagatcgc tgagataggt gcctcactga ttaagcattg gtaactgtca gaccaagttt   1560
actcatatat actttagatt gatttaaaac ttcattttta atttaaaagg atctaggtga   1620
agatcctttt tgataatctc atgaccaaaa tcccttaacg tgagttttcg ttccactgag   1680
cgtcagaccc cgtagaaaag atcaaaggat cttcttgaga tccttttttt ctgcgcgtaa   1740
tctgctgctt gcaaacaaaa aaaccaccgc taccagcggt ggtttgtttg ccggatcaag   1800
agctaccaac tctttttccg aaggtaactg gcttcagcag agcgcagata ccaaatactg   1860
tccttctagt gtagccgtag ttaggccacc acttcaagaa ctctgtagca ccgcctacat   1920
acctcgctct gctaatcctg ttaccagtgg ctgctgccag tggcgataag tcgtgtctta   1980
ccgggttgga ctcaagacga tagttaccgg ataaggcgca gcggtcgggc tgaacggggg   2040
gttcgtgcac acagcccagc ttggagcgaa cgacctacac cgaactgaga tacctacagc   2100
gtgagctatg agaaagcgcc acgcttcccg aagggagaaa ggcggacagg tatccggtaa   2160
gcggcagggt cggaacagga gagcgcacga gggagcttcc agggggaaac gcctggtatc   2220
tttatagtcc tgtcgggttt cgccacctct gacttgagcg tcgatttttg tgatgctcgt   2280
caggggggcg gagcctatgg aaaaacgcca gcaacgcggc ctttttacgg ttcctggcct   2340
tttgctggcc ttttgctcac atgttctttc ctgcgttatc ccctgattct gtggataacc   2400
gtattaccgc ctttgagtga gctgataccg ctcgccgcag ccgaacgacc gagcgcagcg   2460
agtcagtgag cgaggaagcg gaagagcgcc caatacgcaa accgcctctc cccgcgcgtt   2520
ggccgattca ttaatgcagc tggcacgaca ggtttcccga ctggaaagcg ggcagtgagc   2580
gcaacgcaat taatgtgagt tagctcactc attaggcacc ccaggcttta cactttatgc   2640
ttccggctcg tatgttgtgt ggaattgtga gcggataaca atttcacaca ggaaacagct   2700
atgaccatga ttacgccaag cttgcatgcc tgcaggctag cctaagtacg tactcaaaat   2760
gccaacaaat aaaaaaaaag ttgctttaat aatgccaaaa caaattaata aaacacttac   2820
aacaccggat ttttttaat taaaatgtgc catttaggat aaatagttaa tatttttaat   2880
aattatttaa aaagccgtat ctactaaaat gatttttatt tggttgaaaa tattaatatg   2940
tttaaatcaa cacaatctat caaaattaaa ctaaaaaaaa aataagtgta cgtggttaac   3000
```

```
attagtacag taatataaga ggaaaatgag aaattaagaa attgaaagcg agtctaattt   3060
ttaaattatg aacctgcata tataaaagga aagaaagaat ccaggaagaa aagaaatgaa   3120
accatgcatg gtcccctcgt catcacgagt ttctgccatt tgcaatagaa acactgaaac   3180
acctttctct ttgtcactta attgagatgc cgaagccacc tcacaccatg aacttcatga   3240
ggtgtagcac ccaaggcttc catagccatg catactgaag aatgtctcaa gctcagcacc   3300
ctacttctgt gacgtgtccc tcattcacct tcctctcttc cctataaata accacgcctc   3360
aggttctccg cttcacaact caaacattct ctccattggt ccttaaacac tcatcagtca   3420
tcaccgcggc cgcatgggaa cggaccaagg aaaaaccttc acctgggaag agctggcggc   3480
ccataacacc aaggacgacc tactcttggc catccgcggc agggtgtacg atgtcacaaa   3540
gttcttgagc cgccatcctg gtggagtgga cactctcctg ctcggagctg gccgagatgt   3600
tactccggtc tttgagatgt atcacgcgtt tggggctgca gatgccatta tgaagaagta   3660
ctatgtcggt acactggtct cgaatgagct gcccatcttc ccggagccaa cggtgttcca   3720
caaaaccatc aagacgagag tcgagggcta ctttacggat cggaacattg atcccaagaa   3780
tagaccagag atctggggac gatacgctct tatctttgga tccttgatcg cttcctacta   3840
cgcgcagctc tttgtgcctt tcgttgtcga acgcacatgg cttcaggtgg tgtttgcaat   3900
catcatggga tttgcgtgcg cacaagtcgg actcaaccct cttcatgatg cgtctcactt   3960
ttcagtgacc cacaacccca ctgtctggaa gattctggga gccacgcacg actttttcaa   4020
cggagcatcg tacctggtgt ggatgtacca acatatgctc ggccatcacc cctacaccaa   4080
cattgctgga gcagatcccg acgtgtcgac gtctgagccc gatgttcgtc gtatcaagcc   4140
caaccaaaag tggtttgtca accacatcaa ccagcacatg tttgttcctt tcctgtacgg   4200
actgctggcg ttcaaggtgc gcattcagga catcaacatt ttgtactttg tcaagaccaa   4260
tgacgctatt cgtgtcaatc ccatctcgac atggcacact gtgatgttct ggggcggcaa   4320
ggctttcttt gtctggtatc gcctgattgt tcccctgcag tatctgcccc tgggcaaggt   4380
gctgctcttg ttcacggtcg cggacatggt gtcgtcttac tggctggcgc tgaccttcca   4440
ggcgaaccac gttgttgagg aagttcagtg gccgttgcct gacgagaacg ggatcatcca   4500
aaaggactgg gcagctatgc aggtcgagac tacgcaggat tacgcacacg attcgcacct   4560
ctggaccagc atcactggca gcttgaacta ccaggctgtg caccatctgt tccccaacgt   4620
gtcgcagcac cattatcccg atattctggc catcatcaag aacacctgca gcgagtacaa   4680
ggttccatac cttgtcaagg atacgttttg gcaagcattt gcttcacatt tggagcactt   4740
gcgtgttctt ggactccgtc ccaaggaaga gtaggcggcc gcatttcgca ccaaatcaat   4800
gaaagtaata atgaaaagtc tgaataagaa tacttaggct tagatgcctt tgttacttgt   4860
gtaaaataac ttgagtcatg tacctttggc ggaaacagaa taaataaaag gtgaaattcc   4920
aatgctctat gtataagtta gtaatactta atgtgttcta cggttgtttc aatatcatca   4980
aactctaatt gaaactttag aaccacaaat ctcaatcttt tcttaatgaa atgaaaaatc   5040
ttaattgtac catgtttatg ttaaacacct tacaattggt tggagaggag gaccaaccga   5100
tgggacaaca ttgggagaaa gagattcaat ggagatttgg ataggagaac aacattcttt   5160
ttcacttcaa tacaagatga gtgcaacact aaggatatgt atgagacttt cagaagctac   5220
gacaacatag atgagtgagg tggtgattcc tagcaagaaa gacattagag gaagccaaaa   5280
tcgaacaagg aagacatcaa gggcaagaga caggaccatc catctcagga aaaggagctt   5340
```

```
tgggatagtc cgagaagttg tacaagaaat tttttggagg gtgagtgatg cattgctggt   5400
gactttaact caatcaaaat tgagaaagaa agaaaaggga gggggctcac atgtgaatag   5460
aagggaaacg ggagaatttt acagttttga tctaatgggc atcccagcta gtggtaacat   5520
attcaccatg tttaaccttc acgtacgtct agaggatccc c                       5561
```

<210> SEQ ID NO 104
<211> LENGTH: 11889
<212> TYPE: DNA
<213> ORGANISM: Artificial Sequence
<220> FEATURE:
<223> OTHER INFORMATION: sequence of pKR916
<220> FEATURE:
<221> NAME/KEY: misc_feature
<222> LOCATION: (7810)..(7810)
<223> OTHER INFORMATION: n is a, c, g, or t

<400> SEQUENCE: 104

```
ggagatccaa gcttttgatc catgcccttc atttgccgct tattaattaa tttggtaaca     60
gtccgtacta atcagttact tatccttccc ccatcataat taatcttggt agtctcgaat    120
gccacaacac tgactagtct cttggatcat aagaaaaagc caaggaacaa aagaagacaa    180
aacacaatga gagtatcctt tgcatagcaa tgtctaagtt cataaaattc aaacaaaaac    240
gcaatcacac acagtggaca tcacttatcc actagctgat caggatcgcc gcgtcaagaa    300
aaaaaaactg gaccccaaaa gccatgcaca acaacacgta ctcacaaagg tgtcaatcga    360
gcagcccaaa acattcacca actcaaccca tcatgagccc tcacatttgt tgtttctaac    420
ccaacctcaa actcgtattc tcttccgcca cctcattttt gtttatttca acacccgtca    480
aactgcatgc caccccgtgg ccaaatgtcc atgcatgtta acaagaccta tgactataaa    540
tagctgcaat ctcggcccag gttttcatca tcaagaacca gttcaatatc ctagtacacc    600
gtattaaaga atttaagata tactgcggcc gcaccatgga ggtggtgaat gaaatagtct    660
caattgggca ggaagtttta cccaaagttg attatgccca actctggagt gatgccagtc    720
actgtgaggt gctttacttg tccatcgcat ttgtcatctt gaagttcact cttggccccc    780
ttggtccaaa aggtcagtct cgtatgaagt ttgttttcac caattacaac cttctcatgt    840
ccatttattc gttgggatca ttcctctcaa tggcatatgc catgtacacc atcggtgtta    900
tgtctgacaa ctgcgagaag gcttttgaca acaacgtctt caggatcacc acgcagttgt    960
tctatttgag caagttcctg gagtatattg actccttcta tttgccactg atgggcaagc   1020
ctctgacctg gttgcaattc ttccatcatt tgggggcacc gatggatatg tggctgttct   1080
ataattaccg aaatgaagct gtttggattt ttgtgctgtt gaatggtttc atccactgga   1140
tcatgtacgg ttattattgg accagattga tcaagctgaa gttccccatg ccaaaatccc   1200
tgattacatc aatgcagatc attcaattca atgttggttt ctacattgtc tggaagtaca   1260
ggaacattcc ctgttatcgc caagatggga tgaggatgtt tggctggttc ttcaattact   1320
tttatgttgg cacagtcttg tgtttgttct tgaatttcta tgtgcaaacg tatatcgtca   1380
ggaagcacaa gggagccaaa aagattcagt gagcggccgc aagtatgaac taaaatgcat   1440
gtaggtgtaa gagctcatgg agagcatgga atattgtatc cgaccatgta acagtataat   1500
aactgagctc catctcactt cttctatgaa taaacaaagg atgttatgat atattaacac   1560
tctatctatg caccttattg ttctatgata aatttcctct tattattata aatcatctga   1620
atcgtgacgg cttatggaat gcttcaaata gtacaaaaac aaatgtgtac tataagactt   1680
tctaaacaat tctaacctta gcattgtgaa cgagacataa gtgttaagaa gacataacaa   1740
```

```
ttataatgga agaagtttgt ctccatttat atattatata ttacccactt atgtattata   1800
ttaggatgtt aaggagacat aacaattata aagagagaag tttgtatcca tttatatatt   1860
atatactacc catttatata ttatacttat ccacttattt aatgtcttta taaggtttga   1920
tccatgatat ttctaatatt ttagttgata tgtatatgaa agggtactat ttgaactctc   1980
ttactctgta taaaggttgg atcatcctta aagtgggtct atttaatttt attgcttctt   2040
acagataaaa aaaaaattat gagttggttt gataaaatat tgaaggattt aaaataataa   2100
taaataacat ataatatatg tatataaatt tattataata taacatttat ctataaaaaa   2160
gtaaatattg tcataaatct atacaatcgt ttagccttgc tggacgaatc tcaattattt   2220
aaacgagagt aaacatattt gactttttgg ttatttaaca aattattatt taacactata   2280
tgaaattttt tttttatca gcaaagaata aaattaaatt aagaaggaca atggtgtccc   2340
aatccttata caaccaactt ccacaagaaa gtcaagtcag agacaacaaa aaaacaagca   2400
aaggaaattt tttaatttga gttgtcttgt ttgctgcata atttatgcag taaaacacta   2460
cacataaccc ttttagcagt agagcaatgg ttgaccgtgt gcttagcttc ttttatttta   2520
tttttttatc agcaaagaat aaataaaata aaatgagaca cttcagggat gtttcaacaa   2580
gcttggcgcg ccgttctata gtgtcaccta aatcgtatgt gtatgataca taaggttatg   2640
tattaattgt agccgcgttc taacgacaat atgtccatat ggtgcactct cagtacaatc   2700
tgctctgatg ccgcatagtt aagccagccc cgacacccgc caacacccgc tgacgcgccc   2760
tgacgggctt gtctgctccc ggcatccgct tacagacaag ctgtgaccgt ctccgggagc   2820
tgcatgtgtc agaggttttc accgtcatca ccgaaacgcg cgagacgaaa gggcctcgtg   2880
atacgcctat ttttataggt taatgtcatg accaaaatcc cttaacgtga gttttcgttc   2940
cactgagcgt cagaccccgt agaaaagatc aaaggatctt cttgagatcc tttttttctg   3000
cgcgtaatct gctgcttgca aacaaaaaaa ccaccgctac cagcggtggt ttgtttgccg   3060
gatcaagagc taccaactct ttttccgaag gtaactggct tcagcagagc gcagatacca   3120
aatactgtcc ttctagtgta gccgtagtta ggccaccact tcaagaactc tgtagcaccg   3180
cctacatacc tcgctctgct aatcctgtta ccagtggctg ctgccagtgg cgataagtcg   3240
tgtcttaccg ggttggactc aagacgatag ttaccggata aggcgcagcg gtcgggctga   3300
acggggggtt cgtgcacaca gcccagcttg gagcgaacga cctacaccga actgagatac   3360
ctacagcgtg agcattgaga aagcgccacg cttcccgaag ggagaaaggc ggacaggtat   3420
ccggtaagcg gcagggtcgg aacaggagag cgcacgaggg agcttccagg gggaaacgcc   3480
tggtatcttt atagtcctgt cgggtttcgc cacctctgac ttgagcgtcg atttttgtga   3540
tgctcgtcag gggggcggag cctatggaaa aacgccagca acgcggcctt tttacggttc   3600
ctggcctttt gctggccttt tgctcacatg ttctttcctg cgttatcccc tgattctgtg   3660
gataaccgta ttaccgcctt tgagtgagct gataccgctc gccgcagccg aacgaccgag   3720
cgcagcgagt cagtgagcga ggaagcggaa gagcgcccaa tacgcaaacc gcctctcccc   3780
gcgcgttggc cgattcatta atgcaggttg atcagatctc gatcccgcga aattaatacg   3840
actcactata gggagaccac aacggtttcc ctctagaaat aattttgttt aactttaaga   3900
aggagatata cccatggaaa agcctgaact caccgcgacg tctgtcgaga agtttctgat   3960
cgaaaagttc gacagcgtct ccgacctgat gcagctctcg gagggcgaag aatctcgtgc   4020
tttcagcttc gatgtaggag ggcgtggata tgtcctgcgg gtaaatagct gcgccgatgg   4080
```

-continued

```
tttctacaaa gatcgttatg tttatcggca ctttgcatcg gccgcgctcc cgattccgga   4140
agtgcttgac attggggaat tcagcgagag cctgacctat tgcatctccc gccgtgcaca   4200
gggtgtcacg ttgcaagacc tgcctgaaac cgaactgccc gctgttctgc agccggtcgc   4260
ggaggctatg gatgcgatcg ctgcggccga tcttagccag acgagcgggt tcggcccatt   4320
cggaccgcaa ggaatcggtc aatacactac atggcgtgat ttcatatgcg cgattgctga   4380
tccccatgtg tatcactggc aaactgtgat ggacgacacc gtcagtgcgt ccgtcgcgca   4440
ggctctcgat gagctgatgc tttgggccga ggactgcccc gaagtccggc acctcgtgca   4500
cgcggatttc ggctccaaca atgtcctgac ggacaatggc cgcataacag cggtcattga   4560
ctggagcgag gcgatgttcg gggattccca atacgaggtc gccaacatct tcttctggag   4620
gccgtggttg gcttgtatgg agcagcagac gcgctacttc gagcggaggc atccggagct   4680
tgcaggatcg ccgcggctcc gggcgtatat gctccgcatt ggtcttgacc aactctatca   4740
gagcttggtt gacggcaatt tcgatgatgc agcttgggcg cagggtcgat gcgacgcaat   4800
cgtccgatcc ggagccggga ctgtcgggcg tacacaaatc gcccgcagaa gcgcggccgt   4860
ctggaccgat ggctgtgtag aagtactcgc cgatagtgga aaccgacgcc ccagcactcg   4920
tccgagggca aaggaatagt gaggtacagc ttggatcgat ccggctgcta acaaagcccg   4980
aaaggaagct gagttggctg ctgccaccgc tgagcaataa ctagcataac cccttggggc   5040
ctctaaacgg gtcttgaggg gttttttgct gaaaggagga actatatccg gatgatcggg   5100
cgcgccgtcg acggatccgt acgcaaaggc aaagatttaa actcgaaaac attacaaaag   5160
tctcaaaaca gaggcaaggc catgcacaaa gcacactcta agtgcttcca ttgcctacta   5220
agtagggtac gtacacgatc accattcacc agtgatgatc tttattaata tacaacacac   5280
tcagagacag cttatgttat agctagctag cataaactat cacatcatgt gttagtacga   5340
caagtgacaa cattgctttt aacttcgcgg ccttggatcc tctagaccgg atataatgag   5400
ccgtaaacaa agatgattaa gtagtaatta atacgtacta gtaaaagtgg caaaagataa   5460
cgagaaagaa ccaatttctt tgcattcggc cttagcggaa ggcatatata agctttgatt   5520
attttattta gtgtaatgat ttcgtacaac caaagcattt atttagtact ctcacacttg   5580
tgtcgcggcc gcgaattcac tagtgattcc ttatagagcc ttccccgcgg gttgcttctc   5640
cgccatccgg gcgaacaccg ccagatagcg cagcaggatg accaaccctt catggggcag   5700
cgggttccga tacggcaggt tgtgcttctg gcacagctgt tccacctggt agctaaccgc   5760
tgtcaggttg tggcgaggga gggtcggcca caaatggtgc tcaatctggt aattcaagcc   5820
tccgaaaaac caatctgtga taatccctcg ccgaatgttc atggtctcat ggatctggcc   5880
aaccgagaat ccatggccat cccagactga gtccccgatc ttctccagtg ggtagtggtt   5940
catgaacacc acgatcgcaa tgccgaagcc gccaaccagc tccgaaacga aaaacaccaa   6000
cagcgatgtg aggatgctgg gcataaagaa taagtggaac agggtcttca aggtccagtg   6060
cagggcgagg ccaatggcct ccttcttata ctgagagcga tagaattggt tatctctgtc   6120
cttcaaactg cgcacggtca acacgctctg gaaacaccaa atgaaccgca acaagataca   6180
gatgaccaag aaatagtact gctggaactg aatgagcttg cgggaaatcg gtgacgcccg   6240
tgtgacgtca tcctcagacc aggctaagag gggaggttg tcaatatcag ggtcgtgccc   6300
ttgaacattg gttgccgaat gatgtgcatt gtgtctgtcc ttccaccatg tcacggaaaa   6360
accttgcaga ccattgccaa ataccagtcc cacgaggttg ttccagttcc ggttcttgaa   6420
agtctggtgg tggcaaatgt catgagaaag ccagcccatc tgttgatagt gcatcccaag   6480
```

```
caacactgcc ccaatgaaat acatctgata ctgaaccatc aggaaataac ccagcactcc   6540
aaggcccagt gtggtgctga ttttgtatga gtaccagagg ggggaggcat caaacatgcc   6600
agttgcgatc aactcttctc ggagcttccg gaaatcctct tgagcttcat tcactgcagc   6660
ctggggtggc aactcagaac tgggattgat tttgggcatg cgcttgagct tgtcgaaggc   6720
ttcttgagag tgcataacca tgaaggcatc agtggcatcc cttccttggt aattctctat   6780
aatttccgca ccaccagggt ggaaattgac ccaggcagac acatcatatg ttgttccatc   6840
aattgtaagg ggaagcgctt ggcgctttga cttcatttca atcgaattcc cgcggccgct   6900
tggggggcta tggaagactt tcttagttag ttgtgtgaat aagcaatgtt gggagaatcg   6960
ggactactta taggatagga ataaaacaga aaagtattaa gtgctaatga aatatttaga   7020
ctgataatta aaatcttcac gtatgtccac ttgatataaa aacgtcagga ataaaggaag   7080
tacagtagaa tttaaaggta ctctttttat atatacccgt gttctctttt tggctagcta   7140
gttgcataaa aaataatcta tatttttatc attattttaa atatcttatg agatggtaaa   7200
tatttatcat aatttttttt actattattt attatttgtg tgtgtaatac atatagaagt   7260
taattacaaa ttttatttac tttttcatta ttttgatatg attcaccatt aatttagtgt   7320
tattatttat aatagttcat tttaatcttt ttgtatatat tatgcgtgca gtactttttt   7380
cctacatata actactatta cattttattt atataatatt tttattaatg aattttcgtg   7440
ataaatatgta atattgttca ttattatttc agatttttta aaaatatttg tgttattatt   7500
tatgaaatat gtaatttttt tagtatttga ttttatgatg ataaagtgtt ctaaattcaa   7560
aagaaggggg aaagcgtaaa cattaaaaaa cgtcatcaaa caaaaacaaa atcttgttaa   7620
taaagataaa actgtttgtt ttgatcactg ttatttcgta atataaaaac attatttata   7680
tttatattgt tgacaaccaa atttgcctat caaatctaac caatataatg catgcgtggc   7740
aggtaatgta ctaccatgaa cttaagtcat gacataataa accgtgaatc tgaccaatgc   7800
atgtacctan ctaaattgta tttgtgacac gaagcaaatg attcaattca caatggagat   7860
gggaaacaaa taatgaagaa cccagaacta agaaagcttt tctgaaaaat aaaataaagg   7920
caatgtcaaa agtatactgc atcatcagtc cagaaagcac atgatatttt tttatcagta   7980
tcaatgcagc tagttttatt ttacaatatc gatatagcta gtttaaatat attgcagcta   8040
gatttataaa tatttgtgtt attatttatc atttgtgtaa tcctgttttt agtattttag   8100
tttatatatg atgataatgt attccaaatt taaaagaagg gaaataaatt taaacaagaa   8160
aaaaagtcat caaacaaaaa acaaatgaaa gggtggaaag atgttaccat gtaatgtgaa   8220
tgttacagta tttcttttat tatagagtta acaaattaac taatatgatt ttgttaataa   8280
tgataaaata ttttttttat tattatttca taatataaaa atagtttact taatataaaa   8340
aaaattctat cgttcacaac aaagttggcc acctaattta accatgcatg tacccatgga   8400
ccatattagg taaccatcaa acctgatgaa gagataaaga gatgaagact taagtcataa   8460
cacaaaacca taaaaaacaa aaatacaatc aaccgtcaat ctgaccaatg catgaaaaag   8520
ctgcaatagt gagtggcgac acaaagcaca tgattttctt acaacggaga taaaaccaaa   8580
aaaatatttc atgaacaacc tagaacaaat aaagctttta tataataaat atataaataa   8640
ataaaggcta tggaataata tacttcaata tatttggatt aaataaattg ttggcggggt   8700
tgatatattt atacacacct aaagtcactt caatctcatt ttcacttaac ttttattttt   8760
tttttctttt tatttatcat aaagagaata ttgataatat actttttaac atatttttat   8820
```

-continued

```
gacatttttt attggtgaaa acttattaaa aatcataaat tttgtaagtt agatttattt   8880
aaagagttcc tcttcttatt ttaaattttt taataaattt ttaaataact aaaatttgtg   8940
ttaaaaatgt taaaaaatgt gttattaacc cttctcttcg aggacgtacg agatccggcc   9000
ggccagatcc tgcaggtctc aatagattaa gaagttggcg tctcattgat tgaccatggg   9060
ggatcctcta gacgtacgtg aaggttaaac atggtgaata tgttaccact agctgggatg   9120
cccattagat caaaactgta aaattctccc gtttcccttc tattcacatg tgagcccccct  9180
ccctttttctt tctttctcaa ttttgattga gttaaagtca ccagcaatgc atcactcacc  9240
ctccaaaaaa tttcttgtac aacttctcgg actatcccaa agctcctttt cctgagatgg   9300
atggtcctgt ctcttgccct tgatgtcttc cttgttcgat tttggcttcc tctaatgtct   9360
ttcttgctag gaatcaccac ctcactcatc tatgttgtcg tagcttctga aagtctcata   9420
catatcctta gtgttgcact catcttgtat tgaagtgaaa aagaatgttg ttctcctatc   9480
caaatctcca ttgaatctct ttctcccaat gttgtcccat cggttggtcc tcctctccaa   9540
ccaattgtaa ggtgtttaac ataaacatgg tacaattaag atttttcatt tcattaagaa   9600
aagattgaga tttgtggttc taaagtttca attagagttt gatgatattg aaacaaccgt   9660
agaacacatt aagtattact aacttataca tagagcattg gaatttcacc ttttatttat   9720
tctgtttccg ccaaaggtac atgactcaag ttattttaca caagtaacaa aggcatctaa   9780
gcctaagtat tcttattcag acttttcatt attactttca ttgatttggt gcgaaatgcg   9840
gccgcctact cttccttggg acggagtcca agaacacgca agtgctccaa atgtgaagca   9900
aatgcttgcc aaaacgtatc cttgacaagg tatggaacct tgtactcgct gcaggtgttc   9960
ttgatgatgg ccagaatatc gggataatgg tgctgcgaca cgttggggaa cagatggtgc  10020
acagcctggt agttcaagct gccagtgatg ctggtccaga ggtgcgaatc gtgtgcgtaa  10080
tcctgcgtag tctcgacctg catagctgcc cagtcctttt ggatgatccc gttctcgtca  10140
ggcaacggcc actgaacttc ctcaacaacg tggttcgcct ggaaggtcag cgccagccag  10200
taagacgaca ccatgtccgc gaccgtgaac aagagcagca ccttgcccag gggcagatac  10260
tgcaggggaa caatcaggcg ataccagaca aagaaagcct tgccgcccca gaacatcaca  10320
gtgtgccatg tcgagatggg attgacacga atagcgtcat tggtcttgac aaagtacaaa  10380
atgttgatgt cctgaatgcg caccttgaac gccagcagtc cgtacaggaa aggaacaaac  10440
atgtgctggt tgatgtggtt gacaaaccac ttttggttgg gcttgatacg acgaacatcg  10500
ggctcagacg tcgacacgtc gggatctgct ccagcaatgt tggtgtaggg gtgatggccg  10560
agcatatgtt ggtacatcca caccaggtac gatgctccgt tgaaaaagtc gtgcgtggct  10620
cccagaatct tccagacagt ggggttgtgg gtcactgaaa agtgagacgc atcatgaaga  10680
gggttgagtc cgacttgtgc gcacgcaaat cccatgatga ttgcaaacac cacctgaagc  10740
catgtgcgtt cgacaacgaa aggcacaaag agctgcgcgt agtaggaagc gatcaaggat  10800
ccaaagataa gagcgtatcg tccccagatc tctggtctat tcttgggatc aatgttccga  10860
tccgtaaagt agccctcgac tctcgtcttg atggttttgt ggaacaccgt tggctccggg  10920
aagatgggca gctcattcga gaccagtgta ccgacatagt acttcttcat aatggcatct  10980
gcagccccaa acgcgtgata catctcaaag accggagtaa catctcggcc agctccgagc  11040
aggagagtgt ccactccacc aggatggcgg ctcaagaact ttgtgacatc gtacaccctg  11100
ccgcggatgg ccaagagtag gtcgtccttg gtgttatggg ccgccagctc ttcccaggtg  11160
aaggttttc cttggtccgt tcccatgcgg ccgcggtgat gactgatgag tgtttaagga  11220
```

```
ccaatggaga gaatgtttga gttgtgaagc ggagaacctg aggcgtggtt atttataggg  11280
aagagaggaa ggtgaatgag ggacacgtca cagaagtagg gtgctgagct tgagacattc  11340
ttcagtatgc atggctatgg aagccttggg tgctacacct catgaagttc atggtgtgag  11400
gtggcttcgg catctcaatt aagtgacaaa gagaaaggtg tttcagtgtt tctattgcaa  11460
atggcagaaa ctcgtgatga cgaggggacc atgcatggtt tcatttcttt tcttcctgga  11520
ttctttcttt ccttttatat atgcaggttc ataatttaaa aattagactc gctttcaatt  11580
tcttaatttc tcattttcct cttatattac tgtactaatg ttaaccacgt acacttattt  11640
ttttttagt ttaattttga tagattgtgt tgatttaaac atattaatat tttcaaccaa  11700
ataaaaatca ttttagtaga tacggctttt taaataatta ttaaaaatat taactattta  11760
tcctaaatgg cacattttaa ttaaaaaaaa tccggtgttg taagtgtttt attaatttgt  11820
tttggcatta ttaaagcaac tttttttta tttgttggca ttttgagtac gtacttaggc  11880
tagcctgca                                                          11889
```

<210> SEQ ID NO 105
<211> LENGTH: 7769
<212> TYPE: DNA
<213> ORGANISM: Artificial Sequence
<220> FEATURE:
<223> OTHER INFORMATION: sequence of pZuFmEgD9ES

<400> SEQUENCE: 105

```
ggccgcaagt gtggatgggg aagtgagtgc ccggttctgt gtgcacaatt ggcaatccaa    60
gatggatgga ttcaacacag ggatatagcg agctacgtgg tggtgcgagg atatagcaac   120
ggatatttat gtttgacact tgagaatgta cgatacaagc actgtccaag tacaatacta   180
aacatactgt acatactcat actcgtaccc gggcaacggt ttcacttgag tgcagtggct   240
agtgctctta ctcgtacagt gtgcaatact gcgtatcata gtctttgatg tatatcgtat   300
tcattcatgt tagttgcgta cgagccggaa gcataaagtg taaagcctgg ggtgcctaat   360
gagtgagcta actcacatta attgcgttgc gctcactgcc cgctttccag tcgggaaacc   420
tgtcgtgcca gctgcattaa tgaatcggcc aacgcgcggg gagaggcggt ttgcgtattg   480
ggcgctcttc cgcttcctcg ctcactgact cgctgcgctc ggtcgttcgg ctgcggcgag   540
cggtatcagc tcactcaaag gcggtaatac ggttatccac agaatcaggg gataacgcag   600
gaaagaacat gtgagcaaaa ggccagcaaa aggccaggaa ccgtaaaaag gccgcgttgc   660
tggcgttttt ccataggctc cgcccccctg acgagcatca caaaaatcga cgctcaagtc   720
agaggtggcg aaacccgaca ggactataaa gataccaggc gtttccccct ggaagctccc   780
tcgtgcgctc tcctgttccg accctgccgc ttaccggata cctgtccgcc tttctccctt   840
cgggaagcgt ggcgctttct catagctcac gctgtaggta tctcagttcg gtgtaggtcg   900
ttcgctccaa gctgggctgt gtgcacgaac cccccgttca gcccgaccgc tgcgccttat   960
ccggtaacta tcgtcttgag tccaacccgg taagacacga cttatcgcca ctggcagcag  1020
ccactggtaa caggattagc agagcgaggt atgtaggcgg tgctacagag ttcttgaagt  1080
ggtggcctaa ctacggctac actagaagga cagtatttgg tatctgcgct ctgctgaagc  1140
cagttacctt cggaaaaaga gttggtagct cttgatccgg caaacaaacc accgctggta  1200
gcggtggttt ttttgtttgc aagcagcaga ttacgcgcag aaaaaaagga tctcaagaag  1260
atcctttgat cttttctacg gggtctgacg ctcagtggaa cgaaaactca cgttaaggga  1320
```

```
ttttggtcat gagattatca aaaaggatct tcacctagat ccttttaaat taaaaatgaa   1380
gttttaaatc aatctaaagt atatatgagt aaacttggtc tgacagttac caatgcttaa   1440
tcagtgaggc acctatctca gcgatctgtc tatttcgttc atccatagtt gcctgactcc   1500
ccgtcgtgta gataactacg atacgggagg gcttaccatc tggccccagt gctgcaatga   1560
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt gcgcaacgtt gttgccattg   1740
ctacaggcat cgtggtgtca cgctcgtcgt ttggtatggc ttcattcagc tccggttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttccttttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgccctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca agctctaaat cgggggctcc   2580
ctttagggtt ccgatttagt gctttacggc acctcgaccc caaaaaactt gattagggtg   2640
atggttcacg tagtgggcca tcgccctgat agacggtttt tcgccctttg acgttggagt   2700
ccacgttctt taatagtgga ctcttgttcc aaactggaac aacactcaac cctatctcgg   2760
tctattcttt tgatttataa gggattttgc cgatttcggc ctattggtta aaaaatgagc   2820
tgatttaaca aaaatttaac gcgaatttta acaaaatatt aacgcttaca atttccattc   2880
gccattcagg ctgcgcaact gttgggaagg gcgatcggtg cgggcctctt cgctattacg   2940
ccagctggcg aaagggggat gtgctgcaag gcgattaagt tgggtaacgc cagggttttc   3000
ccagtcacga cgttgtaaaa cgacggccag tgaattgtaa tacgactcac tatagggcga   3060
attgggtacc gggccccccc tcgaggtcga tggtgtcgat aagcttgata tcgaattcat   3120
gtcacacaaa ccgatcttcg cctcaaggaa acctaattct acatccgaga gactgccgag   3180
atccagtcta cactgattaa ttttcgggcc aataatttaa aaaaatcgtg ttatataata   3240
ttatatgtat tatatatata catcatgatg atactgacag tcatgtccca ttgctaaata   3300
gacagactcc atctgccgcc tccaactgat gttctcaata tttaaggggt catctcgcat   3360
tgtttaataa taaacagact ccatctaccg cctccaaatg atgttctcaa aatatattgt   3420
atgaacttat ttttattact tagtattatt agacaactta cttgctttat gaaaaacact   3480
tcctatttag gaaacaattt ataatggcag ttcgttcatt taacaattta tgtagaataa   3540
atgttataaa tgcgtatggg aaatcttaaa tatggatagc ataaatgata tctgcattgc   3600
ctaattcgaa atcaacagca acgaaaaaaa tcccttgtac aacataaata gtcatcgaga   3660
aatatcaact atcaaagaac agctattcac acgttactat tgagattatt attggacgag   3720
```

aatcacacac tcaactgtct ttctctcttc tagaaataca ggtacaagta tgtactattc 3780
tcattgttca tacttctagt catttcatcc cacatattcc ttggatttct ctccaatgaa 3840
tgacattcta tcttgcaaat tcaacaatta taataagata taccaaagta gcggtatagt 3900
ggcaatcaaa aagcttctct ggtgtgcttc tcgtatttat ttttattcta atgatccatt 3960
aaaggtatat atttatttct tgttatataa tccttttgtt tattacatgg gctggataca 4020
taaaggtatt ttgatttaat tttttgctta aattcaatcc cccctcgttc agtgtcaact 4080
gtaatggtag gaaattacca tacttttgaa gaagcaaaaa aaatgaaaga aaaaaaaaat 4140
cgtatttcca ggttagacgt tccgcagaat ctagaatgcg gtatgcggta cattgttctt 4200
cgaacgtaaa agttgcgctc cctgagatat tgtacatttt tgcttttaca agtacaagta 4260
catcgtacaa ctatgtacta ctgttgatgc atccacaaca gtttgttttg tttttttttg 4320
ttttttttt ttctaatgat tcattaccgc tatgtatacc tacttgtact tgtagtaagc 4380
cgggttattg gcgttcaatt aatcatagac ttatgaatct gcacggtgtg cgctgcgagt 4440
tacttttagc ttatgcatgc tacttgggtg taatattggg atctgttcgg aaatcaacgg 4500
atgctcaatc gatttcgaca gtaattaatt aagtcataca caagtcagct ttcttcgagc 4560
ctcatataag tataagtagt tcaacgtatt agcactgtac ccagcatctc cgtatcgaga 4620
aacacaacaa catgccccat tggacagatc atgcggatac acaggttgtg cagtatcata 4680
catactcgat cagacaggtc gtctgaccat catacaagct gaacaagcgc tccatacttg 4740
cacgctctct atatacacag ttaaattaca tatccatagt ctaacctcta acagttaatc 4800
ttctggtaag cctcccagcc agccttctgg tatcgcttgg cctcctcaat aggatctcgg 4860
ttctggccgt acagacctcg gccgacaatt atgatatccg ttccggtaga catgacatcc 4920
tcaacagttc ggtactgctg tccgagagcg tctcccttgt cgtcaagacc caccccgggg 4980
gtcagaataa gccagtcctc agagtcgccc ttaggtcggt tctgggcaat gaagccaacc 5040
acaaactcgg ggtcggatcg ggcaagctca atggtctgct tggagtactc gccagtggcc 5100
agagagccct tgcaagacag ctcggccagc atgagcagac ctctggccag cttctcgttg 5160
ggagagggga ctaggaactc cttgtactgg gagttctcgt agtcagagac gtcctccttc 5220
ttctgttcag agacagtttc ctcggcacca gctcgcaggc cagcaatgat tccggttccg 5280
ggtacaccgt gggcgttggt gatatcggac cactcggcga ttcggtgaca ccggtactgg 5340
tgcttgacag tgttgccaat atctgcgaac tttctgtcct cgaacaggaa gaaaccgtgc 5400
ttaagagcaa gttccttgag gggagcacca gtgccggcgt aggtgaagtc gtcaatgatg 5460
tcgatatggg ttttgatcat gcacacataa ggtccgacct tatcggcaag ctcaatgagc 5520
tccttggtgg tggtaacatc cagagaagca cacaggttgg ttttcttggc tgccacgagc 5580
ttgagcactc gagcggcaaa ggcggacttg tggacgttag ctcgagcttc gtaggagggc 5640
attttggtgg tgaagaggag actgaaataa atttagtctg cagaactttt tatcggaacc 5700
ttatctgggg cagtgaagta tatgttatgg taatagttac gagttagttg aacttataga 5760
tagactggac tatacggcta tcggtccaaa ttagaaagaa cgtcaatggc tctctgggcg 5820
tcgcctttgc cgacaaaaat gtgatcatga tgaaagccag caatgacgtt gcagctgata 5880
ttgttgtcgg ccaaccgcgc cgaaaacgca gctgtcagac ccacagcctc caacgaagaa 5940
tgtatcgtca aagtgatcca agcacactca tagttggagt cgtactccaa aggcggcaat 6000
gacgagtcag acagatactc gtcgacgttt aaacagtgta cgcagatcta ctatagagga 6060

```
acatttaaat tgccccggag aagacggcca ggccgcctag atgacaaatt caacaactca   6120
cagctgactt tctgccattg ccactagggg ggggcctttt tatatggcca agccaagctc   6180
tccacgtcgg ttgggctgca cccaacaata aatgggtagg gttgcaccaa caaagggatg   6240
ggatgggggg tagaagatac gaggataacg gggctcaatg gcacaaataa gaacgaatac   6300
tgccattaag actcgtgatc cagcgactga caccattgca tcatctaagg gcctcaaaac   6360
tacctcggaa ctgctgcgct gatctggaca ccacagaggt tccgagcact ttaggttgca   6420
ccaaatgtcc caccaggtgc aggcagaaaa cgctggaaca gcgtgtacag tttgtcttaa   6480
caaaaagtga gggcgctgag gtcgagcagg gtggtgtgac ttgttatagc ctttagagct   6540
gcgaaagcgc gtatggattt ggctcatcag gccagattga gggtctgtgg acacatgtca   6600
tgttagtgta cttcaatcgc cccctggata tagccccgac aataggccgt ggcctcattt   6660
ttttgccttc cgcacatttc cattgctcga tacccacacc ttgcttctcc tgcacttgcc   6720
aaccttaata ctggtttaca ttgaccaaca tcttacaagc ggggggcttg tctagggtat   6780
atataaacag tggctctccc aatcggttgc cagtctcttt tttcctttct ttccccacag   6840
attcgaaatc taaactacac atcacagaat tccgagccgt gagtatccac gacaagatca   6900
gtgtcgagac gacgcgtttt gtgtaatgac acaatccgaa agtcgctagc aacacacact   6960
ctctacacaa actaacccag ctctggtacc atggaggtcg tgaacgaaat cgtctccatt   7020
ggccaggagg ttcttcccaa ggtcgactat gctcagctct ggtctgatgc ctcgcactgc   7080
gaggtgctgt acctctccat cgccttcgtc atcctgaagt tcacccttgg tcctctcgga   7140
cccaagggtc agtctcgaat gaagtttgtg ttcaccaact acaacctgct catgtccatc   7200
tactcgctgg gctccttcct ctctatggcc tacgccatgt acaccattgg tgtcatgtcc   7260
gacaactgcg agaaggcttt cgacaacaat gtcttccgaa tcaccactca gctgttctac   7320
ctcagcaagt tcctcgagta cattgactcc ttctatctgc ccctcatggg caagcctctg   7380
acctggttgc agttctttca ccatctcgga gctcctatgg acatgtggct gttctacaac   7440
taccgaaacg aagccgtttg gatctttgtg ctgctcaacg gcttcattca ctggatcatg   7500
tacggctact attggacccg actgatcaag ctcaagttcc ctatgcccaa gtccctgatt   7560
acttctatgc agatcattca gttcaacgtt ggcttctaca tcgtctggaa gtaccggaac   7620
attccctgct accgacaaga tggaatgaga atgtttggct ggtttttcaa ctacttctac   7680
gttggtactg tcctgtgtct gttcctcaac ttctacgtgc agacctacat cgtccgaaag   7740
cacaagggag ccaaaaagat tcagtgagc                                     7769
```

<210> SEQ ID NO 106
<211> LENGTH: 7771
<212> TYPE: DNA
<213> ORGANISM: Artificial Sequence
<220> FEATURE:
<223> OTHER INFORMATION: sequence of pZuFmEgD9E

<400> SEQUENCE: 106

```
catggaggtg gtgaatgaaa tagtctcaat tgggcaggaa gttttaccca accagttgat     60
tatgcccaac tctggagtga tgccagtcac tgtgaggtgc tttacttgtc catcgcattt    120
gtcatcttga agttcactct tggcccccct ggtccaaaag gtcagtctcg tatgaagttt    180
gttttcacca attacaacct tctcatgtcc atttattcgt tgggatcatt cctctcaatg    240
gcatatgcca tgtacaccat cggtgttatg tctgacaact gcgagaaggc ttttgacaac    300
aacgtcttca ggatcaccac gcagttgttc tatttgagca agttcctgga gtatattgac    360
```

```
tccttctatt tgccactgat gggcaagcct ctgacctggt tgcaattctt ccatcatttg    420
ggggcaccga tggatatgtg gctgttctat aattaccgaa atgaagctgt ttggattttt    480
gtgctgttga atggtttcat ccactggatc atgtacggtt attattggac cagattgatc    540
aagctgaagt tccccatgcc aaaatccctg attacatcaa tgcagatcat tcaattcaat    600
gttggtttct acattgtctg gaagtacagg aacattccct gttatcgcca agatgggatg    660
aggatgtttg gctggttctt caattacttt tatgttggca cagtcttgtg tttgttcttg    720
aatttctatg tgcaaacgta tatcgtcagg aagcacaagg gagccaaaaa gattcagtga    780
gcggccgcaa gtgtggatgg ggaagtgagt gcccggttct gtgtgcacaa ttggcaatcc    840
aagatggatg gattcaacac agggatatag cgagctacgt ggtggtgcga ggatatagca    900
acggatattt atgtttgaca cttgagaatg tacgatacaa gcactgtcca agtacaatac    960
taaacatact gtacatactc atactcgtac ccgggcaacg gtttcacttg agtgcagtgg   1020
ctagtgctct tactcgtaca gtgtgcaata ctgcgtatca tagtctttga tgtatatcgt   1080
attcattcat gttagttgcg tacgagccgg aagcataaag tgtaaagcct ggggtgccta   1140
atgagtgagc taactcacat taattgcgtt gcgctcactg cccgctttcc agtcgggaaa   1200
cctgtcgtgc cagctgcatt aatgaatcgg ccaacgcgcg gggagaggcg gtttgcgtat   1260
tgggcgctct tccgcttcct cgctcactga ctcgctgcgc tcggtcgttc ggctgcggcg   1320
agcggtatca gctcactcaa aggcggtaat acggttatcc acagaatcag gggataacgc   1380
aggaaagaac atgtgagcaa aaggccagca aaaggccagg aaccgtaaaa aggccgcgtt   1440
gctggcgttt ttccataggc tccgcccccc tgacgagcat cacaaaaatc gacgctcaag   1500
tcagaggtgg cgaaacccga caggactata aagataccag gcgtttcccc ctggaagctc   1560
cctcgtgcgc tctcctgttc cgaccctgcc gcttaccgga tacctgtccg cctttctccc   1620
ttcgggaagc gtggcgcttt ctcatagctc acgctgtagg tatctcagtt cggtgtaggt   1680
cgttcgctcc aagctgggct gtgtgcacga accccccgtt cagcccgacc gctgcgcctt   1740
atccggtaac tatcgtcttg agtccaaccc ggtaagacac gacttatcgc cactggcagc   1800
agccactggt aacaggatta gcagagcgag gtatgtaggc ggtgctacag agttcttgaa   1860
gtggtggcct aactacggct acactagaag gacagtattt ggtatctgcg ctctgctgaa   1920
gccagttacc ttcggaaaaa gagttggtag ctcttgatcc ggcaaacaaa ccaccgctgg   1980
tagcggtggt ttttttgttt gcaagcagca gattacgcgc agaaaaaaag gatctcaaga   2040
agatcctttg atcttttcta cggggtctga cgctcagtgg aacgaaaact cacgttaagg   2100
gattttggtc atgagattat caaaaaggat cttcacctag atccttttaa attaaaaatg   2160
aagttttaaa tcaatctaaa gtatatatga gtaaacttgg tctgacagtt accaatgctt   2220
aatcagtgag gcacctatct cagcgatctg tctatttcgt tcatccatag ttgcctgact   2280
ccccgtcgtg tagataacta cgatacggga gggcttacca tctggcccca gtgctgcaat   2340
gataccgcga gacccacgct caccggctcc agatttatca gcaataaacc agccagccgg   2400
aagggccgag cgcagaagtg gtcctgcaac tttatccgcc tccatccagt ctattaattg   2460
ttgccgggaa gctagagtaa gtagttcgcc agttaatagt ttgcgcaacg ttgttgccat   2520
tgctacaggc atcgtggtgt cacgctcgtc gtttggtatg gcttcattca gctccggttc   2580
ccaacgatca aggcgagtta catgatcccc catgttgtgc aaaaaagcgg ttagctcctt   2640
cggtcctccg atcgttgtca gaagtaagtt ggccgcagtg ttatcactca tggttatggc   2700
```

-continued

```
agcactgcat aattctctta ctgtcatgcc atccgtaaga tgcttttctg tgactggtga   2760
gtactcaacc aagtcattct gagaatagtg tatgcggcga ccgagttgct cttgcccggc   2820
gtcaatacgg gataataccg cgccacatag cagaacttta aaagtgctca tcattggaaa   2880
acgttcttcg gggcgaaaac tctcaaggat cttaccgctg ttgagatcca gttcgatgta   2940
acccactcgt gcacccaact gatcttcagc atcttttact ttcaccagcg tttctgggtg   3000
agcaaaaaca ggaaggcaaa atgccgcaaa aaagggaata agggcgacac ggaaatgttg   3060
aatactcata ctcttccttt ttcaatatta ttgaagcatt tatcagggtt attgtctcat   3120
gagcggatac atatttgaat gtatttagaa aaataaacaa ataggggttc cgcgcacatt   3180
tccccgaaaa gtgccacctg acgcgccctg tagcggcgca ttaagcgcgg cgggtgtggt   3240
ggttacgcgc agcgtgaccg ctacacttgc cagcgcccta gcgcccgctc ctttcgcttt   3300
cttcccttcc tttctcgcca cgttcgccgg ctttccccgt caagctctaa atcgggggct   3360
ccctttaggg ttccgattta gtgctttacg gcacctcgac cccaaaaaac ttgattaggg   3420
tgatggttca cgtagtgggc catcgccctg atagacggtt tttcgccctt tgacgttgga   3480
gtccacgttc tttaatagtg gactcttgtt ccaaactgga acaacactca accctatctc   3540
ggtctattct tttgatttat aagggatttt gccgatttcg gcctattggt taaaaaatga   3600
gctgatttaa caaaaattta acgcgaattt taacaaaata ttaacgctta caatttccat   3660
tcgccattca ggctgcgcaa ctgttgggaa gggcgatcgg tgcgggcctc ttcgctatta   3720
cgccagctgg cgaaaggggg atgtgctgca aggcgattaa gttgggtaac gccagggttt   3780
tcccagtcac gacgttgtaa aacgacggcc agtgaattgt aatacgactc actatagggc   3840
gaattgggta ccgggccccc cctcgaggtc gatggtgtcg ataagcttga tatcgaattc   3900
atgtcacaca aaccgatctt cgcctcaagg aaacctaatt ctacatccga gagactgccg   3960
agatccagtc tacactgatt aattttcggg ccaataattt aaaaaaatcg tgttatataa   4020
tattatatgt attatatata tacatcatga tgatactgac agtcatgtcc cattgctaaa   4080
tagacagact ccatctgccg cctccaactg atgttctcaa tatttaaggg gtcatctcgc   4140
attgtttaat aataaacaga ctccatctac cgcctccaaa tgatgttctc aaaatatatt   4200
gtatgaactt atttttatta cttagtatta ttagacaact tacttgcttt atgaaaaaca   4260
cttcctattt aggaaacaat ttataatggc agttcgttca tttaacaatt tatgtagaat   4320
aaatgttata aatgcgtatg ggaaatctta aatatggata gcataaatga tatctgcatt   4380
gcctaattcg aaatcaacag caacgaaaaa aatcccttgt acaacataaa tagtcatcga   4440
gaaatatcaa ctatcaaaga acagctattc acacgttact attgagatta ttattggacg   4500
agaatcacac actcaactgt ctttctctct tctagaaata caggtacaag tatgtactat   4560
tctcattgtt catacttcta gtcatttcat cccacatatt ccttggattt ctctccaatg   4620
aatgacattc tatcttgcaa attcaacaat tataataaga tataccaaag tagcggtata   4680
gtggcaatca aaaagcttct ctggtgtgct tctcgtattt atttttattc taatgatcca   4740
ttaaaggtat atatttattt cttgttatat aatccttttg tttattacat gggctggata   4800
cataaaggta ttttgattta attttttgct taaattcaat ccccccctcgt tcagtgtcaa   4860
ctgtaatggt aggaaattac catacttttg aagaagcaaa aaaaatgaaa gaaaaaaaaa   4920
atcgtatttc caggttagac gttccgcaga atctagaatg cggtatgcgg tacattgttc   4980
ttcgaacgta aaagttgcgc tccctgagat attgtacatt tttgctttta caagtacaag   5040
tacatcgtac aactatgtac tactgttgat gcatccacaa cagtttgttt tgttttttt    5100
```

-continued

```
tgttttttt ttttctaatg attcattacc gctatgtata cctacttgta cttgtagtaa   5160
gccgggttat tggcgttcaa ttaatcatag acttatgaat ctgcacggtg tgcgctgcga   5220
gttactttta gcttatgcat gctacttggg tgtaatattg ggatctgttc ggaaatcaac   5280
ggatgctcaa tcgatttcga cagtaattaa ttaagtcata cacaagtcag ctttcttcga   5340
gcctcatata agtataagta gttcaacgta ttagcactgt acccagcatc tccgtatcga   5400
gaaacacaac aacatgcccc attggacaga tcatgcggat acacaggttg tgcagtatca   5460
tacatactcg atcagacagg tcgtctgacc atcatacaag ctgaacaagc gctccatact   5520
tgcacgctct ctatatacac agttaaatta catatccata gtctaacctc taacagttaa   5580
tcttctggta agcctcccag ccagccttct ggtatcgctt ggcctcctca ataggatctc   5640
ggttctggcc gtacagacct cggccgacaa ttatgatatc cgttccggta gacatgacat   5700
cctcaacagt tcggtactgc tgtccgagag cgtctccctt gtcgtcaaga cccaccccgg   5760
gggtcagaat aagccagtcc tcagagtcgc ccttaggtcg gttctgggca atgaagccaa   5820
ccacaaactc ggggtcggat cgggcaagct caatggtctg cttggagtac tcgccagtgg   5880
ccagagagcc cttgcaagac agctcggcca gcatgagcag acctctggcc agcttctcgt   5940
tgggagaggg gactaggaac tccttgtact gggagttctc gtagtcagag acgtcctcct   6000
tcttctgttc agagacagtt tcctcggcac cagctcgcag gccagcaatg attccggttc   6060
cgggtacacc gtgggcgttg gtgatatcgg accactcggc gattcggtga caccggtact   6120
ggtgcttgac agtgttgcca atatctgcga actttctgtc ctcgaacagg aagaaaccgt   6180
gcttaagagc aagttccttg agggggagca cagtgccggc gtaggtgaag tcgtcaatga   6240
tgtcgatatg ggttttgatc atgcacacat aaggtccgac cttatcggca agctcaatga   6300
gctccttggt ggtggtaaca tccagagaag cacacaggtt ggttttcttg gctgccacga   6360
gcttgagcac tcgagcggca aaggcggact tgtggacgtt agctcgagct tcgtaggagg   6420
gcattttggt ggtgaagagg agactgaaat aaatttagtc tgcagaactt tttatcggaa   6480
ccttatctgg ggcagtgaag tatatgttat ggtaatagtt acgagttagt tgaacttata   6540
gatagactgg actatacggc tatcggtcca aattagaaag aacgtcaatg gctctctggg   6600
cgtcgccttt gccgacaaaa atgtgatcat gatgaaagcc agcaatgacg ttgcagctga   6660
tattgttgtc ggccaaccgc gccgaaaacg cagctgtcag acccacagcc tccaacgaag   6720
aatgtatcgt caaagtgatc caagcacact catagttgga gtcgtactcc aaaggcggca   6780
atgacgagtc agacagatac tcgtcgacgt ttaaacagtg tacgcagatc tactatagag   6840
gaacatttaa attgccccgg agaagacggc caggccgcct agatgacaaa ttcaacaact   6900
cacagctgac tttctgccat tgccactagg ggggggcctt tttatatggc caagccaagc   6960
tctccacgtc ggttgggctg cacccaacaa taaatgggta gggttgcacc aacaaaggga   7020
tgggatgggg ggtagaagat acgaggataa cggggctcaa tggcacaaat aagaacgaat   7080
actgccatta agactcgtga tccagcgact gacaccattg catcatctaa gggcctcaaa   7140
actacctcgg aactgctgcg ctgatctgga caccacagag gttccgagca ctttaggttg   7200
caccaaatgt cccaccaggt gcaggcagaa aacgctggaa cagcgtgtac agtttgtctt   7260
aacaaaaagt gagggcgctg aggtcgagca gggtggtgtg acttgttata gcctttagag   7320
ctgcgaaagc gcgtatggat ttggctcatc aggccagatt gagggtctgt ggacacatgt   7380
catgttagtg tacttcaatc gccccctgga tatagccccg acaataggcc gtggcctcat   7440
```

tttttgcct tccgcacatt tccattgctc gatacccaca ccttgcttct cctgcacttg 7500
ccaaccttaa tactggttta cattgaccaa catcttacaa gcgggggct tgtctagggt 7560 atatataaac agtggctctc ccaatcggtt gccagtctct tttttccttt ctttccccac 7620
agattcgaaa tctaaactac acatcacaga attccgagcc gtgagtatcc acgacaagat 7680
cagtgtcgag acgacgcgtt ttgtgtaatg acacaatccg aaagtcgcta gcaacacaca 7740
ctctctacac aaactaaccc agctctggta c 7771

<210> SEQ ID NO 107
<211> LENGTH: 39
<212> TYPE: DNA
<213> ORGANISM: Artificial Sequence
<220> FEATURE:
<223> OTHER INFORMATION: sequence of the SMART(TM) IV oligonucleotide

<400> SEQUENCE: 107
aagcagtggt atcaacgcag agtggccatt acggccggg 39

<210> SEQ ID NO 108
<211> LENGTH: 59
<212> TYPE: DNA
<213> ORGANISM: Artificial Sequence
<220> FEATURE:
<223> OTHER INFORMATION: sequence of the CDSIII/3' PCR primer
<220> FEATURE:
<221> NAME/KEY: misc_feature
<222> LOCATION: (28)..(57)
<220> FEATURE:
<221> NAME/KEY: misc_feature
<222> LOCATION: (28)..(57)
<223> OTHER INFORMATION: thymidine (dT); see BD Biosciences Clontech's SMART cDNA technology
<220> FEATURE:
<221> NAME/KEY: misc_feature
<222> LOCATION: (59)..(59)
<223> OTHER INFORMATION: n is a, c, g, or t

<400> SEQUENCE: 108
attctagagg ccgaggcggc cgacatgttt tttttttttt tttttttttt tttttttvn 59

<210> SEQ ID NO 109
<211> LENGTH: 23
<212> TYPE: DNA
<213> ORGANISM: Artificial Sequence
<220> FEATURE:
<223> OTHER INFORMATION: sequence of 5'-PCR primer

<400> SEQUENCE: 109
aagcagtggt atcaacgcag agt 23

<210> SEQ ID NO 110
<211> LENGTH: 7779
<212> TYPE: DNA
<213> ORGANISM: Artificial Sequence
<220> FEATURE:
<223> OTHER INFORMATION: sequence of pFBAIN-389Elo

<400> SEQUENCE: 110
ggccgcaagt gtggatgggg aagtgagtgc ccggttctgt gtgcacaatt ggcaatccaa 60
gatggatgga ttcaacacag ggatatagcg agctacgtgg tggtgcgagg atatagcaac 120
ggatatttat gtttgacact tgagaatgta cgatacaagc actgtccaag tacaatacta 180
aacatactgt acatactcat actcgtaccc gggcaacggt ttcacttgag tgcagtggct 240
agtgctctta ctcgtacagt gtgcaatact gcgtatcata gtctttgatg tatatcgtat 300

```
tcattcatgt tagttgcgta cgagccggaa gcataaagtg taaagcctgg ggtgcctaat    360
gagtgagcta actcacatta attgcgttgc gctcactgcc cgctttccag tcgggaaacc    420
tgtcgtgcca gctgcattaa tgaatcggcc aacgcgcggg gagaggcggt ttgcgtattg    480
ggcgctcttc cgcttcctcg ctcactgact cgctgcgctc ggtcgttcgg ctgcggcgag    540
cggtatcagc tcactcaaag gcggtaatac ggttatccac agaatcaggg gataacgcag    600
gaaagaacat gtgagcaaaa ggccagcaaa aggccaggaa ccgtaaaaag gccgcgttgc    660
tggcgttttt ccataggctc cgcccccctg acgagcatca caaaaatcga cgctcaagtc    720
agaggtggcg aaacccgaca ggactataaa gataccaggc gtttccccct ggaagctccc    780
tcgtgcgctc tcctgttccg accctgccgc ttaccggata cctgtccgcc tttctccctt    840
cgggaagcgt ggcgctttct catagctcac gctgtaggta tctcagttcg gtgtaggtcg    900
ttcgctccaa gctgggctgt gtgcacgaac cccccgttca gcccgaccgc tgcgccttat    960
ccggtaacta tcgtcttgag tccaacccgg taagacacga cttatcgcca ctggcagcag   1020
ccactggtaa caggattagc agagcgaggt atgtaggcgg tgctacagag ttcttgaagt   1080
ggtggcctaa ctacggctac actagaagga cagtatttgg tatctgcgct ctgctgaagc   1140
cagttacctt cggaaaaaga gttggtagct cttgatccgg caaacaaacc accgctggta   1200
gcggtggttt ttttgtttgc aagcagcaga ttacgcgcag aaaaaaagga tctcaagaag   1260
atcctttgat cttttctacg gggtctgacg ctcagtggaa cgaaaactca cgttaaggga   1320
ttttggtcat gagattatca aaaaggatct tcacctagat ccttttaaat taaaaatgaa   1380
gttttaaatc aatctaaagt atatatgagt aaacttggtc tgacagttac caatgcttaa   1440
tcagtgaggc acctatctca gcgatctgtc tatttcgttc atccatagtt gcctgactcc   1500
ccgtcgtgta gataactacg atacgggagg gcttaccatc tggccccagt gctgcaatga   1560
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt gcgcaacgtt gttgccattg   1740
ctacaggcat cgtggtgtca cgctcgtcgt ttggtatggc ttcattcagc tccggttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttccttttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgccctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca agctctaaat cgggggctcc   2580
ctttagggtt ccgatttagt gctttacggc acctcgaccc caaaaaactt gattagggtg   2640
```

```
atggttcacg tagtgggcca tcgccctgat agacggtttt tcgccctttg acgttggagt   2700
ccacgttctt taatagtgga ctcttgttcc aaactggaac aacactcaac cctatctcgg   2760
tctattcttt tgatttataa gggattttgc cgatttcggc ctattggtta aaaaatgagc   2820
tgatttaaca aaaatttaac gcgaatttta acaaaatatt aacgcttaca atttccattc   2880
gccattcagg ctgcgcaact gttgggaagg gcgatcggtg cgggcctctt cgctattacg   2940
ccagctggcg aaagggggat gtgctgcaag gcgattaagt tgggtaacgc cagggttttc   3000
ccagtcacga cgttgtaaaa cgacggccag tgaattgtaa tacgactcac tatagggcga   3060
attgggtacc gggccccccc tcgaggtcga tggtgtcgat aagcttgata tcgaattcat   3120
gtcacacaaa ccgatcttcg cctcaaggaa acctaattct acatccgaga gactgccgag   3180
atccagtcta cactgattaa ttttcgggcc aataatttaa aaaaatcgtg ttatataata   3240
ttatatgtat tatatatata catcatgatg atactgacag tcatgtccca ttgctaaata   3300
gacagactcc atctgccgcc tccaactgat gttctcaata tttaaggggt catctcgcat   3360
tgtttaataa taaacagact ccatctaccg cctccaaatg atgttctcaa aatatattgt   3420
atgaacttat ttttattact tagtattatt agacaactta cttgctttat gaaaaacact   3480
tcctatttag gaaacaattt ataatggcag ttcgttcatt taacaattta tgtagaataa   3540
atgttataaa tgcgtatggg aaatcttaaa tatggatagc ataaatgata tctgcattgc   3600
ctaattcgaa atcaacagca acgaaaaaaa tcccttgtac aacataaata gtcatcgaga   3660
aatatcaact atcaaagaac agctattcac acgttactat tgagattatt attggacgag   3720
aatcacacac tcaactgtct ttctctcttc tagaaataca ggtacaagta tgtactattc   3780
tcattgttca tacttctagt catttcatcc cacatattcc ttggatttct ctccaatgaa   3840
tgacattcta tcttgcaaat tcaacaatta taataagata taccaaagta gcggtatagt   3900
ggcaatcaaa aagcttctct ggtgtgcttc tcgtatttat ttttattcta atgatccatt   3960
aaaggtatat atttatttct tgttatataa tccttttgtt tattacatgg gctggataca   4020
taaaggtatt ttgatttaat tttttgctta aattcaatcc cccctcgttc agtgtcaact   4080
gtaatggtag gaaattacca tacttttgaa gaagcaaaaa aaatgaaaga aaaaaaaaat   4140
cgtatttcca ggttagacgt tccgcagaat ctagaatgcg gtatgcggta cattgttctt   4200
cgaacgtaaa agttgcgctc cctgagatat tgtacatttt tgcttttaca agtacaagta   4260
catcgtacaa ctatgtacta ctgttgatgc atccacaaca gtttgttttg tttttttttg   4320
tttttttttt ttctaatgat tcattaccgc tatgtatacc tacttgtact tgtagtaagc   4380
cgggttattg gcgttcaatt aatcatagac ttatgaatct gcacggtgtg cgctgcgagt   4440
tacttttagc ttatgcatgc tacttgggtg taatattggg atctgttcgg aaatcaacgg   4500
atgctcaatc gatttcgaca gtaattaatt aagtcataca caagtcagct ttcttcgagc   4560
ctcatataag tataagtagt tcaacgtatt agcactgtac ccagcatctc cgtatcgaga   4620
aacacaacaa catgccccat tggacagatc atgcggatac acaggttgtg cagtatcata   4680
catactcgat cagacaggtc gtctgaccat catacaagct gaacaagcgc tccatacttg   4740
cacgctctct atatacacag ttaaattaca tatccatagt ctaacctcta acagttaatc   4800
ttctggtaag cctcccagcc agccttctgg tatcgcttgg cctcctcaat aggatctcgg   4860
ttctggccgt acagacctcg gccgacaatt atgatatccg ttccggtaga catgacatcc   4920
tcaacagttc ggtactgctg tccgagagcg tctcccttgt cgtcaagacc caccccgggg   4980
gtcagaataa gccagtcctc agagtcgccc ttaggtcggt tctgggcaat gaagccaacc   5040
```

```
acaaactcgg ggtcggatcg ggcaagctca atggtctgct tggagtactc gccagtggcc   5100
agagagccct tgcaagacag ctcggccagc atgagcagac ctctggccag cttctcgttg   5160
ggagagggga ctaggaactc cttgtactgg gagttctcgt agtcagagac gtcctccttc   5220
ttctgttcag agacagtttc ctcggcacca gctcgcaggc cagcaatgat tccggttccg   5280
ggtacaccgt gggcgttggt gatatcggac cactcggcga ttcggtgaca ccggtactgg   5340
tgcttgacag tgttgccaat atctgcgaac tttctgtcct cgaacaggaa gaaaccgtgc   5400
ttaagagcaa gttccttgag ggggagcaca gtgccggcgt aggtgaagtc gtcaatgatg   5460
tcgatatggg ttttgatcat gcacacataa ggtccgacct tatcggcaag ctcaatgagc   5520
tccttggtgg tggtaacatc cagagaagca cacaggttgg ttttcttggc tgccacgagc   5580
ttgagcactc gagcggcaaa ggcggacttg tggacgttag ctcgagcttc gtaggagggc   5640
attttggtgg tgaagaggag actgaaataa atttagtctg cagaactttt tatcggaacc   5700
ttatctgggg cagtgaagta tatgttatgg taatagttac gagttagttg aacttataga   5760
tagactggac tatacggcta tcggtccaaa ttagaaagaa cgtcaatggc tctctgggcg   5820
tcgcctttgc cgacaaaaat gtgatcatga tgaaagccag caatgacgtt gcagctgata   5880
ttgttgtcgg ccaaccgcgc cgaaaacgca gctgtcagac ccacagcctc caacgaagaa   5940
tgtatcgtca aagtgatcca agcacactca tagttggagt cgtactccaa aggcggcaat   6000
gacgagtcag acagatactc gtcgaaaaca gtgtacgcag atctactata gaggaacatt   6060
taaattgccc cggagaagac ggccaggccg cctagatgac aaattcaaca actcacagct   6120
gactttctgc cattgccact aggggggggc ctttttatat ggccaagcca agctctccac   6180
gtcggttggg ctgcacccaa caataaatgg gtagggttgc accaacaaag ggatgggatg   6240
gggggtagaa gatacgagga taacggggct caatggcaca aataagaacg aatactgcca   6300
ttaagactcg tgatccagcg actgacacca ttgcatcatc taagggcctc aaaactacct   6360
cggaactgct gcgctgatct ggacaccaca gaggttccga gcactttagg ttgcaccaaa   6420
tgtcccacca ggtgcaggca gaaaacgctg gaacagcgtg tacagtttgt cttaacaaaa   6480
agtgagggcg ctgaggtcga gcagggtggt gtgacttgtt atagccttta gagctgcgaa   6540
agcgcgtatg gatttggctc atcaggccag attgagggtc tgtggacaca tgtcatgtta   6600
gtgtacttca atcgccccct ggatatagcc ccgacaatag gccgtggcct catttttttg   6660
ccttccgcac atttccattg ctcggtaccc acaccttgct tctcctgcac ttgccaacct   6720
taatactggt ttacattgac caacatctta caagcggggg gcttgtctag ggtatatata   6780
aacagtggct ctcccaatcg gttgccagtc tcttttttcc tttctttccc cacagattcg   6840
aaatctaaac tacacatcac agaattccga gccgtgagta tccacgacaa gatcagtgtc   6900
gagacgacgc gttttgtgta atgacacaat ccgaaagtcg ctagcaacac acactctcta   6960
cacaaactaa cccagctctg gtaccatggc tgcggtgata gaggtcgcca acgagtttgt   7020
agccatcacg gcagaaacgc tccccaaagt tgactatcaa cgactatggc gagacattta   7080
cagttgtgag ctactgtatt tctccattgc cttcgtgatc ttgaagttta cgttgggcga   7140
gttgagcgac agcggaaaaa agattttgag agtgttgttc aagtggtaca atctcttcat   7200
gtccgtgttc tccttggtgt ctttcctttg catgggctat gccatttata ccgtgggcct   7260
atactctaac gaatgcgaca gggctttcga caactcgttg ttccgctttg caacaaaggt   7320
gttctactac agtaagtttt tggagtacat cgactctttt tatcttccgc tcatggccaa   7380
```

gccgctgtct ttcctgcaat tcttccatca cttgggagcc cccatggaca tgtggctctt 7440
tgtccaatat tctggggaat ctatttggat ctttgtgttt ttgaatgggt tcattcactt 7500
tgttatgtac gggtactact ggactcggct gatgaagttc aatttcccaa tgcccaagca 7560
gttgattacc gcgatgcaga tcacgcagtt caacgttggt ttctacctcg tgtggtggta 7620
caaagatatt ccctgctacc gaaaggatcc catgcgaatg ttggcctgga tcttcaatta 7680
ctggtatgtt gggactgtct tgctgctgtt cattaatttc ttcgtcaaat cctatgtgtt 7740
cccaaagccg aagactgcag ataaaaaggt ccaataggc 7779

<210> SEQ ID NO 111
<211> LENGTH: 1504
<212> TYPE: DNA
<213> ORGANISM: Eutreptiella sp. CCMP389
<220> FEATURE:
<221> NAME/KEY: misc_feature
<222> LOCATION: (1487)..(1487)
<223> OTHER INFORMATION: n is a, c, g, or t

<400> SEQUENCE: 111
tccatttcgc ccgtcaagcc agagtggcca ttacggctgg tcggacacaa catggctgcg 60
gtgatagagg tcgccaacga gtttgtagcc atcacggcag aaacgctccc caaagttgac 120
tatcaacgac tatggcgaga catttacagt tgtgagctac tgtatttctc cattgccttc 180
gtgatcttga agtttacgtt gggcgagttg agcgacagcg gaaaaaagat tttgagagtg 240
ttgttcaagt ggtacaatct cttcatgtcc gtgttctcct tggtgtcttt cctttgcatg 300
ggctatgcca tttataccgt gggcctatac tctaacgaat gcgacagggc tttcgacaac 360
tcgttgttcc gctttgcaac aaaggtgttc tactacagta agtttttgga gtacatcgac 420
tctttttatc ttccgctcat ggccaagccg ctgtctttcc tgcaattctt ccatcacttg 480
ggagccccca tggacatgtg gctctttgtc caatattctg ggaatctat ttggatcttt 540
gtgtttttga atgggttcat tcactttgtt atgtacgggt actactggac tcggctgatg 600
aagttcaatt tcccaatgcc caagcagttg attaccgcga tgcagatcac gcagttcaac 660
gttggtttct acctcgtgtg gtggtacaaa gatattccct gctaccgaaa ggatcccatg 720
cgaatgttgg cctggatctt caattactgg tatgttggga ctgtcttgct gctgttcatt 780
aatttcttcg tcaaatccta tgtgttccca aagccgaaga ctgcagataa aaaggtccaa 840
tagctgcaca cacacaatta tgcagctccc caccactttc tccccaaaac agccagccag 900
cccccttccc atgaaacaag aacctacccc ctccctgctc ctcttttttt aatctcttat 960
tccaccatac acttgatgac aacagttgcc gtgcagtgga gctatgtggt gcatgctgca 1020
atgcactggg gcatcatatt aagattattg ttattagtgg tgcccttgct tctctgcttt 1080
gtgcccctgg taccagggtg cacccatgat gcagtacaca agttgttcaa tgtgtgcact 1140
gtggtattct ctgaattcct tgaggagcca tttagtttaa ccaagcatga ctcggctgga 1200
ttggctcgag gtcattgcgg aagcaaaagt tttgcgaggc agctgccgaa ggtgctgcta 1260
agttcggctt caaactggcc tttgcacacc caggtaccca gggattccaa gtctcatggc 1320
tggcatattt taggtttcat gcatccgcag tggcgtttat gcaaggcaca gacgtttata 1380
tttatggata tgcgagtgaa ggttggcttg ccagcattgg catcgcctgc ctgcatactg 1440
agttttgttg taaaagtaca aactcagtat caacaataca atttttnttt gaaaaaaaaa 1500
aaaa 1504

<210> SEQ ID NO 112
<211> LENGTH: 20
<212> TYPE: DNA
<213> ORGANISM: Artificial Sequence
<220> FEATURE:
<223> OTHER INFORMATION: sequence of degenerate primer EuEF3
<220> FEATURE:
<221> NAME/KEY: misc_feature
<222> LOCATION: (3)..(3)
<223> OTHER INFORMATION: n is a, c, g, or t

<400> SEQUENCE: 112
ytncarttyt tycaycaytt 20

<210> SEQ ID NO 113
<211> LENGTH: 7
<212> TYPE: PRT
<213> ORGANISM: Artificial Sequence
<220> FEATURE:
<223> OTHER INFORMATION: deduced amino acid sequence of the nucleotide sequence of degenerate primer EuEF3

<400> SEQUENCE: 113

Leu Gln Phe Phe His His Leu
1 5

<210> SEQ ID NO 114
<211> LENGTH: 20
<212> TYPE: DNA
<213> ORGANISM: Artificial Sequence
<220> FEATURE:
<223> OTHER INFORMATION: the nucleotide sequence of degenerate primer EuER3

<400> SEQUENCE: 114
ttraaytgda tdatytgcat 20

<210> SEQ ID NO 115
<211> LENGTH: 7
<212> TYPE: PRT
<213> ORGANISM: Artificial Sequence
<220> FEATURE:
<223> OTHER INFORMATION: deduced amino acid sequence of the nucleotide sequence of degenerate primer EuER3

<400> SEQUENCE: 115

Met Gln Ile Ile Gln Phe Asn
1 5

<210> SEQ ID NO 116
<211> LENGTH: 22
<212> TYPE: DNA
<213> ORGANISM: Artificial Sequence
<220> FEATURE:
<223> OTHER INFORMATION: sequence of 389Elo-5-1 primer

<400> SEQUENCE: 116
gaatgaaccc attcaaaaac ac 22

<210> SEQ ID NO 117
<211> LENGTH: 22
<212> TYPE: DNA
<213> ORGANISM: Artificial Sequence
<220> FEATURE:
<223> OTHER INFORMATION: sequence of 389Elo-5-2 primer

<400> SEQUENCE: 117
gatccaaata gattccccag aa 22

<210> SEQ ID NO 118
<211> LENGTH: 22
<212> TYPE: DNA
<213> ORGANISM: Artificial Sequence
<220> FEATURE:
<223> OTHER INFORMATION: sequence of DNR CDS 5'-2 primer

<400> SEQUENCE: 118
caacgcagag tggccattac gg 22

<210> SEQ ID NO 119
<211> LENGTH: 406
<212> TYPE: DNA
<213> ORGANISM: Eutreptiella sp. CCMP389
<220> FEATURE:
<221> NAME/KEY: misc_feature
<222> LOCATION: (1)..(406)
<223> OTHER INFORMATION: the sequence of the Eutreptiella sp. CCMP389 (E389D9e) 5' cDNA fragment #1
<220> FEATURE:
<221> NAME/KEY: misc_feature
<222> LOCATION: (1)..(406)
<223> OTHER INFORMATION: sequence of the Eutreptiella sp. CCMP389 (E389D9e) 5' cDNA fragment #1

<400> SEQUENCE: 119
atggcgagac atttacagtt gtgagctact gtatttctcc attgccttcg tgatcttgaa 60
gtttacgttg ggcgagttga gcgacagcgg aaaaaagatt ttgagagtgt tgttcaagtg 120
gtacaatctc ttcatgtccg tgttctcctt ggtgtctttc ctttgcatgg gctatgccat 180
ttataccgtg ggcctatact ctaacgaatg cgacagggct ttcgacaact cgttgttccg 240
ctttgcaaca aaggtgttct actacagtaa gtttttggag tacatcgact ctttttatct 300
tccgctcatg gccaagccgc tgtctttcct gcaattcttc catcacttgg gagcccccat 360
ggacatgtgg ctctttgtcc aatattctgg ggaatctatt tggatc 406

<210> SEQ ID NO 120
<211> LENGTH: 21
<212> TYPE: DNA
<213> ORGANISM: Artificial Sequence
<220> FEATURE:
<223> OTHER INFORMATION: sequence of 389Elo-5-4 primer

<400> SEQUENCE: 120
gtaaacttca agatcacgaa g 21

<210> SEQ ID NO 121
<211> LENGTH: 197
<212> TYPE: DNA
<213> ORGANISM: Eutreptiella sp. CCMP389
<220> FEATURE:
<221> NAME/KEY: misc_feature
<222> LOCATION: (1)..(197)
<223> OTHER INFORMATION: is the sequence of the Eutreptiella sp. CCMP389 (E389D9e) 5' cDNA fragment #2
<220> FEATURE:
<221> NAME/KEY: misc_feature
<222> LOCATION: (1)..(197)
<223> OTHER INFORMATION: sequence of the Eutreptiella sp. CCMP389 (E389D9e) 5' cDNA fragment #2

<400> SEQUENCE: 121
tccatttcgc ccgtcaagcc agagtggcca ttacggctgg tcggacacaa catggctgcg 60
gtgatagagg tcgccaacga gtttgtagcc atcacggcag aaacgctccc caaagttgac 120
tatcaacgac tatggcgaga catttacagt tgtgagctac tgtatttctc cattgccttc 180
gtgatcttga agtttac 197

<210> SEQ ID NO 122
<211> LENGTH: 22
<212> TYPE: DNA
<213> ORGANISM: Artificial Sequence
<220> FEATURE:
<223> OTHER INFORMATION: sequence of 389Elo-3-1 primer

<400> SEQUENCE: 122
gttcattcac tttgttatgt ac 22

<210> SEQ ID NO 123
<211> LENGTH: 22
<212> TYPE: DNA
<213> ORGANISM: Artificial Sequence
<220> FEATURE:
<223> OTHER INFORMATION: sequence of 389Elo-3-2 primer

<400> SEQUENCE: 123
ctggactcgg ctgatgaagt tc 22

<210> SEQ ID NO 124
<211> LENGTH: 920
<212> TYPE: DNA
<213> ORGANISM: Eutreptiella sp. CCMP389
<220> FEATURE:
<221> NAME/KEY: misc_feature
<222> LOCATION: (1)..(920)
<223> OTHER INFORMATION: is the nucleotiden sequence of the Eutreptiella sp. CCMP389 (E389D9e) 3' cDNA fragment

<400> SEQUENCE: 124
ctggactcgg ctgatgaagt tcaatttccc aatgcccaag cagttgatta ccgcgatgca 60
gatcacgcag ttcaacgttg gtttctacct cgtgtggtgg tacaaagata ttccctgcta 120
ccgaaaggat cccatgcgaa tgttggcctg gatcttcaat tactggtatg ttgggactgt 180
cttgctgctg ttcattaatt tcttcgtcaa atcctatgtg ttcccaaagc cgaagactgc 240
agataaaaag gtccaatagc tgcacacaca caattatgca gctccccacc actttctccc 300
caaaacagcc agccagcccc cttcccatga aacaagaacc taccccctcc ctgctcctct 360
ttttttaatc tcttattcca ccatacactt gatgacaaca gttgccgtgc agtggagcta 420
tgtggtgcat gctgcaatgc actggggcat catattaaga ttattgttat tagtggtgcc 480
cttgcttctc tgctttgtgc ccctggtacc agggtgcacc catgatgcag tacacaagtt 540
gttcaatgtg tgcactgtgg tattctctga attccttgag gagccattta gtttaaccaa 600
gcatgactcg gctggattgg ctcgaggtca ttgcggaagc aaaagttttg cgaggcagct 660
gccgaaggtg ctgctaagtt cggcttcaaa ctggcctttg cacacccagg tacccaggga 720
ttccaagtct catggctggc atattttagg tttcatgcat ccgcagtggc gtttatgcaa 780
ggcacagacg tttatattta tggatatgcg agtgaaggtt ggcttgccag cattggcatc 840
gcctgcctgc atactgagtt ttgttgtaaa agtacaaact cagtatcaac aatacaattt 900
ttktttgaaa aaaaaaaaaa 920

<210> SEQ ID NO 125
<211> LENGTH: 1504
<212> TYPE: DNA
<213> ORGANISM: Eutreptiella sp. CCMP389

<220> FEATURE:
<221> NAME/KEY: misc_feature
<222> LOCATION: (1)..(1504)
<223> OTHER INFORMATION: the nucleotide sequence of the Eutreptiella sp. CCMP389 (E389D9e) complete assembled contig
<220> FEATURE:
<221> NAME/KEY: misc_feature
<222> LOCATION: (1)..(1504)
<223> OTHER INFORMATION: sequence of the Eutreptiella sp. CCMP389 (E389D9e) complete assembled contig

<400> SEQUENCE: 125

```
tccatttcgc ccgtcaagcc agagtggcca ttacggctgg tcggacacaa catggctgcg     60

gtgatagagg tcgccaacga gtttgtagcc atcacggcag aaacgctccc caaagttgac    120

tatcaacgac tatggcgaga catttacagt tgtgagctac tgtatttctc cattgccttc    180

gtgatcttga agtttacgtt gggcgagttg agcgacagcg gaaaaaagat tttgagagtg    240

ttgttcaagt ggtacaatct cttcatgtcc gtgttctcct tggtgtcttt cctttgcatg    300

ggctatgcca tttataccgt gggcctatac tctaacgaat gcgacagggc tttcgacaac    360

tcgttgttcc gctttgcaac aaaggtgttc tactacagta agtttttgga gtacatcgac    420

tctttttatc ttccgctcat ggccaagccg ctgtctttcc tgcaattctt ccatcacttg    480

ggagccccca tggacatgtg gctctttgtc caatattctg ggaatctat ttggatcttt    540

gtgtttttga atgggttcat tcactttgtt atgtacgggt actactggac tcggctgatg    600

aagttcaatt tcccaatgcc caagcagttg attaccgcga tgcagatcac gcagttcaac    660

gttggtttct acctcgtgtg gtggtacaaa gatattccct gctaccgaaa ggatcccatg    720

cgaatgttgg cctggatctt caattactgg tatgttggga ctgtcttgct gctgttcatt    780

aatttcttcg tcaaatccta tgtgttccca aagccgaaga ctgcagataa aaaggtccaa    840

tagctgcaca cacacaatta tgcagctccc caccactttc tccccaaaac agccagccag    900

ccccccttccc atgaaacaag aacctacccc ctccctgctc ctctttttt aatctcttat    960

tccaccatac acttgatgac aacagttgcc gtgcagtgga gctatgtggt gcatgctgca   1020

atgcactggg gcatcatatt aagattattg ttattagtgg tgcccttgct tctctgcttt   1080

gtgcccctgg taccagggtg cacccatgat gcagtacaca agttgttcaa tgtgtgcact   1140

gtggtattct ctgaattcct tgaggagcca tttagtttaa ccaagcatga ctcggctgga   1200

ttggctcgag gtcattgcgg aagcaaaagt tttgcgaggc agctgccgaa ggtgctgcta   1260

agttcggctt caaactggcc tttgcacacc caggtaccca gggattccaa gtctcatggc   1320

tggcatattt taggtttcat gcatccgcag tggcgtttat gcaaggcaca gacgtttata   1380

tttatggata tgcgagtgaa ggttggcttg ccagcattgg catcgcctgc ctgcatactg   1440

agttttgttg taaaagtaca aactcagtat caacaataca atttttnttt gaaaaaaaaa   1500

aaaa                                                                1504
```

<210> SEQ ID NO 126
<211> LENGTH: 792
<212> TYPE: DNA
<213> ORGANISM: Eutreptiella sp. CCMP389

<400> SEQUENCE: 126

```
atggctgcgg tgatagaggt cgccaacgag tttgtagcca tcacggcaga aacgctcccc     60

aaagttgact atcaacgact atggcgagac atttacagtt gtgagctact gtatttctcc    120

attgccttcg tgatcttgaa gtttacgttg ggcgagttga gcgacagcgg aaaaaagatt    180
```

```
ttgagagtgt tgttcaagtg gtacaatctc ttcatgtccg tgttctcctt ggtgtctttc    240

ctttgcatgg gctatgccat ttataccgtg ggcctatact ctaacgaatg cgacagggct    300

ttcgacaact cgttgttccg ctttgcaaca aaggtgttct actacagtaa gtttttggag    360

tacatcgact ctttttatct tccgctcatg gccaagccgc tgtctttcct gcaattcttc    420

catcacttgg gagcccccat ggacatgtgg ctctttgtcc aatattctgg ggaatctatt    480

tggatctttg tgtttttgaa tgggttcatt cactttgtta tgtacgggta ctactggact    540

cggctgatga agttcaattt cccaatgccc aagcagttga ttaccgcgat gcagatcacg    600

cagttcaacg ttggtttcta cctcgtgtgg tggtacaaag atattccctg ctaccgaaag    660

gatcccatgc gaatgttggc ctggatcttc aattactggt atgttgggac tgtcttgctg    720

ctgttcatta atttcttcgt caaatcctat gtgttcccaa agccgaagac tgcagataaa    780

aaggtccaat ag                                                        792


<210> SEQ ID NO 127
<211> LENGTH: 263
<212> TYPE: PRT
<213> ORGANISM: Eutreptiella sp. CCMP389

<400> SEQUENCE: 127

Met Ala Ala Val Ile Glu Val Ala Asn Glu Phe Val Ala Ile Thr Ala
1               5                   10                  15

Glu Thr Leu Pro Lys Val Asp Tyr Gln Arg Leu Trp Arg Asp Ile Tyr
            20                  25                  30

Ser Cys Glu Leu Leu Tyr Phe Ser Ile Ala Phe Val Ile Leu Lys Phe
        35                  40                  45

Thr Leu Gly Glu Leu Ser Asp Ser Gly Lys Lys Ile Leu Arg Val Leu
    50                  55                  60

Phe Lys Trp Tyr Asn Leu Phe Met Ser Val Phe Ser Leu Val Ser Phe
65                  70                  75                  80

Leu Cys Met Gly Tyr Ala Ile Tyr Thr Val Gly Leu Tyr Ser Asn Glu
                85                  90                  95

Cys Asp Arg Ala Phe Asp Asn Ser Leu Phe Arg Phe Ala Thr Lys Val
            100                 105                 110

Phe Tyr Tyr Ser Lys Phe Leu Glu Tyr Ile Asp Ser Phe Tyr Leu Pro
        115                 120                 125

Leu Met Ala Lys Pro Leu Ser Phe Leu Gln Phe Phe His His Leu Gly
    130                 135                 140

Ala Pro Met Asp Met Trp Leu Phe Val Gln Tyr Ser Gly Glu Ser Ile
145                 150                 155                 160

Trp Ile Phe Val Phe Leu Asn Gly Phe Ile His Phe Val Met Tyr Gly
                165                 170                 175

Tyr Tyr Trp Thr Arg Leu Met Lys Phe Asn Phe Pro Met Pro Lys Gln
            180                 185                 190

Leu Ile Thr Ala Met Gln Ile Thr Gln Phe Asn Val Gly Phe Tyr Leu
        195                 200                 205

Val Trp Trp Tyr Lys Asp Ile Pro Cys Tyr Arg Lys Asp Pro Met Arg
    210                 215                 220

Met Leu Ala Trp Ile Phe Asn Tyr Trp Tyr Val Gly Thr Val Leu Leu
225                 230                 235                 240
```

```
Leu Phe Ile Asn Phe Phe Val Lys Ser Tyr Val Phe Pro Lys Pro Lys
                245                 250                 255

Thr Ala Asp Lys Lys Val Gln
            260


<210> SEQ ID NO 128
<211> LENGTH: 7222
<212> TYPE: DNA
<213> ORGANISM: Artificial Sequence
<220> FEATURE:
<223> OTHER INFORMATION: sequence of pFBAIN-MOD-1

<400> SEQUENCE: 128

catggatcca ggcctgttaa cggccattac ggcctgcagg atccgaaaaa acctcccaca     60

cctccccctg aacctgaaac ataaaatgaa tgcaattgtt gttgttaact tgtttattgc    120

agcttataat ggttacaaat aaagcaatag catcacaaat ttcacaaata aagcattttt    180

ttcactgcat tctagttgtg gtttgtccaa actcatcaat gtatcttatc atgtctgcgg    240

ccgcaagtgt ggatggggaa gtgagtgccc ggttctgtgt gcacaattgg caatccaaga    300

tggatggatt caacacaggg atatagcgag ctacgtggtg gtgcgaggat atagcaacgg    360

atatttatgt ttgacacttg agaatgtacg atacaagcac tgtccaagta caatactaaa    420

catactgtac atactcatac tcgtacccgg gcaacggttt cacttgagtg cagtggctag    480

tgctcttact cgtacagtgt gcaatactgc gtatcatagt ctttgatgta tatcgtattc    540

attcatgtta gttgcgtacg agccggaagc ataaagtgta aagcctgggg tgcctaatga    600

gtgagctaac tcacattaat tgcgttgcgc tcactgcccg ctttccagtc gggaaacctg    660

tcgtgccagc tgcattaatg aatcggccaa cgcgcgggga gaggcggttt gcgtattggg    720

cgctcttccg cttcctcgct cactgactcg ctgcgctcgg tcgttcggct gcggcgagcg    780

gtatcagctc actcaaaggc ggtaatacgg ttatccacag aatcagggga taacgcagga    840

aagaacatgt gagcaaaagg ccagcaaaag gccaggaacc gtaaaaaggc cgcgttgctg    900

gcgtttttcc ataggctccg cccccctgac gagcatcaca aaaatcgacg ctcaagtcag    960

aggtggcgaa acccgacagg actataaaga taccaggcgt ttccccctgg aagctccctc   1020

gtgcgctctc ctgttccgac cctgccgctt accggatacc tgtccgcctt tctcccttcg   1080

ggaagcgtgg cgctttctca tagctcacgc tgtaggtatc tcagttcggt gtaggtcgtt   1140

cgctccaagc tgggctgtgt gcacgaaccc cccgttcagc ccgaccgctg cgccttatcc   1200

ggtaactatc gtcttgagtc caacccggta agacacgact tatcgccact ggcagcagcc   1260

actggtaaca ggattagcag agcgaggtat gtaggcggtg ctacagagtt cttgaagtgg   1320

tggcctaact acggctacac tagaaggaca gtatttggta tctgcgctct gctgaagcca   1380

gttaccttcg gaaaaagagt tggtagctct tgatccggca aacaaaccac cgctggtagc   1440

ggtggttttt ttgtttgcaa gcagcagatt acgcgcagaa aaaaaggatc tcaagaagat   1500

cctttgatct tttctacggg gtctgacgct cagtggaacg aaaactcacg ttaagggatt   1560

ttggtcatga gattatcaaa aaggatcttc acctagatcc ttttaaatta aaaatgaagt   1620

tttaaatcaa tctaaagtat atatgagtaa acttggtctg acagttacca atgcttaatc   1680

agtgaggcac ctatctcagc gatctgtcta tttcgttcat ccatagttgc ctgactcccc   1740

gtcgtgtaga taactacgat acgggagggc ttaccatctg gccccagtgc tgcaatgata   1800

ccgcgagacc cacgctcacc ggctccagat ttatcagcaa taaaccagcc agccggaagg   1860

gccgagcgca gaagtggtcc tgcaacttta tccgcctcca tccagtctat taattgttgc   1920
```

-continued

```
cgggaagcta gagtaagtag ttcgccagtt aatagtttgc gcaacgttgt tgccattgct   1980
acaggcatcg tggtgtcacg ctcgtcgttt ggtatggctt cattcagctc cggttcccaa   2040
cgatcaaggc gagttacatg atcccccatg ttgtgcaaaa aagcggttag ctccttcggt   2100
cctccgatcg ttgtcagaag taagttggcc gcagtgttat cactcatggt tatggcagca   2160
ctgcataatt ctcttactgt catgccatcc gtaagatgct tttctgtgac tggtgagtac   2220
tcaaccaagt cattctgaga atagtgtatg cggcgaccga gttgctcttg cccggcgtca   2280
atacgggata ataccgcgcc acatagcaga actttaaaag tgctcatcat tggaaaacgt   2340
tcttcggggc gaaaactctc aaggatctta ccgctgttga gatccagttc gatgtaaccc   2400
actcgtgcac ccaactgatc ttcagcatct tttactttca ccagcgtttc tgggtgagca   2460
aaaacaggaa ggcaaaatgc cgcaaaaaag ggaataaggg cgacacggaa atgttgaata   2520
ctcatactct tcctttttca atattattga agcatttatc agggttattg tctcatgagc   2580
ggatacatat ttgaatgtat ttagaaaaat aaacaaatag gggttccgcg cacatttccc   2640
cgaaaagtgc cacctgacgc gccctgtagc ggcgcattaa gcgcggcggg tgtggtggtt   2700
acgcgcagcg tgaccgctac acttgccagc gccctagcgc ccgctccttt cgctttcttc   2760
ccttcctttc tcgccacgtt cgccggcttt ccccgtcaag ctctaaatcg ggggctccct   2820
ttagggttcc gatttagtgc tttacggcac ctcgacccca aaaaacttga ttagggtgat   2880
ggttcacgta gtgggccatc gccctgatag acggtttttc gccctttgac gttggagtcc   2940
acgttcttta atagtggact cttgttccaa actggaacaa cactcaaccc tatctcggtc   3000
tattcttttg atttataagg gattttgccg atttcggcct attggttaaa aaatgagctg   3060
atttaacaaa aatttaacgc gaattttaac aaaatattaa cgcttacaat ttccattcgc   3120
cattcaggct gcgcaactgt tgggaagggc gatcggtgcg ggcctcttcg ctattacgcc   3180
agctggcgaa agggggatgt gctgcaaggc gattaagttg ggtaacgcca gggttttccc   3240
agtcacgacg ttgtaaaacg acggccagtg aattgtaata cgactcacta tagggcgaat   3300
tgggtaccgg gccccccctc gaggtcgatg gtgtcgataa gcttgatatc gaattcatgt   3360
cacacaaacc gatcttcgcc tcaaggaaac ctaattctac atccgagaga ctgccgagat   3420
ccagtctaca ctgattaatt ttcgggccaa taatttaaaa aaatcgtgtt atataatatt   3480
atatgtatta tatatataca tcatgatgat actgacagtc atgtcccatt gctaaataga   3540
cagactccat ctgccgcctc caactgatgt tctcaatatt taaggggtca tctcgcattg   3600
tttaataata aacagactcc atctaccgcc tccaaatgat gttctcaaaa tatattgtat   3660
gaacttattt ttattactta gtattattag acaacttact tgctttatga aaaacacttc   3720
ctatttagga aacaatttat aatggcagtt cgttcattta acaatttatg tagaataaat   3780
gttataaatg cgtatgggaa atcttaaata tggatagcat aaatgatatc tgcattgcct   3840
aattcgaaat caacagcaac gaaaaaaatc ccttgtacaa cataaatagt catcgagaaa   3900
tatcaactat caaagaacag ctattcacac gttactattg agattattat tggacgagaa   3960
tcacacactc aactgtcttt ctctcttcta gaaatacagg tacaagtatg tactattctc   4020
attgttcata cttctagtca tttcatccca catattcctt ggatttctct ccaatgaatg   4080
acattctatc ttgcaaattc aacaattata ataagatata ccaaagtagc ggtatagtgg   4140
caatcaaaaa gcttctctgg tgtgcttctc gtatttattt ttattctaat gatccattaa   4200
aggtatatat ttatttcttg ttatataatc cttttgttta ttacatgggc tggatacata   4260
aaggtatttt gatttaattt tttgcttaaa ttcaatcccc cctcgttcag tgtcaactgt   4320
```

-continued

```
aatggtagga aattaccata cttttgaaga agcaaaaaaa atgaaagaaa aaaaaaatcg   4380
tatttccagg ttagacgttc cgcagaatct agaatgcggt atgcggtaca ttgttcttcg   4440
aacgtaaaag ttgcgctccc tgagatattg tacatttttg cttttacaag tacaagtaca   4500
tcgtacaact atgtactact gttgatgcat ccacaacagt ttgttttgtt tttttttgtt   4560
tttttttttt ctaatgattc attaccgcta tgtataccta cttgtacttg tagtaagccg   4620
ggttattggc gttcaattaa tcatagactt atgaatctgc acggtgtgcg ctgcgagtta   4680
cttttagctt atgcatgcta cttgggtgta atattgggat ctgttcggaa atcaacggat   4740
gctcaatcga tttcgacagt aattaattaa gtcatacaca agtcagcttt cttcgagcct   4800
catataagta taagtagttc aacgtattag cactgtaccc agcatctccg tatcgagaaa   4860
cacaacaaca tgccccattg gacagatcat gcggatacac aggttgtgca gtatcataca   4920
tactcgatca gacaggtcgt ctgaccatca tacaagctga acaagcgctc catacttgca   4980
cgctctctat atacacagtt aaattacata tccatagtct aacctctaac agttaatctt   5040
ctggtaagcc tcccagccag ccttctggta tcgcttggcc tcctcaatag gatctcggtt   5100
ctggccgtac agacctcggc cgacaattat gatatccgtt ccggtagaca tgacatcctc   5160
aacagttcgg tactgctgtc cgagagcgtc tcccttgtcg tcaagaccca ccccgggggt   5220
cagaataagc cagtcctcag agtcgccctt aggtcggttc tgggcaatga agccaaccac   5280
aaactcgggg tcggatcggg caagctcaat ggtctgcttg gagtactcgc cagtggccag   5340
agagcccttg caagacagct cggccagcat gagcagacct ctggccagct tctcgttggg   5400
agaggggact aggaactcct tgtactggga gttctcgtag tcagagacgt cctccttctt   5460
ctgttcagag acagtttcct cggcaccagc tcgcaggcca gcaatgattc cggttccggg   5520
tacaccgtgg gcgttggtga tatcggacca ctcggcgatt cggtgacacc ggtactggtg   5580
cttgacagtg ttgccaatat ctgcgaactt tctgtcctcg aacaggaaga aaccgtgctt   5640
aagagcaagt tccttgaggg ggagcacagt gccggcgtag gtgaagtcgt caatgatgtc   5700
gatatgggtt ttgatcatgc acacataagg tccgacctta tcggcaagct caatgagctc   5760
cttggtggtg gtaacatcca gagaagcaca caggttggtt ttcttggctg ccacgagctt   5820
gagcactcga gcggcaaagg cggacttgtg gacgttagct cgagcttcgt aggagggcat   5880
tttggtggtg aagaggagac tgaaataaat ttagtctgca gaacttttta tcggaacctt   5940
atctggggca gtgaagtata tgttatggta atagttacga gttagttgaa cttatagata   6000
gactggacta tacggctatc ggtccaaatt agaaagaacg tcaatggctc tctgggcgtc   6060
gcctttgccg acaaaaatgt gatcatgatg aaagccagca atgacgttgc agctgatatt   6120
gttgtcggcc aaccgcgccg aaaacgcagc tgtcagaccc acagcctcca acgaagaatg   6180
tatcgtcaaa gtgatccaag cacactcata gttggagtcg tactccaaag gcggcaatga   6240
cgagtcagac agatactcgt cgaaaacagt gtacgcagat ctactataga ggaacattta   6300
aattgccccg gagaagacgg ccaggccgcc tagatgacaa attcaacaac tcacagctga   6360
ctttctgcca ttgccactag gggggggcct ttttatatgg ccaagccaag ctctccacgt   6420
cggttgggct gcacccaaca ataaatgggt agggttgcac caacaaaggg atgggatggg   6480
gggtagaaga tacgaggata acggggctca atggcacaaa taagaacgaa tactgccatt   6540
aagactcgtg atccagcgac tgacaccatt gcatcatcta agggcctcaa aactacctcg   6600
gaactgctgc gctgatctgg acaccacaga ggttccgagc actttaggtt gcaccaaatg   6660
tcccaccagg tgcaggcaga aaacgctgga acagcgtgta cagtttgtct taacaaaaag   6720
```

-continued

```
tgagggcgct gaggtcgagc agggtggtgt gacttgttat agcctttaga gctgcgaaag   6780

cgcgtatgga tttggctcat caggccagat tgagggtctg tggacacatg tcatgttagt   6840

gtacttcaat cgccccctgg atatagcccc gacaataggc cgtggcctca tttttttgcc   6900

ttccgcacat ttccattgct cggtacccac accttgcttc tcctgcactt gccaacctta   6960

atactggttt acattgacca acatcttaca agcgggggc ttgtctaggg tatatataaa    7020

cagtggctct cccaatcggt tgccagtctc ttttttcctt tctttcccca cagattcgaa   7080

atctaaacta cacatcacag aattccgagc cgtgagtatc cacgacaaga tcagtgtcga   7140

gacgacgcgt tttgtgtaat gacacaatcc gaaagtcgct agcaacacac actctctaca   7200

caaactaacc cagctctggt ac                                            7222
```

```
<210> SEQ ID NO 129
<211> LENGTH: 200
<212> TYPE: DNA
<213> ORGANISM: Eutreptiella sp. CCMP389
<220> FEATURE:
<221> NAME/KEY: misc_feature
<222> LOCATION: (1)..(200)
<223> OTHER INFORMATION: the nucleotide sequence of the Eutreptiella sp.
      CCMP389 (E389D9e) internal cDNA fragment
<220> FEATURE:
<221> NAME/KEY: misc_feature
<222> LOCATION: (1)..(200)
<223> OTHER INFORMATION: sequence of the Eutreptiella sp. CCMP389
      (E389D9e) internal cDNA fragment

<400> SEQUENCE: 129

ttacagttct tccaccactt gggagccccc atggacatgt ggctctttgt ccaatattct     60

ggggaatcta tttggatctt tgtgtttttg aatgggttca ttcactttgt tatgtacggg    120

tactactgga ctcggctgat gaagttcaat ttcccaatgc ccaagcagtt gattaccgcg    180

atgcagatca tccaattcaa                                                200
```

```
<210> SEQ ID NO 130
<211> LENGTH: 13
<212> TYPE: PRT
<213> ORGANISM: Artificial Sequence
<220> FEATURE:
<223> OTHER INFORMATION: motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: X = L or F
<220> FEATURE:
<221> NAME/KEY: misc_feature
<222> LOCATION: (5)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 130

Tyr Asn Xaa Xaa Xaa Xaa Xaa Xaa Ser Xaa Xaa Ser Phe
1               5                   10
```

```
<210> SEQ ID NO 131
<211> LENGTH: 15
<212> TYPE: PRT
<213> ORGANISM: Artificial Sequence
```

<220> FEATURE:
<223> OTHER INFORMATION: motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: X = E or D
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (12)..(12)
<223> OTHER INFORMATION: X = T or S
<220> FEATURE:
<221> NAME/KEY: misc_feature
<222> LOCATION: (13)..(14)
<223> OTHER INFORMATION: Xaa can be any naturally occurring amino acid

<400> SEQUENCE: 131

Phe Tyr Xaa Ser Lys Xaa Xaa Xaa Tyr Xaa Asp Xaa Xaa Xaa Leu
1               5                   10                  15

<210> SEQ ID NO 132
<211> LENGTH: 9
<212> TYPE: PRT
<213> ORGANISM: Artificial Sequence
<220> FEATURE:
<223> OTHER INFORMATION: motif
<220> FEATURE:
<221> NAME/KEY: MISC_FEATURE
<222> LOCATION: (2)..(2)
<223> OTHER INFORMATION: X = Q or H
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 132

Leu Xaa Xaa Phe His His Xaa Gly Ala
1               5

<210> SEQ ID NO 133
<211> LENGTH: 14
<212> TYPE: PRT
<213> ORGANISM: Artificial Sequence
<220> FEATURE:
<223> OTHER INFORMATION: motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(12)
<223> OTHER INFORMATION: Xaa can be any naturally occurring amino acid
<220> FEATURE:
<221> NAME/KEY: MISC_FEATURE
<222> LOCATION: (13)..(13)
<223> OTHER INFORMATION: X = K or R or N -continued

<400> SEQUENCE: 133

Met Tyr Xaa Tyr Tyr Xaa Xaa Xaa Xaa Xaa Xaa Xaa Xaa Phe
1               5                   10

<210> SEQ ID NO 134
<211> LENGTH: 8
<212> TYPE: PRT
<213> ORGANISM: Artificial Sequence
<220> FEATURE:
<223> OTHER INFORMATION: motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: X = I or L or M
<220> FEATURE:
<221> NAME/KEY: misc_feature
<222> LOCATION: (6)..(7)
<223> OTHER INFORMATION: Xaa can be any naturally occurring amino acid

<400> SEQUENCE: 134

Lys Xaa Leu Xaa Thr Xaa Xaa Gln
1               5

<210> SEQ ID NO 135
<211> LENGTH: 7
<212> TYPE: PRT
<213> ORGANISM: Artificial Sequence
<220> FEATURE:
<223> OTHER INFORMATION: motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 135

Trp Xaa Phe Asn Tyr Xaa Tyr
1               5

<210> SEQ ID NO 136
<211> LENGTH: 9
<212> TYPE: PRT
<213> ORGANISM: Artificial Sequence
<220> FEATURE:
<223> OTHER INFORMATION: motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 136

Tyr Xaa Gly Xaa Val Xaa Xaa Leu Phe
1               5

DELTA-9 ELONGASES AND THEIR USE IN MAKING POLYUNSATURATED FATTY ACIDS

This application is a divisional of U.S. patent application Ser. No. 12/725,482 filed Mar. 17, 2010, now U.S. Pat. No. 8,420,892, which is a divisional of U.S. patent application Ser. No. 11/601,563 filed Nov. 16, 2006, now abandoned, which claims the benefit of U.S. Provisional Application No. 60/739,989, filed Nov. 23, 2005, the entire contents of which are herein incorporated by reference.

FIELD OF THE INVENTION

This invention pertains to polynucleotide sequences encoding delta-9 elongases and the use of these elongase in making long-chain polyunsaturated fatty acids (PUFAs).

BACKGROUND OF THE INVENTION

Fatty acids (lipids) are water-insoluble organic biomolecules that can be extracted from cells and tissues by nonpolar solvents such as chloroform, ether or benzene. Lipids have several important biological functions, serving as (1) structural components of membranes; (2) storage and transport forms of metabolic fuels; (3) a protective coating on the surface of many organisms; and, (4) cell-surface components concerned in cell recognition, species specificity and tissue immunity. More specifically, polyunsaturated fatty acids (PUFAs) are important components of the plasma membrane of the cell, where they may be found in such forms as phospholipids and also can be found in triglycerides. PUFAs also serve as precursors to other molecules of importance in human beings and animals, including the prostacyclins, leukotrienes and prostaglandins. There are two main families of PUFAs (i.e., the omega-3 fatty acids and the omega-6 fatty acids).

The human body is capable of producing most of the PUFAs which it requires to function. However, eicosapentaenoic acid (EPA; 20:5, delta-5,8,11,14,17) and docosahexaenoic acid (DHA; 22:6, delta-4,7,10,13,16,19) cannot be synthesized efficiently by the human body and thus must be supplied through the diet. Since the human body cannot produce adequate quantities of these PUFAs, they are called essential fatty acids. Because of their important roles in human health and nutrition, EPA and DHA are the subject of much interest as discussed herein.

DHA is a fatty acid of the omega-3 series according to the location of the last double bond in the methyl end. It is synthesized via alternating steps of desaturation and elongation (see FIG. 15). Production of DHA is important because of its beneficial effect on human health. For example, increased intake of DHA has been shown to be beneficial or have a positive effect in inflammatory disorders (e.g., rheumatoid arthritis), Type II diabetes, hypertension, atherosclerosis, depression, myocardial infarction, thrombosis, some cancers and for prevention of the onset of degenerative disorders such as Alzheimer's disease. Currently the major sources of DHA are oils from fish and algae.

EPA and arachidonic acid (AA or ARA; 20:4, delta-5,8,11,14) are both delta-5 essential fatty acids. EPA belongs to the omega-3 series with five double bonds in the acyl chain, is found in marine food, and is abundant in oily fish from the North Atlantic. Beneficial or positive effects of increased intake of EPA have been shown in patients with coronary heart disease, high blood pressure, inflammatory disorders, lung and kidney diseases, Type II diabetes, obesity, ulcerative colitis, Crohn's disease, anorexia nervosa, burns, osteoarthritis, osteoporosis, attention deficit/hyperactivity disorder and early stages of colorectal cancer (see, for example, the review of McColl, *J., NutraCos.* 2(4):35-40 (2003)).

AA belongs to the omega-6 series with four double bonds. The lack of a double bond in the omega-3 position confers on AA different properties than those found in EPA. The eicosanoids produced from AA have strong inflammatory and platelet aggregating properties, whereas those derived from EPA have anti-inflammatory and anti-platelet aggregating properties. AA is recognized as the principal omega-6 fatty acid found in the human brain and an important component of breast milk and many infant formulas, based on its role in early neurological and visual development. AA can be obtained from some foods (such as meat, fish, and eggs), but the concentration is low.

Gamma-linolenic acid (GLA; 18:3, delta-6,9,12) is another essential fatty acid found in mammals. GLA is the metabolic intermediate for very long-chain omega-6 fatty acids and for various active molecules. In mammals, formation of long-chain PUFAs is rate-limited by delta-6 desaturation. Many physiological and pathological conditions such as aging, stress, diabetes, eczema, and some infections have been shown to depress the delta-6 desaturation step. In addition, GLA is readily catabolized from the oxidation and rapid cell division associated with certain disorders (e.g., cancer or inflammation).

As described above, research has shown that various omega fatty acids reduce the risk of heart disease, have a positive effect on children's development and on certain mental illnesses, autoimmune diseases and joint complaints. However, although there are many health benefits associated with a diet supplemented with these fatty acids, it is recognized that different PUFAs exert different physiological effects in the body (e.g., most notably, the opposing physiological effects of GLA and AA). Thus, production of oils using recombinant means is expected to have several advantages over production from natural sources. For example, recombinant organisms having preferred characteristics for oil production can be used, since the naturally occurring fatty acid profile of the host can be altered by the introduction of new biosynthetic pathways in the host and/or by the suppression of undesired pathways, thereby resulting in increased levels of production of desired PUFAs (or conjugated forms thereof) and decreased production of undesired PUFAs. Optionally, recombinant organisms can provide PUFAs in particular forms which may have specific uses; or, oil production can be manipulated such that the ratio of omega-3 to omega-6 fatty acids so produced is modified and/or a specific PUFA is produced without significant accumulation of other PUFA downstream or upstream products (e.g., production of oils comprising AA and lacking GLA).

The mechanism of PUFA synthesis frequently occurs via the delta-6 desaturation pathway. For example, long-chain PUFA synthesis in mammals proceeds predominantly by a delta-6 desaturation pathway, in which the first step is the delta-6 desaturation of linoleic acid (LA; 18:2, delta-9,12) and alpha-linolenic acid (ALA; 18:3, delta-9,12,15) to yield gamma-linolenic acid (GLA; 18:3, delta-6,9,12)) and stearidonic acid (STA; 18:4, delta-6,9,12,15), respectively. Further fatty acid elongation and desaturation steps give rise to arachidonic acid (AA or ARA) and eicosapentaenoic acid (EPA). Accordingly, genes encoding delta-6 desaturases, delta-6 elongase components (also identified as $C_{18/20}$ elongases) and delta-5 desaturases have been cloned from a variety of organisms including higher plants, algae, mosses, fungi, nematodes and humans. Humans can synthesize long-chain PUFAs from the essential fatty acids, LA and ALA; however biosynthesis of long-chain PUFAs is somewhat limited (they are regulated by dietary and hormonal changes), and LA and ALA must be obtained from the diet.

Elongases which have been identified in the past differ in terms of the substrates upon which they act. They are present in both animals and plants. Those found in mammals can act upon saturated, monounsaturated and polyunsaturated fatty acids. However, those found in plants are specific for saturated and monounsaturated fatty acids. Thus, there is a need for a PUFA-specific elongase to produce polyunsaturated fatty acids (PUFAs) in plants.

The elongation process in plants involves a four-step process initiated by the crucial step of condensation of malonate and a fatty acid with release of a carbon dioxide molecule. The substrates in fatty acid elongation are CoA-thioesters. The condensation step is mediated by a 3-ketoacyl synthase, which is generally rate limiting to the overall cycle of four reactions and provides some substrate specificity. The product of one elongation cycle regenerates a fatty acid that has been extended by two carbon atoms (Browse et al., *Trends in Biochemical Sciences* 27(9):467-473 (September 2002); Napier, *Trends in Plant Sciences* 7(2): 51-54 (February 2002)).

WO 02/077213 (published Oct. 3, 2002) describes isolated nucleic acid molecules encoding a fatty acid elongase with specificity for linoleic acid or alpha-linolenic acid from *Isochrysis galbana* (i.e., delta-9 elongase).

U.S. Pat. No. 6,403,349 (issued to Mukerji et al. on Jun. 11, 2002) concerns the identification of nucleotide and amino acid sequences of an elongase gene derived from *Mortierella alpina*.

WO 02/26946 (published Apr. 4, 2002) describes isolated nucleic acid molecules encoding FAD4, FAD5, FAD5-2 and FAD6 fatty acid desaturase family members which are expressed in long-chain PUFA-producing organisms, e.g., *Thraustochytrium, Pythium irregulare, Schizichytrium* and *Crypthecodinium*. It is indicated that constructs containing the desaturase genes can be used in any expression system including plants, animals, and microorganisms for the production of cells capable of producing long-chain PUFAs.

WO 98/55625 (published Dec. 19, 1998) describes the production of PUFAs by expression of polyketide-like synthesis genes in plants.

WO 98/46764 (published Oct. 22, 1998) describes compositions and methods for preparing long-chain fatty acids in plants, plant parts and plant cells which utilize nucleic acid sequences and constructs encoding fatty acid desaturases, including delta-5 desaturases, delta-6 desaturases and delta-12 desaturases.

U.S. Pat. No. 6,075,183 (issued to Knutzon et al. on Jun. 13, 2000) describes methods and compositions for synthesis of long-chain PUFAs in plants.

U.S. Pat. No. 6,459,018 (issued to Knutzon et al. on Oct. 1, 2002) describes a method for producing STA in plant seed utilizing a construct comprising a DNA sequence encoding a delta-6 desaturase.

Spychalla et al. (*Proc. Natl. Acad. Sci. USA,* 94:1142-1147 (1997)) describes the isolation and characterization of a cDNA from *Caenorhabditis elegans* that, when expressed in *Arabidopsis*, encodes a fatty acid desaturase which can catalyze the introduction of an omega-3 double bond into a range of 18- and 20-carbon fatty acids.

An alternate pathway for the biosynthesis of AA and EPA operates in some organisms (i.e., the delta-9 elongase/delta-8 desaturase pathway). Whereby LA and ALA are first elongated to eicosadienoic acid (EDA; 20:2, delta-11,14) and eicosatrienoic acid (EtrA; 20:3, delta-11,14,17), respectively, by a delta-9 elongase. Subsequent delta-8 and delta-5 desaturation of these products yields AA and EPA. The delta-8 pathway is present inter alia, in euglenoid species where it is the dominant pathway for formation of 20-carbon PUFAs.

WO 2000/34439 (published Jun. 15, 2000) discloses amino acid and nucleic acid sequences for delta-5 and delta-8 desaturase enzymes. Based on the information presented herein, it is apparent that the delta-8 nucleotide and amino acid sequences of WO 2000/34439 are not correct. However, the correct sequence is set forth in corresponding U.S. Pat. No. 6,825,017 (issued to Browse et al. on Nov. 30, 2004) that describes desaturases, in particular, delta-5 and delta-8 desaturases and their use in synthesizing PUFAs.

Applicants' Assignee's co-pending application having application Ser. No. 11/166,003 filed Jun. 24, 2005 (Attorney Docket No. 1547 USNA) discloses a delta-8 desaturase from *Euglena gracilis*.

Wallis et al. (*Arch. Biochem. and Biophys.* 365(2):307-316 (May 1999)) describes the cloning of a gene that appears to encode a delta-8 desaturase in *Euglena gracilis*. This sequence appears to be the same sequence disclosed in WO 2000/34439.

Qi et al. (*Nat. Biotech.* 22(6):739-45 (2004)) describes the production of long-chain PUFAs using, among other things, a delta-8 desaturase from *Euglena gracilis*; however, the complete sequence of the delta-8 desaturase is not provided.

WO 2004/057001 (published Jul. 8, 2004) discloses amino acid and nucleic acid sequences for a delta-8 desaturase enzyme from *Euglena gracilis*.

An expansive study of PUFAs from natural sources and from chemical synthesis are not sufficient for commercial needs. Therefore, it is of interest to find alternative means to allow production of commercial quantities of PUFAs. Biotechnology offers an attractive route for producing long-chain PUFAs in a safe, cost efficient manner in microorganisms and plants.

With respect to microorganisms, many algae, bacteria, molds and yeast can synthesize oils in the ordinary course of cellular metabolism. Thus, oil production involves cultivating the microorganism in a suitable culture medium to allow for oil synthesis, followed by separation of the microorganism from the fermentation medium and treatment for recovery of the intracellular oil. Attempts have been made to optimize production of fatty acids by fermentative means involving varying such parameters as microorganisms used, media and conditions that permit oil production. However, these efforts have proved largely unsuccessful in improving yield of oil or the ability to control the characteristics of the oil composition produced.

One class of microorganisms that has not been previously examined as a production platform for PUFAs (prior to work by the Applicants' Assignee), however, are the oleaginous yeasts. These organisms can accumulate oil up to 80% of their dry cell weight. The technology for growing oleaginous yeast with high oil content is well developed (for example, see EP 0 005 277B1; Ratledge, C., *Prog. Ind. Microbiol.* 16:119-206 (1982)), and may offer a cost advantage compared to commercial micro-algae fermentation for production of omega-3 or omega-6 PUFAs. Whole yeast cells may also represent a convenient way of encapsulating omega-3 or omega-6 PUFA-enriched oils for use in functional foods and animal feed supplements.

WO 2004/101757 and WO 2004/101753 (published Nov. 25, 2004) concern the production of PUFAs in oleaginous yeasts and are Applicants' Assignee's copending applications.

WO 2004/071467 (published Aug. 26, 2004) concerns the production of PUFAs in plants, while WO 2004/071178 (published Aug. 26, 2004) concerns annexin promoters and their use in expression of transgenes in plants; both are Applicants' Assignee's copending applications.

Applicants' Assignee's copending applications also include CL2698 (U.S. patent application Ser. No. 11/265,761, filed Nov. 2, 2005), CL3136 (U.S. patent application Ser. No. 11/264,784, filed Nov. 1, 2005) and CL3160 (U.S. patent application Ser. No. 11/264,737, filed Nov. 1, 2005) (methods of making EPA, ARA and DHA, respectively, in *Yarrowia lipolytica*), each claiming benefit of the earlier provisional filing date of CL2698 on Nov. 4, 2004.

SUMMARY OF THE INVENTION

The invention concerns an isolated polynucleotide comprising:

(a) a nucleotide sequence encoding a polypeptide having delta-9 elongase activity, wherein the polypeptide has at least 70% amino acid identity, based on the Clustal V method of alignment, when compared to an amino acid sequence as set forth in SEQ ID NO:5 or SEQ ID NO:127;

(b) a nucleotide sequence encoding a polypeptide having delta-9 elongase activity, wherein the nucleotide sequence has at least 70% sequence identity, based on the BLASTN method of alignment, when compared to a nucleotide sequence as set forth in SEQ ID NO:4, SEQ ID NO:90 or SEQ ID NO:126;

(c) a nucleotide sequence encoding a polypeptide having delta-9 elongase activity, wherein the nucleotide sequence hybridizes with a nucleotide sequence as set forth in SEQ ID NO:4, SEQ ID NO:90 or SEQ ID NO:126 under the following stringent hybridization conditions: 0.1×SSC, 0.1% SDS, 65° C. and washed with 2×SSC, 0.1% SDS followed by 0.1×SSC, 0.1% SDS; or (d) a complement of the nucleotide sequence of (a), (b) or (c), wherein the complement and the nucleotide sequence consist of the same number of nucleotides and are 100% complementary.

In a second embodiment, the invention concerns codon optimization, specifically, an isolated nucleic acid molecule which encodes a delta-9 elongase enzyme as set forth in SEQ ID NO:90 wherein at least 106 codons are codon-optimized for expression in *Yarrowia* sp.

In a third embodiment, the invention concerns a recombinant DNA construct comprising any of the polynucleotides of the invention operably linked to at least one regulatory sequence.

In a fourth embodiment, the invention concerns a cell comprising the recombinant DNA construct of the invention. Of interest are cells selected from the group consisting of plants and yeast.

In a fifth embodiment, the invention concerns a method for transforming a cell, comprising transforming a cell with the recombinant construct of the invention and selecting those cells transformed with the recombinant construct of the invention.

In a sixth embodiment, the invention concerns a method for producing a transformed plant comprising transforming a plant cell with a polynucleotide of the invention and regenerating a plant from the transformed plant cell. A preferred plant is soybean.

In an eighth embodiment, the invention concerns a seed comprising the recombinant construct of the invention.

In a ninth embodiment, the invention concerns method for making long-chain polyunsaturated fatty acids in a cell comprising:

(a) transforming a cell with the recombinant construct of the invention;

(b) selecting those transformed cells that make long-chain polyunsaturated fatty acids.

In a tenth embodiment, the invention concerns oil obtained from seed comprising the recombinant construct of the invention.

In an eleventh embodiment, the invention concerns a method for making long-chain polyunsaturated fatty acids in a plant cell comprising:

(a) transforming a cell with the recombinant construct of the invention; and (b) selecting those transformed cells that make long-chain polyunsaturated fatty acids.

In a twelfth embodiment, the invention concerns a method for producing at least one polyunsaturated fatty acid in a soybean cell comprising:

(a) transforming a soybean cell with a first recombinant DNA construct comprising an isolated polynucleotide encoding at least one delta-9 elongate polypeptide, operably linked to at least one regulatory sequence and at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-12 desaturase, a delta-15 desaturase, a delta-17 desaturase, a delta-9 desaturase, a $C_{14/16}$ elongase, a $C_{16/18}$ elongase, a $C_{18/20}$ elongase and a $C_{20/22}$ elongase;

(b) regenerating a soybean plant from the transformed cell of step (a); and (c) selecting those seeds obtained from the plants of step (b) having an altered level of polyunsaturated fatty acids when compared to the level in seeds obtained from a nontransformed soybean plant.

In a thirteenth embodiment, the invention concerns an oilseed plant comprising:

(a) a first recombinant DNA construct comprising an isolated polynucleotide encoding at least one delta-9 elongase polypeptide, operably linked to at least one regulatory sequence; and (b) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-12 desaturase, a delta-15 desaturase, a delta-17 desaturase, a delta-9 desaturase, a $C_{14/16}$ elongase, a $C_{16/18}$ elongase, a $C_{18/20}$ elongase and a $C_{20/22}$ elongase.

Also of interest are seeds obtained from such oilseed plants and oil obtained from these seeds.

In a fourteenth embodiment, the invention concerns food or feed which incorporates oil of the invention.

In a fifteenth embodiment, the invention concerns food or feed comprising an ingredient derived from the processing of the seeds of the invention.

In a sixteenth embodiment, the invention concerns an isolated nucleic acid fragment comprising a nucleic acid sequence encoding a delta-9 elongase, excluding SEQ ID NO:27, wherein the amino acid sequence comprising said elongase contains at least one of the following amino acid sequence motifs selected from the group consisting of:

(SEQ ID NO: 130)

a)
Y N X (L or F) X X X X S X X S F;

(SEQ ID NO: 131)

b)
F Y X S K X X (E or D) Y X D (T or S)

X X L;

(SEQ ID NO: 132)

c)
L (Q or H) X F H H X G A;

(SEQ ID NO: 133)

d)
M Y X Y Y X X X X X X X (K or R or N)

F;

(SEQ ID NO: 134)

e)
K X L (I or L or M) T X X Q;

(SEQ ID NO: 135)

f)
W X F N Y X Y;
and (SEQ ID NO: 136)

g)
Y X G X V X X L F;

wherein X can be any amino acid.

In a seventeenth embodiment, the invention concerns an isolated polynucleotide comprising a nucleotide sequence encoding a polypeptide having delta-9 elongase activity, wherein the nucleotide sequence has at least 70% sequence identity, based on the BLASTN method of alignment, when compared to a nucleotide sequence as set forth in SEQ ID NO:4, SEQ ID NO:90 it SEQ ID NO:126.

In an eighteenth embodiment, the invention concerns progeny plants obtained from obtained from a plant made by the method of the invention or an oilseed plant of the invention.

Biological Deposits

The following plasmids have been deposited with the American Type Culture Collection (ATCC), 10801 University Boulevard, Manassas, Va. 20110-2209, and bear the following designations, Accession Numbers and dates of deposit (Table 1).

TABLE 1

ATCC Deposits

| Plasmid | Accession Number | Date of Deposit |
|---|---|---|
| pKR72 | PTA-6019 | May 28, 2004 |
| pKR275 | PTA-4989 | Jan. 30, 2003 |
| pKR585 | PTA-6279 | Nov. 4, 2004 |
| pKR578 | PTA-6280 | Nov. 4, 2004 |

BRIEF DESCRIPTION OF THE DRAWINGS AND SEQUENCE LISTINGS

The invention can be more fully understood from the following detailed description and the accompanying drawings and Sequence Listing, which form a part of this application.

A Sequence Listing is provided herewith on Compact Disk. The contents of the Compact Disk containing the Sequence Listing are hereby incorporated by reference in compliance with 37 C.F.R. §1.52(e). The Compact Disks are submitted in triplicate and are identical to one another. The disks are labeled "Copy 1—Sequence Listing", "Copy 2—Sequence Listing", and "CRF—Sequence Listing". The disks contain the following file: BB1562 US NA Sequence Listing.ST25 having the following size: 572,000 bytes and which were created Nov. 16, 2006.

The sequence descriptions summarize the Sequences Listing provided herewith. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219(2): 345-373 (1984).

FIG. 14 are the results of functional analysis of the *Euglena gracilis* delta-9 elongase in *Saccharomyces cerevisiae.*

FIG. 16 shows a Clustal V alignment (with default parameters) of SEQ ID NO:5 (amino acid sequence of the delta-9 elongase of the instant invention) and SEQ ID NO:27 (amino acid sequence of the long-chain PUFA elongation enzyme from *Isochrysis galbana* (NCBI Accession No. AAL37626 (GI 17226123)).

FIG. 20 are the results of the fatty acid analysis of transgenic somatic soybean embryos expressing pKR912.

FIG. 21 are the lipid profiles of the somatic soybean embryos expressing the *Euglena gracilis* delta-9 elongase and the *Euglena gracilis* delta-8 desaturase for the top 5 events.

FIG. 22 are the lipid profiles of T2 bulk seed seed for the 22 wild-type-transformed events as well as for untransformed wild-type.

FIG. 23 are the lipid profiles of T2 bulk seed seed for the 16 fad3/fae1-transformed events as well as for untransformed fad3/fae1.

FIG. 24 are the lipid profiles for ten single seeds for wild-type pKR926-8 and ff pKR926-1.

FIG. 25A are the average fatty acid profiles for the ten best EPA events (average of nine or ten individual embryos) for pKR916 and pKR873.

FIG. 25B are the fatty acid profiles for the five best EPA seed from two independent events.

Figure 26A:
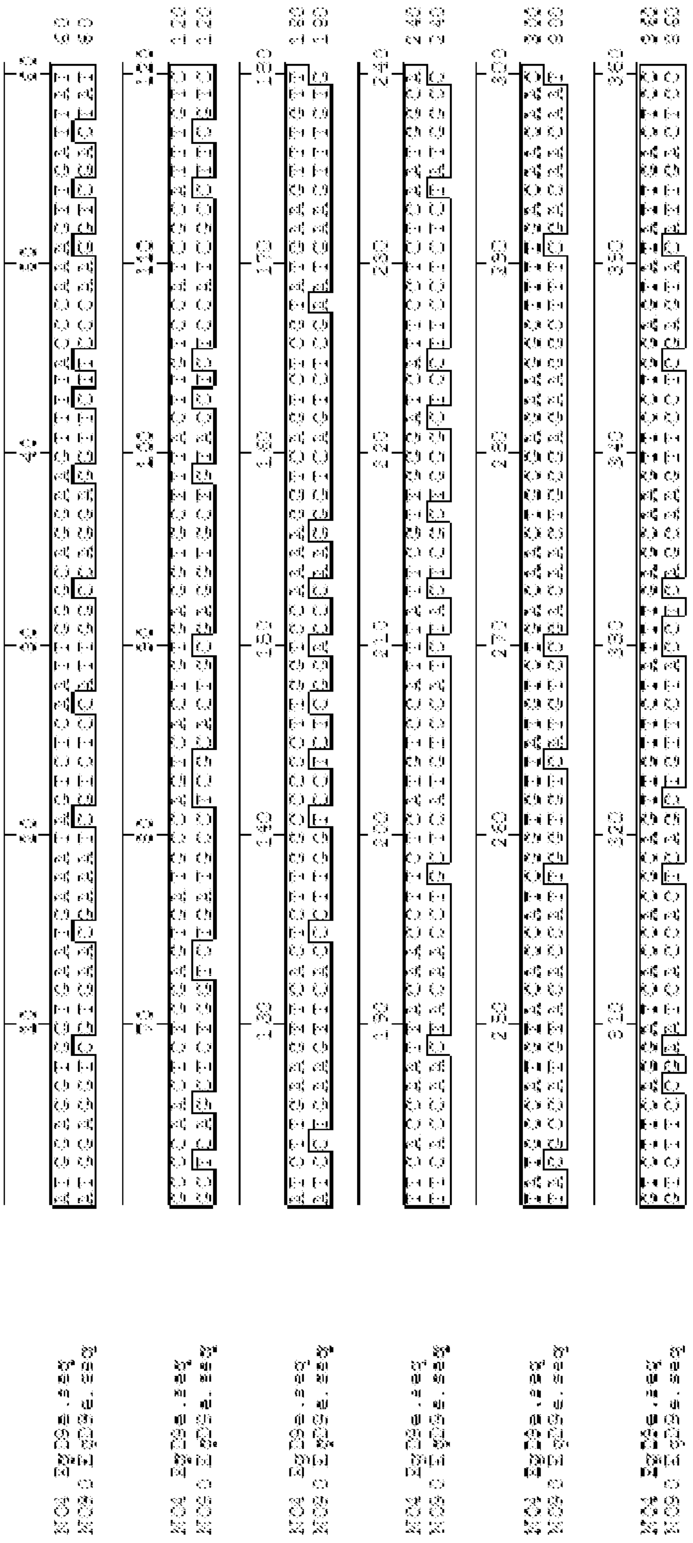
Figure 26B:
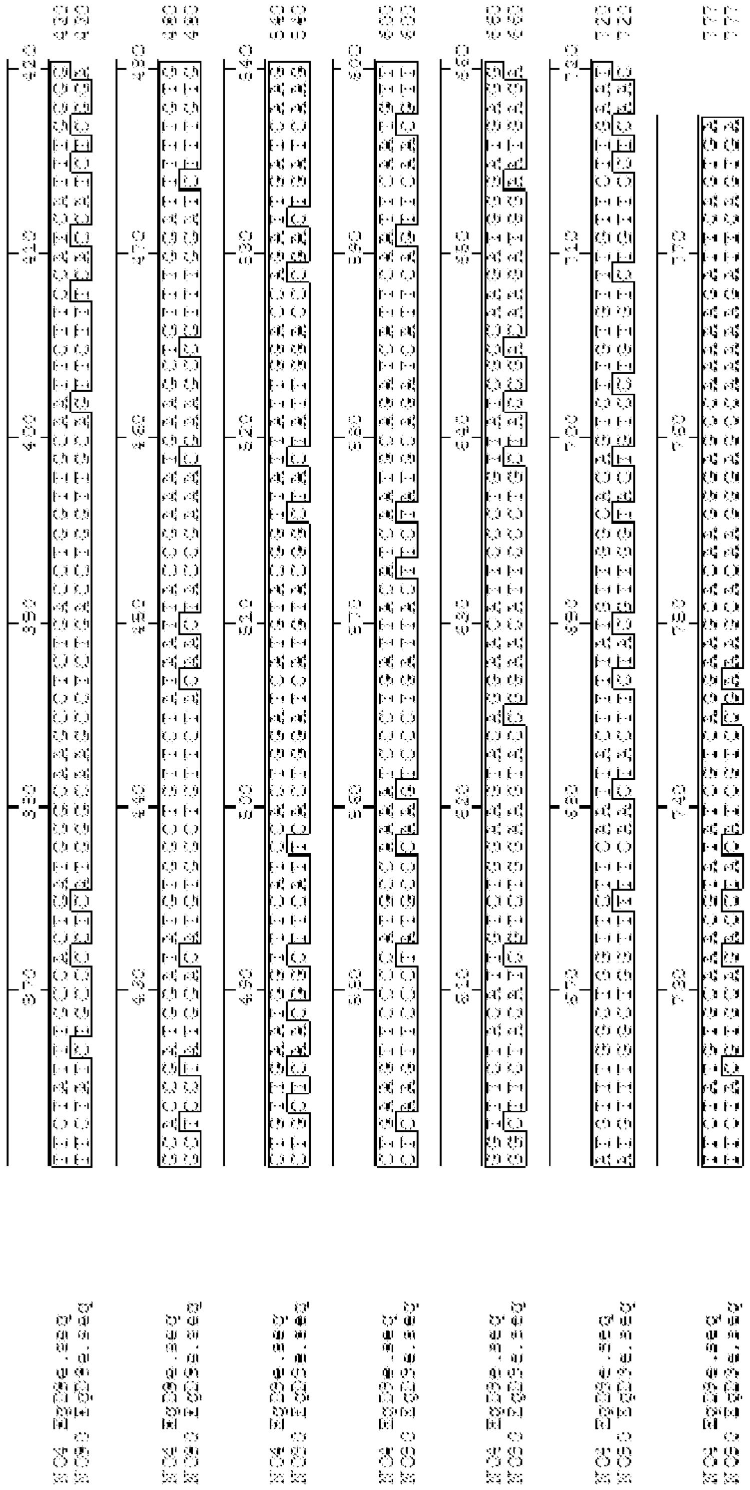

FIGS. 26A and B show a comparison of the nucleotide sequences of *Euglena gracilis* delta-9 elongase (EgD9e) (SEQ ID NO:4) and the synthetic delta-9 elongase, derived from *Euglena gracilis* and codon-optimized for expression in *Yarrowia lipolytica* (EgD9eS) (SEQ ID NO:90).

FIG. 27 show a Clustal W alignment (with default parameters) of SEQ ID NO:5 (amino acid sequence of the delta-9 elongase of the instant invention) and SEQ ID NO:27 (amino acid sequence of the long-chain PUFA elongation enzyme from *Isochrysis galbana* (NCBI Accession No. AAL37626 (GI 17226123)).

Figure 28:
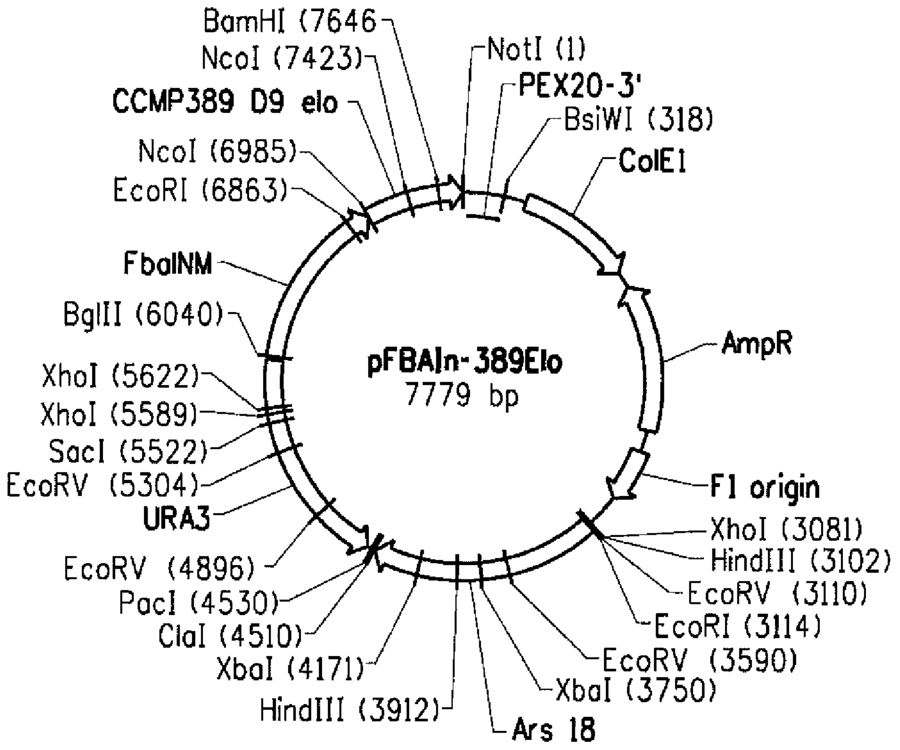

FIG. 28 is a map of plasmid pFBAIn-389Elo.

FIG. 29 shows a Clustal V alignment (with default parameters) of the amino acid sequence of the *Euglena gracilis* delta-9 elongase of the instant invention (SEQ ID NO:5), the amino acid sequence of the *Eutreptiella* sp. CCMP389 delta-9 elongase of the instant invention (SEQ ID NO:127) and the amino acid sequence of the long-chain PUFA elongation enzyme from *Isochrysis galbana* (NCBI Accession No. AAL37626 (GI 17226123)) (SEQ ID NO:27).

SEQ ID NO:1 is the 5' sequence of the cDNA insert from clone eeg1c.pk001.n5.f.

SEQ ID NO:2 is the 3' sequence of the cDNA insert from clone eeg1c.pk001.n5.f.

SEQ ID NO:3 is the sequence aligned from SEQ ID NO:1 and SEQ ID NO:2 (full cDNA sequence excluding polyA tail).

SEQ ID NO:4 is nucleotide sequence of the CDS of the *Euglena gracilis* delta-9 elongase of the instant invention (clone eeg1c.pk001.n5.f) (abbreviated EgD9e).

SEQ ID NO:5 is the deduced amino acid sequence of SEQ ID NO:4 (*Euglena gracilis* delta-9 elongase of the instant invention—clone eeg1c.pk001.n5.f).

SEQ ID NO:6 is the sequence of the ig-s primer.

SEQ ID NO:7 is the sequence of the ig-as primer.

SEQ ID NO:8 is the sequence of the oEugEL1-1 primer.

SEQ ID NO:9 is the sequence of the oEugEL1-2 primer.

SEQ ID NO:10 is the sequence of the Eg5-1 primer.

SEQ ID NO:11 is the sequence of the Eg3-3 primer.

SEQ ID NO:12 is the sequence of T7.

SEQ ID NO:13 is the sequence of M13-28Rev.

SEQ ID NO:14 is the sequence of Eg3-2.

SEQ ID NO:15 is the sequence of Eg5-2.

SEQ ID NO:16 is the nucleotide sequence for the *Euglena gracilis* delta-8 desaturase (Eg5).

SEQ ID NO:17 is the amino acid sequence for the *Euglena gracilis* delta-8 desaturase (Eg5) shown in SEQ ID NO:16.

SEQ ID NO:18 is the sequence of the KTi cassette 5' end MCS for pKR457.

SEQ ID NO:19 is the sequence of the KTi cassette 3' end MCS for pKR457 including the soy albumin transcription 3' terminator.

SEQ ID NO:20 is the sequence of the oSaIb-12 primer.

SEQ ID NO:21 is the sequence of the oSaIb-13 primer.

SEQ ID NO:22 is the sequence of restriction sites added to pKR287 to make pKR767.

SEQ ID NO:23 is the sequence of the oSAIb-9 primer.

SEQ ID NO:24 is the sequence of the oSAIb-2 primer.

SEQ ID NO:25 is the sequence of pZUF17.

SEQ ID NO:26 is the sequence of pDMW237.

SEQ ID NO:27 amino acid sequence of the long-chain PUFA elongation enzyme from *Isochrysis galbana* (NCBI Accession No. AAL37626 (GI 17226123), locus AAL37626, CDS AF390174).

SEQ ID NO:28 is the sequence of the M13F universal primer.

SEQ ID NO:29 is the nucleotide sequence of the long-chain PUFA elongation enzyme from *Isochrysis galbana* (NCBI Accession No. AAL37626 (GI 17226123), locus AAL37626, CDS AF390174) shown in SEQ ID NO:27.

Figure 1:
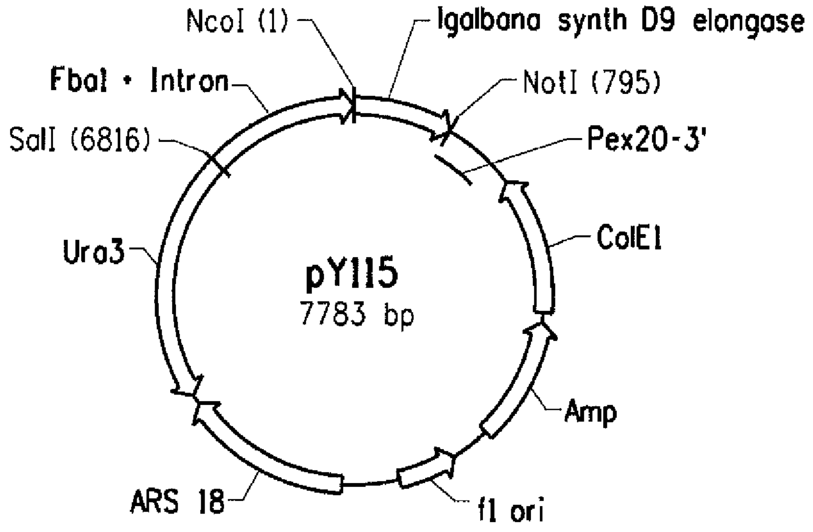
FIG. 1 is a map of plasmid pY115.

SEQ ID NO:30 is the sequence of pY115 (see FIG. 1).

Figure 2:
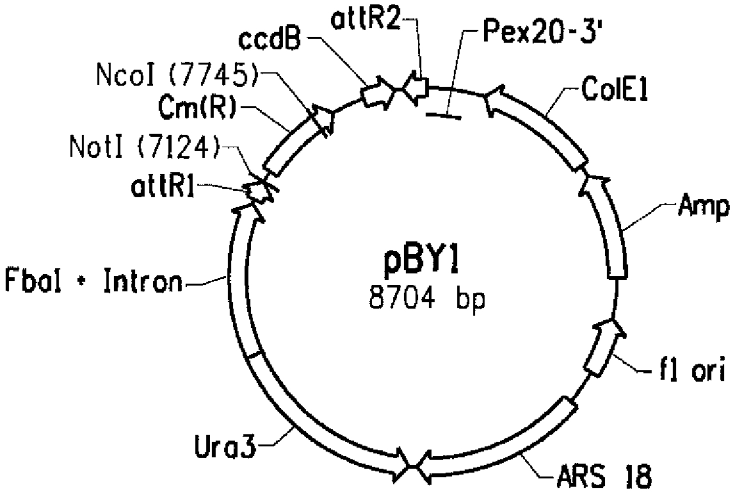
FIG. 2 is a map of *Yarrowia lipolytica* Gateway® destination vector pBY1.

SEQ ID NO:31 is the sequence of pBY1 (see FIG. 2).

Figure 3:
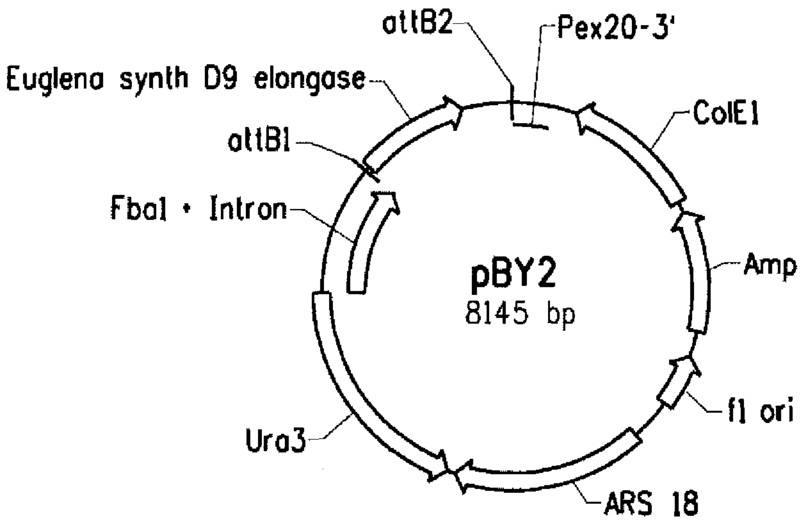
FIG. 3 is a map of plasmid pBY2.

SEQ ID NO:32 is the sequence of pBY2 (see FIG. 3).

Figure 4:
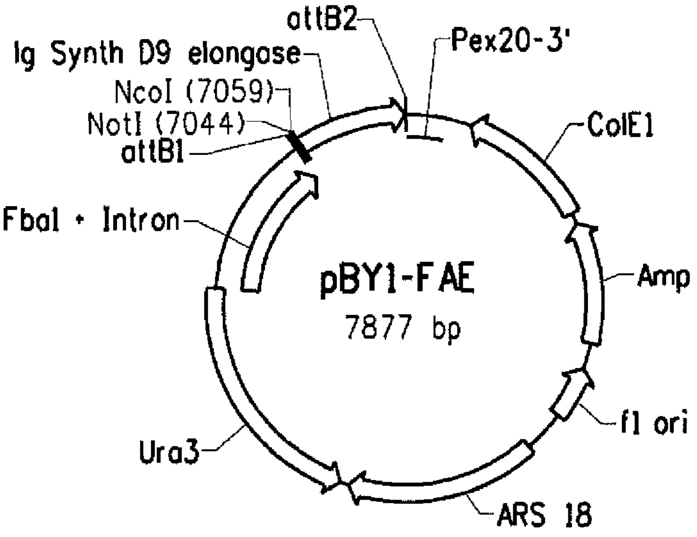
FIG. 4 is a map of plasmid pBY1-FAE.

SEQ ID NO:33 is the sequence of pBY1-FAE (see FIG. 4).

Figure 5:
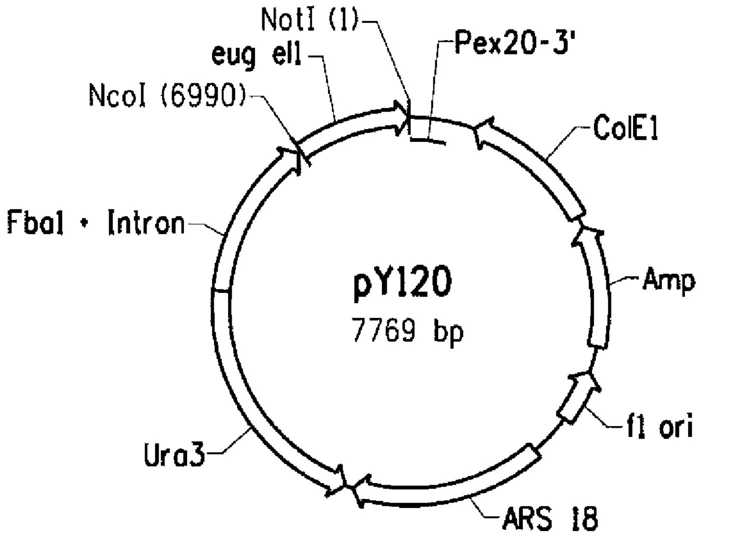
FIG. 5 is a map of plasmid pY120.

SEQ ID NO:34 is the sequence of pY120 (see FIG. 5).

Figure 6:
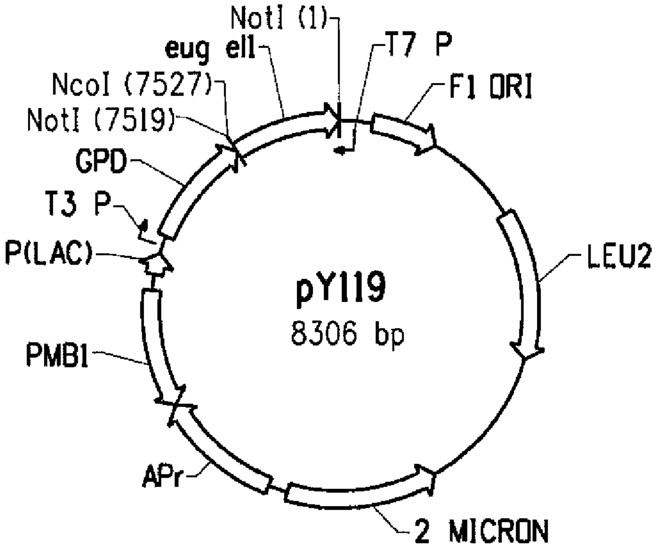
FIG. 6 is a map of plasmid pY119.

SEQ ID NO:35 is the sequence of pY119 (see FIG. 6).

SEQ ID NO:36 is the sequence of pKR72.

Figure 7:
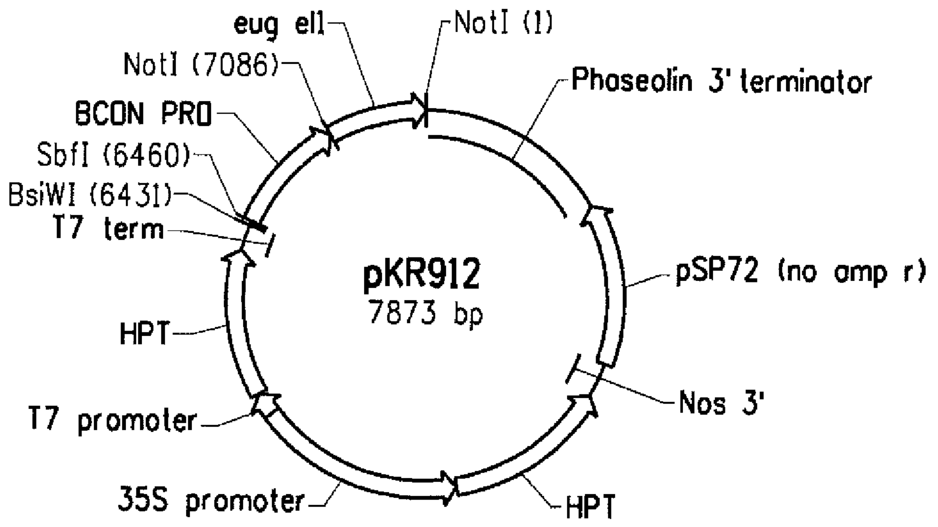
FIG. 7 is a map of plasmid pKR912.

SEQ ID NO:37 is the sequence of pKR912 (see FIG. 7).

SEQ ID NO:38 is the sequence of pKS102.

SEQ ID NO:39 is the sequence of pKR197.

Figure 8:
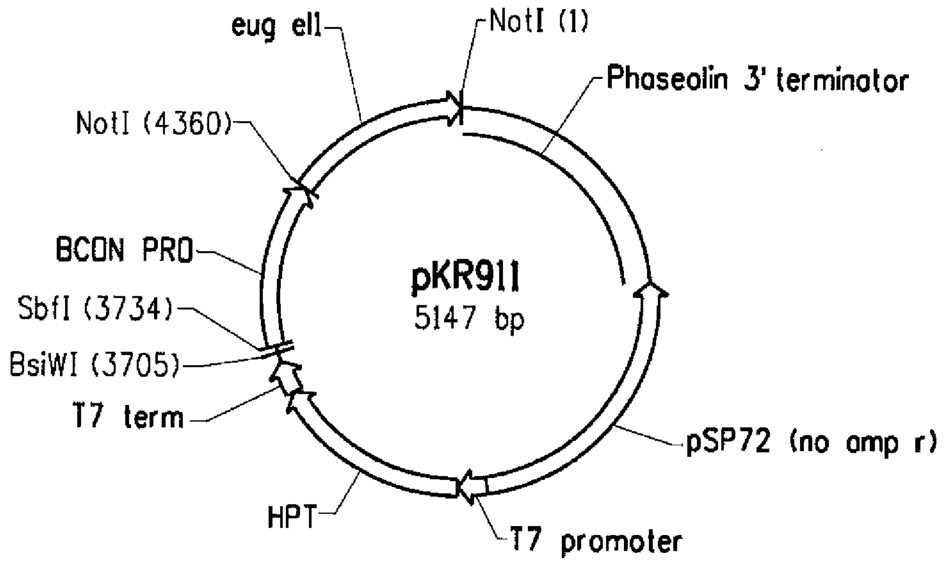
FIG. 8 is a map of plasmid pKR911.

SEQ ID NO:40 is the sequence of pKR911 (see FIG. 8).

SEQ ID NO:41 is the sequence of pKS121.

SEQ ID NO:42 is the sequence of pKR457.

SEQ ID NO:43 is the sequence of pKR680.

Figure 9:
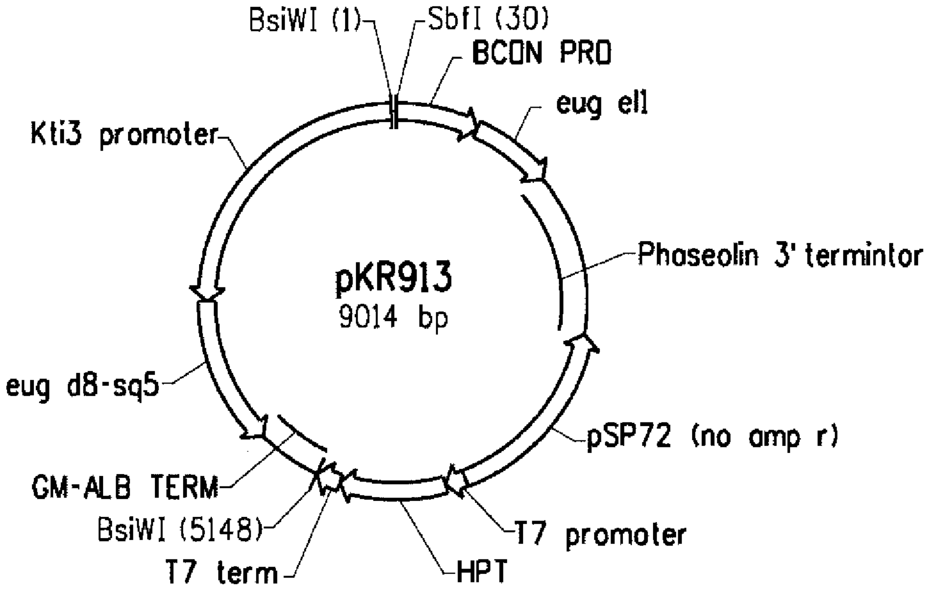
FIG. 9 is a map of plasmid pKR913.

SEQ ID NO:44 is the sequence of pKR913 (see FIG. 9).

SEQ ID NO:45 is the sequence of pKR767.

SEQ ID NO:46 is the sequence of pKR328.

Figure 10A:
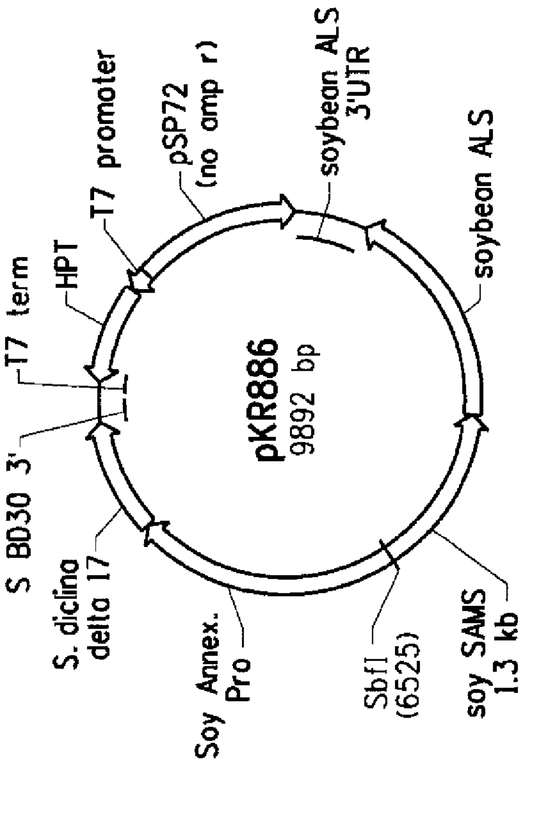
FIG. 10A is a map of plasmid pKR886.
Figure 10B:
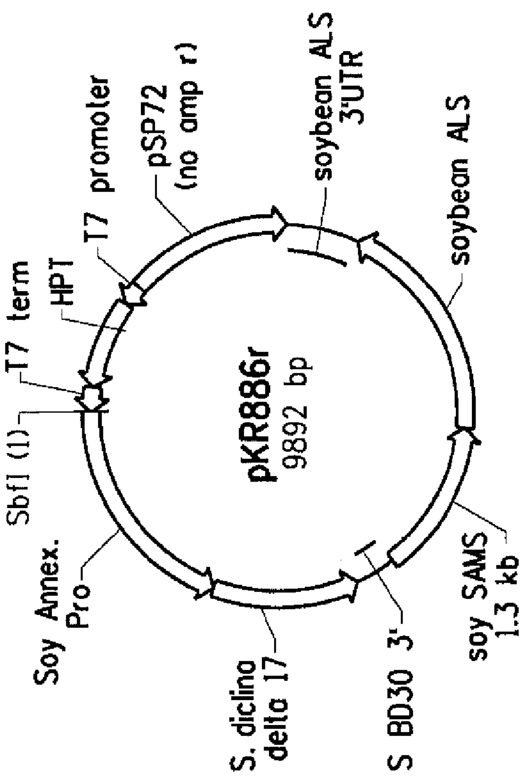
FIG. 10B is a map of plasmid pKR886r.

SEQ ID NO:47 is the sequence of pKR886 (see FIG. 10).

SEQ ID NO:48 is the sequence of pKR886r (see FIG. 10).

SEQ ID NO:49 is the sequence of pKR271.

SEQ ID NO:50 is the sequence of pKR226.

SEQ ID NO:51 is the sequence of pKR275.

SEQ ID NO:52 is the sequence of pKR329.

SEQ ID NO:53 is the sequence of pKR585.

SEQ ID NO:54 is the sequence of pKR578.

SEQ ID NO:55 is the sequence of pKR667.

Figure 12:
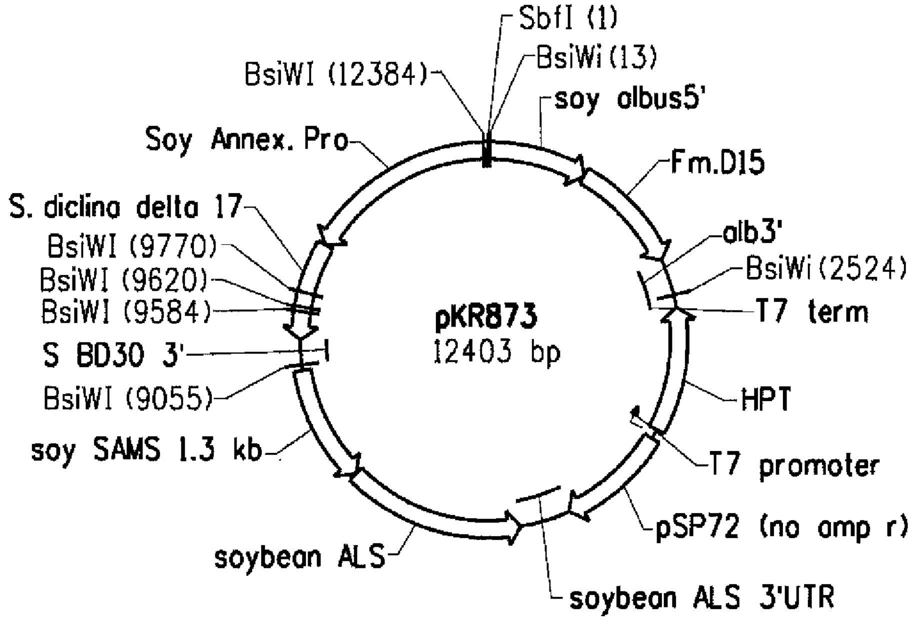
FIG. 12 is a map of plasmid pKR873.

SEQ ID NO:56 is the sequence of pKR873 (see FIG. 12).

SEQ ID NO:57 is the sequence of pKR132.

SEQ ID NO:58 is the sequence of pKR160.

SEQ ID NO:59 is the sequence of pKR124.

SEQ ID NO:60 is the sequence of pKR163.

SEQ ID NO:61 is the sequence of pY34.

SEQ ID NO:62 is the sequence of pKR863.

SEQ ID NO:63 is the sequence of pKR869.

SEQ ID NO:64 is the sequence of pKR270.

SEQ ID NO:65 is the nucleotide sequence for the synthetic delta-9 elongase derived from *Isochrysis galbana* codon-optimized for expression in *Yarrowia lipolytica*.

SEQ ID NOs:66-81 correspond to primers IL3-1A, IL3-1B, IL3-2A, IL3-2B, IL3-3A, IL3-3B, IL3-4A, IL3-4B, IL3-5A, IL3-5B, IL3-6A, IL3-6B, IL3-7A, IL3-7B, IL3-8A and IL3-8B, respectively, used for amplification as described in Example 4.

SEQ ID NOs:82-85 correspond to primers IL3-1F, IL3-4R, IL3-5F and IL3-8R, respectively, used for amplification as described in Example 4.

SEQ ID NO:86 is the 417 bp NcoI/PstI fragment described in Example 4.

SEQ ID NO:87 is the 377 bp PstI/NotI fragment described in Example 4.

SEQ ID NO:88 is the sequence of the *Mortierella alpine* delta-5 desaturase.

SEQ ID NO:89 is the sequence of pDMW263.

SEQ ID NO:90 is the nucleotide sequence for the synthetic delta-9 elongase derived from *Euglena gracilis* codon-optimized for expression in *Yarrowia lipolytica*.

Figure 17:
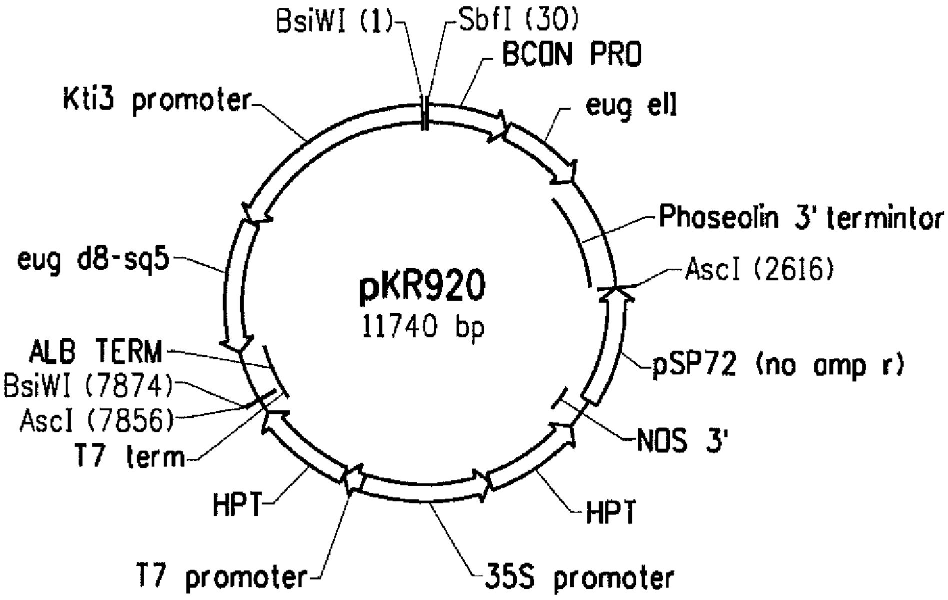
FIG. 17 is a map of plasmid pKR920.

SEQ ID NO:91 is the sequence of pKR920 (see FIG. 17).

SEQ ID NO:92 is the sequence of cal a24-4.

SEQ ID NO:93 is the sequence of primer oCal-15.

SEQ ID NO:94 is the sequence of primer oCal-6.

SEQ ID NO:95 is the sequence of pKR53B

SEQ ID NO:96 is the sequence of pKR85.

SEQ ID NO:97 is the sequence of primer oKR85-1.

SEQ ID NO:98 is the sequence of primer oKR85-2.

SEQ ID NO:99 is the sequence of pPCR85.

SEQ ID NO:100 is the sequence of pKR91.

SEQ ID NO:101 is the sequence of pKR92.

Figure 18:
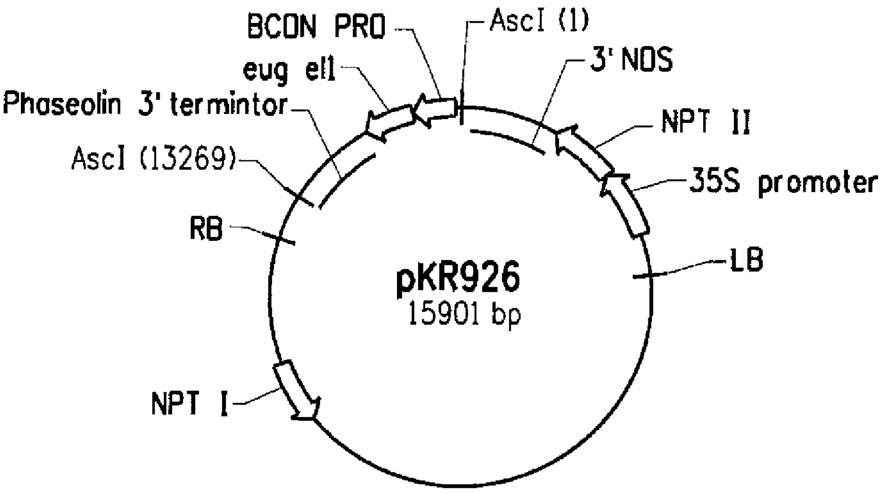
FIG. 18 is a map of plasmid pKR926.

SEQ ID NO:102 is the sequence of pKR926 (see FIG. 18)

SEQ ID NO:103 is the sequence of pKR767.

Figure 19:
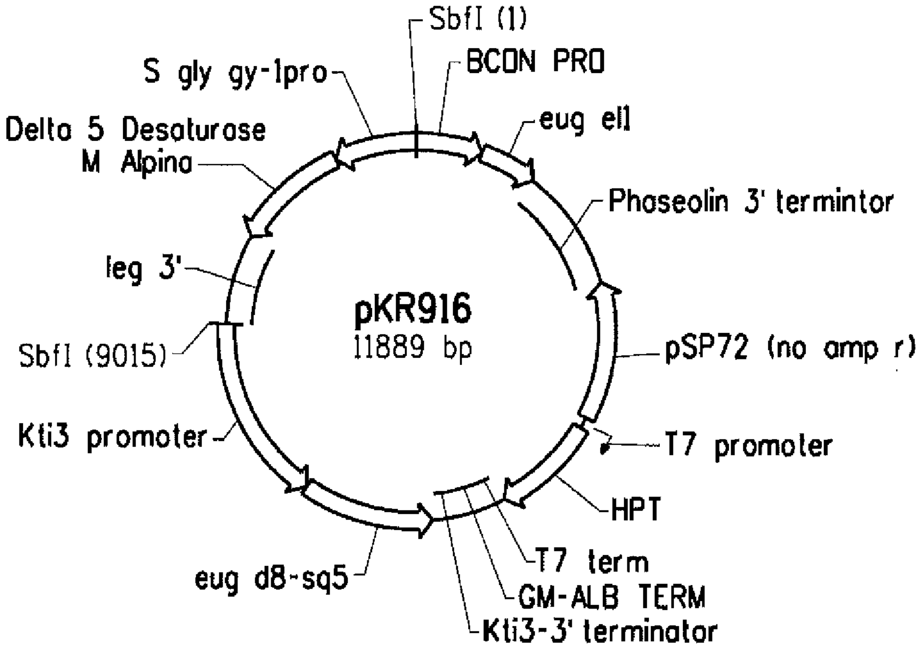
FIG. 19 is a map of plasmid pKR916.

SEQ ID NO:104 is the sequence of pKR916 (see FIG. 19)

SEQ ID NO:105 is the sequence of pZuFmEgD9ES.

SEQ ID NO:106 is the sequence of pZuFmEgD9E.

SEQ ID NO:107 is the sequence of the SMART™ IV oligonucleotide.

SEQ ID NO:108 is the sequence of the CDSIII/3' PCR primer.

SEQ ID NO:109 is the sequence of the 5'-PCR primer.

SEQ ID NO:110 is the sequence of pFBAIN-389Elo.

SEQ ID NO:111 is the sequence of the *Eutreptiella* sp. CCMP389 (E389D9e) complete assembled contig.

SEQ ID NO:112 is the nucleotide sequence of degenerate primer EuEF3.

SEQ ID NO:113 is the deduced amino acid sequence of SEQ ID NO:112.

SEQ ID NO:114 is the nucleotide sequence of degenerate primer EuER3.

SEQ ID NO:115 is the deduced amino acid sequence of SEQ ID NO:114.

SEQ ID NO:116 is the sequence of the 389Elo-5-1 primer.

SEQ ID NO:117 is the sequence of the 389Elo-5-2 primer.

SEQ ID NO:118 is the sequence of the DNR CDS 5'-2 primer.

SEQ ID NO:119 is the sequence of the *Eutreptiella* sp. CCMP389 (E389D9e) 5' cDNA fragment #1.

SEQ ID NO:120 is the sequence of the 389Elo-5-4 primer.

SEQ ID NO:121 is the sequence of the *Eutreptiella* sp. CCMP389 (E389D9e) 5' cDNA fragment #2.

SEQ ID NO:122 is the sequence of the 389Elo-3-1 primer.

SEQ ID NO:123 is the sequence of the 389Elo-3-2 primer.

SEQ ID NO:124 is the sequence of the *Eutreptiella* sp. CCMP389 (E389D9e) 3' cDNA fragment.

SEQ ID NO:125 is the sequence of the *Eutreptiella* sp. CCMP389 (E389D9e) complete assembled contig.

SEQ ID NO:126 is the nucleotide sequence of the *Eutreptiella* sp. CCMP389 (E389D9e) delta-9 elongase.

SEQ ID NO:127 is the deduced amino acid sequence of SEQ ID NO:126 (*Eutreptiella* sp. CCMP389 (E389D9e) delta-9 elongase).

SEQ ID NO:128 is the sequence of pFBAIN-MOD-1.

SEQ ID NO:129 is the sequence of the *Eutreptiella* sp. CCMP389 (E389D9e) internal cDNA fragment.

SEQ ID NOs:130-136 are the motif sequences associated with a delta-9 elongase.

DETAILED DESCRIPTION OF THE INVENTION

All patents, patent applications, and publications cited herein are incorporated by reference in their entirety.

In the context of this disclosure, a number of terms shall be utilized.

The term "fatty acids" refers to long-chain aliphatic acids (alkanoic acids) of varying chain lengths, from about $C_{12}$ to $C_{22}$ (although both longer and shorter chain-length acids are known). The predominant chain lengths are between $C_{16}$ and $C_{22}$. Additional details concerning the differentiation between "saturated fatty acids" versus "unsaturated fatty acids", "monounsaturated fatty acids" versus "polyunsaturated fatty acids" (or "PUFAs"), and "omega-6 fatty acids" (ω-6 or n-6) versus "omega-3 fatty acids" (ω-3 or n-3) are provided in WO 2004/101757.

Fatty acids are described herein by a simple notation system of "X:Y", wherein the number before the colon indicates the number of carbon atoms in the fatty acid and the number after the colon is the number of double bonds that are present. The number following the fatty acid designation indicates the position of the double bond from the carboxyl end of the fatty acid with the "c" affix for the cis-configuration of the double bond (e.g., palmitic acid (16:0), stearic acid (18:0), oleic acid (18:1, 9c), petroselinic acid (18:1, 6c), LA (18:2, 9c,12c), GLA (18:3, 6c,9c,12c) and ALA (18:3, 9c,12c,15c)). Unless otherwise specified 18:1, 18:2 and 18:3 refer to oleic, LA and linolenic fatty acids. If not specifically written as otherwise, double bonds are assumed to be of the cis configuration. For instance, the double bonds in 18:2 (9,12) would be assumed to be in the cis configuration.

Figure 15:
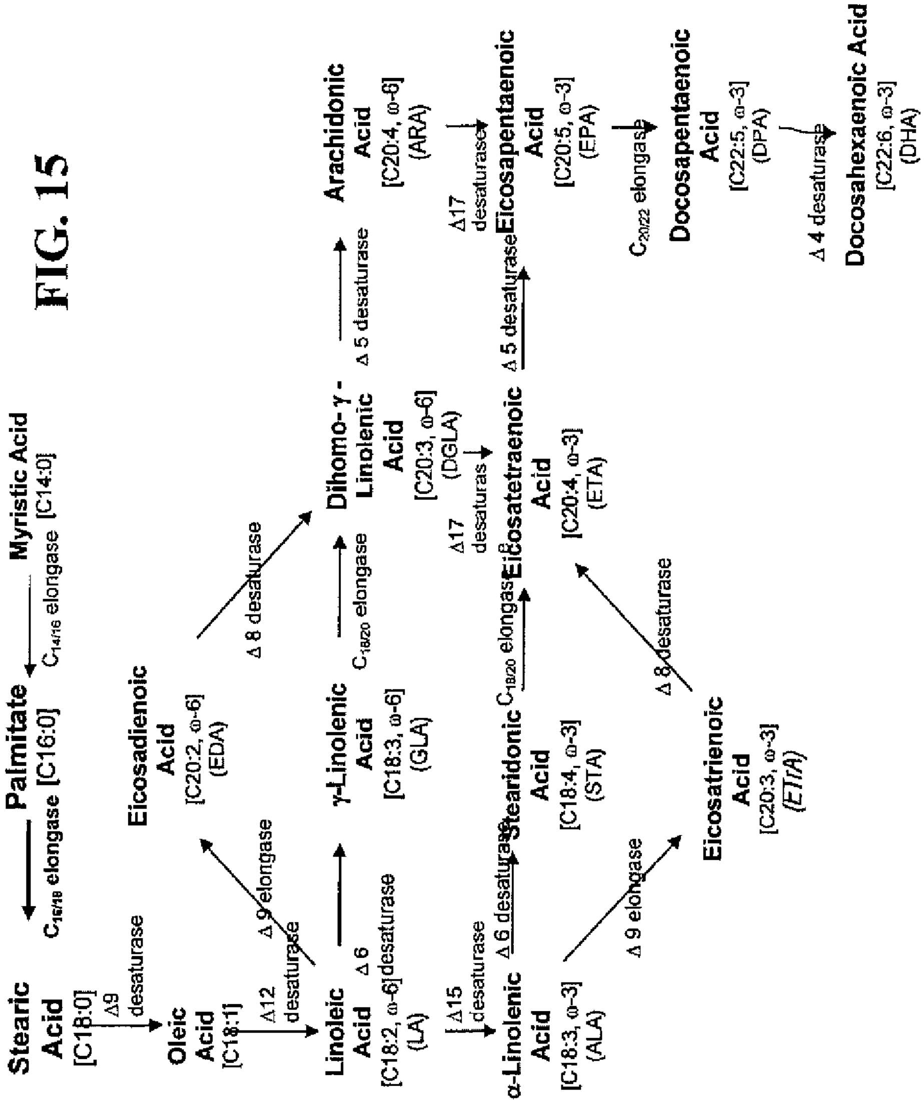
FIG. 15 is a representative omega-3 and omega-6 fatty acid pathway providing for the conversion of myristic acid through various intermediates to docosahexaenoic acid (DHA).

A representative pathway is illustrated in FIG. 15, providing for the conversion of myristic acid through various intermediates to DHA, which demonstrates how both omega-3 and omega-6 fatty acids may be produced from a common source.

Nomenclature used to describe PUFAs in the present disclosure is shown below in Table 2. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the Table summarizes the common names of omega-3 and omega-6 fatty acids, the abbreviations that will be used throughout the remainder of the specification, and each compounds' chemical name.

TABLE 2

Nomenclature of Polyunsaturated Fatty Acids

| Common Name | Abbreviation | Chemical Name | Shorthand Notation |
|---|---|---|---|
| oleic | — | cis-9-octadecenoic | 18:1 |
| linoleic | LA | cis-9,12-octadecadienoic | 18:2 ω-6 |
| gamma-linolenic | GLA | cis-6,9,12-octadecatrienoic | 18:3 ω-6 |
| eicosadienoic | EDA | cis-11,14-eicosadienoic | 20:2 ω-6 |
| dihomo-gamma-linolenic | DGLA or HGLA | cis-8,11,14-eicosatrienoic | 20:3 ω-6 |
| arachidonic | AA or ARA | cis-5,8,11,14-eicosatetraenoic | 20:4 ω-6 |
| alpha-linolenic | ALA | cis-9,12,15-octadecatrienoic | 18:3 ω-3 |
| stearidonic | STA | cis-6,9,12,15-octadecatetraenoic | 18:4 ω-3 |
| eicosatrienoic | ETrA or ERA | cis-11,14,17-eicosatrienoic | 20:3 ω-3 |
| eicosa-tetraenoic | ETA | cis-8,11,14,17-eicosatetraenoic | 20:4 ω-3 |
| eicosa-pentaenoic | EPA | cis-5,8,11,14,17-eicosapentaenoic | 20:5 ω-3 |
| docosa-pentaenoic | DPA | cis-7,10,13,16,19-docosapentaenoic | 22:5 ω-3 |
| docosa-hexaenoic | DHA | cis-4,7,10,13,6,19-docosahexaenoic | 22:6 ω-3 |

Other abbreviations that may be used are as follows (the terms and abbreviations may be used interchangeably):

EgD9e=*Euglena gracilis* delta-9 elongase (wild-type)

EgD9eS=synthetic delta-9 elongase, derived from *Euglena gracilis* and codon-optimized for expression in *Yarrowia lipolytica*

E389D9e=*Eutreptiella* sp. CCMP389delta-9 elongase (wild-type)

E389D9eS=synthetic delta-9 elongase, derived from *Eutreptiella* sp. CCMP389 and codon-optimized for expression in *Yarrowia lipolytica*

The term "essential fatty acid" refers to a particular PUFA that an organism must ingest in order to survive, being unable to synthesize the particular essential fatty acid de novo. For example, mammals can not synthesize the essential fatty acid LA. Other essential fatty acids include, but are not limited to, GLA, DGLA, AA, EPA and DHA.

The term "fat" refers to a lipid substance that is solid at 25° C. and usually saturated.

The term "oil" refers to a lipid substance that is liquid at 25° C. and usually polyunsaturated. PUFAs are found in the oils of some algae, oleaginous yeasts and filamentous fungi. "Microbial oils" or "single cell oils" are those oils naturally produced by microorganisms during their lifespan. Such oils can contain long-chain PUFAs.

The term "PUFA biosynthetic pathway" refers to a metabolic process that converts oleic acid to LA, EDA, GLA, DGLA, AA, ALA, STA, ETrA, ETA, EPA, DPA and DHA. This process is well described in the literature (e.g., see WO 2005/003322 and WO 2006/052870). Simplistically, this process involves elongation of the carbon chain through the addition of carbon atoms and desaturation of the molecule through the addition of double bonds, via a series of special desaturation and elongation enzymes (i.e., "PUFA biosynthetic pathway enzymes") present in the endoplasmic reticulim membrane. More specifically, "PUFA biosynthetic pathway enzymes" refer to any of the following enzymes (and genes which encode said enzymes) associated with the biosynthesis of a PUFA, including: a delta-4 desaturase, a delta-5 desaturase, a delta-6 desaturase, a delta-12 desaturase, a delta-15 desaturase, a delta-17 desaturase, a delta-9 desaturase, a delta-8 desaturase, a delta-9 elongase, a $C_{14/16}$ elongase, a $C_{16/18}$ elongase, a $C_{18/20}$ elongase and/or a $C_{20/22}$ elongase.

"Desaturase" is a polypeptide which can desaturate one or more fatty acids to produce a mono- or poly-unsaturated fatty acid or precursor which is of interest. Of particular interest herein are delta-8 desaturases that will desaturate a fatty acid between the eighth and ninth carbon atom numbered from the carboxyl-terminal end of the molecule and that can, for example, catalyze the conversion of EDA to DGLA and/or ETrA to ETA. Other useful fatty acid desaturases include, for example, (1) delta-5 desaturases that catalyze the conversion of DGLA to AA and/or ETA to EPA; (2) delta-6 desaturases that catalyze the conversion of LA to GLA and/or ALA to STA; (3) delta-4 desaturases that catalyze the conversion of DPA to DHA; (4) delta-12 desaturases that catalyze the conversion of oleic acid to LA; (5) delta-15 desaturases that catalyze the conversion of LA to ALA and/or GLA to STA; (6) delta-17 desaturases that catalyze the conversion of AA to EPA and/or DGLA to ETA; and (7) delta-9 desaturases that catalyze the conversion of palmitate to palmitoleic acid (16:1) and/or stearate to oleic acid (18:1).

The term "elongase system" refers to a suite of four enzymes that are responsible for elongation of a fatty acid carbon chain to produce a fatty acid that is two carbons longer than the fatty acid substrate that the elongase system acts upon. More specifically, the process of elongation occurs in association with fatty acid synthase, whereby CoA is the acyl carrier (Lassner et al., *Plant Cell* 8:281-292 (1996)). In the first step, which has been found to be both substrate-specific and also rate-limiting, malonyl-CoA is condensed with a long-chain acyl-CoA to yield carbon dioxide ($CO_2$) and a β-ketoacyl-CoA (where the acyl moiety has been elongated by two carbon atoms). Subsequent reactions include reduction to β-hydroxyacyl-CoA, dehydration to an enoyl-CoA and a second reduction to yield the elongated acyl-CoA. Examples of reactions catalyzed by elongase systems are the conversion of GLA to DGLA, STA to ETA and EPA to DPA.

For the purposes herein, an enzyme catalyzing the first condensation reaction (i.e., conversion of malonyl-CoA to β-ketoacyl-CoA) will be referred to generically as an "elongase". In general, the substrate selectivity of elongases is somewhat broad but segregated by both chain length and the degree of unsaturation. Accordingly, elongases can have different specificities. For example, a $C_{14/16}$ elongase will utilize a $C_{14}$ substrate (e.g., myristic), a $C_{16/18}$ elongase will utilize a $C_{16}$ substrate (e.g., palmitate), a $C_{18/20}$ elongase will utilize a $C_{18}$ substrate (e.g., GLA, STA) and a $C_{20/22}$ elongase will utilize a $C_{20}$ substrate (e.g., EPA). In like manner, and of particular interest herein, a "delta-9 elongase" is able to catalyze the conversion of LA and ALA to EDA and ETrA. It is important to note that some elongases have broad specificity and thus a single enzyme may be capable of catalyzing several elongase reactions (e.g., thereby acting as both a $C_{16/18}$ elongase and a $C_{18/20}$ elongase). In preferred embodiments, it is desirable to empirically determine the specificity of a fatty acid elongase by transforming a suitable host with the gene for the fatty acid elongase and determining its effect on the fatty acid profile of the host.

The term "delta-9 elongase/delta-8 desaturase pathway" refers to a biosynthetic pathway for production of long-chain PUFAs. This pathway, at a minimum, comprises a delta-9 elongase and a delta-8 desaturase, thereby enabling biosynthesis of DGLA and/or ETA from LA and ALA, respectively.

The term "delta-9 elongase" refers to an enzyme that is capable of catalyzing at least one elongase reaction such as the elongation of linoleic or alpha-linolenic acid to EDA or ETrA, respectively. It may act as both a $C_{16/18}$ elongase and a $C_{18/20}$ elongase.

The term "amino acid" will refer to the basic chemical structural unit of a protein or polypeptide. Amino acids are identified by either the one-letter code or the three-letter codes for amino acids, in conformity with the IUPAC-IYUB standards described in *Nucleic Acids Research,* 13:3021-3030 (1985) and in the *Biochemical Journal,* 219 (2):345-373 (1984), which are herein incorporated by reference.

The term "conservative amino acid substitution" refers to a substitution of an amino acid residue in a given protein with another amino acid, without altering the chemical or functional nature of that protein. For example, it is well known in the art that alterations in a gene that result in the production of a chemically equivalent amino acid at a given site (but that do not affect the structural and functional properties of the encoded, folded protein) are common. For the purposes of the present invention, "conservative amino acid substitutions" are defined as exchanges within one of the following five groups:

1. small aliphatic, nonpolar or slightly polar residues: Ala [A], Ser [S], Thr [T] (Pro [P], Gly [G]);
2. polar, negatively charged residues and their amides: Asp [D], Asn [N], Glu [E], Gln [Q];
3. polar, positively charged residues: His [H], Arg [R], Lys [K];
4. large aliphatic, nonpolar residues: Met [M], Leu [L], Ile [I], Val [V] (Cys [C]); and,
5. large aromatic residues: Phe [F], Tyr [Y], Trp [W].

Conservative amino acid substitutions generally maintain: 1) the structure of the polypeptide backbone in the area of the substitution; 2) the charge or hydrophobicity of the molecule at the target site; or 3) the bulk of the side chain. Additionally, in many cases, alterations of the N-terminal and C-terminal portions of the protein molecule would also not be expected to alter the activity of the protein.

The term "non-conservative amino acid substitution" refers to an amino acid substitution that is generally expected to produce the greatest change in protein properties. Thus, for example, a non-conservative amino acid substitution would be one whereby: 1.) a hydrophilic residue is substituted for/by a hydrophobic residue (e.g., Ser or Thr for/by Leu, Ile, Val); 2.) a Cys or Pro is substituted for/by any other residue; 3.) a residue having an electropositive side chain is substituted for/by an electronegative residue (e.g., Lys, Arg or His for/by Asp or Glu); or, 4.) a residue having a bulky side chain is substituted for/by one not having a side chain (e.g., Phe for/by Gly). Sometimes, non-conservative amino acid substitutions between two of the five groups will not affect the activity of the encoded protein.

The terms "polynucleotide", "polynucleotide sequence", "nucleic acid sequence", "nucleic acid fragment" and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric genes to produce the desired phenotype in a transformed plant. Chimeric genes can be designed for use in suppression by linking a nucleic acid fragment or subfragment thereof, whether or not it encodes an active enzyme, in the sense or antisense orientation relative to a plant promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Other exemplary stringent hybridization conditions include 0.1×SSC, 0.1% SDS, 65° C. and washed with 2×SSC, 0.1% SDS followed by 0.1×SSC, 0.1% SDS.

Specificity is typically the function of post-hybridization washes, the critical factors being the ionic strength and temperature of the final wash solution. For DNA-DNA hybrids, the $T_m$ can be approximated from the equation of Meinkoth et al., *Anal. Biochem.* 138:267-284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel et al., Eds., Greene Publishing and Wiley-Interscience, New York (1995). Hybridization and/or wash conditions can be applied for at least 10, 30, 60, 90, 120, or 240 minutes.

"Sequence identity" or "identity" in the context of nucleic acid or polypeptide sequences refers to the nucleic acid bases or amino acid residues in the two sequences that are the same when aligned for maximum correspondence over a specified comparison window.

Thus, "percentage of sequence identity" refers to the valued determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 50% to 100%, such as such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. These identities can be determined using any of the programs described herein.

Sequence alignments and percent identity or similarity calculations may be determined using a variety of comparison methods designed to detect homologous sequences including, but not limited to, the MegAlign™ program of the LASARGENE bioinformatics computing suite (DNASTAR Inc., Madison, Wis.). Multiple alignment of the sequences are performed using the Clustal V method of alignment (Higgins, D. G. and Sharp, P. M. (1989) *Comput. Appl. Biosci.* 5:151-153; Higgins, D. G. et al. (1992) *Comput. Appl. Biosci.* 8:189-191) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

It is well understood by one skilled in the art that many levels of sequence identity are useful in identifying polypeptides, from other species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 50% to 100%, such as such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Indeed, any integer amino acid identity from 50% to 100% may be useful in describing the present invention. Also, of interest is any full-length or partial complement of this isolated nucleotide fragment.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

A "codon-optimized gene" is a gene having its frequency of codon usage designed to mimic the frequency of preferred codon usage of the host cell.

An "allele" is one of several alternative forms of a gene occupying a given locus on a chromosome. When all the alleles present at a given locus on a chromosome are the same that plant is homozygous at that locus. If the alleles present at a given locus on a chromosome differ that plant is heterozygous at that locus.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, introns, polyadenylation recognition sequences, RNA processing sites, effector binding sites and stem-loop structures.

"Promoter" refers to a DNA sequence capable of controlling the expression of a coding sequence or functional RNA.

The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters". New promoters of various types useful in plant cells are constantly being discovered; numerous examples may be found in the compilation by Okamuro, J. K., and Goldberg, R. B. *Biochemistry of Plants* 15:1-82 (1989).

"Translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., *Mol. Biotechnol.* 3:225-236 (1995)).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. *Plant Cell* 1:671-680 (1989).

"RNA transcript" refers to the product resulting from RNA polymerase-catalyzed transcription of a DNA sequence. When the RNA transcript is a perfect complementary copy of the DNA sequence, it is referred to as the primary transcript. A RNA transcript is referred to as the mature RNA when it is a RNA sequence derived from post-transcriptional processing of the primary transcript. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory: Cold Spring Harbor, N.Y. (1989). Transformation methods are well known to those skilled in the art and are described below.

"PCR" or "polymerase chain reaction" is a technique for the synthesis of large quantities of specific DNA segments and consists of a series of repetitive cycles (Perkin Elmer Cetus Instruments, Norwalk, Conn.). Typically, the double-stranded DNA is heat denatured, the two primers complementary to the 3' boundaries of the target segment are annealed at low temperature and then extended at an intermediate temperature. One set of these three consecutive steps is referred to as a "cycle".

The term "recombinant" refers to an artificial combination of two otherwise separated segments of sequence, e.g., by chemical synthesis or by the manipulation of isolated segments of nucleic acids by genetic engineering techniques.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The term "expression", as used herein, refers to the production of a functional end-product (e.g., a mRNA or a protein [either precursor or mature]).

The term "expression cassette" as used herein, refers to a discrete nucleic acid fragment into which a nucleic acid sequence or fragment can be moved.

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms.

"Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020). Co-suppression constructs in plants previously have been designed by focusing on overexpression of a nucleic acid sequence having homology to an endogenous mRNA, in the sense orientation, which results in the reduction of all RNA having homology to the overexpressed sequence (Vaucheret et al., *Plant J.* 16:651-659 (1998); Gura, *Nature* 404:804-808 (2000)). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (WO 99/53050, published Oct. 21, 1999; WO 02/00904, published Jan. 3, 2002). This increases the frequency of co-suppression in the recovered transgenic plants. Another variation describes the use of plant viral sequences to direct the suppression, or "silencing", of proximal mRNA encoding sequences (WO 98/36083, published Aug. 20, 1998). Both of these co-suppressing phenomena have not been elucidated mechanistically, although genetic evidence has begun to unravel this complex situation (Elmayan et al., *Plant Cell* 10:1747-1757 (1998)).

The term "oleaginous" refers to those organisms that tend to store their energy source in the form of lipid (Weete, In: Fungal Lipid Biochemistry, 2$^{nd}$ Ed., Plenum, 1980). Generally, the cellular oil content of these microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419-25 (1991)).

The term "oleaginous yeast" refers to those microorganisms classified as yeasts that make oil. It is not uncommon for oleaginous microorganisms to accumulate in excess of about 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces*.

The "Clustal V method of alignment" corresponds to the alignment method labeled Clustal V (described by Higgins and Sharp, *CABIOS.* 5:151-153 (1989)) and found in the MegAlign™ program of the LASERGENE bioinformatics computing suite (DNASTAR Inc., Madison, Wis.). The "default parameters" are the parameters preset by the manufacturer of the program. For multiple alignments, they correspond to GAP PENALTY=10 and GAP LENGTH PENALTY=10; and, for pairwise alignments, they are KTUPLE 1, GAP PENALTY=3, WINDOW=5 and DIAGONALS SAVED=5. After alignment of the sequences using the Clustal V program, it is possible to obtain a "percent identity" by viewing the "sequence distances" table in the same program.

"BLASTN method of alignment" is an algorithm provided by the National Center for Biotechnology Information (NCBI) to compare nucleotide sequences using default parameters.

The present invention concerns an isolated polynucleotide comprising:

(a) a nucleotide sequence encoding a polypeptide having delta-9 elongase activity, wherein the polypeptide has at least 70% amino acid identity, based on the Clustal V method of alignment, when compared to an amino acid sequence as set forth in SEQ ID NO:5 or SEQ ID NO:127;

(b) a nucleotide sequence encoding a polypeptide having delta-9 elongase activity, wherein the nucleotide sequence has at least 70% sequence identity, based on the BLASTN method of alignment, when compared to a nucleotide sequence as set forth in SEQ ID NO:4, SEQ ID NO:90 or SEQ ID NO:126;

(c) a nucleotide sequence encoding a polypeptide having delta-9 elongase activity, wherein the nucleotide sequence hybridizes with a nucleotide sequence as set forth in SEQ ID NO:4, SEQ ID NO:90 or SEQ ID NO:126 under the following stringent hybridization conditions: 0.1×SSC, 0.1% SDS, 65° C. and washed with 2×SSC, 0.1% SDS followed by 0.1×SSC, 0.1% SDS; or (d) a complement of the nucleotide sequence of (a), (b) or (c), wherein the complement and the nucleotide sequence consist of the same number of nucleotides and are 100% complementary.

In another aspect this invention concerns an isolated nucleic acid fragment comprising a nucleic acid sequence encoding a delta-9 elongase, excluding SEQ ID NO:27, wherein the amino acid sequence comprising said elongase contains at least one of the following amino acid sequence motifs selected from the group consisting of:

```
                                        (SEQ ID NO: 130)
a)
Y N X (L or F) X X X X S X X S F;

                                        (SEQ ID NO: 131)
b)
F Y X S K X X (E or D) Y X D (T or S)

X X L;

                                        (SEQ ID NO: 132)
c)
L (Q or H) X F H H X G A;

                                        (SEQ ID NO: 133)
d)
M Y X Y Y X X X X X X X (K or R or N)

F;

                                        (SEQ ID NO: 134)
e)
K X L (I or L or M) T X X Q;

                                        (SEQ ID NO: 135)
f) W X F N Y X Y;
and

                                        (SEQ ID NO: 136)
g)
Y X G X V X X L F;
```

wherein X can be any amino acid.

The underlined amino acids may be unique to delta-9 elongases. FIG. 16 (see also FIG. 29) sets forth a comparison of the delta-9 elongase of the invention with a delta-9 elongase from *Isochrysis galbana* using Clustal V alignment (with default parameters). Specifically, SEQ ID NO:5 (amino acid sequence of the delta-9 elongase of the instant invention) and SEQ ID NO:27 (amino acid sequence of the long-chain PUFA elongation enzyme from *Isochrysis galbana* (NCBI Accession No. AAL37626 (GI 17226123)) were compared.

In still another aspect, this invention concerns an isolated polynucleotide comprising a nucleotide sequence encoding a polypeptide having delta-9 elongase activity, wherein the nucleotide sequence has at least 84% sequence identity, based on the BLASTN method of alignment, when compared to a nucleotide sequence as set forth in SEQ ID NO:4.

It was found that a comparison of SEQ ID NO:4 and SEQ ID NO:90 using the BLASTN method of alignment with default parameters showed that these sequences had at least 84% sequence identity.

This delta-9 elongase may be used alone or in combination with other desaturase and elongase components to produce various omega-6 and omega-3 PUFAs, including e.g., DGLA, ETA, AA, EPA, DPA and/or DHA (FIG. 15). One skilled in the art will recognize the appropriate combinations of the delta-9 elongase of the invention herein in conjunction with a delta-4 desaturase, a delta-5 desaturase, a delta-6 desaturase, a delta-12 desaturase, a delta-15 desaturase, a delta-17 desaturase, a delta-9 desaturase, a delta-8 desaturase, a $C_{14/16}$ elongase, a $C_{16/18}$ elongase, a $C_{18/20}$ elongase and/or a $C_{20/22}$ elongase, based on the particular host cell (and its native PUFA profile and/or desaturase and/or elongase profile), the availability of substrate, and the desired end product(s).

In another embodiment, this invention concerns a recombinant construct comprising the polynucleotide of the invention operably linked to at least one regulatory sequence.

As was noted above, a promoter is a DNA sequence that directs cellular machinery of a plant to produce RNA from the contiguous coding sequence downstream (3') of the promoter. The promoter region influences the rate, developmental stage, and cell type in which the RNA transcript of the gene is made. The RNA transcript is processed to produce mRNA which serves as a template for translation of the RNA sequence into the amino acid sequence of the encoded polypeptide. The 5' non-translated leader sequence is a region of the mRNA upstream of the protein coding region that may play a role in initiation and translation of the mRNA. The 3' transcription termination/polyadenylation signal is a non-translated region downstream of the protein coding region that functions in the plant cell to cause termination of the RNA transcript and the addition of polyadenylate nucleotides to the 3' end of the RNA.

The origin of the promoter chosen to drive expression of the coding sequence is not important as long as it has sufficient transcriptional activity to accomplish the invention by expressing translatable mRNA for the desired nucleic acid fragments in the desired host tissue at the right time. Either heterologous or non-heterologous (i.e., endogenous) promoters can be used to practice the invention. For example, suitable promoters include, but are not limited to: the alpha prime subunit of beta conglycinin promoter, Kunitz trypsin inhibitor 3 promoter, annexin promoter, Gly1 promoter, beta subunit of beta conglycinin promoter, P34/Gly Bd m 30K promoter, albumin promoter, Leg A1 promoter and Leg A2 promoter.

The annexin, or P34, promoter is described in WO 2004/071178 (published Aug. 26, 2004). The level of activity of the annexin promoter is comparable to that of many known strong promoters, such as: (1) the CaMV 35S promoter (Atanassova et al., *Plant Mol. Biol.* 37:275-285 (1998); Battraw and Hall, *Plant Mol. Biol.* 15:527-538 (1990); Holtorf et al., *Plant Mol. Biol.* 29:637-646 (1995); Jefferson et al., *EMBO J.* 6:3901-3907 (1987); Wilmink et al., *Plant Mol. Biol.* 28:949-955 (1995)); (2) the *Arabidopsis* oleosin promoters (Plant et al., *Plant Mol. Biol.* 25:193-205 (1994); Li, Texas A&M University Ph.D. dissertation, pp. 107-128 (1997)); (3) the *Arabidopsis* ubiquitin extension protein promoters (Callis et al., *J Biol. Chem.* 265(21):12486-93 (1990)); (4) a tomato ubiquitin gene promoter (Rollfinke et al., *Gene.* 211(2):267-76 (1998)); (5) a soybean heat shock protein promoter (Schoffl et al., *Mol Gen Genet.* 217(2-3):246-53 (1989)); and, (6) a maize H3 histone gene promoter (Atanassova et al., *Plant Mol Biol.* 37(2):275-85 (1989)).

Another useful feature of the annexin promoter is its expression profile in developing seeds. The annexin promoter is most active in developing seeds at early stages (before 10 days after pollination) and is largely quiescent in later stages. The expression profile of the annexin promoter is different from that of many seed-specific promoters, e.g., seed storage protein promoters, which often provide highest activity in later stages of development (Chen et al., *Dev. Genet.* 10:112-122 (1989); Ellerstrom et al., *Plant Mol. Biol.* 32:1019-1027 (1996); Keddie et al., *Plant Mol. Biol.* 24:327-340 (1994); Plant et al., (supra); Li, (supra)). The annexin promoter has a more conventional expression profile but remains distinct from other known seed specific promoters. Thus, the annexin promoter will be a very attractive candidate when overexpression, or suppression, of a gene in embryos is desired at an early developing stage. For example, it may be desirable to overexpress a gene regulating early embryo development or a gene involved in the metabolism prior to seed maturation.

Following identification of an appropriate promoter suitable for expression of a specific coding sequence, the promoter is then operably linked in a sense orientation using conventional means well known to those skilled in the art.

Standard recombinant DNA and molecular cloning techniques used herein are well known in the art and are described more fully in Sambrook, J. et al., In *Molecular Cloning: A*

*Laboratory Manual;* $2^{nd}$ ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In *Current Protocols in Molecular Biology*; John Wiley and Sons: New York, 1990 (hereinafter "Ausubel et al., 1990").

Once the recombinant construct has been made, it may then be introduced into a plant cell of choice by methods well known to those of ordinary skill in the art (e.g., transfection, transformation and electroporation). Oilseed plant cells are the preferred plant cells. The transformed plant cell is then cultured and regenerated under suitable conditions permitting expression of the long-chain PUFA which is then optionally recovered and purified.

The recombinant constructs of the invention may be introduced into one plant cell; or, alternatively, each construct may be introduced into separate plant cells.

Expression in a plant cell may be accomplished in a transient or stable fashion as is described above.

The desired long-chain PUFAs can be expressed in seed. Also within the scope of this invention are seeds or plant parts obtained from such transformed plants.

The term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores.

"Progeny" comprises any subsequent generation of a plant.

Plant parts include differentiated and undifferentiated tissues including, but not limited to the following: roots, stems, shoots, leaves, pollen, seeds, tumor tissue and various forms of cells and culture (e.g., single cells, protoplasts, embryos and callus tissue). The plant tissue may be in plant or in a plant organ, tissue or cell culture.

The term "plant organ" refers to plant tissue or group of tissues that constitute a morphologically and functionally distinct part of a plant. The term "genome" refers to the following: (1) the entire complement of genetic material (genes and non-coding sequences) is present in each cell of an organism, or virus or organelle; (2) a complete set of chromosomes inherited as a (haploid) unit from one parent.

Thus, this invention also concerns a method for transforming a cell, comprising transforming a cell with the recombinant construct of the invention and selecting those cells transformed with the recombinant construct of Claim 5.

Also of interest is a method for producing a transformed plant comprising transforming a plant cell with the polynucleotide of the instant invention and regenerating a plant from the transformed plant cell.

Methods for transforming dicots (primarily by use of *Agrobacterium tumefaciens*) and obtaining transgenic plants have been published, among others, for: cotton (U.S. Pat. Nos. 5,004,863; 5,159,135); soybean (U.S. Pat. Nos. 5,569,834; 5,416,011); *Brassica* (U.S. Pat. No. 5,463,174); peanut (Cheng et al. *Plant Cell Rep.* 15:653-657 (1996); McKently et al. *Plant Cell Rep.* 14:699-703 (1995)); papaya (Ling, K. et al. *Bio/technology* 9:752-758 (1991)); and pea (Grant et al. *Plant Cell Rep.* 15:254-258 (1995)). For a review of other commonly used methods of plant transformation see Newell, C. A. (*Mol. Biotechnol.* 16:53-65 (2000)). One of these methods of transformation uses *Agrobacterium rhizogenes* (Tepfler, M. and Casse-Delbart, F. *Microbiol. Sci.* 4:24-28 (1987)). Transformation of soybeans using direct delivery of DNA has been published using PEG fusion (WO 92/17598), electroporation (Chowrira, G. M. et al. *Mol. Biotechnol.* 3:17-23 (1995); Christou, P. et al. *Proc. Natl. Acad. Sci. U.S.A.* 84:3962-3966 (1987)), microinjection, or particle bombardment (McCabe, D. E. et. al. *Bio/Technology* 6:923 (1988); Christou et al. *Plant Physiol.* 87:671-674 (1988)).

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, In: Methods for Plant Molecular Biology, (Eds.), Academic: San Diego, Calif. (1988)). This regeneration and growth process typically includes the steps of selection of transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones. See, for example: Sambrook et al., Molecular Cloning: A Laboratory Manual, Cold Spring Harbor: NY (1989); Maliga et al., Methods in Plant Molecular Biology, Cold Spring Harbor: NY (1995); Birren et al., Genome Analysis: Detecting Genes, Vol. 1, Cold Spring Harbor: NY (1998); Birren et al., Genome Analysis: Analyzing DNA, Vol. 2, Cold Spring Harbor: NY (1998); Plant Molecular Biology: A Laboratory Manual, eds. Clark, Springer: NY (1997).

Examples of oilseed plants include, but are not limited to, soybean, *Brassica* species, sunflower, maize, cotton, flax and safflower.

Examples of polyunsaturated fatty acids having at least twenty carbon atoms and five or more carbon-carbon double bonds include, but are not limited to, omega-3 fatty acids such as EPA, DPA and DHA. Seeds obtained from such plants are also within the scope of this invention as well as oil obtained from such seeds.

In one embodiment this invention concerns an oilseed plant comprising: a) a first recombinant DNA construct comprising an isolated polynucleotide encoding a delta-9 elongase polypeptide, operably linked to at least one regulatory sequence; and b) at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-9 desaturase, a delta-12 desaturase, a delta-15 desaturase, and a delta-17 desaturase, a $C_{18/20}$ elongase and a $C_{20/22}$ elongase.

Such desaturases are discussed, for example, in U.S. Pat. Nos. 6,075,183, 5,968,809, 6,136,574, 5,972,664, 6,051,754, 6,410,288 and WO 98/46763, WO 98/46764, WO 00/12720 and WO 00/40705.

The choice of combination of cassettes used depends in part on the PUFA profile and/or desaturase/elongase profile of the oilseed plant cells to be transformed and the long-chain PUFA which is to be expressed.

In another aspect, this invention concerns a method for making long-chain polyunsaturated fatty acids in a plant cell comprising:

(a) transforming a cell with the recombinant construct of the invention; and (b) selecting those transformed cells that make long-chain polyunsaturated fatty acids.

In still another aspect, this invention concerns a method for producing at least one polyunsaturated fatty acid in a soybean cell comprising:

(a) transforming a soybean cell with a first recombinant DNA construct comprising an isolated polynucleotide encoding a delta-9 elongase polypeptide, operably linked to at least one regulatory sequence and at least one additional recombinant DNA construct comprising an isolated polynucleotide, operably linked to at least one regulatory sequence, encoding a polypeptide selected from the group consisting of a delta-4 desaturase, a delta-5 desaturase, a delta-6 desaturase, a delta-8 desaturase, a delta-9 desaturase, a delta-12 desaturase, a delta-15 desaturase, and a delta-17 desaturase, a $C_{18/20}$ elongase and a $C_{20/22}$ elongase;

(b) regenerating a soybean plant from the transformed cell of step (a); and (c) selecting those seeds obtained from the plants of step (b) having an altered level of polyunsaturated fatty acids when compared to the level in seeds obtained from a nontransformed soybean plant.

Methods of isolating seed oils are well known in the art: (Young et al., Processing of Fats and Oils, In *The Lipid Handbook*, Gunstone et al., eds., Chapter 5 pp 253-257; Chapman & Hall: London (1994)). For example, soybean oil is produced using a series of steps involving the extraction and purification of an edible oil product from the oil-bearing seed. Soybean oils and soybean byproducts are produced using the generalized steps shown in Table 3.

TABLE 3

Generalized Steps for Soybean Oil and Byproduct Production

| Process Step | Process | Impurities Removed and/or By-Products Obtained |
|---|---|---|
| #1 | soybean seed | |
| #2 | oil extraction | meal |
| #3 | degumming | lecithin |
| #4 | alkali or physical refining | gums, free fatty acids, pigments |
| #5 | water washing | soap |
| #6 | bleaching | color, soap, metal |
| #7 | (hydrogenation) | |
| #8 | (winterization) | stearine |
| #9 | deodorization | free fatty acids, tocopherols, sterols, volatiles |
| #10 | oil products | |

More specifically, soybean seeds are cleaned, tempered, dehulled and flaked, thereby increasing the efficiency of oil extraction. Oil extraction is usually accomplished by solvent (e.g., hexane) extraction but can also be achieved by a combination of physical pressure and/or solvent extraction. The resulting oil is called crude oil. The crude oil may be degummed by hydrating phospholipids and other polar and neutral lipid complexes that facilitate their separation from the nonhydrating, triglyceride fraction (soybean oil). The resulting lecithin gums may be further processed to make commercially important lecithin products used in a variety of food and industrial products as emulsification and release (i.e., antisticking) agents. Degummed oil may be further refined for the removal of impurities (primarily free fatty acids, pigments and residual gums). Refining is accomplished by the addition of a caustic agent that reacts with free fatty acid to form soap and hydrates phosphatides and proteins in the crude oil. Water is used to wash out traces of soap formed during refining. The soapstock byproduct may be used directly in animal feeds or acidulated to recover the free fatty acids. Color is removed through adsorption with a bleaching earth that removes most of the chlorophyll and carotenoid compounds. The refined oil can be hydrogenated, thereby resulting in fats with various melting properties and textures. Winterization (fractionation) may be used to remove stearine from the hydrogenated oil through crystallization under carefully controlled cooling conditions. Deodorization (principally via steam distillation under vacuum) is the last step and is designed to remove compounds which impart odor or flavor to the oil. Other valuable byproducts such as tocopherols and sterols may be removed during the deodorization process. Deodorized distillate containing these byproducts may be sold for production of natural vitamin E and other high-value pharmaceutical products. Refined, bleached, (hydrogenated, fractionated) and deodorized oils and fats may be packaged and sold directly or further processed into more specialized products. A more detailed reference to soybean seed processing, soybean oil production and byproduct utilization can be found in Erickson, Practical Handbook of Soybean Processing and Utilization, The American Oil Chemists' Society and United Soybean Board (1995).

Soybean oil is liquid at room temperature because it is relatively low in saturated fatty acids when compared with oils such as coconut, palm, palm kernel and cocoa butter. Many processed fats (including spreads, confectionary fats, hard butters, margarines, baking shortenings, etc.) require varying degrees of solidity at room temperature and can only be produced from soybean oil through alteration of its physical properties. This is most commonly achieved through catalytic hydrogenation.

Hydrogenation is a chemical reaction in which hydrogen is added to the unsaturated fatty acid double bonds with the aid of a catalyst such as nickel. High oleic soybean oil contains unsaturated oleic, LA and linolenic fatty acids and each of these can be hydrogenated. Hydrogenation has two primary effects. First, the oxidative stability of the oil is increased as a result of the reduction of the unsaturated fatty acid content. Second, the physical properties of the oil are changed because the fatty acid modifications increase the melting point resulting in a semi-liquid or solid fat at room temperature.

There are many variables which affect the hydrogenation reaction, which in turn alter the composition of the final product. Operating conditions including pressure, temperature, catalyst type and concentration, agitation and reactor design are among the more important parameters that can be controlled. Selective hydrogenation conditions can be used to hydrogenate the more unsaturated fatty acids in preference to the less unsaturated ones. Very light or brush hydrogenation is often employed to increase stability of liquid oils. Further hydrogenation converts a liquid oil to a physically solid fat. The degree of hydrogenation depends on the desired performance and melting characteristics designed for the particular end product. Liquid shortenings (used in the manufacture of baking products, solid fats and shortenings used for commercial frying and roasting operations) and base stocks for margarine manufacture are among the myriad of possible oil and fat products achieved through hydrogenation. A more detailed description of hydrogenation and hydrogenated products can be found in Patterson, H. B. W., Hydrogenation of Fats and Oils: Theory and Practice. The American Oil Chemists' Society (1994).

Hydrogenated oils have also become controversial due to the presence of trans-fatty acid isomers that result from the hydrogenation process. Ingestion of large amounts of trans-isomers has been linked with detrimental health effects including increased ratios of low density to high density lipoproteins in the blood plasma and increased risk of coronary heart disease.

Compared to other vegetable oils, the oils of the invention are believed to function similarly to other oils in food applications from a physical standpoint. Partially hydrogenated oils, such as soybean oil, are widely used as ingredients for soft spreads, margarine and shortenings for baking and frying.

In general, lipid accumulation in oleaginous microorganisms is triggered in response to the overall carbon to nitrogen ratio present in the growth medium. This process, leading to the de novo synthesis of free palmitate (16:0) in oleaginous microorganisms, is described in detail in WO 2004/101757. Palmitate is the precursor of longer-chain saturated and unsaturated fatty acid derivates, which are formed through the action of elongases and desaturases. For example, palmitate is converted to its unsaturated derivative (palmitoleic acid (16:1)) by the action of a delta-9 desaturase. Similarly, palmitate is elongated by a $C_{16/18}$ fatty acid elongase to form stearic acid (18:0), which can be converted to its unsaturated derivative by a delta-9 desaturase to thereby yield oleic acid (18:1).

Triacylglycerols (the primary storage unit for fatty acids) are formed by the esterification of two molecules of acyl-CoA to glycerol-3-phosphate to yield 1,2-diacylglycerol phosphate (commonly identified as phosphatidic acid). The phosphate is then removed, by phosphatidic acid phosphatase, to yield 1,2-diacylglycerol. Triacylglycerol is formed upon the addition of a third fatty acid by the action of a diacylglycerol-acyl transferase.

Many microorganisms, including algae, bacteria, molds and yeasts, can synthesize PUFAs and omega fatty acids in the ordinary course of cellular metabolism. Particularly well-studied are fungi including *Schizochytrium aggregatm*, species of the genus *Thraustochytrium* and *Morteriella alpina*. Additionally, many dinoflagellates (Dinophyceaae) naturally produce high concentrations of PUFAs. As such, a variety of genes involved in oil production have been identified through genetic means and the DNA sequences of some of these genes are publicly available. See, for example, AY131238, Y055118, AY055117, AF296076, AF007561, L11421, NM_031344, AF465283, AF465281, AF110510, AF465282, AF419296, AB052086, AJ250735, AF126799, AF126798 (delta-6 desaturases); AF199596, AF226273, AF320509, AB072976, AF489588, AJ510244, AF419297, AF07879, AF067654, AB022097 (delta-5 desaturases); AAG36933, AF110509, AB020033, AAL13300, AF417244, AF161219, AY332747, AAG36933, AF110509, X86736, AF240777, AB007640, AB075526, AP002063 (delta-12 desaturases); NP_441622, BAA18302, BAA02924, AAL36934 (delta-15 desaturases); AF338466, AF438199, E11368, E11367, D83185, U90417, AF085500, AY504633, NM_069854, AF230693 (delta-9 desaturases); AF390174 (delta-9 elongase); AF139720 and CQ831420 (delta-8 desaturase); and AX464731, NM_119617, NM_134255, NM_134383, NM_134382, NM_068396, NM_068392, NM_070713, NM_068746, NM_064685 (elongases).

Additionally, the patent literature provides many additional DNA sequences of genes (and/or details concerning several of the genes above and their methods of isolation) involved in PUFA production (e.g., WO 02/077213 (delta-9 elongases); WO 00/34439, WO 04/057001 and U.S. Pat. No. 6,825,017 (delta-8 desaturases); U.S. Pat. No. 5,968,809 (delta-6 desaturases); U.S. Pat. No. 5,972,664 and U.S. Pat. No. 6,075,183 (delta-5 desaturases); WO 94/11516, U.S. Pat. No. 5,443,974, WO 03/099216 and WO 05/047485 (delta-12 desaturases); WO 93/11245 (delta-15 desaturases); WO 91/13972 and U.S. Pat. No. 5,057,419 (delta-9 desaturases); U.S. Patent Application Publication No. 2003/0196217 A1 (delta-17 desaturase); and WO 00/12720 and WO 2002/077213, U.S. Pat. Nos. 6,403,349, 6,677,145, and U.S. Patent Application Publication No. 2004/0111763 ($C_{14/16}$, $C_{16/18}$ and $C_{18/20}$ elongases)). Each of these patents and applications are herein incorporated by reference in their entirety.

As will be obvious to one skilled in the art, the particular functionalities required to be introduced into a microbial host organism for production of a particular PUFA final product will depend on the host cell (and its native PUFA profile and/or desaturase/elongase profile), the availability of substrate and the desired end product(s). LA, GLA, EDA, DGLA, AA, ALA, STA, ETrA, ETA, EPA, DPA and DHA may all be produced in oleaginous yeasts, by introducing various combinations of the following PUFA enzyme functionalities: a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and/or a $C_{20/22}$ elongase. One skilled in the art will be able to identify various candidate genes encoding each of the above enzymes, according to publicly available literature (e.g., GenBank), the patent literature, and experimental analysis of microorganisms having the ability to produce PUFAs. The sequences may be derived from any source, e.g., isolated from a natural source (from bacteria, algae, fungi, plants, animals, etc.), produced via a semi-synthetic route or synthesized de novo. In some embodiments, manipulation of genes endogenous to the host is preferred; for other purposes, it is necessary to introduce heterologous genes.

Although the particular source of the desaturase and elongase genes introduced into the host is not critical to the invention, considerations for choosing a specific polypeptide having desaturase or elongase activity include (1) the substrate specificity of the polypeptide, (2) whether the polypeptide or a component thereof is a rate-limiting enzyme, (3) whether the desaturase or elongase is essential for synthesis of a desired PUFA, and/or (4) co-factors required by the polypeptide. The expressed polypeptide preferably has parameters compatible with the biochemical environment of its location in the host cell. For example, the polypeptide may have to compete for substrate with other enzymes in the host cell. Analyses of the $K_M$ and specific activity of the polypeptide are therefore considered in determining the suitability of a given polypeptide for modifying PUFA production in a given host cell. The polypeptide used in a particular host cell is one that can function under the biochemical conditions present in the intended host cell but otherwise can be any polypeptide having desaturase or elongase activity capable of modifying the desired PUFA.

In some cases, the host organism in which it is desirable to produce PUFAs will possess endogenous genes encoding some PUFA biosynthetic pathway enzymes. For example, oleaginous yeast can typically produce 18:2 fatty acids (and some have the additional capability of synthesizing 18:3 fatty acids); thus, oleaginous yeast typically possess native delta-12 desaturase activity and may also have delta-15 desaturases. In some embodiments, therefore, expression of the native desaturase enzyme is preferred over a heterologous (or "foreign") enzyme since (1) the native enzyme is optimized for interaction with other enzymes and proteins within the cell, and (2) heterologous genes are unlikely to share the same codon preference in the host organism. Additionally, advantages are incurred when the sequence of the native gene is known, as it permits facile disruption of the endogenous gene by targeted disruption.

In many instances, however, the appropriate desaturases and elongases are not present in the host organism of choice to enable production of the desired PUFA products. Thus, it is necessary to introduce heterologous genes. In one embodiment of the present invention, work was conducted toward the goal of the development of an oleaginous yeast that accumulates oils enriched in long-chain omega-3 and/or omega-6 fatty acids via expression of a delta-9 elongase/delta-8 desaturase pathway, to enable production of EDA, DGLA, ARA, ALA, ETrA, ETA, EPA, DPA and/or DHA.

In order to express genes encoding the delta-9 elongase/delta-8 desaturase pathway for the biosynthesis of long-chain PUFAs (e.g., AA and EPA) in these organisms, it was therefore necessary to (1) identify a suitable delta-9 elongase and delta-8 desaturase that functioned relatively efficiently in oleaginous yeast based on substrate-feeding trials, and, (2) subject the delta-9 elongase and delta-9 desaturase gene to codon-optimization techniques (infra) to further enhance the expression of the heterologous enzymes in the alternate oleaginous yeast host, to thereby enable maximal production of omega-3 and/or omega-6 fatty acids.

It will be obvious to one of skill in the art that heterologous genes will be expressed with variable efficiencies in an alternate host. Thus, omega-3 and/or omega-6 PUFA production may be optimized by selection of a particular desaturase or elongase whose level of expression in a heterologous host is preferred relative to the expression of an alternate desaturase or elongase in the host organism of interest. Furthermore, it may be desirable to modify the expression of particular PUFA biosynthetic pathway enzymes to achieve optimal conversion efficiency of each, according to the specific PUFA product composition of interest. A variety of genetic engineering techniques are available to optimize expression of a particular enzyme. Two such techniques include codon optimization and gene mutation, as described below. Genes produced by, for example, either of these two methods, having desaturase and/or elongase activity(s) would be useful in the invention herein for synthesis of omega-3 and/or omega-6 PUFAs.

As will be appreciated by one skilled in the art, it is frequently useful to modify a portion of the codons encoding a particular polypeptide that is to be expressed in a foreign host, such that the modified polypeptide uses codons that are preferred by the alternate host. Use of host-preferred codons can substantially enhance the expression of the foreign gene encoding the polypeptide.

In general, host-preferred codons can be determined within a particular host species of interest by examining codon usage in proteins (preferably those expressed in the largest amount) and determining which codons are used with highest frequency. Then, the coding sequence for a polypeptide of interest having desaturase or elongase activity can be synthesized in whole or in part using the codons preferred in the host species. All (or portions) of the DNA also can be synthesized to remove any destabilizing sequences or regions of secondary structure that would be present in the transcribed mRNA. All (or portions) of the DNA also can be synthesized to alter the base composition to one more preferable in the desired host cell.

In the present invention, it is desirable to modify a portion of the codons encoding the polypeptide having delta-9 elongase activity, to enhance the expression of the gene in a host organism including, but not limited to, a plant, plant parts and/or oleaginous yeast *Yarrowia lipolytica*. The nucleic acid sequence of the native gene (i.e., the *Euglena gracilis* delta-9 elongase defined herein as SEQ ID NOs:3 and 4) is modified to employ host-preferred codons. This wildtype elongase has 258 amino acids (SEQ ID NO:5); in the codon-optimized gene (SEQ ID NO:90), 117 bp of the 777 bp coding region (15.1%) and 106 codons) are codon-optimized (41.1%) and the translation initiation site is modified.

The skilled artisan will appreciate that modulation of the *Euglena gracilis* delta-9 elongase as well as numerous other heterologous delta-9 elongases from variable sources can be codon-optimized to improve their expression in an oleaginous yeast host (e.g, see Example 4 herein, wherein a synthetic codon-optimized delta-9 elongase derived from *Isochrysis galbana* was created for expression in *Yarrowia lipolytica*). The present invention comprises the complete sequence of the synthetic codon-optimized gene as reported in the accompanying Sequence Listing (SEQ ID NO:90), the complement of those complete sequences, and substantial portions of those sequences. Furthermore, the codon-optimization method described in WO 2004/101753 and described herein for optimization of the *Euglena gracilis* delta-9 elongase is equally applicable to other genes in the omega-3/omega-6 fatty acid biosynthetic pathway.

Methods for synthesizing sequences and bringing sequences together are well established in the literature. For example, in vitro mutagenesis and selection, site-directed mutagenesis, error prone PCR (Melnikov et al., *Nucleic Acids Research,* 27(4):1056-1062 (February 1999)), "gene shuffling" or other means can be employed to obtain mutations of naturally occurring desaturase or elongase genes (wherein such mutations may include deletions, insertions and point mutations, or combinations thereof). This would permit production of a polypeptide having desaturase or elongase activity, respectively, in vivo with more desirable physical and kinetic parameters for function in the host cell such as a longer half-life or a higher rate of production of a desired PUFA. Or, if desired, the regions of a polypeptide of interest (i.e., a desaturase or an elongase) important for enzymatic activity can be determined through routine mutagenesis, expression of the resulting mutant polypeptides and determination of their activities. An overview of these techniques are described in WO 2004/101757. All such mutant proteins and nucleotide sequences encoding them that are derived from the codon-optimized gene described herein are within the scope of the present invention.

Microbial production of omega-3 and/or omega-6 fatty acids has several advantages. For example, (1) many microbes are known with greatly simplified oil compositions compared with those of higher organisms, making purification of desired components easier, (2) microbial production is not subject to fluctuations caused by external variables, such as weather and food supply, (3) microbially produced oil is substantially free of contamination by environmental pollutants, (4) microbes can provide PUFAs in particular forms which may have specific uses, and (5) microbial oil production can be manipulated by controlling culture conditions, notably by providing particular substrates for microbially expressed enzymes, or by addition of compounds/genetic engineering to suppress undesired biochemical pathways.

In addition to these advantages, production of omega-3 and/or omega-6 fatty acids from recombinant microbes provides the ability to alter the naturally occurring microbial fatty acid profile by providing new biosynthetic pathways in the host or by suppressing undesired pathways, thereby increasing levels of desired PUFAs, or conjugated forms thereof, and decreasing levels of undesired PUFAs. For example, it is possible to modify the ratio of omega-3 to omega-6 fatty acids so produced, produce either omega-3 or omega-6 fatty acids exclusively while eliminating production of the alternate omega fatty acid, or engineer production of a specific PUFA without significant accumulation of other PUFA downstream or upstream products (e.g., enable biosynthesis of AA, EPA and/or DHA via the delta-9 elongase/delta-8 desaturase pathway, thereby avoiding synthesis of GLA and/or STA).

The genes and gene products described herein may be produced in heterologous microbial host cells, particularly in the cells of oleaginous yeasts (e.g., *Yarrowia lipolytica*). Expression in recombinant microbial hosts may be useful for the production of various PUFA pathway intermediates, or for the modulation of PUFA pathways already existing in the host for the synthesis of new products heretofore not possible using the host.

Microbial expression systems and expression vectors containing regulatory sequences that direct high level expression of foreign proteins are well known to those skilled in the art. Any of these could be used to construct chimeric genes for production of any of the gene products of the preferred desaturase and/or elongase sequences. These chimeric genes could then be introduced into appropriate microorganisms via transformation to provide high-level expression of the encoded enzymes.

Accordingly, it is expected that introduction of chimeric genes encoding a PUFA biosynthetic pathway, under the control of the appropriate promoters will result in increased production of omega-3 and/or omega-6 fatty acids. It is contemplated that it will be useful to express various combinations of these PUFA desaturase and elongase genes together in a host microorganism. It will be obvious to one skilled in the art that the particular genes included within a particular expression cassette(s) will depend on the host cell, its ability to synthesize PUFAs using native desaturases and elongases, the availability of substrate and the desired end product(s). For example, it may be desirable for an expression cassette to be constructed comprising genes encoding one or more of the following enzymatic activities: a delta-4 desaturase, a delta-5 desaturase, a delta-6 desaturase, a delta-8 desaturase, a delta-12 desaturase, a delta-15 desaturase, a delta-17 desaturase, a delta-9 desaturase, a delta-9 elongase, a $C_{14/16}$ elongase, a $C_{16/18}$ elongase, a $C_{18/20}$ elongase and/or a $C_{20/22}$ elongase. As such, the present invention encompasses a method of producing PUFAs comprising exposing a fatty acid substrate to the PUFA enzyme(s) described herein, such that the substrate is converted to the desired fatty acid product. Thus, each PUFA gene and corresponding enzyme product described herein (e.g., a wildtype, codon-optimized, synthetic and/or mutant enzyme having appropriate desaturase or elongase activity) can be used directly or indirectly for the production of PUFAs. Direct production of PUFAs occurs wherein the fatty acid substrate is converted directly into the desired fatty acid product without any intermediate steps or pathway intermediates. For example, production of AA would occur in a host cell which produces or which is provided DGLA, by adding or introducing into said cell an expression cassette that provides delta-5 desaturase activity. Similarly, expression of the delta-9 elongase of the invention permits the direct synthesis of EDA and ETrA (when provided LA and ALA, respectively, as substrate). Thus, for example, the present invention may encompass a method of producing either EDA or ETrA, respectively, comprising:

a) providing a host organism including, but not limited to, an oleaginous yeast comprising: (i) a gene encoding a delta-9 elongase polypeptide as set forth in SEQ ID NO:5 or SEQ ID NO:127; and
   (ii) a source of elongase substrate consisting of either LA or ALA, respectively; and,
b) growing the yeast of step (a) in the presence of a suitable fermentable carbon source wherein the gene encoding a delta-9 elongase polypeptide is expressed and LA is converted to EDA or ALA is converted to ETrA, respectively; and,
c) optionally recovering the EDA or ETrA, respectively, of step (b).

In some preferred embodiments, the nucleotide sequence of a gene encoding a delta-9 elongase polypeptide is set forth in SEQ ID NO:90 wherein at least 106 codons have been optimized for expression in *Yarrowia*.

In contrast, multiple genes encoding the PUFA biosynthetic pathway may be used in combination, such that a series of reactions occur to produce a desired PUFA. For example, expression cassette(s) encoding delta-9 elongase, delta-8 desaturase, delta-5 desaturase and delta-17 desaturase activity would enable a host cell that naturally produces LA, to instead produce ARA (such that LA is converted to EDA by delta-9 elongase; EDA may then be converted to DGLA by a delta-8 desaturase; DGLA is then converted to ARA by a delta-5 desaturase). In a related manner, expression of the delta-9 elongase of the invention enables the indirection production of ETA, EPA, DPA and/or DHA as down-stream PUFAs, if subsequent desaturase and elongation reactions are catalyzed. In a preferred embodiment, wherein the host cell is an oleaginous yeast, expression cassettes encoding each of the enzymes necessary for PUFA biosynthesis will need to be introduced into the organism, since naturally produced PUFAs in these organisms are limited to 18:2 fatty acids (i.e., LA), and less commonly, 18:3 fatty acids (i.e., ALA). Alternatively, substrate feeding may be required.

Vectors or DNA cassettes useful for the transformation of suitable microbial host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation (e.g., a promoter) and a region 3' of the DNA fragment that controls transcriptional termination (i.e., a terminator). It is most preferred when both control regions are derived from genes from the transformed host cell, although it is to be understood that such control regions need not be derived from the genes native to the specific species chosen as a production host.

Initiation control regions or promoters which are useful to drive expression of desaturase and/or elongase ORFs in the desired microbial host cell are numerous and familiar to those skilled in the art. Virtually any promoter capable of directing expression of these genes in the selected host cell is suitable for the present invention. Expression in a microbial host cell can be accomplished in a transient or stable fashion. Transient expression can be accomplished by inducing the activity of a regulatable promoter operably linked to the gene of interest, alternatively, stable expression can be achieved by the use of a constitutive promoter operably linked to the gene of interest.

As an example, when the host cell is yeast, transcriptional and translational regions functional in yeast cells are provided, particularly from the host species. The transcriptional initiation regulatory regions can be obtained, for example, from (1) genes in the glycolytic pathway, such as alcohol dehydrogenase, glyceraldehyde-3-phosphate-dehydrogenase (WO 2005/003310), phosphoglycerate mutase (WO 2005/003310), fructose-bisphosphate aldolase (WO 2005/049805), phosphoglucose-isomerase, phosphoglycerate kinase, glycerol-3-phosphate O-acyltransferase (see U.S. patent application Ser. No. 11/225,354), etc.; or (2) regulatable genes such as acid phosphatase, lactase, metallothionein, glucoamylase, the translation elongation factor EF1-α (TEF) protein (U.S. Pat. No. 6,265,185), ribosomal protein S7 (U.S. Pat. No. 6,265,185)), ammonium transporter proteins (U.S. patent application Ser. No. 11/185,301), export proteins, etc. Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, as demonstrated in the invention herein in *Yarrowia lipolytica*, one can determine the consensus translation initiation sequence in the host and engineer this sequence into heterologous genes for their optimal expression in the host of interest.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, the termination region is derived from a yeast gene, particularly *Saccharomyces, Schizosaccharomyces, Candida, Yarrowia* or *Kluyveromyces*. The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation and secretion from the host cell. More specifically, some of the molecular features that have been manipulated to control gene expression include: (1) the nature of the relevant transcriptional promoter and terminator sequences; (2) the number of copies of the cloned gene and whether the gene is plasmid-borne or integrated into the genome of the host cell; (3) the final cellular location of the synthesized foreign protein; (4) the efficiency of translation in the host organism; (5) the intrinsic stability of the cloned gene protein within the host cell; and (6) the codon usage within the cloned gene, such that its frequency approaches the frequency of preferred codon usage of the host cell. Each of these types of modifications are encompassed in the present invention, as means to further optimize expression of the PUFA biosynthetic pathway enzymes.

Once the DNA encoding a desaturase or elongase polypeptide suitable for expression in an oleaginous yeast has been obtained, it is placed in a plasmid vector capable of autonomous replication in a host cell; or, it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

A method of expressing genes in *Yarrowia lipolytica* is by integration of linear DNA into the genome of the host; and, integration into multiple locations within the genome can be particularly useful when high level expression of genes are desired. Toward this end, it is desirable to identify a sequence within the genome that is present in multiple copies.

Schmid-Berger et al. (*J. Bact.* 176(9):2477-2482 (1994)) discovered the first retrotransposon-like element Ylt1 in *Yarrowia lipolytica*. This retrotransposon is characterized by the presence of long terminal repeats (LTRs; each approximately 700 bp in length) called zeta regions. Ylt1 and solo zeta elements were present in a dispersed manner within the genome in at least 35 copies/genome and 50-60 copies/genome, respectively; both elements were determined to function as sites of homologous recombination. Further, work by Juretzek et al. (*Yeast* 18:97-113 (2001)) demonstrated that gene expression could be dramatically increased by targeting plasmids into the repetitive regions of the yeast genome (using linear DNA with LTR zeta regions at both ends), as compared to the expression obtained using low-copy plasmid transformants. Thus, zeta-directed integration can be ideal as a means to ensure multiple integration of plasmid DNA into *Yarrowia lipolytica*, thereby permitting high-level gene expression. Unfortunately, however, not all strains of *Yarrowia lipolytica* possess zeta regions (e.g., the strain identified as ATCC Accession No. #20362). When the strain lacks such regions, it is also possible to integrate plasmid DNA comprising expression cassettes into alternate loci to reach the desired copy number for the expression cassette. For example, preferred alternate loci include: the Ura3 locus (GenBank Accession No. AJ306421), the Leu2 gene locus (GenBank Accession No. AF260230), the Lys5 gene (GenBank Accession No. M34929), the Aco2 gene locus (GenBank Accession No. AJ001300), the Pox3 gene locus (Pox3: GenBank Accession No. XP_503244; or, Aco3: GenBank Accession No. AJ001301), the delta-12 desaturase gene locus, the Lip1 gene locus (GenBank Accession No. Z50020) and/or the Lip2 gene locus (GenBank Accession No. AJ012632).

Advantageously, the Ura3 gene can be used repeatedly in combination with 5-fluoroorotic acid (5-fluorouracil-6-carboxylic acid monohydrate; "5-FOA") selection (infra), to readily permit genetic modifications to be integrated into the *Yarrowia* genome in a facile manner.

Where two or more genes are expressed from separate replicating vectors, it is desirable that each vector has a different means of selection and should lack homology to the other constructs to maintain stable expression and prevent reassortment of elements among constructs. Judicious choice of regulatory regions, selection means and method of propagation of the introduced construct can be experimentally determined so that all introduced genes are expressed at the necessary levels to provide for synthesis of the desired products.

Constructs comprising the gene of interest may be introduced into a host cell by any standard technique. These techniques include transformation (e.g., lithium acetate transformation [*Methods in Enzymology,* 194:186-187 (1991)]), protoplast fusion, bolistic impact, electroporation, microinjection, or any other method that introduces the gene of interest into the host cell. More specific teachings applicable for oleaginous yeasts (i.e., *Yarrowia lipolytica*) include U.S. Pat. No. 4,880,741 and U.S. Pat. No. 5,071,764 and Chen, D. C. et al. (*Appl Microbiol Biotechnol.* 48(2):232-235 (1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified or is present on an extrachromosomal element having multiple copy numbers.

The transformed host cell can be identified by various selection techniques, as described in WO 04/101757. Preferred selection methods for use herein are resistance to kanamycin, hygromycin and the amino glycoside G418, as well as ability to grow on media lacking uracil, leucine, lysine, tryptophan or histidine. In alternate embodiments, 5-FOA is used for selection of yeast Ura-mutants. The compound is toxic to yeast cells that possess a functioning URA3 gene encoding orotidine 5'-monophosphate decarboxylase (OMP decarboxylase); thus, based on this toxicity, 5-FOA is especially useful for the selection and identification of $Ura^-$ mutant yeast strains (Bartel, P. L. and Fields, S., Yeast 2-Hybrid System, Oxford University: New York, v. 7, pp 109-147, 1997). More specifically, one can first knockout the native Ura3 gene to produce a strain having a Ura− phenotype, wherein selection occurs based on 5-FOA resistance. Then, a cluster of multiple chimeric genes and a new Ura3 gene could be integrated into a different locus of the *Yarrowia* genome to thereby produce a new strain having a Ura+ phenotype. Subsequent integration would produce a new Ura3− strain (again identified using 5-FOA selection), when the introduced Ura3 gene is knocked out. Thus, the Ura3 gene (in combination with 5-FOA selection) can be used as a selection marker in multiple rounds of transformation.

Following transformation, substrates suitable for the recombinantly expressed desaturases and/or elongases (and optionally other PUFA enzymes that are expressed within the host cell) may be produced by the host either naturally or transgenically, or they may be provided exogenously.

Methods for manipulating biochemical pathways are well known to those skilled in the art; and, it is expected that numerous manipulations will be possible to maximize omega-3 and/or omega-6 fatty acid biosynthesis in oleaginous yeasts, and particularly, in *Yarrowia lipolytica*. This may require metabolic engineering directly within the PUFA biosynthetic pathway or additional manipulation of pathways that contribute carbon to the PUFA biosynthetic pathway.

In the case of manipulations within the PUFA biosynthetic pathway, it may be desirable to increase the production of LA to enable increased production of omega-6 and/or omega-3 fatty acids. Introducing and/or amplifying genes encoding delta-9 and/or delta-12 desaturases may accomplish this.

To maximize production of omega-6 unsaturated fatty acids, it is well known to one skilled in the art that production is favored in a host microorganism that is substantially free of ALA. Thus, preferably, the host is selected or obtained by removing or inhibiting delta-15 or omega-3 type desaturase activity that permits conversion of LA to ALA. The endogenous desaturase activity can be reduced or eliminated by, for example, (1) providing a cassette for transcription of antisense sequences to the delta-15 desaturase transcription product, (2) disrupting the delta-15 desaturase gene through insertion, substitution and/or deletion of all or part of the target gene; or (3) using a host cell which naturally has [or has been mutated to have] low or no delta-15 desaturase activity. Inhibition of undesired desaturase pathways can also be accomplished through the use of specific desaturase inhibitors such as those described in U.S. Pat. No. 4,778,630.

Alternatively, it may be desirable to maximize production of omega-3 fatty acids (and minimize synthesis of omega-6 fatty acids). Thus, one could utilize a host microorganism wherein the delta-12 desaturase activity that permits conversion of oleic acid to LA is removed or inhibited, using any of the means described above (see also e.g., WO 2004/104167, herein incorporated entirely by reference). Subsequently, appropriate expression cassettes would be introduced into the host, along with appropriate substrates (e.g., ALA) for conversion to omega-3 fatty acid derivatives of ALA (e.g., STA, ETrA, ETA, EPA, DPA, DHA).

Beyond the immediate PUFA biosynthetic pathway, it is expected that manipulation of several other enzymatic pathways leading to the biosynthesis of precursor fatty acids may contribute to the overall net biosynthesis of specific PUFAs. Identification and manipulation of these related pathways will be useful in the future.

Additional copies of desaturase and elongase genes may be introduced into the host to increase the output of omega-3 and/or omega-6 fatty acid biosynthetic pathways. Expression of the desaturase or elongase genes also can be increased at the transcriptional level through the use of a stronger promoter (either regulated or constitutive) to cause increased expression, by removing/deleting destabilizing sequences from either the mRNA or the encoded protein, or by adding stabilizing sequences to the mRNA (U.S. Pat. No. 4,910,141). Yet another approach to increase expression of the desaturase or elongase genes, as demonstrated in the instant invention, is to increase the translational efficiency of the encoded mRNAs by replacement of codons in the native gene with those for optimal gene expression in the selected host microorganism.

Conversely, biochemical pathways competing with the omega-3 and/or omega-6 fatty acid biosynthetic pathways for energy or carbon, or native PUFA biosynthetic pathway enzymes that interfere with production of a particular PUFA end-product, may be eliminated by gene disruption or down-regulated by other means (e.g., antisense mRNA). For gene disruption, a foreign DNA fragment (typically a selectable marker gene) is inserted into the structural gene to be disrupted in order to interrupt its coding sequence and thereby functionally inactivate the gene. Transformation of the disruption cassette into the host cell results in replacement of the functional native gene by homologous recombination with the non-functional disrupted gene (see, for example: Hamilton et al. *J. Bacteriol.* 171:4617-4622 (1989); Balbas et al. *Gene* 136:211-213 (1993); Gueldener et al. *Nucleic Acids Res.* 24:2519-2524 (1996); and Smith et al. *Methods Mol. Cell. Biol.* 5:270-277 (1996)).

Antisense technology is another method of down-regulating genes when the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA that encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down-regulating genes where the sequence is known, other less specific methodologies have been developed that are not sequence-based (e.g., mutagenesis via UV radiation/chemical agents or use of transposable elements/transposons; see WO 2004/101757).

Within the context of the present invention, it may be useful to modulate the expression of the fatty acid biosynthetic pathway by any one of the methods described above. For example, the present invention provides methods whereby genes encoding key enzymes in the biosynthetic pathways are introduced into oleaginous yeasts for the production of omega-3 and/or omega-6 fatty acids. It will be particularly useful to express these genes in oleaginous yeasts that do not naturally possess omega-3 and/or omega-6 fatty acid biosynthetic pathways and coordinate the expression of these genes, to maximize production of preferred PUFA products using various means for metabolic engineering of the host organism.

Microbial host cells for production of omega fatty acids may include microbial hosts that grow on a variety of feedstocks, including simple or complex carbohydrates, organic acids and alcohols, and/or hydrocarbons over a wide range of temperature and pH values.

Preferred microbial hosts, however, are oleaginous yeasts. These organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia, Candida, Rhodotorula, Rhodosporidium, Cryptococcus, Trichosporon* and *Lipomyces* . More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis* and *Yarrowia lipolytica* (formerly classified as *Candida lipolytica*).

Most preferred is the oleaginous yeast *Yarrowia lipolytica*; and, in a further embodiment, most preferred are the *Yarrowia lipolytica* strains designated as ATCC Accession Nos. #20362, ATCC #8862, ATCC #18944, ATCC #76982 and/or LGAM S(7)1 (Papanikolaou S., and Aggelis G., *Bioresour. Technol.* 82(1):43-9 (2002)).

The transformed microbial host cell is grown under conditions that optimize desaturase and elongase activities and produce the greatest and the most economical yield of the preferred PUFAs. In general, media conditions that may be optimized include the type and amount of carbon source, the type and amount of nitrogen source, the carbon-to-nitrogen ratio, the oxygen level, growth temperature, pH, length of the biomass production phase, length of the oil accumulation phase and the time of cell harvest. Microorganisms of interest, such as oleaginous yeast, are grown in complex media (e.g., yeast extract-peptone-dextrose broth (YPD)) or a defined minimal media that lacks a component necessary for growth and thereby forces selection of the desired expression cassettes (e.g., yeast nitrogen base (Difco Laboratories, Detroit, Mich.)).

Fermentation media in the present invention must contain a suitable carbon source. Suitable carbon sources may include, but are not limited to: monosaccharides (e.g., glucose, fructose), disaccharides (e.g., lactose, sucrose), oligosaccharides, polysaccharides (e.g., starch, cellulose or mixtures thereof), sugar alcohols (e.g., glycerol) or mixtures from renewable feedstocks (e.g., cheese whey permeate, cornsteep liquor, sugar beet molasses, barley malt). Additionally, carbon sources may include alkanes, fatty acids, esters of fatty acids, monoglycerides, diglycerides, triglycerides, phospholipids and various commercial sources of fatty acids including vegetable oils (e.g., soybean oil) and animal fats. Additionally, the carbon source may include one-carbon sources (e.g., carbon dioxide, methanol, formaldehyde, formate and carbon-containing amines) for which metabolic conversion into key biochemical intermediates has been demonstrated. Hence it is contemplated that the source of carbon utilized in the present invention may encompass a wide variety of carbon-containing sources and will only be limited by the choice of the host organism. Although all of the above mentioned carbon sources and mixtures thereof are expected to be suitable in the present invention, preferred carbon sources are sugars and/or fatty acids. Most preferred is glucose and/or fatty acids containing between 10-22 carbons.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the microorganism and promotion of the enzymatic pathways necessary for PUFA production. Particular attention is given to several metal ions (e.g., $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as yeast nitrogen base (Difco Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.0 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast. This approach is described in WO 2004/101757, as are various suitable fermentation process designs (i.e., batch, fed-batch and continuous) and considerations during growth.

The PUFAs may be found in the host microorganism as free fatty acids or in esterified forms such as acylglycerols, phospholipids, sulfolipids or glycolipids, and may be extracted from the host cell through a variety of means well-known in the art. One review of extraction techniques, quality analysis and acceptability standards for yeast lipids is that of Z. Jacobs (*Critical Reviews in Biotechnology* 12(5/6):463-

491 (1992)). A brief review of downstream processing is also available by A. Singh and O. Ward (*Adv. Appl. Microbiol.* 45:271-312 (1997)).

In general, means for the purification of PUFAs may include extraction with organic solvents, sonication, supercritical fluid extraction (e.g., using carbon dioxide), saponification and physical means such as presses, or combinations thereof. One is referred to the teachings of WO 2004/101757 for additional details.

The market place currently supports a large variety of food and feed products, incorporating omega-3 and/or omega-6 fatty acids (particularly ARA, EPA and DHA). It is contemplated that the plant oils of the invention and the yeast oils of the invention comprising long-chain PUFAs will function in food and feed products to impart the health benefits of current formulations. More specifically, oils of the invention containing omega-3 and/or omega-6 fatty acids will be suitable for use in a variety of food and feed products including, but not limited to food analogs, meat products, cereal products, baked foods, snack foods and dairy products.

Additionally the present oils may be used in formulations to impart health benefit in medical foods including medical nutritionals, dietary supplements, infant formula as well as pharmaceutical products. One of skill in the art of food processing and food formulation will understand how the amount and composition of the present oils may be added to the food or feed product. Such an amount will be referred to herein as an "effective" amount and will depend on the food or feed product, the diet that the product is intended to supplement or the medical condition that the medical food or medical nutritional is intended to correct or treat.

A "food analog" is a food-like product manufactured to resemble its food counterpart, whether meat, cheese, milk or the like, and is intended to have the appearance, taste, and texture of its counterpart. Thus, the term "food" as used herein also encompasses food analogs. Food analogs can be made use processes well known to those skilled in the art. U.S. Pat. Nos. 6,355,296 B1 and 6,187,367 B1 describe emulsified meat analogs and emulsified meat extenders. U.S. Pat. No. 5,206,050 B1 describes soy protein curd useful for cooked food analogs (also can be used as a process to form a curd useful to make food analogs). U.S. Pat. No. 4,284,656 to Hwa describes a soy protein curd useful for food analogs. U.S. Pat. No. 3,988,485 to Hibbert et al. describes a meat-like protein food formed from spun vegetable protein fibers. U.S. Pat. No. 3,950,564 to Puski et al. describes a process of making a soy based meat substitute and U.S. Pat. No. 3,925, 566 to Reinhart et al. describes a simulated meat product. For example, soy protein that has been processed to impart a structure, chunk or fiber for use as a food ingredient is called "textured soy protein" (TSP). TSPs are frequently made to resemble meat, seafood, or poultry in structure and appearance when hydrated.

Food analogs can be classified as imitation or substitutes depending on their functional and compositional characteristics. For example, an imitation cheese need only resemble the cheese it is designed to replace. However, a product can generally be called a substitute cheese only if it is nutritionally equivalent to the cheese it is replacing and meets the minimum compositional requirements for that cheese. Thus, substitute cheese will often have higher protein levels than imitation cheeses and be fortified with vitamins and minerals.

Milk analogs or nondairy food products include, but are not limited to, imitation milks and nondairy frozen desserts (e.g., those made from soybeans and/or soy protein products).

Meat products encompass a broad variety of products. In the United States "meat" includes "red meats" produced from cattle, hogs and sheep. In addition to the red meats there are poultry items which include chickens, turkeys, geese, guineas, ducks and the fish and shellfish. There is a wide assortment of seasoned and processed meat products: fresh, cured and fried, and cured and cooked. Sausages and hot dogs are examples of processed meat products. Thus, the term "meat products" as used herein includes, but is not limited to, processed meat products.

A cereal food product is a food product derived from the processing of a cereal grain. A cereal grain includes any plant from the grass family that yields an edible grain (seed). The most popular grains are barley, corn, millet, oats, quinoa, rice, rye, sorghum, triticale, wheat and wild rice. Examples of a cereal food product include, but are not limited to: whole grain, crushed grain, grits, flour, bran, germ, breakfast cereals, extruded foods, pastas, and the like.

A baked goods product comprises any of the cereal food products mentioned above and has been baked or processed in a manner comparable to baking (i.e., to dry or harden by subjecting to heat). Examples of a baked good product include, but are not limited to: bread, cakes, doughnuts, bars, pastas, bread crumbs, baked snacks, mini-biscuits, mini-crackers, mini-cookies, and mini-pretzels. As was mentioned above, oils of the invention can be used as an ingredient.

A snack food product comprises any of the above or below described food products.

A fried food product comprises any of the above or below described food products that has been fried.

The beverage can be in a liquid or in a dry powdered form.

For example, there can be mentioned non-carbonated drinks such as fruit juices, fresh, frozen, canned or concentrate; flavored or plain milk drinks, etc. Adult and infant nutritional formulas are well known in the art and commercially available (e.g., Similac®, Ensure®, Jevity®, and Alimentum® from Ross Products Division, Abbott Laboratories).

Infant formulas are liquids or reconstituted powders fed to infants and young children. "Infant formula" is defined herein as an enteral nutritional product which can be substituted for human breast milk in feeding infants and typically is composed of a desired percentage of fat mixed with desired percentages of carbohydrates and proteins in an aqueous solution (e.g., see U.S. Pat. No. 4,670,285). Based on the worldwide composition studies, as well as levels specified by expert groups, average human breast milk typically contains about 0.20% to 0.40% of total fatty acids (assuming about 50% of calories from fat); and, generally the ratio of DHA to ARA would range from about 1:1 to 1:2 (see, e.g., formulations of Enfamil LIPIL™ (Mead Johnson & Company) and Similac Advance™ (Ross Products Division, Abbott Laboratories)). Infant formulas have a special role to play in the diets of infants because they are often the only source of nutrients for infants; and, although breast-feeding is still the best nourishment for infants, infant formula is a close enough second that babies not only survive but thrive.

A dairy product is a product derived from milk. A milk analog or nondairy product is derived from a source other than milk, for example, soymilk as was discussed above. These products include, but are not limited to: whole milk, skim milk, fermented milk products such as yogurt or sour milk, cream, butter, condensed milk, dehydrated milk, coffee whitener, coffee creamer, ice cream, cheese, etc.

Additional food products into which the long-chain PUFA-containing oils of the invention could be included are, for example, chewing gums, confections and frostings, gelatins and puddings, hard and soft candies, jams and jellies, white granulated sugar, sugar substitutes, sweet sauces, toppings and syrups, and dry-blended powder mixes.

A health food product is any food product that imparts a health benefit and include functional foods, medical foods, medical nutritionals and dietary supplements. Additionally, the oils of the invention may be used in standard pharmaceutical compositions (e.g., the long-chain PUFA containing oils could readily be incorporated into the any of the above mentioned food products, to thereby produce a functional or medical food). For example, more concentrated formulations comprising ARA, EPA or DHA include capsules, powders, tablets, softgels, gelcaps, liquid concentrates and emulsions which can be used as a dietary supplement in humans or animals other than humans.

Animal feeds are generically defined herein as products intended for use as feed or for mixing in feed for animals other than humans. The long-chain PUFA containing oils of the invention can be used as an ingredient in various animal feeds.

More specifically, although not limited therein, it is expected that the oils of the invention can be used within pet food products, ruminant and poultry food products and aquacultural food products. Pet food products are those products intended to be fed to a pet (e.g., dog, cat, bird, reptile, rodent). These products can include the cereal and health food products above, as well as meat and meat byproducts, soy protein products, grass and hay products (e.g., alfalfa, timothy, oat or brome grass, vegetables). Ruminant and poultry food products are those wherein the product is intended to be fed to an animal (e.g., turkeys, chickens, cattle, swine). As with the pet foods above, these products can include cereal and health food products, soy protein products, meat and meat byproducts, and grass and hay products as listed above. Aquacultural food products (or "aquafeeds") are those products intended to be used in aquafarming which concerns the propagation, cultivation or farming of aquatic organisms and/or animals in fresh or marine waters.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The meaning of abbreviations is as follows: "sec" means second(s), "min" means minute(s), "h" means hour(s), "d" means day(s), "μl" means microliter(s), "mL" means milliliter(s), "L" means liter(s), "μM" means micromolar, "mM" means millimolar, "M" means molar, "mmol" means millimole(s), "μmole" mean micromole(s), "g" means gram(s), "μg" means microgram(s), "ng" means nanogram(s), "U" means unit(s), "bp" means base pair(s) and "kB" means kilobase(s).

Transformation and Cultivation of *Yarrowia lipolytica*

*Yarrowia lipolytica* strains with ATCC Accession Nos. #20362, #76982 and #90812 were purchased from the American Type Culture Collection (Rockville, Md.). *Yarrowia lipolytica* strains were typically grown at 28° C. on YPD agar (1% yeast extract, 2% bactopeptone, 2% glucose, 2% agar).

Transformation of *Yarrowia lipolytica* was performed according to the method of Chen, D. C. et al. (*Appl. Microbiol. Biotechnol.* 48(2):232-235 (1997)), unless otherwise noted. Briefly, *Yarrowia* was streaked onto a YPD plate and grown at 30° C. for approximately 18 h. Several large loopfuls of cells were scraped from the plate and resuspended in 1 mL of transformation buffer containing: 2.25 mL of 50% PEG, average MW 3350; 0.125 mL of 2 M Li acetate, pH 6.0; 0.125 mL of 2 M DTT; and 50 μg sheared salmon sperm DNA. Then, approximately 500 ng of linearized plasmid DNA was incubated in 100 μL of resuspended cells, and maintained at 39° C. for 1 h with vortex mixing at 15 min intervals. The cells were plated onto selection media plates and maintained at 30° C. for 2 to 3 days.

For selection of transformants, minimal medium ("MM") was generally used; the composition of MM is as follows: 0.17% yeast nitrogen base (Difco Laboratories, Detroit, Mich.) without ammonium sulfate or amino acids, 2% glucose, 0.1% proline, pH 6.1). Supplements of uracil were added as appropriate to a final concentration of 0.01% (thereby producing "MMU" selection media, prepared with 20 g/L agar).

Alternatively, transformants were selected on 5-fluoroorotic acid ("FOA"; also 5-fluorouracil-6-carboxylic acid monohydrate) selection media, comprising: 0.17% yeast nitrogen base (Difco Laboratories, Detroit, Mich.) without ammonium sulfate or amino acids, 2% glucose, 0.1% proline, 75 mg/L uracil, 75 mg/L uridine, 900 mg/L FOA (Zymo Research Corp., Orange, Calif.) and 20 g/L agar.

Fatty Acid Analysis of *Yarrowia lipolytica*

For fatty acid analysis, cells were collected by centrifugation and lipids were extracted as described in Bligh, E. G. & Dyer, W. J. (*Can. J. Biochem. Physiol.* 37:911-917 (1959)). Fatty acid methyl esters were prepared by transesterification of the lipid extract with sodium methoxide (Roughan, G., and Nishida I. *Arch Biochem Biophys.* 276(1):38-46 (1990)) and subsequently analyzed with a Hewlett-Packard 6890 GC fitted with a 30 m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 μL of 1%) was added to the sample, and then the sample was vortexed and rocked for 20 min. After adding 3 drops of 1 M NaCl and 400 μL hexane, the sample was vortexed and spun. The upper layer was removed and analyzed by GC as described above.

Example 1

*Euglena gracilis* Growth Conditions, Lipid Profile and mRNA Isolation

*Euglena gracilis* was obtained from Dr. Richard Triemer's lab at Michigan State University (East Lansing, Mich.). From 10 mL of actively growing culture, a 1 mL aliquot was transferred into 250 mL of *Euglena gracilis* (Eg) Medium in a 500 mL glass bottle. Eg medium was made by combining 1 g of sodium acetate, 1 g of beef extract (U126-01, Difco Laboratories, Detroit, Mich.), 2 g of Bacto® tryptone (0123-17-3, Difco Laboratories), 2 g of Bacto® yeast extract (0127-17-9, Difco Laboratories) in 970 mL of water. After filter sterilizing, 30 mL of soil-water supernatant (15-3790, Carolina Biological Supply Company, Burlington, N.C.) was aseptically added to give the final Eg medium. *Euglena gracilis* cultures were grown at 23° C. with a 16 h light, 8 h dark cycle for 2 weeks with no agitation.

Figure 13:
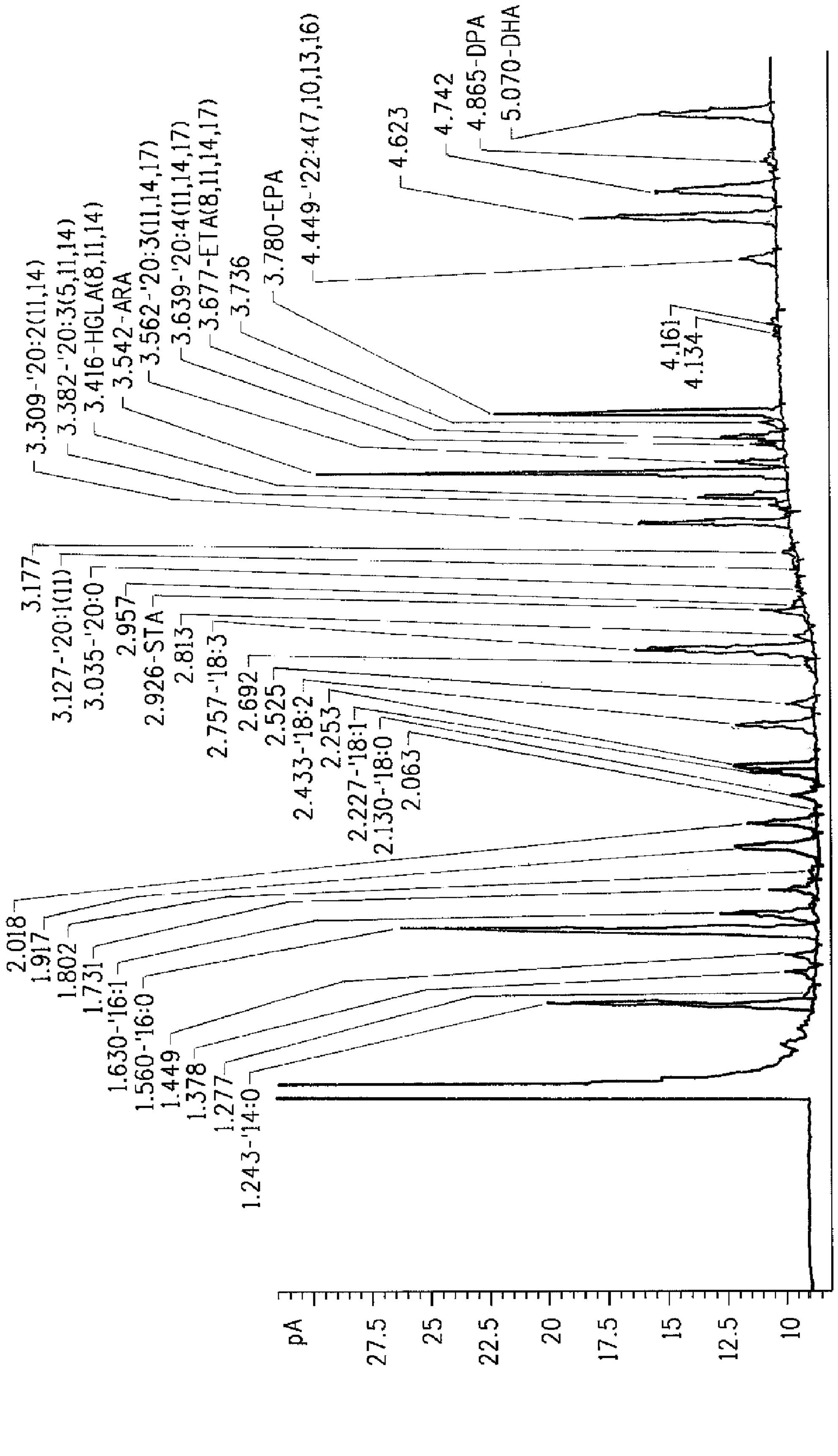
FIG. 13 shows a chromatogram of the lipid profile of an *Euglena gracilis* cell extract as described in the Examples.

After 2 weeks, 10 mL of culture was removed for lipid analysis and centrifuged at 1,800×g for 5 min. The pellet was washed once with water and re-centrifuged. The resulting pellet was dried for 5 min under vacuum, resuspended in 100 μL of trimethylsulfonium hydroxide (TMSH) and incubated at room temperature for 15 min with shaking. After this, 0.5 mL of hexane was added and the vials were incubated for 15 min at room temperature with shaking. Fatty acid methyl esters (5 μL injected from hexane layer) were separated and quantified using a Hewlett-Packard 6890 Gas Chromatograph fitted with an Omegawax 320 fused silica capillary column (Supelco Inc., Cat. No. 24152). The oven temperature was programmed to hold at 220° C. for 2.7 min, increase to 240° C. at 20° C./min and then hold for an additional 2.3 min. Carrier gas was supplied by a Whatman hydrogen generator. Retention times were compared to those for methyl esters of standards commercially available (Nu-Chek Prep, Inc. Cat. No. U-99-A) and the resulting chromatogram is shown in FIG. 13.

The remaining 2 week culture (240 mL) was pelleted by centrifugation at 1,800×g for 10 min, washed once with water and re-centrifuged. Total RNA was extracted from the resulting pellet using the RNA STAT-60™ reagent (TEL-TEST, Inc., Friendswood, Tex.) and following the manufacturer's protocol provided (use 5 mL of reagent, dissolved RNA in 0.5 mL of water). In this way, 1 mg of total RNA (2 mg/mL) was obtained from the pellet. The mRNA was isolated from 1 mg of total RNA using the mRNA Purification Kit (Amersham Biosciences, Piscataway, N.J.) following the manufacturer's protocol provided. In this way, 85 μg of mRNA was obtained.

Example 2

*Euglena gracilis* cDNA Synthesis, Library Construction and Sequencing

A cDNA library was generated using the Cloneminer™ cDNA Library Construction Kit (Cat. No. 18249-029, Invitrogen Corporation, Carlsbad, Calif.) and following the manufacturer's protocol provided (Version B, 25-0608). Using the non-radiolabeling method, cDNA was synthesized from 3.2 μg of mRNA (described above) using the Biotin-attB2-Oligo (dT) primer. After synthesis of the first and second strand, the attB1 adapter was added, ligated and the cDNA was size fractionated using column chromatography. DNA from fractions 7 and 8 (size ranging from ~800-1500 bp) were concentrated, recombined into pDONR™ 222 and transformed into *E. coli* ElectroMAX™ DH10B™ T1 Phage-Resistant cells (Invitrogen Corporation). The *Euglena gracilis* library was named eeg1c.

For sequencing, clones first were recovered from archived glycerol cultures grown/frozen in 384-well freezing media plates, and replicated with a sterile 384 pin replicator (Genetix, Boston, Mass.) in 384-well microtiter plates containing LB+75 μg/mL Kanamycin (replicated plates). Plasmids then were isolated, using the Templiphi DNA sequencing template amplification kit method (Amersham Biosciences) following the manufacturer's protocol. Briefly, the Templiphi method uses bacteriophage ϕ29 DNA polymerase to amplify circular single-stranded or double-stranded DNA by isothermal rolling circle amplification (Dean et al., *Genome Res.* 11:1095-1099 (2001); Nelson et al., *Biotechniques* 32:S44-S47 (2002)). After growing 20 h at 37° C., cells from the replicated plate were added to 5 μL of dilution buffer and denatured at 95° C. for 3 min to partially lyse cells and release the denatured template. 5 μL of Templiphi premix then were added to each sample and the resulting reaction mixture was incubated at 30° C. for 16 h, then at 65° C. for 10 min to inactivate the ϕ29 DNA polymerase activity. DNA quantification with the PicoGreen® dsDNA Quantitation Reagent (Molecular Probes) was performed after diluting the amplified samples 1:3 in distilled water.

The amplified products then were denatured at 95° C. for 10 min and end-sequenced in 384-well plates, using the M13F universal primer (SEQ ID NO:28), and the ABI BigDye version 3.1 Prism Sequencing Kit. For the sequencing reaction, 100-200 ng of templates and 6.4 pmol of primers were used, and the following reaction conditions were repeated 25 times: 96° C. for 10 sec, 50° C. for 5 sec and 60° C. for 4 min. After ethanol-based cleanup, cycle sequencing reaction products were resolved and detected on Perkin-Elmer ABI 3730×1 automated sequencers.

Example 3

Identification of Long-Chain Polyunsaturated Fatty Acid Elongation Enzyme Homologs from *Euglena gracilis* cDNA Library eeg1c cDNA clones encoding long-chain polyunsaturated fatty acid elongation enzyme homologs (LC-PUFA ELO homologs or delta-9 elongases) were identified by conducting BLAST (Basic Local Alignment Search Tool; Altschul et al., *J. Mol. Biol.* 215:403-410 (1993)) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 2 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States, *Nat. Genet.* 3:266-272 (1993)) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

The BLASTX search using the nucleotide sequences from clone eeg1c.pk001.n5.f revealed similarity of the protein encoded by the cDNA to the long-chain PUFA elongation enzyme from *Isochrysis galbana* (SEQ ID NO:27) (NCBI Accession No. AAL37626 (GI 17226123), locus AAL37626, CDS AF390174; Qi et al., *FEBS Lett.* 510(3):159-165 (2002)). The sequence of a portion of the cDNA insert from clone eeg1c.pk001.n5.f is shown in SEQ ID NO:1 (5' end of cDNA insert). Additional sequence was obtained from the 3' end of the cDNA insert of eeg1c.pk001.n5.1 as described above, but using the poly(A) tail-primed WobbleT oligonucleotides. Briefly, the WobbleT primer is an equimolar mix of 21 mer poly(T)A, poly(T)C, and poly(T)G, used to sequence the 3' end of cDNA clones.

The 3' end sequence is shown in SEQ ID NO:2. Both the 5' and 3' sequences were aligned using Sequencher™ (Version 4.2, Gene Codes Corporation, Ann Arbor, Mich.) and the resulting sequence for the cDNA is shown in SEQ ID NO:3. Sequence for the coding sequence from the cDNA in eeg1c.pk001.n5.f and the corresponding deduced amino acid sequence is shown in SEQ ID NO:4 and SEQ ID NO:5, respectively.

The amino acid sequence set forth in SEQ ID NO:5 was evaluated by BLASTP, yielding a pLog value of 38.70 (E value of 2e-39) versus the *Isochrysis galbana* sequence (SEQ ID NO:27). The *Euglena gracilis* delta-9 elongase is 39.4% identical to the *Isochrysis galbana* delta-9 elongase sequence using the Jotun Hein method. Sequence percent identity calculations performed by the Jotun Hein method (Hein, J. J., *Meth. Enz.* 183:626-645 (1990)) were done using the MegAlign™ v6.1 program of the LASARGENE bioinformatics computing suite (DNASTAR Inc., Madison, Wis.) with the default parameters for pairwise alignment (KTUPLE=2). The *Euglena gracilis* delta-9 elongase is 31.8% (SEQ ID NO:5) identical to the *Isochrysis galbana* delta-9 elongase (SEQ ID NO:27) sequence using the Clustal V method (see FIG. 16 and FIG. 29). Sequence percent identity calculations performed by the Clustal V method (Higgins, D. G. and Sharp, P. M., *Comput. Appl. Biosci.* 5:151-153 (1989); Higgins et al., *Comput. Appl. Biosci.* 8:189-191 (1992)) were done using the MegAlign™ v6.1 program of the LASARGENE bioinformatics computing suite (DNASTAR Inc., Madison, Wis.) with the default parameters for pairwise alignment (KTUPLE=1, GAP PENALTY=3, WINDOW=5 and DIAGONALS SAVED=5 and GAP LENGTH PENALTY=10). BLAST scores and probabilities indicate that the instant nucleic acid fragment (SEQ ID NO:3) encode an entire *Euglena gracilis* delta-9 elongase.

Example 4

Synthesis and Functional Expression of a Codon-Optimized Delta-9 Elongase Gene (Derived from *Isochrysis galbana*) in *Yarrowia lipolytica*

The codon usage of the delta-9 elongase gene of *Isochrysis galbana* (SEQ ID NO:27, GenBank Accession No. AF390174) was optimized for expression in *Yarrowia lipolytica*. According to the *Yarrowia* codon usage pattern, the consensus sequence around the ATG translation initiation codon, and the general rules of RNA stability (Guhaniyogi, G. and J. Brewer, *Gene* 265(1-2):11-23 (2001)), a codon-optimized delta-9 elongase gene was designed, affording SEQ ID NO:65, based on the DNA sequence of *Isochrysis galbana* (SEQ ID NO:29). In addition to modification of the translation initiation site, 127 bp of the 792 bp coding region were modified, and 122 codons were optimized. None of the modifications in the codon-optimized gene changed the amino acid sequence of the encoded protein (GenBank Accession No. AF390174; SEQ ID NO:27).

In Vitro Synthesis of a Codon-Optimized Delta-9 Elongase Gene for *Yarrowia lipolytica:*

Eight pairs of oligonucleotides were designed to extend the entire length of the codon-optimized coding region of the *Isochrysis galbana* delta-9 elongase gene (e.g., IL3-1A, IL3-1B, IL3-2A, IL3-2B, IL3-3A, IL3-3B, IL3-4A, IL3-4B, IL3-5A, IL3-5B, IL3-6A, IL3-6B, IL3-7A, IL3-7B, IL3-8A, IL3-8B, corresponding to SEQ ID NOs:66-81). Each pair of sense (A) and anti-sense (B) oligonucleotides were complementary, with the exception of a 4 bp overhang at each 5'-end. Additionally, primers IL3-1F, IL3-4R, IL3-5F and IL3-8R (SEQ ID NOs:82-85) also introduced NcoI, PstI, PstI and Not1 restriction sites, respectively, for subsequent subcloning.

Each oligonucleotide (100 ng) was phosphorylated at 37° C. for 1 h in a volume of 20 μL containing 50 mM Tris-HCl (pH 7.5), 10 mM $MgCl_2$, 10 mM DTT, 0.5 mM spermidine, 0.5 mM ATP and 10 U of T4 polynucleotide kinase. Each pair of sense and antisense oligonucleotides was mixed and annealed in a thermocycler using the following parameters: 95° C. (2 min), 85° C. (2 min), 65° C. (15 min), 37° C. (15 min), 24° C. (15 min) and 4° C. (15 min). Thus, IL3-1A (SEQ ID NO:66) was annealed to IL3-1B (SEQ ID NO:67) to produce the double-stranded product "IL3-1AB". Similarly, IL3-2A (SEQ ID NO:68) was annealed to IL3-2B (SEQ ID NO:69) to produce the double-stranded product "IL3-2AB", etc.

Two separate pools of annealed, double-stranded oligonucleotides were then ligated together, as shown below: Pool 1 (comprising IL3-1AB, IL3-2AB, IL3-3AB and IL3-4AB); and Pool 2 (comprising IL3-5AB, IL3-6AB, IL3-7AB and IL3-8AB). Each pool of annealed oligonucleotides was mixed in a volume of 20 μL with 10 U of T4 DNA ligase and the ligation reaction was incubated overnight at 16° C.

The product of each ligation reaction was then used as template to amplify the designed DNA fragment by PCR. Specifically, using the ligated "Pool 1" mixture (e.g., IL3-1AB, IL3-2AB, IL3-3AB and IL3-4AB) as template, and oligonucleotides IL3-1F and IL3-4R (SEQ ID NOs:82 and 83) as primers, the first portion of the codon-optimized delta-9 elongase gene was amplified by PCR. The 417 bp PCR fragment was subcloned into the pGEM-T easy vector (Promega) to generate pT9(1-4) (SEQ ID NO:86).

Using the ligated "Pool 2" mixture (e.g. IL3-5AB, IL3-6AB, IL3-7AB and IL3-8AB) as the template, and oligonucleotides IL3-5F and IL3-8R (SEQ ID NOs:84 and 85) as primers, the second portion of the codon-optimized delta-9 elongase gene was amplified similarly by PCR and cloned into the pGEM-T-easy vector to generate pT9(5-8) (SEQ ID NO:87).

*E. coli* was transformed separately with pT9(1-4) (SEQ ID NO:86) and pT9(5-8) (SEQ ID NO:87) and the plasmid DNA was isolated from ampicillin-resistant transformants. Plasmid DNA was purified and digested with the appropriate restriction endonucleases to liberate the 417 bp NcoI/PstI fragment of pT9(1-4) (SEQ ID NO:86) and the 377 bp PstI/NotI fragment of pT9(5-8) (SEQ ID NO:87). These two fragments were then combined and directionally ligated together with NcoI/NotI digested pZUF17 (SEQ ID NO:25) to generate pDMW237 (SEQ ID NO:26). The DNA sequence of the resulting synthetic delta-9 elongase gene ("IgD9e") in pDMW237 was exactly the same as the originally designed codon-optimized gene (e.g., SEQ ID NO:65) for *Yarrowia lipolytica.*

Example 5

Construction of pDMW263

Plasmid pY5-30 (which was previously described in PCT Publication No. WO 05/003310 (the contents of which are hereby incorporated by reference)) is a shuttle plasmid that can replicate both in *E. coli* and *Yarrowia lipolytica*. Plasmid pY5-30 contains the following: a *Yarrowia* autonomous replication sequence (ARS18); a ColE1 plasmid origin of replication; an ampicillin-resistance gene ($Amp^R$), for selection in *E. coli*; a *Yarrowia* LEU2 gene, for selection in *Yarrowia*; and a chimeric TEF::GUS::XPR gene. Plasmid pDMW263 (SEQ ID NO:89) was created from pY5-30, by replacing the TEF promoter with the *Yarrowia lipolytica* FBAINm promoter (PCT Publication No. WO 05/049805) using techniques well known to one skilled in the art. Briefly, this promoter refers to a modified promoter which is located in the 5' upstream untranslated region in front of the 'ATG' translation initiation codon of the fructose-bisphosphate aldolase enzyme (E.C. 4.1.2.13) encoded by the fba1 gene and that is necessary for expression, plus a portion of 5' coding region that has an intron, wherein FBAINm has a 52 bp deletion between the ATG translation initiation codon and the intron of the FBAIN promoter (thereby including only 22 amino acids of the N-terminus) and a new translation consensus motif after the intron. Table 4 summarizes the components of pDMW263.

TABLE 4

Components of Plasmid pDMW263

| RE Sites and Nucleotides Within SEQ ID NO: 89 | Description of Fragment and Chimeric Gene Components |
|---|---|
| 4992-4296 | ARS18 sequence (GenBank Accession No. A17608) |
| SalI/SacII (8505-2014) | FBAINm::GUS::XPR, comprising: FBAINm: FBAINm promoter (WO2005/049805) GUS: *E. coli* gene encoding β-glucuronidase (Jefferson, R. A. *Nature.* 14: 342: 837-838 (1989) XPR: ~100 bp of the 3' region of the *Yarrowia* Xpr gene (GenBank Accession No. M17741) |
| 6303-8505 | *Yarrowia* Leu2 gene (GenBank Accession No. AF260230) |

Example 6

Construction of *Yarrowia lipolytica* Expression Vector pY115 and Gateway® Destination Vector pBY1

The NcoI/SalI DNA fragment from pDMW263 (see construction in Example 5), containing the *Yarrowia lipolytica* FBAINm promoter, was cloned into the NcoI/SalI DNA fragment of pDMW237 (see construction in Example 4), containing the synthetic delta-9 elongase gene (IgD9e), to produce pY115 (SEQ ID NO:30; FIG. 1).

Plasmid pY115 (SEQ ID NO:30) was digested with NcoI/NotI and the resulting DNA ends were filled using Klenow. After filling to form blunt ends, the DNA fragments were treated with calf intestinal alkaline phosphatase and separated using agarose gel electrophoresis. The 6989 bp fragment containing the *Yarrowia lipolytica* FBAINm promoter was excised from the agarose gel and purified using the QIAquick® Gel Extraction Kit (Qiagen Inc., Valencia, Calif.) following the manufacturer's protocol. The purified 6989 bp fragment was ligated with cassette rfA using the Gateway Vector Conversion System (Cat. No. 11823-029, Invitrogen Corporation) following the manufacturer's protocol to form *Yarrowia lipolytica* Gateway® destination vector pBY1 (SEQ ID NO:31; FIG. 2).

Example 7

Construction of *Yarrowia lipolytica* Expression Vectors pBY2 and pBY1-FAE

Plasmid was purified from eeg1c.pk001.n5.f using the QIAprep® Spin Miniprep Kit (Qiagen Inc., Valencia, Calif.) following the manufacturer's protocol. Using the Gateway® LR Clonase™ II enzyme mix (Cat. No. 11791-020, Invitrogen Corporation) and following the manufacturer's protocol, the cDNA from eeg1c.pk001.n5.f was transferred to pBY1 to form pBY2 (SEQ ID NO:32; FIG. 3). Since sequencing was performed with the WobbleT primer, the full sequence of the 3' end of eeg1c.pk001.n5.f, containing the polyA tail, was not known. Based on restriction digest and agarose gel analysis, the poly A tail appeared to be less than 100 bp long. pBY2 (SEQ ID NO:32) was transformed into *E. coli* DH10B™ (Invitrogen Corporation), cells were grown and pBY2 was isolated using the QIAprep® Spin Miniprep Kit (Qiagen Inc., Valencia, Calif.) as above.

The *Isochrysis galbana* synthetic delta-9 elongase gene (IgD9e) was amplified from pY115 (SEQ ID NO:30) with oligonucleotide primers ig-s (SEQ ID NO:6) and ig-as (SEQ ID NO:7) using the AccuPrime™ Taq Polymerase High Fidelity (Cat. No. 12346-086, Invitrogen Corporation) following the manufacturer's protocol. The resulting DNA fragment was cloned into pENTR™/D-TOPO® using the pENTR™ Directional TOPO® Cloning Kit (Invitrogen Corporation), following the manufacturer's protocol, to produce pENTR-FAE. Plasmid pENTR-FAE was purified using the QIAprep® Spin Miniprep Kit (Qiagen Inc., Valencia, Calif.) following the manufacturer's protocol as above. Using the Gateway® LR Clonase™ II enzyme mix (Cat. No. 11791-020, Invitrogen Corporation) and following the manufacturer's protocol, the CDS for the *Isochrysis galbana* synthetic delta-9 elongase gene (IgD9e) was transferred to pBY1 to form pBY1-FAE (SEQ ID NO:33; FIG. 4). pBY1-FAE was transformed into *E. coli* DH10B™ (Invitrogen Corporation), cells were grown and pBY1-FAE was isolated using the QIAprep® Spin Miniprep Kit (Qiagen Inc., Valencia, Calif.) as above.

Example 8

Construction of *Yarrowia lipolytica* Expression Vector pY120

The *Euglena gracilis* delta-9 elongase was amplified from eeg1c.pk001.n5.f with oligonucleotide primers oEugEL1-1 (SEQ ID NO:8) and oEugEL1-2 (SEQ ID NO:9) using the VentR® DNA Polymerase (Cat. No. M0254S, New England Biolabs Inc., Beverly, Mass.) following the manufacturer's protocol. The resulting DNA fragment was cloned into the pCR-Blunt® cloning vector using the Zero Blunt® PCR Cloning Kit (Invitrogen Corporation), following the manufacturer's protocol, to produce pKR906. The NcoI/NotI DNA fragment from pKR906, containing the *Eulgena gracilis* delta-9 elongase, was cloned into the NcoI/NotI DNA fragment from pY115, containing the *Yarrowia lipolytica* FBAINm promoter, to produce pY120 (SEQ ID NO:34; FIG. 5).

Example 9

Cloning the *Euglena gracilis* Delta-9 Elongase into a Yeast Expression Vector

The yeast episomal plasmid (YEp)-type vector pRS425 (Christianson et al., *Gene* 110:119-122 (1992)) contains sequences from the *Saccharomyces cerevisiae* 2μ endogenous plasmid, a LEU2 selectable marker and sequences based on the backbone of a multifunctional phagemid, pBluescript II SK(+). The *Saccharomyces cerevisiae* strong, constitutive glyceraldehyde-3-phosphate dehydrogenase (GPD) promoter was cloned between the SacII and SpeI sites of pRS425 in the same way as described by Jia et al. (*Physiol.*

*Genomics,* 3, 83-92 (2000)) to produce pGPD-425. A NotI site was introduced into the BamHI site of pGPD-425, thus giving a NotI site flanked by BamHI sites, and this plasmid was called pY-75. The *Euglena gracilis* delta-9 elongase was released from pKR906 (see Example 8) by digestion with NotI and cloned into the NotI site of pY-75 to produce pY119 (SEQ ID NO:35; FIG. 6).

Example 10

Cloning the *Euglena gracilis* Delta-9 Elongase into a Soybean Expression Vector A starting plasmid pKR72 (ATCC Accession No. PTA-6019; SEQ ID NO:36, 7085 bp sequence), a derivative of pKS123 which was previously described in PCT Publication No. WO 02/008269 (the contents of which are hereby incorporated by reference), contains the hygromycin B phosphotransferase gene (HPT) (Gritz, L. and Davies, J., *Gene* 25:179-188 (1983)), flanked by the T7 promoter and transcription terminator (T7prom/hpt/T7term cassette), and a bacterial origin of replication (ori) for selection and replication in bacteria (e.g., *E. coli*). In addition, pKR72 also contains the hygromycin B phosphotransferase gene, flanked by the 35S promoter (Odell et al., *Nature* 313:810-812 (1985)) and NOS 3' transcription terminator (Depicker et al., *J. Mol. Appl. Genet.* 1:561-570 (1982)) (35S/hpt/NOS3' cassette) for selection in plants such as soybean. pKR72 also contains a NotI restriction site, flanked by the promoter for the α' subunit of β-conglycinin (Beachy et al., *EMBO J.* 4:3047-3053 (1985)) and the 3' transcription termination region of the phaseolin gene (Doyle et al., *J. Biol. Chem.* 261:9228-9238 (1986)), thus allowing for strong tissue-specific expression in the seeds of soybean of genes cloned into the NotI site.

The gene for the *Euglena gracilis* delta-9 elongase was released from pKR906 (see Example 8) by digestion with NotI and cloned into the NotI site of pKR72 to produce pKR912 (SEQ ID NO:37). A schematic depiction of pKR912 is shown in FIG. 7.

Example 11

Cloning the *Euglena gracilis* Delta-9 Elongase into an Intermediate Cloning Vector Vector pKS102 (SEQ ID NO:38), previously described in PCT Publication No. WO 02/00905 (the contents of which are hereby incorporated by reference), contains the hygromycin B phosphotransferase gene (HPT) (Gritz, L. and Davies, J., *Gene* 25:179-188 (1983)), flanked by the T7 promoter and transcription terminator (T7prom/hpt/T7term cassette), and a bacterial origin of replication (ori) for selection and replication in bacteria (e.g., *E. coli*).

Vector pKR197 (SEQ ID NO:39), previously described in PCT Publication No. WO 04/071467 (the contents of which are hereby incorporated by reference) was constructed by combining the AscI fragment from plasmid pKS102 (SEQ ID NO:38), containing the T7prom/hpt/T7term cassette and bacterial ori, with the AscI fragment of plasmid pKR72, containing the βcon/NotI/Phas cassette.

The gene for the *Euglena gracilis* delta-9 elongase was released from pKR906 (see Example 6) by digestion with NotI and cloned into the NotI site of pKR197 to produce intermediate cloning vector pKR911 (SEQ ID NO:40). A schematic depiction of pKR911 is shown in FIG. 8.

Example 12 cDNA Synthesis and PCR of *Euglena gracilis* Delta-8 Desaturase cDNA was synthesized from 765 ng of mRNA (described in Example 1 above) using the SuperScript™ Choice System for cDNA synthesis (Invitrogen™ Life Technologies, Carlsbad, Calif.) with the provided oligo(dT) primer according to the manufacturer's protocol. The synthesized cDNA was dissolved in 20 μL of water.

The *Euglena gracilis* delta-8 desaturase was amplified from cDNA with oligonucleotide primers Eg5-1 (SEQ ID NO:10) and Eg3-3 (SEQ ID NO:11) using the conditions described below.

cDNA (1 μL) from the reaction described above was combined with 50 pmol of Eg5-1 (SEQ ID NO:10), 50 pmol of Eg5-3 (SEQ ID NO:11), 1 □μL of PCR nucleotide mix (10 mM, Promega, Madison, Wis.), 5 μL of 10×PCR buffer (Invitrogen Corporation), 1.5 μL of $MgCl_2$ (50 mM, Invitrogen Corporation), 0.5 μL of Taq polymerase (Invitrogen Corporation) and water to 50 μL. The reaction conditions were 94° C. for 3 min followed by 35 cycles of 94° C. for 45 sec, 55° C. for 45 sec and 72° C. for 1 min. The PCR was finished at 72° C. for 7 min and then held at 4° C. The PCR reaction was analyzed by agarose gel electrophoresis on 5 μL and a DNA band with molecular weight around 1.3 kb was observed. The remaining 45 μL of product was separated by agarose gel electrophoresis and DNA band purified using the Zymoclean™ Gel DNA Recovery Kit (Zymo Research, Orange, Calif.) following the manufacturer's protocol. The resulting DNA was cloned into the pGEM®-T Easy Vector (Promega) following the manufacturer's protocol. Multiple clones were sequenced using T7 (SEQ ID NO:12), M13-28Rev (SEQ ID NO:13), Eg3-2 (SEQ ID NO:14) and Eg5-2 (SEQ ID NO:15).

Thus, a DNA sequence for the *Euglena gracilis* delta-8 desaturase (Eg5) was obtained (SEQ ID NO:16). Translation of Eg5 gave rise to the protein sequence set forth in SEQ ID NO:17.

Example 13

Cloning the *Euglena gracilis* Delta-8 Desaturase with the *Euglena gracilis* Delta-9 Elongase Vector pKS121 (SEQ ID NO:41), which was previously described in PCT Publication No. WO 02/00904 (the contents of which are hereby incorporated by reference), contains a NotI site flanked by the Kunitz soybean Trypsin Inhibitor (KTi) promoter (Jofuku et al., *Plant Cell* 1:1079-1093 (1989)) and the KTi 3' termination region, the isolation of which is described in U.S. Pat. No. 6,372,965 (KTi/NotI/KTi3' cassette). Vector pKR457 (SEQ ID NO:42), which was previously described in PCT Publication No. WO 05/047479 (the contents of which are hereby incorporated by reference), is a derivative of pKS121 where the restriction sites upstream and downstream of the KTi/NotI/KTi3' cassette have been altered through a number of subcloning steps. Vector pKR457 also contains the soy albumin transcription terminator, which was previously described in PCT Publication No. WO 04/071467 (the contents of which are hereby incorporated by reference), downstream of the KTi terminator to lengthen and strengthen termination of transcription. In pKR457, the BamHI site upstream of the KTi promoter in the KTi/NotI/KTi3' cassette was removed and a new sequence (SEQ ID NO:18) added containing a BsiWI, SalI, SbfI and HindIII site with the BsiWI site being closest the 5' end of the KTi promoter.

In addition, the SalI site downstream of the KTi terminator in the KTi/NotI/KTi3' cassette from pKS121 was removed and a new sequence (SEQ ID NO:19) added containing an XbaI (closest to 3' end of KTi terminator), a BamHI site, the soy albumin transcription terminator sequence, a BsiWI site and another BamHI site. The albumin transcription terminator had been previously amplified from soy genomic DNA using primer oSalb-12 (SEQ ID NO:20), designed to introduce a BsiWI site at the 3' end of the terminator, and primer oSalb-13 (SEQ ID NO:21), designed to introduce a BamHI site at the 5' end of the terminator.

Eg5 (SEQ ID NO:16) was released from the pGEM®-T Easy Vector described in Example 12 bp digestion with NotI and cloned into the NotI site of pKR457 to produce pKR680 (SEQ ID NO:43). Plasmid pKR680 was then digested with BsiWI and the fragment containing Eg5 (SEQ ID NO:16) was cloned into the BsiWI site of pKR911 (SEQ ID NO:40) to produce pKR913 (SEQ ID NO:44). A schematic depiction of pK913 is shown in FIG. 9.

Example 14

Cloning the *Euglena gracilis* Delta-8 Desaturase into a Soybean Expression Vector and Co-Expression with the *Euglena gracilis* Delta-9 Elongase Plasmid pKR680 (SEQ ID NO:43) is digested with BsiWI and the fragment containing Eg5 (SEQ ID NO:16) is cloned into the BsiWI site of pKR912 (SEQ ID NO:37). In this way, the *Euglena gracilis* delta-8 desaturase is co-expressed with the *Euglena gracilis* delta-9 elongase behind strong, seed-specific promoters.

Example 15

Cloning the *Mortierella alpina* Delta-5 Desaturase into a Soybean Expression Vector and Co-Expression with the *Euglena gracilis* Delta-9 Elongase and the *Euglena gracilis* Delta-8 Desaturase A soybean expression vector containing the *Euglena gracilis* delta-8 desaturase (SEQ ID NO:16), the *Euglena gracilis* delta-9 elongase (SEQ ID NO:4) and the *Mortierella alpina* delta-5 desaturase (SEQ ID NO:88), which is described in U.S. Pat. No. 6,075,183 and PCT Publication Nos. WO 04/071467 and WO 05/0479479 (the contents of which are hereby incorporated by reference), all under the control of strong seed-specific promoters, is constructed in the following way.

Through a number of sub-cloning steps, a sequence of DNA (SEQ ID NO:22) is effectively added into the SmaI site of vector pKR287 (which is described in PCT Publication No. WO 04/071467, the contents of which are hereby incorporated by reference), to produce pKR767 (SEQ ID NO:45). In this way, a SbfI restriction site is added to the 3' end of the leg1A transcription terminator of the Gy1/Mad5/legA2 cassette, which is described in PCT Publication Nos. WO 04/071467 and WO 05/0479479.

The Gy1/Mad5/legA2 cassette is released from pKR767 by digestion with SbfI and the resulting fragment is cloned into the SbfI site of the vector described in Example 14 to produce a new vector that co-expresses all three genes under control of strong seed-specific promoters.

Example 16

Co-Expressing the *Mortierella alpina* Delta-5 Desaturase, the *Euglena gracilis* Delta-9 Elongase and the *Euglena gracilis* Delta-8 Desaturase with the *Saprolegnia diclina* Delta-17 Desaturase The soybean expression vector described in Example 15 is co-transformed along with other vectors expressing multiple different seed-specific promoter/LCPUFA-biosynthetic gene combinations. Whole plasmids or purified AscI fragments from the plasmids, containing the appropriate gene combinations, are used, as could any combination of either fragment of plasmid.

For instance, the vector described in Example 15 could be co-transformed with pKR328 (SEQ ID NO:46, described in PCT Publication No. WO 04/071467) containing the *Saprolegnia diclina* delta-17 desaturase under control of the annexin promoter and having a hygromycin resistance gene for selection in plants.

Similarly, the vector described in Example 15, could be co-transformed with pKR886 or pKR886r (FIG. 10), two vectors similar to pKR328 but having the SAMS/ALS/ALS3' cassette (which is described in PCT Publication No. WO 04/071467) for selection in plants. Vectors pKR886 (SEQ ID NO:47) and pKR886r (SEQ ID NO:48) are made by cloning the PstI fragment, containing the Ann/Sdd17/BD30 cassette from pKR271 (SEQ ID NO:49, which is described in PCT Publication No. WO 04/071467) into the SbfI site of pKR226 (SEQ ID NO:50, which is described in PCT Publication No. WO 04/071467).

Example 17

Co-Expressing the *Mortierella alpina* Delta-5 Desaturase, the *Euglena qracilis* Delta-9 Elongase and the *Euglena gracilis* Delta-8 Desaturase with the *Saprolegnia diclina* Delta-17 Desaturase and *Arabidopsis* Fad3

Alternatively, the vector described in Example 15 could be co-transformed into soybeans with either pKR275 (SEQ ID NO:51, which is described in PCT Publication No. WO 04/071467 and has ATCC Accession Number PTA-4989) or pKR329 (SEQ ID NO:52, which is described in PCT Publication No. WO 04/07146). Plasmids pKR275 and pKR329 have ALS or hygromycin selection, respectively, and contain the KTi/Fad3/KTi3' gene cassette (which is described in PCT Publication No. WO 04/071467) in addition to the Ann/Sdd17/BD30 cassette. In this way, the *Arabidopsis* Fad3 gene could be co-expressed with the *Saprolegnia diclina* delta-17 desaturase behind strong, seed-specific promoters.

Example 18

Co-Expressing the *Mortierella alpina* Delta-5 Desaturase, the *Euglena gracilis* Delta-9 Elongase and the *Euglena gracilis* Delta-8 Desaturase with the *Saprolegnia diclina* Delta-17 Desaturase and *Fusarium moniliforme* Delta-15 Desaturase The vector described in Example 15 could be co-transformed into soybeans with pKR585 (SEQ ID NO:53, which is described in PCT Publication No. WO 05/0479479 and has ATCC Accession No. PTA-6019), having hygromycin selection and containing the *Fusarium moniliforme* delta-15 desaturase under control of the KTi promoter.

Figure 11:
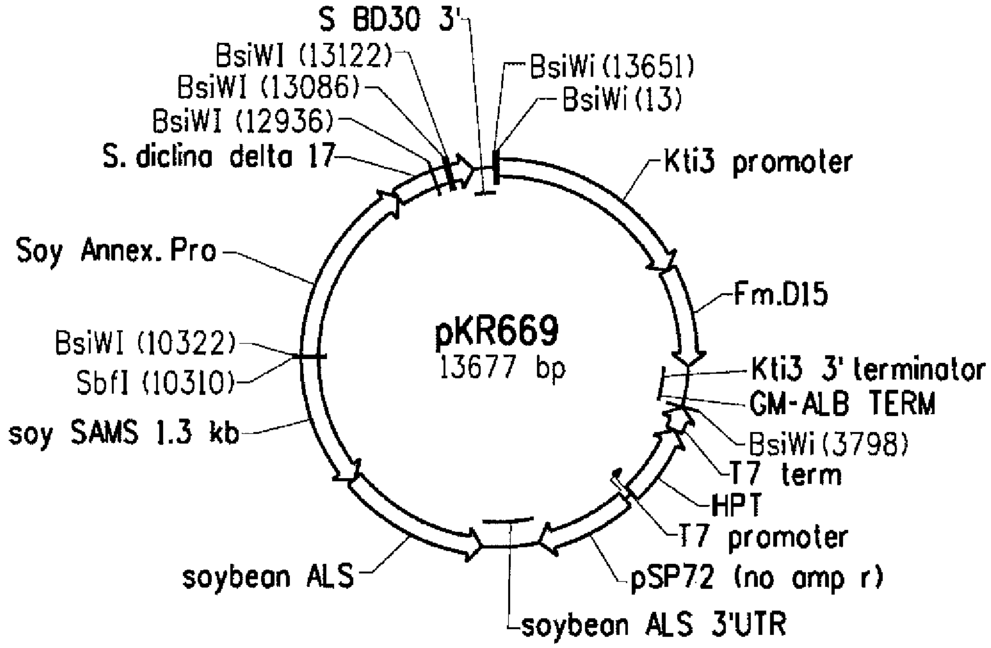
FIG. 11 is a map of plasmid pKR669.

The vector described in Example 15 could also be co-transformed into soybeans with pKR669, having ALS selection and containing the *Fusarium moniliforme* delta-15 desaturase under control of the KTi promoter in addition to the Ann/Sdd17/BD30 cassette. Plasmid pKR669 is produced in the following way. The KTi promoter:Fm delta-15 desaturase ORF:KTi terminator cassette is released from plasmid pKR578 (SEQ ID NO:54, which is described in PCT Publication No. WO 05/0479479 and has ATCC Accession No. PTA-6280) by digestion with BsiWI and is cloned into the BsiWI site of plasmid pKR226 (SEQ ID NO:50, which is described in PCT Publication No. WO 04/071467), containing the ALS gene for selection, the T7prom/hpt/T7term cassette and the bacterial on region, to produce pKR667 (SEQ ID NO:55). Plasmid pKR271 (SEQ ID NO: 49, which is described in PCT Publication No. WO 04/071467) is digested with PstI and the fragment containing the *Saprolegnia diclina* delta-17 desaturase is cloned into the SbfI site of pKR667 to produce pKR669. In this way, the *Fusarium moniliforme* delta-15 desaturase could be co-expressed with the *Saprolegnia diclina* delta-17 desaturase behind strong, seed-specific promoters. A schematic depiction of pKR669 is shown in FIG. 11.

The vector described in Example 15 could also be co-transformed into soybeans with pKR873 (SEQ ID NO:56), having ALS selection and containing the *Fusarium moniliforme* delta-15 desaturase under control of the soy albumin promoter (which is described in PCT Publication No. WO 04/071467) in addition to the Ann/Sdd17/BD30 cassette. Plasmid pKR873 is produced in the following way. The SA/NotI/SA3' cassette is amplified from plasmid pKR132 (SEQ ID NO:57, which is described in PCT Publication No. WO 04/071467) using PCR. Primer oSAIb-9 (SEQ ID NO:23) is designed to introduce XbaI and BsiWI sites at the 5' end of the promoter and primer oSAIb-2 (SEQ ID NO:24) is designed to introduce BsiWI and XbaI sites at the 3' end of the terminator. The resulting PCR fragment is subsequently cloned into pCR-Script AMP SK(+) (Stratagene Company, San Diego, Calif.) to produce pKR160 (SEQ ID NO:58). Plasmid pKR160 is then digested with BsiWI and the SA/NotI/SA3' cassette ligated into the BsiWI site of pKR124 (SEQ ID NO:59, which is described in PCT Publication No. WO 05/0479479) to produce pKR163 (SEQ ID NO:60). The NotI fragment from pY34 (SEQ ID NO:61, which is described in PCT Publication No. WO 05/0479479), containing the *Fusarium moniliforme* delta-15 desaturase, is cloned into the NotI site of pKR163 (SEQ ID NO:60) to produce pKR863 (SEQ ID NO:62). The SA/Fusd15/SA3' cassette is released from plasmid pKR863 by digestion with BsiWI and is cloned into the BsiWI site of plasmid pKR226 (SEQ ID NO:50, which is described in PCT Publication No. WO 04/071467), containing the ALS gene for selection, the T7prom/hpt/T7term cassette and the bacterial on region, to produce pKR869 (SEQ ID NO:63). Plasmid pKR271 (SEQ ID NO:49, which is described in PCT Publication No. WO 04/071467) is digested with PstI and the fragment containing the *Saprolegnia diclina* delta-17 desaturase is cloned into the SbfI site of pKR869 (SEQ ID NO:63) to produce pKR873 (SEQ ID NO:56). In this way, the *Fusarium moniliforme* delta-15 desaturase could be co-expressed with the *Saprolegnia diclina* delta-17 desaturase behind strong, seed-specific promoters. A schematic depiction of pKR873 is shown in FIG. 12. Subsequent to the writing of this Example in the Provisional Application, the work describing the preparation of pKR873 was done and is described in Example 29 below.

Example 19

Co-Expressing the *Mortierella alpina* Delta-5 Desaturase, the *Euglena gracilis* Delta-9 Elongase and the *Euglena gracilis* Delta-8 Desaturase with the *Saprolegnia diclina* Delta-17 Desaturase and *Mortierella alpina* Elongase The vector described in Example 15 could also be co-transformed into soybeans with a vector having ALS selection and containing the *Mortierella alpina* elongase (which is described in PCT Publication Nos. WO 04/071467 and WO 00/12720) under control of the soy albumin promoter (which is described in PCT Publication No. WO 04/071467) in addition to the Ann/Sdd17/BD30 cassette. This plasmid could be produced in a similar way as to those described supra. For instance, the NotI fragment from pKR270 (SEQ ID NO:64, which is described in PCT Publication No. WO 04/071467), containing the *Mortierella alpina* elongase, could be cloned into the NotI site of pKR163 (SEQ ID NO:60) to produce a vector having the SA/Maelo/SA3' cassette. The SA/Maelo/SA3' cassette could be released from that plasmid by digestion with BsiWI and could be cloned into the BsiWI site of plasmid pKR226 (SEQ ID NO:50, which is described in PCT Publication No. WO 04/071467), containing the ALS gene for selection, the T7prom/hpt/T7term cassette and the bacterial on region, to produce a new plasmid. Plasmid pKR271 (SEQ ID NO:49, which is described in PCT Publication No. WO 04/071467) could then be digested with PstI and the fragment containing the *Saprolegnia diclina* delta-17 desaturase could be cloned into the SbfI site of the new plasmid containing the SA/Maelo/SA3' cassette. In this way, the *Mortierella alpina* elongase could be co-expressed with the *Saprolegnia diclina* delta-17 desaturase behind strong, seed-specific promoters.

Example 20

Functional Analysis of the *Euglena gracilis* Delta-9 Elongase in *Saccharomyces cerevisiae*

Plasmids pY119 and pY-75 (Example 9, cloning vector used to insert the *Euglena gracilis* delta-9 elongase yielding pY119) were transformed into *Saccharomyces cerevisiae* INVSC1 (Invitrogen Corporation) using standard lithium acetate transformation procedures. Transformants were selected on DOBA media supplemented with CSM-leu (Qbiogene, Carlsbad, Calif.). Transformants from each plate were inoculated into 2 mL of DOB medium supplemented with CSM-leu (Qbiogene) and 0.2% tergitol. Cells were grown for 1 day at 30° C. after which, 0.1 mL was transferred to 3 mL of the same medium supplemented with either linoleic acid [LA-18:2(9,12)], α-linolenic acid [ALA-18:3(9,12,15)], γ-linolenic acid [GLA-18:3(6,9,12)], stearidonic acid [STA-18:4(6,9,12,15)], arachiconic acid [AA-20:4(5,8,11,14)] or eicosapentaenoic acid [EPA-20:5(5,8,11,14,17)] to 0.175 mM. These were incubated for 16 h at 30° C., 250 rpm and then pellets were obtained by centrifugation. Cells were washed once with water, pelleted by centrifugation and air dried. Pellets were transesterified (Roughan, G., and Nishida I. *Arch Biochem Biophys.* 276(1):38-46 (1990)) with 500 μL of 1% sodium methoxide for 30 min. at 50° C. after which 500 μL of 1M sodium chloride and 100 μL of heptane were added. After thorough mixing and centrifugation, fatty acid methyl esters (FAMEs) were analyzed by GC as described supra. Results for feeding cells containing pY75 (vector control) or pY119 (3 independent transformants;

pY119-5, pY119-6, pY119-8) are shown in FIG. 14. The elongation efficiency (% Elo) was calculated for each fatty acid fed as [% $FA_{product}$/(% $FA_{product}$+% $FA_{substrate}$)×100].

The data in FIG. 14 demonstrated that the cloned *Euglena gracilis* delta-9 elongase efficiently elongated linoleic acid [LA-18:2(9,12)] and α-linolenic acid [ALA-18:3(9,12,15)] to eicosadienoic acid [EDA-20:2(11,14)] and eicosatrienoic acid [ETrA-20:3(11,14,17)], respectively.

Additionally, FAMEs from cells where no fatty acid had been fed were analyzed by GC using slightly different temperature profiles in order to achieve separation of oleic acid [OA-18:1(9)] and vaccenic acid [VA-18:1(11)], the elongation product of palmitoleic acid-[PA-16:1(9)] elongation. Fatty acid methyl esters (3 μL injected from hexane layer) were separated and quantified using a Hewlett-Packard 6890 Gas Chromatograph fitted with an Omegawax 320 fused silica capillary column (Supelco Inc., Cat. No. 24152). The oven temperature was programmed to hold at 200° C. for 2.7 min, increase to 240° C. at 20° C./min and then hold for an additional 2.3 min. Results are shown in Table 5.

TABLE 5

Lipid Profiles Having No Exogenous Fatty Acid Added

| Sample Name | 16:0 | 16:1 (9) | 18:0 | 18:1 (9) | 18:1 (11) | % Elo 16:0 | % Elo 16:1 |
|---|---|---|---|---|---|---|---|
| pY75 | 13.1 | 54.7 | 3.5 | 27.6 | 1.2 | 20.9 | 2.1 |
| pY119-5 | 12.9 | 55.6 | 3.6 | 26.0 | 1.8 | 21.6 | 3.2 |
| pY119-6 | 13.4 | 54.0 | 3.6 | 27.3 | 1.6 | 21.2 | 3.0 |
| pY119-8 | 12.7 | 53.3 | 3.5 | 29.0 | 1.5 | 21.7 | 2.8 |

Example 21

Functional Analysis of the *Euglena gracilis* Delta-9 Elongase in *Yarrowia lipolytica*

A uracil ura3 auxotrophic strain of *Yarrowia lipolytica* (strain Y2224) was used for functional assays. *Yarrowia lipolytica* (ATCC Accession No. 20362) cells from a YPD plate were streaked onto a minimal medium plate (75 mg/L each of uracil and uridine, 6.7 g/L YNB with ammonia sulfate, without amino acid, and 20 g/L glucose) containing 250 mg/L 5-FOA (Zymo Research). Plates were incubated at 28° C. and four of the resulting colonies were patched separately onto minimal medium plates containing 200 mg/mL 5-FOA and minimal medium plates lacking uracil and uridine to confirm uracil ura3 auxotrophy.

*Yarrowia lipolytica* strain Y2224 was grown at 28° C. on YPD agar (1% yeast extract, 2% bactopeptone, 2% glucose, 2% agar). For selection of transformants, minimal medium (0.17% yeast nitrogen base (DIFCO Laboratories, Detroit, Mich.) without ammonium sulfate or amino acids, 2% glucose, 0.1% proline, pH 6.1) was used. Supplements of adenine, leucine, lysine and/or uracil are added to a final concentration of 0.01%.

Transformation of *Yarrowia lipolytica* pBY1-FAE, containing the *Isochrysis galbana* delta-9 elongase (SEQ ID NO:27), and pBY2, containing the *Euglena gracilis* delta-9 elongase were transformed into *Yarrowia lipolytica* strain Y2224 as described in the General Methods.

Briefly, *Yarrowia lipolytica* Strain #2224 was streaked onto a YPD plate and grown at 30° C. for approximately 18 h. Several large loopfuls of cells were scraped from the plate and resuspended in 1 mL of transformation buffer containing:

2.25 mL of 50% PEG, average MW 3350;
0.125 mL of 2 M Li acetate, pH 6.0;
0.125 mL of 2M DTT; and
50 μg sheared salmon sperm DNA.

About 500 ng of pBY1-FAE or pBY2 plasmid DNA was incubated in 100 μL of resuspended cells, and maintained at 39° C. for 1 h with vortex mixing at 15 min intervals. The cells were plated onto minimal media plates lacking uracil and maintained at 30° C. for 2 to 3 days Single colonies of transformant *Yarrowia lipolytica* containing pBY1-FAE or pBY2 were grown in 3 mL minimal media lacking uracil at 30° C. to an $OD_{600}$ ~1.0. Y2224 was also grown in a similar way on minimal media supplemented with uracil. Cells were subsequently washed with water, collected by centrifugation and lipids transesterified as described supra. FAMEs from cells containing pBY1-FAE or pBY2 were analyzed by GC as were those for cells containing pY119 in Example 13. Results for the average of three replications of each are shown in Table 6.

TABLE 6

Comparison of Lipid Profiles of *Yarrowis* Expressing Delta-9 Elongases

| Sample Name | 16:0 | 16:1 (9) | 17.1 (9) | 18:0 | 18:1 (9) | LA | EDA | % Elo LA |
|---|---|---|---|---|---|---|---|---|
| Y2224-1 | 13.4 | 12.6 | 0.8 | 2.8 | 43.1 | 27.2 | 0.1 | 0.2 |
| Y2224-2 | 12.2 | 12.3 | 0.8 | 2.3 | 46.1 | 26.2 | 0.1 | 0.2 |
| Y2224-3 | 11.7 | 10.8 | 1.1 | 2.8 | 48.4 | 25.0 | 0.1 | 0.2 |
| pBY1-FAE-1 | 11.9 | 11.9 | 0.8 | 3.1 | 50.6 | 20.2 | 1.6 | 7.5 |
| pBY1-FAE-2 | 12.9 | 11.4 | 0.9 | 3.6 | 46.7 | 23.0 | 1.4 | 5.9 |
| pBY1-FAE-3 | 12.1 | 12.5 | 0.8 | 3.2 | 50.0 | 19.8 | 1.6 | 7.4 |
| pBY2-1 | 12.3 | 11.7 | 0.8 | 3.4 | 48.4 | 21.1 | 2.2 | 9.5 |
| pBY2-2 | 12.1 | 12.5 | 0.8 | 3.2 | 50.1 | 19.1 | 2.3 | 10.6 |
| pBY2-3 | 12.1 | 12.2 | 0.8 | 3.3 | 50.0 | 19.4 | 2.1 | 9.9 |

Example 22

Cloning Other Delta-8 Desaturases or Elongases into Soybean Expression Vectors In addition to the delta-8 desaturase or delta-9 elongase from *Euglena gracilis*, other delta-8 desaturases or delta-9 elongases can be cloned into the soybean expression vectors described in the preceding Examples. For instance, a suitable delta-8 desaturase or delta-9 elongase from an organism other than *Euglena gracilis* can be cloned using methods similar to, but not limited to, the methods described herein. PCR primers designed to introduce NotI sites at the 5' and 3' ends of the delta-8 desaturase can be used to amplify the gene. The resulting PCR product can then be digested with NotI and can be cloned into a suitable soybean expression vector containing a NotI site flanked by a strong seed-specific promoter and a transcription terminator. Further sub-cloning into other vectors such as those described herein, or in WO 04/071467 or WO 05/047479, but not limited to these, should yield vectors suitable for expression and co-expression of the delta-8 desaturase and or delta-9 elongase in soybean.

Example 23

Co-Expressing Delta-5 Elongases and Delta-4 Desaturases

Delta-4 desaturases or delta-5 elongases can also be co-expressed in soybean expression vectors similar to those described herein. For instance, a delta-4 desaturase from *Schizochytrium aggregatum* (WO 02/090493) or a delta-5 elongase (EPA elongase or $C_{20/22}$ elongase) from *Pavlova* (WO 04/071467), can be cloned into suitable soybean expression vectors such as those described in WO 04/071467. PCR primers designed to introduce NotI sites at the 5' and 3' ends of the delta-4 desaturase or delta-5 elongase can be used to amplify the gene. The resulting PCR product can then be digested with NotI and can be cloned into a suitable soybean expression vector containing a NotI site flanked by a strong seed-specific promoter and a transcription terminator. Further sub-cloning into other vectors such as those described herein, or in WO 04/071467 or WO 05/047479, but not limited to these, should yield vectors suitable for expression and co-expression of the delta-4 desaturase and or delta-5 elongase in soybean.

Example 24

Transformation of Somatic Soybean Embryo Cultures

Please also see Example 30.

Culture Conditions:

Soybean embryogenic suspension cultures (cv. Jack) can be maintained in 35 mL liquid medium SB196 (see recipes below) on rotary shaker, 150 rpm, 26° C. with cool white fluorescent lights on 16:8 h day/night photoperiod at light intensity of 60-85 µE/m2/s. Cultures are subcultured every seven days to two weeks by inoculating approximately 35 mg of tissue into 35 mL of fresh liquid SB196 (the preferred subculture interval is every seven days).

Soybean embryogenic suspension cultures can be transformed with the plasmids and DNA fragments described earlier by the method of particle gun bombardment (Klein et al., *Nature* (London) 327:70-73 (1987); U.S. Pat. No. 4,945,050). A DuPont Biolistic™ PDS1000/HE instrument (helium retrofit) would be used for all transformations.

Soybean Embryogenic Suspension Culture Initiation:

Soybean cultures are initiated twice each month with five-seven days between each initiation. Pods with immature seeds from available soybean plants 45-55 days after planting are picked, removed from their shells and placed into a sterilized magenta box. The soybean seeds are sterilized by shaking them for 15 min in a 5% Clorox solution with 1 drop of ivory soap (95 mL of autoclaved distilled water plus 5 mL Clorox and 1 drop of soap—mix well. Seeds are rinsed using 2 1-liter bottles of sterile distilled water and those less than 4 mm were placed on individual microscope slides. The small end of the seed is cut and the cotyledons pressed out of the seed coat. Cotyledons are transferred to plates containing SB1 medium (25-30 cotyledons per plate). Plates are wrapped with fiber tape and stored for eight weeks. After this time secondary embryos are cut and placed into SB196 liquid media for seven days.

Preparation of DNA for Bombardment:

Either an intact plasmid or a DNA plasmid fragment containing the genes of interest and the selectable marker gene can be used for bombardment. Fragments from plasmids such pKR274 (ATCC Accession No. PTA-4988) and pKR685 (ATCC Accession No. PTA-6047) or pKR681 (ATCC Accession No. PTA-6046) and/or other expression plasmids can be obtained by gel isolation of digested plasmids. In each case, 100 µg of plasmid DNA can be used in 0.5 mL of the specific enzyme mix described below. Plasmids could be digested with AscI (100 units) in NEBuffer 4 (20 mM Tris-acetate, 10 mM magnesium acetate, 50 mM potassium acetate, 1 mM dithiothreitol, pH 7.9), 100 µg/mL BSA, and 5 mM beta-mercaptoethanol at 37° C. for 1.5 h. The resulting DNA fragments could be separated by gel electrophoresis on 1% SeaPlaque® GTG agarose (BioWhitaker Molecular Applications) and the DNA fragments containing EPA biosynthetic genes could be cut from the agarose gel. DNA can be purified from the agarose using the GELase® digesting enzyme following the manufacturer's protocol. Alternatively, whole plasmids or a combination of whole plasmid with fragment could be used.

A 50 µL aliquot of sterile distilled water containing 3 mg of gold particles (3 mg gold) can be added to 5 µL of a 1 µg/µL DNA solution (either intact plasmid or DNA fragment prepared as described above), 50 µL 2.5M $CaCl_2$ and 20 µL of 0.1 M spermidine. The mixture is shaken 3 min on level 3 of a vortex shaker and spun for 10 sec in a bench microfuge. After a wash with 400 µL 100% ethanol the pellet is suspended by sonication in 40 µL of 100% ethanol. Five µL of DNA suspension is dispensed to each flying disk of the Biolistic PDS1000/HE instrument disk. Each 5 µL aliquot contained approximately 0.375 mg gold per bombardment (e.g., per disk). Tissue Preparation and Bombardment with DNA:

Approximately 150-200 mg of seven day old embryonic suspension cultures are placed in an empty, sterile 60×15 mm petri dish and the dish is covered with plastic mesh. Tissue is bombarded one or two shots per plate with membrane rupture pressure set at 1100 PSI and the chamber is evacuated to a vacuum of 27-28 inches of mercury. Tissue is placed approximately 3.5 inches from the retaining/stopping screen.

Selection of Transformed Embryos:

Transformed embryos are selected either using hygromycin (when the hygromycin B phosphotransferase (HPT) gene was used as the selectable marker) or chlorsulfuron (when the acetolactate synthase (ALS) gene was used as the selectable marker).

Hygromycin (HPT) Selection:

Following bombardment, the tissue is placed into fresh SB196 media and cultured as described above. Six days post-bombardment, the SB196 is exchanged with fresh SB196 containing a selection agent of 30 mg/L hygromycin. The selection media is refreshed weekly. Four to six weeks post selection, green, transformed tissue may be observed growing from untransformed, necrotic embryogenic clusters. Isolated, green tissue is removed and inoculated into multiwell plates to generate new, clonally propagated, transformed embryogenic suspension cultures.

Chlorsulfuron (ALS) Selection:

Following bombardment, the tissue is divided between two flasks with fresh SB196 media and cultured as described above. Six to seven days post-bombardment, the SB196 is exchanged with fresh SB196 containing selection agent of 100 ng/mL chlorsulfuron. The selection media is refreshed weekly. Four to six weeks post selection, green, transformed tissue may be observed growing from untransformed, necrotic embryogenic clusters. Isolated, green tissue is removed and inoculated into multiwell plates containing SB196 to generate new, clonally propagated, transformed embryogenic suspension cultures.

Regeneration of Soybean Somatic Embryos into Plants:

In order to obtain whole plants from embryogenic suspension cultures, the tissue needs to be regenerated.

Embryo Maturation:

Embryos can be cultured for four-six weeks at 26° C. in SB196 under cool white fluorescent (Phillips cool white Econowatt F40/CW/RS/EW) and Agro (Phillips F40 Agro) bulbs (40 watt) on a 16:8 h photoperiod with light intensity of 90-120 µE/m2/s. After this time embryo clusters are removed to a solid agar media, SB166, for one-two weeks. Clusters are then subcultured to medium SB103 for three weeks. During this period, individual embryos can be removed from the clusters and screened for alterations in their fatty acid compositions as described supra. It should be noted that any detectable phenotype, resulting from the expression of the genes of interest, could be screened at this stage. This detectable phenotype would include, but not be limited to, alterations in fatty acid profile, protein profile and content, carbohydrate content, growth rate, viability, or the ability to develop normally into a soybean plant.

Embryo Desiccation and Germination:

Matured individual embryos can be desiccated by placing them into an empty, small petri dish (35×10 mm) for approximately four-seven days. The plates are sealed with fiber tape (creating a small humidity chamber). Desiccated embryos can be planted into SB71-4 medium where they are left to germinate under the same culture conditions described above. Germinated plantlets are removed from germination medium and rinsed thoroughly with water and then planted in Redi-Earth in 24-cell pack tray, covered with clear plastic dome. After two weeks the dome is removed and plants hardened off for a further week. If plantlets look hardy they are transplanted to a 10 inch pot of Redi-Earth with up to 3 plantlets per pot. After ten to sixteen weeks, mature seeds can be harvested, chipped and analyzed for fatty acids as described above.

Media Recipes:

SB 196 - FN Lite Liquid Proliferation Medium (per liter)

| | |
|---|---|
| MS FeEDTA - 100x Stock 1 | 10 mL |
| MS Sulfate - 100x Stock 2 | 10 mL |
| FN Lite Halides - 100x Stock 3 | 10 mL |
| FN Lite P, B, Mo - 100x Stock 4 | 10 mL |
| B5 vitamins (1 mL/L) | 1.0 mL |
| 2,4-D (10 mg/L final concentration) | 1.0 mL |
| $KNO_3$ | 2.83 gm |
| $(NH_4)_2SO_4$ | 0.463 gm |
| asparagine | 1.0 gm |
| sucrose (1%) | 10 gm |
| pH 5.8 | |

FN Lite Stock Solutions

| Stock Number | 1000 mL | 500 mL |
|---|---|---|
| 1 - MS Fe EDTA 100x Stock | | |
| $Na_2$ EDTA* | 3.724 g | 1.862 g |
| $FeSO_4$—$7H_2O$ | 2.784 g | 1.392 g |
| 2 - MS Sulfate 100x stock | | |
| $MgSO_4$—$7H_2O$ | 37.0 g | 18.5 g |
| $MnSO_4$—$H_2O$ | 1.69 g | 0.845 g |
| $ZnSO_4$—$7H_2O$ | 0.86 g | 0.43 g |
| $CuSO_4$—$5H_2O$ | 0.0025 g | 0.00125 g |
| 3 - FN Lite Halides 100x Stock | | |
| $CaCl_2$—$2H_2O$ | 30.0 g | 15.0 g |
| KI | 0.083 g | 0.0715 g |
| $CoCl_2$—$6H_2O$ | 0.0025 g | 0.00125 g |
| 4 - FN Lite P, B, Mo 100x Stock | | |
| $KH_2PO_4$ | 18.5 g | 9.25 g |
| $H_3BO_3$ | 0.62 g | 0.31 g |
| $Na_2MoO_4$—$2H_2O$ | 0.025 g | 0.0125 g |

SB1 Solid Medium (per liter)

1 package MS salts (Gibco/BRL - Cat. No. 11117-066)
1 mL B5 vitamins 1000X stock
31.5 g sucrose -continued Media Recipes:

2 mL 2,4-D (20 mg/L final concentration)
pH 5.7
8 g TC agar

SB 166 Solid Medium (per liter)

1 package MS salts (Gibco/BRL - Cat. No. 11117-066)
1 mL B5 vitamins 1000X stock
60 g maltose
750 mg $MgCl_2$ hexahydrate
5 g activated charcoal
pH 5.7
2 g gelrite SB 103 Solid Medium (per liter)

1 package MS salts (Gibco/BRL - Cat. No. 11117-066)
1 mL B5 vitamins 1000X stock
60 g maltose
750 mg MgCl2 hexahydrate
pH 5.7
2 g gelrite SB 71-4 Solid Medium (per liter)

1 bottle Gamborg's B5 salts w/sucrose (Gibco/BRL - Cat. No. 21153-036)
pH 5.7
5 g TC agar 2,4-D Stock Obtain premade from Phytotech Cat. No. D 295 - concentration 1 mg/mL B5 Vitamins Stock (per 100 mL)

Store aliquots at −20° C.
10 g myo-inositol
100 mg nicotinic acid
100 mg pyridoxine HCl
1 g thiamine
If the solution does not dissolve quickly enough, apply a low level of heat via the hot stir plate.

Chlorsulfuron Stock 1 mg/mL in 0.01N Ammonium Hydroxide

*Add first, dissolve in dark bottle while stirring

To induce somatic embryos, cotyledons, 3-5 mm in length dissected from surface sterilized, immature seeds of the soybean cultivar A2872, can be cultured in the light or dark at 26° C. on an appropriate agar medium for six-ten weeks. Somatic embryos, which produce secondary embryos, are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 h day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al., *Nature* (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a recombinant DNA construct composed of the 35S promoter from Cauliflower Mosaic Virus (Odell et al., *Nature* 313:810-812 (1985)), the hygromycin B phosphotransferase gene from plasmid pJR225 (from *E. coli*; Gritz et al., *Gene* 25:179-188 (1983)) and the 3' region of the nopaline synthase gene from the T-DNA of the Ti plasmid of *Agrobacterium tumefaciens*. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL $CaCl_2$ (2.5 M). The particle preparation is then agitated for three minutes, spun in a microfuge for 10 sec and the supernatant removed. The DNA-coated particles are then washed once in 400 μL 70% ethanol and resuspended in 40 μL of anhydrous ethanol. The DNA/particle suspension can be sonicated three times for one sec each. Five μL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately five-ten plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 25

Synthesis and Functional Expression of a Codon-Optimized Delta-9 Elongase Gene (Derived from *Euglena gracilis*) in *Yarrowia lipolytica*

The codon usage of the delta-9 elongase gene of *Euglena gracilis* (SEQ ID NOs:3 and 4) is optimized for expression in *Yarrowia lipolytica*, in a manner similar to that described in Example 4 (supra) and PCT Publication No. WO 2004/101753. Specifically, a codon-optimized delta-9 elongase gene (designated “EgD9S”), SEQ ID NO:90) is designed, based on the coding sequence of the delta-9 elongase of the instant invention (clone eeg1c.pk001.n5.f), according to the *Yarrowia* codon usage pattern (PCT Publication No. WO 2004/101753), the consensus sequence around the ‘ATG’ translation initiation codon, and the general rules of RNA stability (Guhaniyogi, G. and J. Brewer, *Gene* 265(1-2):11-23 (2001)). In addition to the modification of the translation initiation site, 117 bp of the 777 bp coding region are modified (15.1%) and 106 codons are optimized (40.9%). None of the modifications in the codon-optimized gene change the amino acid sequence of the encoded protein (SEQ ID NO:5). The designed EgD9 gene can be synthesized by GenScript Corporation (Piscataway, N.J.) and can be cloned into pUC57 (GenBank Accession No. Y14837) to generate pEgD9S.

Subsequent to the writing of this Example in the Provisional Application, the work describing the preparation codon-optimized *Euglena gracilis* delta-9 elongase gene (designated “EgD9S”) was done and is described in Example 36 below.

Example 26

Cloning the *Euglena gracilis* Delta-8 Desaturase into a Soybean Expression Vector and Co-Expression with the *Euglena gracilis* Delta-9 Elongase Plasmid pKR680 (SEQ ID NO:43) was digested with BsiWI and the fragment containing *Euglena gracilis* delta-8 desaturase (Eg5) (SEQ ID NO:16) was cloned into the BsiWI site of pKR912 (SEQ ID NO:37) to produce pKR920 (SEQ ID NO:91). A schematic depiction of pK920 is shown in FIG. 17. In this way, the *Euglena gracilis* delta-8 desaturase (called eug d8-sq5 in FIG. 17) was co-expressed with the *Euglena gracilis* delta-9 elongase (called eug el1 in FIG. 17) behind strong, seed-specific promoters.

Example 27

Cloning the *Euglena gracilis* Delta-9 Elongase into an *Arabidopsis thaliana* Binary Expression Vector (pKR926)

Various restriction sites were added, through a number of cloning steps, to the ends of the Bcon/NotI/Phas3' cassette from KS123, which was previously described in PCT Publication No. WO 02/008269 (the contents of which are hereby incorporated by reference). Briefly, a DNA fragment (cal a24-4; SEQ ID NO:92) was amplified from plasmid CalFad2-2 (described in PCT Publication No. WO 01/12800) using primers oCal-15 (SEQ ID NO:93) and oCal-6 (SEQ ID NO:94). DNA fragment cal a24-4 was digested with BglII and BamHI and cloned into the BamHI site of pKS123 to give pKR53B (SEQ ID NO:95). The XbaI/SbfI fragment of pKR53B, containing the Bcon/NotI/Phas3' cassette was cloned into the XbaI/SbfI fragment of pKR72, containing the bacterial hygromycin phosphotransferase gene, to give pKR85 (SEQ ID NO:96).

The Bcon/NotI/Phas3' cassette was amplified from plasmid pKR85 using primers oKR85-1 (SEQ ID NO:97) and oKR85-2 (SEQ ID NO:98) and the resulting DNA fragment was cloned into PCR-Script® (Stratgene) following the manufacture’s protocol, to give pPCR85 (SEQ ID NO:99).

The EcoRI/BglII fragment of pPCR85, containing the Bcon/NotI/Phas3' cassette was cloned into the EcoRI/BamHI fragment of plasmid pZS199 (PCT Publication No. WO 93/11245 (also U.S. Pat. No. 5,952,544) which was published on Jun. 10, 1993, the disclosures of which are hereby incorporated by reference), containing the *Arabidopsis* binary vector backbone to produce pKR91 (SEQ ID NO:100).

The Bcon/NotI/Phas3' cassette was removed from pKR91 by digestion with AscI and the re-ligated binary vector containing a unique AscI cloning site was produced called pKR92 (SEQ ID NO:101).

The AscI fragment of pKR911 (SEQ ID NO:40; Example 11), containing the *Euglena gracilis* delta-9 elongase was cloned into the AscI site of pKR92 to give pKR926 (SEQ ID NO:102). A schematic depiction of pK926 is shown in FIG. 18. In this way, the *Euglena gracilis* delta-9 elongase (called eug el1 in FIG. 18) was expressed in *Arabidopsis* behind the soybean beta-conglycinin promoter. The soybean beta-conglycinin promoter functions as a strong, seed-specific promoter in *Arabidopsis* (see U.S. application Ser. No. 11/258,704).

Example 28

Cloning the *Mortierella alpina* Delta-5 Desaturase into a Soybean Expression Vector and Co-Expression with the *Euglena gracilis* Delta-9 Elongase and the *Euglena gracilis* Delta-8 Desaturase (pKR916)

A soybean expression vector containing the *Euglena gracilis* delta-8 desaturase (SEQ ID NO:16), the *Euglena gracilis* delta-9 elongase (SEQ ID NO:4) and the *Mortierella alpina* delta-5 desaturase (SEQ ID NO:88), which is described in U.S. Pat. No. 6,075,183 and PCT Publication Nos. WO 04/071467 and WO 05/0479479 (the contents of which are hereby incorporated by reference), all under the control of strong seed-specific promoters, was constructed in the following way.

The Gy1/Mad5/legA2 cassette was released from pKR767 (SEQ ID NO:103) by digestion with SbfI and the resulting fragment was cloned into the SbfI site of pKR913 (SEQ ID NO:44; Example 13) to produce pKR916 (SEQ ID NO:104). A schematic depiction of pKR916 is shown in FIG. 19. In this way, the *Euglena gracilis* delta-9 elongase (called eug el1 in FIG. 19) was co-expressed with the *Euglena gracilis* delta-8 desaturase (called eug d8-sq5 in FIG. 19) and the *Mortierella alpina* delta-5 desaturase (called DELTA 5 DESATURASE M ALPINA in FIG. 19) behind strong, seed specific promoters.

Example 29

Co-Expressing the *Saprolegnia diclina* Delta-17 Desaturase with the *Fusarium moniliforme* Delta-15 Desaturase (pKR873)

Plasmid pKR873 (SEQ ID NO:56; FIG. 12) was produced in the following way. The SA/NotI/SA3' cassette was amplified from plasmid pKR132 (SEQ ID NO:57, which is described in PCT Publication No. WO 04/071467) using PCR. Primer oSAIb-9 (SEQ ID NO:23) was designed to introduce XbaI and BsiWI sites at the 5' end of the promoter and primer oSAIb-2 (SEQ ID NO:24) was designed to introduce BsiWI and XbaI sites at the 3' end of the terminator. The resulting PCR fragment was subsequently cloned into pCR-Script AMP SK(+) (Stratagene Company, San Diego, Calif.) to produce pKR160 (SEQ ID NO:58).

Plasmid pKR160 was then digested with BsiWI and the SA/NotI/SA3' cassette ligated into the BsiWI site of pKR124 (SEQ ID NO:59, which is described in PCT Publication No. WO 05/0479479) to produce pKR163 (SEQ ID NO:60). The NotI fragment from pY34 (SEQ ID NO:61, which is described in PCT Publication No. WO 05/0479479), containing the *Fusarium moniliforme* delta-15 desaturase, was cloned into the NotI site of pKR163 (SEQ ID NO:60) to produce pKR863 (SEQ ID NO:62). The SA/Fusd15/SA3' cassette was released from plasmid pKR863 by digestion with BsiWI and was cloned into the BsiWI site of plasmid pKR226 (SEQ ID NO:50, which is described in PCT Publication No. WO 04/071467), containing the ALS gene for selection, the T7prom/hpt/T7term cassette and the bacterial on region, to produce pKR869 (SEQ ID NO:63). Plasmid pKR271 (SEQ ID NO:49, which is described in PCT Publication No. WO 04/071467) was digested with PstI and the fragment containing the *Saprolegnia diclina* delta-17 desaturase was cloned into the SbfI site of pKR869 (SEQ ID NO:63) to produce pKR873 (SEQ ID NO:56). In this way, the *Fusarium moniliforme* delta-15 desaturase was co-expressed with the *Saprolegnia diclina* delta-17 desaturase behind strong, seed-specific promoters. A schematic depiction of pKR873 is shown in FIG. 12.

Example 30

Transformation of Somatic Soybean Embryo Cultures with Soybean Expression Vectors Culture Conditions:

Soybean embryogenic suspension cultures (cv. Jack) were maintained in 35 mL liquid medium SB196 (infra) on a rotary shaker, 150 rpm, 26° C. with cool white fluorescent lights on 16:8 hr day/night photoperiod at light intensity of 60-85 μE/m2/s. Cultures were subcultured every 7 days to two weeks by inoculating approximately 35 mg of tissue into 35 mL of fresh liquid SB196 (the preferred subculture interval is every 7 days).

Soybean embryogenic suspension cultures were transformed with the soybean expression plasmids by the method of particle gun bombardment (Klein et al., *Nature,* 327:70 (1987)) using a DuPont Biolistic PDS1000/HE instrument (helium retrofit) for all transformations.

Soybean Embryogenic Suspension Culture Initiation:

Soybean cultures were initiated twice each month with 5-7 days between each initiation. Pods with immature seeds from available soybean plants were picked 45-55 days after planting. Seeds were removed from the pods and placed into a sterilized magenta box. The soybean seeds were sterilized by shaking them for 15 min in a 5% Clorox solution with 1 drop of ivory soap (i.e., 95 mL of autoclaved distilled water plus 5 mL Clorox and 1 drop of soap, mixed well). Seeds were rinsed using 2 1-liter bottles of sterile distilled water and those less than 4 mm were placed on individual microscope slides. The small end of the seed was cut and the cotyledons pressed out of the seed coat. When cultures were being prepared for production transformation, cotyledons were transferred to plates containing SB1 medium (25-30 cotyledons per plate). Plates were wrapped with fiber tape and were maintained at 26° C. with cool white fluorescent lights on 16:8 h day/night photoperiod at light intensity of 60-80 μE/m2/s for eight weeks, with a media change after 4 weeks. When cultures were being prepared for model system experiments, cotyledons were transferred to plates containing SB199 medium (25-30 cotyledons per plate) for 2 weeks, and then transferred to SB1 for 2-4 weeks. Light and temperature conditions were the same as described above. After incubation on SB1 medium, secondary embryos were cut and placed into SB196 liquid media for 7 days.

Preparation of DNA for Bombardment:

Either an intact plasmid or a DNA plasmid fragment containing the genes of interest and the selectable marker gene were used for bombardment. Fragments from soybean expression plasmids, the construction of which is described herein, were obtained by gel isolation of digested plasmids. In each case, 100 μg of plasmid DNA was used in 0.5 mL of the specific enzyme mix described below. Plasmids were digested with AscI (100 units) in NEBuffer 4 (20 mM Tris-acetate, 10 mM magnesium acetate, 50 mM potassium acetate, 1 mM dithiothreitol, pH 7.9), 100 μg/mL BSA, and 5 mM beta-mercaptoethanol at 37° C. for 1.5 hr. The resulting DNA fragments were separated by gel electrophoresis on 1% SeaPlaque GTG agarose (BioWhitaker Molecular Applications) and the DNA fragments containing gene cassettes were cut from the agarose gel. DNA was purified from the agarose using the GELase digesting enzyme following the manufacturer's protocol.

A 50 μL aliquot of sterile distilled water containing 3 mg of gold particles (3 mg gold) was added to 30 μL of a 10 ng/μL DNA solution (either intact plasmid or DNA fragment prepared as described herein), 25 μL 5M $CaCl_2$ and 20 μL of 0.1 M spermidine. The mixture was shaken 3 min on level 3 of a vortex shaker and spun for 10 sec in a bench microfuge. The supernatant was removed, followed by a wash with 400 μL 100% ethanol and another brief centrifugation. The 400 ul ethanol was removed and the pellet was resuspended in 40 μL of 100% ethanol. Five μL of DNA suspension was dispensed to each flying disk of the Biolistic PDS1000/HE instrument disk. Each 5 μL aliquot contained approximately 0.375 mg gold per bombardment (e.g., per disk).

For model system transformations, the protocol was identical except for a few minor changes (ie, 1 mg of gold particles was added to 5 μL of a 1 μg/μL DNA solution, 50 μL of a 2.5M $CaCl_2$ was used and the pellet was ultimately resuspended in 85 μL of 100% ethanol thus providing 0.058 mg of gold particles per bombardment).

Tissue Preparation and Bombardment with DNA:

Approximately 150-200 mg of seven day old embryogenic suspension cultures was placed in an empty, sterile 60×15 mm petri dish and the dish was covered with plastic mesh. The chamber was evacuated to a vacuum of 27-28 inches of mercury, and tissue was bombarded one or two shots per plate with membrane rupture pressure set at 1100 PSI. Tissue was placed approximately 3.5 inches from the retaining/stopping screen. Model system transformation conditions were identical except 100-150 mg of embryogenic tissue was used, rupture pressure was set at 650 PSI and tissue was place approximately 2.5 inches from the retaining screen.

Selection of Transformed Embryos:

Transformed embryos were selected either using hygromycin (when the hygromycin B phosphotransferase (HPT) gene was used as the selectable marker) or chlorsulfuron (when the acetolactate synthase (ALS) gene was used as the selectable marker).

Following bombardment, the tissue was placed into fresh SB196 media and cultured as described above. Six to eight days post-bombardment, the SB196 was exchanged with fresh SB196 containing either 30 mg/L hygromycin or 100 ng/mL chlorsulfuron, depending on the selectable marker used. The selection media was refreshed weekly. Four to six weeks post-selection, green, transformed tissue was observed growing from untransformed, necrotic embryogenic clusters. Isolated, green tissue was removed and inoculated into multiwell plates to generate new, clonally propagated, transformed embryogenic suspension cultures.

Embryo Maturation:

Transformed embryogenic clusters from production transformation were cultured for four-six weeks (one-three weeks for model system) in multiwell plates as described above at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 $\mu E/m^2s$. After this time embryo clusters were removed to a solid agar media, SB166, for one-two weeks (1 week for model system) and then subcultured to SB103 medium for 3-4 weeks to mature embryos. After maturation on plates in SB103, individual embryos were removed from the clusters, dried and screened for alterations in their fatty acid compositions as described supra. When desired, plants were obtained from some events as described below.

Alternatively, in some model system experiments, embryos were matured in soybean histodifferentiation and maturation liquid medium (SHaM liquid media; Schmidt et al., *Cell Biology and Morphogenesis* 24:393 (2005)) using a modified procedure. Briefly, after 4 weeks of selection in SB196 as described above, embryo clusters were removed to 35 mL of SB228 (SHaM liquid media) in a 250 mL Erlenmeyer flask. Tissue was maintained in SHaM liquid media on a rotary shaker at 130 rpm and 26° C. with cool white fluorescent lights on a 16:8 hr day/night photoperiod at a light intensity of 60-85 μE/m2/s for 2-3 weeks as embryos matured. Embryos grown for 2-3 weeks in SHaM liquid media were equivalent in size and fatty acid content to embryos cultured on SB166/SB103 for 5-8 weeks.

After maturation in SHaM liquid media, individual embryos were removed from the clusters, dried and screened for alterations in their fatty acid compositions as described supra. When desired, plants were obtained from some events as described below.

Embryo Desiccation and Germination:

Matured individual embryos were desiccated by placing them into an empty, small petri dish (60×15 mm) for approximately four-seven days. The plates were sealed with fiber tape (creating a small humidity chamber). Desiccated embryos were planted into SB71-4 medium where they were left to germinate under the same culture conditions described above. Germinated plantlets were removed from germination medium and rinsed thoroughly with water and then planted in Redi-Earth in a 24-cell pack tray, and covered with a clear plastic dome. After one-two weeks the dome was removed and plants hardened off for a further week. If plantlets look hardy they were transplanted to a 10 inch pot of Redi-Earth with up to 3 plantlets per pot. After ten to sixteen weeks, mature seeds were harvested, chipped and analyzed for fatty acids as described herein.

| Media Recipes: | |
|---|---|
| SB 196 - FN Lite Liquid Proliferation Medium (per liter) | |
| MS FeEDTA - 100x Stock 1 | 10 mL |
| MS Sulfate - 100x Stock 2 | 10 mL |
| FN Lite Halides - 100x Stock 3 | 10 mL |
| FN Lite P, B, Mo - 100x Stock 4 | 10 mL |
| B5 vitamins (1 mL/L) | 1.0 mL |
| 2,4-D (10 mg/L final concentration) | 1.0 mL |
| $KNO_3$ | 2.83 gm |
| $(NH_4)_2SO_4$ | 0.463 gm |
| asparagine | 1.0 gm |
| sucrose (1%) | 10 gm |
| pH 5.8 | |

-continued

Media Recipes:

FN Lite Stock Solutions

| Stock Number | 1000 mL | 500 mL |
|---|---|---|
| 1 MS Fe EDTA 100x Stock | | |
| $Na_2$ EDTA* | 3.724 g | 1.862 g |
| $FeSO_4$—$7H_2O$ | 2.784 g | 1.392 g |
| 2 MS Sulfate 100x stock | | |
| $MgSO_4$—$7H_2O$ | 37.0 g | 18.5 g |
| $MnSO_4$—$H_2O$ | 1.69 g | 0.845 g |
| $ZnSO_4$—$7H_2O$ | 0.86 g | 0.43 g |
| $CuSO_4$—$5H_2O$ | 0.0025 g | 0.00125 g |
| 3 FN Lite Halides 100x Stock | | |
| $CaCl_2$—$2H_2O$ | 30.0 g | 15.0 g |
| KI | 0.083 g | 0.0715 g |
| $CoCl_2$—$6H_2O$ | 0.0025 g | 0.00125 g |
| 4 FN Lite P, B, Mo 100x Stock | | |
| $KH_2PO_4$ | 18.5 g | 9.25 g |
| $H_3BO_3$ | 0.62 g | 0.31 g |
| $Na_2MoO_4$—$2H_2O$ | 0.025 g | 0.0125 g |

*Add first, dissolve in dark bottle while stirring

SB1 Solid Medium (per liter)

1 package MS salts (Gibco/BRL - Cat. No. 11117-066)
1 mL B5 vitamins 1000X stock
31.5 g glucose
2 mL 2,4-D (20 mg/L final concentration)
pH 5.7
8 g TC agar SB199 Solid Medium (per liter)

1 package MS salts (Gibco/BRL - Cat. No. 11117-066)
1 mL B5 vitamins 1000X stock
30 g Sucrose
4 ml 2,4-D (40 mg/L final concentration)
pH 7.0
2 gm Gelrite SB 166 Solid Medium (per liter)

1 package MS salts (Gibco/BRL - Cat. No. 11117-066)
1 mL B5 vitamins 1000X stock
60 g maltose
750 mg $MgCl_2$ hexahydrate
5 g activated charcoal
pH 5.7
2 g gelrite SB 103 Solid Medium (per liter)

1 package MS salts (Gibco/BRL - Cat. No. 11117-066)
1 mL B5 vitamins 1000X stock
60 g maltose
750 mg MgCl2 hexahydrate
pH 5.7
2 g gelrite SB 71-4 Solid Medium (per liter)

1 bottle Gamborg's B5 salts w/sucrose (Gibco/BRL - Cat. No. 21153-036)
pH 5.7
5 g TC agar 2,4-D Stock Obtain premade from Phytotech Cat. No. D 295 - concentration 1 mg/mL B5 Vitamins Stock (per 100 mL)

Store aliquots at −20° C.
10 g myo-inositol
100 mg nicotinic acid
100 mg pyridoxine HCl
1 g thiamine
If the solution does not dissolve quickly enough, apply a low level of heat via the hot stir plate.

-continued

| Media Recipes: | | |
|---|---|---|
| SB 228- Soybean Histodifferentiation & Maturation (SHaM) (per liter) | | |
| DDI $H_2O$ | 600 | mL |
| FN-Lite Macro Salts for SHaM 10X | 100 | mL |
| MS Micro Salts 1000x | 1 | mL |
| MS FeEDTA 100x | 10 | mL |
| CaCl 100x | 6.82 | mL |
| B5 Vitamins 1000x | 1 | mL |
| L-Methionine | 0.149 | g |
| Sucrose | 30 | g |
| Sorbitol | 30 | g |
| Adjust volume to 900 mL | | |
| pH 5.8 | | |
| Autoclave | | |
| Add to cooled media (≤30° C.): | | |
| *Glutamine (final concentration 30 mM) 4% | 110 | mL |
| FN-lite Macro for SHAM 10X- Stock #1 (per liter) | | |
| $(NH_4)2SO_4$ (ammonium sulfate) | 4.63 | g |
| $KNO_3$ (potassium nitrate) | 28.3 | g |
| $MgSO_4$*$7H_20$ (magnesium sulfate heptahydrate | 3.7 | g |
| $KH_2PO_4$ (potassium phosphate, monobasic) | 1.85 | g |
| Bring to volume | | |
| Autoclave | | |
| MS Micro 1000X- Stock #2 (per 1 liter) | | |
| $H_3BO_3$ (boric acid) | 6.2 | g |
| $MnSO_4$*$H_2O$ (manganese sulfate monohydrate) | 16.9 | g |
| ZnSO4*7H20 (zinc sulfate heptahydrate) | 8.6 | g |
| $Na_2MoO_4$*2H20 (sodium molybdate dihydrate) | 0.25 | g |
| $CuSO_4$*$5H_20$ (copper sulfate pentahydrate) | 0.025 | g |
| $CoCl_2$*$6H_20$ (cobalt chloride hexahydrate) | 0.025 | g |
| KI (potassium iodide) | 0.8300 | g |
| Bring to volume | | |
| Autoclave | | |
| FeEDTA 100X- Stock #3 (per liter) | | |
| $Na_2EDTA$* (sodium EDTA) | 3.73 | g |
| $FeSO_4$*$7H_20$ (iron sulfate heptahydrate) | 2.78 | g |
| Bring to Volume | | |
| Solution is photosensitive. Bottle(s) should be wrapped in foil to omit light. | | |
| Autoclave | | |
| Ca 100X- Stock #4 (per liter) | | |
| $CaCl_2$*$2H_20$ (calcium chloride dihydrate) | 44 | g |
| Bring to Volume | | |
| Autoclave | | |
| B5 Vitamin 1000X- Stock #5 (per liter) | | |
| Thiamine*HCl | 10 | g |
| Nicotinic Acid | 1 | g |
| Pyridoxine*HCl | 1 | g |
| Myo-Inositol | 100 | g |
| Bring to Volume | | |
| Store frozen | | |
| 4% Glutamine- Stock #6 (per liter) | | |
| DDI water heated to 30° C. | 900 | mL |
| L-Glutamine | 40 | g |
| Gradually add while stirring and applying low heat. | | |
| Do not exceed 35° C. | | |
| Bring to Volume | | |
| Filter Sterilize | | |
| Store frozen* | | |

*Note:
Final volume will be 1010 mL after glutamine addition.
Since glutamine degrades relatively rapidly, it may be preferable to add immediately prior to using media. Expiration 2 weeks after glutamine is added; base media can be kept longer w/o glutamine.
*EDTA must be completely dissolved before adding iron.
*Note:
Warm thawed stock in 31° C. bath to fully dissolve crystals.

Example 31

Functional Analysis of the *Euglena gracilis* Delta-9 Elongase in Somatic Soybean Embryos Transformed with Soybean Expression Vector pKR912

Mature somatic soybean embryos are a good model for zygotic embryos. While in the globular embryo state in liquid culture, somatic soybean embryos contain very low amounts of triacylglycerol or storage proteins typical of maturing, zygotic soybean embryos. At this developmental stage, the ratio of total triacylglyceride to total polar lipid (phospholipids and glycolipid) is about 1:4, as is typical of zygotic soybean embryos at the developmental stage from which the somatic embryo culture was initiated. At the globular stage as well, the mRNAs for the prominent seed proteins, α'-subunit of β-conglycinin, kunitz trypsin inhibitor 3, and seed lectin are essentially absent. Upon transfer to hormone-free media to allow differentiation to the maturing somatic embryo state, triacylglycerol becomes the most abundant lipid class. As well, mRNAs for α'-subunit of β-conglycinin, kunitz trypsin inhibitor 3 and seed lectin become very abundant messages in the total mRNA population. On this basis, the somatic soybean embryo system behaves very similarly to maturing zygotic soybean embryos in vivo, and is thus a good and rapid model system for analyzing the phenotypic effects of modifying the expression of genes in the fatty acid biosynthesis pathway (see PCT Publication No. WO 2002/00904, Example 3). Most importantly, the model system is also predictive of the fatty acid composition of seeds from plants derived from transgenic embryos.

Fatty Acid Analysis of Transgenic Somatic Soybean Embryos Expressing pKR912

Individual single, matured, somatic soybean embryos that had been transformed with pKR912 (SEQ ID NO:37; FIG. 7) and matured in the model system on SB103 plates as described in Example 30, with hygromycin as selection, were picked into glass GC vials and fatty acid methyl esters were prepared by transesterification. For transesterification, 50 μL of trimethylsulfonium hydroxide (TMSH) and 0.5 mL of hexane were added to the embryos in glass vials and incubated for 30 min at room temperature while shaking. Fatty acid methyl esters (5 μL injected from hexane layer) were separated and quantified using a Hewlett-Packard 6890 Gas Chromatograph fitted with an Omegawax 320 fused silica capillary column (Catalog #24152, Supelco Inc.). The oven temperature was programmed to hold at 220° C. for 2.6 min, increase to 240° C. at 20° C./min and then hold for an additional 2.4 min. Carrier gas was supplied by a Whatman hydrogen generator. Retention times were compared to those for methyl esters of standards commercially available (Nu-Chek Prep, Inc.). Routinely, 5-10 embryos per event were analyzed by GC, using the methodology described above.

Individual embryo fatty acid profiles for each event (5 embryos each) containing pKR912 were obtained from a total of 44 events. Of the 44 events, 37 events had at least 1 embryo with greater than 1% EDA and/or ERA. The lipid profiles of somatic soybean embryos expressing the *Euglena gracilis* delta-9 elongase for the top 5 events are shown in FIG. 20. Fatty acids are identified as 16:0 (palmitate), 18:0 (stearic acid), 18:1 (oleic acid), LA, ALA, EDA, and ERA; and, fatty acid compositions listed in FIG. 20 are expressed as a weight percent (wt. %) of total fatty acids. The activity of the *Euglena gracilis* delta-9 elongase is expressed as percent delta-9 elongation (% Elong), calculated according to the following formula: ([product]/[substrate+product])*100.

More specifically, the combined percent elongation for LA and ALA is shown as "delta-9% Elong", determined as: ([EDA+ERA]/[LA+ALA+EDA+ERA])*100. This elongation is also referred to as the overall % elongation. The individual omega-6 delta-9 elongation ("LA % Elong") was calculated as: ([EDA]/[LA+EDA])*100. Similarly, the individual omega-3 delta-9 elongation ("ALA % Elong") was calculated as: ([ERA]/[ALA+ERA])*100. The ratio of delta-9 elongation for omega-6 versus omega-3 substrates ("ratio [LA/ALA] % Elong") was obtained by dividing the LA % delta-9 elongation by the ALA % delta-9 elongation.

In summary of FIG. 20, the *Euglena gracilis* delta-9 elongase functioned in soybean to convert both LA and ALA to EDA and ERA, respectively. The line with the highest average EDA content (i.e., 1936-6-26) had embryos with an average EDA content of 36.1% and an average ERA content of 6.7%. The highest EDA and ERA content for an individual embryo from this line was 44.0% and 10.5%, respectively. The highest average overall % delta-9 elongation was 67.4% with the highest overall % delta-9 elongation for an individual embryo being 75.7%. When broken down into % delta-9 elongation for the omega-6 and omega-3 substrates, the highest average % delta-9 elongation was 67.3% and 67.1% for LA and ALA, respectively. The highest % delta-9 elongation for an individual embryo was 74.7% and 80.0% for LA and ALA, respectively. In this example, the *Euglena gracilis* delta-9 elongase may have a slight preference for ALA over LA, with the average desaturation ratio ranging from 0.8 to 1.0.

Example 32

Functional Analysis of the *Euglena gracilis* Delta-9 Elongase Co-Expressed with the *Euglena gracilis* Delta-8 Desaturase in Somatic Soybean Embryos Transformed with Soybean Expression Vector pKR920

Individual single, matured, somatic soybean embryos that had been transformed with pKR920 (SEQ ID NO:91) and matured in the model system on SB103 plates as described in Example 30, with hygromycin as selection, were picked into glass GC vials and fatty acid methyl esters were prepared by transesterification and analyzed as described in Example 31.

Individual embryo fatty acid profiles for each event (six embryos each) containing pKR920 were obtained from a total of 48 events. Of the 48 events, 40 events had at least one embryo with greater than 1% C20 fatty acids (sum of EDA, ERA, DGLA and ETA) and 29 of these also had a functional *Euglena gracilis* delta-8 desaturase (at least one embryo with greater than 1% DGLA and/or ETA). The lipid profiles of somatic soybean embryos expressing the *Euglena gracilis* delta-9 elongase and the *Euglena gracilis* delta-8 desaturase for the top 5 events are shown in FIG. 21. Fatty acids are identified as 16:0 (palmitate), 18:0 (stearic acid), 18:1 (oleic acid), LA, ALA, EDA, HGLA, ERA and ETA; and, fatty acid compositions listed in FIG. 21 are expressed as a weight percent (wt. %) of total fatty acids. The activity of the *Euglena gracilis* delta-9 elongase is expressed as percent delta-9 elongation (% Elong), calculated according to the following formula: ([product]/[substrate+product])*100.

More specifically, the combined percent elongation for LA and ALA is shown as "Total delta-9% Elong", determined as: ([EDA+HGLA+ERA+ETA]/[LA+ALA+EDA+HGLA+ERA+ETA])*100. This elongation is also referred to as the overall % elongation. The individual omega-6 delta-9 elongation ("LA % Elong") was calculated as: ([EDA+HGLA]/

[LA+EDA+HGLA])*100. Similarly, the individual omega-3 delta-9 elongation ("ALA % Elong") was calculated as: ([ERA+ETA]/[ALA+ERA+ETA])*100. The ratio of delta-9 elongation for omega-6 versus omega-3 substrates ("ratio [LA/ALA] % Elong") was obtained by dividing the LA % delta-9 elongation by the ALA % delta-9 elongation.

In summary of FIG. 21, the *Euglena gracilis* delta-9 elongase functioned in soybean to convert both LA and ALA to EDA and ERA, respectively, and these were further converted to HGLA and ETA, respectively, when the *Euglena gracilis* delta-8 desaturase was functional. The line with the highest average overall % delta-9 elongation (i.e., 1919-6-8) had embryos with an average total C20 fatty acid (EDA+HGLA+ERA+ETA) content of 42.2%. The highest total C20 fatty acid (EDA+HGLA+ERA+ETA) content for an individual embryo from this line was 50.1%. The highest average overall % delta-9 elongation was 65.5% with the highest overall % delta-9 elongation for an individual embryo being 80.8%. When broken down into % delta-9 elongation for the omega-6 and omega-3 substrates, the highest average % delta-9 elongation in this event was 64.7% and 69.3% for LA and ALA, respectively. The highest % delta-9 elongation for an individual embryo in this event was 80.4% and 83.8% for LA and ALA, respectively.

Example 33

Transformation of *Arabidopsis*

Transformed *Arabidopsis* plants were created by whole plant *Agrobacterium* transformation. Binary vector pKR926 (SEQ ID NO:102) was transformed into *Agrobacterium tumefaciens* NTL4 (Luo et al., *Molecular Plant-Microbe Interactions* 14(1):98-103 (2001)) by electroporation. Briefly, 1 μg plasmid DNA was mixed with 100 μL of electro-competent cells on ice. The cell suspension was transferred to a 100 μL electro oration curette (1 mm gap width) and electro orated using a BIORAD electro orator set to 1 kV, 400Ω and 25 μF. Cells were transferred to 1 mL LB medium and incubated for 2 h at 30° C. Cells were plated onto LB medium containing 50 μg/mL kanamycin. Plates were incubated at 30° C. for 60 h. Recombinant *agrobacterium* cultures (500 mL LB, 50 μg/mL kanamycin) were inoculated from single colonies of transformed *Agrobacterium* cells and grown at 30° C. for 60 h.

Cells were harvested by centrifugation (5000×g, 10 min) and resuspended in 1 L of 5% (W/V) sucrose containing 0.05% (V/V) Silwet L-77 (OSI Specialties, Inc). *Arabidopsis* plants were grown in soil at a density of 10 plants per 100 $cm^2$ pot in metromix 360 soil mixture for 4 weeks (22° C., 16 h light/8 h dark, 100 μE $m^{-2}s^{-1}$). At early bolting, *Arabidopsis* plants were dipped into the *Agrobacterium* suspension. Two days later, the same plants were dipped again with the same *Agrobacterium* strain in sucrose/Silwet. Plants were grown for three to four weeks under standard plant growth conditions described above and plant material was harvested and dried for one week at ambient temperatures in paper bags. Seeds were harvested using a 0.425 mm mesh brass sieve.

Cleaned *Arabidopsis* seeds (2 grams, corresponding to about 100,000 seeds) were sterilized by washes in 45 mL of 80% ethanol, 0.01% triton X-100, followed by 45 mL of 30% (V/V) household bleach in water, 0.01% triton X-100 and finally by repeated rinsing in sterile water. Aliquots of 20,000 seeds were transferred to square plates (20×20 cm) containing 150 mL of sterile plant growth medium comprised of 0.5×MS salts, 1.0% (W/V) sucrose, 0.05 MES/KOH (pH 5.8), 200 μg/mL timentin, and 50 μg/mL kanamycin solidified with 10 g/L agar. Homogeneous dispersion of the seed on the medium was facilitated by mixing the aqueous seed suspension with an equal volume of melted plant growth medium. Plates were incubated under standard growth conditions for fourteen days. Kanamycin-resistant seedlings were transferred to soil and grown to maturity as described above. T2 seed was obtained from these individual transformants.

Example 34

Functional Analysis of the *Euglena gracilis* Delta-9 Elongase in *Arabidopsis* Seed Transformed with *Arabidopsis* Expression Vector pKR926

Wild-type *Arabidopsis thaliana* (Columbia ecotype) and a fad3/fae1 double mutant (Smith et al., *Planta* 217:507-516 (2003)) were transformed with pKR926 (SEQ ID NO:102) as described in Example 33 and segregating T2 seed was obtained from a number of individual events for each. Bulk T2 seed lipid profiles for each event were obtained by transesterification with TMSH as described in Example 31 with the following modificiations. For each event, a small scoopful of seeds (approximately 25-50 seed each scoopful) was crushed in 50 μL of TMSH in a 1.5 mL eppendorf tube. After shaking in TMSH for 15 min., 400 μL of heptane was added and the tubes were vortexed well, shaken for an additional 15 min and centrifuged at 13,000×g for 1 min. After shaking, the heptane layer was removed into glass GC vials and the fatty acid methyl esters were analyzed as described in Example 31.

Bulk T2 seed fatty acid profiles were obtained for 22 events where wild-type *Arabidopsis* was transformed with pKR926 (SEQ ID NO:102) and for 16 events where the fad3/fae1 mutant was transformed. The lipid profiles of T2 bulk seed seed for the 22 wild-type-transformed events as well as for untransformed wild-type are shown in FIG. 22. The lipid profiles of T2 bulk seed seed for the 16 fad3/fae1-transformed events as well as for untransformed fad3/fae1 are shown in FIG. 23. Fatty acids are identified as 16:0 (palmitate), 18:0 (stearic acid), 18:1 (oleic acid), LA, ALA, 20:0 (arachidic acid), 20:1 (eicosenoic acid), EDA and ERA; and, fatty acid compositions listed in FIG. 22 and FIG. 23 are expressed as a weight percent (wt. %) of total fatty acids.

Individual T2 seed lipid profiles (ten seed per event) for one representative wild-type- and fad3/fae1-transformed event each (i.e., wt pKR926-8 and ff pKR926-1) were obtained by transesterification with TMSH as described in Example 31 with the following modifications. For each event, one seed was crushed in 10 μL of TMSH in a 1.5 mL eppendorf tube. After shaking in TMSH for 15 min, 75 μL of heptane was added and the tubes were vortexed well, shaken for an additional 15 min and centrifuged at 13,000×g for 1 min. After centrifugation, the heptane layer was removed into glass GC vials containing 200 μL inserts and the fatty acid methyl esters were analyzed as described in Example 31. In addition to having a representative T2 bulk seed fatty acid profile, each event chosen for single seed analysis also segregated both for resistance to kanamycin and for phenotype as a single loci insertion (i.e., 3:1).

The lipid profiles for ten single seeds for wt pKR926-8 and ff pKR926-1 are shown in FIG. 24. The activity of the *Euglena gracilis* delta-9 elongase is expressed as percent delta-9 elongation (% Elong), calculated according to the following formula: ([product]/[substrate+product])*100 as described in Example 31. Since the seed are T2 and are segregating, some of the seed have a wt or ff phenotype, respectively and these are indicated with shading (rows 1, 7-8, 12, 16-17 and 20).

Example 35

Co-Expression of the *Euglena gracilis* Delta-9 Elongase with the *Euglena gracilis* Delta-8 Desaturase, the *Mortierella alpina* Delta-5 Desaturase, the *Saprolegnia diclina* Delta-17 Desaturase and the *Fusarium moniliforme* Delta-15 Desaturase in Soybean Embryos Transformed with Soybean Expression Vectors pKR916 and pKR873

Soybean embryogenic suspension culture (cv. Jack) was transformed with the AscI fragments of pKR916 (SEQ ID NO:104; FIG. 19) and pKR873 (SEQ ID NO:56; FIG. 12) (fragments containing the expression cassettes), as described for production in Example 30. A subset of soybean embryos generated from each event (ten embryos per event) were harvested and analyzed for fatty acid composition as described in Example 31. Fatty acids were identified by comparison of retention times to those for authentic standards.

In this way, 169 events transformed with pKR916 and pKR873 were analyzed. From the 169 events analyzed, 127 were identified that produced EPA in at least one embryo out of ten analyzed at a relative abundance greater than 1.0% of the total fatty acids. Of these, 49 were identified that produced EPA in at least one embryo out of ten analyzed at a relative abundance greater than 10.0% of the total fatty acids. The average fatty acid profile for the ten best EPA events (average of nine or ten individual embryos) is shown in FIG. 25A. Fatty acids are identified as 16:0 (palmitate), 18:0 (stearic acid), 18:1 (oleic acid), LA, GLA, ALA, EDA, HGLA, ARA, ERA, JUN, ETA, EPA and DPA; and, fatty acid compositions listed in FIG. 25A are expressed as a weight percent (wt. %) of total fatty acids. For FIG. 25A., fatty acids listed as "others" include: 18:2 (5,9), STA, 20:0, 20:1(11), 20:2 (7,11) or 20:2 (8,11) and 20:3 (5,11,14). Each of these fatty acids is present at a relative abundance of less than 1% of the total fatty acids. The activity of the *Euglena gracilis* delta-9 elongase is expressed as percent delta-9 elongation (% Elong), calculated according to the following formula: ([product]/[substrate+product])*100.

More specifically, the combined percent elongation for LA and ALA is shown as "Total delta-9% Elong", determined as: ([EDA+HGLA+ARA+ERA+JUN+ETA+EPA+DPA]/[LA+ALA+EDA+HGLA+ARA+ERA+JUN+ETA+EPA+DPA])*100. This elongation is also referred to as the overall % elongation.

In summary of FIG. 25A, the *Euglena gracilis* delta-9 elongase functioned in soybean to convert both LA and ALA to EDA and ERA, respectively and these were further converted to other LC-PUFAs. The high EPA line with the highest average overall % delta-9 elongation (i.e., AFS 4697-7-5) had embryos with an average total C20 fatty acid (EDA+HGLA+ARA+ERA+JUN+ETA+EPA+DPA) content of 38.2%. The highest total C20 fatty acid (EDA+HGLA+ARA+ERA+JUN+ETA+EPA+DPA) content for a high EPA individual embryo was 51.4% (embryo from AFS 4709-8-6) and in this embryo, EPA was 24.4%.

Four plants each from top EPA events were regenerated and grown as described in Example 30. Seeds were harvested and a small chip was taken from part of each seed (from directly opposite the embryonic axis) using a razor blade. The seed chips were analyzed for fatty acids as described above. Fatty acid profiles for five seeds with highest EPA from 2 representative events (4697-6-1 and 6697-6-5) as well for a segregating wild-type seed for each are shown in FIG. 25B. Seed names are designated by a five number series separated by hyphens where the first three numbers indicate a particular event, the fourth number indicates the plant and the fifth number indicates the seed analyzed.

The seed with the highest total C20 fatty acid (EDA+HGLA+ARA+ERA+JUN+ETA+EPA+DPA) content for a high EPA event had total C20 fatty acids of 48.0% (seed number 4697-6-5-2-4) with a overall % elongation of 77.1% and in this seed, EPA was 16.2%.

Example 36

Construction and Functional Analysis of *Yarrowia lipolytica* Expression Vector pZuFmEgD9ES, Comprising a Synthetic Delta-9 Elongase Gene (Derived from *Euglena gracilis*), Codon-Optimized for Expression in *Yarrowia lipolytica* (EgD9eS)

The present Example describes the expression of *Yarrowia lipolytica* vector pZuFmEgD9ES, comprising a chimeric FBAINm::EgD9ES::Pex20 gene, wherein EgD9eS is a synthetic delta-9 elongase derived from *Euglena gracilis* and codon-optimized for expression in *Yarrowia*. This analysis included: (1) synthesis of EgD9eS; (2) construction and transformation of pZuFmEgD9ES into *Yarrowia lipolytica* strain Y2224; and (3) analysis of lipid profiles within transformant organisms of *Yarrowia lipolytica* strain Y2224 that were comprising pZuFmEgD9ES (expressing EgD9eS).

Synthesis of EgD9eS

The codon usage of the delta-9 elongase gene of *Euglena gracilis* (EgD9e; SEQ ID NOs:4 and 5) was optimized for expression in *Yarrowia lipolytica*, in a manner similar to that described in Example 4 and PCT Publication No. WO 2004/101753. Specifically, a codon-optimized delta-9 elongase gene (designated "EgD9eS"; SEQ ID NO:90) was designed, based on the coding sequence of EgD9e (i.e., from clone eeg1c.pk001.n5.f), according to the *Yarrowia* codon usage pattern (PCT Publication No. WO 2004/101753), the consensus sequence around the 'ATG' translation initiation codon, and the general rules of RNA stability (Guhaniyogi et al., *Gene,* 265(1-2):11-23 (2001)). In addition to modification of the translation initiation site, 117 bp of the 777 bp coding region were modified (15.1%) and 106 codons were optimized (40.9%). FIGS. 26A and B show a comparison of the nucleotide sequences of EgD9e and EgD9eS. None of the modifications in the codon-optimized gene changed the amino acid sequence of the encoded protein (SEQ ID NO:5). The designed EgD9eS gene was synthesized by GenScript Corporation (Piscataway, N.J.) and cloned into pUC57 (GenBank Accession No. Y14837) to generate pEgD9S.

Generation of Construct pZuFmEgD9E (Comprising EgD9E) and pZuFmEgD9ES (Comprising EgD9ES)

Plasmid pZuFmEgD9ES (SEQ ID NO:105), comprising a chimeric FBAINm::EgD9ES::Pex20 gene, was constructed by replacing the Nco I/Not I fragment of pZUF17 (SEQ ID NO:25) with the Nco I/Not I fragment from pEgD9S comprising EgD9eS. The product of this ligation was auto-replicating expression vector pZuFmEgD9ES, which thereby contained the following components:

TABLE 7

| Components of Plasmid pZuFmEgD9ES (SEQ ID NO: 105) | |
|---|---|
| RE Sites and Nucleotides Within SEQ ID NO: 105 | Description of Fragment and Chimeric Gene Components |
| Swa I/BsiW I (6067-318) | FBAINm::EgD9eS::Pex20, comprising: FBAINm: *Yarrowia lipolytica* FBAINm promoter (WO 2005/049805) EgD9eS: codon-optimized delta-9 elongase (SEQ ID NO: 5, described herein as EgD9eS), derived from *Euglena gracilis* Pex20: Pex20 terminator sequence of *Yarrowia* Pex20 gene (GenBank Accession No. AF054613) |
| 1354-474 | ColE1 plasmid origin of replication |
| 2284-1424 | Ampicillin-resistance gene ($Amp^R$) for selection in *E. coli* |
| 3183-4487 | *Yarrowia* autonomous replication sequence (ARS18; GenBank Accession No. A17608) |
| 6020-4533 | *Yarrowia* Ura 3 gene (GenBank Accession No. AJ306421) |

Plasmid pZuFmEgD9E (SEQ ID NO:106), comprising a chimeric FBAINm::EgD9E::Pex20 gene, was synthesized in a similar manner using the pZUF17 plasmid backbone.

Functional Analysis of *Yarrowia lipolytica* Transformants Comprising pZuFmEgD9E and pZuFmEgD9ES Plasmid pZuFmEgD9E and pZuFmEgD9ES (comprising a chimeric FBAINm::EgD9e::Pex20 gene and FBAINm::EgD9eS::Pex20 gene, respectively) were transformed into strain Y2224 (the FOA resistant mutant from an autonomous mutation of the Ura3 gene of wildtype *Yarrowia* strain ATCC #20362; Example 21), as described in the General Methods. The transformants were selected on MM plates. After 2 days growth at 30° C., 3 transformants grown on the MM plates were picked and re-streaked onto fresh MM plates. Once grown, these strains were individually inoculated into 3 mL liquid MM at 30° C. and shaken at 250 rpm/min for 2 days. The cells were collected by centrifugation, lipids were extracted, and fatty acid methyl esters were prepared by trans-esterification, and subsequently analyzed with a Hewlett-Packard 6890 GC.

GC analyses showed that there were about 3.2% EDA (C20:2) of total lipids produced in all seven transformants with pZuFmEgD9E, wherein the average conversion efficiency of LA (C18:2) to EDA in these seven strains was determined to be about 18.3% (average; calculated as described in Example 20).

In contrast, GC analyses showed that there were about 3.6% EDA (C20:2) of total lipids produced in all seven transformants with pZuFmEgD9ES, wherein the average conversion efficiency of LA (C18:2) to EDA in these seven strains was determined to be about 20.1% (average). Thus, the experimental data demonstrated that the synthetic *Euglena gracilis* delta-9 elongase codon-optimized for expression in *Yarrowia lipolytica* (i.e., EgD9eS; SEQ ID NO:90) was about 16.2% more efficient elongating LA to EDA than the wild-type EgD9e gene (i.e., SEQ ID NO:4).

Example 37

Preparation of *Eutreptiella* sp. CCMP389 Genomic DNA, RNA And cDNA

The present Example describes the preparation of genomic DNA, RNA and cDNA from *Eutreptiella* sp. CCMP389, which had been purchased from The Provasoli-Guillard National Center for Culture of Marine Phytoplankton (CCMP) (Bigelow Laboratory for Ocean Sciences, West Boothbay Harbor, Me.).

Preparation of RNA and Genomic DNA From *Eutreptiella* sp. CCMP389

Total RNA and genomic DNA were isolated from 1 liter of culture using Trizol reagent (Invitrogen, Carlsbad, Calif.), according to the manufacturer's protocol. Specifically, the cell pellet was resuspended in 0.75 mL of Trizol reagent, mixed with 0.5 mL of 0.5 mm glass beads, and homogenized in a Biospec mini beadbeater (Bartlesville, Okla.) at the highest setting for 3 min. The mixtures were centrifuged in an Eppendorf centrifuge for 30 sec at 14,000 rpm to remove debris and glass beads. The supernatant was extracted with 150 μL of 24:1 chloroform:isoamyl alcohol (Invitrogen). The upper aqueous phase was used for RNA isolation and the lower organic phase was used for DNA isolation.

For RNA isolation, the aqueous phase was mixed with 0.375 mL of isopropyl alcohol and allowed to incubate at room temperature for 5 min. Precipitated RNA was collected by centrifugation at 8,000 rpm and 4° C. for 5 min. The pellet was washed once with 0.7 mL of 80% ethanol and air-dried. In this way, 360 μg of total RNA were obtained.

For genomic DNA isolation, the lower organic phase was mixed with 75 μL of ethanol and incubated at room temperature for 5 min. The sample was then centrifuged at 5,000 rpm for 2 min in an Eppendorf centrifuge. The pellet was washed with 0.75 mL of 0.1 M sodium citrate: 10% ethanol twice. Each time, the sample was incubated for 15 min at room temperature in the wash solution, followed by centrifugation at 5,000 rpm for 5 min at 4° C. The pellet was air-dried and re-dissolved in 300 μL of 8 mM NaOH. The pH of the sample was adjusted to 7.5 with 1 M HEPES. The genomic DNA was then further purified with a Qiagen PCR purification kit (Valencia, Calif.) exactly as described in the manufacturer's protocol. Thus, 40 μg of genomic DNA was isolated.

Preparation of cDNA from *Eutreptiella* sp. CCMP389

Double-stranded cDNA was generated, using the Creator™ SMART™ cDNA Library Construction Kit from BD Bioscience Clontech (Palo Alto, Calif.). Specifically, for first strand cDNA synthesis, 1 μL of the total RNA sample (1.2 μg) was mixed individually with 1 μL of SMART™ IV oligonucleotide (SEQ ID NO:107), 1 μlL CDSIII/3' PCR primer (SEQ ID NO:108) and 2 μL of water. The mixture was heated to 75° C. for 5 min and cooled on ice for 5 min. To the sample was added 2 μL of 5× first strand buffer, 1 μL 20 mM DTT, 1 μL of dNTP mix (10 mM each of dATP, dCTP, dGTP and dTTP) and 1 μL of PowerScript reverse transcriptase. The sample was incubated at 42° C. for 1 hr.

The first strand cDNA synthesis mixture was used as template for amplification. Specifically, the reaction mixture contained 2 μL of the above first strand cDNA sample, 80 μL of water, 10 μL of 10× Advantage 2 PCR buffer, 2 μL 50×dNTP mix (10 mM each of dATP, dCTP, dGTP and dTTP), 2 μL of 5'-PCR primer (SEQ ID NO:109), 2 μL CDSIII/3'-PCR primer (SEQ ID NO:108) and 2 μL 50× Advantage 2 polymerase mix. PCR amplification was performed using the following conditions: 95° C. for 1 min, followed by 20 cycles of 95° C. for 10 sec and 68° C. for 6 min. Amplification products were purified with a Qiagen PCR purification kit following the manufacturer's protocol exactly. Purified products were eluted with 50 μL of water.

Example 38

Isolation of the Full-Length Delta-9 Elongase from *Eutreptiella* sp. CCMP389

The present Example describes the identification of a partial cDNA fragment encoding a delta-9 elongase from *Eutrep-*

*tiella* sp. CCMP389, by use of primers derived from conserved regions of the *Euglena gracilis* (EgD9e; Example 3) and *Isochrysis galbana* (IgD9e) delta-9 elongase sequences. Then, based on the sequence of the partial cDNA fragment, the 5' and 3' ends of the gene were isolated. This enabled assembly of a contig (SEQ ID NO:111), extending 51 bases upstream of the *Eutreptiella* sp. CCMP389 delta-9 elongase translation initiation 'ATG' codon and 662 bp beyond the delta-9 elongase termination codon.

Identification of a cDNA Fragment Encoding a Partial Delta-9 Elongase from *Eutreptiella* sp. CCMP389

It was assumed that a delta-9 elongase/delta-8 desaturase pathway operated in *Eutreptiella* sp. CCMP389, based on the Applicants' Assignee's previous identification of a delta-8 desaturase within the organism (co-pending U.S. Patent Application No. 60/853,563; filed Oct. 23, 2006; Attorney Docket No. BB1574). Design of degenerate primers suitable to isolate the *Eutreptiella* sp. CCMP389 delta-9 elongase was based on the identification of several stretches of conserved amino acid sequences common to both EgD9e (SEQ ID NO:5) and IgD9e (SEQ ID NO:27), when an alignment of the two elongases was produced using the method of Clustal W (slow, accurate, Gonnet option; Thompson et al., *Nucleic Acids Res.,* 22:4673-4680 (1994)) of the MegAlign™ program of DNASTAR software (see FIG. 27).

Based on this alignment, the following set of degenerate oligonucleotides were designed to amplify a portion of the coding region of the delta-9 elongase gene from *Eutreptiella* sp. CCMP389, as shown in Table 8.

TABLE 8

Degenerate Oligonucleotides used to Amplify the Delta-9 Elongase Gene From *Eutreptiella* sp. CCMP389

| Primer | Nucleotide Sequence | Amino Acid Sequence | Position Within SEQ ID NO: 2 (EgD9e) |
|---|---|---|---|
| EuEF3 | YTNCARTTYTTYCAYCA YTT (SEQ ID NO: 112) | LQFFHHL (SEQ ID NO: 113) | 150-156 |
| EuER3 | TTRAAYTGDATDATYTG CAT (SEQ ID NO: 114) | MQIIQFN (SEQ ID NO: 115) | 210-216 |

[Note:
The nucleic acid degeneracy code used for SEQ ID NOs: 112 and 114 was as follows: R = A/G; Y = C/T; D = G/A/T; and N = A/C/T/G.]

The reaction mixture contained 1 μL of 1:20 diluted cDNA, 5 μL each of the forward and reverse primers (20 μM), 14 μL water and 25 μL of TaKaRa ExTaq 2× premix (TaKaRa Bio, Mountain View, Calif.). PCR amplification was performed using the following parameters: 94° C. for 1 min, then 35 cycles of 94° C. for 20 sec, 55° C. for 20 sec, and 72° C. for 1 min, followed by a final elongation cycle at 72° C. for 5 min.

Agarose gel analysis of the PCR products showed that a ~200 bp fragment was obtained. The fragments were purified with a Qiagen PCR purification kit, cloned into pCR2.1-TOPO (Invitrogen) and sequenced. The resultant sequence (SEQ ID NO:129), when translated, had homology with the known delta-9 elongase from *Isochrysis galbana* (IgD9e; SEQ ID NO:27), based on BLAST program analysis (Basic Local Alignment Search Tool; Altschul, S. F., et al., *J. Mol. Biol.,* 215:403-410 (1993)).

Isolation of the 5'-End Sequence of the *Eutreptiella* sp. CCMP389 Delta-9 Elongase Double-stranded cDNA of *Eutreptiella* sp. CCMP389 (Example 37) was used as template in two separate rounds of PCR amplification. In the first round of PCR amplification, the oligonucleotide primers consisted of a gene specific oligonucleotide (i.e., 389Elo-5-1 (SEQ ID NO:116)) and the generic oligonucleotide 5'-PCR primer (SEQ ID NO:109) from the BD-Clontech Creator™ SMART™ cDNA Library Kit. The PCR amplifications were carried out in a 50 μL total volume, comprising: 1 μL of 1:10 diluted *Eutreptiella* sp. CCMP389 cDNA as template, 1 μL of each primer (20 μM), 22 μL water and 25 μL TaKaRa ExTaq 2× premix. Amplification was carried out at 94° C. for 90 sec, then 30 cycles of 94° C. for 30 sec, 55° C. for 30 sec and 72° C. for 1 min, followed by a final elongation cycle at 72° C. for 7 min.

The second round of PCR amplification used 1 μL of diluted product (1:50) from the first round PCR reaction as template. Primers consisted of a gene specific oligonucleotide (i.e., 389Elo-5-2 (SEQ ID NO:117)) and the oligonucleotide DNR CDS 5'-2 (SEQ ID NO:118). Amplification was conducted as described above.

The products of the second round PCR reaction were electrophoresed in 1% (w/v) agarose and appeared as a diffused band spanning the size range of 200 to 800 bp. Products between 400 bp to 600 bp were isolated using a Qiagen Gel purification kit according to the manufacturer's protocol, cloned into pCR2.1-TOPO (Invitrogen), and transformed into *E. coli*. Transformants were selected on LB agar containing ampicillin (100 μg/mL).

Sequence analysis of the plasmid DNA from one transformant comprising the 5' region of the putative delta-9 elongase cDNA revealed a fragment of 406 bp (i.e., 5'-cDNA fragment 1; SEQ ID NO:119). This fragment extended to near the gene's 'ATG' translation initiation codon, but neither the start codon nor the first 20 to 30 amino acids were included in SEQ ID NO:119.

An additional oligonucleotide (i.e., 389Elo-5-4 (SEQ ID NO:120)) was then designed to obtain the complete 5' end of the gene by PCR, based on the sequence of 5'-cDNA fragment 1 (SEQ ID NO:119). The reaction mixture and amplification conditions were identical to those used for the second round of PCR above, except that primer 389Elo-5-2 was replaced with 389Elo-5-4. When analyzed by agarose gel electrophoresis, PCR products again appeared as a diffused band between 200 and 800 bp and fragments with a size of 200 to 500 bp were isolated, cloned and transformed as described above.

Sequence analysis of the plasmid DNA from one transformant comprising the 5' region of the putative delta-9 elongase cDNA revealed a fragment of 197 bp (5'-cDNA fragment 2; SEQ ID NO:121). This included the 5'-end of the cDNA and 51 bp of upstream untranslated region.

Isolation of the 3'-End of the *Eutreptiella* sp. CCMP389 Delta-9 Elongase

The 3' end of the putative delta-9 delta elongase was also isolated by PCR amplification using cDNA as template. The methodology was as described above for isolation of the 5' end; however, the primers used on both the first and second round of PCR amplification were as shown below in Table 9 and were 10 μM instead of 20 μM. Additionally, the final elongation cycle at 72° C. was decreased from 7 min to 5 min.

TABLE 9

Oligonucleotide Primers Used For 3' cDNA Isolation

| PCR Amplification | Gene Specific Oligonucleotide | Generic Oligonucleotide |
|---|---|---|
| 1st Round | 389Elo-3-1 (SEQ ID NO: 122) | CDSIII/3' PCR primer (SEQ ID NO: 108) |
| 2nd Round | 389Elo-3-2 (SEQ ID NO: 123) | CDSIII/3' PCR primer (SEQ ID NO: 108) |

* CDSIII/3' PCR primer was supplied in Clontech's Creator ™ SMART ™ cDNA Library Construction Kit.

A ~1 kB DNA fragment was generated from the 2nd round PCR amplification, which was purified with a Qiagen PCR purification kit, cloned into pCR2.1-TOPO, transformed and sequenced. Sequence analysis of several clones showed that the ~1 kB DNA fragment contained the 3'-region of the putative delta-9 elongase cDNA, including the polyA tail. The 920 bp assembled contig sequence of the 3'-region is shown as SEQ ID NO:124.

Assembly of the Full-Length Delta-9 Elongase Sequence from *Eutreptiella* sp. CCMP389

Assembly of the original partial cDNA fragment (SEQ ID NO:116), the two 5' cDNA fragments (SEQ ID NOs:119 and 121) and 3'-cDNA fragment (SEQ ID NO:124) resulted in the complete sequence of the delta-9 elongase from *Eutreptiella* sp. CCMP389, plus 51 bp of 5' untranslated region and 662 bp of 3' untranslated region (SEQ ID NO:125; 1504 bp). The coding region is 792 bp long and encodes a protein of 263 amino acids (SEQ ID NO:126). SEQ ID NO:127 is the nucleotide sequence of the coding sequence of *Eutreptiella* sp. CCMP389 delta-9 elongase (designated herein as E389D9e).

Comparison of the Delta-9 Elongase Sequence of *Eutreptiella* sp. CCMP389 (E389D9e) to Known Delta-9 Elongases Identity of SEQ ID NO:127 (i.e., E389D9e) was determined by conducting BLAST searches for similarity to sequences contained in the BLAST "nr" database (Example 3). The results of the BLAST comparison summarizing the sequence to which SEQ ID NO:127 has the most similarity are reported according to the % identity, % similarity, and Expectation value. "% Identity" is defined as the percentage of amino acids that are identical between the two proteins. "% Similarity" is defined as the percentage of amino acids that are identical or conserved between the two proteins. "Expectation value" estimates the statistical significance of the match, specifying the number of matches, with a given score, that are expected in a search of a database of this size absolutely by chance.

Thus, the amino acid fragment described herein as SEQ ID NO:126 shared 38% identity and 56% similarity with IgD9e, the delta-9 elongase of *Isochrysis galbana* (SEQ ID NO:27), with an expectation value of 2E-43. Similarly, E389D9e is 33.1% identical to IgD9e using the Clustal V method and E389D9e is 65.1% identical to EgD9e using the Clustal V method (see FIG. 29). Sequence percent identity calculations performed by the Clustal V method (Higgins, D. G. and Sharp, P. M., *Comput. Appl. Biosci.,* 5:151-153 (1989); Higgins et al., *Comput. Appl. Biosci.,* 8:189-191 (1992)) were done using the MegAlign™ v6.1 program of the LASERGENE bioinformatics computing suite with the default parameters for pairwise alignment (KTUPLE=1, GAP PENALTY=3, WINDOW=5, DIAGONALS SAVED=5 and GAP LENGTH PENALTY=10).

Additionally, pairwise alignment of SEQ ID NO:126 to the EgD9e sequence of SEQ ID NO:5 using default parameters of Vector NTI®'s AlignX program revealed 65% identity and 76.5% similarity between the two proteins over a length of the 258 amino acids of EgD9e.

Example 39

Construction and Functional Analysis of *Yarrowia lipolytica* Expression Vector pFBAIN-389Elo (Comprising the *Eutreptiella* sp. CCMP389 Delta-9 Elongase (E389D9e)) in *Yarrowia lipolytica* Strain Y2224)

The present Example describes synthesis of *Yarrowia lipolytica* expression vector pFBAIN-389Elo (comprising a chimeric FBAINm::E389D9e::Pex20 gene). Delta-9 elongase activity of E389D9e when expressed in *Yarrowia lipolytica* strain Y2224 was subsequently determined.

Construction of *Yarrowia lipolytica* Expression Vector pFBAIN-389Elo

Oligonucleotides 389Elo-F and 389Elo-R1 (SEQ ID NOs: 116 and 117, respectively) were used as primers to amplify the full length cDNA of E389D9e (SEQ ID NO:127). The PCR reactions, with *Eutreptiella* sp. CCMP389 cDNA (Example 27) as template, were individually carried out in a 50 μL total volume comprising: 1 μL each of 20 μM forward and reverse primers, 1 μL cDNA, 10 μL 5×PCR buffer, 1 μL dNTP mix (10 μM each), 35 μL water and 1 μL Phusion polymerase (New England Biolabs, Inc., Ipswich, Mass.). Amplification was carried out at 98° C. for 1 min, then 30 cycles of 98° C. for 10 sec, 55° C. for 10 sec, and 72° C. for 30 sec, followed by a final elongation cycle at 72° C. for 5 min. The PCR product was digested with NcoI and EarI to generate a ~210 bp fragment that contained the 5' region of the delta-9 elongase cDNA. It was also digested with EarI and NotI to generate a ~600 bp fragment that contained the 3' region of the cDNA. The NcoI/EarI and the EarI/NotI digested fragments were purified following gel electrophoresis in 1% (w/v) agarose.

The NcoI/EarI and the EarI/NotI delta-9 elongase digested fragments were directionally ligated with NcoI/NotI digested pFBAIN-MOD-1 (SEQ ID NO:128), such that the E389D9e gene was under the control of the *Yarrowia lipolytica* FBAINm promoter and the PEX20-3' terminator region. Specifically, the ligation reaction contained: 10 μL 2× ligation buffer, 1 μL T4 DNA ligase (Promega), 4 μL each of the ~210 bp and the ~600 bp fragment (~300 ng each), and 1 μL pFBAIN-MOD-1 (~150 ng). The reaction mixture was incubated at room temperature for 2 h and used to transform *E. coli* Top10 competent cells (Invitrogen). Plasmid DNA from transformants was recovered using a Qiagen Miniprep kit. Correct clones were identified by restriction mapping and the final construct was designated "pFBAIN-389Elo".

Thus, pFBAIN-389Elo (FIG. 28; SEQ ID NO:110) thereby contained the following components:

TABLE 10

Components of Plasmid pFBAIN-389Elo (SEQ ID NO: 110)

| RE Sites and Nucleotides Within SEQ ID NO: 110 | Description of Fragment and Chimeric Gene Components |
|---|---|
| BglII-BsiWI (6040-301) | FBAINm::E389D9e::Pex20, comprising:<br>FBAINm: *Yarrowia lipolytica* FBAINm promoter (PCT Publication No. WO 2005/049805)<br>E389D9e: *Eutreptiella* sp. CCMP389 delta-9 elongase (SEQ ID NO: 127 described herein)<br>Pex20: Pex20 terminator sequence of *Yarrowia* Pex20 gene (GenBank Accession No. AF054613) |

TABLE 10-continued

Components of Plasmid pFBAIN-389Elo (SEQ ID NO: 110)

| RE Sites and Nucleotides Within SEQ ID NO: 110 | Description of Fragment and Chimeric Gene Components |
|---|---|
| PacI-BglII (4533-6040) | *Yarrowia* Ura 3 gene (GenBank Accession No. AJ306421) |
| (3123-4487) | *Yarrowia* autonomous replication sequence (ARS18; GenBank Accession No. A17608) |
| (2464-2864) | f1 origin |
| (1424-2284) | Ampicillin-resistance gene ($Amp^R$) for selection in *E. coli* |
| (474-1354) | ColE1 plasmid origin of replication |

Functional Analysis of *Yarrowia lipolytica* Transformants Comprising pFBAIN-389Elo Five (5) individual clones of pFBAIN-389Elo (comprising E389D9e) and control plasmid pFBAIN-MOD-1 were transformed into *Yarrowia lipolytica* strain Y2224 (Example 20) as described in the General Methods. The cells were plated onto MM plates lacking uracil and maintained at 30° C. for 2 to 3 days. Then, cells from each plate were scraped off, lipids were extracted, and fatty acid methyl esters were prepared by trans-esterification, and subsequently analyzed with a Hewlett-Packard 6890 GC.

GC analyses showed that EDA was produced in all five of the transformants comprising pFBAIN-389Elo, while no EDA was produced in the control strain (Table 11). Fatty acids are identified as 18:2 (LA) and 20:2 (EDA); and the composition of each is presented as a % of the total fatty acids. The conversion efficiency was calculated according to the following formula: ([product]/[substrate+product])*100, where 'product' includes the immediate product and all products in the pathway derived from it.

TABLE 11

Lipid Composition in *Yarrowia lipolytica* Strain Y2224 Engineered to Over-Express *Eutreptiella* sp. CCMP389 Delta-9 Elongase (E389D9e)

| Plasmid | Clone | C18:2 | C20:2 | Conversion Efficiency |
|---|---|---|---|---|
| pFBAIN-MOD-1 | 1 | 17.4 | 0 | 0 |
| pFBAIN-389Elo | 1 | 13.49 | 2.16 | 13.80 |
| | 2 | 13.16 | 1.79 | 11.97 |
| | 3 | 14.11 | 1.92 | 11.98 |
| | 4 | 15.55 | 0.78 | 4.78 |
| | 5 | 13.24 | 1.79 | 11.91 |

The results shown above confirmed that the cloned cDNA from *Eutreptiella* sp. CCMP389, described herein as SEQ ID NOs:126 and 127, efficiently desaturated LA to EDA and thus functioned as a delta-9 elongase.

Example 40

Construction of Alternate Soybean Expression Vectors for Expression of Other PUFA Genes In addition to the genes, promoters, terminators and gene cassettes described herein, one skilled in the art can appreciate that other promoter/gene/terminator cassette combinations can be synthesized in a way similar to, but not limited to, that described herein for expression of EgD9e, EgD9eS, E389D9e or E389D9eS. Similarly, it may be desirable to express other PUFA genes (such as those described below in Table 14), for co-expression with any of the delta-9 elongases of the present invention.

For instance, PCT Publication Nos. WO 2004/071467 and WO 2004/071178 describe the isolation of a number of promoter and transcription terminator sequences for use in embryo-specific expression in soybean. Furthermore, PCT Publication Nos. WO 2004/071467, WO 2005/047479 and WO 2006/012325 describe the synthesis of multiple promoter/gene/terminator cassette combinations by ligating individual promoters, genes and transcription terminators together in unique combinations. Generally, a NotI site flanked by the suitable promoter (such as those listed in, but not limited to, Table 12) and a transcription terminator (such as those listed in, but not limited to, Table 13) is used to clone the desired gene. NotI sites can be added to a gene of interest such as those listed in, but not limited to, Table 14 using PCR amplification with oligonucleotides designed to introduce NotI sites at the 5' and 3' ends of the gene. The resulting PCR product is then digested with NotI and cloned into a suitable promoter/NotI/terminator cassette.

In addition, PCT Publication Nos. WO 2004/071467, WO 2005/047479 and WO 2006/012325 describe the further linking together of individual gene cassettes in unique combinations, along with suitable selectable marker cassettes, in order to obtain the desired phenotypic expression. Although this is done mainly using different restriction enzymes sites, one skilled in the art can appreciate that a number of techniques can be utilized to achieve the desired promoter/gene/transcription terminator combination. In so doing, any combination of embryo-specific promoter/gene/transcription terminator cassettes can be achieved. One skilled in the art can also appreciate that these cassettes can be located on individual DNA fragments or on multiple fragments where co-expression of genes is the outcome of co-transformation of multiple DNA fragments.

TABLE 12

Seed-specific Promoters

| Promoter | Organism | Promoter Reference |
|---|---|---|
| β-conglycinin α'-subunit | soybean | Beachy et al., *EMBO J.* 4: 3047-3053 (1985) |
| kunitz trypsin inhibitor | soybean | Jofuku et al., *Plant Cell* 1: 1079-1093 (1989) |
| annexin | soybean | WO 2004/071467 |
| glycinin Gy1 | soybean | WO 2004/071467 |
| albumin 2S | soybean | U.S. Pat. No. 6,177,613 |
| legumin A1 | pea | Rerie et al., *Mol. Gen. Genet.* 225: 148-157 (1991) |
| β-conglycinin β-subunit | soybean | WO 2004/071467 |
| BD30 (also called P34) | soybean | WO 2004/071467 |
| legumin A2 | pea | Rerie et al., *Mol. Gen. Genet.* 225: 148-157 (1991) |

TABLE 13

Transcription Terminators

| Transcription Terminator | Organism | Reference |
|---|---|---|
| phaseolin 3' | bean | WO 2004/071467 |
| kunitz trypsin inhibitor 3' | soybean | WO 2004/071467 |
| BD30 (also called P34) 3' | soybean | WO 2004/071467 |
| legumin A2 3' | pea | WO 2004/071467 |
| albumin 2S 3' | soybean | WO 2004/071467 |

TABLE 14

| PUFA Biosynthetic Pathway Genes | | |
|---|---|---|
| Gene | Organism | Reference |
| delta-6 desaturase | *Saprolegnia diclina* | WO 2002/081668 |
| delta-6 desaturase | *Mortierella alpina* | U.S. Pat. No. 5,968,809 |
| elongase | *Mortierella alpina* | WO 2000/12720<br>U.S. Pat. No. 6,403,349 |
| delta-5 desaturase | *Mortierella alpina* | U.S. Pat. No. 6,075,183 |
| delta-5 desaturase | *Saprolegnia diclina* | WO 2002/081668 |
| delta-15 desaturase | *Fusarium moniliforme* | WO 2005/047479 |
| delta-17 desaturase | *Saprolegnia diclina* | WO 2002/081668 |
| elongase | *Thraustochytrium aureum* | WO 2002/08401<br>U.S. Pat. No. 6,677,145 |
| elongase | *Pavlova* sp. | Pereira et al., *Biochem. J.* 384: 357-366 (2004) |
| delta-4 desaturase | *Schizochytrium aggregatum* | WO 2002/090493 |
| delta-9 elongase | *Isochrysis galbana* | WO 2002/077213 |
| delta-9 elongase | *Euglena gracilis* | U.S. Provisional Application No. 60/739,989 |
| delta-8 desaturase | *Euglena gracilis* | WO 2000/34439<br>U.S. Pat. No. 6,825,017<br>WO 2004/057001<br>WO 2006/012325 |
| delta-8 desaturase | *Acanthamoeba castellanii* | Sayanova et al., *FEBS Lett.* 580: 1946-1952 (2006) |
| delta-8 desaturase | *Pavlova salina* | WO 2005/103253 |
| delta-8 desaturase | *Pavlova lutheri* | U.S. Provisional Application No. 60/795,810 |
| delta-8 desaturase | *Tetruetreptia pomquetensis* CCMP1491 | U.S. Provisional Application No. 60/853,563 |
| delta-8 desaturase | *Eutreptiella* sp. CCMP389 | U.S. Provisional Application No. 60/853,563 |
| delta-8 desaturase | *Eutreptiella* cf *gymnastica* CCMP1594 | U.S. Provisional Application No. 60/853,563 |

What is claimed is:

1. A recombinant construct comprising an isolated polynucleotide comprising:

(a) a nucleotide sequence encoding a polypeptide having delta-9 elongase activity, wherein the polypeptide has at least 95% amino acid identity, based on the Clustal V method of alignment, when compared to an amino acid sequence as set forth in SEQ ID NO:127; or (b) a nucleotide sequence encoding a polypeptide having delta-9 elongase activity, wherein the nucleotide sequence has at least 95% sequence identity, based on the BLASTN method of alignment, when compared to a nucleotide sequence as set forth in SEQ ID NO:126;

wherein said isolated polynucleotide is operably linked to at least one heterologous regulatory sequence.

2. A method for producing a transgenic plant comprising transforming a plant cell with the recombinant construct of claim 1 and regenerating a transgenic plant from the transformed plant cell.

3. The method of claim 2 wherein the transgenic plant is a soybean plant.

4. A transgenic seed comprising the recombinant construct of claim 1.

5. A transgenic seed obtained from the plant made by the method of claim 2 or 3, wherein said transgenic seed comprises said recombinant construct.

6. An oilseed plant comprising the recombinant construct of claim 1.

7. The oilseed plant of claim 6, wherein the oilseed plant is selected from the group consisting of soybean, *Brassica* species, sunflower, maize, cotton, flax and safflower.

8. A seed obtained from the oilseed plant of claim 6, wherein said seed comprises said recombinant construct.

9. A progeny plant obtained from the transgenic seed of claim 4, wherein said progeny plant comprises said recombinant construct.

10. A progeny plant obtained from the transgenic seed of claim 5, wherein said progeny plant comprises said recombinant construct.

11. A progeny plant obtained from the seed of claim 8, wherein said progeny plant comprises said recombinant construct.

* * * * *